US012673109B2

(12) United States Patent
Soares et al.

(10) Patent No.: US 12,673,109 B2
(45) Date of Patent: Jul. 7, 2026

(54) COMPOUNDS, COMPOSITIONS, METHODS, AND USES FOR TREATING CANCER AND IMMUNOLOGICAL DISORDERS

(71) Applicant: IL-2RX, Inc., Los Altos, CA (US)

(72) Inventors: Luis R.B. Soares, San Jose, CA (US); Clarence Ray Hurt, San Jose, CA (US)

(73) Assignee: IL-2RX, San Jose, CA (US)

(*) Notice: Subject to any disclaimer, the term of this patent is extended or adjusted under 35 U.S.C. 154(b) by 1264 days.

(21) Appl. No.: 17/147,179

(22) Filed: Jan. 12, 2021

(65) Prior Publication Data

US 2021/0252160 A1 Aug. 19, 2021

Related U.S. Application Data

(63) Continuation of application No. PCT/US2019/041486, filed on Jul. 11, 2019.

(60) Provisional application No. 62/770,651, filed on Nov. 21, 2018, provisional application No. 62/697,978, filed on Jul. 13, 2018.

(51) Int. Cl.

| | |
|---|---|
| *A61K 47/65* | (2017.01) |
| *A61K 31/519* | (2006.01) |
| *A61K 39/00* | (2006.01) |
| *A61K 39/395* | (2006.01) |
| *A61P 3/10* | (2006.01) |
| *A61P 13/08* | (2006.01) |
| *A61P 35/00* | (2006.01) |
| *A61P 37/02* | (2006.01) |
| *C07K 16/28* | (2006.01) |

(52) U.S. Cl.

CPC ............ *A61K 47/65* (2017.08); *A61K 31/519* (2013.01); *A61K 39/39558* (2013.01); *A61P 3/10* (2018.01); *A61P 35/00* (2018.01); *A61P 37/02* (2018.01); *C07K 16/2818* (2013.01); *A61K 2039/505* (2013.01); *A61K 2039/55* (2013.01); *A61P 13/08* (2018.01); *C07K 16/28* (2013.01); *C07K 2317/24* (2013.01); *C07K 2319/30* (2013.01); *C12Q 2600/106* (2013.01); *C12Q 2600/156* (2013.01)

(58) Field of Classification Search

CPC .................. A61K 47/65; A61K 31/519; A61K 39/39558; A61K 2039/505; A61K 2039/55; A61K 47/642; A61P 3/10; A61P 35/00; A61P 37/02; A61P 13/08; C07K 16/2818; C07K 16/28; C07K 2317/24; C07K 2319/30; C12Q 2600/106; C12Q 2600/156

See application file for complete search history.

(56) References Cited

U.S. PATENT DOCUMENTS

| | | | | |
|---|---|---|---|---|
| 7,951,810 | B2 | 5/2011 | Critchley et al. | |
| 8,901,136 | B2 | 12/2014 | Critchley et al. | |
| 2008/0241128 | A1 | 10/2008 | Jeffrey | |
| 2011/0136834 | A1 | 6/2011 | Critchley et al. | |
| 2012/0107332 | A1 | 5/2012 | Jeffrey | |
| 2016/0151515 | A1 | 6/2016 | Joubert et al. | |
| 2017/0066772 | A1 | 3/2017 | Mizutani et al. | |
| 2018/0162864 | A1 | 6/2018 | Mizutani et al. | |
| 2020/0040052 | A1* | 2/2020 | Winston | C07K 14/55 |
| 2021/0060169 | A1* | 3/2021 | Ikeda | A61P 37/04 |

FOREIGN PATENT DOCUMENTS

| | | | |
|---|---|---|---|
| CN | 107106654 | A | 6/2021 |
| EP | 0 319 012 | A2 | 6/1989 |
| EP | 2 478 891 | A1 | 7/2012 |
| EP | 3 103 802 | A1 | 12/2016 |
| WO | WO-00/04926 | A2 | 2/2000 |
| WO | WO-0004926 | A3 | 2/2000 |
| WO | WO-03/015697 | A2 | 2/2003 |
| WO | WO-03/015697 | A3 | 2/2003 |

(Continued)

OTHER PUBLICATIONS

Burke, et al., Bioconjugate Chem 2009 20:1242 (Year: 2009).*

(Continued)

*Primary Examiner* — Julie Wu
*Assistant Examiner* — Sydney Van Druff
(74) *Attorney, Agent, or Firm* — Gary P. Katz; Katz Law Group LLC

(57) ABSTRACT

The present disclosure provides novel polypeptide-therapeutic compound or hormone-therapeutic compound conjugates using cleavable or non-cleavable linkers, whereby the polypeptide or hormone serves to target specific cells using receptor expression on the targeted cell to bind the ligand (polypeptide or hormone) carrying the therapeutic compound unlike antibody drug conjugates. Upon binding, the ligand and the therapeutic compound (multiples of the therapeutic compound in some embodiments) enter the cell by receptor-mediated endocytosis, and release drugs conjugated to the ligand by linkers, to interact with intracellular components to enhance, restore, or block a signal transduction process. The ligands for the polypeptide-therapeutic compound or hormone-therapeutic compound conjugates include, but are not limited to: cytokines, growth factors and hormones among other proteins with corresponding cell surface specific receptors. The disorders targeted by such polypeptide-therapeutic compound or hormone-therapeutic compound conjugates include, but are not limited to: immunological disorders (e.g., allergy and autoimmune disorders) and cancer.

13 Claims, 18 Drawing Sheets

Specification includes a Sequence Listing.

(56) References Cited

FOREIGN PATENT DOCUMENTS

WO WO-2007/092213 A2 8/2007
WO WO-2007/092213 A3 8/2007
WO WO-2018218119 A1 * 11/2018 .......... A61K 31/352

OTHER PUBLICATIONS

Shi Chunqin, Jiang Yufeng, Hu Qiaohong (2011). "Progress in research on receptor-mediated active targeting drug delivery carriers," Chin. Pharm. J. 46(21):1617-1621 (with English Summary Provided).
Wang, Y. et al. (2017). "Peptide drug conjugates as effective prodrug strategies for targeted delivery," Adv. Drug Deliv. 110-111:112-126, 35 total pages.
Altschul et al. (1990). "Basic local alignment search tool," J. Mol. Biol. 215:403-10.
Babon, J. et al. (2012). "The biology mechanism of action of suppressor of cytokine signaling 3 (SOCS3)," Growth Factors 30:207-219.
Bart de Goeij and John M Lambert. "New developments for antibody-drug conjugate-based therapeutic approaches." In: Current Opinion in Immunology 40 (2016), pp. 14-23.
Basle, N. Joubert, and M. Pucheault. "Protein chemical modification on endogenous amino acids." In: Chem Biol 17.3 (2010), pp. 213-227.
Beck et al. "Strategies and challenges for the next generation of antibody drug conjugates." In: Nat Rev Drug Discov 16.5 (2017), pp. 315-337.
Brownell, J.E. et al. (2010). "Substrate-Assisted Inhibition of Ubiquitin-like Protein-Activating Enzymes: The NEDD8 E1 Inhibitor MLN4924 Forms a NEDD8-AMP Mimetic In Situ," Mol. Cell 37:102-111.
Burslem and C.M. Crews. "Small-Molecule Modulation of Protein Homeostasis. Chem Rev." In: Chem. Rev. 117.17 (2017), pp. 11269-11301.
Cazzamalli et al. "Enhanced Therapeutic Activity of Non-Internalizing Small Molecule-Drug Conjugates Targeting Carbonic Anhydrase IX in Combination With Targeted Interleukin-2." In: Clinical Cancer Research 17 (2018), p. 3458.
Dal Corso et al. "Protease-Cleavable Linkers Modulate the Anticancer Activity of Noninternalizing Antibody-Drug Conjugates." In: Bioconjug Chem 28.7 (2017), pp. 1826-1833.
De Graaf et al. "Beta-Glucuronidase-Mediated Drug Release." In: Current Pharmaceutical Design 18 (2002).
DeGruyter, L. R. Malins, and P. S. Baran. "Residue-Specific Peptide Modification: A Chemist's Guide." In: Biochemistry 56.30 (2017), pp. 3863-3873.
Dorywalska et al. "Molecular Basis of Valine-Citrulline-P ABC Linker Instability in Site-Specific ADCs and Its Mitigation by Linker Design." In: Mol Cancer Ther 15.5 (2016), pp. 958-970.
Dubowchik, A. Raymond, and I. Firestone. "Cathepsin B-sensitive dipeptide prodrugs. 1. A model study of structural requirements for efficient release of doxorubicin." In: Bioorganic & Medicinal Chemistry Letters 8 (1998), pp. 3341-3346.
Dubowchik, A. Raymond, et al. "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity." In: Bioconjugate Chem. 13 (2002), pp. 855-869.
Emanuele, M.J. et al. (2011). "Global Identification of Modular Cullin-Ring Ligase Substrates," Cell 147:459-474.
Friend, S.F. et al. (2013). "The Discovery of a Reciprocal Relationship between Tyrosine-Kinase Signaling and Cullin Neddylation," PLOS One 8:e75200, 9 total pages.
Gadducci et al. "Treatment options in recurrent cervical cancer." In: Oncology Letters (2010), pp. 3-11.
Hartemann, A. et al. (2013). "Low-dose interleukin 2 in patients with type 1 diabetes: a phase ½ randomised, double-blind, placebo-controlled trial," Lancet Diabetes Endocrinal 1:295-305.
Hatanaka Yasumaru, Hashimoto Makoto, and Yuichi Kanaoka. "A Novel Biotinylated Heterobifunctional Cross-linking Reagent Bearing an Aromatic Diazirine." In: Bioorganic & Medicinal Chemistry 2.12 (1994 ).
He, J. et al. (2016). "Low-dose interleukin-2 treatment selectively modulates $CD4^+$ T cell subsets in patients with systemic lupus erythematosus," Nature Medicine 22:991-993, 5 total pages.
Hwa, V. et al. (2011). "STAT5b deficiency: Lessons from STAT5b gene mutations," Best Practice & Research Clinical Endocrinology & Metabolism 25:61-75.
International Search Report mailed on Jan. 8, 2020, for PCT Application No. PCT/US2019/041486, filed on Jul. 11, 2019, 12 pages.
Jain, N. et al. (2015). "Current ADC Linker Chemistry," Pharm. Res. 32:3526-3540.
Jeffrey et al. "Development and Properties of β-Glucuronide Linkers for Monoclonal Antibody-Drug Conjugates." In: Bioconjugate Chem 17 (2006).
Jeffrey, M. T. Nguyen, et al. "Minor groove binder antibody conjugates employing a water soluble beta-glucuronide linker." In: Bioorg Med Chem Lett 17.8 (2007).
Kanai, T. et al. (2012). "The STAT5b pathway defect and autoimmunity," Frontiers in Immunol. 3:1-8.
Kanai, T. et al. (2014). "Identification of STAT5A and STAT5B Target Genes in Human T Cells," Plos One 9:e86790, 12 total pages.
Kennedy-Nasser, A.A. et al. (2014). "Ultra low-dose IL-2 for GVHD prophylaxis after allogeneic hematopoietic stem cell transplantation mediates expansion of regulatory T cells without diminishing antiviral and antileukemic activity," Clin. Can. Res. 20:2215-2225.
Kida et al. "Studies on Heterobifunctional Cross-Linking Reagents, 6- Maleimidohexanoic Acid Active Esters." In: Chem. Pharm. Bull. 55.4 (2007), pp. 685-687.
Kolodych, C. Michel, et al. "Development and evaluation of beta-galactosidase sensitive antibody-drug conjugates." In: Eur J Med Chem 142 (2017).
Koniev and A. Wagner. "Developments and recent advancements in the field of endogenous amino acid selective bond forming reactions for bioconjugation." In: Chem Soc Rev 448.15 (2015), pp. 5495-5551.
Koreth, J. et al. (2011). "Interleukin-2 and regulatory T cells in graft-versus-host disease," N. Engl. J. of Med. 365:2055-2066.
Kottke et al. "Treg Depletion-enhanced IL-2 Treatment Facilitates Therapy of Established Tumors Using Systemically Delivered Oncolytic Virus." In: Molecular Therapy 16.7 (2008), pp. 1217-1226.
Leung, C-H. et al. (2011). "A natural product-like inhibitor of NEDD8-activating enzyme," Chem. Commun. (Camb). 47:2511-2513.
List, T. et al. (2014). "A chemically defined trifunctional antibody-cytokine-drug conjugate with potent antitumor activity," Mol. Cancer Ther. 13:2641-2652.
Lu, P. et al. (2016). "Discovery of a novel NEDD8 activating enzyme inhibitor with piperidin-4-amine scaffold by structure-based virtual screening," ACS Chem. Biol. 11:1901-1907.
Lukkarila, J.L. et al. (2011). "Identification of NAE Inhibitors Exhibiting Potent Activity in Leukemia Cells: Exploring the Structural Determinants of NAE Specificity," ACS Med. Chem. Lett. 2:577-582.
Ma, H. et al. (2017). "Discovery of benzothiazole derivatives as novel non-sulfamide NEDD8 activating enzyme inhibitors by target-based virtual screening," Eur. J. Med. Chem. 133:174-183.
MacKenzie, D.A. et al. (2007). "GRAIL Is Up-regulated in CD4+ CD25+ T Regulatory Cells and Is Sufficient for Conversion of T Cells to a Regulatory Phenotype," J. Biol. Chem. 282:9696-9702.
Matsuoka, K-I, et al. (2013). "Low-dose interleukin-2 therapy restores regulatory T cell homeostasis in patients with chronic graft-versus-host disease," Clin. Can. Res. 5:179ra43, 25 total pages.
McKay and M. G. Finn. "Click chemistry in complex mixtures: bioorthogonal bioconjugation." In: Chem Biol 21.9 (2014), pp. 1075-1101.
Merlet, J. et al. (2009). "Regulation of cullin-RING E3 ubiquitin-ligases by neddylation and dimerization," Cell Mol. Life Sci. 66:1924-1938.

(56) References Cited

OTHER PUBLICATIONS

Oo, Y.H. et al. (2012). "Low-Dose Interleukin-2 and HCV-Induced Vasculitis," N. Engl. J. Med. 366:1353-1354.
Pescovitz, H.K.C. et al. (2013). "Immune intervention therapy in type 1 diabetes: Safety first," The Lancet 1:263-265.
Petroski, M.D. (2010). "Mechanism-based neddylation inhibitor," Chem. & Biol. 17:6-8.
Rhee, H-W. et al. (2013). "Proteomic Mapping of Mitochondria in Living Cells via Spatially-Restricted Enzymatic Tagging," Science 339:1328-1331.
Rosenberg, S.A. et al. Biological activity of recombinant human interleukin-2 produced in *Escherichia coli*, Mar. 30, 1984;223(4643):1412-4.
Saadoun, D. et al. (2011). "Regulatory T-Cell Responses to Low-Dose Interleukin-2 in HCV-Induced Vasculitis," N. Engl. J. Med. 365:2067-2077.
Seroogy, C.M. et al. (2004). "The gene related to anergy in lymphocytes, an E3 ubiquitin ligase, is necessary for anergy induction in CD4 T cells," J. Immunol. 173:79-85.
Song, H. et al. (2016). "MLN4924, a first-in-class NEDD8-activating enzyme inhibitor, attenuates IFN-β production," J. Immunol. 196:3117-3123.
Soucy, T.A. et al. (2009). "Targeting NEDD8-activated Cullin-RING ligases for the treatment of cancer," Clin. Can. Res. 15:3912-3916.
Soucy, T.A. et al. (2009). "An inhibitor of NEDD8-activating enzyme as a new approach to treat cancer," Nature 458:732-737.
Su, L. et al. CD4+CD25+ regulatory T cells fail to undergo chromatin remodeling across the proximal promoter region of the IL-2 gene. J Immunol. Oct. 15, 2004;173(8):4994-5001.
Tan, Y-C. et al. (2014). "Sequencing Antibody Repertoires Provides Evidence for Original Antigenic Sin Shaping the Antibody Response to Influenza Vaccination," Clin. Immunol. 151:55-65.
Tsuchikama and Z. An. "Antibody-drug conjugates: recent advances in conjugation and linker chemistries." In: Protein Cell 9.1 (2018), pp. 33-46.
Vhora et al. (2015). "Protein and Peptide-Drug Conjugates: an Emerging Drug Delivery Technology." In: Advances in Protein Chemistry and Structural Biology, vol. 98, pp. 1-55.
Wakankar, A. et al. Analytical methods for physicochemical characterization of antibody drug conjugates. mAbs. 2011:3(2): 161-172.
Warnecke et al. "Synthesis, cleavage profile, and antitumor efficacy of an albumin-binding prodrug of methotrexate that is cleaved by plasmin and cathepsin B." In: Arch Pharm (Weinheim) 340.8 (2007), pp. 389-395.
Wang et al. "Ontak-like human IL-2 fusion toxin." In: J Immunol. Methods 448 (2017), pp. 51-58.
Wang et al. "Development and Properties of Valine-Alanine based Antibody-Drug Conjugates with Monomethyl Auristatin E as the Potent Payload." In: Int. J Mol. Sci. 18 (2007), p. 1860.
Williams, J.J.L. et al. (2014). "Role of Ubiquitylation in Controlling Suppressor of Cytokine Signalling 3 (SOCS3) Function and Expression," Cells 3:546-562.
Written Opinion of the International Searching Authority mailed on Jan. 8, 2020, for PCT Application No. PCT/US2019/041486, filed on Jul. 11, 2019, 16 pages.
Yao, Z. et al. (2007). "Nonredundant roles for Stat5a/b in directly regulating Foxp3," Blood 109:4368-4375.
Zacharie, B. et al. "A Simple One-Step Conversion of Carboxylic Acids to Esters Using EEDQ." In: J Org. Chem 60 (1995), pp. 7072-7074.
Zhong, H-J. et al. (2014). "Structure-based repurposing of FDA-approved drugs as inhibitors of NEDD8-activating enzyme," Biochimie. 102:211-215.
Zhong, H-J. et al. (2015). "Discovery of deoxyvasicinone derivatives as inhibitors of NEDD8-activating enzyme," Methods 71:71-76.

* cited by examiner

FIG. 3

| Series | AA Linkage | Family Names | Protein Drug Conjugate |
|---|---|---|---|
| A | Cys | (R)-N-((R)-1-(l1-azaneyl)-3-mercapto-1-oxopropan-2-yl)-2-(l2-azaneyl)propanamide | 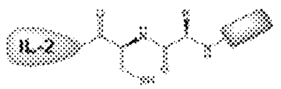 |
| B | Cys | (S)-(l1-azaneyl)(2-(benzo[d]thiazol-2-yl)-4,5-dihydrothiazol-4-yl)methanone | 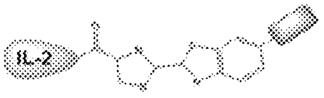 |
| C | Cys | (R)-2-amino-1-(l1-azaneyl)-3-(propylthio)propan-1-one |  |
| D | Cys | (R)-2-((2-amino-3-(l1-azaneyl)-3-oxopropyl)thio)-N-methylacetamide | 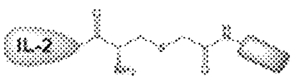 |
| E | Cys | 3-(((R)-2-amino-3-(l1-azaneyl)-3-oxopropyl)thio)pyrrolidine-2,5-dione |  |
| F | Cys | (R)-2-amino-1-(l1-azaneyl)-3-((2-(ethylsulfonyl)ethyl)thio)propan-1-one | 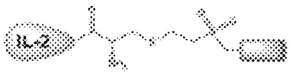 |
| G | Cys | (R)-2-amino-1-(l1-azaneyl)-3-(methyldisulfaneyl)propan-1-one |  |
| H | Cys | (R)-3-((2-amino-3-(l1-azaneyl)-3-oxopropyl)thio)-1l2-pyrrole-2,5-dione | 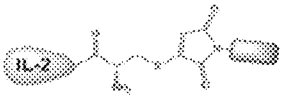 |
| I | Cys | 3,4-bis(((R)-2-amino-3-(l1-azaneyl)-3-oxopropyl)thio)-1l2-pyrrole-2,5-dione | 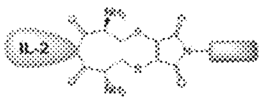 |
| J | Cys | (R,E)-3-((2-amino-3-(l1-azaneyl)-3-oxopropyl)thio)-3-phenylacrylonitrile | 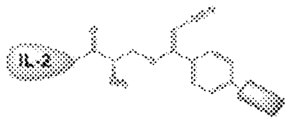 |

FIG. 3 (con't)

| Series | AA Linkage | Family Names | Protein Drug Conjugate |
|---|---|---|---|
| K | Cys | (R)-3-((2-amino-3-(l1-azaneyl)-3-oxopropyl)thio)-1-(l2-azaneyl)but-3-en-1-one | 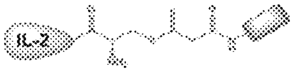 |
| L | Cys | (R)-(l1-azaneyl)(thiazolidin-4-yl)methanone | 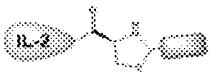 |
| M | Cys | (R)-2-amino-1-(l1-azaneyl)-3-((5-phenyl-1,3,4-oxadiazol-2-yl)thio)propan-1-one | 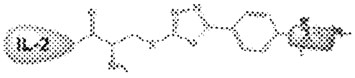 |
| N | Cys | (R)-4-(3-((2-amino-3-(l1-azaneyl)-3-oxopropyl)thio)propanoyl)-N-methylbenzamide | 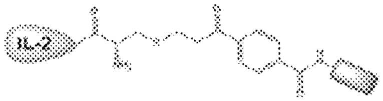 |
| O | Cys | (R)-2-amino-1-(l1-azaneyl)-3-((2,3,5,6-tetrafluorophenyl)thio)propan-1-one | 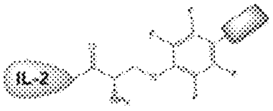 |
| P | Cys | (R)-2-amino-1-(l1-azaneyl)-3-(propylthio)propan-1-one | 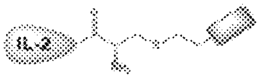 |
| Q | Cys | (2R)-2-amino-1-(l1-azaneyl)-3-(((E)-3-hydroxy-1,3-diaryl-prop-1-en-2-yl)thio)propan-1-one | 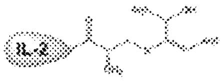 |
| R | Cys | (R)-3-(allylthio)-2-amino-1-(l1-azaneyl)propan-1-one | 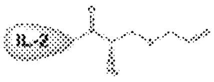 |
| S | Cys | (S)-4-(4-((E)-(4-((((R)-2-amino-3-(l1-azaneyl)-3-oxopropyl)thio)methyl)phenyl)diazenyl)phenyl)-3-(l2-azaneyl)butan-2-one | 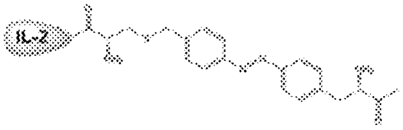 |
| T | Cys | dialkyl(1S,2R,3S,4R)-3-(((S)-2-amino-3-(l1-azaneyl)-3-oxopropyl)thio)-1-methyl-7-oxabicyclo[2.2.1]hept-5-ene-2,3-dicarboxylate | 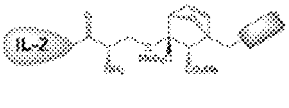 |

FIG. 3 (con't)

| Series | AA Linkage | Family Names | Protein Drug Conjugate |
|---|---|---|---|
| U | Lys | (S)-N-(5-amino-6-(l1-azaneyl)-6-oxohexyl)acetamide | 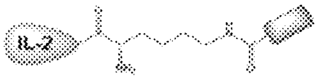 |
| V | Lys | (S)-N-(5-amino-6-(l1-azaneyl)-6-oxohexyl)acetamide | 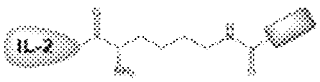 |
| W | Lys | (S)-N-(5-amino-6-(l1-azaneyl)-6-oxohexyl)acetamide | 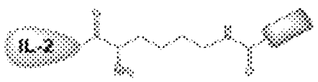 |
| X | Lys | (S)-N-(5-amino-6-(l1-azaneyl)-6-oxohexyl)-l2-azanecarbothioamide | 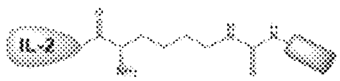 |
| Y | Lys | (S)-2-amino-1-(l1-azaneyl)-6-(ethylamino)hexan-1-one | 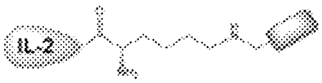 |
| Z | Lys | (S,Z)-N-(5-amino-6-(l1-azaneyl)-6-oxohexyl)-2-((5-(diethylamino)-2-(methylcarbamoyl)-4-oxocyclohexa-2,5-dien-1-ylidene)amino)benzamide | 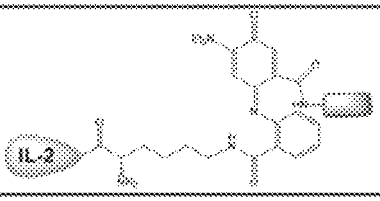 |
| AA | Lys | (S)-1-(5-amino-6-(l1-azaneyl)-6-oxohexyl)-4-(methoxycarbonyl)pyridin-1-ium | 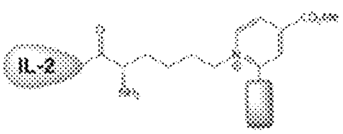 |
| AB | Lys | (S)-2-amino-1-(l1-azaneyl)-6-(1,1-dihydroxy-3-alkyl-1H-1l4,2l4-benzo[c][1,2]azaborol-2-yl)hexan-1-one | 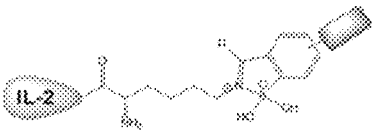 |
| AC | Lys | (S)-7-((l2-azaneyl)carbonyl)-3-(5-amino-6-(l1-azaneyl)-6-oxohexyl)benzo[d][1,2,3]triazin-4(3H)-one | 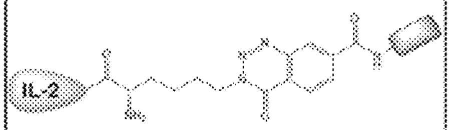 |

SEQUENCE LISTING

```
<160> NUMBER OF SEQ ID NOS: 4

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80
```

```
Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130


<210> SEQ ID NO 2
<211> LENGTH: 242
<212> TYPE: PRT
<213> ORGANISM: Artificial Sequence
<220> FEATURE:
<223> OTHER INFORMATION: TXN / GSAM linker / IL-2 C125S mutant

<400> SEQUENCE: 2

Met Val Lys Gln Ile Glu Ser Lys Thr Ala Phe Gln Glu Ala Leu Asp
1               5                   10                  15

Ala Ala Gly Asp Lys Leu Val Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val Gly Ser Ala Met Ala Pro Thr
            100                 105                 110

Ser Ser Ser Thr Lys Lys Thr Gln Leu Gln Leu Glu His Leu Leu Leu
        115                 120                 125

Asp Leu Gln Met Ile Leu Asn Gly Ile Asn Asn Tyr Lys Asn Pro Lys
    130                 135                 140

Leu Thr Arg Met Leu Thr Phe Lys Phe Tyr Met Pro Lys Lys Ala Thr
145                 150                 155                 160

Glu Leu Lys His Leu Gln Cys Leu Glu Glu Glu Leu Lys Pro Leu Glu
                165                 170                 175

Glu Val Leu Asn Leu Ala Gln Ser Lys Asn Phe His Leu Arg Pro Arg
            180                 185                 190

Asp Leu Ile Ser Asn Ile Asn Val Ile Val Leu Glu Leu Lys Gly Ser
        195                 200                 205

Glu Thr Thr Phe Met Cys Glu Tyr Ala Asp Glu Thr Ala Thr Ile Val
    210                 215                 220

Glu Phe Leu Asn Arg Trp Ile Thr Phe Ser Gln Ser Ile Ile Ser Thr
225                 230                 235                 240

Leu Thr


<210> SEQ ID NO 3
<211> LENGTH: 133
<212> TYPE: PRT
<213> ORGANISM: Homo sapiens

<400> SEQUENCE: 3

Ala Pro Thr Ser Ser Ser Thr Lys Lys Thr Gln Leu Gln Leu Glu His
```

-continued

```
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130


<210> SEQ ID NO 4
<211> LENGTH: 134
<212> TYPE: PRT
<213> ORGANISM: Artificial Sequence
<220> FEATURE:
<223> OTHER INFORMATION: IL-2 WT Cys-N-positions

<400> SEQUENCE: 4

Cys Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130
```

COMPOUNDS, COMPOSITIONS, METHODS, AND USES FOR TREATING CANCER AND IMMUNOLOGICAL DISORDERS

CROSS-REFERENCE TO RELATED APPLICATIONS

This application is a continuation of International Patent Application No. PCT/US2019/041486, filed Jul. 11, 2019, which claims priority to U.S. Provisional Application No. 62/770,651, filed Nov. 21, 2018, and U.S. Provisional Application No. 62/697,978, filed Jul. 13, 2018, each of which is incorporated herein by reference in its entirety.

BACKGROUND OF THE DISCLOSURE

Description of the Text File Submitted Electronically

The contents of the text file submitted electronically herewith are incorporated herein by reference in their entirety: A computer readable format copy of the Sequence Listing (filename: IL2R_003_02US_SeqList_ST25.txt, date recorded: Jan. 11, 2021, file size ~7 kilobytes).

Field of the Disclosure

The present disclosure relates to compounds, modified polypeptides or modified hormones, and pharmaceutical compositions comprising said compounds for therapeutic use in the treatment of disorders. More particularly, the modifications to the polypeptides or hormones include the attachment of therapeutic compounds to the polypeptides or hormones using linkers. In some embodiments, the polypeptides are IL-2 polypeptides or homologs thereof, and the disorders include immunological disorders and cancer. The present disclosure has applications in the fields of pharmacology, oncology, immunology, chemistry, and biochemistry.

Background Information

Antibody-drug conjugates ("ADCs") have long held promise of delivering the holy grail of pharmacology: the precise targeting of drugs to specifically targeted tissues and cells, by using antibody-receptor specificity as a means to deliver drugs conjugated to the antibody to a target. [1,2] The ADC approach in certain cases enables the delivery of oncolytics or other conjugated drugs at effective drug concentrations in excess of those available using traditional approaches, given the typically narrow therapeutic windows of such drugs. [3] Currently four ADCs (Mylotarg, Adcetris, Kadcyla, and Besponsa) have been approved for clinical use in the U.S., Europe, and Japan. [4]

Some non-antibody protein-drug conjugates have been made and examined. [5] These include albumin-drug conjugates, transferrin-drug conjugates, and gelatin-drug conjugates. [6] Some proteins have been used in combination with drug conjugates. [7, 8] However, there remains a need for new protein and other drug conjugates for therapeutic use. In particular, protein and other conjugates (e.g., hormone-drug conjugates) that improve the therapeutic properties such as half-life of the protein and the related protein-conjugate. Additionally, in certain cases, the protein component may contribute to the therapeutic properties. In some cases, the conjugates may make possible the effective administration of therapeutic and non-toxic amounts of the drug component, for example, where the administration of the drug component is unacceptably toxic when adminstered alone. Or, in some cases, certain conjugates have improved solubility or other properties that allow production and use of the conjugate and/or the protein portion of the conjugate in commercially and therapeutically relevant amounts.

SUMMARY OF THE DISCLOSURE

The present disclosure provides a novel approach for polypeptide-therapeutic compound or hormone-therapeutic compound conjugates to selectively target specific receptors and thereby exert a modulating effect on specified targets in concert with a conjugated therapeutic compound payload. Polypeptide-therapeutic compound or hormone-therapeutic compound conjugates that are developed as treatments for cancer and utilize endogenous proteins to selectively target diseased tissue for the delivery of toxic payloads to their high affinity, such as cytokines, growth factors ("GFs"), and hormones, may all be used with the disclosure described herein. Without being bound to any particular theory of action, the foregoing polypeptides and hormones function as chemical messengers that mediate intercellular communication. Regulation of cellular and nuclear functions by cytokines, growth factors, and hormones may be initiated through the activation of cell surface receptors ("Rc"). Signaling receptors typically have two main components: 1) a ligand-binding domain that ensures ligand specificity and 2) an effector signaling domain that initiates the generation of the biological response upon ligand binding. The activated receptor may then undergo receptor mediated endocytosis and release drugs conjugated to the ligand by cleavable linkers to interact with other intracellular components to complete, enhance, restore or block the signal transduction process, and thus provide a means for delivering therapeutic compounds using a "Trojan Horse" approach as described herein.

The therapeutic compounds can be conjugated to polypeptides or hormones using cleavable or non-cleavable linkers, whereby the polypeptides or hormones serve to target specific cells using receptor expression on the targeted cell to bind the ligand (polypeptide or hormone) carrying the therapeutic compound to effect specificity in targeted therapeutic compound delivery. Unlike antibody-therapeutic compound conjugates, the conjugates of the disclosure use a receptor-specific ligand to deliver the therapeutic compound to the cell expressing the receptor. Upon binding, the ligand and the therapeutic compound (or multiples of the therapeutic compound in some embodiments) may enter the cell by receptor mediated endocytosis and be released following cleavage of the linker. Non-cleavable linked therapeutic compounds will act directly absent release. The ligands for such polypeptide-therapeutic compound or hormone-therapeutic compound conjugates may be composed of cytokine polypeptides, growth factor polypeptides and/or hormones as well as other polypeptides with cell surface specific receptors. The disorders targeted by such therapeutic compound-polypeptide or hormone-therapeutic compound conjugates include immunological disorders (e.g., allergy, autoimmune, etc.) and certain cancers.

Some exemplary embodiments of the present disclosure include a compound having the structure of Formula (I):

$$X_{2a}\text{—}(X_3)_m \quad \text{(I)},$$

and pharmaceutically acceptable salts, solvates, hydrates, isomers, or tautomers thereof, wherein:

m is 1, 2, 3, 4, 5, 6, 7, 8, 9, or 10;

$X_{2a}$ is a linker; and $X_3$ is a therapeutic compound.

In some embodiments of the compound of Formula (I), m is 1. In some embodiments of the compound of Formula (I), m is 2, 3, 4, 5, 6, 7, or 8. In some embodiments of the compound of Formula (I), m is 1, 2, or 3. In some embodiments of the compound of Formula (I), m is 2, 3, 4, or 5.

In some embodiments of the compound of Formula (I), $X_{2a}$ is a cleavable linker. In some embodiments of the compound of Formula (I), $X_{2a}$ is a non-cleavable linker. In some embodiments of the compound of Formula (I), $X_{2a}$ is selected from the group consisting of L-1, L-2, L-3, L-4, L-5, L-6, L-7, L-8, L-9, L-10, L-11, L-12, L-13, L-14, L-15, L-16, and L-19, as disclosed herein, wherein R is H, alkyl, aryl, arylalkyl, a glycol ether, or a glycol linker. In some embodiments of the compound of Formula (I), $X_{2a}$ is selected from the group consisting of L-1 and L-19. In some embodiments of the compound of Formula (I), $X_{2a}$ is selected from the group consisting of L-17 and L-18, as disclosed herein.

In some embodiments of the compound of Formula (I), $X_3$ is an immunomodulating agent. In some embodiments of the compound of Formula (I), $X_3$ is selected from the group consisting of an immunosuppressive drug, an antianemic, an antianginal, an antiarryhythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a ubiquitin-activating enzyme inhibitor, a ubiquitin-activating enzyme E1 inhibitor, and a proteasome inhibitor. In some embodiments of the compound of Formula (I), $X_3$ is selected from the group consisting of: pevonedistat; TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate); Piperacillin; M22 (1-benzyl-N-(2,4-dichlorophenethyl) piperidin-4-amine); 6,6'-Biapigenin; Thieno-pyridine; Imidazo-pyrimidine; Largazole; Pyr-41 (4 [4-(5-nitro-furan-2-ylmethylene)-3,5-dioxo-pyrazolidin-1-yl]-benzoic acid ethyl ester); Phorbol 12-myristate 13-acetate; 2,3-dihydropyrrolo[2,1-b]quinazolin-9 (1H)-one; Ofloxacin; Panepophenanthin; Himeic Acid A; Hyrtioreticulins A; Phytol; ABPA3 ([(2R,3S,4R,5R)-5-[6-(3-ethynylanilino) purin-9-yl]-3,4-dihydroxyoxolan-2-yl]methyl sulfamate); Benzothiazole; a Deoxyvasicinone derivative; Coumarin A; Coumarin B; and Imidazolium-quinoxaline, wherein $R_1$ is alkyl, aryl, arylalkyl, arylalkyne, arylalkene, heterocyclyl, or heteroaryl and $R_2$ is H, alkyl, or aryl. In some embodiments of the compound of Formula (I), $X_3$ is selected from the group consisting of: Pevonedistat, TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl) methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), and TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate). In some embodiments, $X_3$ is Pevonedistat. In some embodiments of the compound of Formula (I), $X_3$ is selected from the group consisting of: pevonedistat; TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate); Piperacillin; M22 (1-benzyl-N-(2,4-dichlorophenethyl) piperidin-4-amine); 6,6'-Biapigenin; Thieno-pyridine; Imidazo-pyrimidine; Largazole; Pyr-41 (4 [4-(5-nitro-furan-2-ylmethylene)-3,5-dioxo-pyrazolidin-1-yl]-benzoic acid ethyl ester); Phorbol 12-myristate 13-acetate; 2,3-dihydropyrrolo[2,1-b]quinazolin-9 (1H)-one; Ofloxacin; Panepophenanthin; Himeic Acid A; Hyrtioreticulins A; Phytol; ABPA3 ([(2R,3S,4R,5R)-5-[6-(3-ethynylanilino) purin-9-yl]-3,4-dihydroxyoxolan-2-yl]methyl sulfamate); Benzothiazole; a Deoxyvasicinone derivative; Coumarin A; Coumarin B; Imidazolium-quinoxaline, and TAS4464 (7H-Pyrrolo[2,3-d]pyrimidin-4-amine, 7-[5-[(aminosulfonyl)amino]-5-deoxy-beta-D-ribofuranosyl]-5-[2-(2-ethoxy-6-fluorophenyl) ethynyl]-), wherein $R_1$ is alkyl, aryl, arylalkyl, arylalkyne, arylalkene, heterocyclyl, or heteroaryl and $R_2$ is H, alkyl, or aryl. In some embodiments of the compound of Formula (I), $X_3$ is selected from the group consisting of: Pevonedistat, TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl) methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate), and TAS4464 (7H-Pyrrolo[2,3-d]pyrimidin-4-amine, 7-[5-[(aminosulfonyl)amino]-5-deoxy-beta-D-ribofuranosyl]-5-[2-(2-ethoxy-6-fluorophenyl) ethynyl]-).

In some embodiments of the compound of Formula (I), $X_3$ is a cancer chemotherapeutic. In some embodiments of the compound of Formula (I), $X_3$ is selected from the group consisting of an oncolytic drug, a genotoxic agent, an alkylating agent, a tubulin inhibitor, a microtubule assembly inhibitor, an antineoplastic drug, a kinase inhibitor, a vinca alkaloid, an antibiotic, an anthracycline, an antimetabolite, an aromatase inhibitor, a topoisomerase inhibitor, a mTor inhibitor, a retinoid, an antimitotic agent, a protease inhibitor, a tyrosine kinase inhibitor, a microtubule destabilizer, and a proteasome inhibitor. In some embodiments of the compound of Formula (I), $X_3$ is selected from the group consisting of vincristine, vinorelbine, vinflunine, crytophycin 52, a halichondrin, a dolastatin, a hemiasterlin, colchicine, a combretastatin, 2-methoxyestradiol, a methoxy benzenesulfonamide, epothilone, and discodermolide. In some embodiments of the compound of Formula (I), $X_3$ is selected from the group consisting of: Monomethyl Auristatin E; Docetaxel; Etoposide; Gemcitabine; Vinblastine; Paclitaxel; Irinotecan; Fluorouracil; Methotrexate; Carboplatin; Oxaliplatin; Cisplatin; Doxorubicin HCl; Fulvestrant; Isotretinoin; Buserelin; Everolimus; Carfilzomib; Rifabutin; Clindamycin; Tubulysin A; Indibulin; Gefitinib; and Dasatinib. In some embodiments of the compound of Formula (I), $X_3$ is Monomethyl Auristatin E.

In some embodiments of the compound of Formula (I), the compound of Formula (I) is selected from the group consisting of: A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32 A-33, A-34, A-35, A-36, A-37, A-38, A-39, A-40, A-41, A-42, A-43, A-44, A-45, A-46, A-47, A-48, A-49, A-50, and A-51 as disclosed herein, wherein R is H, alkyl, aryl, arylalkyl, a glycol ether, or a glycol linker and p is 1, 2, 3, 4, 5, or 6. In some embodiments of the compound of Formula (I), the compound of Formula (I) is selected from the group consisting of A-1, A-2, A-3, A-4, A-5, A-6, A-7, A-8, A-9, A-10, A-11, A-12, A-13, A-14, A-15, A-16, A-17, A-18, A-30, A-31, and A-51. In some embodiments of the compound of Formula (I), the compound of Formula (I) is selected from the group consisting of A-1, A-30, A-31, and A-51. In some embodiments of the compound of Formula (I), the compound of Formula (I) is A-32.

Some exemplary embodiments of the present disclosure include a compound having the structure of Formula (II):

$$X_1—[X_2—(X_3)_m]_n \quad \text{(II),}$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is a biologically active polypeptide or hormone;

$X_2$ is a linker; and $X_3$ is a therapeutic compound.

Some exemplary embodiments of the present disclosure include a compound having the structure of Formula (III):

$$X_1—[X_2—(X_3)_m]_n \quad \text{(III),}$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is an IL-2 polypeptide or a bio-active homolog polypeptide thereof;

$X_2$ is a linker; and $X_3$ is a therapeutic compound.

In some embodiments of the compound of Formula (II) or Formula (III), $X_3$ is an oncolytic drug. In some embodiments of the compound of Formula (II) or Formula (III), $X_3$ is an immunomodulatory drug.

In some embodiments of the compound of Formula (II) or Formula (III), $X_2$ is a cleavable linker. In some embodiments of the compound of Formula (II) or Formula (III), $X_2$ is a non-cleavable linker.

In some embodiments of the compound of Formula (II) or Formula (III), $X_2$ is bound to $X_1$ at a Cys residue thereof. Among these are embodiments in which $X_3$ is a oncolytic drug or $X_3$ is an immunomodulatory drug. Among these embodiments are those in which $X_2$ is a cleavable linker, and those in which $X_2$ is a non-cleavable linker.

In some embodiments of the compound of Formula (II) or Formula (III), $X_2$ is bound to $X_1$ at a Lys residue thereof. Among these are embodiments in which $X_3$ is an oncolytic drug or $X_3$ is an immunomodulatory drug. Among these embodiments are those in which $X_2$ is a cleavable linker, and those in which $X_2$ is a non-cleavable linker.

In some embodiments of the compound of Formula (II) or Formula (III), n is 2, 3, 4, 5, 6, 7, 8, or 9. In some embodiments of the compound of Formula (II) or Formula (III), n is 3, 4, 5, 6, 7, or 8. In some embodiments of the compound of Formula (II) or Formula (III), n is 4, 5, 6, or 7. In some embodiments of the compound of Formula (II) or Formula (III), n is 5 or 6. In some embodiments of the compound of Formula (II) or Formula (III), m=n. In some embodiments of the compound of Formula (II) or Formula (III), n is greater than m. In some embodiments of the compound of Formula (II) or Formula (III), m is 1 and n is 1, 2, 3, 4, 5, 6, 7, 8, 9, 10, or 11. In some embodiments of the compound of Formula (II) or Formula (III), m is 2 and n is 1, 2, 3, 4, 5, 6, 7, 8, 9, 10, or 11. In some embodiments of the compound of Formula (II) or Formula (III), n is an integer between 2 and 9, an integer between 3 and 8, an integer between 4 and 7, or n can be 5 or 6. In some embodiments of the compound of Formula (II) or Formula (III), n is an integer between 1 and 11. In some embodiments of the compound of Formula (II) or Formula (III), m is an integer between 1 and 10. In some embodiments of the compound of Formula (II) or Formula (III), m is 1. In some embodiments of the compound of Formula (II) or Formula (III), m is 2, 3, 4, 5, 6, 7, or 8. In some embodiments of the compound of Formula (II) or Formula (III), m is 1, 2, or 3. In some embodiments of the compound of Formula (II) or Formula (III), m is 2, 3, 4, or 5.

In another aspect, the present disclosure provides a method of treating a disorder in a subject, comprising administering to said subject a therapeutically effective amount of a compound of the disclosure, or a pharmaceutically acceptable salt, hydrate, solvate, isomer, or tautomer thereof, in a pharmaceutically acceptable carrier.

In some embodiments of the compound of Formula (II) or Formula (III), $X_1$ is selected from the group consisting of an Acylation stimulating protein polypeptide, an Adipokine polypeptide, an Albinterferon polypeptide, a Cerberus polypeptide, a Colony-stimulating factor polypeptide, an Erythropoietin polypeptide, a FMS-like tyrosine kinase 3 ligand polypeptide, a Globulin component polypeptide, a Macrophage Activating Factor polypeptide, a Granulocyte colony-stimulating factor polypeptide, a Granulocyte-macrophage colony-stimulating factor polypeptide, a Hepatocyte growth factor polypeptide, an IL-17 polypeptide, an IL-10 polypeptide, an Inflammasome polypeptide, an Interferome polypeptide, an Interferon polypeptide, an Interferon beta-la polypeptide, an Interferon beta-1b polypeptide, an Interferon gamma polypeptide, an Interferon type I polypeptide, an Interferon type II polypeptide, an Interferon type III polypeptide, an Interleukin polypeptide, an Interleukin 1 receptor antagonist polypeptide, an Interleukin 8 polypeptide, a Leukemia inhibitory factor polypeptide, a Leukocyte-promoting factor polypeptide, a Lymphokine polypeptide, a Lymphotoxin polypeptide, a Lymphotoxin alpha polypeptide, a Lymphotoxin beta polypeptide, a Macrophage colony-stimulating factor polypeptide, a Macrophage inflammatory protein polypeptide, a Macrophage-activating factor polypeptide, a Monokine polypeptide, a Myokine polypeptide, a Myonectin polypeptide, a Nicotinamide phosphoribosyltransferase polypeptide, an Oncostatin M polypeptide, an Oprelvekin polypeptide, a Platelet factor 4 polypeptide, a Proinflammatory cytokine polypeptide, a Promegapoietin polypeptide, a Receptor activator of nuclear factor kappa-B ligand polypeptide, a Stromal cell-derived factor 1 polypeptide, an adrenomedullin polypeptide, an angiopoietin polypeptide, an Autocrine motility factor polypeptide, a Bone morphogenetic protein polypeptide, a Ciliary neurotrophic factor polypeptide, an Interleukin-6 polypeptide, an Epidermal growth factor polypeptide, an Ephrin A1 polypeptide, an Ephrin A2 polypeptide, an Ephrin A3 polypeptide, an Ephrin A4 polypeptide, an Ephrin A5 polypeptide, an Ephrin B1 polypeptide, an Ephrin B2 polypeptide, an Ephrin B3 polypeptide, a Fibroblast growth factor polypeptide, a Fibroblast growth factor 1 polypeptide, a fibroblast growth factor 2 polypeptide, a Fibroblast growth factor 3 polypeptide, a Fibroblast growth factor 4 polypeptide, a fibroblast growth factor 5 polypeptide, a Fibroblast growth factor 6 polypeptide, a Fibroblast growth factor 7 polypeptide, a fibroblast growth factor 8 polypeptide, a Fibroblast growth factor 9 polypeptide, a Fibroblast growth factor 10 polypeptide, a Fibroblast growth factor 11 polypeptide, a Fibroblast growth factor 12 polypeptide, a Fibroblast growth factor 13 polypeptide, a Fibroblast growth factor 14 polypeptide, a Fibroblast growth factor 15 polypeptide, a Fibroblast growth factor 16 polypeptide, a Fibroblast growth factor 17 polypeptide, a Fibroblast growth factor 18 polypeptide, a Fibroblast growth factor 19 polypeptide, a Fibroblast growth factor 20 polypeptide, a Fibroblast growth factor 21 polypeptide, a Fibroblast growth factor 22 polypeptide, a Fibroblast growth factor 23 polypeptide, a Foetal Bovine Somatotrophin polypeptide, a Glial cell line-derived neurotrophic factor polypeptide, a Neurturin polypeptide, a Persephin polypeptide, an Artemin polypeptide, a Growth differentiation factor-9 polypeptide, a Hepatoma-derived growth factor polypeptide, an Insulin polypeptide, an Insulin-like growth factor polypeptide, an Insulin-like growth factor-1 polypeptide, an Insulin-like growth factor-2 polypeptide, an IL-1 polypeptide, an IL-2 polypeptide or bio-active homolog thereof, an IL-3 polypeptide, an IL-4 polypeptide, an IL-5 polypeptide, an IL-6 polypeptide, an IL-7 polypeptide, a Keratinocyte growth factor polypeptide, a Migration-stimulating factor polypeptide, a Macrophage-stimulating protein polypeptide, a Myostatin polypeptide, a Neuregulin 1 polypeptide, a Neuregulin 2 polypeptide, a Neuregulin 3 polypeptide, a Neuregulin 4 polypeptide, a Brain-derived neurotrophic factor polypeptide, a Nerve growth factor polypeptide, a Neurotrophin-3 polypeptide, a Neurotrophin-4 polypeptide, a Placental growth factor polypeptide, a Platelet-derived growth factor polypeptide, a Renalase polypeptide, an anti-apoptotic survival factor polypeptide, a T-cell growth factor polypeptide, a Thrombopoietin polypeptide, a Transforming growth factor alpha polypeptide, a Transforming growth factor beta polypeptide, a Tumor necrosis factor-alpha polypeptide, a Vascular endothelial growth factor polypeptide, and a Wnt Signaling Pathway polypeptide. In some embodiments of the compound of Formula (II) or Formula (III), the IL-2 polypeptide or the bio-active homolog polypeptide thereof comprises an amino acid sequence set forth in Table 4. In some embodiments of the compound of Formula (II) or Formula (III), the IL-2 polypeptide or the bio-active homolog polypeptide thereof comprises an amino acid sequence set forth in SEQ ID NO: 1 or SEQ ID NO:2.

In some embodiments of the compound of Formula (II) or Formula (III), $X_2$ is a cleavable linker. In some embodiments of the compound of Formula (II) or Formula (III), $X_2$ is a non-cleavable linker. In some embodiments of the compound of Formula (II) or Formula (III), $X_2$ is selected from the group consisting of: K-1, K-2, K-3, K-4, K-5, K-6, K-7, K-8, K-9, K-10, K-11, K-12, K-13, K-14, K-15, K-16, K-19, and K-20, as disclosed herein, wherein the left side of $X_2$, as drawn, is bound to $X_1$, and the right side of $X_2$, as drawn, is bound to $X_3$ and R is H, alkyl, aryl, arylalkyl, a glycol ether, or a glycol linker. In some embodiments of the compound of Formula (II) or Formula (III), $X_2$ is selected from the group consisting of K-1 and K-19. In some embodiments of the compound of Formula (II) or Formula (III), $X_2$ is selected from the group consisting of K-17 and K-18, wherein the left side of $X_2$, as drawn, is bound to $X_1$, and the right side of $X_2$, as drawn, is bound to $X_3$. In some embodiments of the compound of Formula (II) or Formula (III), $X_2$ is bound to $X_1$ at a Cys residue thereof. In some embodiments of the compound of Formula (II) or Formula (III), $X_2$ is bound to $X_1$ at a Lys residue thereof. In some embodiments of the compound of Formula (II) or Formula (III), $X_2$ is bound to $X_1$ at two different sites on $X_1$. In some embodiments of the compound of Formula (II) or Formula (III), $X_2$ is bound to $X_1$ at two different Cys residues on $X_1$. In some embodiments of the compound of Formula (II) or Formula (III), $X_2$ is bound to $X_1$ at two different Lys residues on $X_1$. In some embodiments of the compound of Formula (II) or Formula (III), $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and the combination of n1 and n2 has a sum of 2, 3, 4, 5, 6, 7, 8, 9, 10, or 11. In certain such embodiments, $X_{2b}$ is K-1 and $X_{2c}$ is K-19. In some embodiments, $X_{2b}$ is selected from the group consisting of K-1, K-2, K-4, K-6, K-8, K-11, K-13, K-15, K-17, and K-18 and $X_{2c}$ is K-19. In some embodiments, each $X_2$ bound to $X_1$ is an $X_{2b}$ moiety. In certain such embodiments, n is n1, wherein n1 corresponds to the number of $X_{2b}$ moieties bound to $X_1$. In some embodiments, each $X_2$ bound to $X_1$ is an $X_{2c}$ moiety. In certain such embodiments, n is n2, wherein n2 corresponds to the number of $X_{2c}$ moieties bound to $X_1$.

The description of n as used in the disclosure is inclusive of n1, n2, or the combination of n1 and n2, with the sum of the combination of n1 and n2 being between 2 and 11, inclusive thereof. In some embodiments of the compound of Formula (II) or Formula (III), n1 is 2 or 3 and n2 is 1. In some embodiments of the compound of Formula (II) or Formula (III), n1 is 2 and n2 is 1. In some embodiments of the compound of Formula (II) or Formula (III), n1 is 3 and n2 is 1. In some embodiments of the compound of Formula (II) or Formula (III), n1 is 1, 2, 3, 4, or 5 and n2 is 1, 2 or 3.

In some embodiments of the compound of Formula (II) or Formula (III), $X_3$ is an immunomodulating agent. In some embodiments of the compound of Formula (II) or Formula (III), $X_3$ is selected from the group consisting of an immunosuppressive drug, an antianemic, an antianginal, an antiarryhythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a ubiquitin-activating enzyme inhibitor, a ubiquitin-activating enzyme E1 inhibitor, and a proteasome inhibitor. In some embodiments of the compound of Formula (II) or Formula (III), $X_3$ is selected from the group consisting of: pevonedistat; TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate); Piperacillin; M22 (1-benzyl-N-(2,4-dichlorophenethyl) piperidin-4-amine); 6,6'-Biapigenin; Thieno-pyridine; Imidazo-pyrimidine; Largazole; Pyr-41 (4 [4-(5-nitro-furan-2-ylmethylene)-3,5-dioxo-pyrazolidin-1-yl]-benzoic acid ethyl ester); Phorbol 12-myristate 13-acetate; 2,3-dihydropyrrolo[2,1-b]quinazolin-9 (1H)-one; Ofloxacin; Panepophenanthin; Himeic Acid A; Hyrtioreticulins A; Phytol; ABPA3 ([(2R,3S,4R,5R)-5-

[6-(3-ethynylanilino) purin-9-yl]-3,4-dihydroxyoxolan-2-yl]methyl sulfamate); Benzothiazole; a Deoxyvasicinone derivative; Coumarin A; Coumarin B; and Imidazolium-quinoxaline, $R_1$ is alkyl, aryl, arylalkyl, arylalkyne, arylalkene, heterocyclyl, or heteroaryl, and $R_2$ is H, alkyl, or aryl. In some embodiments of the compound of Formula (II) or Formula (III), $X_3$ is selected from the group consisting of: Pevonedistat, TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate), TAS2 (((1S,2R,3S,4R)-4-(4-amino-5-((4,7-dimethyl-3,4-dihydro-2H-benzo[b][1,4] oxazin-8-yl) ethynyl)-7H-pyrrolo[2,3-d]pyrimidin-7-yl)-2,3-dihydroxycyclopentyl)methyl sulfamate), and TAK7243 (((1R,2R,3S,4R)-2,3-dihydroxy-4-((2-(3-(trifluoromethyl) phenyl) pyrazolo[1,5-a]pyrimidin-7-yl)amino)cyclopentyl) methyl sulfamate). In some embodiments, $X_3$ is Pevonedistat. In some embodiments of the compound of Formula (II) or Formula (III), $X_3$ is selected from the group consisting of: pevonedistat; TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); TAS2 (((1S,2R,3S,4R)-4-(4-amino-5-((4,7-dimethyl-3,4-dihydro-2H-benzo[b][1,4] oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl) phenyl) pyrazolo[1,5-a]pyrimidin-7-yl)amino)cyclopentyl) methyl sulfamate); Piperacillin; M22 (1-benzyl-N-(2,4-dichlorophenethyl) piperidin-4-amine); 6,6'-Biapigenin; Thieno-pyridine; Imidazo-pyrimidine; Largazole; Pyr-41 (4 [4-(5-nitro-furan-2-ylmethylene)-3,5-dioxo-pyrazolidin-1-yl]-benzoic acid ethyl ester); Phorbol 12-myristate 13-acetate; 2,3-dihydropyrrolo[2,1-b]quinazolin-9 (1H)-one; Ofloxacin; Panepophenanthin; Himeic Acid A; Hyrtioreticulins A; Phytol; ABPA3 ([(2R,3S,4R,5R)-5-[6-(3-ethynylanilino) purin-9-yl]-3,4-dihydroxyoxolan-2-yl]methyl sulfamate); Benzothiazole; a Deoxyvasicinone derivative; Coumarin A; Coumarin B; Imidazolium-quinoxaline, and TAS4464 (7H-Pyrrolo[2,3-d]pyrimidin-4-amine, 7-[5-[(aminosulfonyl)amino]-5-deoxy-beta-D-ribofuranosyl]-5-[2-(2-ethoxy-6-fluorophenyl) ethynyl]-), $R_1$ is alkyl, aryl, arylalkyl, arylalkyne, arylalkene, heterocyclyl, or heteroaryl, and $R_2$ is H, alkyl, or aryl.

In some embodiments of the compound of Formula (II) or Formula (III), $X_3$ is a cancer chemotherapeutic. In some embodiments of the compound of Formula (II) or Formula (III), $X_3$ is selected from the group consisting of an oncolytic drug, a genotoxic agent, an alkylating agent, a tubulin inhibitor, a microtubule assembly inhibitor, an antineoplastic drug, a kinase inhibitor, a vinca alkaloid, an antibiotic, an anthracycline, an antimetabolite, an aromatase inhibitor, a topoisomerase inhibitor, a mTor inhibitor, a retinoid, an antimitotic agent, a protease inhibitor, a tyrosine kinase inhibitor, a microtubule destabilizer, and a proteasome inhibitor. In some embodiments of the compound of Formula (II) or Formula (III), $X_3$ is selected from the group consisting of vincristine, vinorelbine, vinflunine, crytophycin 52, a halichondrin, a dolastatin, a hemiasterlin, colchicine, a combretastatin, 2-methoxyestradiol, a methoxybenzenesulfonamide, epothilone, and discodermolide. In some embodiments of the compound of Formula (II) or Formula (III), $X_3$ is selected from the group consisting of: Monomethyl Auristatin E; Docetaxel; Etoposide; Gemcitabine; Vinblastine; Paclitaxel; Irinotecan; Fluorouracil; Methotrexate; Carboplatin; Oxaliplatin; Cisplatin; Doxorubicin HCl; Fulvestrant; Isotretinoin; Buserelin; Everolimus; Carfilzomib; Rifabutin; Clindamycin; Tubulysin A; Indibulin; Gefitinib; and Dasatinib. In some embodiments of the compound of Formula (II) or Formula (III), $X_3$ is Monomethyl Auristatin E.

In some embodiments of the compound of Formula (II) or Formula (III), the compound of Formula (II) or Formula (III) is selected from the group consisting of: B-1, B-2, B-3, B-4, B-5, B-6, B-7, B-8, B-9, B-10, B-11, B-12, B-13, B-14, B-15, B-16, B-17, B-18, B-19, B-20, B-21, B-22, B-23, B-24, B-25, B-26, B-27, B-28, B-29, B-30, B-31, B-48, and B-49, R is H, alkyl, aryl, arylalkyl, a glycol ether, or a glycol linker, and q is 1, 2, 3, or 4. In some embodiments of the compound of Formula (II) or Formula (III), the compound of Formula (II) or Formula (III) is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49. In some embodiments of the compound of Formula (II) or Formula (III), the compound of Formula (II) or Formula (III) is selected from the group consisting of B-1, B-30, B-31, B-48, and B-49. In some embodiments of the compound of Formula (II) or Formula (III), the compound of Formula (II) or Formula (III) is selected from the group consisting of: B-32, B-33, B-34, B-35, B-36, B-37, B-38, B-39, B-40, B-41, B-42, B-43, B-44, B-45, B-46, B-47, and B-50. In some embodiments of the compound of Formula (II) or Formula (III), the compound of Formula (II) or Formula (III) is B-32.

In some embodiments of the compound of Formula (II) or Formula (III), the compound of Formula (II) or Formula (III) is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 2, 3, 4, 5, or 6, and $X_1$ is an IL-2 polypeptide or a bio-active homolog polypeptide thereof comprising an amino acid sequence set forth in SEQ ID NO:1 or SEQ ID NO: 2.

In some embodiments of the compound of Formula (II) or Formula (III), the compound of Formula (II) or Formula (III) is selected from the group consisting of B-1, B-30, B-31, B-48, and B-49, wherein n is 2, 3, 4, 5, or 6, and $X_1$ is an IL-2 polypeptide or a bio-active homolog polypeptide thereof comprising an amino acid sequence set forth in SEQ ID NO:1 or SEQ ID NO: 2.

In some embodiments of the compound of Formula (II) or Formula (III), $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein the combination of n1 and n2 has a sum of 2, 3, 4, 5, or 6, and $X_1$ is an IL-2 polypeptide or a bio-active homolog polypeptide thereof comprising an amino acid sequence set forth in SEQ ID NO: 1 or SEQ ID NO:2.

In some embodiments of the compound of Formula (II) or Formula (III), the compound of Formula (II) or Formula (III) is B-49, wherein $X_1$ is an IL-2 polypeptide or a bio-active homolog polypeptide thereof comprising an amino acid sequence set forth in SEQ ID NO:1 or SEQ ID NO:2, and n1 is 2 or 3 and n2 is 1. In some embodiments of the compound of Formula (II) or Formula (III), the IL-2 polypeptide or the bio-active homolog polypeptide thereof comprises the amino acid sequence set forth in SEQ ID NO:2. An aspect of the disclosure relates to a pharmaceutical composition comprising a compound of Formula (II) or Formula (III), or a pharmaceutically acceptable salt, solvate, hydrate, or tautomer thereof, and a pharmaceutically acceptable carrier.

Another aspect of the disclosure relates to a method for treating a disorder in a subject, comprising administering to a subject in need thereof a therapeutically effective amount of a compound of Formula (II) or Formula (III), or a pharmaceutically acceptable salt, solvate, hydrate, or tautomer thereof, wherein the disorder is an immunological disorder or cancer.

One aspect of the disclosure relates to a method for treating a disorder in a subject, comprising administering to a subject in need thereof a therapeutically effective amount of a pharmaceutical composition comprising a compound of Formula (II) or Formula (III), or a pharmaceutically acceptable salt, solvate, hydrate, or tautomer thereof, wherein the disorder is an immunological disorder or cancer.

An aspect of the disclosure relates to use of a compound of Formula (II) or Formula (III), or a pharmaceutically acceptable salt, solvate, hydrate, or tautomer thereof, in the manufacture of a medicament for treating a disorder in a subject in need thereof, wherein the disorder is an immunological disorder or cancer.

Another aspect of the disclosure relates to use of a pharmaceutical composition comprising a compound of Formula (II) or Formula (III), or a pharmaceutically acceptable salt, solvate, hydrate, or tautomer thereof, in the manufacture of a medicament for treating a disorder in a subject in need thereof, wherein the disorder is an immunological disorder or cancer.

One aspect of the disclosure relates to use of a compound of Formula (II) or Formula (III), or a pharmaceutically acceptable salt, solvate, hydrate, or tautomer thereof, for treating a disorder in a subject in need thereof.

An aspect of the disclosure relates to use of a pharmaceutical composition comprising a compound of Formula (II) or Formula (III), or a pharmaceutically acceptable salt, solvate, hydrate, or tautomer thereof, for treating a disorder in a subject in need thereof.

Another aspect of the disclosure relates to use of a compound of Formula (II) or Formula (III), or a pharmaceutically acceptable salt, solvate, hydrate, or tautomer thereof, for treating a disorder in a subject in need thereof, wherein the disorder is an immunological disorder or cancer.

One aspect of the disclosure relates to use of a pharmaceutical composition comprising a compound of Formula (II) or Formula (III), or a pharmaceutically acceptable salt, solvate, hydrate, or tautomer thereof, for treating a disorder in a subject in need thereof, wherein the disorder is an immunological disorder or cancer.

An aspect of the disclosure relates to a compound of Formula (II) or Formula (III), or a pharmaceutically acceptable salt, solvate, hydrate, or tautomer thereof, for use in a method of treating a disorder in a subject in need thereof, wherein the disorder is an immunological disorder or cancer.

Another aspect of the disclosure relates to a pharmaceutical composition comprising a compound of Formula (II) or Formula (III), or a pharmaceutically acceptable salt, solvate, hydrate, or tautomer thereof, for use in a method of treating a disorder in a subject in need thereof, wherein the disorder is an immunological disorder or cancer.

In some embodiments of the methods, uses, medicaments, compounds for use or pharmaceutical compositions for use of the disclosure, the disorder is an immunological disorder. In some embodiments of the methods, uses, medicaments, compounds for use or pharmaceutical compositions for use of the disclosure wherein the disorder is an immunological disorder, the immunological disorder is multiple sclerosis, type 1 diabetes, inflammatory bowel disease, rheumatoid arthritis, or psoriasis. In some embodiments of the methods, uses, medicaments, compounds for use or pharmaceutical compositions for use of the disclosure wherein the disorder is an immunological disorder, the immunological disorder is multiple sclerosis, type 1 diabetes, inflammatory bowel disease, rheumatoid arthritis, psoriasis, or systemic lupus erythematosus.

In some embodiments of the methods, uses, medicaments, compounds for use or pharmaceutical compositions for use of the disclosure, the disorder is cancer. In some embodiments of the methods, uses, medicaments, compounds for use or pharmaceutical compositions for use of the disclosure wherein the disorder is cancer, the cancer is non-small cell lung cancer (NSCLC), melanoma, kidney cancer, bladder cancer, head and neck cancer, or claudin-low breast cancer.

One aspect of the disclosure relates to an IL-2 polypeptide or a bio-active homolog polypeptide thereof comprising an amino acid sequence set forth in Table 4.

An aspect of the disclosure relates to an IL-2 polypeptide or a bio-active homolog polypeptide thereof comprising an amino acid sequence set forth in SEQ ID NO:1 or SEQ ID NO: 2.

BRIEF DESCRIPTION OF THE DRAWINGS

FIG. 3 is a table showing various Cys and Lys-specific IL-2 polypeptide-Linker-therapeutic compound conjugations in accordance with some embodiments of the disclosure. R groups=alkyl, aryl, and arylalkyl; and Ar=aryl groups such as phenyl groups, substituted phenyl groups, aromatic heterocycles, and the like.

FIG. 6A, bottom panel, illustrates IL-2 (60 pM)-stimulated CD3+ T cell blasts (measures viability) after treatment with MMAE (50 nM, combo) or Conj.=MMAE-IL2 polypeptide conjugates with estimated molar ratios of 1:1 or 3:1 MMAE:IL-2. Med=media. FIG. 6B, bottom panel, illustrates IL-2 (100 pM)-stimulated CD3+ T cell blasts (measures pSTAT5 via ELISA) after treatment with MLN4924 (200 nM, combo) or Conj.=MLN4924-IL2 polypeptide conjugate with estimated molar ratios of 1:1 or 3-4:1 MLN4924:IL-2. Med=media.

DETAILED DESCRIPTION OF THE DISCLOSURE

Figure 1:
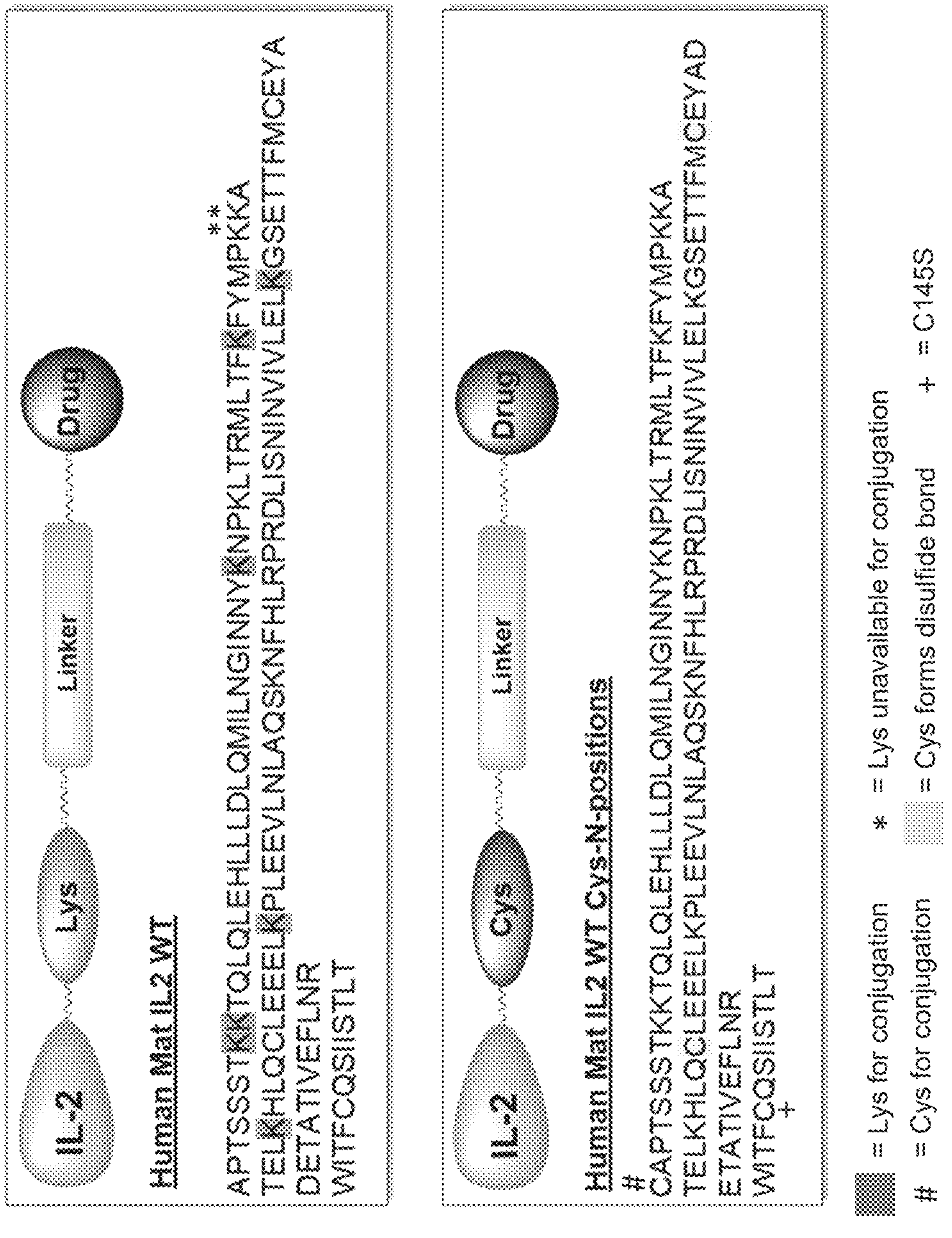
FIG. 1 is a schematic showing sequence-specific IL-2 polypeptide-Linker-therapeutic compound conjugations in accordance with some embodiments of the disclosure.

The present disclosure provides compounds (e.g., compounds of formula II or III), or pharmaceutically acceptable salts, hydrates, solvates, isomers, or tautomers thereof, useful for the treatment of disorders, such as immunological disorders and cancer. The compounds of the disclosure, or pharmaceutically acceptable salts, hydrates, solvates, isomers, or tautomers thereof, may comprise biologically active polypeptides or hormones modified to include the attachment of therapeutic compounds using linkers. Further, the present disclosure provides pharmaceutical compositions comprising compounds of the disclosure, or pharmaceutically acceptable salts, hydrates, solvates, isomers, or tautomers thereof, as well as methods, uses, compounds for use, medicaments, and including pharmaceutical compositions for use comprising said compounds. The present disclosure also provides compounds comprising therapeutic compounds and a linker, useful for the preparation of the compounds comprising biologically active polypeptides or hormones modified to include the attachment of therapeutic compounds using linkers (e.g., compounds of Formula I, or pharmaceutically acceptable salts, hydrates, solvates, isomers, or tautomers thereof). The present disclosure also provides bio-active homolog polypeptides of IL-2.

The compounds of the disclosure, or pharmaceutically acceptable salts, hydrates, solvates, isomers, or tautomers thereof, comprising biologically active polypeptides or hormones modified to include the attachment of therapeutic compounds using linkers provide a highly targeted therapy useful in the treatment of immunological disorders or cancer. The biologically active polypeptide or hormone selectively interacts with its cell surface receptor and is taken up by the cell through receptor mediated endocytosis. The compound of the disclosure is then taken up and degraded by the cell, releasing the therapeutic compound within the cell. Treatment of immunological disorders or cancer with the compounds of the disclosure, or pharmaceutically acceptable salts, hydrates, solvates, isomers, or tautomers thereof, comprising biologically active polypeptides or hormones modified to include the attachment of therapeutic compounds using linkers is specific, potentially reducing off-target effects compared to standard therapies, and may exhibit high affinity for target cells, resulting in low immunogenicity. The compounds of the disclosure, or pharmaceutically acceptable salts, hydrates, solvates, isomers, or tautomers thereof, comprising biologically active polypeptides or hormones modified to include the attachment of therapeutic compounds using linkers may be very potent in the treatment of cancer or immunological disorders and are may be stable at physiological pH, in circulation, and in storage.

Due to the specificity of the compounds of the disclosure, or pharmaceutically acceptable salts, hydrates, solvates, isomers, or tautomers thereof, comprising biologically active polypeptides or hormones modified to include the attachment of therapeutic compounds using linkers for their targeted cells and receptors, a lower therapeutic dose of therapeutic compound may be required, reducing side effects and potentially providing a wider therapeutic window. For example, the therapeutic compounds TAS2 and pevonedistat, both neddylation inhibitors detailed herein, show promise for the treatment of cancer and immunological disorders. But these compounds have apparently struggled in clinical trials due to issues with toxicity. Using the compounds of the disclosure, or pharmaceutically acceptable salts, hydrates, solvates, isomers, or tautomers thereof, reduced amounts of therapeutic compound should be required to exhibit a therapeutic effect, likely only picomolar therapeutic compound concentration doses instead of nanomolar or micromolar concentration doses of therapeutic compound, possibly reducing the therapeutic compound's toxicity. Remarkably, these dose concentrations are consistent with the dose concentrations typically utilized in low dose IL-2 polypeptide therapy, wherein the IL-2 polypeptide concentration cannot exceed 100 picomolar to 200 picomolar without losing therapeutic effect.

Figure 9:
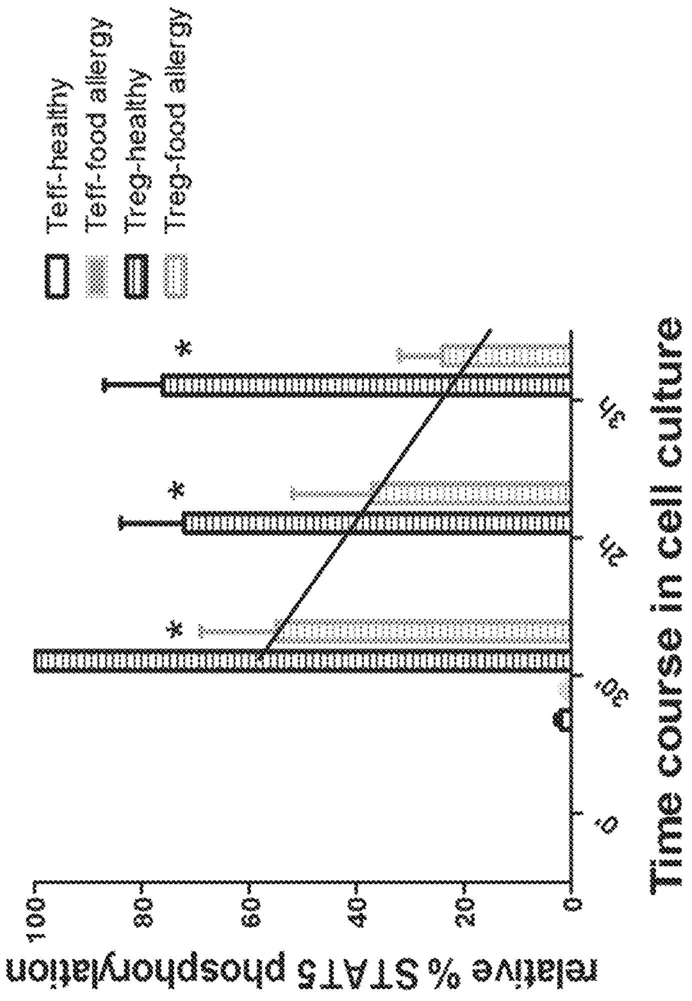
FIG. 9 illustrates low dose IL-2 activation of Tregs from three food allergic patients compared with three normal blood bank controls, in which defective inhibition of Treg IL-2R desensitization is demonstrated in the Tregs from the allergic subjects by a more rapid loss of pSTAT5 in their Tregs than in normal subjects' Tregs, when activated by low dose IL-2 in vitro. pSTAT5 is the transcription factor that controls the expression of genes required for Treg function.

The present disclosure provides in particular bioactive polypeptide, hormone, IL-2 polypeptide, or bio-active IL-2 homolog polypeptide conjugates that are effective immunotherapeutics for disorders, including, but not limited to, oncological and immunological (including autoimmune) disease. Again without wishing to be bound to any particular theory of action, the adaptive immune system is normally held in balance by a subset of white blood cells called regulatory T cells. Regulatory T cells are the key to keeping the immune system in check by controlling the immune response to self-antigens to help prevent autoimmune disease. Complex innate and adaptive systems consisting of cells and molecules work together to maintain human health (immune homeostasis). [9] A major adaptive immune defect in autoimmunity, allergy and inflammatory disorders involves dysregulated signaling through the regulatory T cell (Treg) IL-2 receptor (IL-2R) and IL-2. In such immunological disorders, there is ineffective immune regulation due to defective inhibition of regulatory T cell IL-2R desensitization and IL-2R signaling is turned off too soon, stopping transcription of the genes required for regulatory T cell function (FIG. 9).

Signaling from IL-2 receptor (IL-2R) after binding to IL-2 and activating Janus kinase (JAK1) leads to activation of the signal transducer and activator of transcription-5 (STAT-5). pSTAT5 is the transcription factor that controls the expression of the genes required for Treg function, not for survival or expansion, both controlled by other signaling molecules. JAK1 is inactivated by the suppressors of cytokine signaling (SOCS3) that binds to pJAK1, inhibiting JAK's phosphorylation of STAT-5. SOCS3 then forms a multi-component cullin ring ligase (CRL) protein complex with elongin, Cullin5, RBX, and ubiquitin transferase (E2). The CRL complex normally degrades the IL-2R associated pJAK1 to desensitize the IL-2R, but in Tregs, this activity is blocked. The SOCS3 CRL activity depends upon a post translational modification of a specific lysine on cullin 5 by neddylation. In normal Tregs, the lysine is ubiquitinated by a ubiquitin E3 called GRAIL. This ubiquitination competes with neddylation and inhibits desensitization of the IL-2R and allows pJAK1 to continue to phosphorylate STAT5 and maintain its expression for up to the 5 hours required for the Treg transcriptome controlling function to be transcribed. Tregs from patients with autoimmunity and food allergy have a defect in this inhibition of desensitization of the IL-2R that does not allow pSTAT5 expression for the 5 hours required to transcribe the genes required for Treg function. Inhibiting neddylation of Cullin5 by a NAE inhibitor like MLN4924 enhances or restores this feedback control loop of inhibition of desensitization of the IL-2R, allowing JAK to continue to function as a kinase to phosphorylate and activate STAT-5, preventing desensitization of IL-2R signaling. This inhibition of receptor desensitization results in transcription of the genes required for regulatory T cell proliferation.

The present disclosure thus provides a platform strategy for the integration of IL-2 proteins and distinct small molecules as single compounds (protein drug conjugates) to specifically target the high affinity receptor for IL-2 (IL-2R) that is constitutively expressed on regulatory T cells. Targeting of regulatory T cells with the compounds of the disclosure, or pharmaceutically acceptable salts, hydrates, solvates, isomers, or tautomers thereof, restores or enhances regulatory T cell function in order to treat immunological disorders. In some embodiments, the compound of the disclosure, or pharmaceutically acceptable salts, hydrates, solvates, isomers, or tautomers thereof, comprises a neddylation inhibitor, preventing neddylation of Cullin5, thus, blocking the transfer of ubiquitin to pJAK1, maintaining pJAK1 function.

Utilizing IL-2 polypeptides, or bio-active homolog polypeptides thereof, cytokine polypeptides, growth factor polypeptides, or hormones, the present disclosure also provides new treatments for treating cancer by decreasing immune regulation where tumor infiltrating regulatory T cells block rejection (or destruction) of the tumor. [10] The approach for treating cancer described herein focuses on killing tumor infiltrating Tregs or inactivating them to treat cancer. Thus, using IL-2 conjugated with cytolytic or cytostatic drugs can inactivate tumor infiltrating Tregs to allow the adaptive immune response to destroy the tumor.

Other targets in addition to IL-2R, such as receptors for cytokines, growth factors, or hormones, can also be targeted using cytokine polypeptides, growth factor polypeptides, or hormones conjugated to therapeutic small molecules disclosed herein.

General Information

The articles "a" and "an" are used in this disclosure and may refer to one or more than one (e.g., to at least one) of the grammatical object of the article. By way of example, "an element" may mean one element or more than one element.

The term "and/or" is used in this disclosure and may mean either "and" or "or" unless indicated otherwise.

Unless specifically stated, as used herein, the term "about" may refer to a range of values±10% of a specified value. For example, the phrase "about 200" may include ±10% of 200, or from 180 to 220. When stated otherwise, the term about may refer to a range of values that include ±20%, ±10%, or ±5%, etc.

An "IL-2 bio-active homolog polypeptide" may refer to a non-wild-type IL-2 polypeptide which can include coded and non-coded amino acids, chemically or biochemically modified or derivatized amino acids, a variants of a wild-type IL-2 polypeptide, a fusion IL-2 polypeptide, or an IL-2 polypeptide having modified peptide backbones. The IL-2 bio-active homolog polypeptides disclosed herein may also be variants differing from a wild-type IL-2 polypeptide by amino acid insertions, deletions, mutations, and/or substitutions. The IL-2 bio-active homolog polypeptides disclosed herein may be a fusion of an IL-2 polypeptide with another non-IL-2 polypeptide (e.g., thioredoxin). For examples, the IL-2 bio-active homolog polypeptides disclosed herein may be a fusion of a non-wild-type IL-2 polypeptide, which may include coded and non-coded amino acids, chemically or biochemically modified or derivatized amino acids, a variants of a wild-type IL-2 polypeptide, or an IL-2 polypeptide having a modified peptide backbone with another non-IL-2 polypeptide (e.g., thioredoxin).

The terms "peptide," "polypeptide," and "protein" may be used interchangeably herein, and may refer to a polymeric form of amino acids of any length, which can include coded and non-coded amino acids, chemically or biochemically modified or derivatized amino acids, full-length polypeptides, fragments of polypeptides, variants of polypeptides, truncated polypeptides, fusion polypeptides, or polypeptides having modified peptide backbones. The polypeptides disclosed herein may also be variants differing from a specifically recited "reference" polypeptide (e.g., a wild-type polypeptide) by amino acid insertions, deletions, mutations, and/or substitutions.

In some embodiments, conservative substitutions may be made in the amino acid sequence of a polypeptide without disrupting the three-dimensional structure or function of the polypeptide. Conservative substitutions may be accomplished by the skilled artisan by substituting amino acids with similar hydrophobicity, polarity, and R-chain length for one another. Additionally, by comparing aligned sequences of homologous proteins from different species, conservative substitutions may be identified by locating amino acid residues that have been mutated between species without altering the basic functions of the encoded proteins. The term "conservative amino acid substitution" may refer to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide containing side chains consisting of asparagine and glutamine; a group of amino acids having aromatic side chains consists of phenylalanine, tyrosine, and tryptophan; a group of amino acids having basic side chains consists of lysine, arginine, and histidine; a group of amino acids having acidic side chains consists of glutamate and aspartate; and a group of amino acids having sulfur containing side chains consists of cysteine and methionine. Exemplary conservative amino acid substitution groups are: valine-leucine-isoleucine, phenylalanine-tyrosine, lysine-arginine, alanine-valine, and asparagine-glutamine.

A polypeptide has a certain percent "sequence identity" to another polypeptide, meaning that, when aligned, that percentage of bases or amino acids are the same, and in the same relative position, when comparing the two sequences. Sequence identity can be determined in a number of different manners. To determine sequence identity, sequences can be aligned using various methods and computer programs (e.g., BLAST, T-COFFEE, MUSCLE, MAFFT, etc.), available over the world wide web at sites including ncbi.nlm.nili.gov/BLAST.ebi.ac.uk/Tools/msa/tcoffee/ebi.ac.uk/Tools/msa/muscle/mafft.cbrc.jp/alignment/software/. See, e.g., Altschul et al. (1990), J. Mol. Biol. 215:403-10.

"Optionally substituted" may refer to the replacement of hydrogen with a monovalent or divalent radical. Suitable substitution groups include, for example, hydroxyl, nitro, amino, imino, cyano, halo, thio, thioamido, amidino, oxo, oxamidino, methoxamidino, imidino, guanidino, sulfonamido, carboxyl, formyl, lower alkyl, halo lower alkyl, lower alkoxy, halo lower alkoxy, lower alkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like as defined herein. The substitution group can itself be substituted. The group substituted onto the substitution group can be, for example, carboxyl, halo; nitro, amino, cyano, hydroxyl, lower alkyl, lower alkoxy, aminocarbonyl, —SR, thioamido, $—SO_3H$, $—SO_2R$ or cycloalkyl, where R is typically hydrogen, hydroxyl or lower alkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

"Lower alkyl" as used herein may refer to branched or straight chain alkyl groups comprising one to ten carbon atoms that independently are unsubstituted or substituted, e.g., with one or more halogen, hydroxyl or other groups. Examples of lower alkyl groups include, but are not limited to, methyl, ethyl, propyl, isopropyl, n-butyl, t-butyl, n-hexyl, neopentyl, trifluoromethyl, pentafluoroethyl, and the like.

"Alkylenyl" may refer to a divalent straight chain or branched chain saturated aliphatic radical having from 1 to 20 carbon atoms. Typical alkylenyl groups employed in compounds of the present disclosure are lower alkylenyl groups that have from 1 to about 6 carbon atoms in their backbone.

"Alkenyl" may refer herein to straight chain, branched, or cyclic radicals having one or more double bonds and from 2 to 20 carbon atoms.

"Alkynyl" may refer herein to straight chain, branched, or cyclic radicals having one or more triple bonds and from 2 to 20 carbon atoms.

"Halo lower alkyl" may refer to a lower alkyl radical substituted with one or more halogen atoms.

"Lower alkoxy" as used herein may refer to RO—, wherein R is lower alkyl. Representative examples of lower alkoxy groups include methoxy, ethoxy, t-butoxy, trifluoromethoxy and the like.

"Lower alkythio" as used herein may refer to RS—, wherein R is lower alkyl.

"Alkoxyalkyl" refers to the group $-alk_1-O-alk_2$, where $alk_1$ is alkylenyl or alkenyl, and $alk_2$ is alkyl or alkenyl.

"Lower alkoxyalkyl" refers to an alkoxyalkyl as defined herein, where $alk_1$ is lower alkylenyl or lower alkenyl, and $alk_2$ is lower alkyl or lower alkenyl.

"Aryloxyalkyl" refers to the group alkylenyl-O-aryl.

"Aralkoxyalkyl" refers to the group alkylenyl-O-aralkyl, where aralkyl is a lower aralkyl.

"Cycloalkyl" refers to a monoor polycyclic, lower alkyl substituent. Typical cycloalkyl substituents have from 3 to 8 backbone (i.e., ring) atoms in which each backbone atom is optionally substituted carbon. When used in context with cycloalkyl substituents, the term polycyclic refers herein to fused, nonfused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

"Cycloheteroalkyl" refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

"(Cycloalkyl)alkyl" and "(cycloheteroalkyl)alkyl" refer to alkyl chains substituted with cycloalkyl and cycloheteroalkyl groups respectively.

"Haloalkoxy" refers to an alkoxy radical substituted with one or more halogen atoms. The term "halo lower alkoxy" refers to a lower alkoxy radical substituted with one or more halogen atoms.

"Halo" refers herein to a halogen radical, such as fluorine, chlorine, bromine, or iodine.

"Aryl" refers to monocyclic and polycyclic aromatic groups, or fused ring systems having at least one aromatic ring, having from 3 to 14 backbone carbon atoms. Examples of aryl groups include without limitation phenyl, naphthyl, dihydronaphtyl, tetrahydronaphthyl, and the like.

"Aralkyl" refers to an alkyl group substituted with an aryl group. Typically, aralkyl groups employed in compounds of the present disclosure have from 1 to 6 carbon atoms incorporated within the alkyl portion of the aralkyl group. Suitable aralkyl groups employed in compounds of the present disclosure include, for example, benzyl, picolyl, and the like.

"Heteroaryl" refers herein to aryl groups having from one to four heteroatoms as ring atoms in an aromatic ring with the remainder of the ring atoms being aromatic or non-aromatic carbon atoms. When used in connection with aryl substituents, the term polycyclic refers herein to fused and non-fused cyclic structures in which at least one cyclic structure is aromatic, such as, for example, benzodioxozolo, naphthyl, and the like. Exemplary heteroaryl moieties employed as substituents in compounds of the present disclosure include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

"Amino" refers herein to the group $-NH_2$. The term "lower alkylamino" refers herein to the group $-NRR^1$ where R and $R^1$ are each independently selected from hydrogen or lower alkyl. The term "arylamino" refers herein to the group $-NRR^1$ where R is aryl and $R^1$ is hydrogen, lower alkyl, aryl, or aralkyl. The term "aralkylamino" refers herein to the group $-NRR^1$ where R is aralkyl and $R^1$ is hydrogen, lower alkyl, aryl, or aralkyl. The terms "heteroarylamino" and "heteroaralkylamino" are defined by analogy to arylamino and aralkylamino.

"Aminocarbonyl" refers herein to the group $-C(O)NH_2$. The terms "lower alkylaminocarbonyl," "arylaminocarbonyl," "aralkylaminocarbonyl," "heteroarylaminocarbonyl," and "heteroaralkylaminocarbonyl" refer to $-C(O)NRR^1$ where R and $R^1$ independently are hydrogen and optionally substituted lower alkyl, aryl, aralkyl, heteroaryl, and heteroaralkyl respectively by analogy to the corresponding terms herein.

"Thio" refers to —SH. The terms lower alkylthio, arylthio, heteroarylthio, cycloalkylthio, cycloheteroalkylthio, aralkylthio, heteroaralkylthio, (cycloalkyl)alkylthio, and (cycloheteroalkyl)alkylthio refer to —SR, where R is optionally substituted lower alkyl, aryl, heteroaryl, cycloalkyl, cycloheteroalkyl, aralkyl, heteroaralkyl, (cycloalkyl) alkyl, and (cycloheteroalkyl)alkyl respectively.

"Sulfonyl" refers herein to the group $-SO_2-$. The terms lower alkylsulfonyl, arylsulfonyl, textitheteroarylsulfonyl, cycloalkylsulfonyl, cycloheteroalkylsulfonyl, aralkylsulfonyl, heteroaralkylsulfonyl, (cycloalkyl)alkylsulfonyl, and (cycloheteroalkyl)alkylsulfonyl refer to $-SO_2R$ where R is optionally substituted lower alkyl, aryl, heteroaryl, cycloalkyl, cycloheteroalkyl, aralkyl, heteroaralkyl, (cycloalkyl) alkyl, and (cycloheteroalkyl)alkyl respectively.

"Sulfinyl" refers herein to the group —SO—. The terms lower alkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, and (cycloheteroalkyl)alkylsulfinyl refer to —SOR where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Nitrilo" refers to —CN.

"Formyl" refers to —C(O) H.

"Carboxyl" refers to —C(O) OH.

"Carbonyl" refers to the divalent group —C(O)—. The terms lower alkylcarbonyl, arylcarbonyl, heteroarylcarbonyl, cycloalkylcarbonyl, cycloheteroalkylcarbonyl, aralkycarbonyl, heteroaralkylcarbonyl, (cycloalkyl)alkylcarbonyl, and (cycloheteroalkyl)alkylcarbonyl refer to —C(OR)—, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Thiocarbonyl" refers to the group —C(S)—. The terms lower alkylthiocarbonyl, arylthiocarbonyl, heteroarylthiocarbonyl, cycloalkylthiocarbonyl, cycloheteroalkylthiocarbonyl, aralkylthiocarbonyloxlthiocarbonyl, heteroaralkylthiocarbonyl, (cycloalkyl)alkylthiocarbonyl, and (cycloheteroalkyl)alkylthiocarbonyl refer to —C(S)R—, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonyloxy" refers generally to the group —C(O)O—. The terms lower alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl) alkylcarbonyloxy refer to —C(O)OR, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Oxycarbonyl" refers to the group —OC(O)—. The terms lower alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, (cycloheteroalkyl) alkyloxycarbonyl refer to —OC(O)R, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkylrespectively.

"Carbonylamino" refers to the group —NHC(O)—. The terms lower alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, and (cycloheteroalkyl)alkylcarbonylamino refer to —NHC(O) R—, where R is optionally substituted lower alkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present disclosure includes n-substituted carbonylamino ($-NR^1C(O)R$), where $R^1$ is optionally substituted lower alkyl, aryl, heteroaryl, aralkyl, or heteroaralkyl and R retains the previous defintion.

"Carbonylthio" refers to the group —C(O)S—. The terms lower alkylcarbonylthio, arylcarbonylthio, heteroarylcarbonylthio, cycloalkylcarbonylthio, cycloheteroalkylcarbonylthio, aralkylcarbonylthio, heteroaralkylcarbonylthio, (cycloalkyl)alkylcarbonylthio, (cycloheteroalkyl) alkylcarbonylthio refer to —C(O)SR, where R is optionally substituted lower alkyl, aryl, heteroaryl, cycloalkyl, cycloheteroalkyl, aralkyl, heteroaralkyl, (cycloalkyl)alkyl, and (cycloheteroalkyl)alkyl respectively.

"Guanidino" or "Guanidyl" refers to moieties derived from guanidine, $H_2N—C(=NH)—NH_2$. Such moieties include those bonded at the nitrogen atom carrying the formal double bond (the 2-position of the guanidine, e.g., diaminomethyleneamino, $((H_2N)_2—C=NH—)$ and those bonded at either of the nitrogen atoms carrying a formal single bond (the 1 or 3-positions of the guanidine, e.g., $H_2NC(=NH)—NH—$). The hydrogen atoms at either nitrogen can be replaced with a suitable substituent, such as lower alkyl, aryl, or lower aralkyl.

"Amidino" refers to the moieties $R—C(=N)—NR^1$-(the radical being at the $N^1$ nitrogen) and $R—(NR^1)CN—$ (the radical being at the $N^2$ nitrogen), where R and $R^1$ can be hydrogen, lower alkyl, aryl, or lower aralkyl.

"Imino" refers to the group —C(=NR)—, where R can be hydrogen or optionally substituted lower alkyl, aryl, heteroaryl, or heteroaralkyl respectively. The terms "imino lower alkyl," "iminocycloalkyl," "iminocycloheteroalkyl," "iminoaralkyl," "iminoheteroaralkyl," "(cycloalkyl)iminoalkyl," "(cycloiminoalkyl)alkyl," "(cycloiminoheteroalkyl) alkyl," and "(cycloheteroalkyl)iminoalkyl" refer to optionally substituted lower alkyl, cycloalkyl, cycloheteroalkyl, aralkyl, heteroaralkyl, (cycloalkyl)alkyl, and (cycloheteroalkyl)alkyl groups that include an imino group, respectively.

"Oximino" refers to the group —C(=NOR)—, where R can be hydrogen ("hydroximino") or optionally substituted lower alkyl, aryl, heteroaryl, or heteroaralkyl respectively. The terms "oximino lower alkyl," "oximinocycloalkyl," "oximinocycloheteroalkyl," "oximinoaralkyl," "oximinoheteroaralkyl," "(cycloalkyl) oximinoalkyl," "(cyclooximinoalkyl)alkyl," "(cyclooximinoheteroalkyl)alkyl," and "(cycloheteroalkyl) oximinoalkyl" refer to optionally substituted lower alkyl, cycloalkyl, cycloheteroalkyl, aralkyl, heteroaralkyl, (cycloalkyl)alkyl, and (cycloheteroalkyl)alkyl groups that include an oximino group, respectively.

"Methylene" as used herein refers to an unsubstituted, monosubstituted, or disubstituted carbon atom having a formal $sp^3$ hybridization (i.e., $—CRR^1—$, where R and $R^1$ are hydrogen or independent substituents).

"Methine" as used herein refers to an unsubstituted or substituted carbon atom having a formal $sp^2$ hybridization (i.e., CR= or =CR—, where R is hydrogen or a substituent).

Compounds of the Disclosure

The present disclosure relates to compounds (e.g., Formulae II and III), or pharmaceutically acceptable salts, hydrates, solvates, isomers, or tautomers thereof, useful for the treatment of disorders, such as immunological disorders and cancer. More particularly, the compounds of the disclosure (e.g., Formulae II and III), or pharmaceutically acceptable salts, hydrates, solvates, isomers, or tautomers thereof, may comprise biologically active polypeptides or hormones modified to include the attachment of therapeutic compounds using linkers. The compounds of the disclosure, or pharmaceutically acceptable salts, hydrates, solvates, isomers, or tautomers thereof, also comprise therapeutic compounds connected to linkers.

In an aspect, the present disclosure provides compounds having the structure of Formula (I):

$$X_{2a}—(X_3)_m \quad (I),$$

and pharmaceutically acceptable salts, solvates, hydrates, isomers, or tautomers thereof, wherein:

m is 1, 2, 3, 4, 5, 6, 7, 8, 9, or 10;

$X_{2a}$ is a linker; and $X_3$ is a therapeutic compound.

As shown in Formula (I), multiple $X_3$ moieties, the number defined by m, may be attached to $X_{2a}$.

In some embodiments of the compound of Formula (I), m is 1. In some embodiments of the compound of Formula (I), m is 2, 3, 4, 5, 6, 7, or 8. In some embodiments of the compound of Formula (I), m is 1, 2, or 3. In some embodiments of the compound of Formula (I), m is 2, 3, 4, or 5. In some embodiments of the compound of Formula (I), m is 2. In some embodiments of the compound of Formula (I), m is 3. In some embodiments of the compound of Formula (I), m is 4. In some embodiments of the compound of Formula (I), m is 5. In some embodiments of the compound of Formula (I), m is 6. In some embodiments of the compound of Formula (I), m is 7. In some embodiments of the compound of Formula (I), m is 8. In some embodiments of the compound of Formula (I), m is 9. In some embodiments of the compound of Formula (I), m is 10. In some embodiments, m is an integer between 1 and 10.

$X_{2a}$ is a linker, which can take many forms as shown herein. In some embodiments of the compound of Formula (I), $X_{2a}$ is a linker which has not yet been reacted with a biologically active polypeptide or hormone. In some embodiments of the compound of Formula (I), $X_{2a}$ is a cleavable linker. In some embodiments of the compound of Formula (I), $X_{2a}$ is an non-cleavable linker. As used herein, a "cleavable linker" may refer to a linker comprising a lysosomal and/or endosomal-specific enzyme cleavage site, such as a β-glucuronidase site, a β-galactosidase site, or a cathepsin site. With a cleavable linker, the therapeutic compound may be liberated only after internalization of the conjugate by the cell, in proximity to the therapeutic compound's intracellular target. This targeted liberation may enable use of toxic, potent therapeutic compounds for treatment of disorders. "Non-cleavable linkers" may refer to linkers conjugated to therapeutic compounds that will act directly absent release.

In some embodiments of the compound of Formula (I), $X_{2a}$ is a linker listed in Table 1, wherein the right side of $X_{2a}$, as drawn, is bound to $X_3$. In Table 1, R=H, alkyl, aryl, arylalkyl, glycol ether, or an additional glycol linker attaching to the therapeutic compound.

TABLE 1
| Exemplary $X_{2a}$ Linkers | |
|---|---|
| Compound Number | Structure |
| L-1 Cleavable linker | 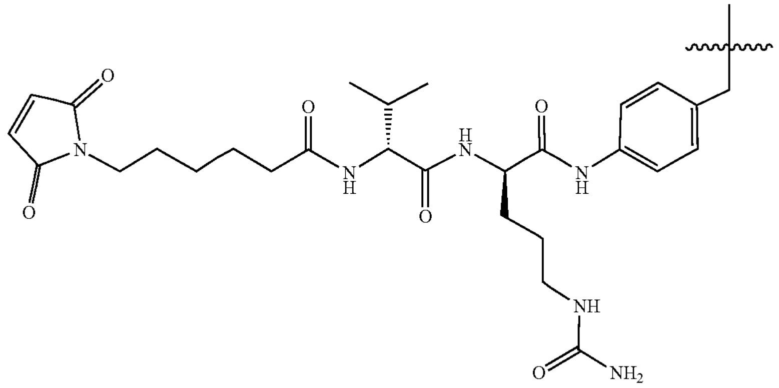 [SMILES: *CC1=CCC=C(NCC(=O)C[C@@H](CCCCCNC(N)=O)NC(=O)C[C@H](NC(=O)CCCCCCCN2C(=O)CC=CC2=C=O)C(C)CC)C=C1] |
| L-2 Cleavable linker | 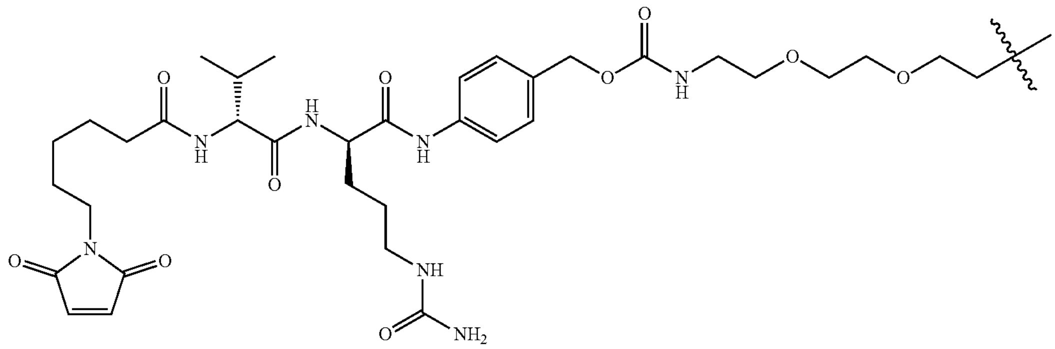 [SMILES: *CCOCCOCCNC(=O)OCc1ccc(NC(=O)[C@@H](CCCNC(N)=O)NC(=O)[C@H](NC(=O)CCCCCN2C(=O)C=CC2=O)C(C)C)cc1] |
| L-3 Cleavable linker | 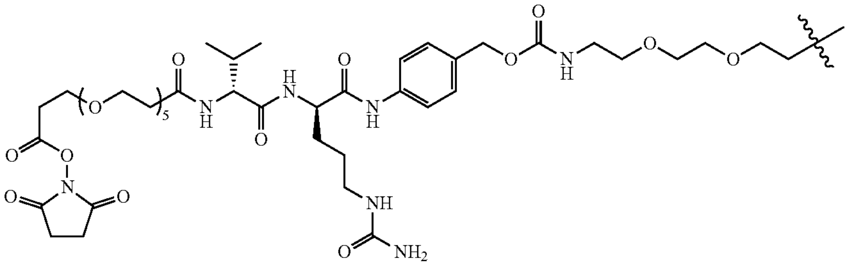 |
| L-4 Cleavable linker | 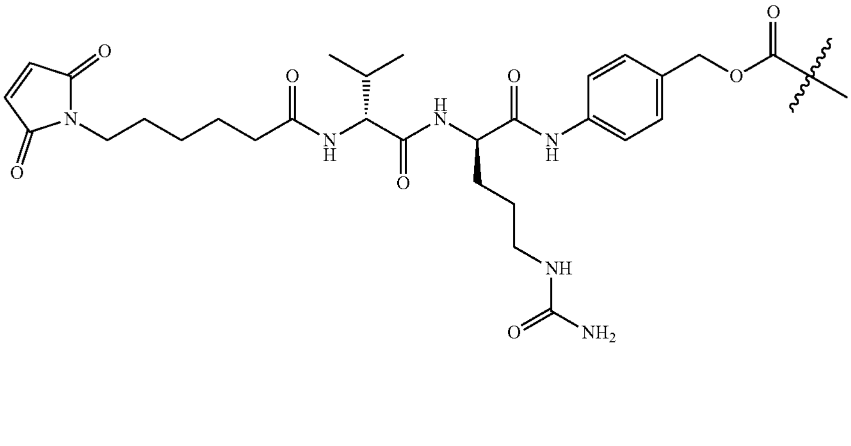 [SMILES: *C(=O)OCc1ccc(NC(=O)[C@@H](CCCNC(N)=O)NC(=O)[C@H](NC(=O)CCCCCN2C(=O)C=CC2=O)C(C)C)cc1] |

TABLE 1-continued
| Exemplary $X_{2a}$ Linkers | |
|---|---|
| Compound Number | Structure |
| L-5 Cleavable linker | 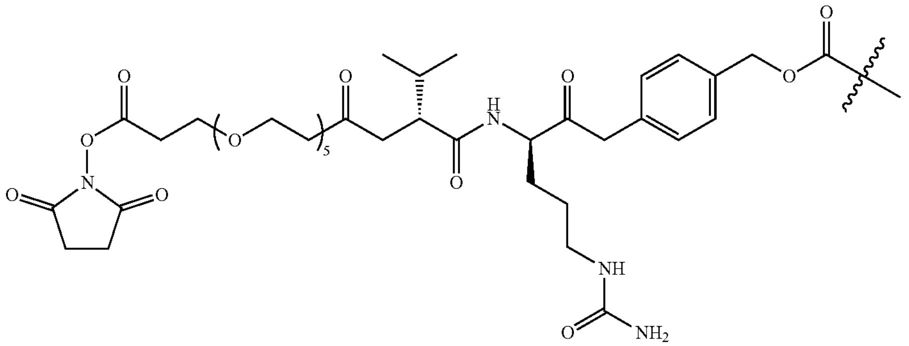 |
| L-6 Cleavable linker | 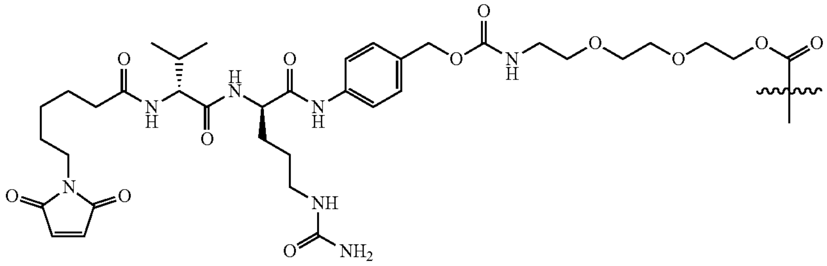 [SMILES: *C(=O)OCCOCCOCCNC(=O)OCc1ccc(NC(=O)[C@@H](CCCNC(N)=O)NC(=O)[C@H](NC(=O)CCCCCN2C(=O)C=CC2=O)C(C)C)cc1] |
| L-7 Cleavable linker | 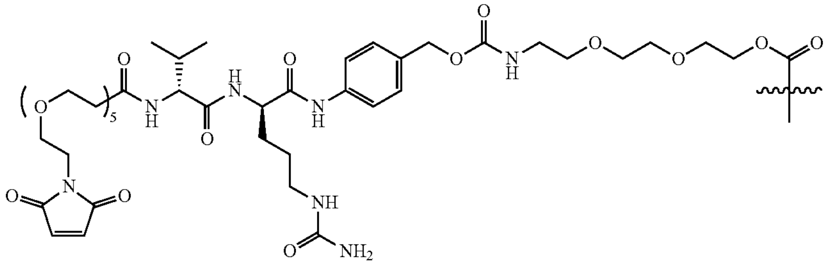 |
| L-8 Cleavable linker | 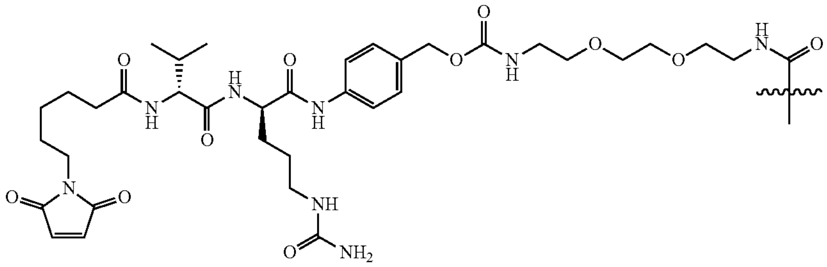 [SMILES: *C(=O)NCCOCCOCCNC(=O)OCc1ccc(NC(=O)[C@@H](CCCNC(N)=O)NC(=O)[C@H](NC(=O)CCCCCN2C(=O)C=CC2=O)C(C)C)cc1] |
| L-9 Cleavable linker | 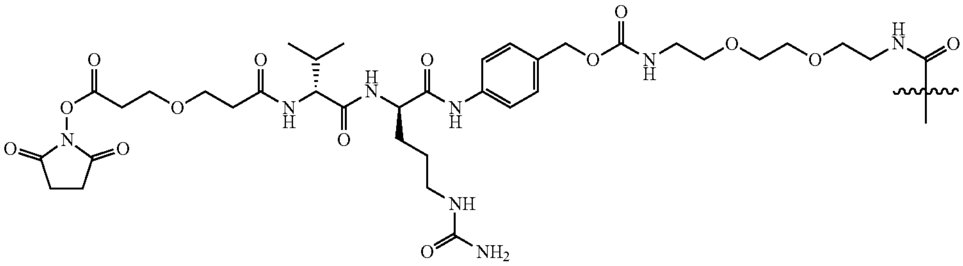 [SMILES: *C(=O)NCCOCCOCCNC(=O)OCc1ccc(NC(=O)[C@@H](CCCNC(N)=O)NC(=O)[C@H](NC(=O)CCOCCC(=O)ON2C(=O)CCC2=O)C(C)C)cc1] |

TABLE 1-continued
| Exemplary $X_{2a}$ Linkers | |
|---|---|
| Compound Number | Structure |
| L-10 Cleavable linker | 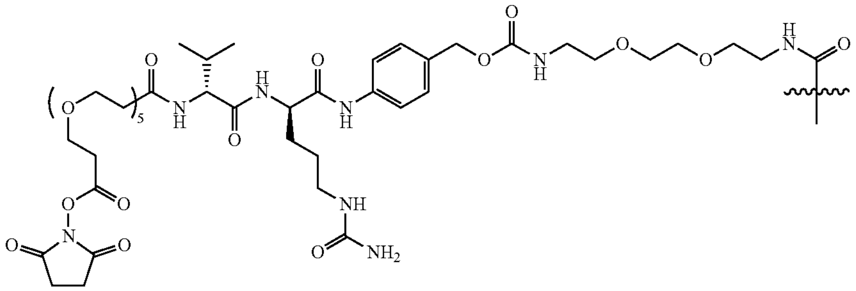 |
| L-11 Cleavable linker | 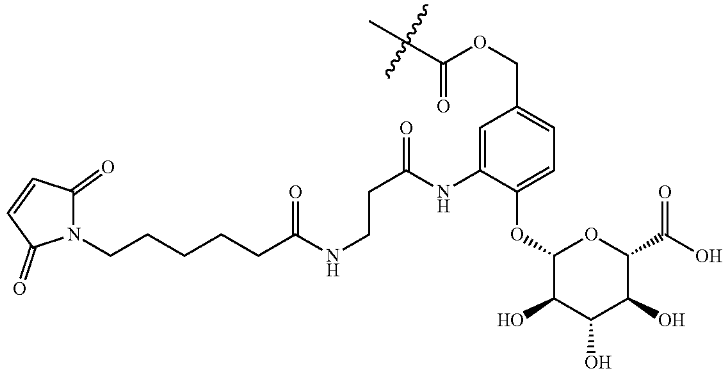 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1] |
| L-12 Cleavable linker | 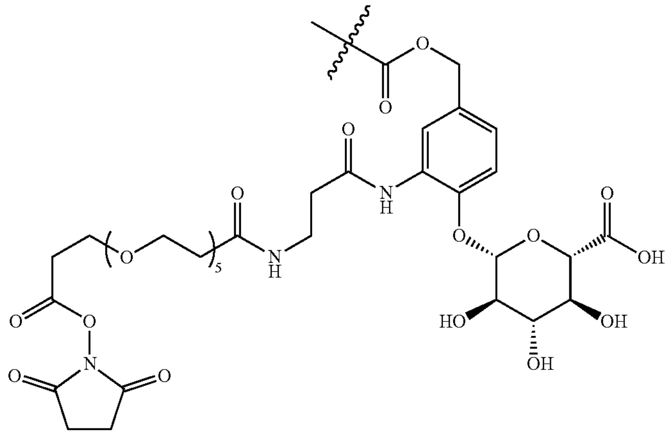 |

TABLE 1-continued
| Exemplary $X_{2a}$ Linkers | |
|---|---|
| Compound Number | Structure |
| L-13 Cleavable linker | 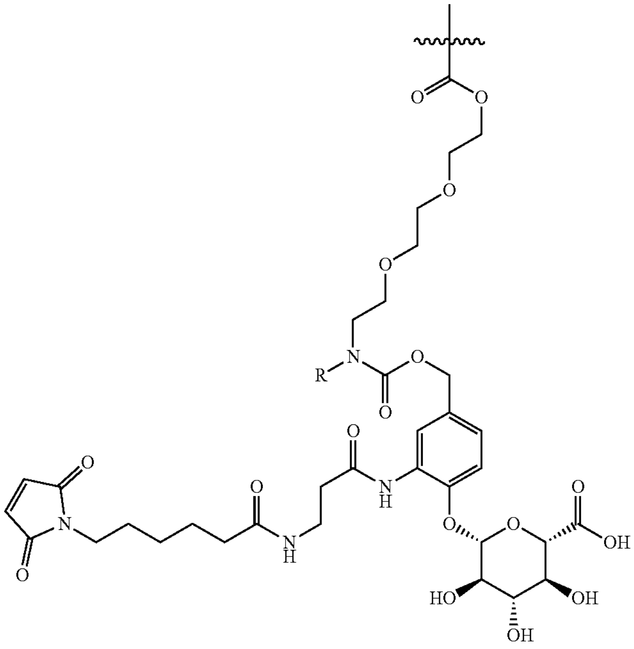 |
| L-14 Cleavable linker | 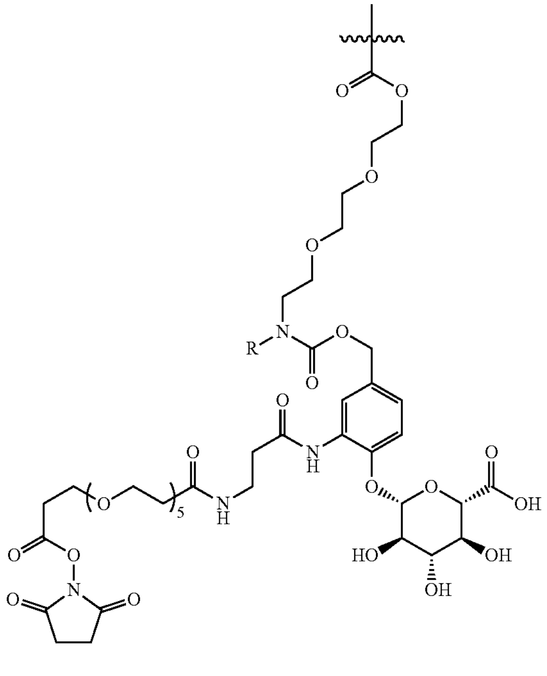 |

TABLE 1-continued
| Exemplary $X_{2a}$ Linkers | |
|---|---|
| Compound Number | Structure |
| L-15 Cleavable linker | 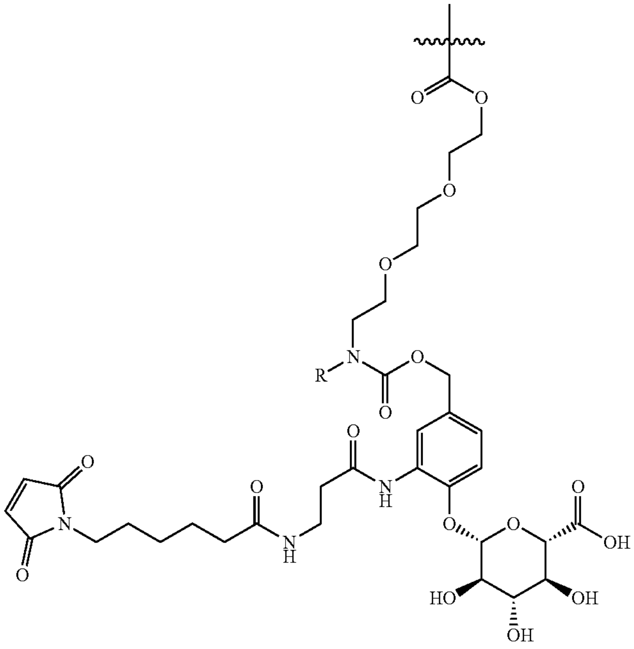 |
| L-16 Cleavable linker | 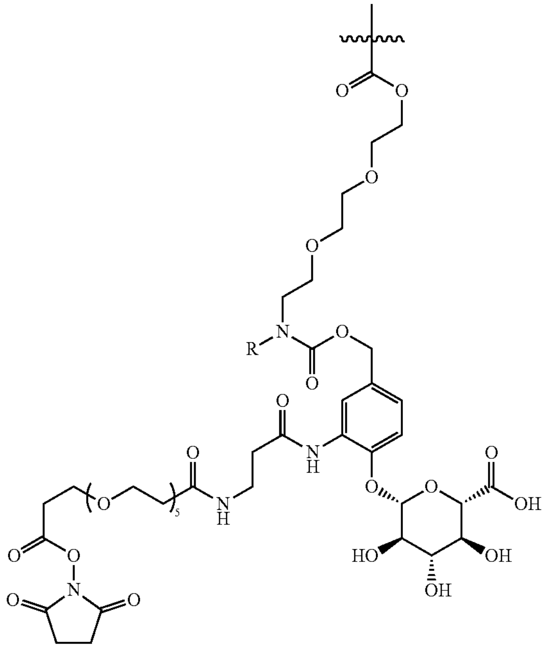 |

TABLE 1-continued

Exemplary $X_{2a}$ Linkers

| Compound Number | Structure |
| --- | --- |
| L-17 Non-cleavable linker | 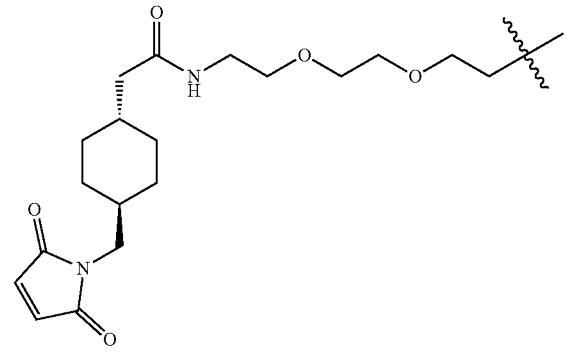 [SMILES: *CCOCCOCCNC(=O)C[C@H]1CC[C@H](CN2C(=O)C=CC2=O)CC1] |
| L-18 Non-cleavable linker | 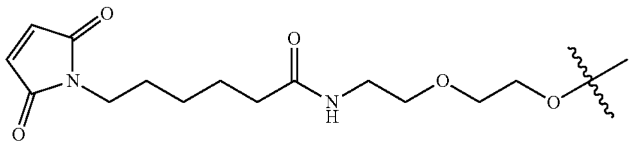 [SMILES: *OCCOCCNC(=O)CCCCCN1C(=O)C=CC1=O] |
| L-19 Cleavable linker | 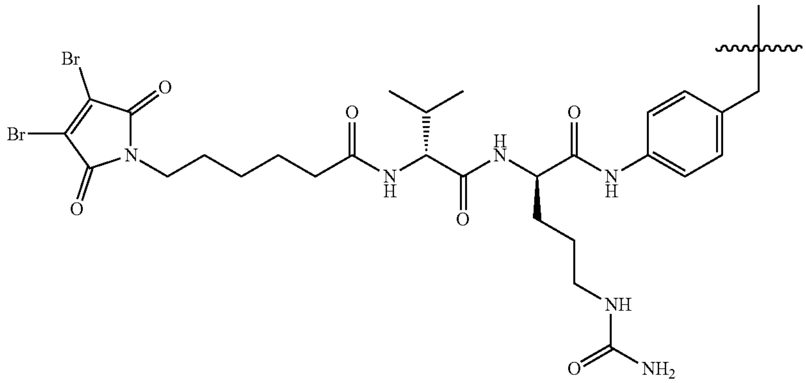 [SMILES: *Cc1ccc(NC(=O)[C@@H](CCCNC(N)=O)NC(=O)[C@H](NC(=O)CCCCCN2C(=O)C(Br)=C(Br)C2=O)C(C)C)cc1] |

In some embodiments of the compound of Formula (I), $X_{2a}$ is a cleavable linker selected from the group consisting of L-1, L-2, L-3, L-4, L-5, L-6, L-7, L-8, L-9, L-10, L-11, L-12, L-13, L-14, L-15, L-16, and L-19.

In some embodiments of the compound of Formula (I), $X_{2a}$ is a cleavable linker selected from the group consisting of L-1 and L-19.

In some embodiments of the compound of Formula (I), $X_{2a}$ is a non-cleavable linker selected from the group consisting of L-17 and L-18.

Figure 5A:
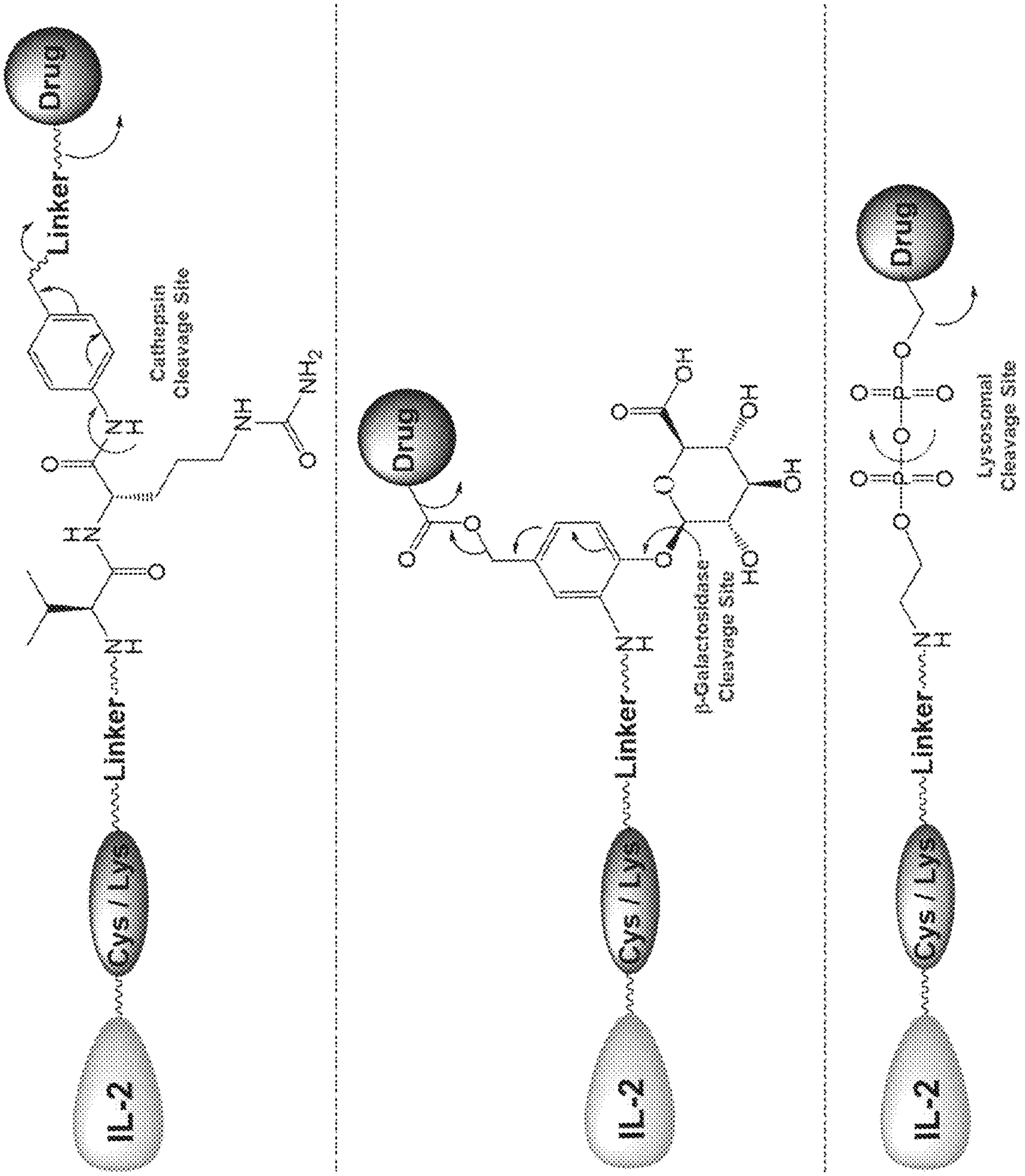
FIGS. 5A and 5B are a schematic showing some cleavable (FIG. 5A) and non-cleavable (FIG. 5B) linkers in accordance with some embodiments of the disclosure.
Figure 5B:
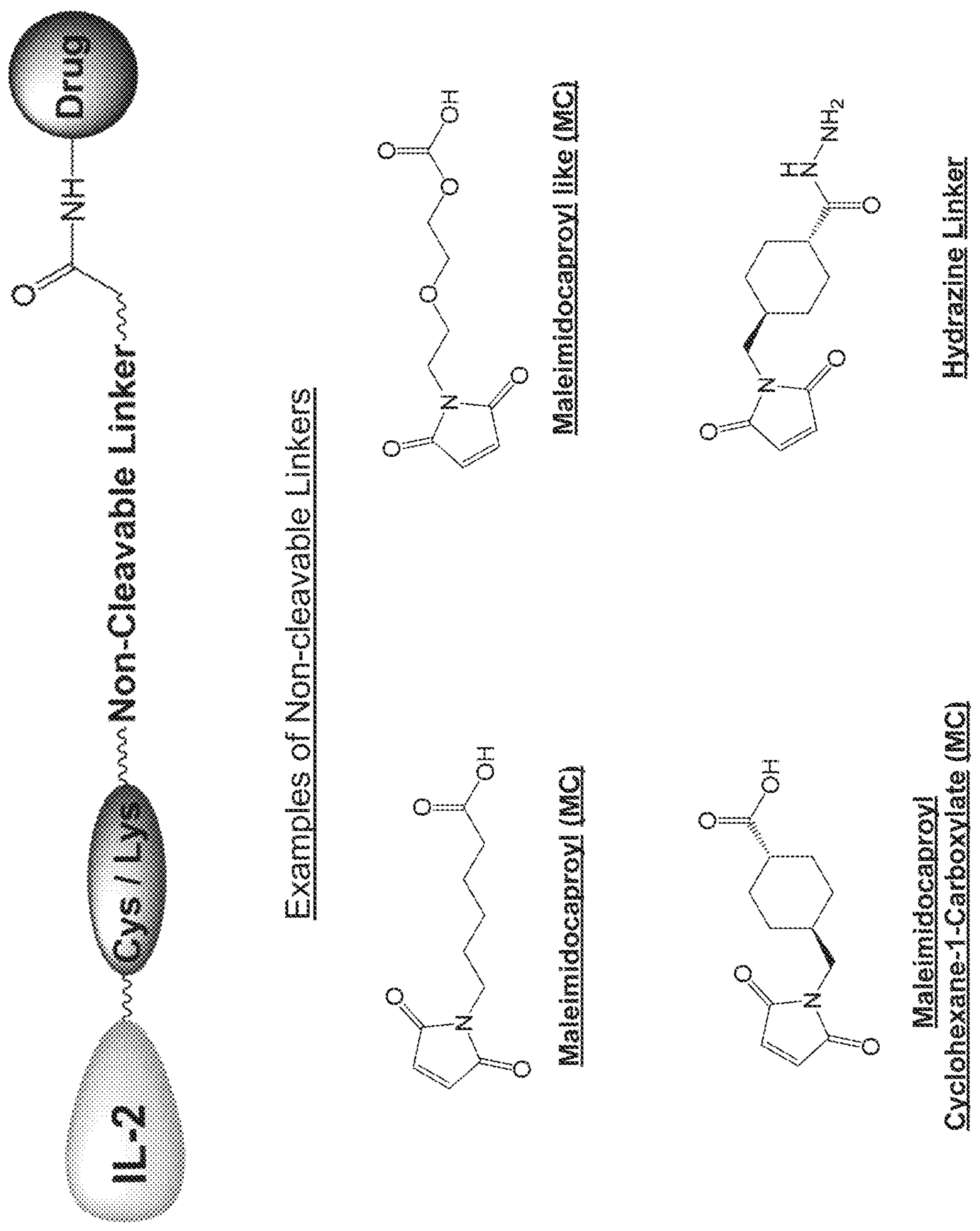

FIGS. 5A and 5B show exemplary cleavable and non-cleavable linkers, which are discussed in more detail herein.

The therapeutic compound $X_3$ can be any suitable therapeutic compound for the desired therapeutic application. Examples of therapeutic compounds useful for the treatment of immunological disorders (e.g., allergy, autoimmune, etc.) include, but are not limited to, the following classes of immunomodulating agents: immunosuppressive drugs, anti-anemics, antianginals, antiarryhythmics, antiarthritics, antiasthmatics, leukotriene antagonists, antibacterials, antibiotics, anticoagulants, anticonvulsants, antidepressants, antidiabetics, antiemetics, glucocorticoids, anti-TNF agents, cytotoxic agents, neddylation inhibitors (e.g., NEDD8 activating enzyme (NAE) inhibitors), ubiquitin-activating enzyme (UAE) inhibitors, ubiquitin-activating enzyme E1 inhibitors (E1 inhibitors), and proteasome inhibitors. Examples of such therapeutic compounds include, but are not limited to: pevonedistat (MLN4924), TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate), Piperacillin, M22 (1-benzyl-N-(2,4-dichlorophenethyl) piperidin-4-amine), 6,6'-Biapigenin, Thieno-pyridine, Imidazo-pyrimidine, Largazole, Pyr-41 (4 [4-(5-nitro-furan-2-ylmethylene)-3,5-dioxo-pyrazolidin-1-yl]-benzoic acid ethyl ester), Phorbol 12-myristate 13-acetate, 2,3-dihydropyrrolo[2,1-b]quinazolin-9 (1H)-one, Ofloxacin, Panepophenanthin, Himeic Acid A, Hyrtioreticulins A, phytol, ABPA3 ([(2R,3S,4R,5R)-5-[6-(3-ethynylanilino) purin-9-yl]-3,4-dihydroxyoxolan-2-yl]methyl sulfamate), Benzothiazole, Deoxyvasicinone derivatives, Coumarins, and Imidazolium-quinoxaline, or pharmaceutically acceptable salts, solvates, hydrates, or tautomers of any of the foregoing. In some embodiments, the immunomodulating agent is pevonedistat (MLN4924), TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl) methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), or TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate). In some embodiments, the immunomodulatory agent is Pevonedistat. Examples of such therapeutic compounds include, but are not limited to: pevonedistat (MLN4924), TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), TAK7243 (((1R,2R,3S,4R)-2,3-dihydroxy-4-((2-(3-(trifluoromethyl) phenyl) pyrazolo[1,5-a]pyrimidin-7-yl)amino)cyclopentyl) methyl sulfamate), Piperacillin, M22 (1-benzyl-N-(2,4-dichlorophenethyl) piperidin-4-amine), 6,6'-Biapigenin, Thieno-pyridine, Imidazo-pyrimidine, Largazole, Pyr-41 (4 [4-(5-nitro-furan-2-ylmethylene)-3,5-dioxo-pyrazolidin-1-yl]-benzoic acid ethyl ester), Phorbol 12-myristate 13-acetate, 2,3-dihydropyrrolo[2,1-b]quinazolin-9 (1H)-one, Ofloxacin, Panepophenanthin, Himeic Acid A, Hyrtioreticulins A, phytol, ABPA3 ([(2R,3S,4R,5R)-5-[6-(3-ethynylanilino) purin-9-yl]-3,4-dihydroxyoxolan-2-yl]methyl sulfamate), Benzothiazole, Deoxyvasicinone derivatives, Coumarins, Imidazolium-quinoxaline, and TAS4464 (7H-Pyrrolo[2,3-d]pyrimidin-4-amine, 7-[5-[(aminosulfonyl) amino]-5-deoxy-beta-D-ribofuranosyl]-5-[2-(2-ethoxy-6-fluorophenyl) ethynyl]-), or pharmaceutically acceptable salts, solvates, hydrates, or tautomers of any of the foregoing. In some embodiments, the immunomodulating agent is pevonedistat (MLN4924), TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate), or TAS4464 (7H-Pyrrolo[2,3-d]pyrimidin-4-amine, 7-[5-[(aminosulfonyl) amino]-5-deoxy-beta-D-ribofuranosyl]-5-[2-(2-ethoxy-6-fluorophenyl) ethynyl]-).

Examples of therapeutic compounds useful for the treatment of cancer include, but are not limited to the following classes of cancer chemotherapeutic agents: oncolytic drugs, genotoxic agents, alkylating agents, tubulin inhibitors, microtubule assembly inhibitors, antineoplastic drugs, kinase inhibitors, vinca alkaloids, antibiotics, anthracyclines, antimetabolites, aromatase inhibitors, topoisomerase inhibitors, mTor inhibitors, retinoids, antimitotic agents, protease inhibitors, tyrosine kinase inhibitors, microtubule destabilizers, and proteasome inhibitors. Examples of such therapeutic compounds include, but are not limited to: buserelin, carboplatin, carfilzomib, cisplatin, clindamycin, dasatinib, docetaxel, doxorubicin, etoposide, everolimus, fluorouracil, fulvestrant, gefitinib, gemcitabine, indibulin, irinotecan, isotretinoin, methotrexate, paclitaxel, oxaliplatin, rifabutin, tubulysin, vinblastine, vincristine, vinorelbine, vinflunine, crytophycin 52, halichondrins, dolastatins, hemiasterlins, colchicine, combretastatins, 2-methoxyestradiol, methoxybenzenesulfonamides, epothilone, discodermolide, and monomethyl auristatin E (MMAE), or pharmaceutically acceptable salts, solvates, hydrates, or tautomers of any of the foregoing. In some embodiments, the therapeutic agent is MMAE.

In some embodiments, $X_3$ can be any suitable therapeutic compound for the desired therapeutic application. Examples of therapeutic compounds useful for the treatment of immunological disorders (e.g., allergy, autoimmune, etc.) include, but are not limited to, the following classes of immunomodulating agents: antianemics, antianginals, antiarryhythmics, antiarthritics, antiasthmatics, leukotriene antagonists, antibacterials, antibiotics, anticoagulants, anticonvulsants, antidepressants, antidiabetics, antiemetics, glucocorticoids, anti-TNF agents, cytotoxic agents, neddylation inhibitors, proteasome inhibitors, and enzyme inhibitors. Examples of therapeutic compounds useful for the treatment of cancer include, but are not limited to the following classes of cancer chemotherapeutic agents: alkylating agents, kinase inhibitors, vinca alkaloids, anthracyclines, antimetabolites, aromatase inhibitors, topoisomerase inhibitors, mTor inhibitors, retinoids, antimitotic agents, antibiotics, and proteasome inhibitors. Examples of such therapeutic compounds include, but are not limited to: buserelin, carboplatin, carfilzomib, cisplatin, clindamycin, dasatinib, docetaxel, doxorubicin, etoposide, everolimus, fluorouracil, fulvestrant, gefitinib, gemcitabine, indibulin, irinotecan, isotretinoin, methotrexate, monomethyl, auristatin E, oxaliplatin, paclitaxel, rifabutin, tubulysin, and vinblastine. In some embodiments, $X_3$ is selected from the group consisting of vincristine, vinorelbine, vinflunine, crytophycin 52, a halichondrin, a dolastatin, a hemiasterlin, colchicine, a combretastatin, 2-methoxyestradiol, a methoxybenzenesulfonamide, epothilone, and discodermolide.

In some embodiments, $X_3$ is selected from the group consisting of: Monomethyl Auristatin E; Docetaxel; Etoposide; Gemcitabine; Vinblastine; Paclitaxel; Irinotecan; Fluorouracil; Methotrexate; Carboplatin; Oxaliplatin; Cisplatin; Doxorubicin HCl; Fulvestrant; Isotretinoin; Buserelin; Everolimus; Carfilzomib; Rifabutin; Clindamycin; Tubulysin A; Indibulin; Gefitinib; and Dasatinib. In some embodiments, $X_3$ is Monomethyl Auristatin E.

Examples of therapeutic compounds, or pharmaceutically acceptable salts, solvates, hydrates, isomers, or tautomers thereof, useful in the disclosure are detailed in Table 2. In Table 2, $R_1$=alkyl, aryl, arylalkyl, arylalkyne, arylalkene, heterocyclyl, heteroaryl, and the like; and $R_2$ is H, alkyl, aryl, and the like.

TABLE 2

| Exemplary Therapeutic Compounds for $X_3$ | |
|---|---|
| Immunological Disorder Therapeutic Compounds | |
| Compound Name and Activity | Structure |
| Pevonedistat<br>NAE Inhibitor | 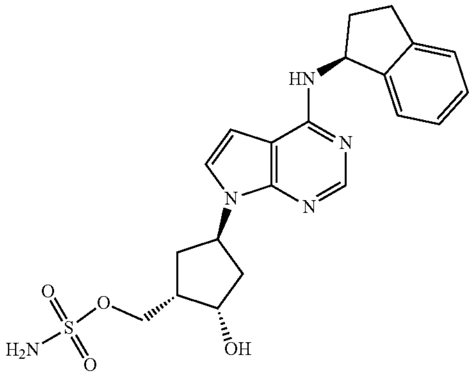 [SMILES: NS(=O)(=O)OC[C@@H]1C[C@@H](n2ccc3c(N[C@H]4CCc5ccccc54)ncnc32)C[C@@H]1O] |
| TAS1 (((2S,3S,4R,5R)-5-(4-amino-5-((4,7-dimethyl-3,4-dihydro-2H-benzo[b][1,4]oxazin-8-yl)ethynyl)-7H-pyrrolo[2,3-d]pyrimidin-7-yl)-3,4-dihydroxytetrahydrofuran-2-yl)methyl sulfamate)<br>NAE Inhibitor | 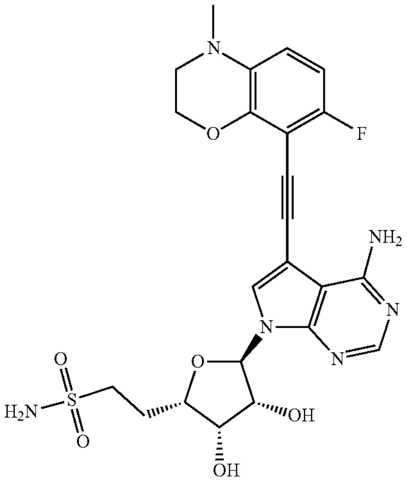 [SMILES: CN1CCOc2c1ccc(F)c2C#Cc1cn([C@@H]2O[C@@H](CCS(N)(=O)=O)[C@@H](O)[C@H]2O)c2ncnc(N)c12] |
| TAS2 (((1S,2R,3S,4R)-4-(4-amino-5-((4,7-dimethyl-3,4-dihydro-2H-benzo[b][1,4]oxazin-8-yl)ethynyl)-7H-pyrrolo[2,3-d]pyrimidin-7-yl)-2,3-dihydroxycyclopentyl)methyl sulfamate)<br>NAE Inhibitor | 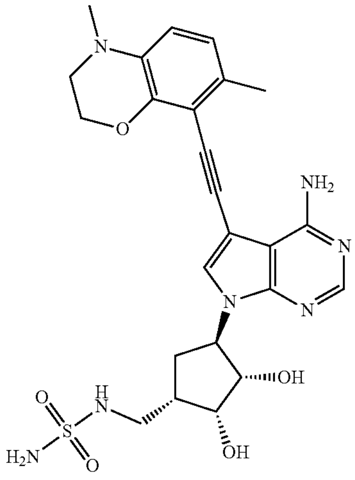 [SMILES: Cc1ccc2c(c1C#Cc1cn([C@@H]3C[C@@H](CNS(N)(=O)=O)[C@@H](O)[C@H]3O)c3ncnc(N)c13)OCCN2C] |

TABLE 2-continued
| Exemplary Therapeutic Compounds for $X_3$ | |
|---|---|
| TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate)<br>NAE/UAE Inhibitor | 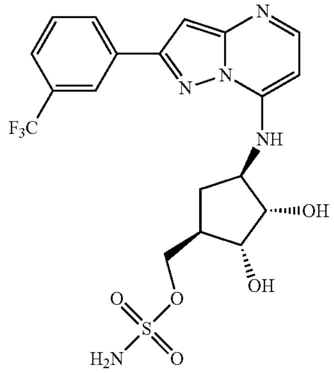 [SMILES: NS(=O)(=O)OC[C@H]1C[C@@H](Nc2ccnc3cc(-c4cccc(C(F)(F)F)c4)nn23)[C@H](O)[C@@H]1O] |
| Piperacillin<br>NAE Inhibitor | 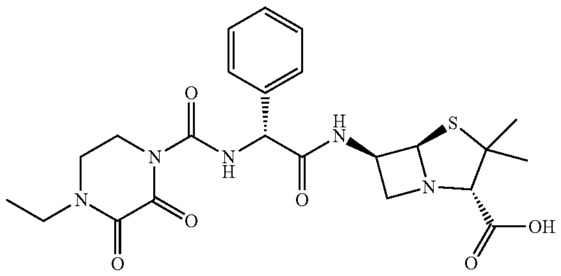 [SMILES: CCN1CCN(C(=O)N[C@@H](C(=O)N[C@@H]2CN3[C@@H]2SC(C)(C)[C@@H]3C(=O)O)c2ccccc2)C(=O)C1=O] |
| M22 (1-benzyl-N-(2,4-dichlorophenethyl)piperidin-4-amine)<br>NAE Inhibitor | 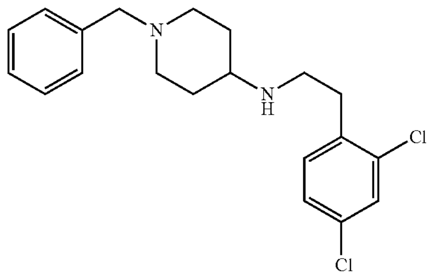 [SMILES: Clc1ccc(CCNC2CCN(Cc3ccccc3)CC2)c(Cl)c1] |
| 6,6'-Biapigenin<br>NAE Inhibitor | 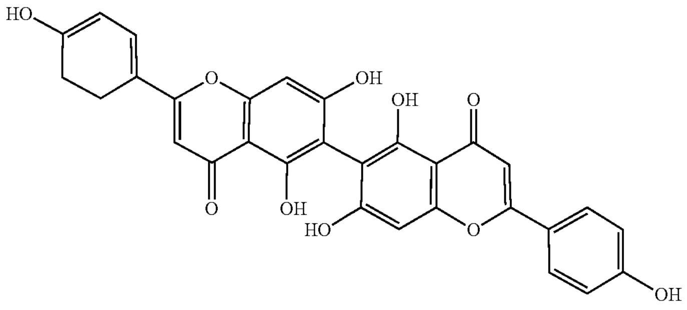 [SMILES: O=c1cc(-c2ccc(O)cc2)oc2c1CC(O)=C(CC1=C(O)c3c(oc(C4=CC=C(O)CC4)cc3=O)CC=C1O)C(CO)=C2] |
| Thieno-pyridine<br>NAE Inhibitor | 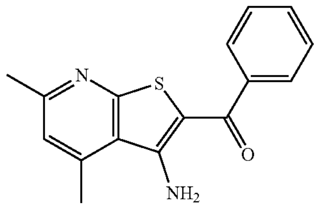 [SMILES: Cc1cc(C)c2c(N)c(C(=O)c3ccccc3)sc2n1] |

TABLE 2-continued
| Exemplary Therapeutic Compounds for $X_3$ | |
|---|---|
| Imidazo-pyrimidine NAE Inhibitor | 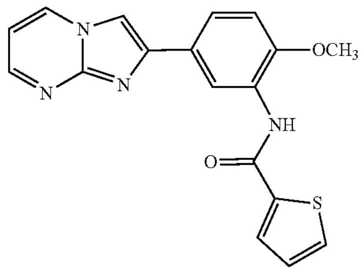 [SMILES: COc1ccc(-c2cn3cccnc3n2)cc1NC(=O)c1cccs1] |
| Largazole E1 inhibitor | 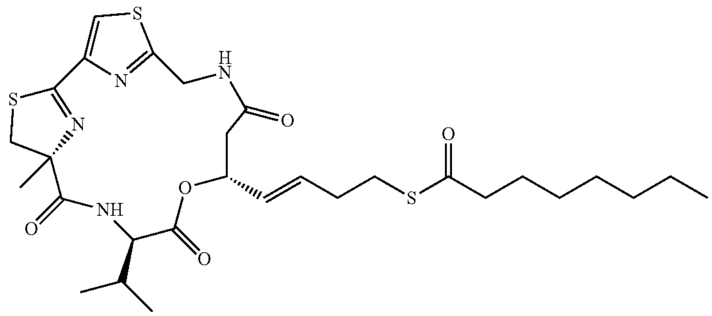 [SMILES: CCCCCCCC(=O)SCC/C=C/[C@H]1CC(=O)NCc2nc(cs2)C2=N[C@](C)(CS2)C(=O)N[C@H](C(C)C)C(=O)O1] |
| Pyr-41 (4[4-(5-nitro-furan-2-ylmethylene)-3,5-dioxo-pyrazolidin-1-yl]-benzoic acid ethyl ester) E1 inhibitor | 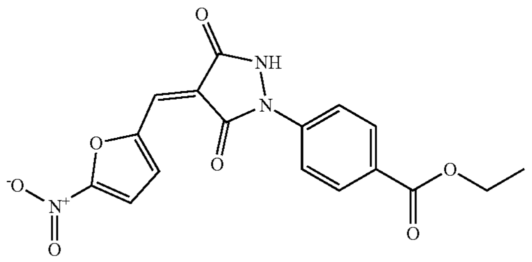 |
| Phorbol 12-myristate 13-acetate Super Oxide Pathway | 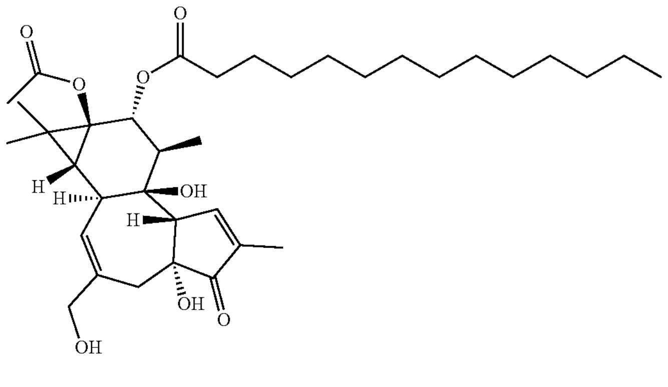 |
| 2,3-dihydropyrrolo[2,1-b] quinazolin-9(1H)-one NAE Inhibitor | 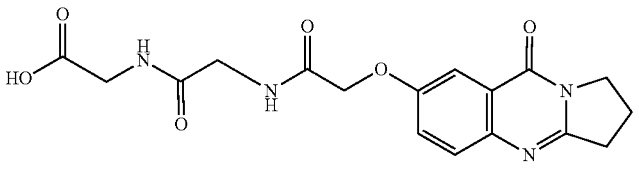 [SMILES: O=C(O)CCNC(=O)CCNC(=O)COc1ccc2nc3n(c(=O)c2c1)CCC3] |

TABLE 2-continued
Exemplary Therapeutic Compounds for $X_3$
Ofloxacin
Super Oxide Pathway
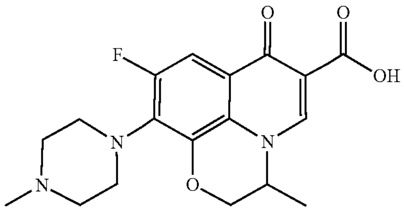
Panepophen-anthin
E1 Inhibitor
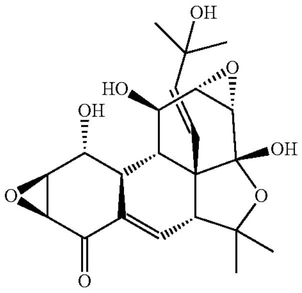 [SMILES: CC(C)(O)/C=C/[C@@]12[C@H]3[C@@H](O)[C@@H]4O[C@@H]4[C@]1(O)OC(C)(C)[C@@H]2C=C1C(=O)[C@H]2O[C@H]2[C@H](O)[C@H]13]
Himeic Acid A
E1 Inhibitor
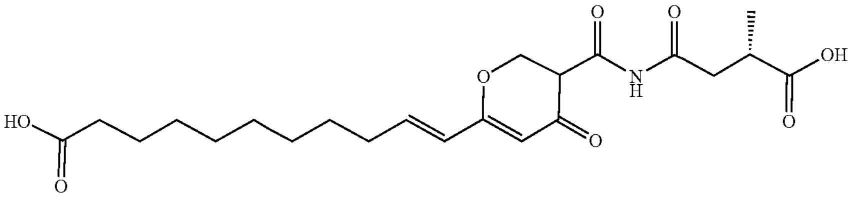 [SMILES: C[C@@H](CCC(=O)NC(=O)C1COC(/C=C/CCCCCCCCCCCCC(=O)O)=CC1=O)C(=O)CO]
Hyrtioreticulins A
E1 Inhibitor
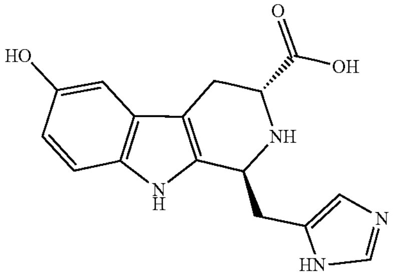 [SMILES: O=C(CO)[C@H]1CCc2c([nH]c3ccc(O)cc23)[C@H](Cc2cnc[nH]2)N1]
Phytol
Super Oxide Pathway
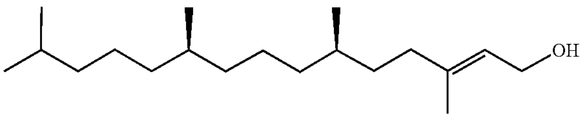 [SMILES: C/C(=C\CO)CC[C@H](C)CCC[C@H](C)CCCC(C)C]

TABLE 2-continued
| Exemplary Therapeutic Compounds for $X_3$ | |
|---|---|
| ABPA3 ([(2R,3S,4R,5R)-5-[6-(3-ethynylanilino)purin-9-yl]-3,4-dihydroxyoxolan-2-yl]methyl sulfamate)<br>NAE Inhibitor | 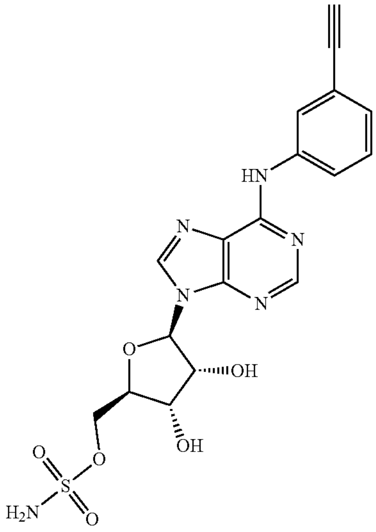 [SMILES: C#Cc1cccc(Nc2ncnc3c2ncn3[C@@H]2O[C@H](COS(N)(=O)=O)[C@@H](O)[C@H]2O)c1] |
| Benzothiazole<br>NAE Inhibitor | 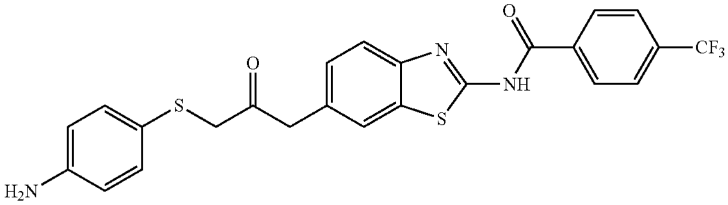 [SMILES: Nc1ccc(SCC(=O)Cc2ccc3nc(NC(=O)c4ccc(C(F)(F)F)cc4)sc3c2)cc1] |
| Deoxy-vasicinone derivative<br>NAE Inhibitor | 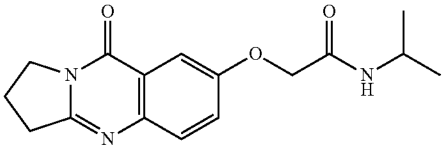 [SMILES: CC(C)NC(=O)COc1ccc2nc3n(c(=O)c2c1)CCC3] |
| Coumarin A<br>NAE Inhibitor | 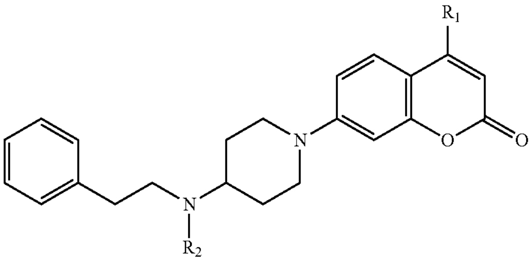 |
| Coumarin B<br>NAE Inhibitor | 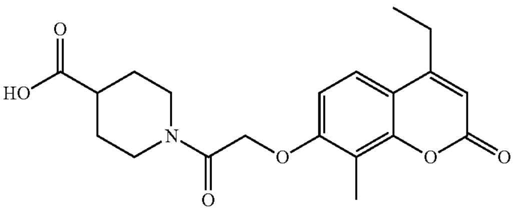 [SMILES: CCc1cc(=O)oc2c(C)c(OCC(=O)N3CCC(C(=O)O)CC3)ccc12] |

TABLE 2-continued

| Exemplary Therapeutic Compounds for $X_3$ | |
|---|---|
| Deoxy-vasicinone derivative<br>NAE Inhibitor | 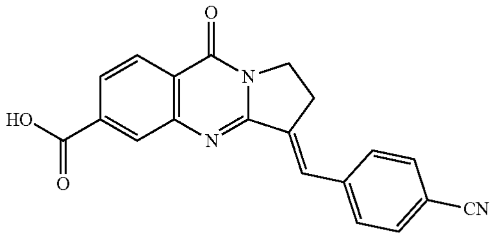 [SMILES: N#Cc1ccc(/C=C2\CCn3c2nc2cc(C(=O)O)ccc2c3=O)cc1] |
| Imidazolium-quinoxaline<br>NAE Inhibitor | 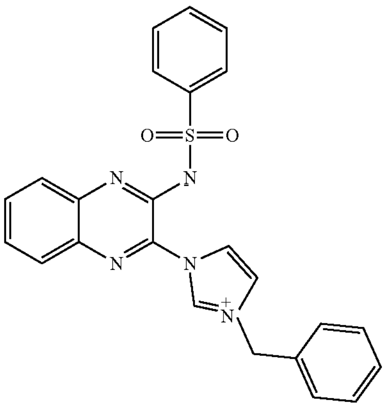 |
| TAS4464 (7H-Pyrrolo[2,3-d]pyrimidin-4-amine, 7-[5-[(aminosulfonyl)amino]-5-deoxy-beta-D-ribofuranosyl]-5-[2-(2-ethoxy-6-fluorophenyl)ethynyl]-)<br>NAE Inhibitor | 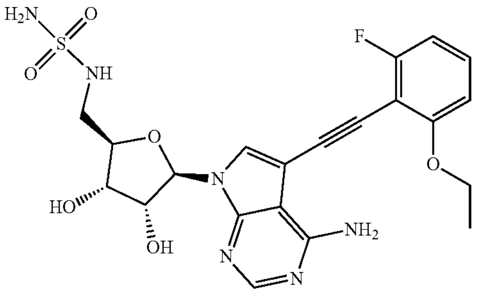 [SMILES: CCOc1cccc(F)c1C#Cc1cn([C@@H]2O[C@H](CNS(N)(=O)=O)[C@@H](O)[C@H]2O)c2ncnc(N)c12] |

Compounds Useful in the Treatment of Cancer

| Compound Name and Activity | Structure |
|---|---|
| Monomethyl Auristatin E<br>Antimitotic | 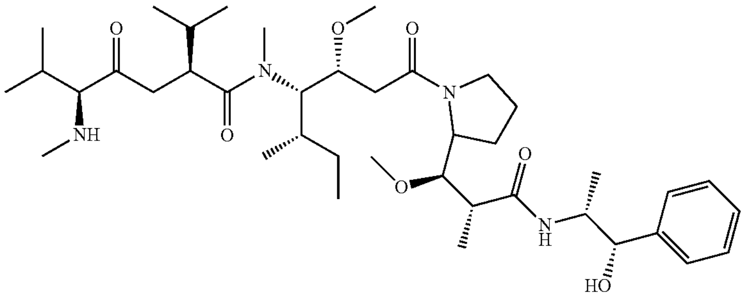 [SMILES: CC[C@H](C)[C@@H]([C@@H](CC(=O)N1CCCC1[C@H](OC)[C@@H](C)C(=O)N[C@H](C)[C@@H](O)c1ccccc1)OC)N(C)C(=O)[C@@H](CC(=O)[C@@H](NC)C(C)C)C(C)C] |

TABLE 2-continued
| Exemplary Therapeutic Compounds for $X_3$ | |
|---|---|
| Docetaxel<br>Antimitotic | 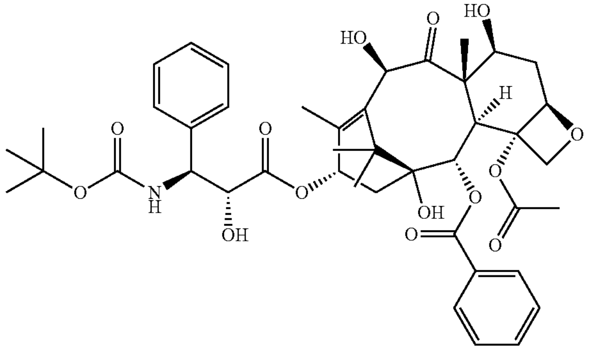 |
| Etoposide<br>Genotoxic agent | 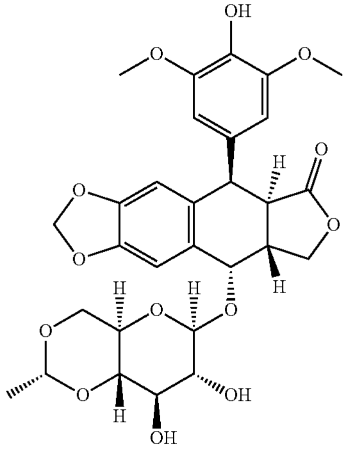 |
| Gemcitabine<br>Antimetabolite | 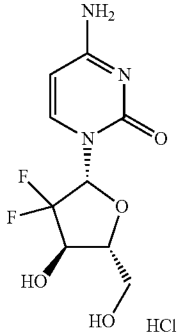 [SMILES: Nc1ccn([C@@H]2O[C@H](CO)[C@@H](O)C2(F)F)c(=O)n1 ; Cl] |
| Vinblastine<br>Microtubule Assembly Inhibitor | 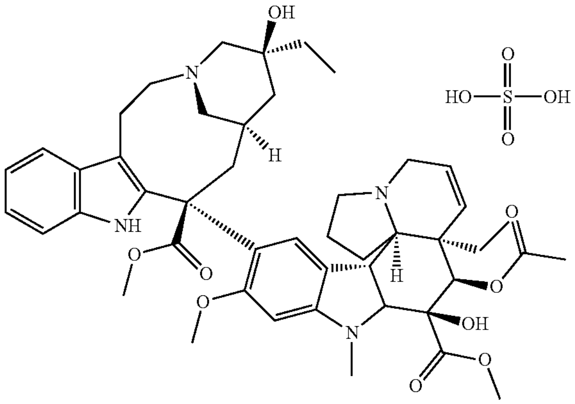 |

TABLE 2-continued
| Exemplary Therapeutic Compounds for $X_3$ | |
|---|---|
| Paclitaxel<br>Antimitotic | 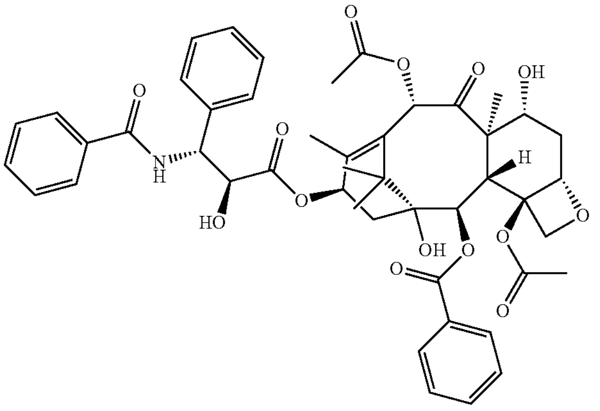 |
| Irinotecan<br>Topoisomerase | 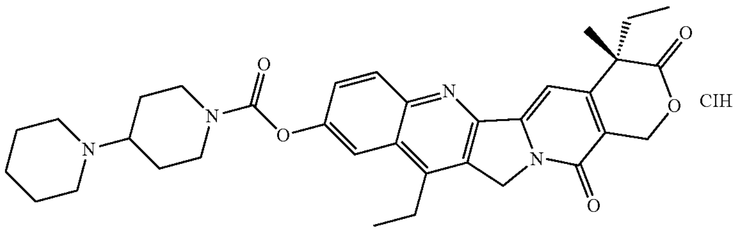 |
| Fluorouracil<br>Antimetabolite | 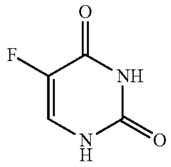 |
| Methotrexate<br>Antimetabolite | 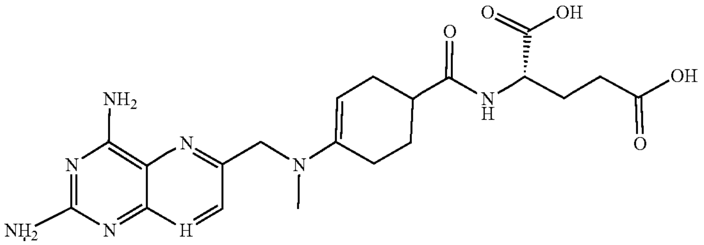 |
| Carboplatin<br>Antineoplastic | 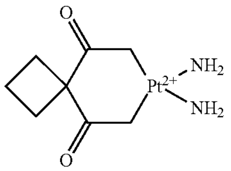 |
| Oxaliplatin<br>Antineoplastic | 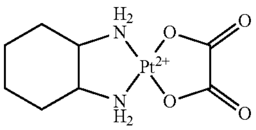 |
| Cisplatin<br>Antineoplastic | 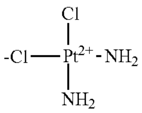 |

TABLE 2-continued
| Exemplary Therapeutic Compounds for $X_3$ | |
|---|---|
| Doxorubicin HCl<br>Anthracycline/Topoisomerase | 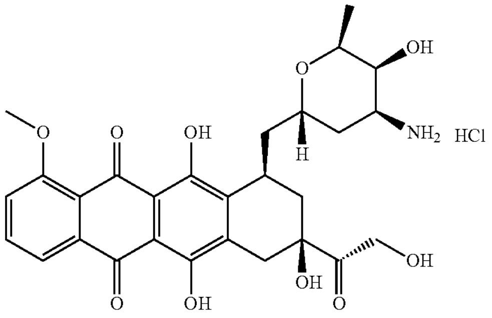 |
| Fulvestrant<br>Aromatase Inhibitor | 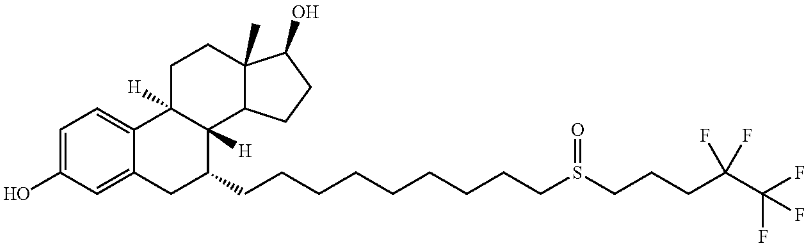 [SMILES: C[C@]12CC[C@@H]3c4ccc(O)cc4C[C@@H](CCCCCCCCCS(=O)CCCC(F)(F)C(F)(F)F)[C@H]3C1CC[C@@H]2O] |
| Isotretinoin<br>Retinoids | 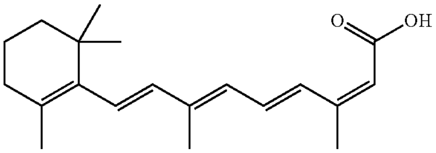 [SMILES: CC1=C(/C=C/C(C)=C/C=C/C(C)=C\C(=O)O)C(C)(C)CCC1] |
| Buserelin<br>Aromatase Inhibitor | 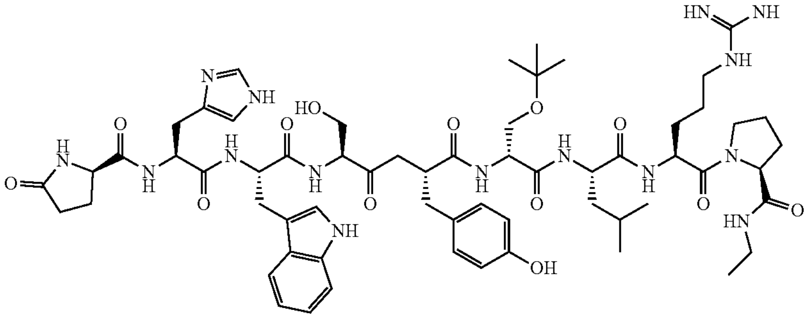 [SMILES: CCNC(=O)[C@@H]1CCCN1C(=O)[C@H](CCCNC(=N)N)NC(=O)[C@H](CC(C)C)NC(=O)[C@@H](COC(C)(C)C)NC(=O)[C@@H](CC(=O)[C@H](CO)NC(=O)[C@H](Cc1c[nH]c2ccccc12)NC(=O)[C@H](Cc1c[nH]cn1)NC(=O)[C@H]1CCC(=O)N1)Cc1ccc(O)cc1] |
| Everolimus<br>mTor Inhibitor | 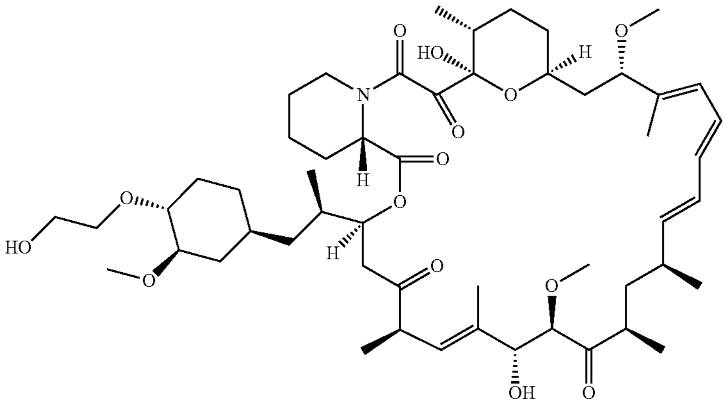 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C] |

TABLE 2-continued
| Exemplary Therapeutic Compounds for $X_3$ | |
|---|---|
| Carfilzomib Protease Inhibitor | 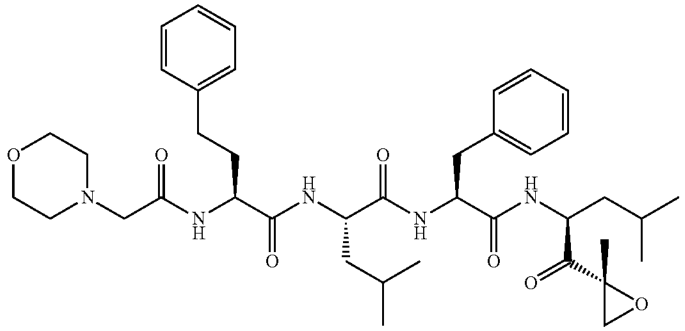 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1] |
| Rifabutin Antibiotic | 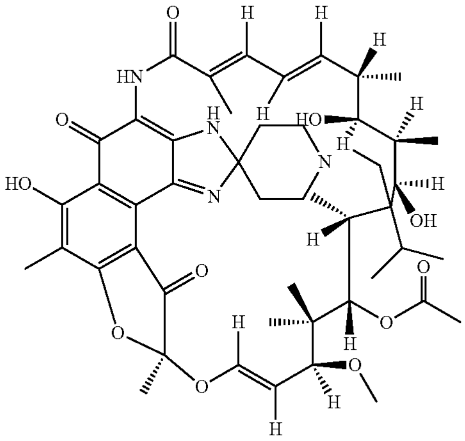 |
| Clindamycin Antibiotic | 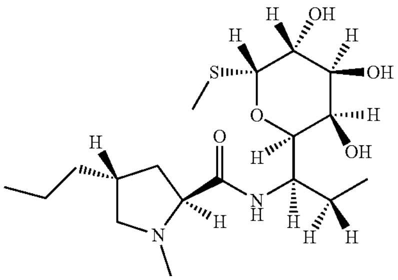 |
| Tubulysin A Antibiotic | 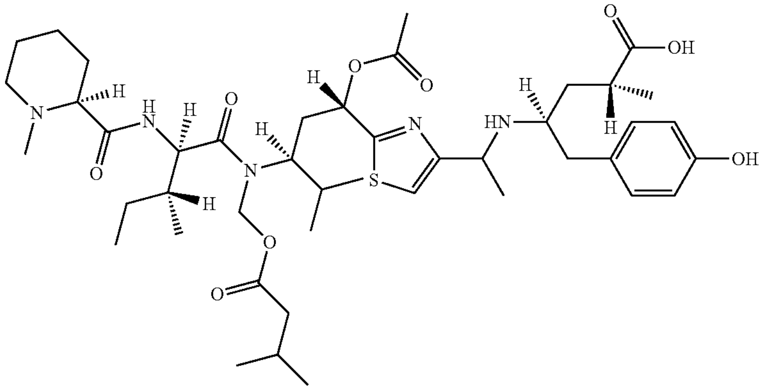 [SMILES: CC[C@@H](C)[C@@H](NC(=O)[C@@H]1CCCCN1C)C(=O)N(COC(=O)CC(C)C)[C@@H](C[C@H](OC(C)=O)c1nc(C(C)N[C@H](Cc2ccc(O)cc2)C[C@@H](C)C(=O)O)cs1)C(C)C] |

TABLE 2-continued

| Exemplary Therapeutic Compounds for $X_3$ | |
|---|---|
| Indibulin<br>Microtubule Destabilizer | 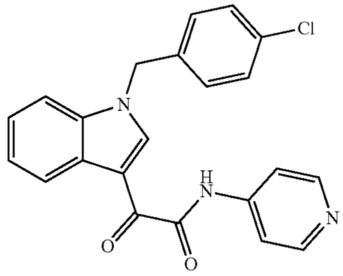 [SMILES: O=C(Nc1ccncc1)C(=O)c1cn(Cc2ccc(Cl)cc2)c2ccccc12] |
| Gefitinib<br>Tyr Kinase Inhibitor | 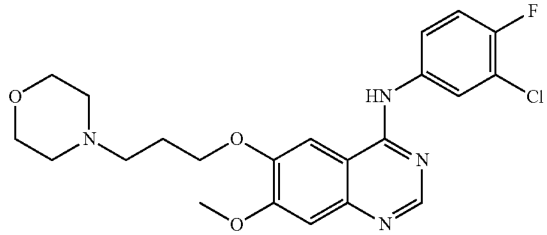 [SMILES: COc1cc2ncnc(Nc3ccc(F)c(Cl)c3)c2cc1OCCCN1CCOCC1] |
| Dasatinib<br>Chemothera-peutic | 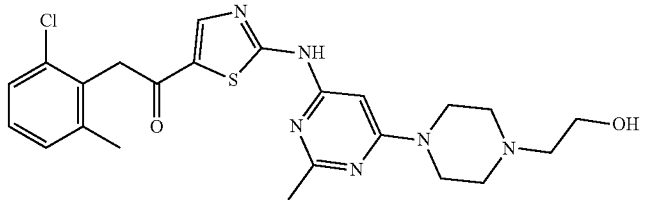 [SMILES: Cc1nc(Nc2ncc(C(=O)Cc3c(C)cccc3Cl)s2)cc(N2CCN(CCO)CC2)n1] |

In some embodiments, the compound of Formula (I) is a compound listed in Table 3, or a pharmaceutically acceptable salt, solvate, hydrate, isomer, or tautomer thereof. In Table 3, R=H, alkyl, aryl, arylalkyl, glycol ether, or an additional glycol linker attaching to the therapeutic compound; and p is 1, 2, 3, 4, 5, or 6.

TABLE 3

| Exemplary Compounds of Formula (I) | |
|---|---|
| Compound Information | Structure |
| A-1<br>Pevonedistat<br>Conjugation<br>Cleavable<br>linker | 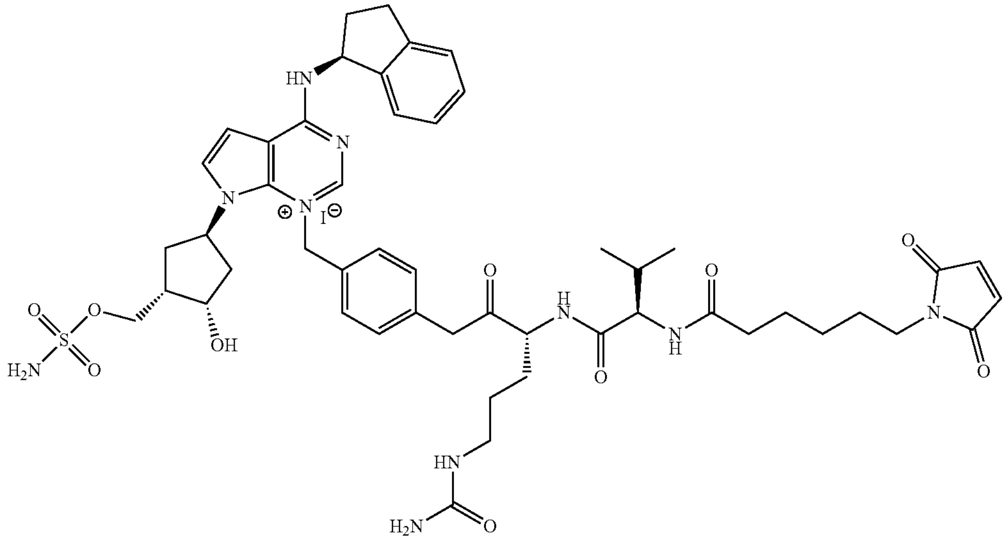 [SMILES: CC(C)[C@@H](NC(=O)CCCCCN1C(=O)C=CC1=O)C(=O)N[C@H](CCCNC(N)=O)C(=O)Cc1ccc(C[n+]2cnc(N[C@H]3CCc4ccccc43)c3ccn([C@@H]4C[C@@H](COS(N)(=O)=O)[C@@H](O)C4)c32)cc1 ; [I-]] |

TABLE 3-continued
| Exemplary Compounds of Formula (I) | |
|---|---|
| Compound Information | Structure |
| A-2 Pevonedistat Conjugation Cleavable linker | 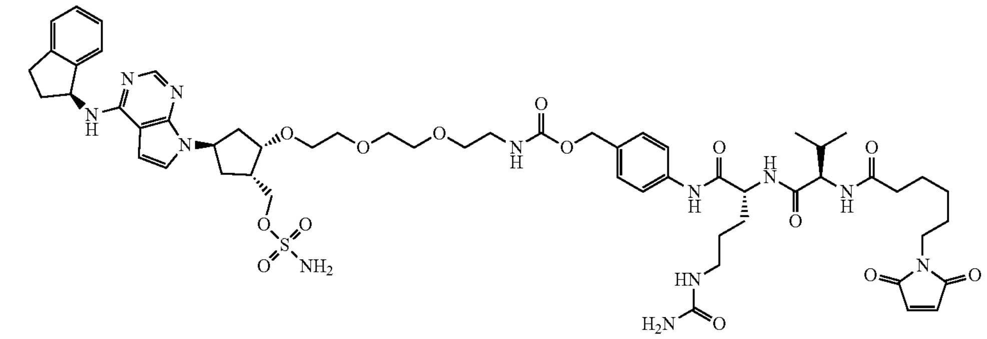 [SMILES: CC(C)[C@@H](NC(=O)CCCCCN1C(=O)C=CC1=O)C(=O)N[C@H](CCCNC(N)=O)C(=O)Nc1ccc(COC(=O)NCCOCCOCCO[C@H]2C[C@H](n3ccc4c(N[C@H]5CCc6ccccc65)ncnc43)C[C@H]2COS(N)(=O)=O)cc1] |
| A-3 Pevonedistat Conjugation Cleavable linker | 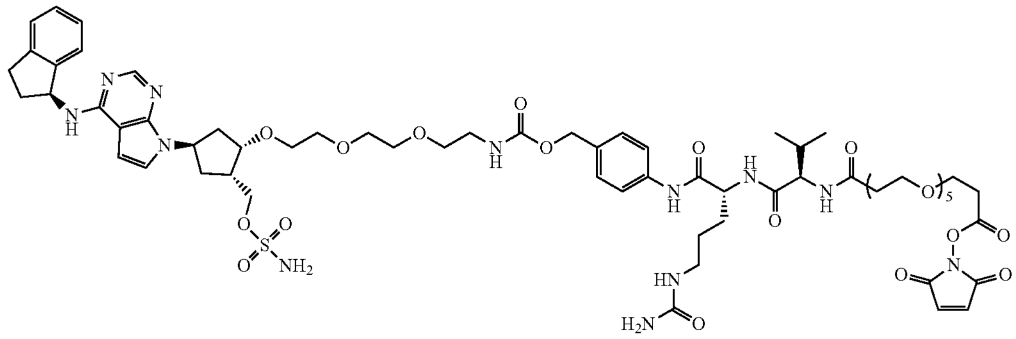 |
| A-4 Pevonedistat Conjugation Cleavable linker | 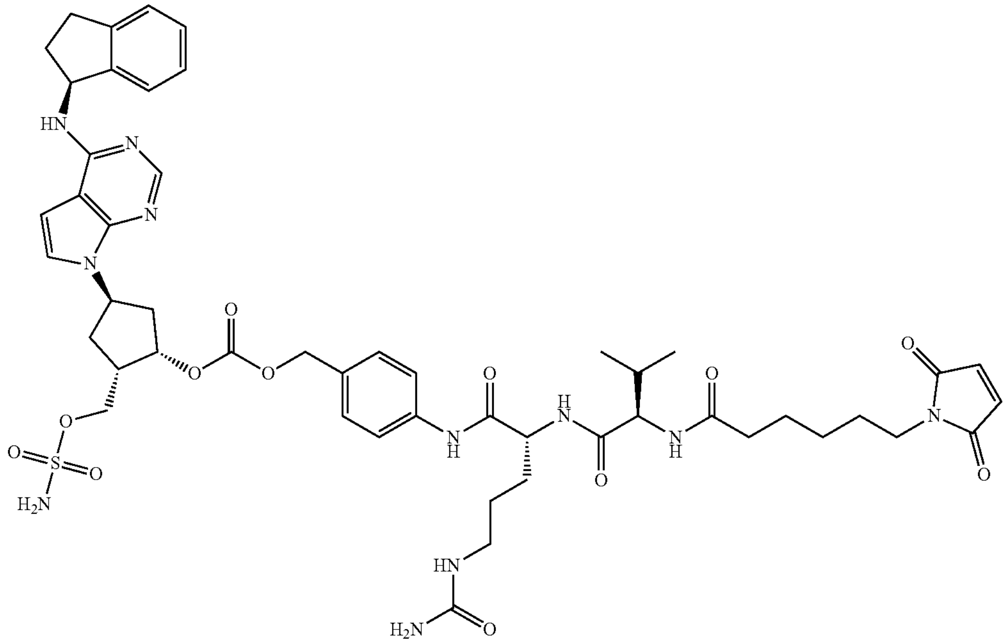 [SMILES: CC(C)[C@@H](NC(=O)CCCCCN1C(=O)C=CC1=O)C(=O)N[C@H](CCCNC(N)=O)C(=O)Nc1ccc(COC(=O)O[C@H]2C[C@H](n3ccc4c(N[C@H]5CCc6ccccc65)ncnc43)C[C@H]2COS(N)(=O)=O)cc1] |

TABLE 3-continued
| Exemplary Compounds of Formula (I) | |
|---|---|
| Compound Information | Structure |
| A-5 Pevonedistat Conjugation Cleavable linker | 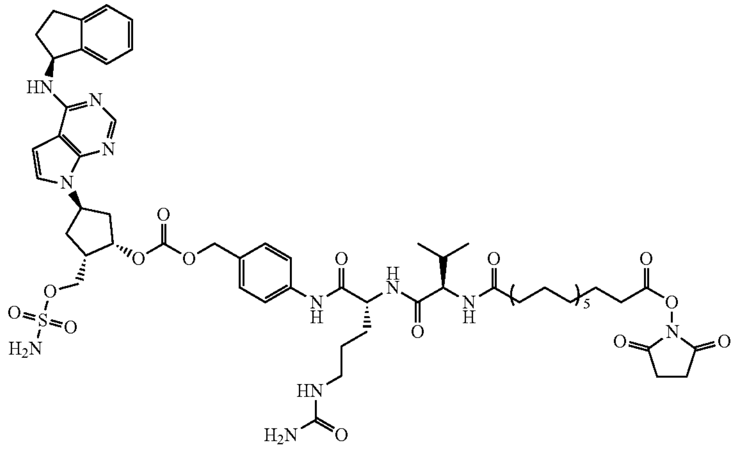 |
| A-6 Pevonedistat Conjugation Cleavable linker | 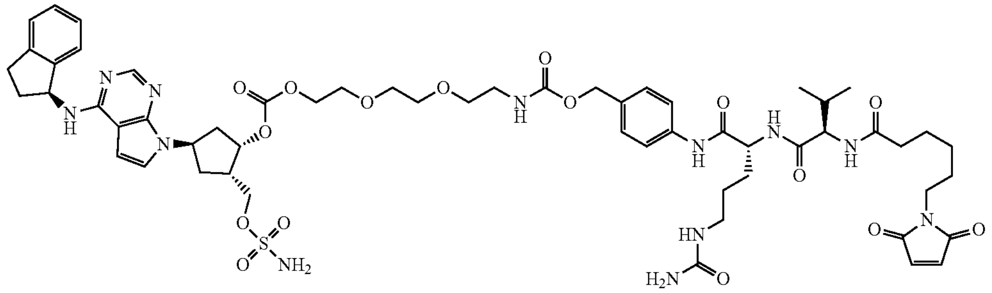 [SMILES: CC(C)[C@@H](NC(=O)CCCCCN1C(=O)C=CC1=O)C(=O)N[C@H](CCCNC(N)=O)C(=O)Nc1ccc(COC(=O)NCCOCCOCCOC(=O)O[C@H]2C[C@H](n3ccc4c(N[C@H]5CCc6ccccc65)ncnc43)C[C@H]2COS(N)(=O)=O)cc1] |
| A-7 Pevonedistat Conjugation Cleavable linker | 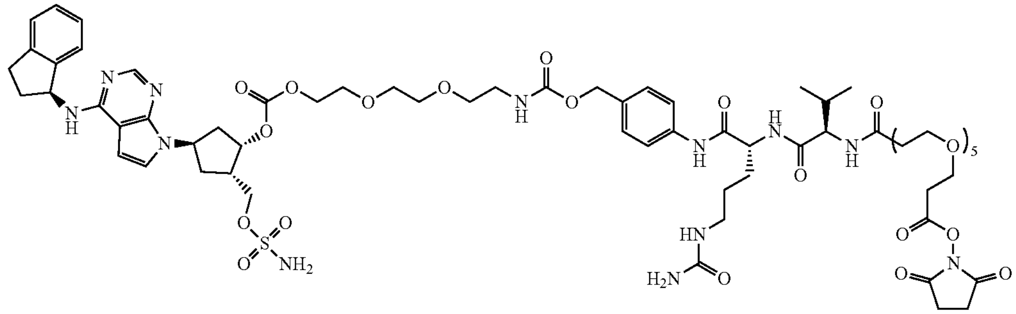 |
| A-8 Pevonedistat Conjugation Cleavable linker | 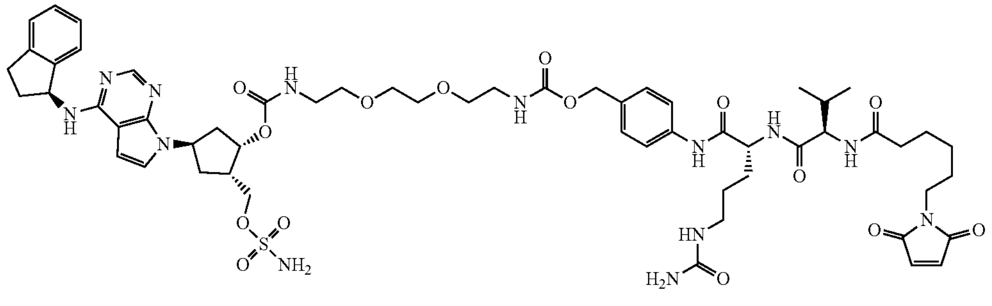 [SMILES: CC(C)[C@@H](NC(=O)CCCCCN1C(=O)C=CC1=O)C(=O)N[C@H](CCCNC(N)=O)C(=O)Nc1ccc(COC(=O)NCCOCCOCCNC(=O)O[C@H]2C[C@H](n3ccc4c(N[C@H]5CCc6ccccc65)ncnc43)C[C@H]2COS(N)(=O)=O)cc1] |

TABLE 3-continued
| Exemplary Compounds of Formula (I) | |
|---|---|
| Compound Information | Structure |
| A-9 Pevonedistat Conjugation Cleavable linker | 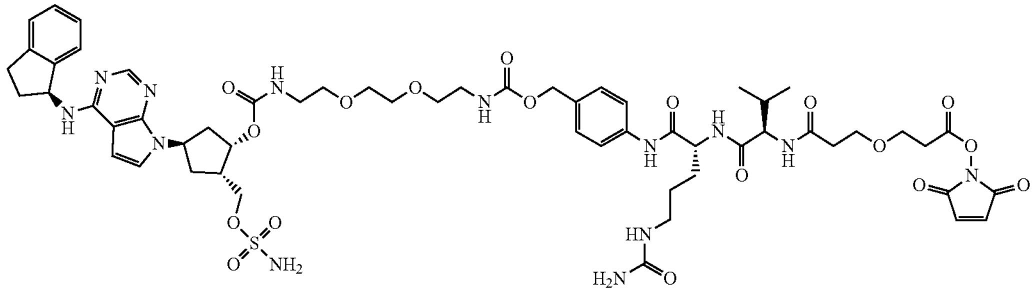 [SMILES: CC(C)[C@@H](NC(=O)CCOCCC(=O)ON1C(=O)C=CC1=O)C(=O)N[C@H](CCCNC(N)=O)C(=O)Nc1ccc(COC(=O)NCCOCCOCCNC(=O)O[C@H]2C[C@H](n3ccc4c(N[C@H]5CCc6ccccc65)ncnc43)C[C@H]2COS(N)(=O)=O)cc1] |
| A-10 Pevonedistat Conjugation Cleavable linker | 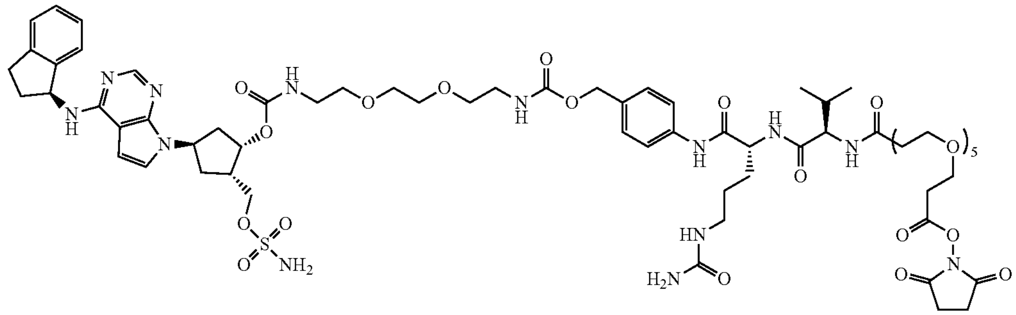 |
| A-11 Pevonedistat Conjugation Cleavable linker | 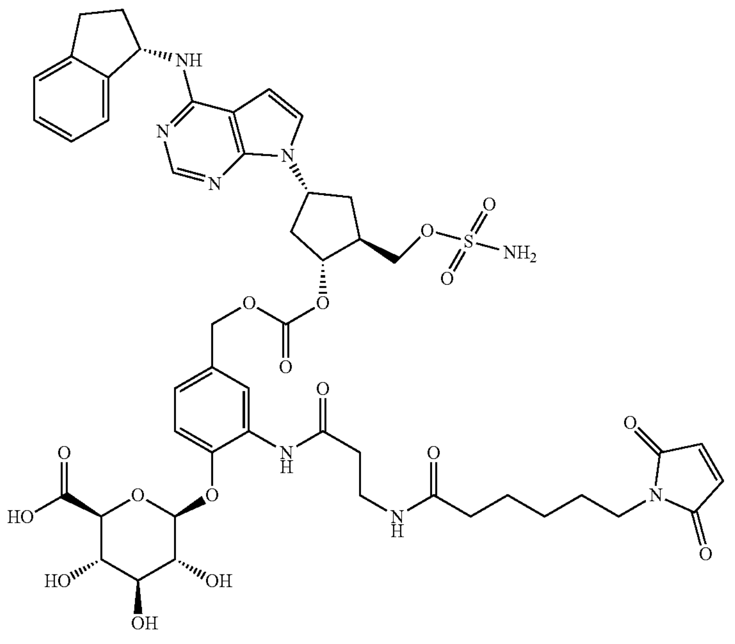 [SMILES: NS(=O)(=O)OC[C@@H]1C[C@@H](n2ccc3c(N[C@H]4CCc5ccccc54)ncnc32)C[C@H]1OC(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1] |

TABLE 3-continued
| Exemplary Compounds of Formula (I) | |
|---|---|
| Compound Information | Structure |
| A-12 Pevonedistat Conjugation Cleavable linker | 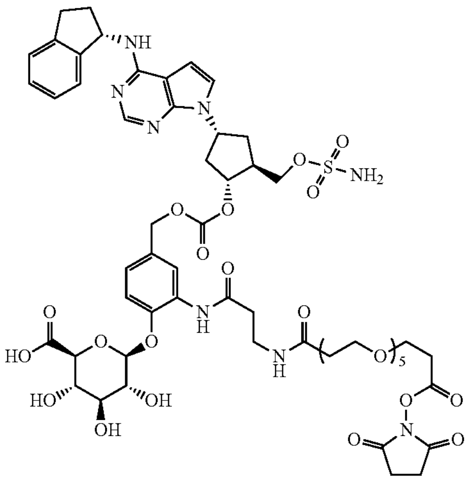 |
| A-13 Pevonedistat Conjugation Cleavable linker | 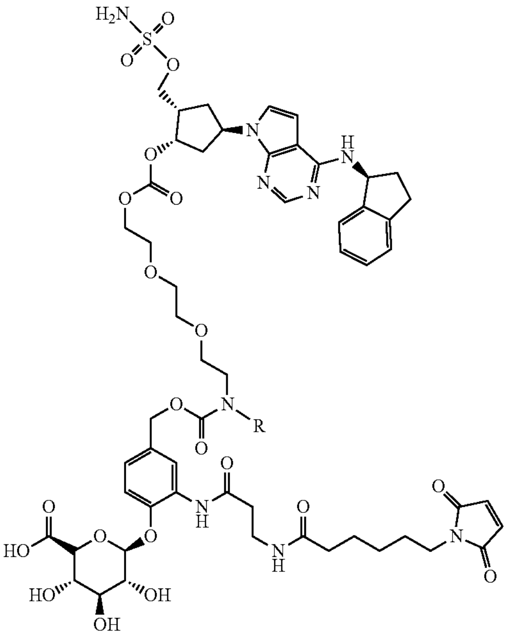 |

TABLE 3-continued
| Exemplary Compounds of Formula (I) | |
|---|---|
| Compound Information | Structure |
| A-14 Pevonedistat Conjugation Cleavable linker | 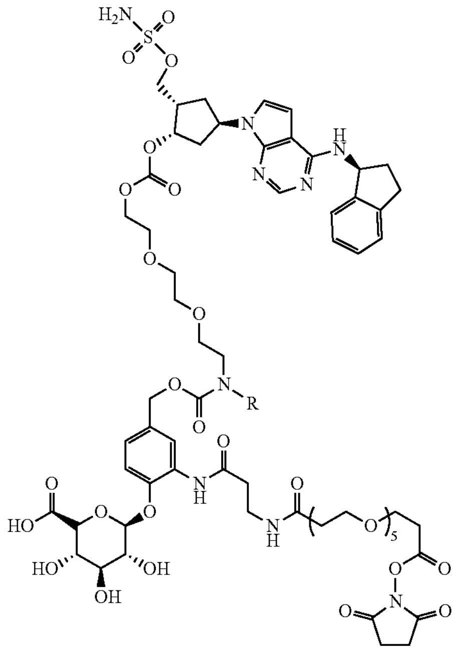 |
| A-15 Pevonedistat Conjugation Cleavable linker | 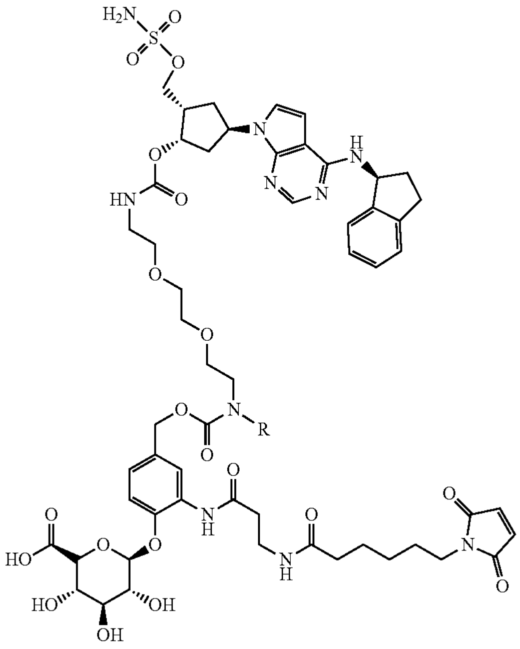 |

TABLE 3-continued
| Exemplary Compounds of Formula (I) | |
|---|---|
| Compound Information | Structure |
| A-16 Pevonedistat Conjugation Cleavable linker | 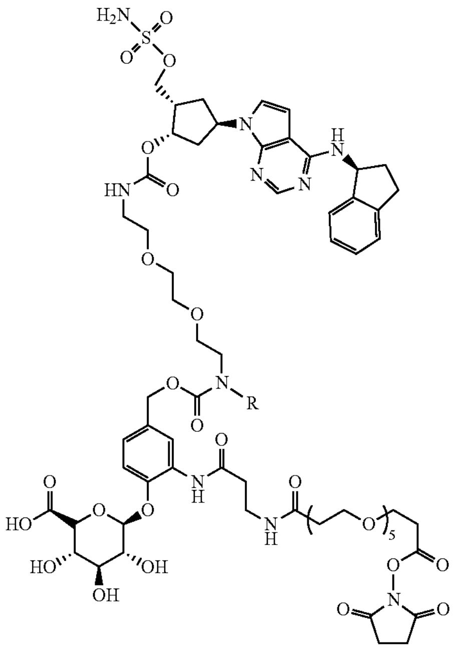 |
| A-17 Pevonedistat Conjugation Non-cleavable linker | 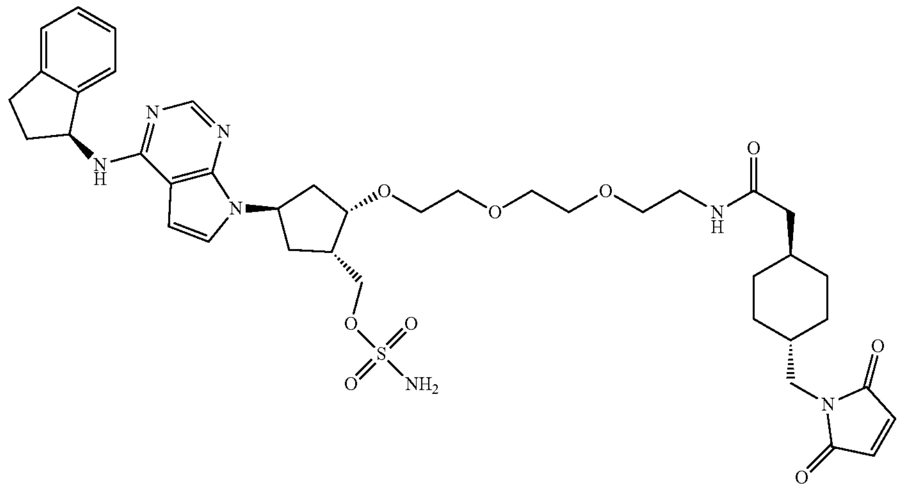 [SMILES: NS(=O)(=O)OC[C@@H]1C[C@@H](n2ccc3c(N[C@H]4CCc5ccccc54)ncnc32)C[C@@H]1OCCOCCOCCNC(=O)C[C@H]1CC[C@H](CN2C(=O)C=CC2=O)CC1] |
| A-18 Pevonedistat Conjugation Non-cleavable linker | 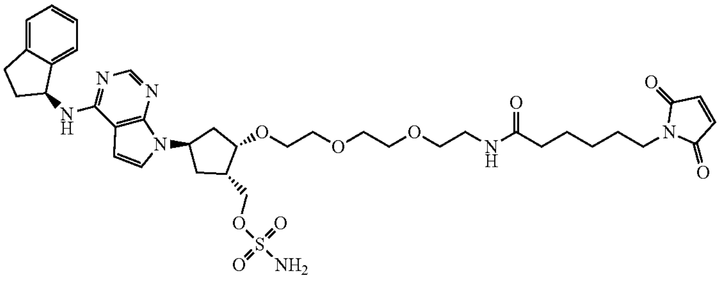 [SMILES: NS(=O)(=O)OC[C@@H]1C[C@@H](n2ccc3c(N[C@H]4CCc5ccccc54)ncnc32)C[C@@H]1OCCOCCOCCNC(=O)CCCCCN1C(=O)C=CC1=O] |

TABLE 3-continued
| Exemplary Compounds of Formula (I) | |
|---|---|
| Compound Information | Structure |
| A-19 Piperacillin Conjugation Cleavable linker | 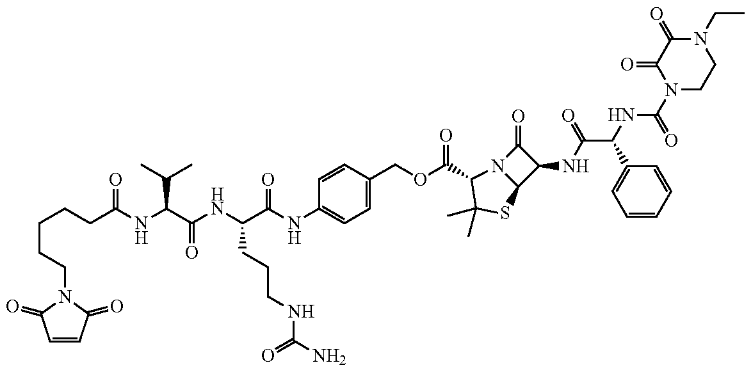 [SMILES: CCN1CCN(C(=O)N[C@@H](C(=O)N[C@@H]2C(=O)N3[C@@H]2SC(C)(C)[C@@H]3C(=O)OCc2ccc(NC(=O)[C@H](CCCNC(N)=O)NC(=O)[C@@H](NC(=O)CCCCCN3C(=O)C=CC3=O)C(C)C)cc2)c2ccccc2)C(=O)C1=O] |
| A-20 M22 (1-benzyl-N-(2,4-dichloro-phenethyl) piperidin-4-amine) Conjugation Cleavable linker | 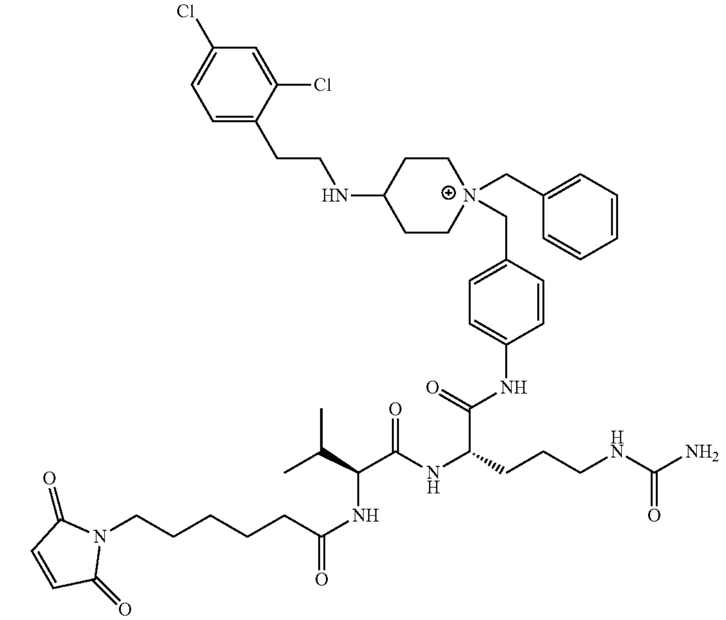 [SMILES: CC(C)[C@H](NC(=O)CCCCCN1C(=O)C=CC1=O)C(=O)N[C@@H](CCCNC(N)=O)C(=O)Nc1ccc(C[N+]2(Cc3ccccc3)CCC(NCCc3ccc(Cl)cc3Cl)CC2)cc1] |
| A-21 6,6'-Biapigenin Conjugation Cleavable linker | 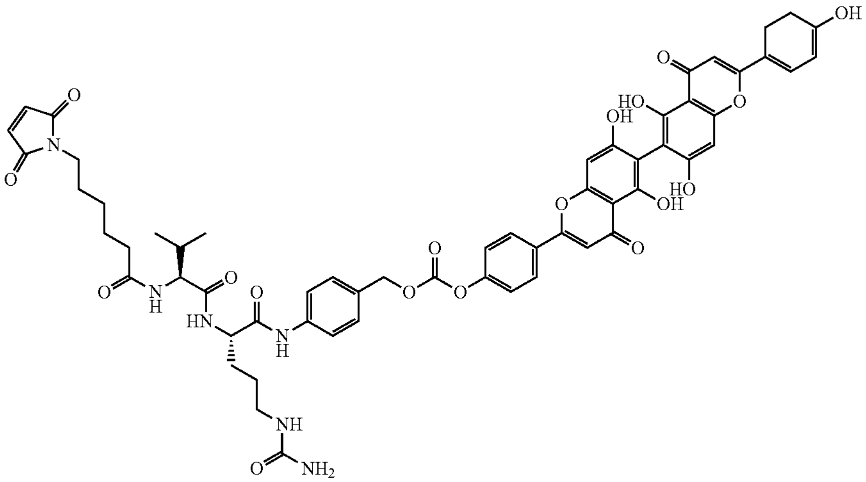 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc(-c3cc(=O)c4c(O)c(-c5c(O)cc6oc(C7=CC=C(O)CC7)cc(=O)c6c5O)c(O)cc4o3)cc2)cc1] |

TABLE 3-continued
| Exemplary Compounds of Formula (I) | |
|---|---|
| Compound Information | Structure |
| A-22 Thieno-pyridine Conjugation Cleavable linker | 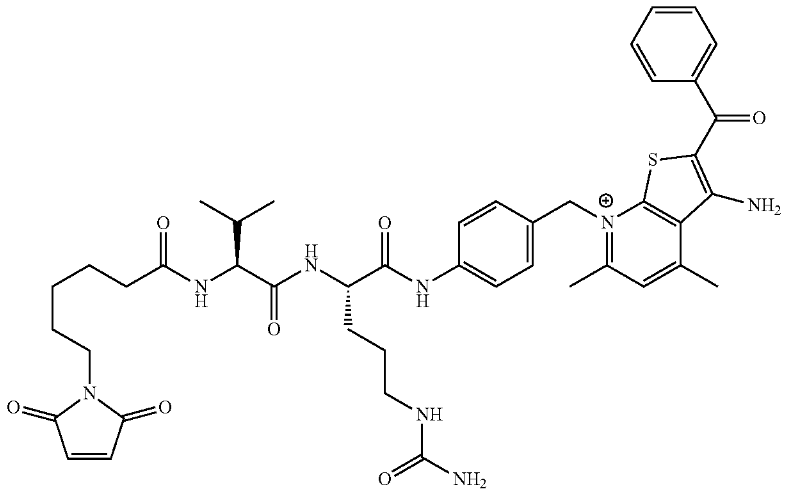 [SMILES: Cc1cc(C)[n+](Cc2ccc(NC(=O)[C@H](CCCNC(N)=O)NC(=O)[C@@H](NC(=O)CCCCCN3C(=O)C=CC3=O)C(C)C)cc2)c2sc(C(=O)c3ccccc3)c(N)c12] |
| A-23 Imidazo-pyrimidine Conjugation Cleavable linker | 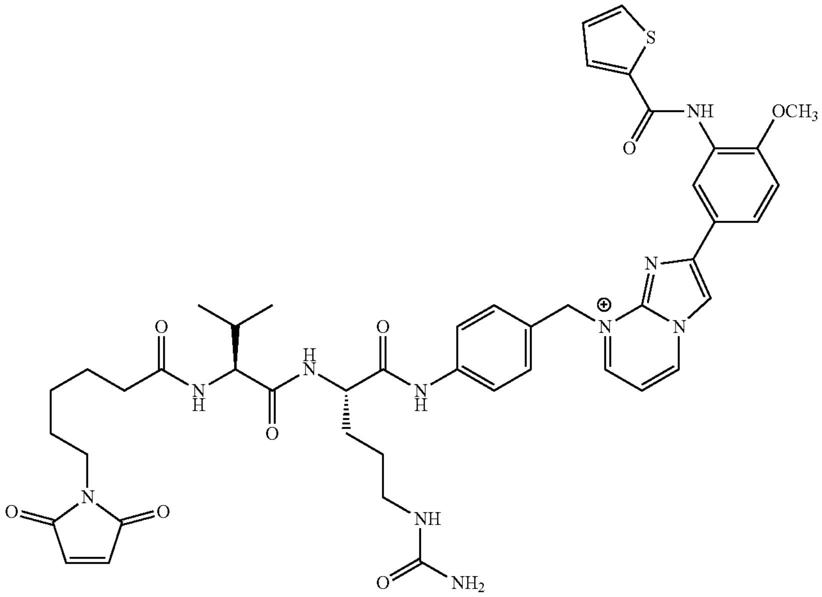 [SMILES: COc1ccc(-c2cn3ccc[n+](Cc4ccc(NC(=O)[C@H](CCCNC(N)=O)NC(=O)[C@@H](NC(=O)CCCCCN5C(=O)C=CC5=O)C(C)C)cc4)c3n2)cc1NC(=O)c1cccs1] |
| A-24 Largazole Conjugation Cleavable linker | 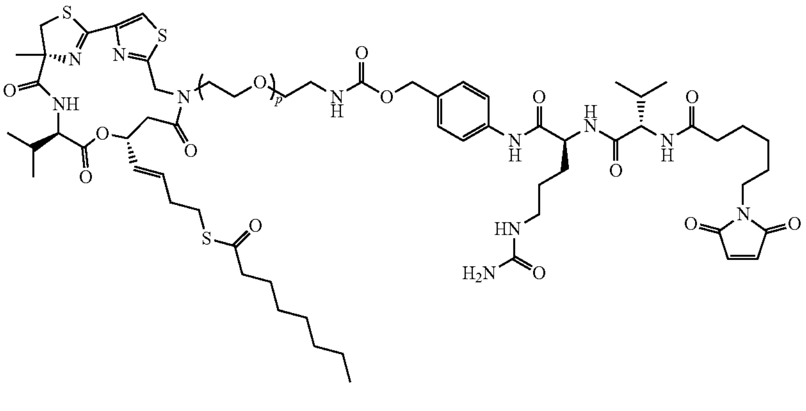 |

TABLE 3-continued
Exemplary Compounds of Formula (I)
| Compound Information | Structure |
|---|---|
| A-25 PYR-41 (4[4-(5-nitro-furan-2-ylmethylene)-3,5-dioxo-pyrazolidin-1-yl]-benzoic acid ethyl ester) Conjugation Cleavable linker | 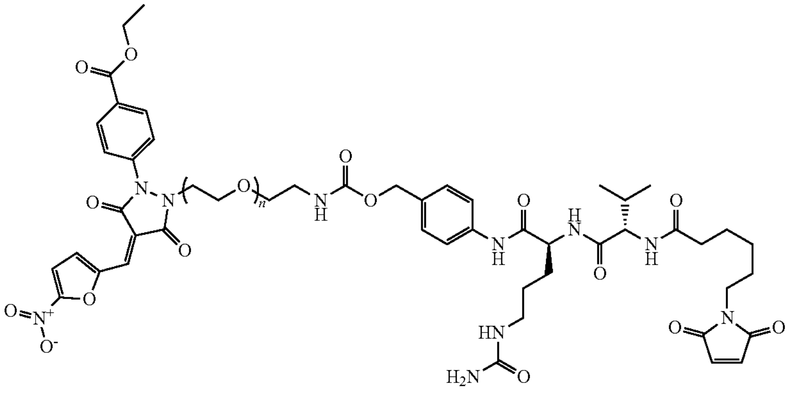 |
| A-26 Phorbol 12-myristate 13-acetate Conjugation Cleavable linker | 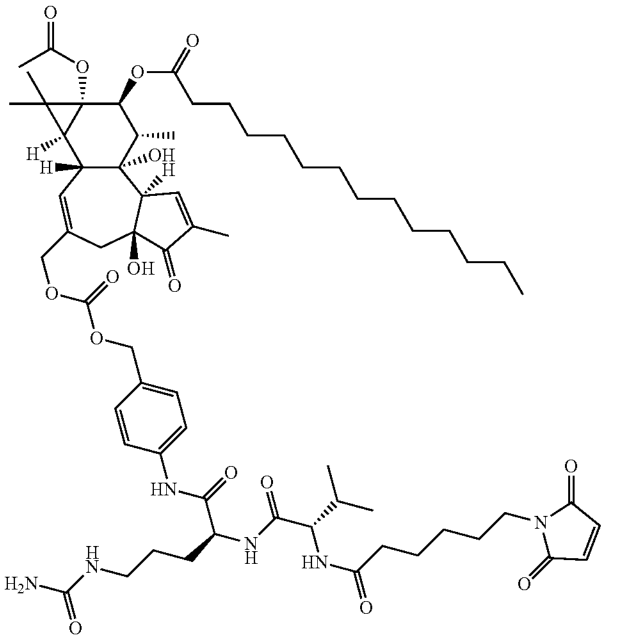 [SMILES: CCCCCCCCCCCCCC(=O)O[C@H]1[C@H](C)[C@]2(O)[C@H](C=C(COC(=O)OCc3ccc(NC(=O)[C@H](CCCNC(N)=O)NC(=O)[C@@H](NC(=O)CCCCCN4C(=O)C=CC4=O)C(C)C)cc3)C[C@@]3(O)C(=O)C(C)=C[C@H]23)[C@H]2C(C)(C)[C@@]12OC(C)=O] |
| A-27 Ofloxacin Conjugation Cleavable linker | 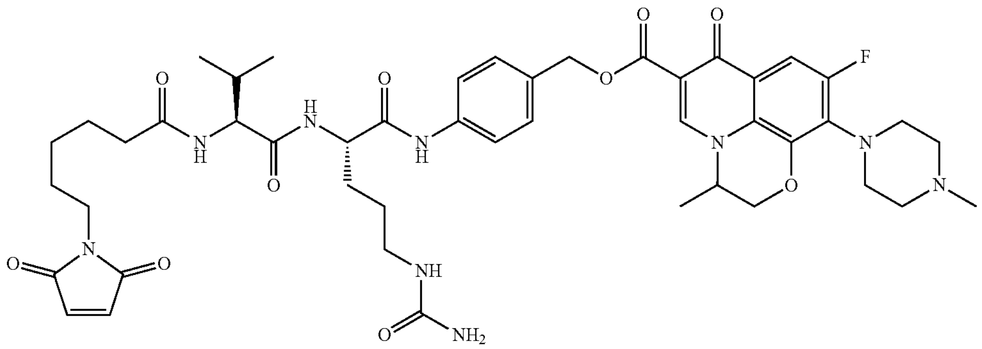 [SMILES: CC(C)[C@H](NC(=O)CCCCCN1C(=O)C=CC1=O)C(=O)N[C@@H](CCCNC(N)=O)C(=O)Nc1ccc(COC(=O)c2cn3c4c(c(N5CCN(C)CC5)c(F)cc4c2=O)OCC3C)cc1] |

TABLE 3-continued
| Exemplary Compounds of Formula (I) | |
|---|---|
| Compound Information | Structure |
| A-28 Ofloxacin Conjugation Cleavable linker | 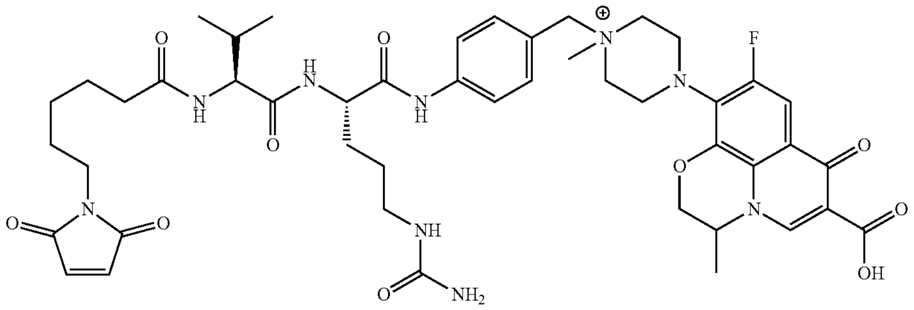 [SMILES: CC(C)[C@H](NC(=O)CCCCCN1C(=O)C=CC1=O)C(=O)N[C@@H](CCCNC(N)=O)C(=O)Nc1ccc(C[N+]2(C)CCN(c3c(F)cc4c(=O)c(C(=O)O)cn5c4c3OCC5C)CC2)cc1] |
| A-29 Pyrrolo[2,1-b]quinazolin-9(1H)-one Conjugation Cleavable linker | 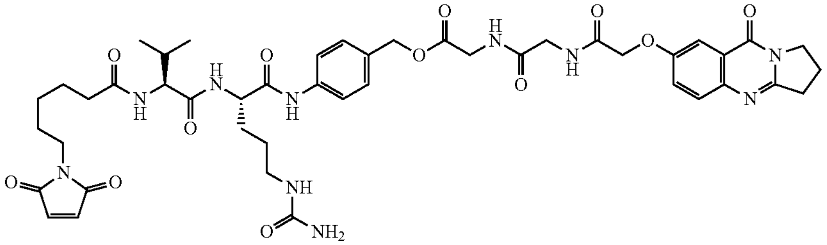 [SMILES: CC(C)[C@H](NC(=O)CCCCCN1C(=O)C=CC1=O)C(=O)N[C@@H](CCCNC(N)=O)C(=O)Nc1ccc(COC(=O)CNC(=O)CNC(=O)COc2ccc3nc4n(c(=O)c3c2)CCC4)cc1] |
| A-30 Drug Conjugate of TAS NAE Inhibitor Cleavable linker | 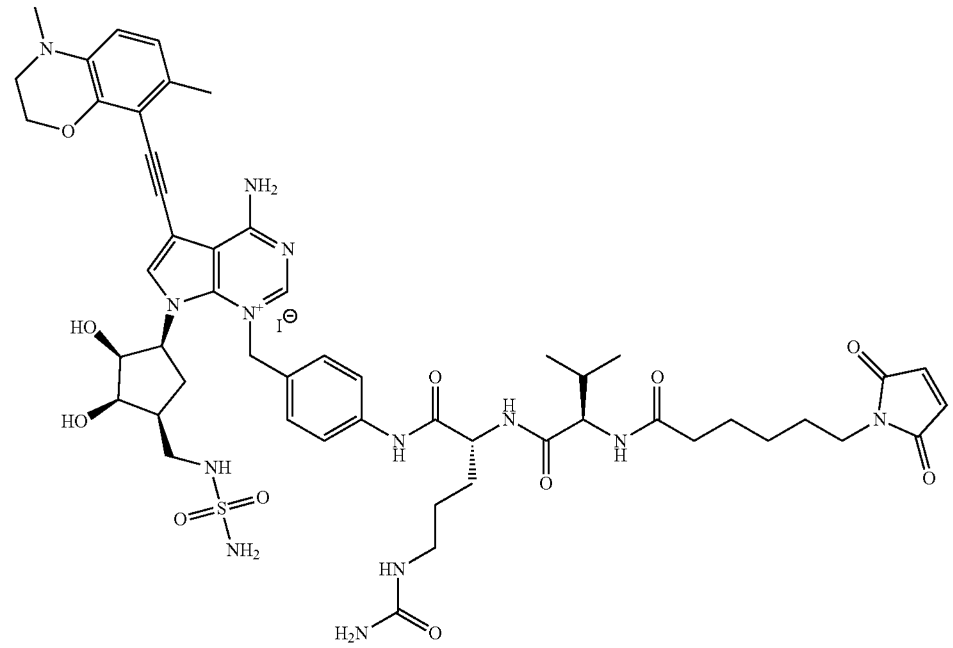 [SMILES: Cc1ccc2c(c1C#Cc1cn([C@H]3C[C@@H](CNS(N)(=O)=O)[C@@H](O)[C@H]3O)c3c1c(N)nc[n+]3Cc1ccc(NC(=O)[C@@H](CCCNC(N)=O)NC(=O)[C@H](NC(=O)CCCCCN3C(=O)C=CC3=O)C(C)C)cc1)OCCN2C ; [I-]] |

TABLE 3-continued
| Exemplary Compounds of Formula (I) | |
|---|---|
| Compound Information | Structure |
| A-31 Drug Conjugate of TAK 7243NAE Inhibitor Cleavable linker | 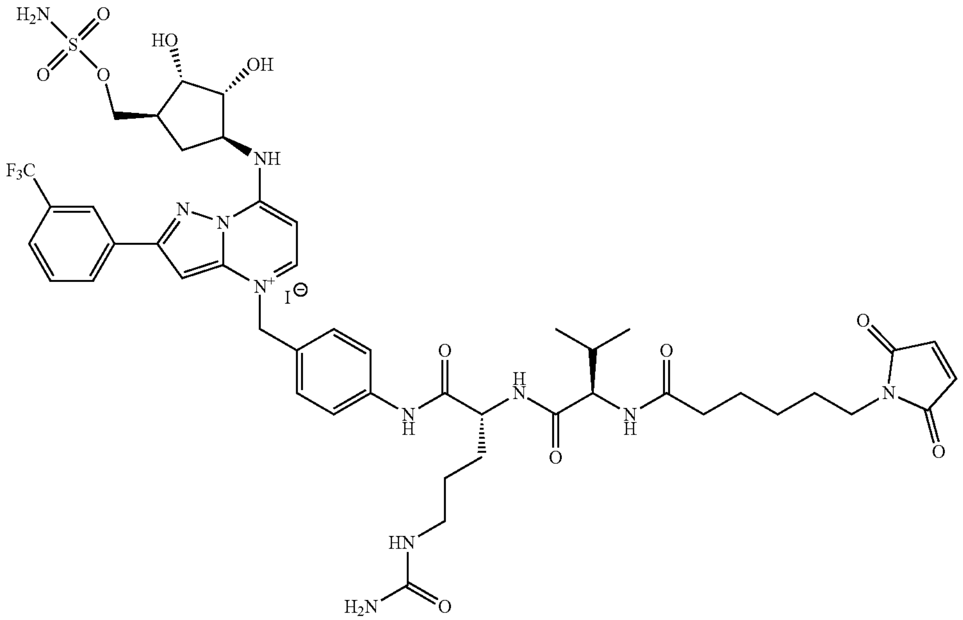 [SMILES: CC(C)[C@@H](NC(=O)CCCCCN1C(=O)C=CC1=O)C(=O)N[C@H](CCCNC(N)=O)C(=O)Nc1ccc(C[n+]2ccc(N[C@H]3C[C@@H](COS(N)(=O)=O)[C@H](O)[C@@H]3O)n3nc(-c4cccc(C(F)(F)F)c4)cc32)cc1 ; [I-]] |
| A-32 Monomethyl auristatin E Conjugation Cleavable linker | 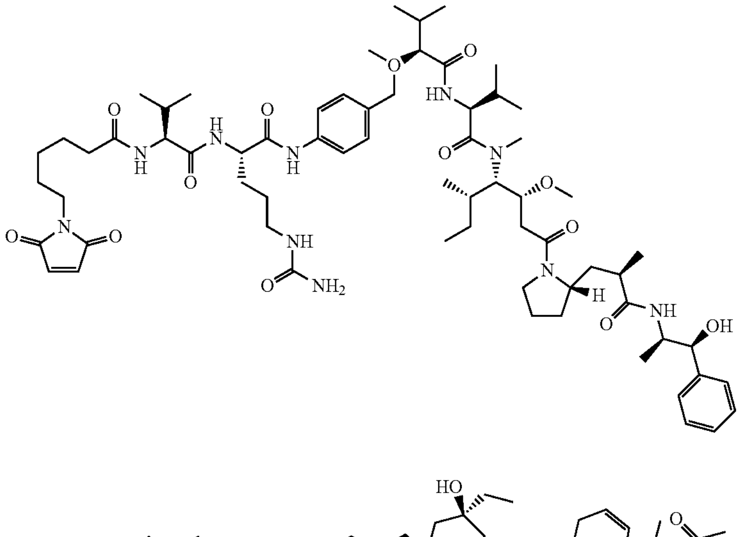 |
| A-33 Viblastine Conjugation Cleavable linker | 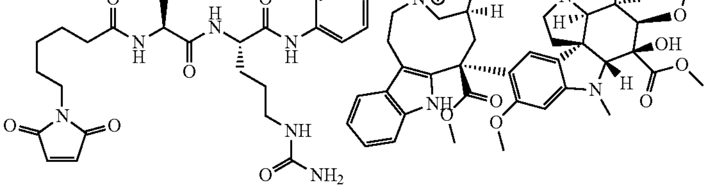 |

TABLE 3-continued
| Exemplary Compounds of Formula (I) | |
|---|---|
| Compound Information | Structure |
| A-34 Carfibzomib Conjugation Cleavable linker | 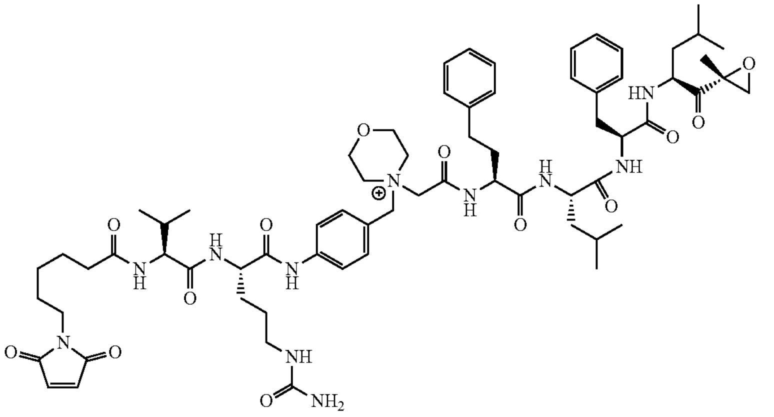 [SMILES: CC(C)C[C@H](NC(=O)[C@H](CCc1ccccc1)NC(=O)C[N+]1(Cc2ccc(NC(=O)[C@H](CCCNC(N)=O)NC(=O)[C@@H](NC(=O)CCCCCN3C(=O)C=CC3=O)C(C)C)cc2)CCOCC1)C(=O)N[C@@H](Cc1ccccc1)C(=O)N[C@@H](CC(C)C)C(=O)[C@@]1(C)CO1] |
| A-35 Rifabutin Conjugation Cleavable linker | 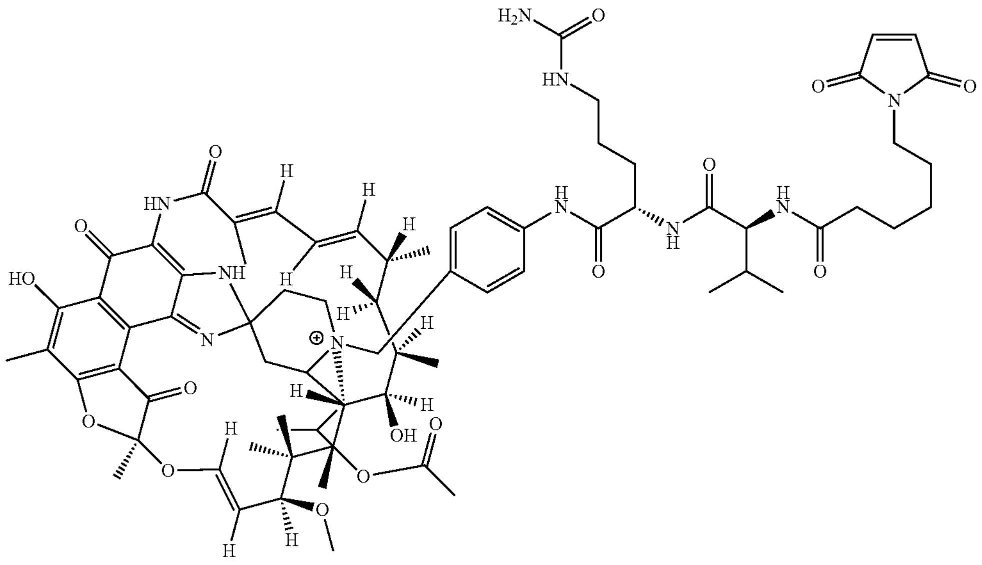 |
| A-36 Clindamycin Conjugation Cleavable linker | 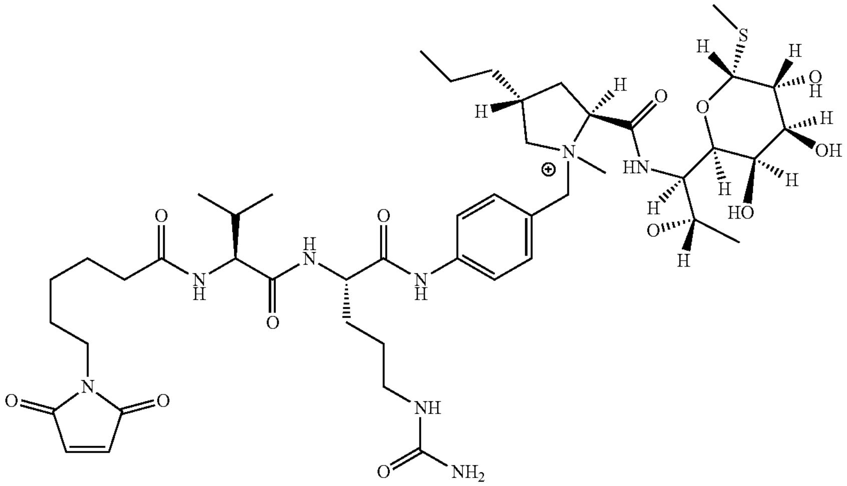 [SMILES: CCC[C@@H]1C[C@@H](C(=O)N[C@@H]([C@H]2O[C@H](SC)[C@H](O)[C@@H](O)[C@H]2O)[C@H](C)O)[N+](C)(Cc2ccc(NC(=O)[C@H](CCCNC(N)=O)NC(=O)[C@@H](NC(=O)CCCCCN3C(=O)C=CC3=O)C(C)C)cc2)C1] |

TABLE 3-continued
| Exemplary Compounds of Formula (I) | |
|---|---|
| Compound Information | Structure |
| A-37 Indibulin Conjugation Cleavable linker | 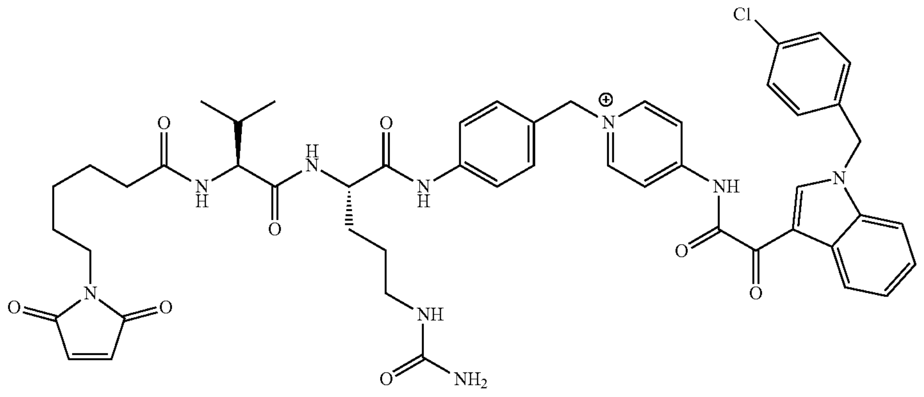 [SMILES: CC(C)[C@H](NC(=O)CCCCCN1C(=O)C=CC1=O)C(=O)N[C@@H](CCCNC(N)=O)C(=O)Nc1ccc(C[n+]2ccc(NC(=O)C(=O)c3cn(Cc4ccc(Cl)cc4)c4ccccc34)cc2)cc1] |
| A-38 Gefitinib Conjugation Cleavable linker | 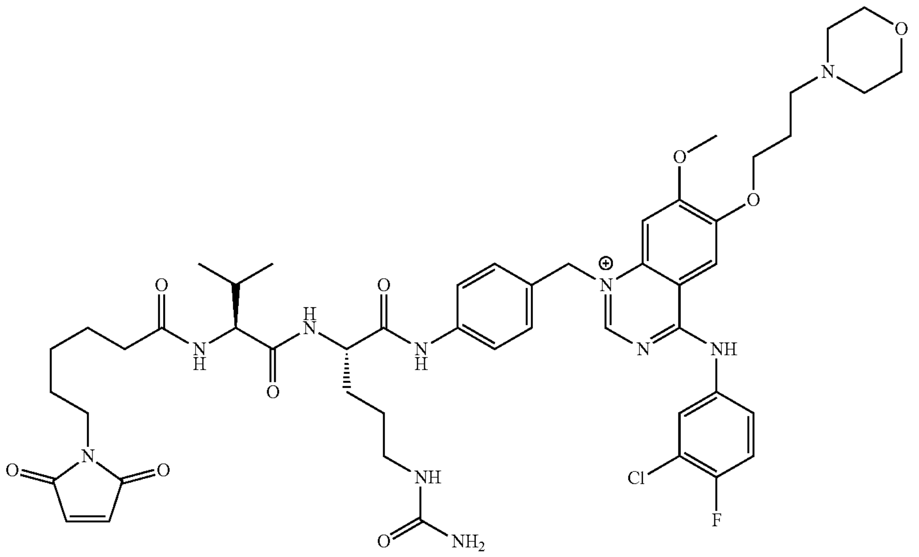 [SMILES: COc1cc2c(cc1OCCCN1CCOCC1)c(Nc1ccc(F)c(Cl)c1)nc[n+]2Cc1ccc(NC(=O)[C@H](CCCNC(N)=O)NC(=O)[C@@H](NC(=O)CCCCCN2C(=O)C=CC2=O)C(C)C)cc1] |
| A-39 Dasatinib Conjugation Cleavable linker | 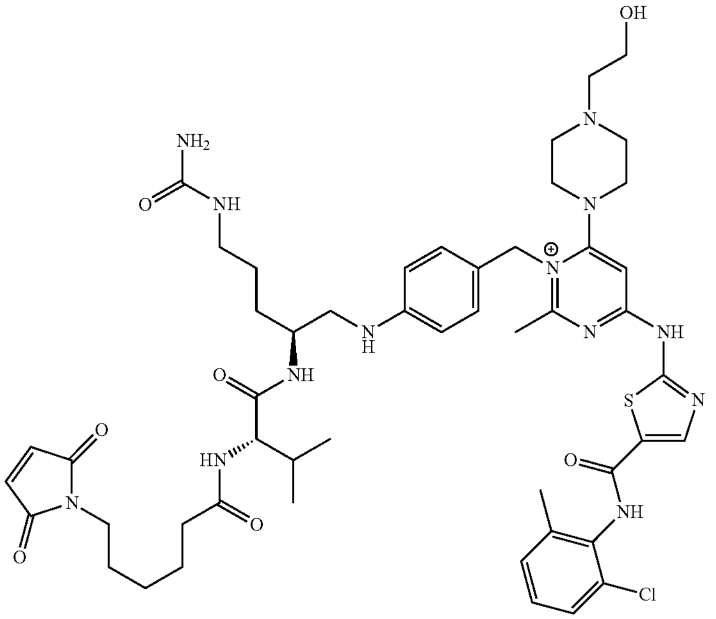 [SMILES: Cc1cccc(Cl)c1NC(=O)c1cnc(Nc2cc(N3CCN(CCO)CC3)[n+](Cc3ccc(NC[C@H](CCCNC(N)=O)NC(=O)[C@@H](NC(=O)CCCCCN4C(=O)C=CC4=O)C(C)C)cc3)c(C)n2)s1] |

TABLE 3-continued
| Exemplary Compounds of Formula (I) | |
|---|---|
| Compound Information | Structure |
| A-40 Docetaxel Conjugation Cleavable linker | 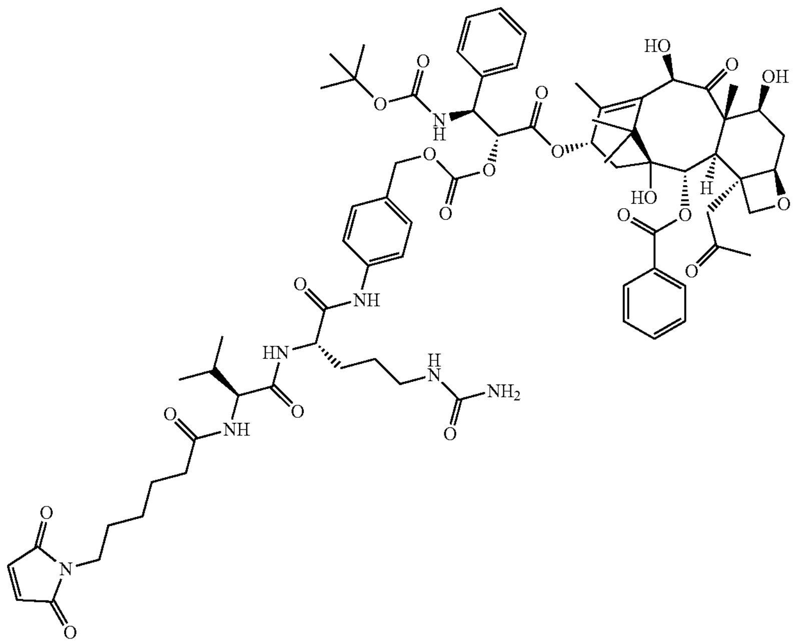 [SMILES: CC(=O)C[C@@]12CO[C@@H]1C[C@H](O)[C@@]1(C)C(=O)[C@H](O)C3=C(C)[C@@H](OC(=O)[C@H](OC(=O)OCc4ccc(NC(=O)[C@H](CCCNC(N)=O)NC(=O)[C@@H](NC(=O)CCCCCN5C(=O)C=CC5=O)C(C)C)cc4)[C@@H](NC(=O)OC(C)(C)C)c4ccccc4)C[C@@](O)([C@@H](OC(=O)c4ccccc4)[C@H]21)C3(C)C] |
| A-41 Paclitaxel Conjugation Cleavable linker | 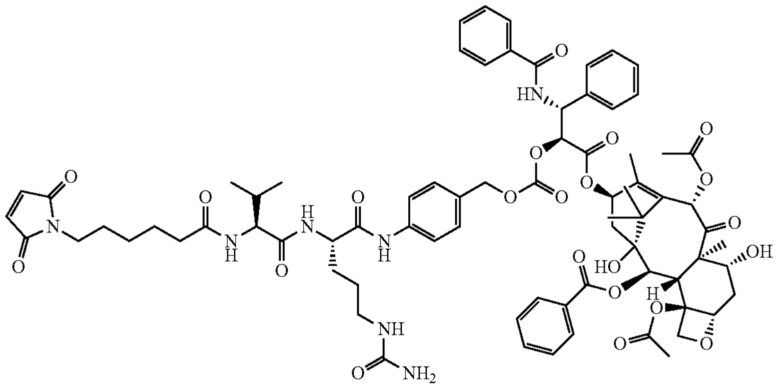 [SMILES: CC(=O)O[C@@H]1C(=O)[C@@]2(C)[C@H](O)C[C@@H]3OC[C@]3(OC(C)=O)[C@@H]2[C@@H](OC(=O)c2ccccc2)[C@@]2(O)C[C@@H](OC(=O)[C@@H](OC(=O)OCc3ccc(NC(=O)[C@H](CCCNC(N)=O)NC(=O)[C@@H](NC(=O)CCCCCN4C(=O)C=CC4=O)C(C)C)cc3)[C@H](NC(=O)c3ccccc3)c3ccccc3)C(C)=C1C2(C)C] |
| A-42 Etoposide Conjugation Cleavable linker | 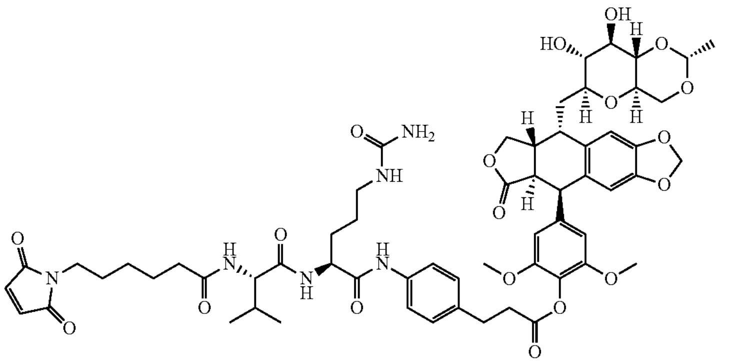 [SMILES: COc1cc([C@@H]2c3cc4c(cc3[C@@H](C[C@@H]3O[C@@H]5CO[C@@H](C)O[C@H]5[C@H](O)[C@H]3O)[C@H]3COC(=O)[C@H]23)OCO4)cc(OC)c1OC(=O)CCc1ccc(NC(=O)[C@H](CCCNC(N)=O)NC(=O)[C@@H](NC(=O)CCCCCN2C(=O)C=CC2=O)C(C)C)cc1] |

TABLE 3-continued
| Exemplary Compounds of Formula (I) | |
|---|---|
| Compound Information | Structure |
| A-43 Gemcitabine Conjugation Cleavable linker | 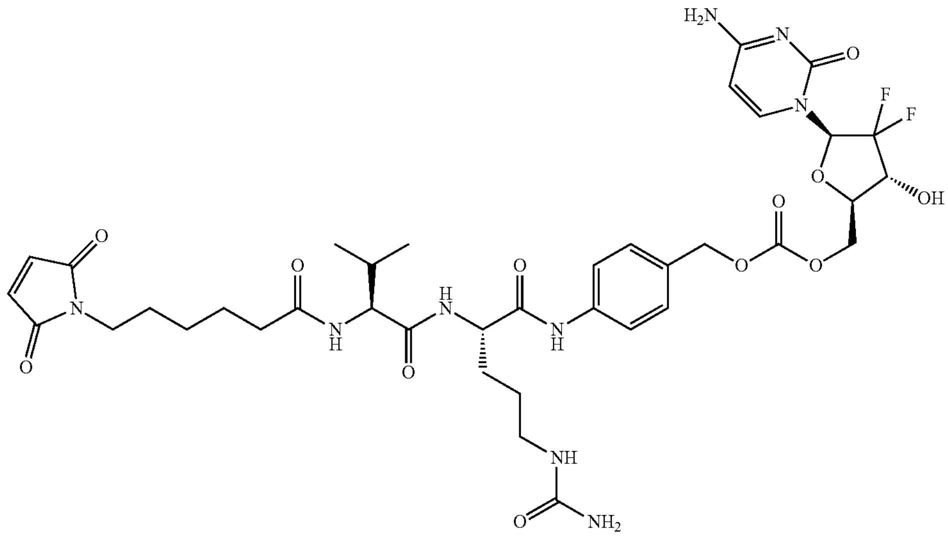 [SMILES: CC(C)[C@H](NC(=O)CCCCCN1C(=O)C=CC1=O)C(=O)N[C@@H](CCCNC(N)=O)C(=O)Nc1ccc(COC(=O)OC[C@H]2O[C@@H](n3ccc(N)nc3=O)C(F)(F)[C@@H]2O)cc1] |
| A-44 Irinotecan Conjugation Cleavable linker | 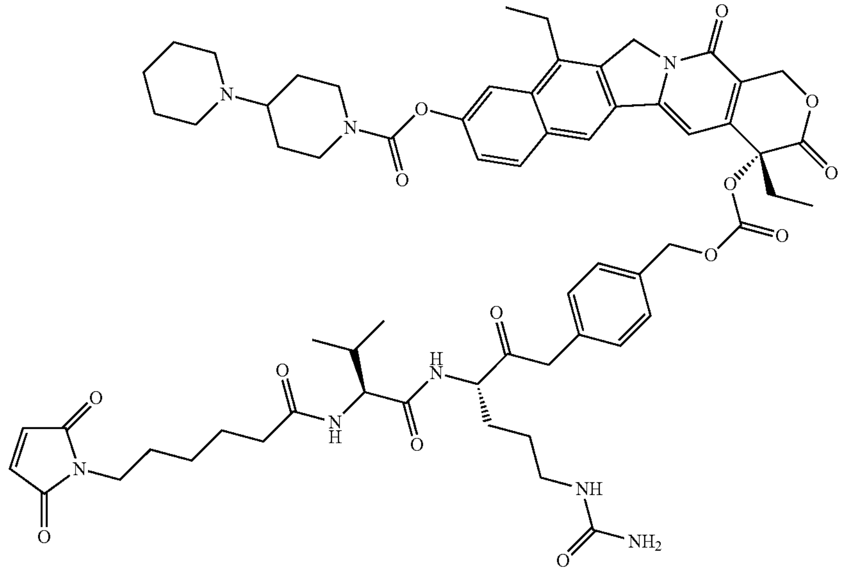 [SMILES: CCc1c2c(cc3ccc(OC(=O)N4CCC(N5CCCCC5)CC4)cc13)-c1cc3c(c(=O)n1C2)COC(=O)[C@]3(CC)OC(=O)OCc1ccc(CC(=O)[C@H](CCCNC(N)=O)NC(=O)[C@@H](NC(=O)CCCCCN2C(=O)C=CC2=O)C(C)C)cc1] |

TABLE 3-continued
| Exemplary Compounds of Formula (I) | |
|---|---|
| Compound Information | Structure |
| A-45 Fluorouracil Conjugation Cleavable linker | 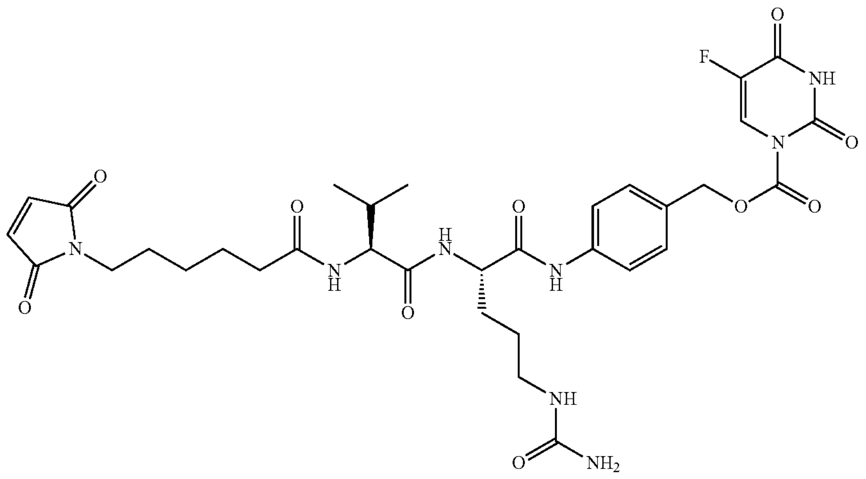 [SMILES: CC(C)[C@H](NC(=O)CCCCCN1C(=O)C=CC1=O)C(=O)N[C@@H](CCCNC(N)=O)C(=O)Nc1ccc(COC(=O)n2cc(F)c(=O)[nH]c2=O)cc1] |
| A-46 Methotrexate Conjugation Cleavable linker | 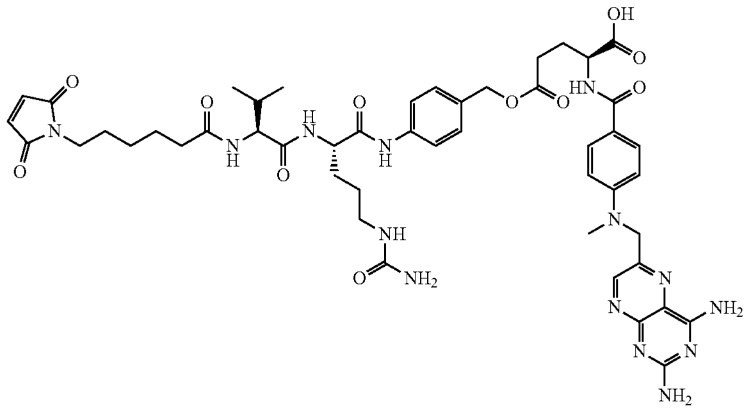 [SMILES: CC(C)[C@H](NC(=O)CCCCCN1C(=O)C=CC1=O)C(=O)N[C@@H](CCCNC(N)=O)C(=O)Nc1ccc(COC(=O)CC[C@H](NC(=O)c2ccc(N(C)Cc3cnc4nc(N)nc(N)c4n3)cc2)C(=O)O)cc1] |
| A-47 Doxorubicin Conjugation Cleavable linker | 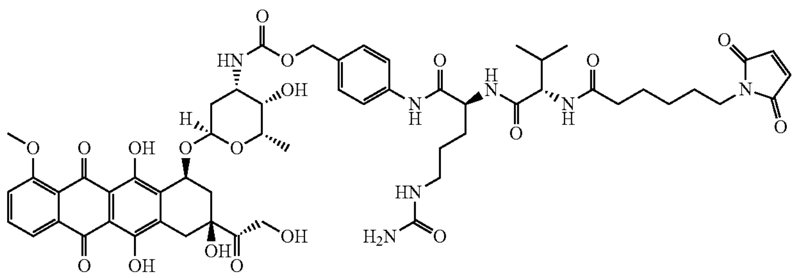 |

TABLE 3-continued
| Exemplary Compounds of Formula (I) | |
|---|---|
| Compound Information | Structure |
| A-48 Pevonedistat Conjugation Carbonyl linker | 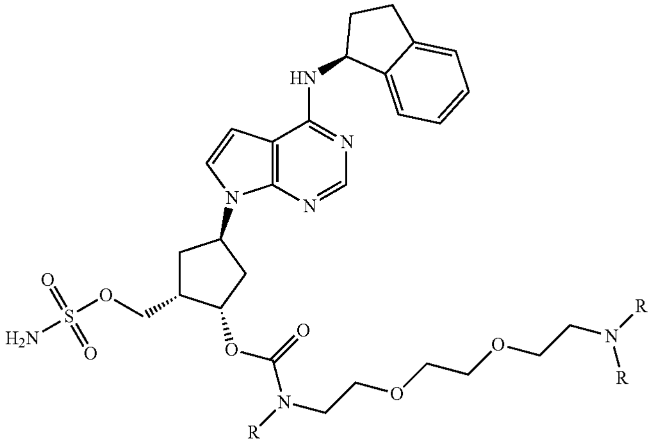 |
| A-49 Pevonedistat Conjugation Carbonyl linker | 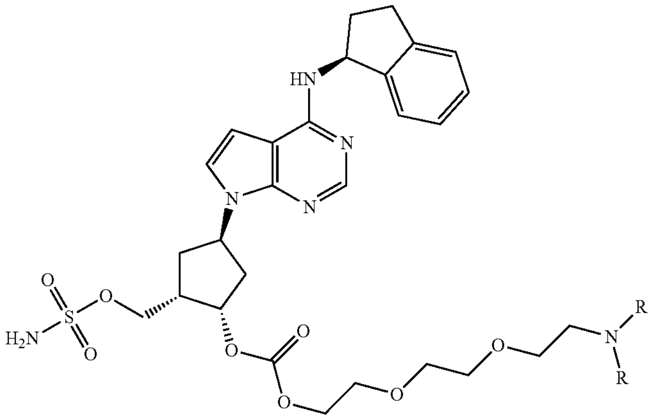 |
| A-50 Pevonedistat Conjugation Ether linker | 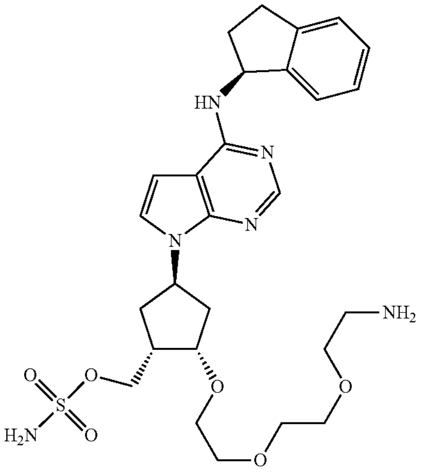 [SMILES: NCCOCCOCCO[C@H]1C[C@H](n2ccc3c(N[C@H]4CCc5ccccc54)ncnc32)C[C@H]1COS(N)(=O)=O] |

TABLE 3-continued

| Exemplary Compounds of Formula (I) | |
|---|---|
| Compound Information | Structure |
| A-51 Pevonedistat Conjugation Cleavable linker | 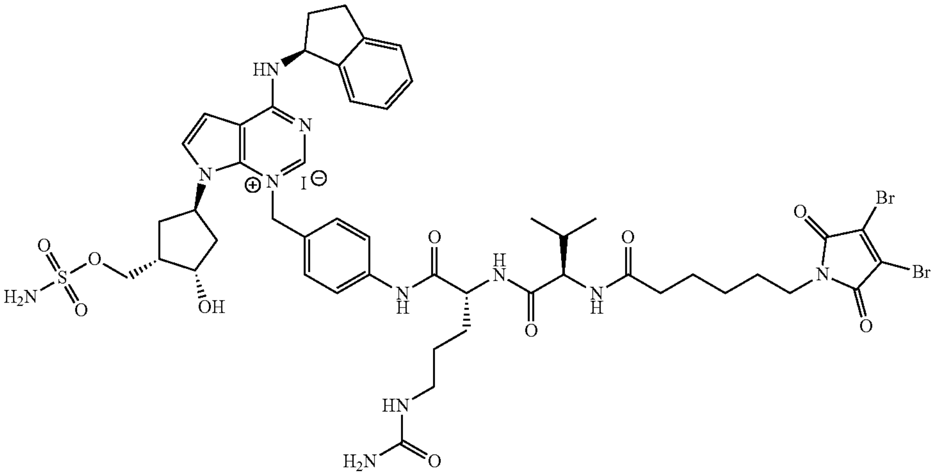 [SMILES: CC(C)[C@@H](NC(=O)CCCCCN1C(=O)C(Br)=C(Br)C1=O)C(=O)N[C@H](CCCNC(N)=O)C(=O)Nc1ccc(C[n+]2cnc(N[C@H]3CCc4ccccc43)c3ccn([C@@H]4C[C@@H](COS(N)(=O)=O)[C@@H](O)C4)c32)cc1 ; [I-]] |

In some embodiments, the compound of Formula (I), or a pharmaceutically acceptable salt, solvate, hydrate, isomer, or tautomer thereof, is selected from the group consisting of A-1, A-2, A-3, A-4, A-5, A-6, A-7, A-8, A-9, A-10, A-11, A-12, A-13, A-14, A-15, A-16, A-17, A-18, A-30, A-31, and A-51.

In some embodiments, the compound of Formula (I), or a pharmaceutically acceptable salt, solvate, hydrate, isomer, or tautomer thereof, is selected from the group consisting of A-1, A-30, A-31, and A-51.

In some embodiments, the compound of Formula (I), or a pharmaceutically acceptable salt, solvate, hydrate, isomer, or tautomer thereof, is A-32.

In an aspect, the present disclosure provides compounds having the structure of Formula (II):

$$X_1—[X_2—(X_3)_m]_n \quad (II),$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is a biologically active polypeptide or hormone;

$X_2$ is a linker; and $X_3$ is a therapeutic compound.

In another aspect, the present disclosure provides compounds having the structure of Formula (III):

$$X_1—[X_2—(X_3)_m]_n \quad (III),$$

and pharmaceutically acceptable salts, solvates, hydrates, isomers, or tautomers thereof, wherein:

m is 1, 2, 3, 4, 5, 6, 7, 8, 9, or 10;

n is 1, 2, 3, 4, 5, 6, 7, 8, 9, 10, or 11;

$X_1$ is an IL-2 polypeptide or a bio-active homolog polypeptide thereof;

$X_2$ is a linker; and $X_3$ is a therapeutic compound.

As shown in Formula (II) and Formula (III), multiple $X_3$ moieties, the number defined by m, may be attached to $X_2$, and multiple $X_2$—$(X_3)$ m moieties, the number defined by n, may be attached to $X_1$. In other words, multiple therapeutic compounds may be linked to a single linker. And the therapeutic drug-linker compound may be attached to the polypeptide or hormone ($X_3$) at one or more positions on the polypeptide or hormone. In some embodiments of the compound of Formula (II) or Formula (III), $X_2$ is bound to $X_1$ at a Cys residue thereof. In some embodiments of the compound of Formula (II) or Formula (III), $X_2$ is bound to $X_1$ at a Lys residue thereof. In some embodiments of the compound of Formula (II) or Formula (III), $X_2$ is bound to $X_1$ at two different sites on $X_1$. In some embodiments of the compound of Formula (II) or Formula (III), $X_2$ is bound to $X_1$ at two different Cys residues on $X_1$. In some embodiments of the compound of Formula (II) or Formula (III), $X_2$ is bound to $X_1$ at two different Lys residues on $X_1$. In some embodiments of the compound of Formula (II) or Formula (III), $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_{2b}$ moieties bound to $X_1$ and n2 corresponds to the number of $X_2c$ moieties bound to $X_1$, and the combination of n1 and n2 has a sum of 2, 3, 4, 5, 6, 7, 8, 9, 10, or 11. By forming bonds with two different Cys residues on the bioactive polypeptide, the two different Cys residues may be rebridged into a disulfide bond, maintaining the structural integrity of the polypeptide and preserving receptor binding and function. The formula of the compound of Formula (II) or Formula (III), when $X_2$ is a mixture of $X_{2b}$ and $X_{2c}$, $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and the combination of n1 and n2 has a sum of 2, 3, 4, 5, 6, 7, 8, 9, 10, or 11, may be illustrated by formula (IV):

$$[(X_3)_m—X_{2b}]_{n1}—X_1—[X_{2c}(X_3)_m]_{n2} \quad (IV),$$

and pharmaceutically acceptable salts, solvates, hydrates, isomers, or tautomers thereof.

In some embodiments of the compound of Formula (II) or Formula (III), each $X_2$ bound to $X_1$ is an $X_{2b}$ moiety. In certain such embodiments, n is n1, wherein n1 corresponds to the number of $X_{2b}$ moieties bound to $X_1$. In some embodiments of the compound of Formula (II) or Formula (III), each $X_2$ bound to $X_1$ is an $X_{2c}$ moiety. In certain such embodiments, n is n2, wherein n2 corresponds to the number of $X_{2c}$ moieties bound to $X_1$.

The description of n as used in the disclosure is inclusive of n1, n2, and the combination of n1 and n2, with, the sum of the combination of n1 and n2 being between 2 and 11, inclusive thereof.

In some embodiments of the compound of Formula (II) or Formula (III), m is 1. In some embodiments of the compound of Formula (II) or Formula (III), m is 2, 3, 4, 5, 6, 7, or 8. In some embodiments of the compound of Formula (II) or Formula (III), m is 1, 2, or 3. In some embodiments of the compound of Formula (II) or Formula (III), m is 2, 3, 4, or 5. In some embodiments of the compound of Formula (II) or Formula (III), m is 2. In some embodiments of the compound of Formula (II) or Formula (III), m is 3. In some embodiments of the compound of Formula (II) or Formula (III), m is 4. In some embodiments of the compound of Formula (II) or Formula (III), m is 5. In some embodiments of the compound of Formula (II) or Formula (III), m is 6. In some embodiments of the compound of Formula (II) or Formula (III), m is 7. In some embodiments of the compound of Formula (II) or Formula (III), m is 8. In some embodiments of the compound of Formula (II) or Formula (III), m is 9. In some embodiments of the compound of Formula (II) or Formula (III), m is 10. In some embodiments, m is an integer between 1 and 10.

In some embodiments of the compound of Formula (II) or Formula (III), n is 2, 3, 4, 5, 6, 7, 8, or 9. In some embodiments of the compound of Formula (II) or Formula (III), n is 3, 4, 5, 6, 7, or 8. In some embodiments of the compound of Formula (II) or Formula (III), n is 4, 5, 6, or 7. In some embodiments of the compound of Formula (II) or Formula (III), n is 1, 2, 3, 4, 5, or 6. In some embodiments of the compound of Formula (II) or Formula (III), n is 2, 3, 4, 5, or 6. In some embodiments of the compound of Formula (II) or Formula (III), n is 1 or 2. In some embodiments of the compound of Formula (II) or Formula (III), n is 3 or 4. In some embodiments of the compound of Formula (II) or Formula (III), n is 5 or 6. In some embodiments of the compound of Formula (II) or Formula (III), n is 1. In some embodiments of the compound of Formula (II) or Formula (III), n is 2. In some embodiments of the compound of Formula (II) or Formula (III), n is 3. In some embodiments of the compound of Formula (II) or Formula (III), n is 4. In some embodiments of the compound of Formula (II) or Formula (III), n is 5. In some embodiments of the compound of Formula (II) or Formula (III), n is 6. In some embodiments of the compound of Formula (II) or Formula (III), n is 7. In some embodiments of the compound of Formula (II) or Formula (III), n is 8. In some embodiments of the compound of Formula (II) or Formula (III), n is 9. In some embodiments of the compound of Formula (II) or Formula (III), n is 10. In some embodiments of the compound of Formula (II) or Formula (III), n is 11. In some embodiments of the compound of Formula (II) or Formula (III), n is an integer between 2 and 9, an integer between 3 and 8, an integer between 4 and 7, or n can be 5 or 6. In some embodiments of the compound of Formula (II) or Formula (III), n is an integer between 1 and 11.

In some embodiments of the compound of Formula (II) or Formula (III), m=n. In some embodiments of the compound of Formula (II) or Formula (III), n is greater than m. In some embodiments of the compound of Formula (II) or Formula (III), m is 1 and n is 1, 2, 3, 4, 5, 6, 7, 8, 9, 10, or 11. In some embodiments of the compound of Formula (II) or Formula (III), m is 2 and n is 1, 2, 3, 4, 5, 6, 7, 8, 9, 10, or 11. In some embodiments of the compound of Formula (II) or Formula (III), m is 3 and n is 1, 2, 3, 4, 5, 6, 7, 8, 9, 10, or 11. In some embodiments of the compound of Formula (II) or Formula (III), m is 4 and n is 1, 2, 3, 4, 5, 6, 7, 8, 9, 10, or 11. In some embodiments of the compound of Formula (II) or Formula (III), m is 5 and n is 1, 2, 3, 4, 5, 6, 7, 8, 9, 10, or 11. In some embodiments of the compound of Formula (II) or Formula (III), m is 1 and n is 1. In some embodiments of the compound of Formula (II) or Formula (III), m is 1 and n is 2. In some embodiments of the compound of Formula (II) or Formula (III), m is 1 and n is 3. In some embodiments of the compound of Formula (II) or Formula (III), m is 1 and n is 4. In some embodiments of the compound of Formula (II) or Formula (III), m is 1 and n is 5. In some embodiments of the compound of Formula (II) or Formula (III), m is 1 and n is 6. In some embodiments of the compound of Formula (II) or Formula (III), m is 1 and n is 7. In some embodiments of the compound of Formula (II) or Formula (III), m is 1 and n is 8. In some embodiments of the compound of Formula (II) or Formula (III), m is 1 and n is 9. In some embodiments of the compound of Formula (II) or Formula (III), m is 1 and n is 10. In some embodiments of the compound of Formula (II) or Formula (III), m is 1 and n is 11. In some embodiments of the compound of Formula (II) or Formula (III), m is 2 and n is 1. In some embodiments of the compound of Formula (II) or Formula (III), m is 2 and n is 2. In some embodiments of the compound of Formula (II) or Formula (III), m is 2 and n is 3. In some embodiments of the compound of Formula (II) or Formula (III), m is 2 and n is 4. In some embodiments of the compound of Formula (II) or Formula (III), m is 2 and n is 5. In some embodiments of the compound of Formula (II) or Formula (III), m is 2 and n is 6. In some embodiments of the compound of Formula (II) or Formula (III), m is 2 and n is 7. In some embodiments of the compound of Formula (II) or Formula (III), m is 2 and n is 8. In some embodiments of the compound of Formula (II) or Formula (III), m is 2 and n is 9. In some embodiments of the compound of Formula (II) or Formula (III), m is 2 and n is 10. In some embodiments of the compound of Formula (II) or Formula (III), m is 2 and n is 11. In some embodiments of the compound of Formula (II) or Formula (III), m is 3 and n is 1. In some embodiments of the compound of Formula (II) or Formula (III), m is 3 and n is 2. In some embodiments of the compound of Formula (II) or Formula (III), m is 3 and n is 3. In some embodiments of the compound of Formula (II) or Formula (III), m is 3 and n is 4. In some embodiments of the compound of Formula (II) or Formula (III), m is 3 and n is 5. In some embodiments of the compound of Formula (II) or Formula (III), m is 3 and n is 6. In some embodiments of the compound of Formula (II) or Formula (III), m is 3 and n is 7. In some embodiments of the compound of Formula (II) or Formula (III), m is 3 and n is 8. In some embodiments of the compound of Formula (II) or Formula (III), m is 3 and n is 9. In some embodiments of the compound of Formula (II) or Formula (III), m is 3 and n is 10. In some embodiments of the compound of Formula (II) or Formula (III), m is 3 and n is 11. In some embodiments of the compound of Formula (II) or Formula (III), m is 4 and n is 1. In some embodiments of the compound of Formula (II) or Formula (III), m is 4 and n is 2. In some embodiments of the compound of Formula (II) or Formula (III), m is 4 and n is 3. In some embodiments of the compound of Formula (II) or Formula (III), m is 4 and n is 4. In some embodiments of the compound of Formula (II) or Formula (III), m is 4 and n is 5. In some embodiments of the compound of Formula (II) or Formula (III), m is 4 and n is 6. In some embodiments of the compound of Formula (II) or Formula (III), m is 4 and n is 7. In some embodiments of the compound of Formula (II) or Formula (III), m is 4 and n is 8. In some embodiments of the compound of Formula (II) or Formula (III), m is 4 and n is 9. In some embodiments of the compound of Formula (II) or Formula (III), m is 4 and n is 10. In some embodiments of the compound of Formula (II) or Formula (III), m is 4 and n is 11. In some embodiments of the compound of Formula (II) or Formula (III), m is 5 and n is 1. In some embodiments of the compound of Formula (II) or Formula (III), m is 5 and n is 2. In some embodiments of the compound of Formula (II) or Formula (III), m is 5 and n is 3. In some embodiments of the compound of Formula (II) or Formula (III), m is 5 and n is 4. In some embodiments of the compound of Formula (II) or Formula (III), m is 5 and n is 5. In some embodiments of the compound of Formula (II) or Formula (III), m is 5 and n is 6. In some embodiments of the compound of Formula (II) or Formula (III), m is 5 and n is 7. In some embodiments of the compound of Formula (II) or Formula (III), m is 5 and n is 8. In some embodiments of the compound of Formula (II) or Formula (III), m is 5 and n is 9. In some embodiments of the compound of Formula (II) or Formula (III), m is 5 and n is 10. In some embodiments of the compound of Formula (II) or Formula (III), m is 5 and n is 11. In some embodiments of the compound of Formula (II) or Formula (III), m is 6 and n is 1. In some embodiments of the compound of Formula (II) or Formula (III), m is 6 and n is 2. In some embodiments of the compound of Formula (II) or Formula (III), m is 6 and n is 3. In some embodiments of the compound of Formula (II) or Formula (III), m is 6 and n is 4. In some embodiments of the compound of Formula (II) or Formula (III), m is 6 and n is 5. In some embodiments of the compound of Formula (II) or Formula (III), m is 6 and n is 6. In some embodiments of the compound of Formula (II) or Formula (III), m is 6 and n is 7. In some embodiments of the compound of Formula (II) or Formula (III), m is 6 and n is 8. In some embodiments of the compound of Formula (II) or Formula (III), m is 6 and n is 9. In some embodiments of the compound of Formula (II) or Formula (III), m is 6 and n is 10. In some embodiments of the compound of Formula (II) or Formula (III), m is 6 and n is 11. In some embodiments of the compound of Formula (II) or Formula (III), m is 7 and n is 1. In some embodiments of the compound of Formula (II) or Formula (III), m is 7 and n is 2. In some embodiments of the compound of Formula (II) or Formula (III), m is 7 and n is 3. In some embodiments of the compound of Formula (II) or Formula (III), m is 7 and n is 4. In some embodiments of the compound of Formula (II) or Formula (III), m is 7 and n is 5. In some embodiments of the compound of Formula (II) or Formula (III), m is 7 and n is 6. In some embodiments of the compound of Formula (II) or Formula (III), m is 7 and n is 7. In some embodiments of the compound of Formula (II) or Formula (III), m is 7 and n is 8. In some embodiments of the compound of Formula (II) or Formula (III), m is 7 and n is 9. In some embodiments of the compound of Formula (II) or Formula (III), m is 7 and n is 10. In some embodiments of the compound of Formula (II) or Formula (III), m is 7 and n is 11. In some embodiments of the compound of Formula (II) or Formula (III), m is 8 and n is 1. In some embodiments of the compound of Formula (II) or Formula (III), m is 8 and n is 2. In some embodiments of the compound of Formula (II) or Formula (III), m is 8 and n is 3. In some embodiments of the compound of Formula (II) or Formula (III), m is 8 and n is 4. In some embodiments of the compound of Formula (II) or Formula (III), m is 8 and n is 5. In some embodiments of the compound of Formula (II) or Formula (III), m is 8 and n is 6. In some embodiments of the compound of Formula (II) or Formula (III), m is 8 and n is 7. In some embodiments of the compound of Formula (II) or Formula (III), m is 8 and n is 8. In some embodiments of the compound of Formula (II) or Formula (III), m is 8 and n is 9. In some embodiments of the compound of Formula (II) or Formula (III), m is 8 and n is 10. In some embodiments of the compound of Formula (II) or Formula (III), m is 8 and n is 11. In some embodiments of the compound of Formula (II) or Formula (III), m is 9 and n is 1. In some embodiments of the compound of Formula (II) or Formula (III), m is 9 and n is 2. In some embodiments of the compound of Formula (II) or Formula (III), m is 9 and n is 3. In some embodiments of the compound of Formula (II) or Formula (III), m is 9 and n is 4. In some embodiments of the compound of Formula (II) or Formula (III), m is 9 and n is 5. In some embodiments of the compound of Formula (II) or Formula (III), m is 9 and n is 6. In some embodiments of the compound of Formula (II) or Formula (III), m is 9 and n is 7. In some embodiments of the compound of Formula (II) or Formula (III), m is 9 and n is 8. In some embodiments of the compound of Formula (II) or Formula (III), m is 9 and n is 9. In some embodiments of the compound of Formula (II) or Formula (III), m is 9 and n is 10. In some embodiments of the compound of Formula (II) or Formula (III), m is 9 and n is 11. In some embodiments of the compound of Formula (II) or Formula (III), m is 10 and n is 1. In some embodiments of the compound of Formula (II) or Formula (III), m is 10 and n is 2. In some embodiments of the compound of Formula (II) or Formula (III), m is 10 and n is 3. In some embodiments of the compound of Formula (II) or Formula (III), m is 10 and n is 4. In some embodiments of the compound of Formula (II) or Formula (III), m is 10 and n is 5. In some embodiments of the compound of Formula (II) or Formula (III), m is 10 and n is 6. In some embodiments of the compound of Formula (II) or Formula (III), m is 10 and n is 7. In some embodiments of the compound of Formula (II) or Formula (III), m is 10 and n is 8. In some embodiments of the compound of Formula (II) or Formula (III), m is 10 and n is 9. In some embodiments of the compound of Formula (II) or Formula (III), m is 10 and n is 10. In some embodiments of the compound of Formula (II) or Formula (III), m is 10 and n is 11.

In some embodiments of the compound of Formula (II) or Formula (III), $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and the combination of n1 and n2 has a sum of 2, 3, 4, 5, 6, 7, 8, 9, 10, or 11. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 1 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 4. In some embodiments of the compound of Formula (II) or Formula (III), when $X_2$ is a mixture of $X_{26}$ and $X_{2c}$ and n is a combination of n1 and n2, m is 2 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 2 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 3 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 4 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 5 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 6 and the combination of n1 and n2 has a sum of 10. In some embodiments of the compound of Formula (II) or Formula (III), when $X_2$ is a mixture of $X_{26}$ and $X_{2c}$ and n is a combination of n1 and n2, m is 6 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 7 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 8 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 9 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 2. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 3. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 4. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 5. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 6. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 7. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 8. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 9. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 10. In some embodiments of the compound of Formula (II) or Formula (III), when $X_2$ is a mixture of $X_{2b}$ and $X_{2c}$ and n is a combination of n1 and n2, m is 10 and the combination of n1 and n2 has a sum of 11. In some embodiments of the compound of Formula (II) or Formula (III), when $X_2$ is a mixture of $X_{2b}$ and $X_{2c}$ and n is a combination of n1 and n2, n1 is 2 or 3 and n2 is 1. In some embodiments of the compound of Formula (II) or Formula (III), when $X_2$ is a mixture of $X_{2b}$ and $X_{2c}$ and n is a combination of n1 and n2, n1 is 2 and n2 is 1. In some embodiments of the compound of Formula (II) or Formula (III), when $X_2$ is a mixture of $X_{2b}$ and $X_{2c}$ and n is a combination of n1 and n2, n1 is 3 and n2 is 1. In some embodiments of the compound of Formula (II) or Formula (III), when $X_2$ is a mixture of $X_{2b}$ and $X_{2c}$ and n is a combination of n1 and n2, n1 is 1, 2, 3, 4, or 5 and n2 is 1, 2 or 3. In some embodiments of the compound of Formula (II) or Formula (III), when $X_2$ is a mixture of $X_{2b}$ and $X_{2c}$ and n is a combination of n1 and n2, n1 is 1, 2, 3, 4, or 5 and n2 is 1. In some embodiments of the compound of Formula (II) or Formula (III), when $X_2$ is a mixture of $X_{2b}$ and $X_{2c}$ and n is a combination of n1 and n2, n1 is 1, 2, 3, 4, or 5 and n2 is 2. In some embodiments of the compound of Formula (II) or Formula (III), when $X_2$ is a mixture of $X_{2b}$ and $X_{2c}$ and n is a combination of n1 and n2, n1 is 1, 2, 3, 4, or 5 and n2 is 3. In some embodiments of the compound of Formula (II) or Formula (III), when $X_2$ is a mixture of $X_{2b}$ and $X_{2c}$ and n is a combination of n1 and n2, n1 is 1 and n2 is 1, 2 or 3. In some embodiments of the compound of Formula (II) or Formula (III), when $X_2$ is a mixture of $X_{2b}$ and $X_{2c}$ and n is a combination of n1 and n2, n1 is 2 and n2 is 1, 2 or 3. In some embodiments of the compound of Formula (II) or Formula (III), when $X_2$ is a mixture of $X_{2b}$ and $X_{2c}$ and n is a combination of n1 and n2, n1 is 3 and n2 is 1, 2 or 3. In some embodiments of the compound of Formula (II) or Formula (III), when $X_2$ is a mixture of $X_{2b}$ and $X_{2c}$ and n is a combination of n1 and n2, n1 is 4 and n2 is 1, 2 or 3. In some embodiments of the compound of Formula (II) or Formula (III), when $X_2$ is a mixture of $X_{2b}$ and $X_{2c}$ and n is a combination of n1 and n2, n1 is 5 and n2 is 1, 2 or 3. In some embodiments of the compound of Formula (II) or Formula (III), when $X_2$ is a mixture of $X_{2b}$ and $X_{2c}$ and n is a combination of n1 and n2, n1=n2. In some embodiments, each $X_2$ bound to $X_1$ is an $X_{2b}$ moiety. In some embodiments, each $X_2$ bound to $X_1$ is an $X_{2c}$ moiety.

In some embodiments of the compound of Formula (II) or Formula (III), each $X_2$ bound to $X_1$ is an $X_{2b}$ moiety. In certain such embodiments, n is n1, wherein n1 corresponds to the number of $X_{2b}$ moieties bound to $X_1$. In some embodiments of the compound of Formula (II) or Formula (III), when $X_2$ is $X_{2b}$ and n is n1, m is 1 and n1 is 2. In some embodiments of the compound of Formula (II) or Formula (III), when $X_2$ is $X_{2b}$ and n is n1, m is 1 and n1 is 3. In some embodiments of the compound of Formula (II) or Formula (III), when $X_2$ is $X_{2b}$ and n is n1, m is 1 and n1 is 4. In some embodiments of the compound of Formula (II) or Formula (III), when $X_2$ is $X_{2b}$ and n is n1, m is 1 and n1 is 5. In some embodiments of the compound of Formula (II) or Formula (III), when $X_2$ is $X_{2b}$ and n is n1, m is 1 and n1 is 6. In some embodiments of the compound of Formula (II) or Formula (III), when $X_2$ is $X_{2b}$ and n is n1, m is 1 and n1 is 7. In some embodiments of the compound of Formula (II) or Formula (III), when $X_2$ is $X_{2b}$ and n is n1, m is 1 and n1 is 8. In some embodiments of the compound of Formula (II) or Formula (III), when $X_2$ is $X_{2b}$ and n is n1, m is 1 and n1 is 9. In some embodiments of the compound of Formula (II) or Formula (III), when $X_2$ is $X_{2b}$ and n is n1, m is 1 and n1 is 10. In some embodiments of the compound of Formula (II) or Formula (III), when $X_2$ is $X_{2b}$ and n is n1, m is 1 and n1 is 11. In some embodiments of the compound of Formula (II) or Formula (III), when $X_2$ is $X_{2b}$ and n is n1, m is 2 and n1 is 2. In some embodiments of the compound of Formula (II) or Formula (III), when $X_2$ is $X_{2b}$ and n is n1, m is 2 and n1 is 3. In some embodiments of the compound of Formula (II) or Formula (III), when $X_2$ is $X_{2b}$ and n is n1, m is 2 and n1 is 4. In some embodiments of the compound of Formula (II) or Formula (III), when $X_2$ is $X_{2b}$ and n is n1, m is 2 and n1 is 5. In some embodiments of the compound of Formula (II) or Formula (III), when $X_2$ is $X_{2b}$ and n is n1, m is 2 and n1 is 6. In some embodiments of the compound of Formula (II) or Formula (III), when $X_2$ is $X_{2b}$ and n is n1, m is 2 and n1 is 7. In some embodiments of the compound of Formula (II) or Formula (III), when $X_2$ is $X_{2b}$ and n is n1, m is 2 and n1 is 8. In some embodiments of the compound of Formula (II) or Formula (III), when $X_2$ is $X_{2b}$ and n is n1, m is 2 and n1 is 9. In some embodiments of the compound of Formula (II) or Formula (III), when $X_2$ is $X_{2b}$ and n is n1, m is 2 and n1 is 10. In some embodiments of the compound of Formula (II) or Formula (III), when $X_2$ is $X_{2b}$ and n is n1, m is 2 and n1 is 11. In some embodiments of the compound of Formula (II) or Formula (III), when $X_2$ is $X_{2b}$ and n is n1, m is 3 and n1 is 2. In some embodiments of the compound of Formula (II) or Formula (III), when $X_2$ is $X_{2b}$ and n is n1, m is 3 and n1 is 3. In some embodiments of the compound of Formula (II) or Formula (III), when $X_2$ is $X_{2b}$ and n is n1, m is 3 and n1 is 4. In some embodiments of the compound of Formula (II) or Formula (III), when $X_2$ is $X_{2b}$ and n is n1, m is 3 and n1 is 5. In some embodiments of the compound of Formula (II) or Formula (III), when $X_2$ is $X_{2b}$ and n is n1, m is 3 and n1 is 6. In some embodiments of the compound of Formula (II) or Formula (III), when $X_2$ is $X_{2b}$ and n is n1, m is 3 and n1 is 7. In some embodiments of the compound of Formula (II) or Formula (III), when $X_2$ is $X_{2b}$ and n is n1, m is 3 and n1 is 8. In some embodiments of the compound of Formula (II) or Formula (III), when $X_2$ is $X_{2b}$ and n is n1, m is 3 and n1 is 9. In some embodiments of the compound of Formula (II) or Formula (III), when $X_2$ is $X_{2b}$ and n is n1, m is 3 and n1 is 10. In some embodiments of the compound of Formula (II) or Formula (III), when $X_2$ is $X_{2b}$ and n is n1, m is 3 and n1 is 11. In some embodiments of the compound of Formula (II) or Formula (III), when $X_2$ is $X_{2b}$ and n is n1, m is 4 and n1 is 2. In some embodiments of the compound of Formula (II) or Formula (III), when $X_2$ is $X_{2b}$ and n is n1, m is 4 and n1 is 3. In some embodiments of the compound of Formula (II) or Formula (III), when $X_2$ is $X_{2b}$ and n is n1, m is 4 and n1 is 4. In some embodiments of the compound of Formula (II) or Formula (III), when $X_2$ is $X_{2b}$ and n is n1, m is 4 and n1 is 5. In some embodiments of the compound of Formula (II) or Formula (III), when $X_2$ is $X_{2b}$ and n is n1, m is 4 and n1 is 6. In some embodiments of the compound of Formula (II) or Formula (III), when $X_2$ is $X_{2b}$ and n is n1, m is 4 and n1 is 7. In some embodiments of the compound of Formula (II) or Formula (III), when $X_2$ is $X_{2b}$ and n is n1, m is 4 and n1 is 8. In some embodiments of the compound of Formula (II) or Formula (III), when $X_2$ is $X_{2b}$ and n is n1, m is 4 and n1 is 9. In some embodiments of the compound of Formula (II) or Formula (III), when $X_2$ is $X_{2b}$ and n is n1, m is 4 and n1 is 10. In some embodiments of the compound of Formula (II) or Formula (III), when $X_2$ is $X_{2b}$ and n is n1, m is 4 and n1 is 11. In some embodiments of the compound of Formula (II) or Formula (III), when $X_2$ is $X_{2b}$ and n is n1, m is 5 and n1 is 2. In some embodiments of the compound of Formula (II) or Formula (III), when $X_2$ is $X_{2b}$ and n is n1, m is 5 and n1 is 3. In some embodiments of the compound of Formula (II) or Formula (III), when $X_2$ is $X_{2b}$ and n is n1, m is 5 and n1 is 4. In some embodiments of the compound of Formula (II) or Formula (III), when $X_2$ is $X_{2b}$ and n is n1, m is 5 and n1 is 5. In some embodiments of the compound of Formula (II) or Formula (III), when $X_2$ is $X_{2b}$ and n is n1, m is 5 and n1 is 6. In some embodiments of the compound of Formula (II) or Formula (III), when $X_2$ is $X_{2b}$ and n is n1, m is 5 and n1 is 7. In some embodiments of the compound of Formula (II) or Formula (III), when $X_2$ is $X_{2b}$ and n is n1, m is 5 and n1 is 8. In some embodiments of the compound of Formula (II) or Formula (III), when $X_2$ is $X_{2b}$ and n is n1, m is 5 and n1 is 9. In some embodiments of the compound of Formula (II) or Formula (III), when $X_2$ is $X_{2b}$ and n is n1, m is 5 and n1 is 10. In some embodiments of the compound of Formula (II) or Formula (III), when $X_2$ is $X_{2b}$ and n is n1, m is 5 and n1 is 11. In some embodiments of the compound of Formula (II) or Formula (III), when $X_2$ is $X_{2b}$ and n is n1, m is 6 and n1 is 2. In some embodiments of the compound of Formula (II) or Formula (III), when $X_2$ is $X_{2b}$ and n is n1, m is 6 and n1 is 3. In some embodiments of the compound of Formula (II) or Formula (III), when $X_2$ is $X_{2b}$ and n is n1, m is 6 and n1 is 4. In some embodiments of the compound of Formula (II) or Formula (III), when $X_2$ is $X_{2b}$ and n is n1, m is 6 and n1 is 5. In some embodiments of the compound of Formula (II) or Formula (III), when $X_2$ is $X_{2b}$ and n is n1, m is 6 and n1 is 6. In some embodiments of the compound of Formula (II) or Formula (III), when $X_2$ is $X_{2b}$ and n is n1, m is 6 and n1 is 7. In some embodiments of the compound of Formula (II) or Formula (III), when $X_2$ is $X_{2b}$ and n is n1, m is 6 and n1 is 8. In some embodiments of the compound of Formula (II) or Formula (III), when $X_2$ is $X_{2b}$ and n is n1, m is 6 and n1 is 9. In some embodiments of the compound of Formula (II) or Formula (III), when $X_2$ is $X_{2b}$ and n is n1, m is 6 and n1 is 10. In some embodiments of the compound of Formula (II) or Formula (III), when $X_2$ is $X_{2b}$ and n is n1, m is 6 and n1 is 11. In some embodiments of the compound of Formula (II) or Formula (III), when $X_2$ is $X_{2b}$ and n is n1, m is 7 and n1 is 2. In some embodiments of the compound of Formula (II) or Formula (III), when $X_2$ is $X_{2b}$ and n is n1, m is 7 and n1 is 3. In some embodiments of the compound of Formula (II) or Formula (III), when $X_2$ is $X_{2b}$ and n is n1, m is 7 and n1 is 4. In some embodiments of the compound of Formula (II) or Formula (III), when $X_2$ is $X_{26}$ and n is n1, m is 7 and n1 is 5. In some embodiments of the compound of Formula (II) or Formula (III), when $X_2$ is $X_{2b}$ and n is n1, m is 7 and n1 is 6. In some embodiments of the compound of Formula (II) or Formula (III), when $X_2$ is $X_{2b}$ and n is n1, m is 7 and n1 is 7. In some embodiments of the compound of Formula (II) or Formula (III), when $X_2$ is $X_{2b}$ and n is n1, m is 7 and n1 is 8. In some embodiments of the compound of Formula (II) or Formula (III), when $X_2$ is $X_{2b}$ and n is n1, m is 7 and n1 is 9. In some embodiments of the compound of Formula (II) or Formula (III), when $X_2$ is $X_{2b}$ and n is n1, m is 7 and n1 is 10. In some embodiments of the compound of Formula (II) or Formula (III), when $X_2$ is $X_{2b}$ and n is n1, m is 7 and n1 is 11. In some embodiments of the compound of Formula (II) or Formula (III), when $X_2$ is $X_{2b}$ and n is n1, m is 8 and n1 is 2. In some embodiments of the compound of Formula (II) or Formula (III), when $X_2$ is $X_{2b}$ and n is n1, m is 8 and n1 is 3. In some embodiments of the compound of Formula (II) or Formula (III), when $X_2$ is $X_{2b}$ and n is n1, m is 8 and n1 is 4. In some embodiments of the compound of Formula (II) or Formula (III), when $X_2$ is $X_{2b}$ and n is n1, m is 8 and n1 is 5. In some embodiments of the compound of Formula (II) or Formula (III), when $X_2$ is $X_{2b}$ and n is n1, m is 8 and n1 is 6. In some embodiments of the compound of Formula (II) or Formula (III), when $X_2$ is $X_{2b}$ and n is n1, m is 8 and n1 is 7. In some embodiments of the compound of Formula (II) or Formula (III), when $X_2$ is $X_{2b}$ and n is n1, m is 8 and n1 is 8. In some embodiments of the compound of Formula (II) or Formula (III), when $X_2$ is $X_{2b}$ and n is n1, m is 8 and n1 is 9. In some embodiments of the compound of Formula (II) or Formula (III), when $X_2$ is $X_{2b}$ and n is n1, m is 8 and n1 is 10. In some embodiments of the compound of Formula (II) or Formula (III), when $X_2$ is $X_{2b}$ and n is n1, m is 8 and n1 is 11. In some embodiments of the compound of Formula (II) or Formula (III), when $X_2$ is $X_{2b}$ and n is n1, m is 9 and n1 is 2. In some embodiments of the compound of Formula (II) or Formula (III), when $X_2$ is $X_{2b}$ and n is n1, m is 9 and n1 is 3. In some embodiments of the compound of Formula (II) or Formula (III), when $X_2$ is $X_{2b}$ and n is n1, m is 9 and n1 is 4. In some embodiments of the compound of Formula (II) or Formula (III), when $X_2$ is $X_{2b}$ and n is n1, m is 9 and n1 is 5. In some embodiments of the compound of Formula (II) or Formula (III), when $X_2$ is $X_{2b}$ and n is n1, m is 9 and n1 is 6. In some embodiments of the compound of Formula (II) or Formula (III), when $X_2$ is $X_{2b}$ and n is n1, m is 9 and n1 is 7. In some embodiments of the compound of Formula (II) or Formula (III), when $X_2$ is $X_{2b}$ and n is n1, m is 9 and n1 is 8. In some embodiments of the compound of Formula (II) or Formula (III), when $X_2$ is $X_{2b}$ and n is n1, m is 9 and n1 is 9. In some embodiments of the compound of Formula (II) or Formula (III), when $X_2$ is $X_{2b}$ and n is n1, m is 9 and n1 is 10. In some embodiments of the compound of Formula (II) or Formula (III), when $X_2$ is $X_{2b}$ and n is n1, m is 9 and n1 is 11. In some embodiments of the compound of Formula (II) or Formula (III), when $X_2$ is $X_{2b}$ and n is n1, m is 10 and n1 is 2. In some embodiments of the compound of Formula (II) or Formula (III), when $X_2$ is $X_{2b}$ and n is n1, m is 10 and n1 is 3. In some embodiments of the compound of Formula (II) or Formula (III), when $X_2$ is $X_{2b}$ and n is n1, m is 10 and n1 is 4. In some embodiments of the compound of Formula (II) or Formula (III), when $X_2$ is $X_{2b}$ and n is n1, m is 10 and n1 is 5. In some embodiments of the compound of Formula (II) or Formula (III), when $X_2$ is $X_{2b}$ and n is n1, m is 10 and n1 is 6. In some embodiments of the compound of Formula (II) or Formula (III), when $X_2$ is $X_{2b}$ and n is n1, m is 10 and n1 is 7. In some embodiments of the compound of Formula (II) or Formula (III), when $X_2$ is $X_{2b}$ and n is n1, m is 10 and n1 is 8. In some embodiments of the compound of Formula (II) or Formula (III), when $X_2$ is $X_{2b}$ and n is n1, m is 10 and n1 is 9. In some embodiments of the compound of Formula (II) or Formula (III), when $X_2$ is $X_{2b}$ and n is n1, m is 10 and n1 is 10. In some embodiments of the compound of Formula (II) or Formula (III), when $X_2$ is $X_{2b}$ and n is n1, m is 10 and n1 is 11. In some embodiments of the compound of Formula (II) or Formula (III), when $X_2$ is $X_{2b}$ and n is n1, n1 is 2 or 3 and n2 is 1. In some embodiments of the compound of Formula (II) or Formula (III), when $X_2$ is $X_{2b}$ and n is n1, n1 is 2 and n2 is 1. In some embodiments of the compound of Formula (II) or Formula (III), when $X_2$ is $X_{2b}$ and n is n1, n1 is 3 and n2 is 1. In some embodiments of the compound of Formula (II) or Formula (III), when $X_2$ is $X_{2b}$ and n is n1, n1 is 1, 2, 3, 4, or 5 and n2 is 1, 2 or 3. In some embodiments of the compound of Formula (II) or Formula (III), when $X_2$ is $X_{2b}$ and n is n1, n1 is 1, 2, 3, 4, or 5 and n2 is 1. In some embodiments of the compound of Formula (II) or Formula (III), when $X_2$ is $X_{2b}$ and n is n1, n1 is 1, 2, 3, 4, or 5 and n2 is 2. In some embodiments of the compound of Formula (II) or Formula (III), when $X_2$ is $X_{2b}$ and n is n1, n1 is 1, 2, 3, 4, or 5 and n2 is 3. In some embodiments of the compound of Formula (II) or Formula (III), when $X_2$ is $X_{2b}$ and n is n1, n1 is 1 and n2 is 1, 2 or 3. In some embodiments of the compound of Formula (II) or Formula (III), when $X_2$ is $X_{2b}$ and n is n1, n1 is 2 and n2 is 1, 2 or 3. In some embodiments of the compound of Formula (II) or Formula (III), when $X_2$ is $X_{2b}$ and n is n1, n1 is 3 and n2 is 1, 2 or 3. In some embodiments of the compound of Formula (II) or Formula (III), when $X_2$ is $X_{2b}$ and n is n1, n1 is 4 and n2 is 1, 2 or 3. In some embodiments of the compound of Formula (II) or Formula (III), when $X_2$ is $X_{2b}$ and n is n1, n1 is 5 and n2 is 1, 2 or 3.

In some embodiments of the compound of Formula (II) or Formula (III), each $X_2$ bound to $X_1$ is an $X_{2c}$ moiety. In certain such embodiments, n is n2, wherein n2 corresponds to the number of $X_{2c}$ moieties bound to $X_1$. In some embodiments of the compound of Formula (II) or Formula (III), when $X_2$ is $X_{2c}$ and n is n2, m is 1 and n2 is 2. In some embodiments of the compound of Formula (II) or Formula (III), when $X_2$ is $X_{2c}$ and n is n2, m is 1 and n2 is 3. In some embodiments of the compound of Formula (II) or Formula (III), when $X_2$ is $X_{2c}$ and n is n2, m is 1 and n2 is 4. In some embodiments of the compound of Formula (II) or Formula (III), when $X_2$ is $X_{2c}$ and n is n2, m is 1 and n2 is 5. In some embodiments of the compound of Formula (II) or Formula (III), when $X_2$ is $X_{2c}$ and n is n2, m is 1 and n2 is 6. In some embodiments of the compound of Formula (II) or Formula (III), when $X_2$ is $X_{2c}$ and n is n2, m is 1 and n2 is 7. In some embodiments of the compound of Formula (II) or Formula (III), when $X_2$ is $X_{2c}$ and n is n2, m is 1 and n2 is 8. In some embodiments of the compound of Formula (II) or Formula (III), when $X_2$ is $X_{2c}$ and n is n2, m is 1 and n2 is 9. In some embodiments of the compound of Formula (II) or Formula (III), when $X_2$ is $X_{2c}$ and n is n2, m is 1 and n2 is 10. In some embodiments of the compound of Formula (II) or Formula (III), when $X_2$ is $X_{2c}$ and n is n2, m is 1 and n2 is 11. In some embodiments of the compound of Formula (II) or Formula (III), when $X_2$ is $X_{2c}$ and n is n2, m is 2 and n2 is 2. In some embodiments of the compound of Formula (II) or Formula (III), when $X_2$ is $X_{2c}$ and n is n2, m is 2 and n2 is 3. In some embodiments of the compound of Formula (II) or Formula (III), when $X_2$ is $X_{2c}$ and n is n2, m is 2 and n2 is 4. In some embodiments of the compound of Formula (II) or Formula (III), when $X_2$ is $X_{2c}$ and n is n2, m is 2 and n2 is 5. In some embodiments of the compound of Formula (II) or Formula (III), when $X_2$ is $X_{2c}$ and n is n2, m is 2 and n2 is 6. In some embodiments of the compound of Formula (II) or Formula (III), when $X_2$ is $X_{2c}$ and n is n2, m is 2 and n2 is 7. In some embodiments of the compound of Formula (II) or Formula (III), when $X_2$ is $X_{2c}$ and n is n2, m is 2 and n2 is 8. In some embodiments of the compound of Formula (II) or Formula (III), when $X_2$ is $X_{2c}$ and n is n2, m is 2 and n2 is 9. In some embodiments of the compound of Formula (II) or Formula (III), when $X_2$ is $X_{2c}$ and n is n2, m is 2 and n2 is 10. In some embodiments of the compound of Formula (II) or Formula (III), when $X_2$ is $X_{2c}$ and n is n2, m is 2 and n2 is 11. In some embodiments of the compound of Formula (II) or Formula (III), when $X_2$ is $X_{2c}$ and n is n2, m is 3 and n2 is 2. In some embodiments of the compound of Formula (II) or Formula (III), when $X_2$ is $X_{2c}$ and n is n2, m is 3 and n2 is 3. In some embodiments of the compound of Formula (II) or Formula (III), when $X_2$ is $X_{2c}$ and n is n2, m is 3 and n2 is 4. In some embodiments of the compound of Formula (II) or Formula (III), when $X_2$ is $X_{2c}$ and n is n2, m is 3 and n2 is 5. In some embodiments of the compound of Formula (II) or Formula (III), when $X_2$ is $X_{2c}$ and n is n2, m is 3 and n2 is 6. In some embodiments of the compound of Formula (II) or Formula (III), when $X_2$ is $X_{2c}$ and n is n2, m is 3 and n2 is 7. In some embodiments of the compound of Formula (II) or Formula (III), when $X_2$ is $X_{2c}$ and n is n2, m is 3 and n2 is 8. In some embodiments of the compound of Formula (II) or Formula (III), when $X_2$ is $X_{2c}$ and n is n2, m is 3 and n2 is 9. In some embodiments of the compound of Formula (II) or Formula (III), when $X_2$ is $X_{2c}$ and n is n2, m is 3 and n2 is 10. In some embodiments of the compound of Formula (II) or Formula (III), when $X_2$ is $X_{2c}$ and n is n2, m is 3 and n2 is 11. In some embodiments of the compound of Formula (II) or Formula (III), when $X_2$ is $X_{2c}$ and n is n2, m is 4 and n2 is 2. In some embodiments of the compound of Formula (II) or Formula (III), when $X_2$ is $X_{2c}$ and n is n2, m is 4 and n2 is 3. In some embodiments of the compound of Formula (II) or Formula (III), when $X_2$ is $X_{2c}$ and n is n2, m is 4 and n2 is 4. In some embodiments of the compound of Formula (II) or Formula (III), when $X_2$ is $X_{2c}$ and n is n2, m is 4 and n2 is 5. In some embodiments of the compound of Formula (II) or Formula (III), when $X_2$ is $X_{2c}$ and n is n2, m is 4 and n2 is 6. In some embodiments of the compound of Formula (II) or Formula (III), when $X_2$ is $X_{2c}$ and n is n2, m is 4 and n2 is 7. In some embodiments of the compound of Formula (II) or Formula (III), when $X_2$ is $X_{2c}$ and n is n2, m is 4 and n2 is 8. In some embodiments of the compound of Formula (II) or Formula (III), when $X_2$ is $X_{2c}$ and n is n2, m is 4 and n2 is 9. In some embodiments of the compound of Formula (II) or Formula (III), when $X_2$ is $X_{2c}$ and n is n2, m is 4 and n2 is 10. In some embodiments of the compound of Formula (II) or Formula (III), when $X_2$ is $X_{2c}$ and n is n2, m is 4 and n2 is 11. In some embodiments of the compound of Formula (II) or Formula (III), when $X_2$ is $X_{2c}$ and n is n2, m is 5 and n2 is 2. In some embodiments of the compound of Formula (II) or Formula (III), when $X_2$ is $X_{2c}$ and n is n2, m is 5 and n2 is 3. In some embodiments of the compound of Formula (II) or Formula (III), when $X_2$ is $X_{2c}$ and n is n2, m is 5 and n2 is 4. In some embodiments of the compound of Formula (II) or Formula (III), when $X_2$ is $X_{2c}$ and n is n2, m is 5 and n2 is 5. In some embodiments of the compound of Formula (II) or Formula (III), when $X_2$ is $X_{2c}$ and n is n2, m is 5 and n2 is 6. In some embodiments of the compound of Formula (II) or Formula (III), when $X_2$ is $X_{2c}$ and n is n2, m is 5 and n2 is 7. In some embodiments of the compound of Formula (II) or Formula (III), when $X_2$ is $X_{2c}$ and n is n2, m is 5 and n2 is 8. In some embodiments of the compound of Formula (II) or Formula (III), when $X_2$ is $X_{2c}$ and n is n2, m is 5 and n2 is 9. In some embodiments of the compound of Formula (II) or Formula (III), when $X_2$ is $X_{2c}$ and n is n2, m is 5 and n2 is 10. In some embodiments of the compound of Formula (II) or Formula (III), when $X_2$ is $X_{2c}$ and n is n2, m is 5 and n2 is 11. In some embodiments of the compound of Formula (II) or Formula (III), when $X_2$ is $X_{2c}$ and n is n2, m is 6 and n2 is 2. In some embodiments of the compound of Formula (II) or Formula (III), when $X_2$ is $X_{2c}$ and n is n2, m is 6 and n2 is 3. In some embodiments of the compound of Formula (II) or Formula (III), when $X_2$ is $X_{2c}$ and n is n2, m is 6 and n2 is 4. In some embodiments of the compound of Formula (II) or Formula (III), when $X_2$ is $X_{2c}$ and n is n2, m is 6 and n2 is 5. In some embodiments of the compound of Formula (II) or Formula (III), when $X_2$ is $X_{2c}$ and n is n2, m is 6 and n2 is 6. In some embodiments of the compound of Formula (II) or Formula (III), when $X_2$ is $X_{2c}$ and n is n2, m is 6 and n2 is 7. In some embodiments of the compound of Formula (II) or Formula (III), when $X_2$ is $X_{2c}$ and n is n2, m is 6 and n2 is 8. In some embodiments of the compound of Formula (II) or Formula (III), when $X_2$ is $X_{2c}$ and n is n2, m is 6 and n2 is 9. In some embodiments of the compound of Formula (II) or Formula (III), when $X_2$ is $X_{2c}$ and n is n2, m is 6 and n2 is 10. In some embodiments of the compound of Formula (II) or Formula (III), when $X_2$ is $X_{2c}$ and n is n2, m is 6 and n2 is 11. In some embodiments of the compound of Formula (II) or Formula (III), when $X_2$ is $X_{2c}$ and n is n2, m is 7 and n2 is 2. In some embodiments of the compound of Formula (II) or Formula (III), when $X_2$ is $X_{2c}$ and n is n2, m is 7 and n2 is 3. In some embodiments of the compound of Formula (II) or Formula (III), when $X_2$ is $X_{2c}$ and n is n2, m is 7 and n2 is 4. In some embodiments of the compound of Formula (II) or Formula (III), when $X_2$ is $X_{2c}$ and n is n2, m is 7 and n2 is 5. In some embodiments of the compound of Formula (II) or Formula (III), when $X_2$ is $X_{2c}$ and n is n2, m is 7 and n2 is 6. In some embodiments of the compound of Formula (II) or Formula (III), when $X_2$ is $X_{2c}$ and n is n2, m is 7 and n2 is 7. In some embodiments of the compound of Formula (II) or Formula (III), when $X_2$ is $X_{2c}$ and n is n2, m is 7 and n2 is 8. In some embodiments of the compound of Formula (II) or Formula (III), when $X_2$ is $X_{2c}$ and n is n2, m is 7 and n2 is 9. In some embodiments of the compound of Formula (II) or Formula (III), when $X_2$ is $X_{2c}$ and n is n2, m is 7 and n2 is 10. In some embodiments of the compound of Formula (II) or Formula (III), when $X_2$ is $X_{2c}$ and n is n2, m is 7 and n2 is 11. In some embodiments of the compound of Formula (II) or Formula (III), when $X_2$ is $X_{2c}$ and n is n2, m is 8 and n2 is 2. In some embodiments of the compound of Formula (II) or Formula (III), when $X_2$ is $X_{2c}$ and n is n2, m is 8 and n2 is 3. In some embodiments of the compound of Formula (II) or Formula (III), when $X_2$ is $X_{2c}$ and n is n2, m is 8 and n2 is 4. In some embodiments of the compound of Formula (II) or Formula (III), when $X_2$ is $X_{2c}$ and n is n2, m is 8 and n2 is 5. In some embodiments of the compound of Formula (II) or Formula (III), when $X_2$ is $X_{2c}$ and n is n2, m is 8 and n2 is 6. In some embodiments of the compound of Formula (II) or Formula (III), when $X_2$ is $X_{2c}$ and n is n2, m is 8 and n2 is 7. In some embodiments of the compound of Formula (II) or Formula (III), when $X_2$ is $X_{2c}$ and n is n2, m is 8 and n2 is 8. In some embodiments of the compound of Formula (II) or Formula (III), when $X_2$ is $X_{2c}$ and n is n2, m is 8 and n2 is 9. In some embodiments of the compound of Formula (II) or Formula (III), when $X_2$ is $X_{2c}$ and n is n2, m is 8 and n2 is 10. In some embodiments of the compound of Formula (II) or Formula (III), when $X_2$ is $X_{2c}$ and n is n2, m is 8 and n2 is 11. In some embodiments of the compound of Formula (II) or Formula (III), when $X_2$ is $X_{2c}$ and n is n2, m is 9 and n2 is 2. In some embodiments of the compound of Formula (II) or Formula (III), when $X_2$ is $X_{2c}$ and n is n2, m is 9 and n2 is 3. In some embodiments of the compound of Formula (II) or Formula (III), when $X_2$ is $X_{2c}$ and n is n2, m is 9 and n2 is 4. In some embodiments of the compound of Formula (II) or Formula (III), when $X_2$ is $X_{2c}$ and n is n2, m is 9 and n2 is 5. In some embodiments of the compound of Formula (II) or Formula (III), when $X_2$ is $X_{2c}$ and n is n2, m is 9 and n2 is 6. In some embodiments of the compound of Formula (II) or Formula (III), when $X_2$ is $X_{2c}$ and n is n2, m is 9 and n2 is 7. In some embodiments of the compound of Formula (II) or Formula (III), when $X_2$ is $X_{2c}$ and n is n2, m is 9 and n2 is 8. In some embodiments of the compound of Formula (II) or Formula (III), when $X_2$ is $X_{2c}$ and n is n2, m is 9 and n2 is 9. In some embodiments of the compound of Formula (II) or Formula (III), when $X_2$ is $X_{2c}$ and n is n2, m is 9 and n2 is 10. In some embodiments of the compound of Formula (II) or Formula (III), when $X_2$ is $X_{2c}$ and n is n2, m is 9 and n2 is 11. In some embodiments of the compound of Formula (II) or Formula (III), when $X_2$ is $X_{2c}$ and n is n2, m is 10 and n2 is 2. In some embodiments of the compound of Formula (II) or Formula (III), when $X_2$ is $X_{2c}$ and n is n2, m is 10 and n2 is 3. In some embodiments of the compound of Formula (II) or Formula (III), when $X_2$ is $X_{2c}$ and n is n2, m is 10 and n2 is 4. In some embodiments of the compound of Formula (II) or Formula (III), when $X_2$ is $X_{2c}$ and n is n2, m is 10 and n2 is 5. In some embodiments of the compound of Formula (II) or Formula (III), when $X_2$ is $X_{2c}$ and n is n2, m is 10 and n2 is 6. In some embodiments of the compound of Formula (II) or Formula (III), when $X_2$ is $X_{2c}$ and n is n2, m is 10 and n2 is 7. In some embodiments of the compound of Formula (II) or Formula (III), when $X_2$ is $X_{2c}$ and n is n2, m is 10 and n2 is 8. In some embodiments of the compound of Formula (II) or Formula (III), when $X_2$ is $X_{2c}$ and n is n2, m is 10 and n2 is 9. In some embodiments of the compound of Formula (II) or Formula (III), when $X_2$ is $X_{2c}$ and n is n2, m is 10 and n2 is 10. In some embodiments of the compound of Formula (II) or Formula (III), when $X_2$ is $X_{2c}$ and n is n2, m is 10 and n2 is 11. In some embodiments of the compound of Formula (II) or Formula (III), when $X_2$ is $X_{2c}$ and n is n2, n2 is 2 or 3 and n2 is 1. In some embodiments of the compound of Formula (II) or Formula (III), when $X_2$ is $X_{2c}$ and n is n2, n2 is 2 and n2 is 1. In some embodiments of the compound of Formula (II) or Formula (III), when $X_2$ is $X_{2c}$ and n is n2, n2 is 3 and n2 is 1. In some embodiments of the compound of Formula (II) or Formula (III), when $X_2$ is $X_{2c}$ and n is n2, n2 is 1, 2, 3, 4, or 5 and n2 is 1, 2 or 3. In some embodiments of the compound of Formula (II) or Formula (III), when $X_2$ is $X_{2c}$ and n is n2, n2 is 1, 2, 3, 4, or 5 and n2 is 1. In some embodiments of the compound of Formula (II) or Formula (III), when $X_2$ is $X_{2c}$ and n is n2, n2 is 1, 2, 3, 4, or 5 and n2 is 2. In some embodiments of the compound of Formula (II) or Formula (III), when $X_2$ is $X_{2c}$ and n is n2, n2 is 1, 2, 3, 4, or 5 and n2 is 3. In some embodiments of the compound of Formula (II) or Formula (III), when $X_2$ is $X_{2c}$ and n is n2, n2 is 1 and n2 is 1, 2 or 3. In some embodiments of the compound of Formula (II) or Formula (III), when $X_2$ is $X_{2c}$ and n is n2, n2 is 2 and n2 is 1, 2 or 3. In some embodiments of the compound of Formula (II) or Formula (III), when $X_2$ is $X_{2c}$ and n is n2, n2 is 3 and n2 is 1, 2 or 3. In some embodiments of the compound of Formula (II) or Formula (III), when $X_2$ is $X_{2c}$ and n is n2, n2 is 4 and n2 is 1, 2 or 3. In some embodiments of the compound of Formula (II) or Formula (III), when $X_2$ is $X_{2c}$ and n is n2, n2 is 5 and n2 is 1, 2 or 3.

In some embodiments of the compound of Formula (II) or Formula (III), the molar ratio of $X_3$ to $X_1$ is between 1:1 and 110:1. In some embodiments of the compound of Formula (II) or Formula (III), the molar ratio of $X_3$ to $X_1$ is between 1:1 and 50:1. In some embodiments of the compound of Formula (II) or Formula (III), the molar ratio of $X_3$ to $X_1$ is between 1:1 and 10:1. In some embodiments of the compound of Formula (II) or Formula (III), the molar ratio of $X_3$ to $X_1$ is between 1:1 and 5:1. In some embodiments of the compound of Formula (II) or Formula (III), the molar ratio of $X_3$ to $X_1$ is between 10:1 and 50:1. In some embodiments of the compound of Formula (II) or Formula (III), the molar ratio of $X_3$ to $X_1$ is between 50:1 and 110:1. In some embodiments of the compound of Formula (II) or Formula (III), the molar ratio of $X_3$ to $X_1$ is 1:1. In some embodiments of the compound of Formula (II) or Formula (III), the molar ratio of $X_3$ to $X_1$ is 2:1. In some embodiments of the compound of Formula (II) or Formula (III), the molar ratio of $X_3$ to $X_1$ is 3:1. In some embodiments of the compound of Formula (II) or Formula (III), the molar ratio of $X_3$ to $X_1$ is 4:1. In some embodiments of the compound of Formula (II) or Formula (III), the molar ratio of $X_3$ to $X_1$ is 5:1. In some embodiments of the compound of Formula (II) or Formula (III), the molar ratio of $X_3$ to $X_1$ is 6:1. In some embodiments of the compound of Formula (II) or Formula (III), the molar ratio of $X_3$ to $X_1$ is 7:1. In some embodiments of the compound of Formula (II) or Formula (III), the molar ratio of $X_3$ to $X_1$ is 8:1. In some embodiments of the compound of Formula (II) or Formula (III), the molar ratio of $X_3$ to $X_1$ is 9:1. In some embodiments of the compound of Formula (II) or Formula (III), the molar ratio of $X_3$ to $X_1$ is 10:1. In some embodiments of the compound of Formula (II) or Formula (III), the molar ratio of $X_3$ to $X_1$ is 11:1. In some embodiments of the compound of Formula (II) or Formula (III), the molar ratio of $X_3$ to $X_1$ is 12:1. In some embodiments of the compound of Formula (II) or Formula (III), the molar ratio of $X_3$ to $X_1$ is 13:1. In some embodiments of the compound of Formula (II) or Formula (III), the molar ratio of $X_3$ to $X_1$ is 14:1. In some embodiments of the compound of Formula (II) or Formula (III), the molar ratio of $X_3$ to $X_1$ is 15:1. In some embodiments of the compound of Formula (II) or Formula (III), the molar ratio of $X_3$ to $X_1$ is 16:1. In some embodiments of the compound of Formula (II) or Formula (III), the molar ratio of $X_3$ to $X_1$ is 17:1. In some embodiments of the compound of Formula (II) or Formula (III), the molar ratio of $X_3$ to $X_1$ is 18:1. In some embodiments of the compound of Formula (II) or Formula (III), the molar ratio of $X_3$ to $X_1$ is 19:1. In some embodiments of the compound of Formula (II) or Formula (III), the molar ratio of $X_3$ to $X_1$ is 20:1.

$X_1$ is a biologically active polypeptide, e.g., a polypeptide exerting its own biological effect on specified targets, or a hormone. Cytokines, growth factors (GF), and hormones are all chemical messengers that mediate intercellular communication. The regulation of intracellular and nuclear functions by cytokines, growth factors, and hormones is initiated through the activation of cell surface receptors (Rc). All receptors generally have two main components: 1) a ligand-binding domain that ensures ligand specificity and 2) an effector domain that initiates the generation of the biological response upon ligand binding. The activated receptor may then interact with other cellular components to complete the signal transduction process. Among such proteins are IL-2 polypeptides and its bio-active homolog polypeptides.

Cytokines are a large group of proteins, peptides or glycoproteins that are secreted by specific cells of the immune system. Cytokines are a category of signaling molecules that mediate and regulate immunity, inflammation and hematopoiesis. Cytokines are produced throughout the body by cells of diverse embryological origin. Cytokines and their receptors exhibit very high affinity for each other. Because of this high affinity, low concentrations, such as picomolar concentrations, of cytokines can mediate a biological effect. Examples of cytokines used in the disclosure include, but are not limited to: an Acylation stimulating protein polypeptide, an Adipokine polypeptide, an Albinterferon polypeptide, a Cerberus polypeptide, a Colony-stimulating factor polypeptide, an Erythropoietin polypeptide, a FMS-like tyrosine kinase 3 ligand polypeptide, a Globulin component Macrophage Activating Factor (GcMAF) polypeptide, a Granulocyte colony-stimulating factor polypeptide, a Granulocyte-macrophage colony-stimulating factor polypeptide, a Hepatocyte growth factor polypeptide, an IL-17 polypeptide, an IL-10 polypeptide, an Inflammasome polypeptide, an Interferome polypeptide, an Interferon polypeptide, an Interferon beta-la polypeptide, an Interferon beta-1b polypeptide, an Interferon gamma polypeptide, an Interferon type I polypeptide, an Interferon type II polypeptide, an Interferon type III polypeptide, an Interleukin polypeptide, an Interleukin 1 receptor antagonist polypeptide, an Interleukin 8 polypeptide, a Leukemia inhibitory factor polypeptide, a Leukocyte-promoting factor polypeptide, a Lymphokine polypeptide, a Lymphotoxin polypeptide, a Lymphotoxin alpha polypeptide, a Lymphotoxin beta polypeptide, a Macrophage colony-stimulating factor polypeptide, a Macrophage inflammatory protein polypeptide, a Macrophage-activating factor polypeptide, a Monokine polypeptide, a Myokine polypeptide, a Myonectin polypeptide, a Nicotinamide phosphoribosyltransferase polypeptide, an Oncostatin M polypeptide, an Oprelvekin polypeptide, a Platelet factor 4 polypeptide, a Proinflammatory cytokine polypeptide, a Promegapoietin polypeptide, a Receptor activator of nuclear factor kappa-B ligand (RANKL) polypeptide, a Stromal cell-derived factor 1 polypeptide, a Tumor necrosis factor alpha polypeptide, a Tumor necrosis factor superfamily polypeptide, and a vascular endothelial growth inhibitor polypeptide.

Growth factors are naturally occurring substances capable of stimulating cellular growth, proliferation, healing, and cellular differentiation. Usually these are proteins or steroid hormones. They are important for regulating a variety of cellular processes, typically act as signaling molecules between cells. Examples are cytokines and hormones that bind to specific receptors on the surface of their target cells. They often promote cell differentiation and maturation, which varies between growth factors. Examples of growth factors used in the disclosure include, but are not limited to: an adrenomedullin (AM) polypeptide, an angiopoietin (Ang) polypeptide, an Autocrine motility factor polypeptide, a Bone morphogenetic proteins (BMPs) polypeptide, a ciliary neurotrophic factor family polypeptide, a Ciliary neurotrophic factor (CNTF) polypeptide, a Leukemia inhibitory factor (LIF) polypeptide, an Interleukin-6 (IL-6) polypeptide, a Colony-stimulating factor polypeptide, a Macrophage colony-stimulating factor (m-CSF) polypeptide, a Granulocyte colony-stimulating factor (G-CSF) polypeptide, a Granulocyte macrophage colony-stimulating factor (GM-CSF) polypeptide, an Epidermal growth factor (EGF) polypeptide, an Ephrin polypeptide (e.g., an Ephrin A1 polypeptide, an Ephrin A2 polypeptide, an Ephrin A3 polypeptide, an Ephrin A4 polypeptide, an Ephrin A5 polypeptide, an Ephrin B1 polypeptide, an Ephrin B2 polypeptide, and an Ephrin B3 polypeptide), an Erythropoietin (EPO) polypeptide, a Fibroblast growth factor (FGF) polypeptide, a Fibroblast growth factor 1 (FGF1) polypeptide, a fibroblast growth factor 2 (FGF2) polypeptide, a Fibroblast growth factor 3 (FGF3) polypeptide, a Fibroblast growth factor 4 (FGF4) polypeptide, a fibroblast growth factor 5 (FGF5) polypeptide, a Fibroblast growth factor 6 (FGF6) polypeptide, a Fibroblast growth factor 7 (FGF7) polypeptide, a fibroblast growth factor 8 (FGF8) polypeptide, a Fibroblast growth factor 9 (FGF9) polypeptide, a Fibroblast growth factor 10 (FGF10) polypeptide, a Fibroblast growth factor 11 (FGF11) polypeptide, a Fibroblast growth factor 12 (FGF12) polypeptide, a Fibroblast growth factor 13 (FGF13) polypeptide, a Fibroblast growth factor 14 (FGF14) polypeptide, a Fibroblast growth factor 15 (FGF15) polypeptide, a Fibroblast growth factor 16 (FGF16) polypeptide, a Fibroblast growth factor 17 (FGF17) polypeptide, a Fibroblast growth factor 18 (FGF18) polypeptide, a Fibroblast growth factor 19 (FGF19) polypeptide, a Fibroblast growth factor 20 (FGF20) polypeptide, a Fibroblast growth factor 21 (FGF21) polypeptide, a Fibroblast growth factor 22 (FGF22) polypeptide, a Fibroblast growth factor 23 (FGF23) polypeptide, a Foetal Bovine Somatotrophin (FBS) polypeptide, a Glial cell line-derived neurotrophic factor (GDNF) polypeptide, a Neurturin polypeptide, a Persephin polypeptide, an Artemin polypeptide, a Growth differentiation factor-9 (GDF9) polypeptide, a Hepatocyte growth factor (HGF) polypeptide, a Hepatoma-derived growth factor (HDGF) polypeptide, an Insulin polypeptide, an Insulin-like growth factor polypeptide, an Insulin-like growth factor-1 (IGF-1) polypeptide, an Insulin-like growth factor-2 (IGF-2) polypeptide, an Interleukin polypeptide, an IL-1 polypeptide, an IL-1 polypeptide, an IL-2 polypeptide or bio-active homolog thereof, an IL-3 polypeptide, an IL-4 polypeptide, an IL-5 polypeptide, an IL-6 polypeptide, an IL-7 polypeptide, a Keratinocyte growth factor (KGF) polypeptide, a Migration-stimulating factor (MSF) polypeptide, a Macrophage-stimulating protein (MSP) polypeptide, a Myostatin (GDF-8) polypeptide, a Neuregulin polypeptide, a Neuregulin 1 (NRG1) polypeptide, a Neuregulin 2 (NRG2) polypeptide, a Neuregulin 3 (NRG3) polypeptide, a Neuregulin 4 (NRG4) polypeptide, a Neurotrophin polypeptide, a Brain-derived neurotrophic factor (BDNF) polypeptide, a Nerve growth factor (NGF) polypeptide, a Neurotrophin-3 (NT-3) polypeptide, a Neurotrophin-4 (NT4) polypeptide, a Placental growth factor (PGF) polypeptide, a Platelet-derived growth factor (PDGF) polypeptide, a Renalase (RNLS) polypeptide, an anti-apoptotic survival factor polypeptide, a T-cell growth factor (TCGF) polypeptide, a Thrombopoietin (TPO) polypeptide, a Transforming growth factor polypeptide, a Transforming growth factor alpha (TGF-$\alpha$) polypeptide, a Transforming growth factor beta (TGF-8) polypeptide, a Tumor necrosis factor-alpha (TNF-$\alpha$) polypeptide, a Vascular endothelial growth factor (VEGF) polypeptide, and a Wnt Signaling Pathway polypeptide.

Figure 2A:
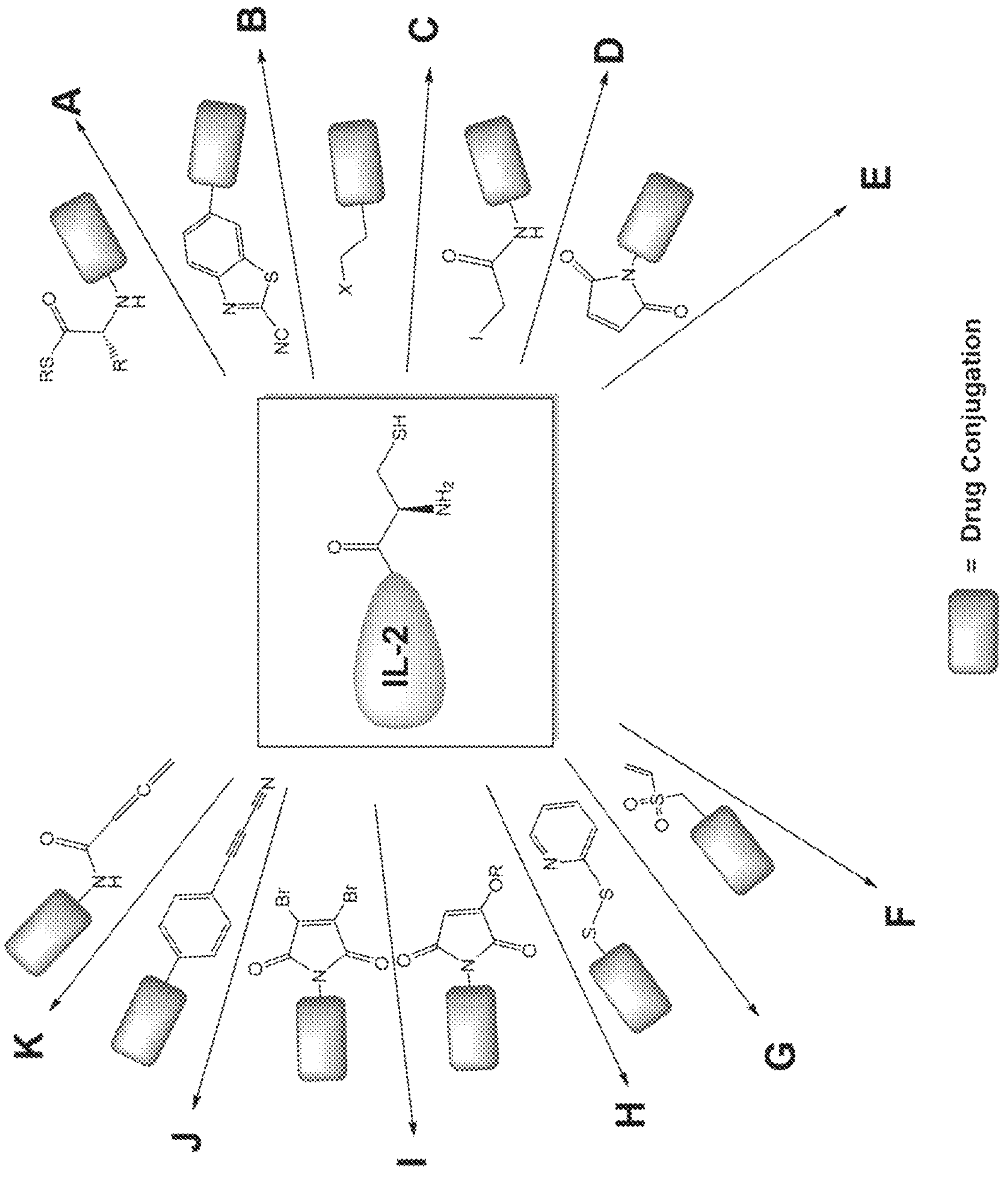
FIGS. 2A and 2B are a schematic showing Cys-specific IL-2 polypeptide-Linker-therapeutic compound conjugations in accordance with some embodiments of the disclosure. Ts=tosyl; R groups=alkyl, aryl, and arylalkyl; E+ groups=electophiles such as alkyl halides, alkynes, alkenes, and the like; Ar=aryl groups such as phenyl groups, substituted phenyl groups, aromatic heterocycles, and the like; X=halogens, alkyl sulfonates, aryl sulfonates and general leaving groups.
Figure 2B:
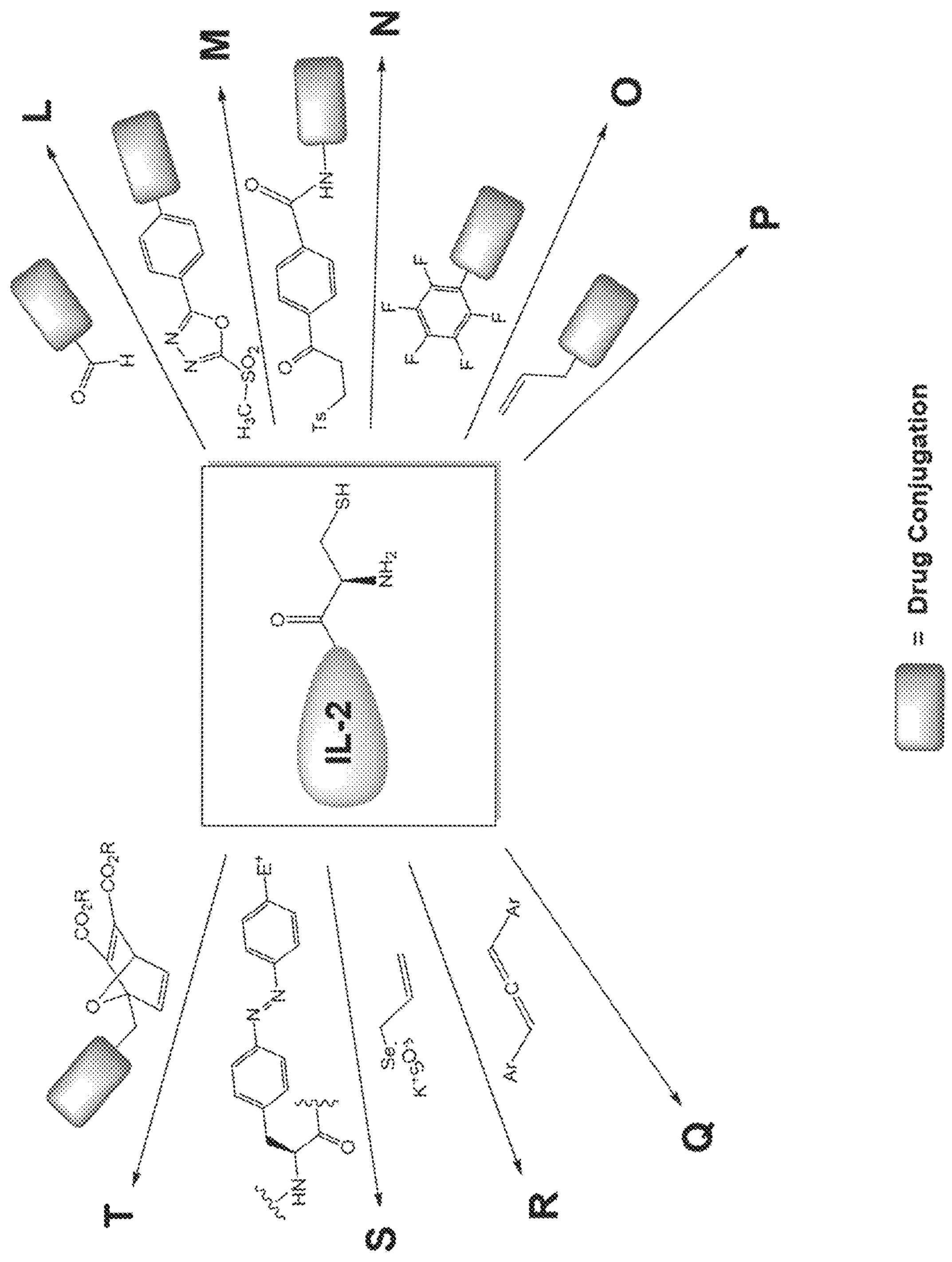
Figure 4:
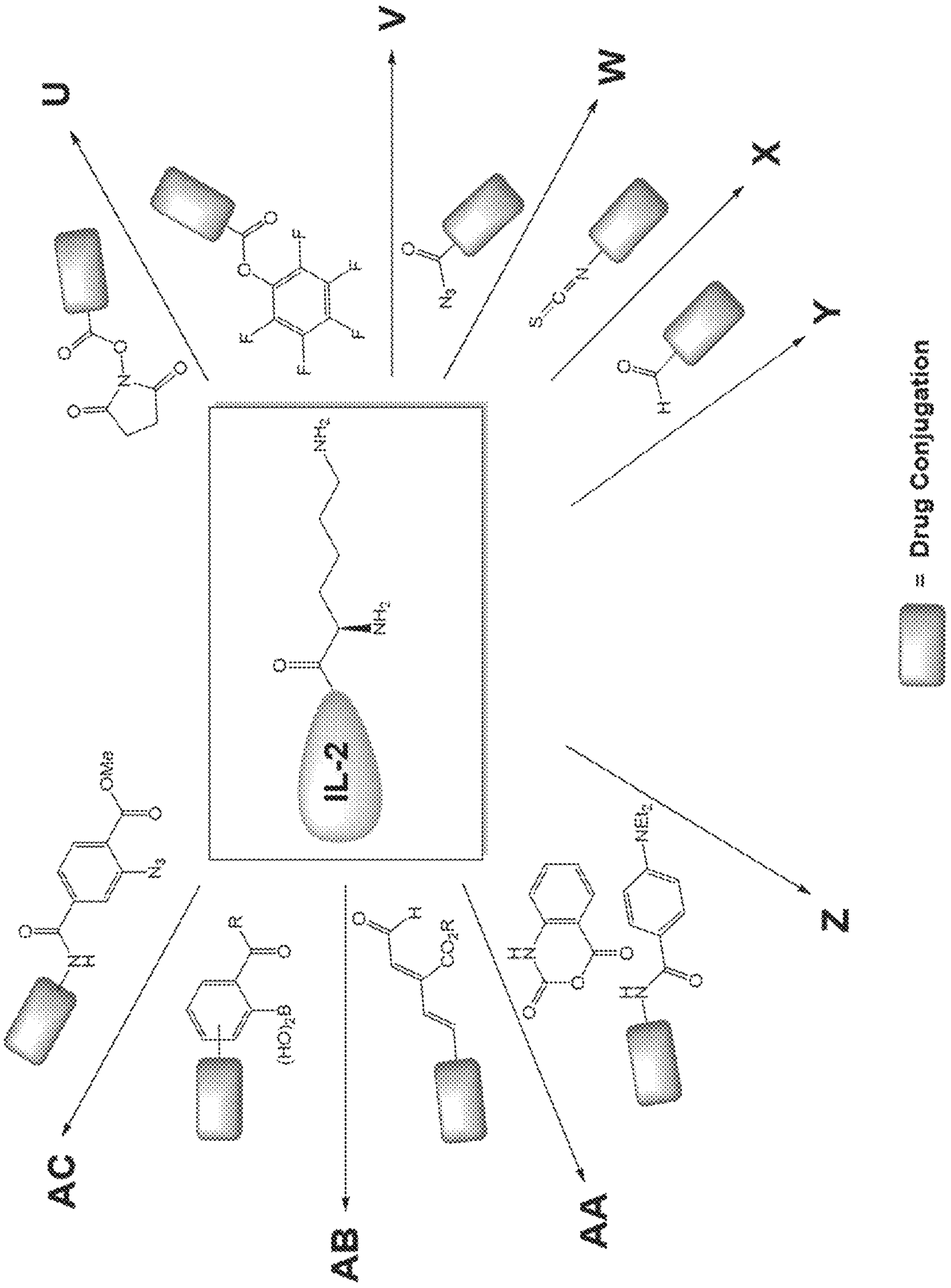
FIG. 4 is a schematic showing Lys-specific IL-2 polypeptide-Linker-therapeutic compound conjugations in accordance with some embodiments of the disclosure. R groups=alkyl, aryl, and arylalkyl.

Distinct IL-2 polypeptides were produced and shown to express activity for the high affinity receptor and each allows for the conjugation of a linker to a distinct amino acid site available to attach the therapeutic compound payload. One IL-2 polypeptide produced is the Human Mat IL2 wild-type, and another is the Human Mat IL2 wild-type Cys-N-positions. There are seven Lys residues identified in the first structure which are available for conjugation (FIG. 1). In the second structure, there are a total of three Cys residues present (two form a disulfide bond and and are not available for bioconjugation). Each of these distinct proteins can be conjugated using either the Cys or Lys amino acid residues through a series of different chemistries (FIGS. 2-4). [11, 12, 13, 14] The Cys residue has been functionalized in the first 20 (Series A through T) reaction shown. The resulting linkage is shown in FIG. 3. The Lys residue has also been functionalized through chemical reactions as shown in FIG. 3. FIG. 3 also shows the resulting products from the conjugation as series U through AC. Other amino acid residues can be used to conjugate linkers and payloads for the formation of site specific therapeutic compound conjugates. FIG. 4 shows examples of additional Lys-specific conjugations. In some embodiments, the IL-2 polypeptide of the compounds of the disclosure (e.g., compounds of Formula (II) or Formula (III), or pharmaceutically acceptable salts, solvates, hydrates, isomers, or tautomers thereof) is a wild-type human IL-2 polypeptide or a known mutant or variant thereof.

IL-2 polypeptides or bio-active homolog polypeptides produced in the disclosure are detailed in Table 4. The IL-2 polypeptides or bio-active homolog polypeptides of Table 4 may exhibit increased half life and solubility compared to wild-type human IL-2. These IL-2 polypeptides or bio-active homolog polypeptides also have an increased number of cysteines compared to wild-type human IL-2 yet retain high affinity for IL-2R, even after conjugation with a linker and a therapeutic compound.

TABLE 4

IL-2 Polypeptides

| SEQ ID NO and Name | Amino acid sequence |
|---|---|
| SEQ ID NO: 1 IL-2 C125S (WT, human) | APTSSSTKKTQLQLEHLLLDLQMILNGINNYKNPKLTRMLTFKFYMPKKATELKHLQCL EEELKPLEEVLNLAQSKNFHLRPRDLISNINVIVLELKGSETTFMCEYADETATIVEFLNR WITFSQSIISTLT |
| SEQ ID NO: 2 UniProtKB/ Swiss-Prot: P10599.3 (TXN)/UniProt KB - P60568 (IL2_HUMAN) + GSAM linker, IL-2 C125S mutant | MVKQIESKTAFQEALDAAGDKLVVVDFSATWCGPCKMIKPFFHSLSE KYSNVIFLEVDVDDCQDVASECEVKCMPTFQFFKKGQKVGEFSGAN KEKLEATINELVGSAMAPTSSSTKKTQLQLEHLLLDLQMILNGINNYK NPKLTRMLTFKFYMPKKATELKHLQCLEEELKPLEEVLNLAQSKNFH LRPRDLISNINVIVLELKGSETTFMCEYADETATIVEFLNRWITFSQSIIS TLT |
| SEQ ID NO: 3 Human Mat IL2 WT | APTSSSTKKTQLQLEHLLLDLQMILNGINNYKNPKLTRMLTFKFYMPKKATELKHLQCL EEELKPLEEVLNLAQSKNFHLRPRDLISNINVIVLELKGSETTFMCEYADETATIVEFLNR WITFCQSIISTLT |
| SEQ ID NO: 4 Human Mat IL-2 WT Cys-N-positions | CAPTSSSTKKTQLQLEHLLLDLQMILNGINNYKNPKLTRMLTFKFYMPKKATELKHLQC LEEELKPLEEVLNLAQSKNFHLRPRDLISNINVIVLELKGSETTFMCEYADETATIVEFLNR WITFCQSIISTLT |

In some embodiments, the IL-2 polypeptides or bio-active homolog polypeptides of the disclosure have at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to an amino acid sequence of Table 4. In some embodiments, the IL-2 polypeptides or bio-active homolog polypeptides of the disclosure have at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2.

Hormones are any member of a class of signaling molecules produced by glands in, multicellular organisms that are transported by the circulatory system to target distant organs to regulate physiology and behavior. Hormones have diverse chemical structures, mainly of three classes: eicosanoids, steroids, and amino acid/protein derivatives (amines, peptides, and proteins). The glands that secrete hormones comprise the endocrine signaling system. The term hormone is sometimes extended to include chemicals produced by cells that affect the same cell (autocrine or intracrine signalling) or nearby cells (paracrine signalling).

Hormones are used to communicate between organs and tissues for physiological regulation and behavioral activities, such as digestion, metabolism, respiration, tissue function, sensory perception, sleep, excretion, lactation, stress, growth and development, movement, reproduction, and mood. Hormones affect distant cells by binding to specific receptor proteins in the target cell resulting in a change in cell function. When a hormone binds to the receptor, it results in the activation of a signal transduction pathway that typically activates gene transcription resulting in increased expression of target proteins; non-genomic effects are more rapid, and can be synergistic with genomic effects. Amino acid-based hormones (amines and peptide or protein hormones) are water-soluble and act on the surface of target cells via second messengers; steroid hormones, being lipid-soluble, move through the plasma membranes of target cells (both cytoplasmic and nuclear) to act within their nuclei. Examples of hormones used in the disclosure include, but are not limited to: Melatonin, Serotonin, Thyroxine, Epinephrine, Norepinephrine, Dopamine, an Antimullerianopolypeptide, an Adiponectin polypeptide, an Adrenocorticotropic Hormone polypeptide, an Angiotensinogen polypeptide, Antidiuretic Hormone, Atrial Natriuretic Peptide, a Calcitonin polypeptide, a Cholecystokinin polypeptide, a Corticotrophin-Releasing Erythropoietin polypeptide, a Follicle Stimulating Hormone polypeptide, a Gastrin polypeptide, a Ghrelin polypeptide, a Glucagon polypeptide, a Growth Hormone-Releasing Hormone polypeptide, a Human Chorionic Growth Hormone polypeptide, an Insulin polypeptide, an Insulin-Like Growth Factor polypeptide, a Leptin polypeptide, a Luteinizing Hormone polypeptide, a Melanocyte Stimulating Hormone, an Orexin polypeptide, an Oxytocin polypeptide, a Parathyroid Hormone polypeptide, a Prolactin polypeptide, a Secretin polypeptide, Aldosterone, Testosterone, Androstenedione, Estradiol, Progesterone, a Lipotropin polypeptide, a Brain natriuretic peptide polypeptide, Histamine, an Endothelin polypeptide, and Enkephalin.

In some embodiments, $X_1$ is selected from the group consisting of an Acylation stimulating protein polypeptide, an Adipokine polypeptide, an Albinterferon polypeptide, a Cerberus polypeptide, a Colony-stimulating factor polypeptide, an Erythropoietin polypeptide, a FMS-like tyrosine kinase 3 ligand polypeptide, a Globulin component polypeptide, a Macrophage Activating Factor polypeptide, a Granulocyte colony-stimulating factor polypeptide, a Granulocyte-macrophage colony-stimulating factor polypeptide, a Hepatocyte growth factor polypeptide, an IL-17 polypeptide, an IL-10 polypeptide, an Inflammasome polypeptide, an Interferome polypeptide, an Interferon polypeptide, an Interferon beta-la polypeptide, an Interferon beta-1b polypeptide, an Interferon gamma polypeptide, an Interferon type I polypeptide, an Interferon type II polypeptide, an Interferon type III polypeptide, an Interleukin polypeptide, an Interleukin 1 receptor antagonist polypeptide, an Interleukin 8 polypeptide, a Leukemia inhibitory factor polypeptide, a Leukocyte-promoting factor polypeptide, a Lymphokine polypeptide, a Lymphotoxin polypeptide, a Lymphotoxin alpha polypeptide, a Lymphotoxin beta polypeptide, a Macrophage colony-stimulating factor polypeptide, a Macrophage inflammatory protein polypeptide, a Macrophage-activating factor polypeptide, a Monokine polypeptide, a Myokine polypeptide, a Myonectin polypeptide, a Nicotinamide phosphoribosyltransferase polypeptide, an Oncostatin M polypeptide, an Oprelvekin polypeptide, a Platelet factor 4 polypeptide, a Proinflammatory cytokine polypeptide, a Promegapoietin polypeptide, a Receptor activator of nuclear factor kappa-B ligand polypeptide, a Stromal cell-derived factor 1 polypeptide, an adrenomedullin polypeptide, an angiopoietin polypeptide, an Autocrine motility factor polypeptide, a Bone morphogenetic protein polypeptide, a Ciliary neurotrophic factor polypeptide, an Interleukin-6 polypeptide, an Epidermal growth factor polypeptide, an Ephrin A1 polypeptide, an Ephrin A2 polypeptide, an Ephrin A3 polypeptide, an Ephrin A4 polypeptide, an Ephrin A5 polypeptide, an Ephrin B1 polypeptide, an Ephrin B2 polypeptide, an Ephrin B3 polypeptide, a Fibroblast growth factor polypeptide, a Fibroblast growth factor 1 polypeptide, a fibroblast growth factor 2 polypeptide, a Fibroblast growth factor 3 polypeptide, a Fibroblast growth factor 4 polypeptide, a fibroblast growth factor 5 polypeptide, a Fibroblast growth factor 6 polypeptide, a Fibroblast growth factor 7 polypeptide, a fibroblast growth factor 8 polypeptide, a Fibroblast growth factor 9 polypeptide, a Fibroblast growth factor 10 polypeptide, a Fibroblast growth factor 11 polypeptide, a Fibroblast growth factor 12 polypeptide, a Fibroblast growth factor 13 polypeptide, a Fibroblast growth factor 14 polypeptide, a Fibroblast growth factor 15 polypeptide, a Fibroblast growth factor 16 polypeptide, a Fibroblast growth factor 17 polypeptide, a Fibroblast growth factor 18 polypeptide, a Fibroblast growth factor 19 polypeptide, a Fibroblast growth factor 20 polypeptide, a Fibroblast growth factor 21 polypeptide, a Fibroblast growth factor 22 polypeptide, a Fibroblast growth factor 23 polypeptide, a Foetal Bovine Somatotrophin polypeptide, a Glial cell line-derived neurotrophic factor polypeptide, a Neurturin polypeptide, a Persephin polypeptide, an Artemin polypeptide, a Growth differentiation factor-9 polypeptide, a Hepatoma-derived growth factor polypeptide, an Insulin polypeptide, an Insulin-like growth factor polypeptide, an Insulin-like growth factor-1 polypeptide, an Insulin-like growth factor-2 polypeptide, an IL-1 polypeptide, an IL-2 polypeptide or bio-active homolog thereof, an IL-3 polypeptide, an IL-4 polypeptide, an IL-5 polypeptide, an IL-6 polypeptide, an IL-7 polypeptide, a Keratinocyte growth factor polypeptide, a Migration-stimulating factor polypeptide, a Macrophage-stimulating protein polypeptide, a Myostatin polypeptide, a Neuregulin 1 polypeptide, a Neuregulin 2 polypeptide, a Neuregulin 3 polypeptide, a Neuregulin 4 polypeptide, a Brain-derived neurotrophic factor polypeptide, a Nerve growth factor polypeptide, a Neurotrophin-3 polypeptide, a Neurotrophin-4 polypeptide, a Placental growth factor polypeptide, a Platelet-derived growth factor polypeptide, a Renalase polypeptide, an anti-apoptotic survival factor polypeptide, a T-cell growth factor polypeptide, a Thrombopoietin polypeptide, a Transforming growth factor alpha polypeptide, a Transforming growth factor beta polypeptide, a Tumor necrosis factor-alpha polypeptide, a Vascular endothelial growth factor polypeptide, and a Wnt Signaling Pathway polypeptide.

In some embodiments of the compound of Formula (II) or Formula (III), $X_2$ is a linker, which can take many forms as shown herein. In some embodiments of the compound of Formula (II) or Formula (III), $X_2$ is a cleavable linker. In some embodiments of the compound of Formula (II) or Formula (III), $X_2$ is a non-cleavable linker. In some embodiments of the compound of Formula (II) or Formula (III), $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_2$b moieties bound to $X_1$ and n2 corresponds to the number of $X_{2c}$ moieties bound to $X_1$, and the combination of n1 and n2 has a sum of 2, 3, 4, 5, 6, 7, 8, 9, 10, or 11. In some embodiments, each $X_2$ bound to $X_1$ is an $X_{2b}$ moiety. In some embodiments, each $X_2$ bound to $X_1$ is an $X_2$c moiety. In some embodiments of the compound of Formula (II) or Formula (III), $X_2$ is a linker listed in Table 5, wherein the left side of $X_2$, as drawn, is bound to $X_1$, and the right side of $X_2$, as drawn, is bound to $X_3$. In Table 5, R=H, alkyl, aryl, arylalkyl, glycol ether, or an additional glycol linker attaching to the therapeutic compound.

TABLE 5

Exemplary $X_2$ Linkers

| Compound Number | Structure |
| --- | --- |
| K-1 Cleavable linker | 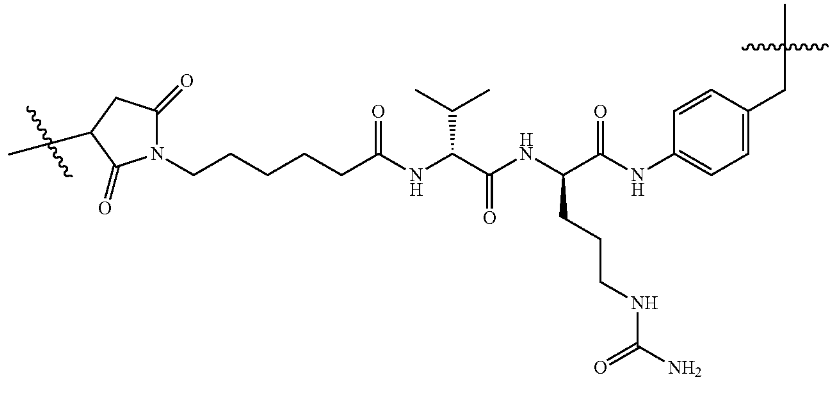 [SMILES: *Cc1ccc(NC(=O)[C@@H](CCCNC(N)=O)NC(=O)[C@H](NC(=O)CCCCCN2C(=O)CC(*)C2=O)C(C)C)cc1] |

TABLE 5-continued
| Exemplary $X_2$ Linkers | |
|---|---|
| Compound Number | Structure |
| K-2 Cleavable linker | 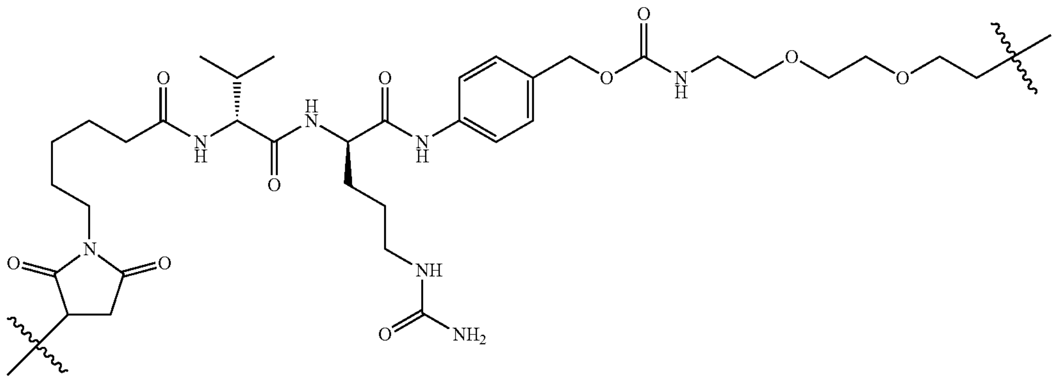 [SMILES: *CCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |
| K-3 Cleavable linker | 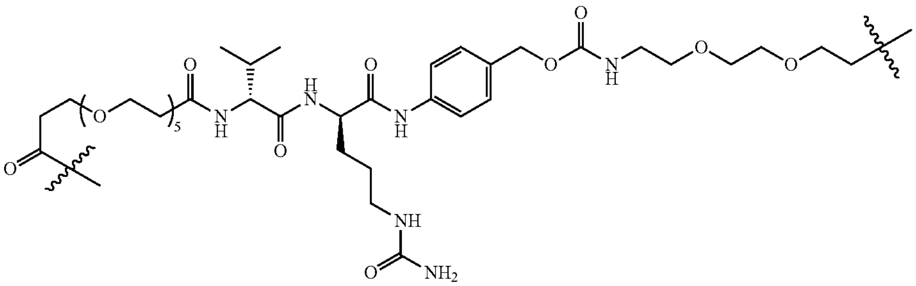 |
| K-4 Cleavable linker | 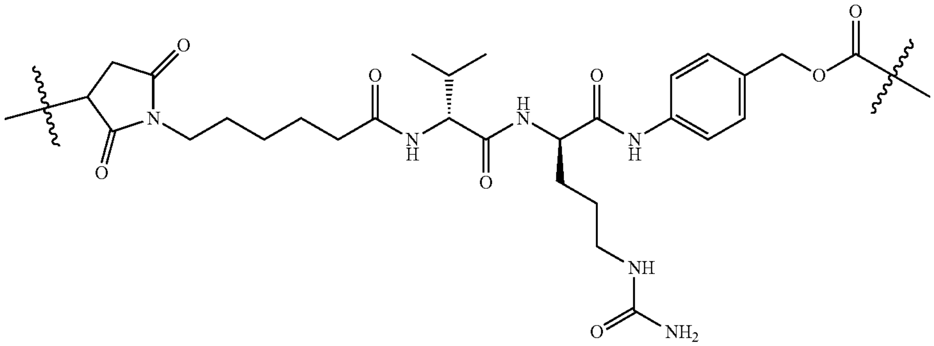 [SMILES: *C(=O)OCc1ccc(NC(=O)[C@@H](CCCNC(N)=O)NC(=O)[C@H](NC(=O)CCCCCN2C(=O)CC(*)C2=O)C(C)C)cc1] |
| K-5 Cleavable linker | 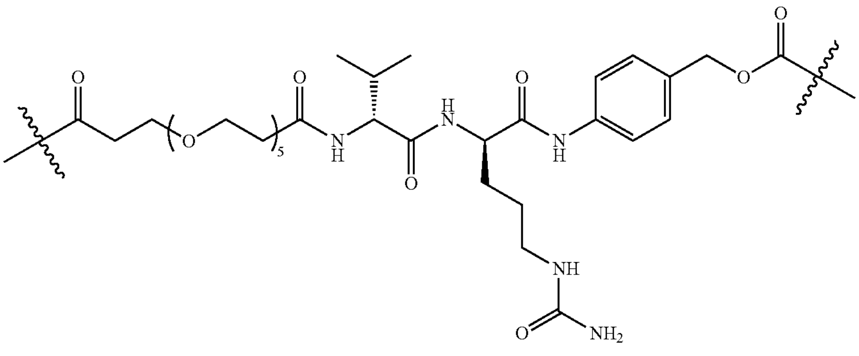 |

TABLE 5-continued
| Exemplary $X_2$ Linkers | |
|---|---|
| Compound Number | Structure |
| K-6 Cleavable linker | 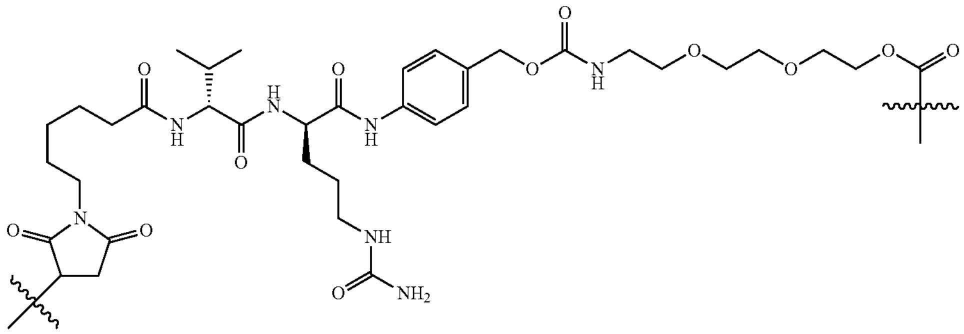 [SMILES: *C(=O)OCCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |
| K-7 Cleavable linker | 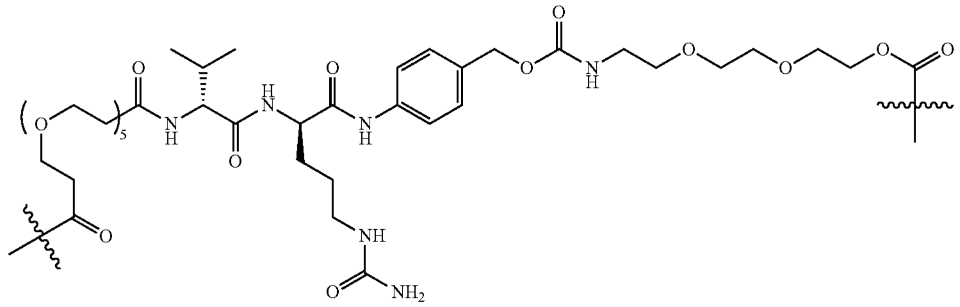 |
| K-8 Cleavable linker | 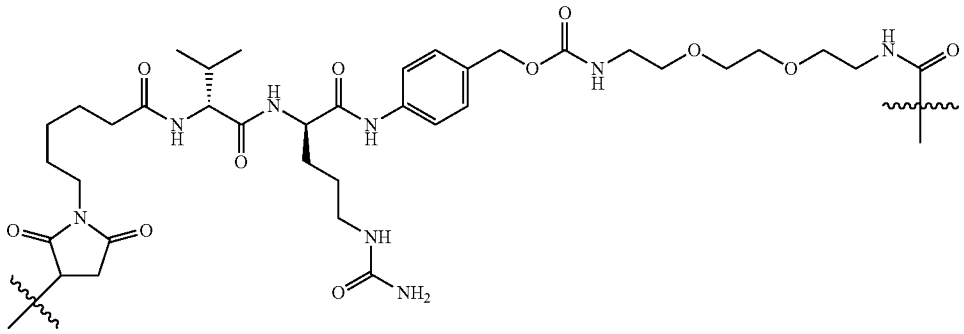 [SMILES: *C(=O)NCCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |
| K-9 Cleavable linker | 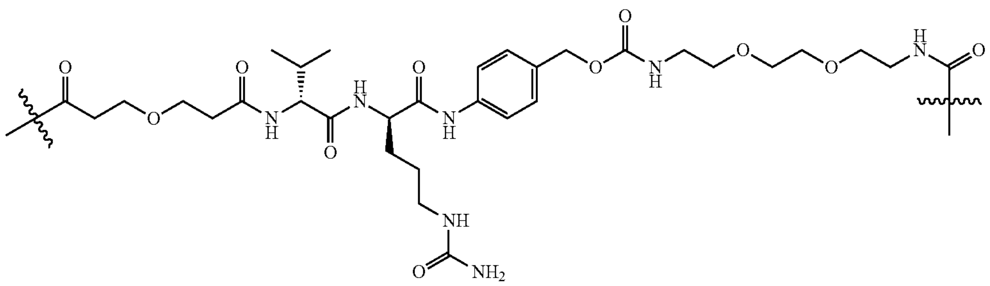 [SMILES: *C(=O)CCOCCC(=O)N[C@@H](C(=O)N[C@H](CCCNC(N)=O)C(=O)Nc1ccc(COC(=O)NCCOCCOCCNC(*)=O)cc1)C(C)C] |

TABLE 5-continued
| Exemplary $X_2$ Linkers | |
|---|---|
| Compound Number | Structure |
| K-10 Cleavable linker | 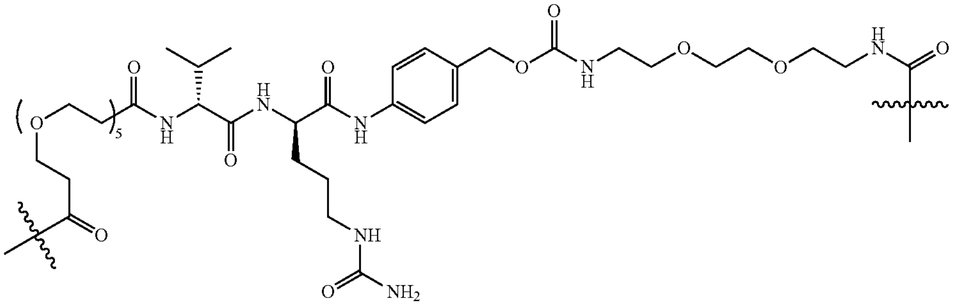 |
| K-11 Cleavable linker | 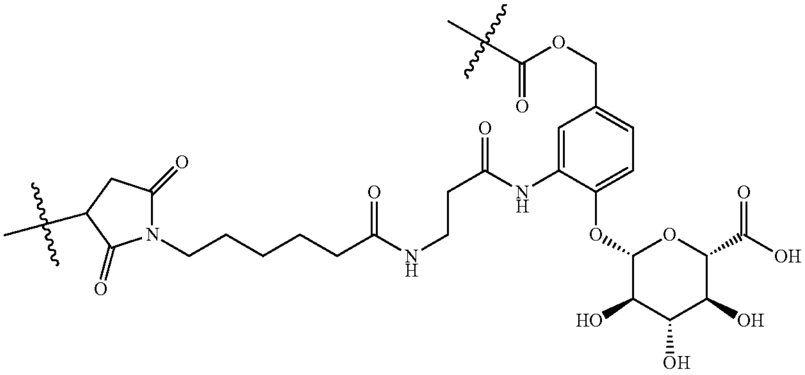 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)CC(*)C2=O)c1] |
| K-12 Cleavable linker | 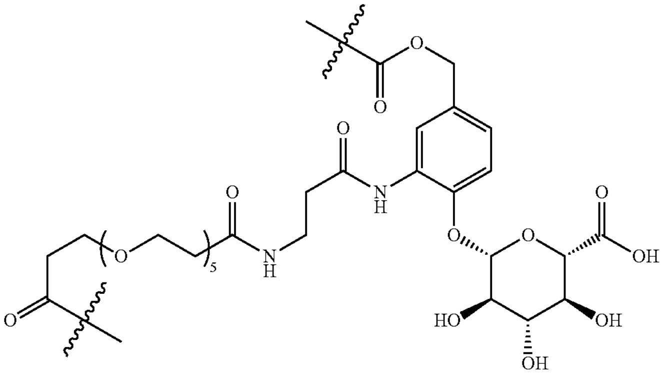 |

TABLE 5-continued
| Exemplary $X_2$ Linkers | |
|---|---|
| Compound Number | Structure |
| K-13 Cleavable linker | 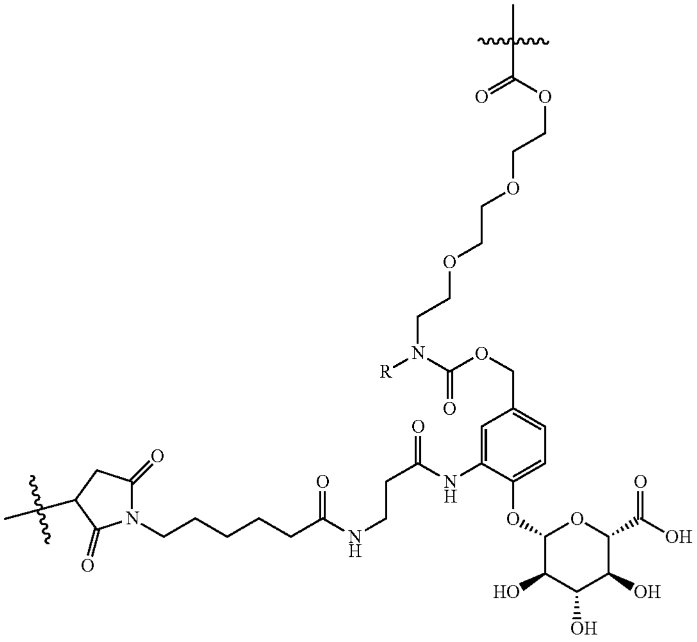 |
| K-14 Cleavable linker | 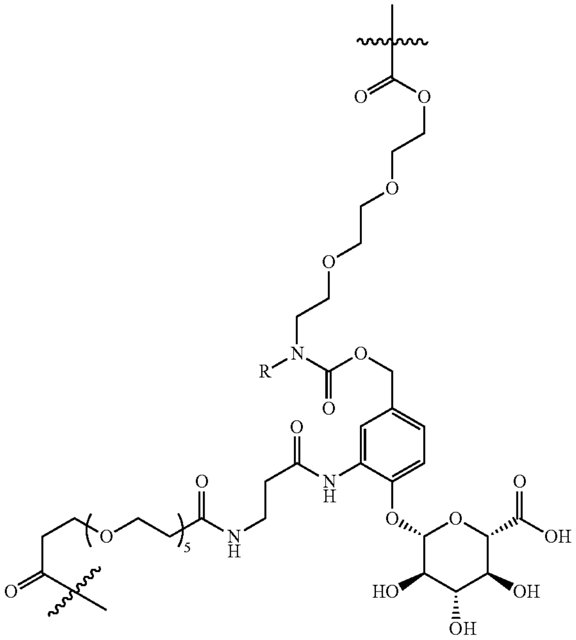 |

TABLE 5-continued
| Exemplary $X_2$ Linkers | |
|---|---|
| Compound Number | Structure |
| K-15 Cleavable linker | 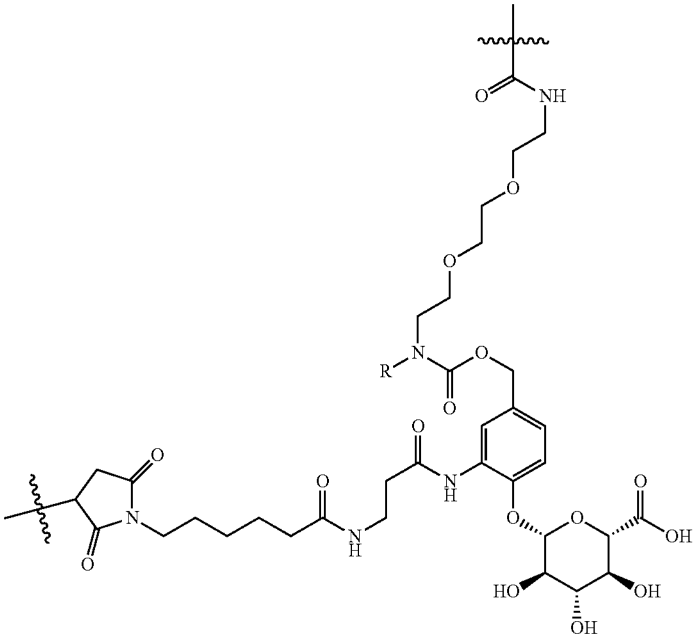 |
| K-16 Cleavable linker | 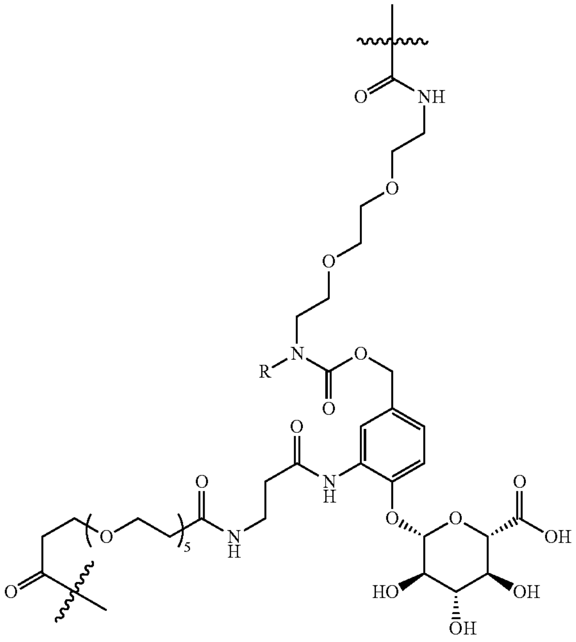 |

TABLE 5-continued
| Exemplary $X_2$ Linkers | |
|---|---|
| Compound Number | Structure |
| K-17 Non-cleavable linker | 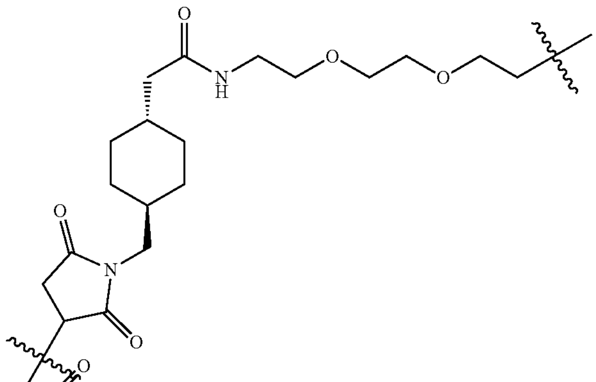 |
| K-18 Non-cleavable linker | 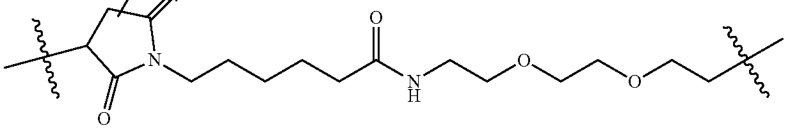 |
| K-19 Cleavable linker | 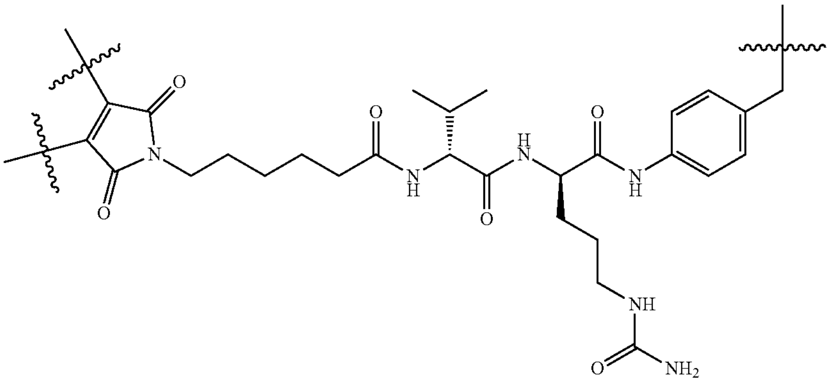 [SMILES: *Cc1ccc(NC(=O)[C@@H](CCCNC(N)=O)NC(=O)[C@H](NC(=O)CCCCCN2C(=O)C(*)=C(*)C2=O)C(C)C)cc1] |
| K-20 Cleavable linker | 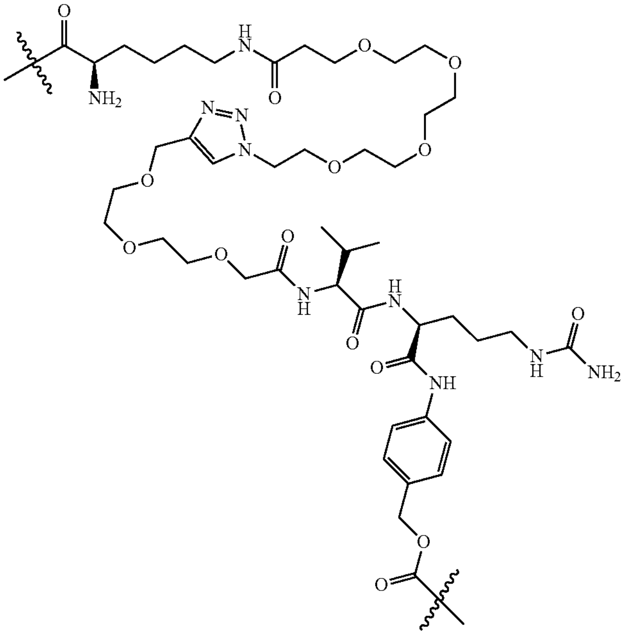 [SMILES: *C(=O)OCc1ccc(NC(=O)[C@H](CCCNC(N)=O)NC(=O)[C@@H](NC(=O)COCCOCCOCc2cn(CCOCCOCCOCCOCCC(=O)NCCCC[C@@H](N)C(*)=O)nn2)C(C)C)cc1] |

In some embodiments of the compound of Formula (II) or Formula (III), $X_2$ is a cleavable linker selected from the group consisting of K-1, K-2, K-3, K-4, K-5, K-6, K-7, K-8, K-9, K-10, K-11, K-12, K-13, K-14, K-15, K-16, K-19, and K-20.

In some embodiments of the compound of Formula (II) or Formula (III), $X_2$ is a cleavable linker and is selected from the group consisting of K-1 and K-19.

In some embodiments of the compound of Formula (II) or Formula (III), $X_2$ is a non-cleavable linker selected from the group consisting of K-17 and K-18.

In some embodiments of the compound of Formula (II) or Formula (III), $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and the combination of n1 and n2 has a sum of 2, 3, 4, 5, 6, 7, 8, 9, 10, or 11. In certain such embodiments, $X_{2b}$ is K-1 and $X_{2c}$ is K-19. In some embodiments of the compound of Formula (II) or Formula (III), when $X_2$ is a mixture of $X_{2b}$ and $X_{2c}$, $X_{2b}$ is selected from the group consisting of K-1, K-2, K-4, K-6, K-8, K-11, K-13, K-15, K-17, and K-18 and $X_{2c}$ is K-19. In some embodiments, each $X_2$ bound to $X_1$ is an $X_{2b}$ moiety. In certain such embodiments, n is n1, wherein n1 corresponds to the number of $X_{2b}$ moieties bound to $X_1$. In some embodiments, each $X_2$ bound to $X_1$ is an $X_{2c}$ moiety. In certain such embodiments, n is n2, wherein n2 corresponds to the number of $X_{2c}$ moieties bound to $X_1$.

In some embodiments of the compound of Formula (II) or Formula (III), $X_3$ is a therapeutic compound as detailed herein.

In some embodiments, the compound of Formula (II) or Formula (III) is a compound listed in Tables 6 and 7, or a pharmaceutically acceptable salt, solvate, hydrate, isomer, or tautomer thereof, wherein $X_1$ is is a biologically active polypeptide or hormone or if the compound is of Formula (III), an IL-2 polypeptide or a bio-active homolog polypeptide thereof, and n is 1, 2, 3, 4, 5, 6, 7, 8, 9, 10 or 11. In Table 6, R=H, alkyl, aryl, arylalkyl, glycol ether, or an additional glycol linker attaching to the therapeutic compound; q is 1, 2, 3, or 4; n1 is 1, 2, 3, 4, 5, 6, 7, 8, 9, or 10; and n2 is 1, 2, 3, 4, 5, 6, 7, 8, 9, or 10, wherein the combination of n1 and n2 has a sum of 2, 3, 4, 5, 6, 7, 8, 9, 10, or 11.

TABLE 6

Exemplary Compounds of Formula (II) or Formula (III) for Treating Immunological Disorders

| Compound Information | Structure |
| --- | --- |
| B-1 Pevonedistat Conjugation Cleavable linker | 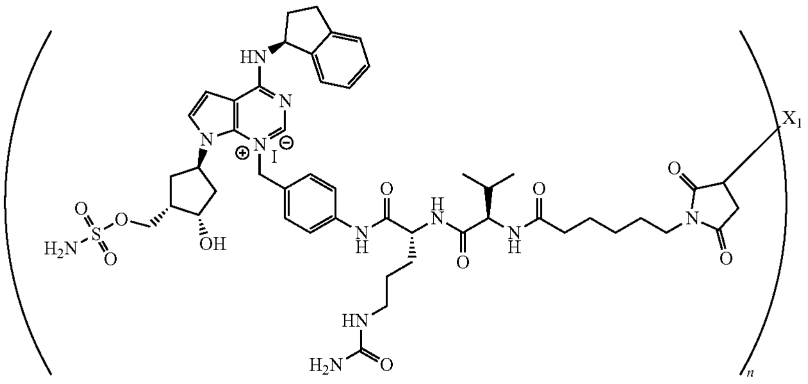 |
| B-2 Pevonedistat Conjugation Cleavable linker | 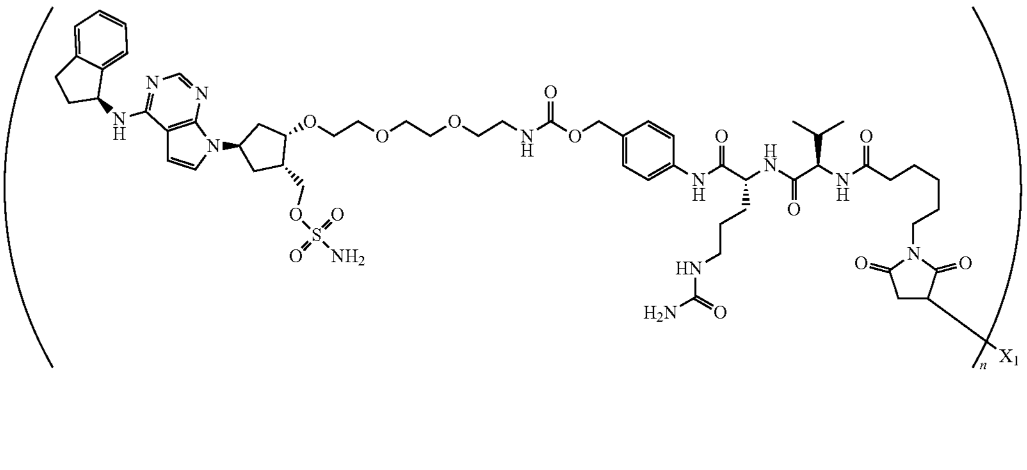 |

TABLE 6-continued
Exemplary Compounds of Formula (II) or Formula (III) for Treating Immunological Disorders
| Compound Information | Structure |
| --- | --- |
| B-3 Pevonedistat Conjugation Cleavable linker | 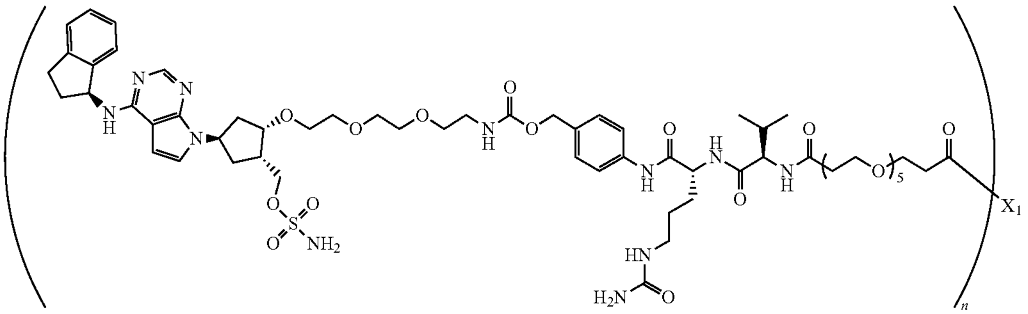 |
| B-4 Pevonedistat Conjugation Cleavable linker | 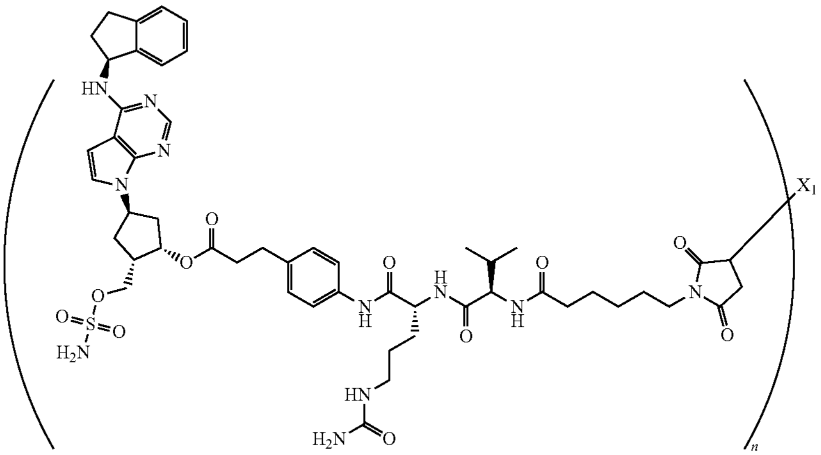 |
| B-5 Pevonedistat Conjugation Cleavable linker | 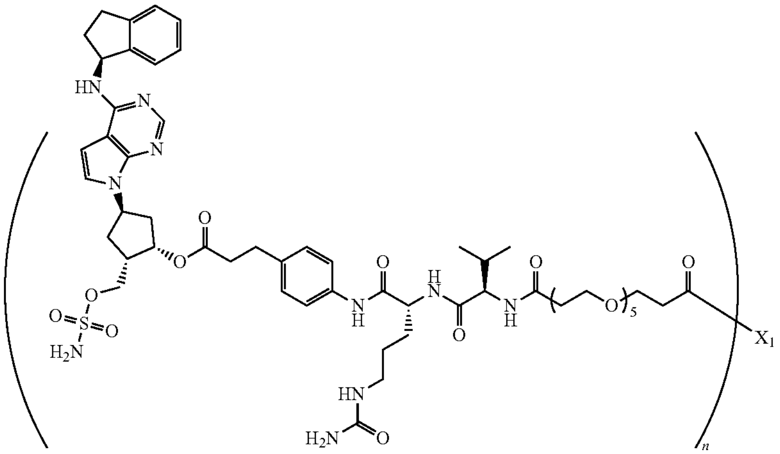 |

TABLE 6-continued

| Exemplary Compounds of Formula (II) or Formula (III) for Treating Immunological Disorders | |
|---|---|
| Compound Information | Structure |
| B-6 Pevonedistat Conjugation Cleavable linker | 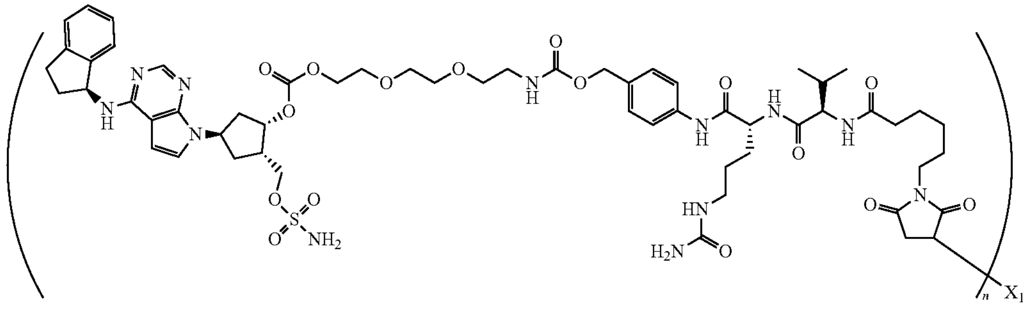 |
| B-7 Pevonedistat Conjugation Cleavable linker | 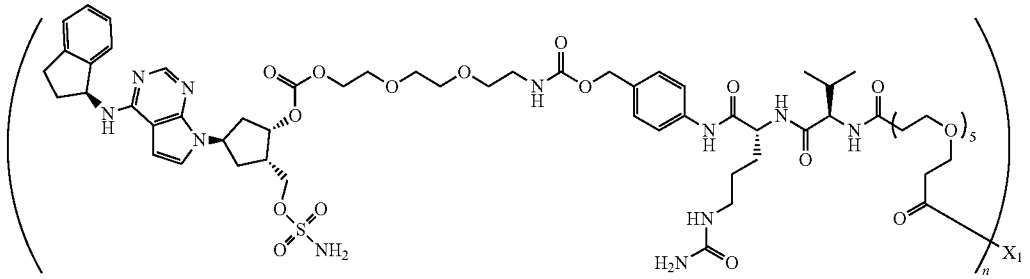 |
| B-8 Pevonedistat Conjugation Cleavable linker | 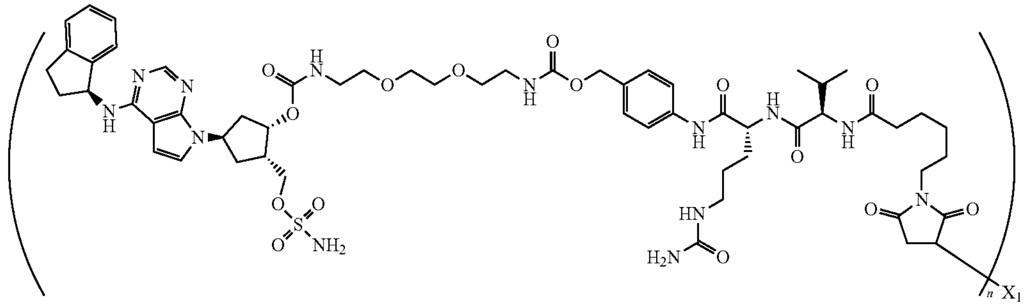 |
| B-9 Pevonedistat Conjugation Cleavable linker | 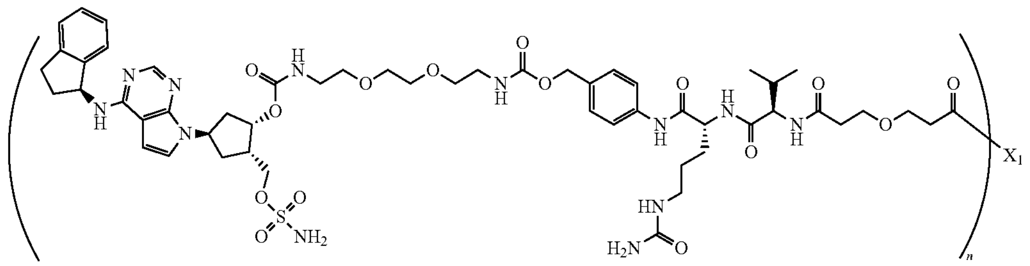 |
| B-10 Pevonedistat Conjugation Cleavable linker | 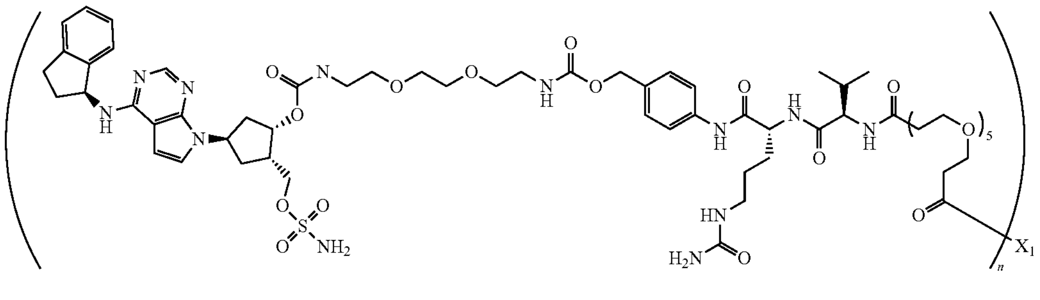 |

TABLE 6-continued
| Exemplary Compounds of Formula (II) or Formula (III) for Treating Immunological Disorders | |
|---|---|
| Compound Information | Structure |
| B-11 Pevonedistat Conjugation Cleavable linker | 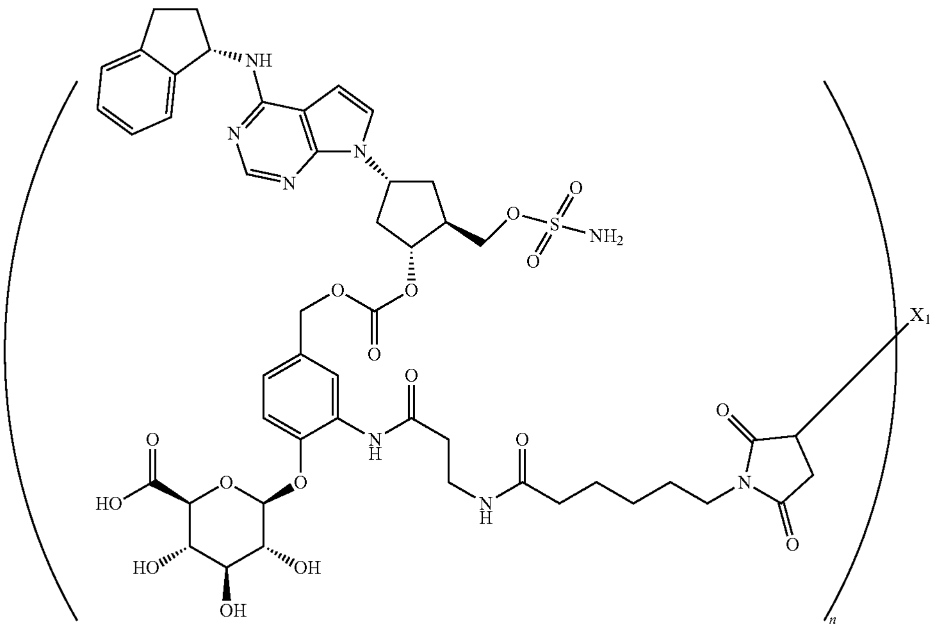 |
| B-12 Pevonedistat Conjugation Cleavable linker | 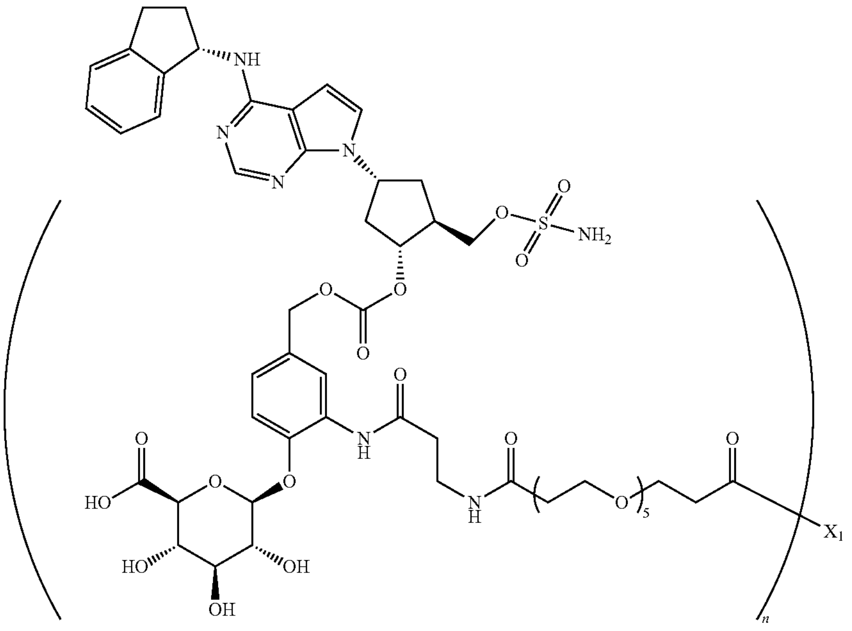 |

TABLE 6-continued
| Exemplary Compounds of Formula (II) or Formula (III) for Treating Immunological Disorders | |
|---|---|
| Compound Information | Structure |
| B-13 Pevonedistat Conjugation Cleavable linker | 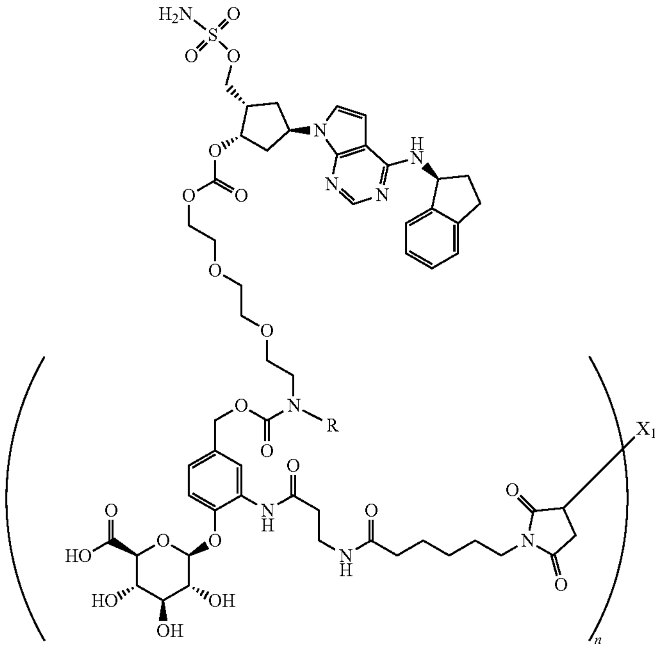 |
| B-14 Pevonedistat Conjugation Cleavable linker | 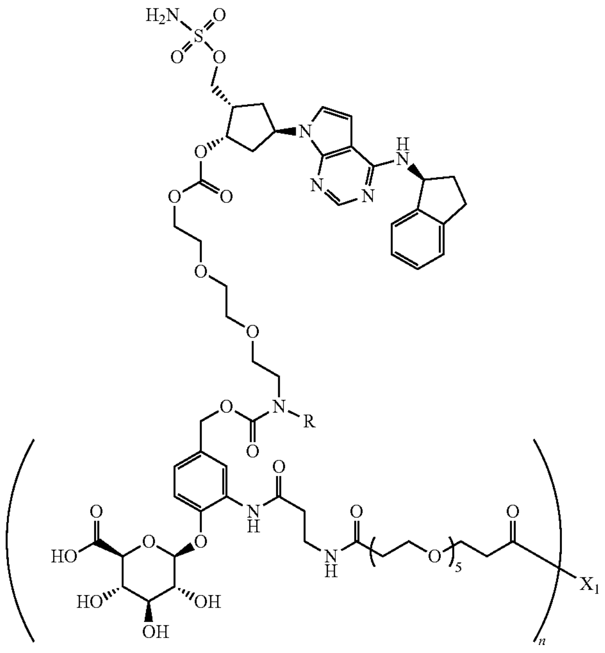 |

TABLE 6-continued
| Exemplary Compounds of Formula (II) or Formula (III) for Treating Immunological Disorders | |
|---|---|
| Compound Information | Structure |
| B-15 Pevonedistat Conjugation Cleavable linker | 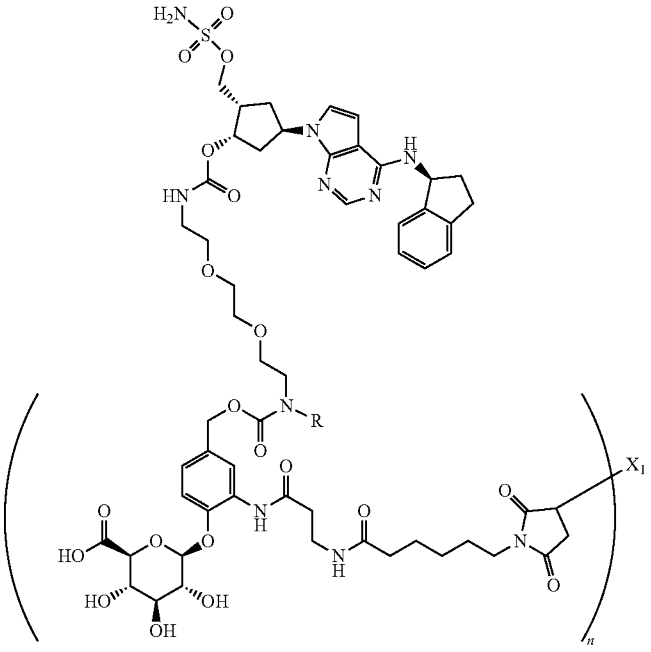 |
| B-16 Pevonedistat Conjugation Cleavable linker | 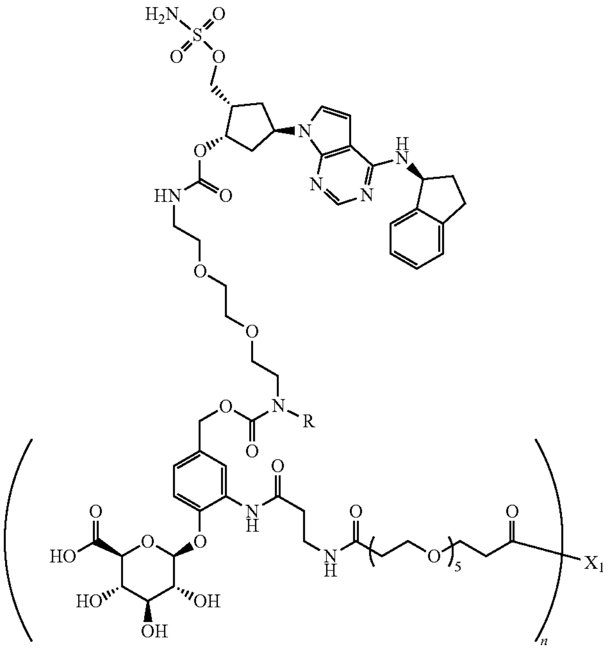 |

TABLE 6-continued
| Exemplary Compounds of Formula (II) or Formula (III) for Treating Immunological Disorders | |
|---|---|
| Compound Information | Structure |
| B-17 Pevonedistat Conjugation Non-cleavable linker | 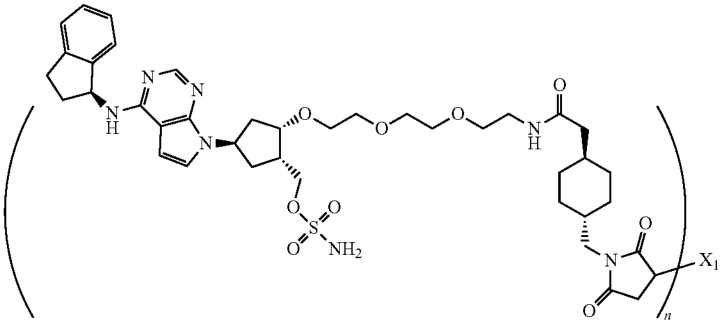 |
| B-18 Pevonedistat Conjugation Non-cleavable linker | 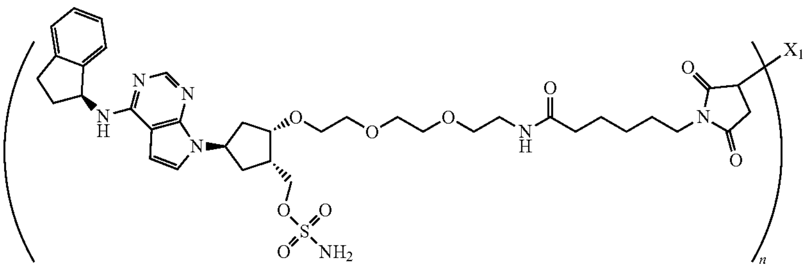 |
| B-19 Piperacillin Conjugation Cleavable linker | 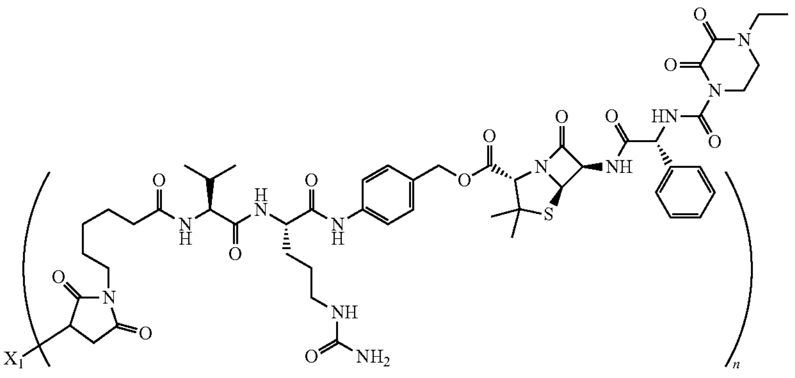 |

TABLE 6-continued
| Exemplary Compounds of Formula (II) or Formula (III) for Treating Immunological Disorders | |
|---|---|
| Compound Information | Structure |
| B-20 M22 (1-benzyl-N-(2,4-dichlorophenethyl) piperidin-4-amine) Conjugation Cleavable linker | 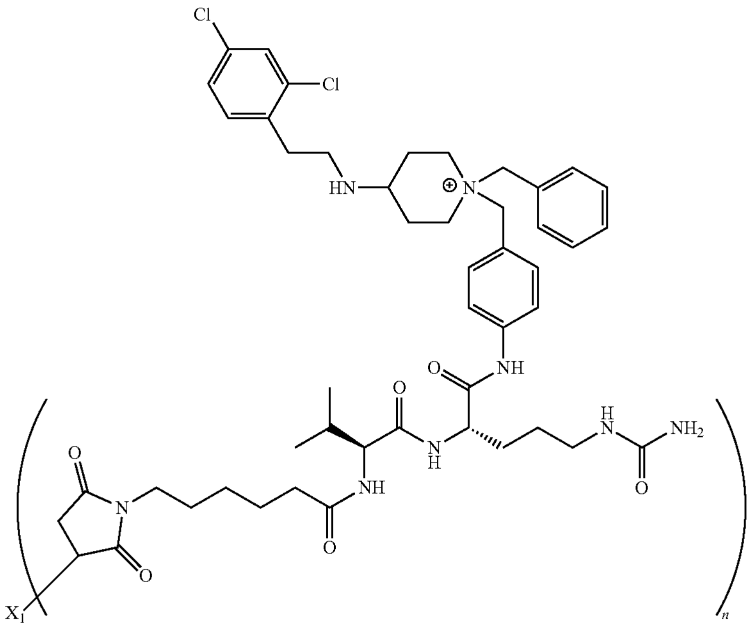 |
| B-21 6,6'-Biapigenin Conjugation Cleavable linker | 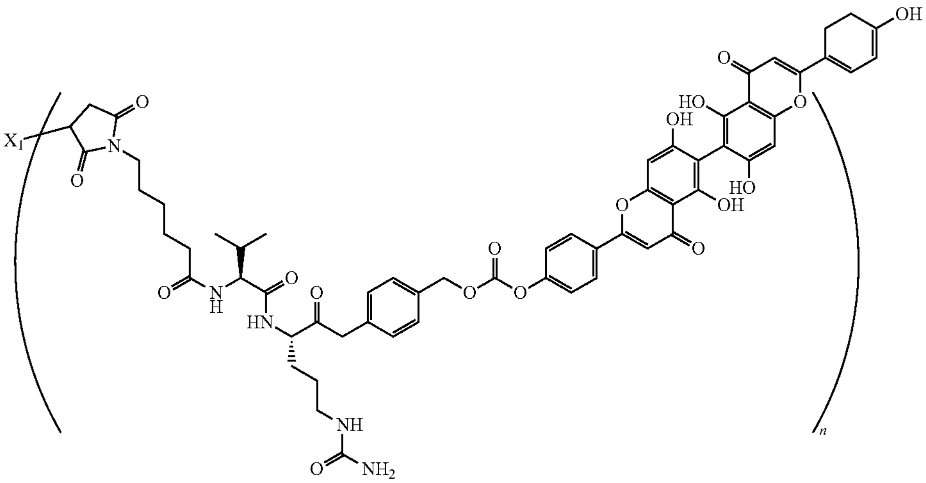 |

TABLE 6-continued
| Exemplary Compounds of Formula (II) or Formula (III) for Treating Immunological Disorders | |
|---|---|
| Compound Information | Structure |
| B-22 Thienopyridine Conjugation Cleavable linker | 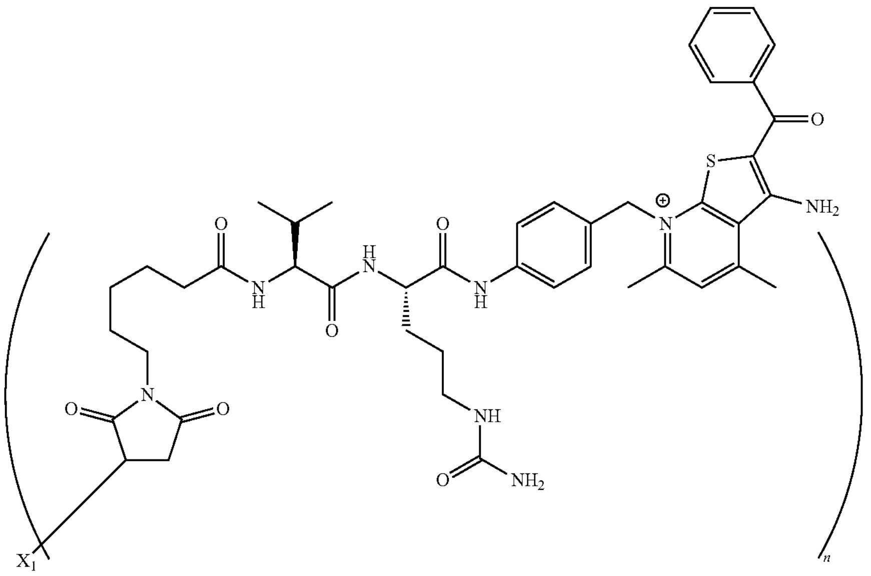 |
| B-23 Imidazopyrimidine Conjugation Cleavable linker | 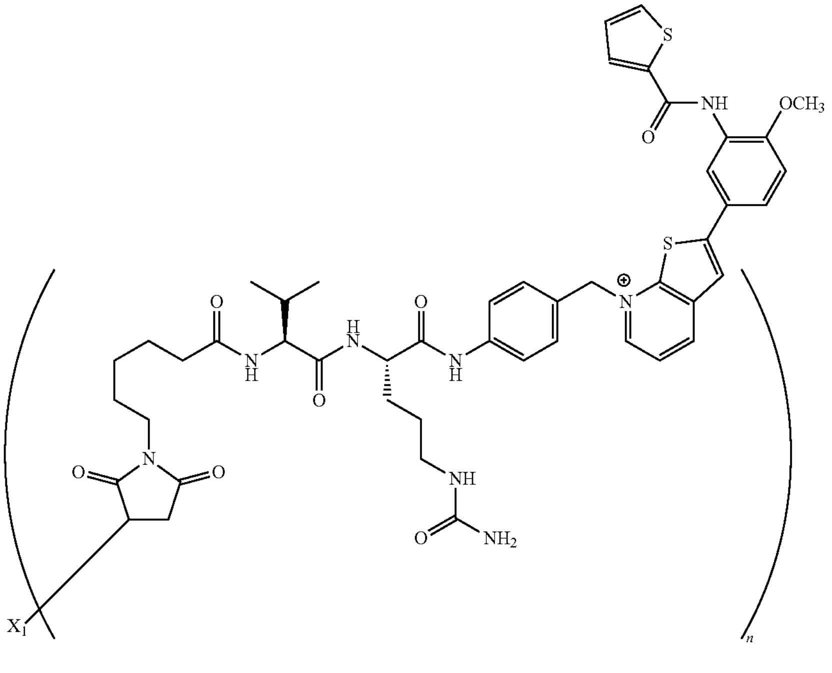 |

TABLE 6-continued
| Exemplary Compounds of Formula (II) or Formula (III) for Treating Immunological Disorders | |
|---|---|
| Compound Information | Structure |
| B-24 Largazole Conjugation Cleavable linker | 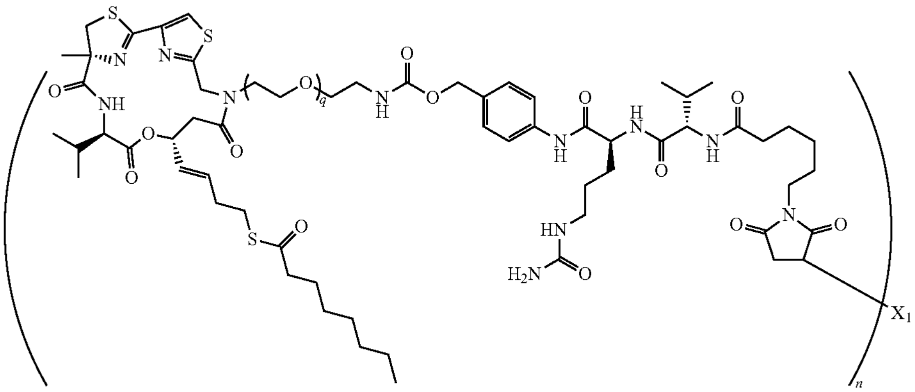 |
| B-25 PYR-41 (4[4-(5-nitro-furan-2-yl-methyl-ene)-3,5-dioxo-pyrazol-idin-1-yl]-benzoic acid ethyl ester) Conjugation Cleavable linker | 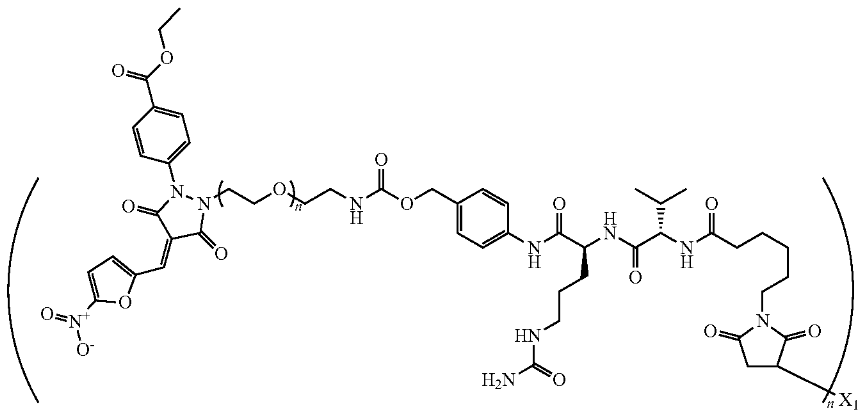 |
| B-26 Phorbol 12-myristate 13-acetate Conjugation Cleavable linker | 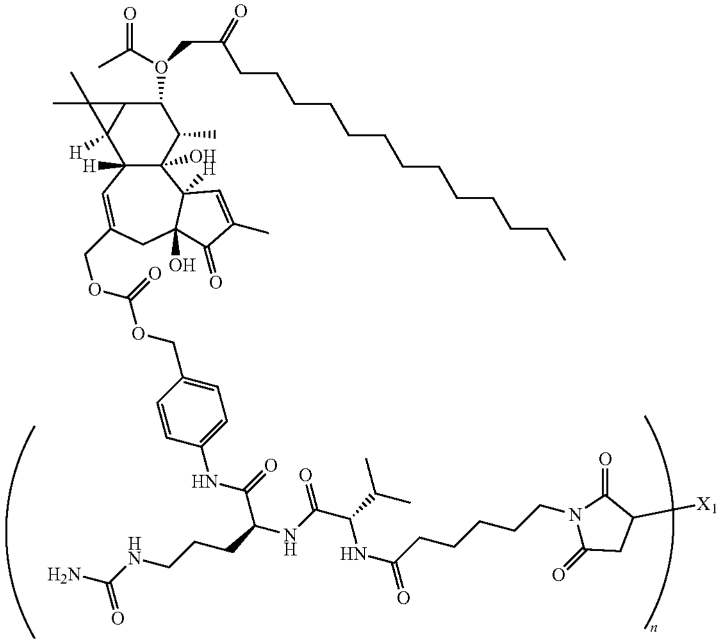 |

TABLE 6-continued
| Exemplary Compounds of Formula (II) or Formula (III) for Treating Immunological Disorders | |
|---|---|
| Compound Information | Structure |
| B-27 Ofloxacin Conjugation Cleavable linker | 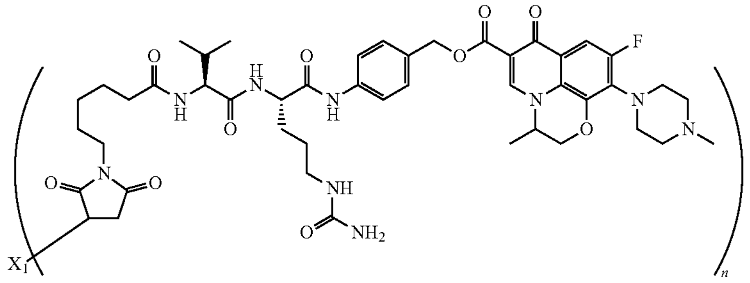 |
| B-28 Ofloxacin Conjugation Cleavable linker | 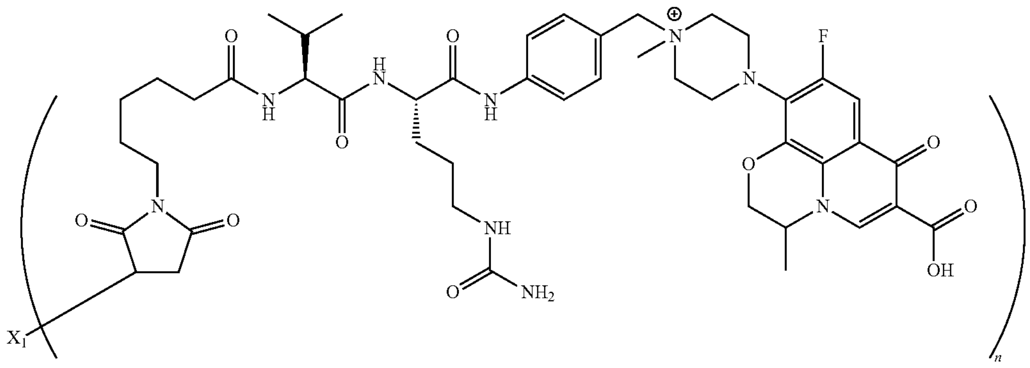 |
| B-29 Pyrrolo [2,1-b] quinazolin-9(1H)-one Conjugation Cleavable linker | 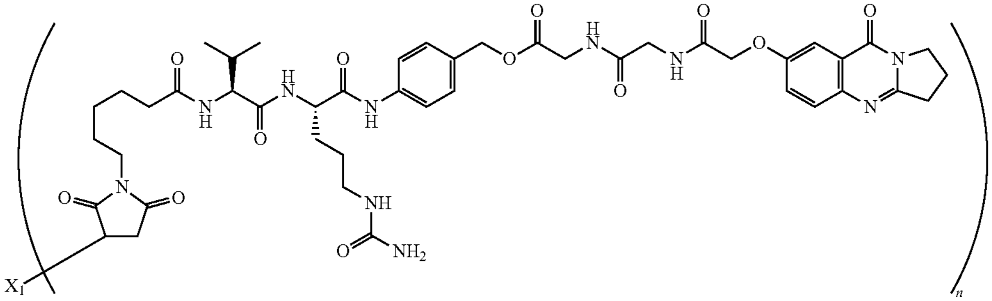 |
| B-30 Drug Conjugate of TAS NAE Inhibitor Cleavable linker | 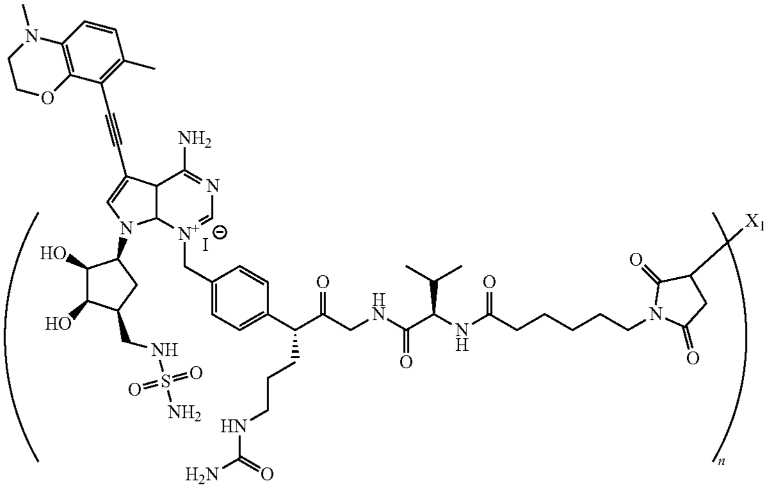 |

TABLE 6-continued
| Exemplary Compounds of Formula (II) or Formula (III) for Treating Immunological Disorders | |
|---|---|
| Compound Information | Structure |
| B-31 Drug Conjugate of TAK 7243NAE Inhibitor Cleavable linker | 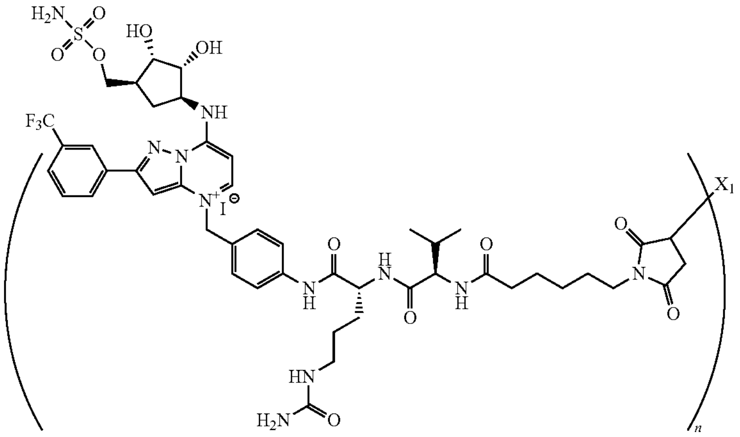 |
| B-48 Pevonedistat Conjugation Cleavable linker | 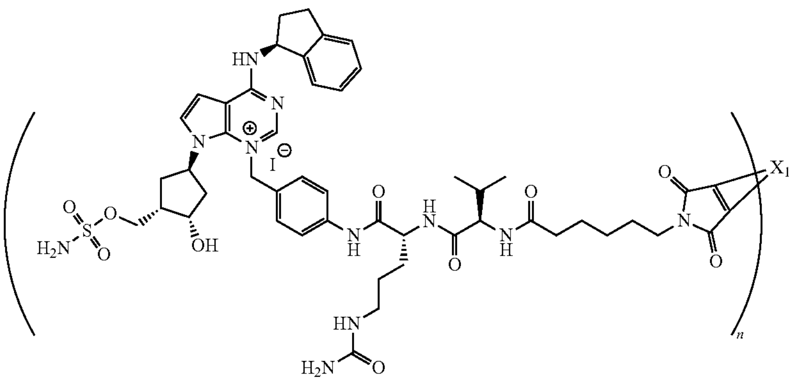 |

TABLE 6-continued
| Exemplary Compounds of Formula (II) or Formula (III) for Treating Immunological Disorders | |
|---|---|
| Compound Information | Structure |
| B-49 Pevonedistat Conjugation Cleavable linker | 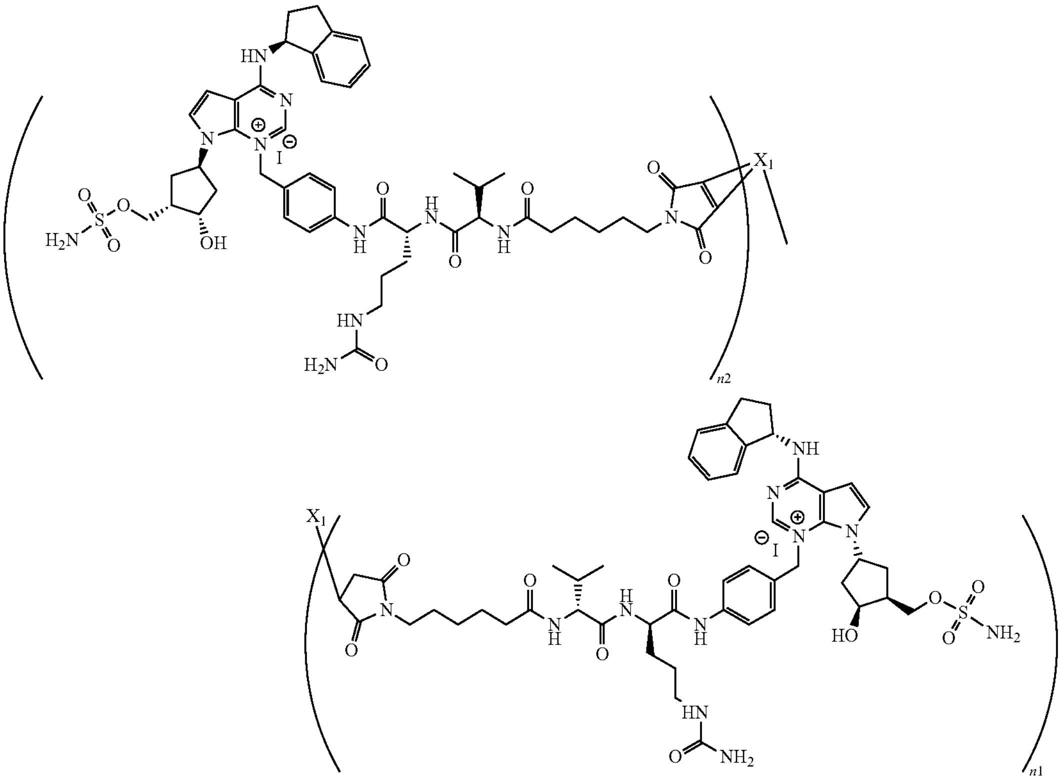 |
TABLE 7
| Exemplary Compounds of Formula (II) or Formula (III) for Treating Cancer | |
|---|---|
| Compound Information | Structure |
| B-32 Monomethyl auristatin E Conjugation Cleavable linker | 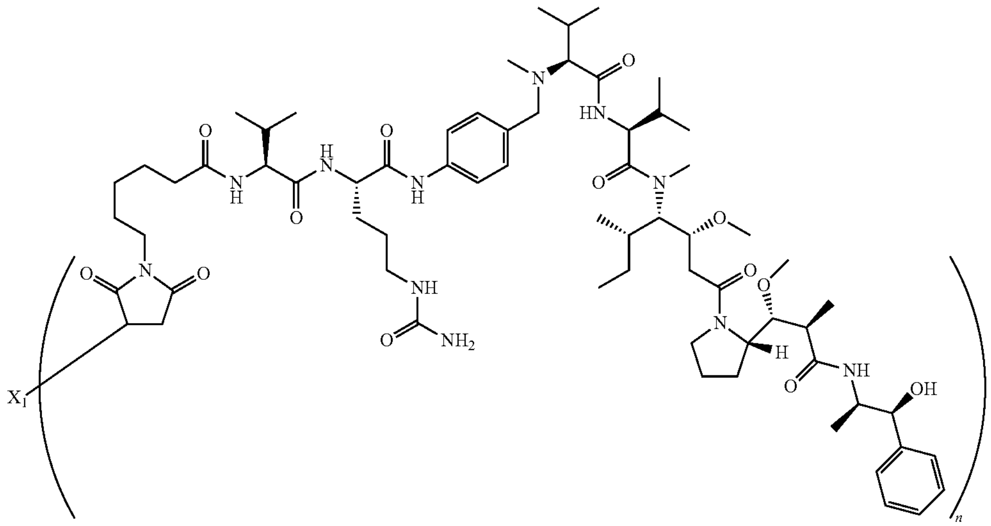 |

TABLE 7-continued
| Exemplary Compounds of Formula (II) or Formula (III) for Treating Cancer | |
|---|---|
| Compound Information | Structure |
| B-33 Viblastine Conjugation Cleavable linker | 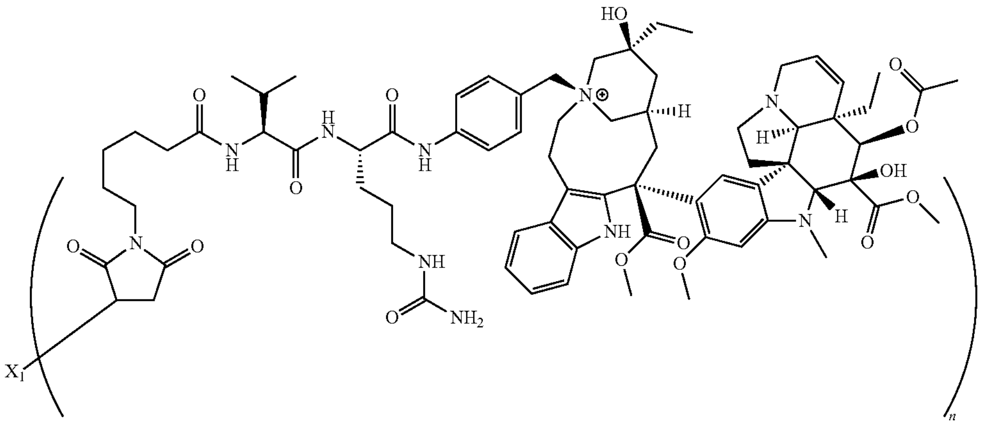 |
| B-34 Carfibzomib Conjugation Cleavable linker | 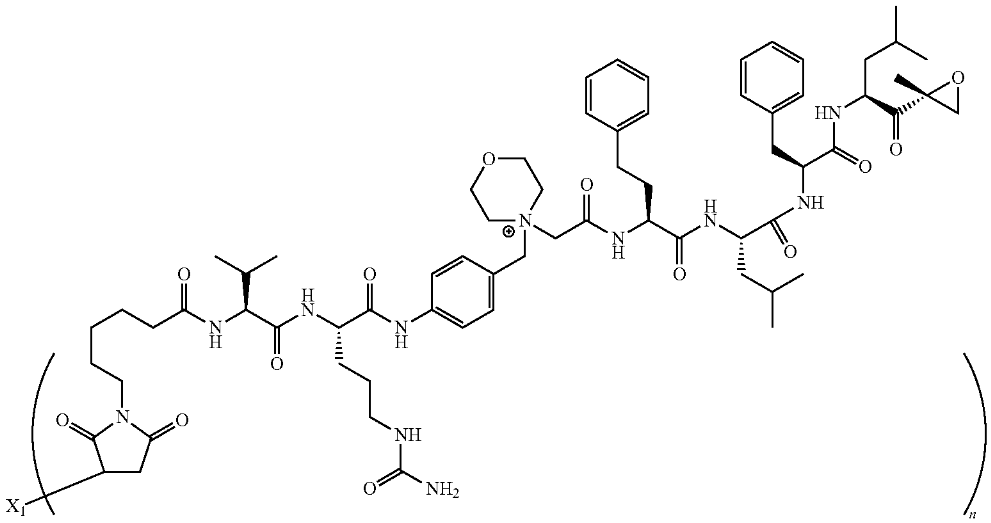 |
| B-35 Rifabutin Conjugation Cleavable linker | 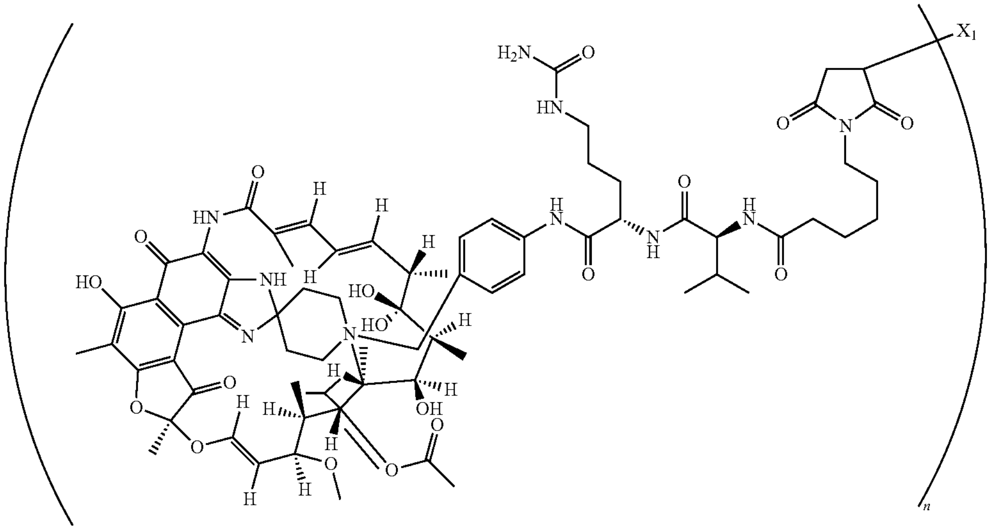 |

TABLE 7-continued
| Exemplary Compounds of Formula (II) or Formula (III) for Treating Cancer | |
|---|---|
| Compound Information | Structure |
| B-36 Clindamycin Conjugation Cleavable linker | 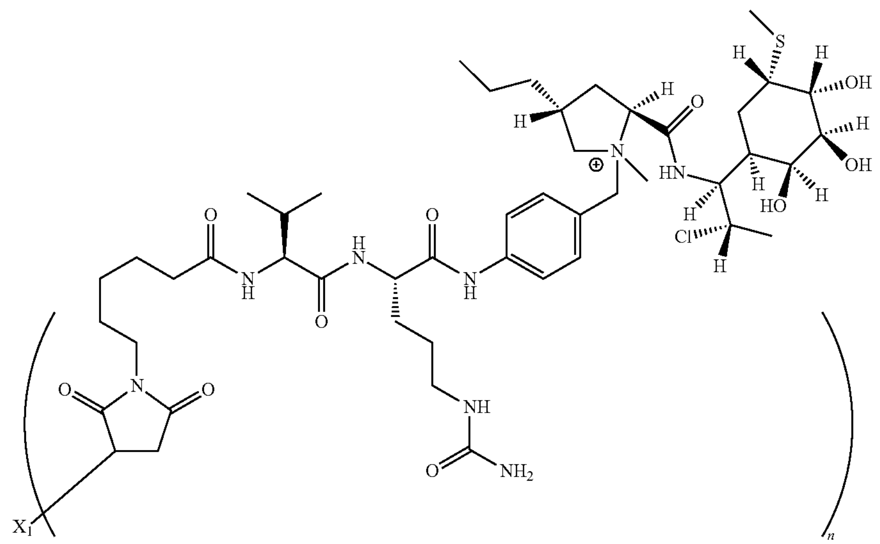 |
| B-37 Indibulin Conjugation Cleavable linker | 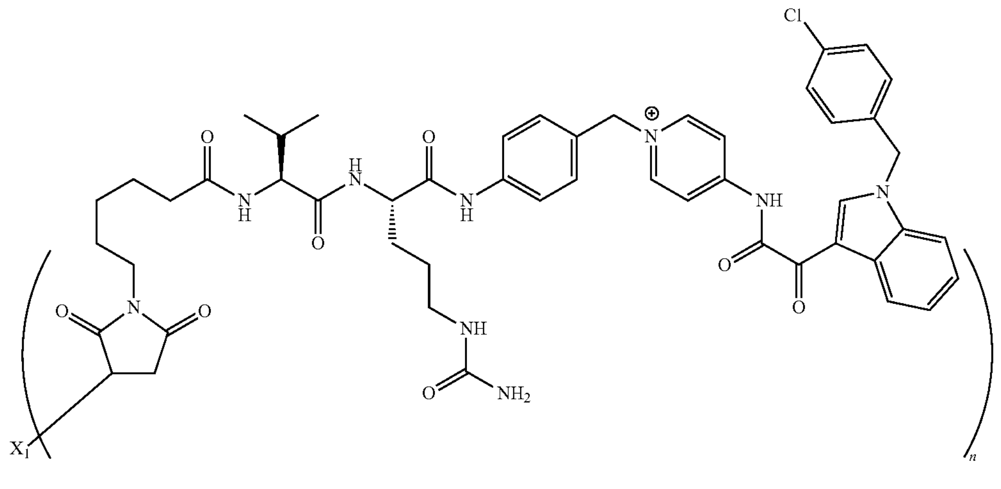 |

TABLE 7-continued
Exemplary Compounds of Formula (II) or Formula (III) for Treating Cancer
| Compound Information | Structure |
|---|---|
| B-38 Gefitinib Conjugation Cleavable linker | 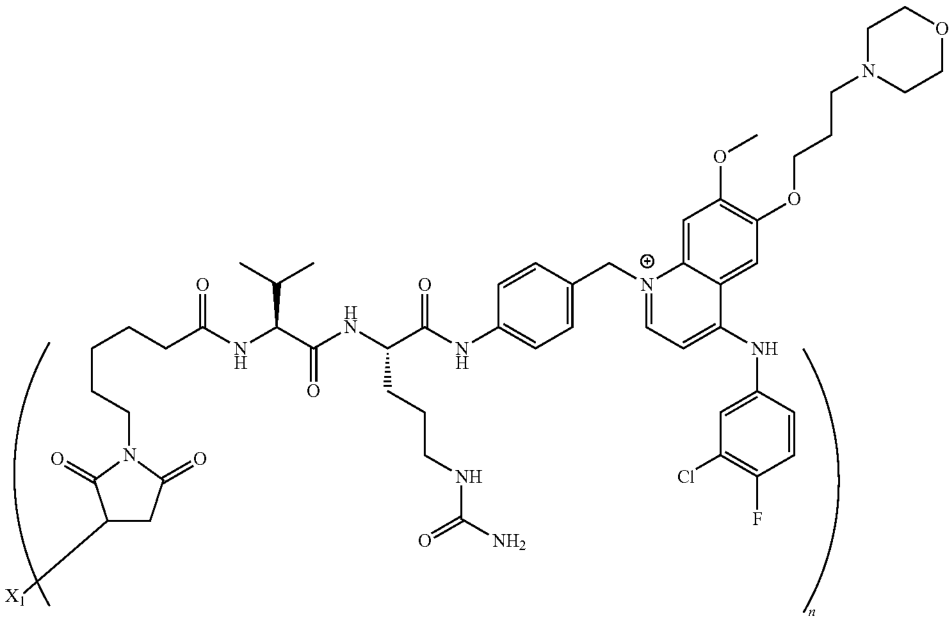 |
| B-39 Dasatinib Conjugation Cleavable linker | 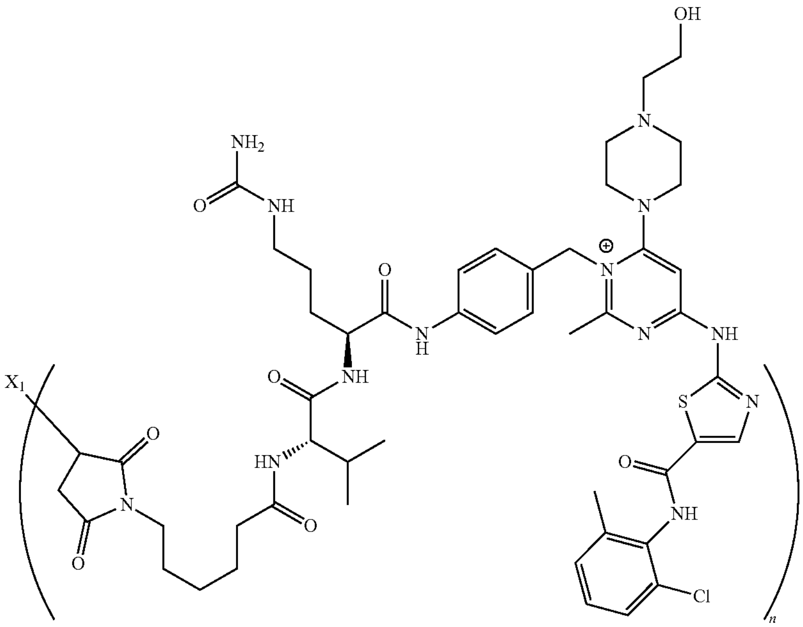 |

TABLE 7-continued
| Exemplary Compounds of Formula (II) or Formula (III) for Treating Cancer | |
|---|---|
| Compound Information | Structure |
| B-40 Docetaxel Conjugation Cleavable linker | 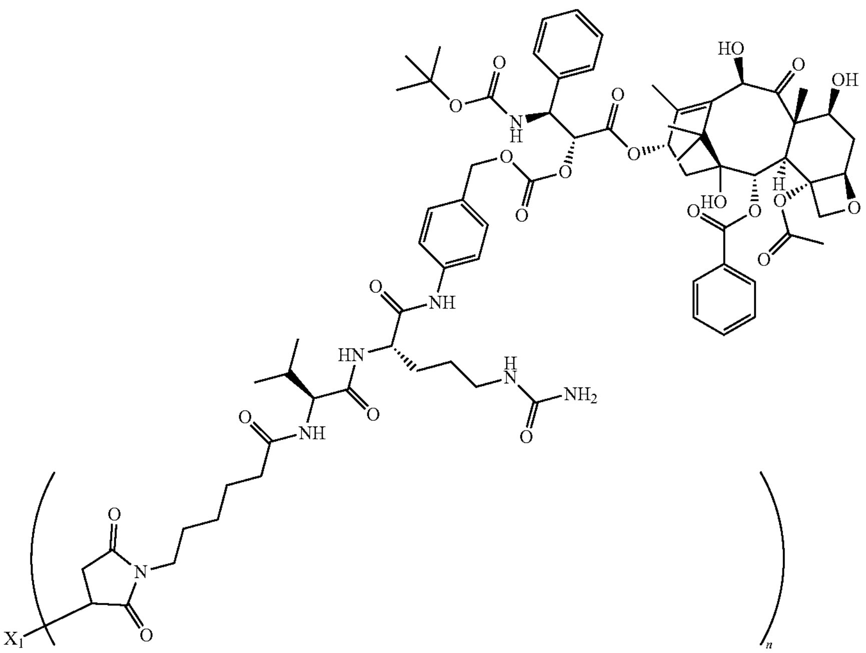 |
| B-41 Paclitaxel Conjugation Cleavable linker | 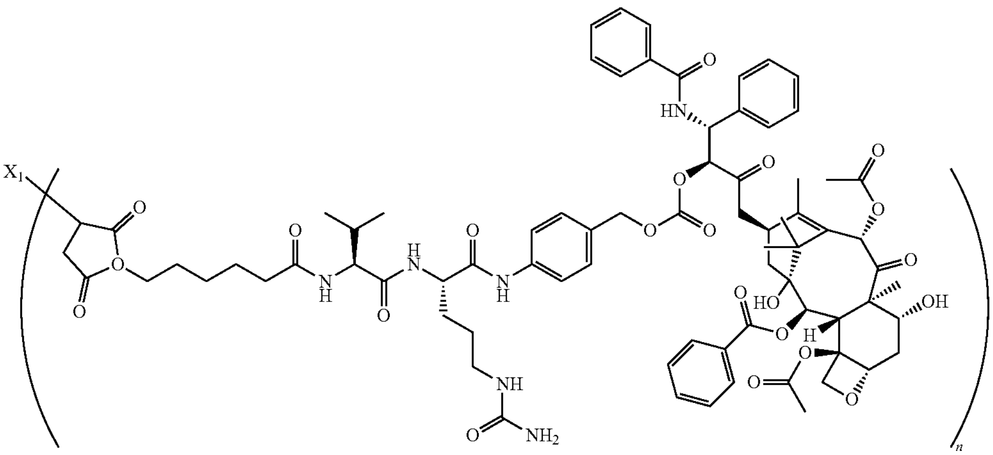 |

TABLE 7-continued
| Exemplary Compounds of Formula (II) or Formula (III) for Treating Cancer | |
|---|---|
| Compound Information | Structure |
| B-42 Etoposide Conjugation Cleavable linker | 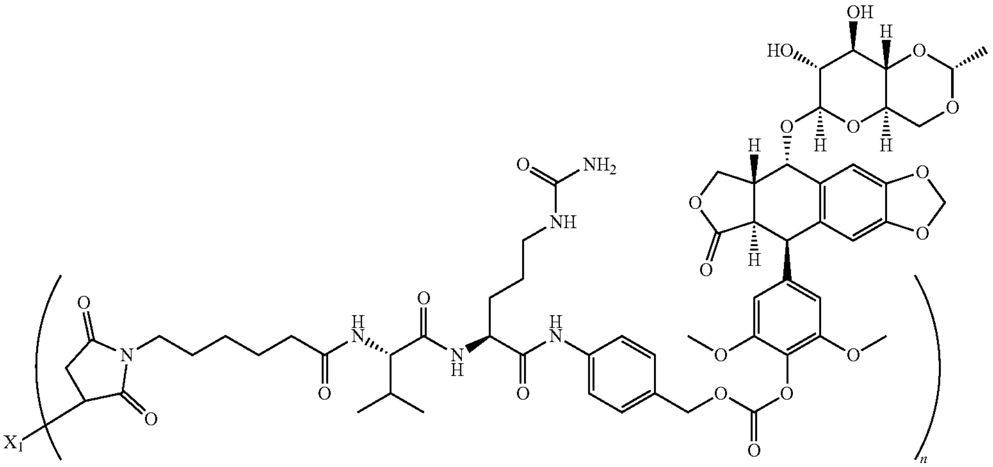 |
| B-43 Gemcitabine Conjugation Cleavable linker | 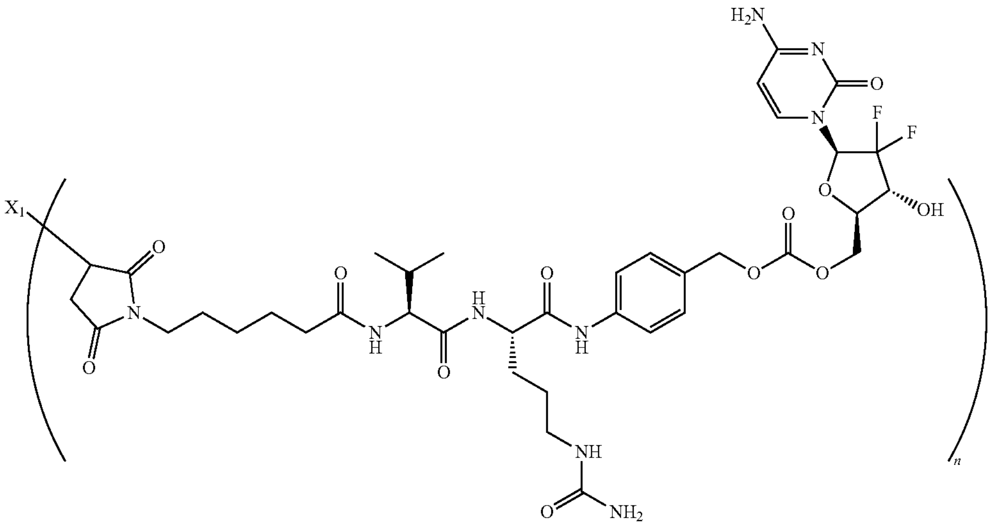 |

TABLE 7-continued
| Exemplary Compounds of Formula (II) or Formula (III) for Treating Cancer | |
|---|---|
| Compound Information | Structure |
| B-44 Irinotecan Conjugation Cleavable linker | 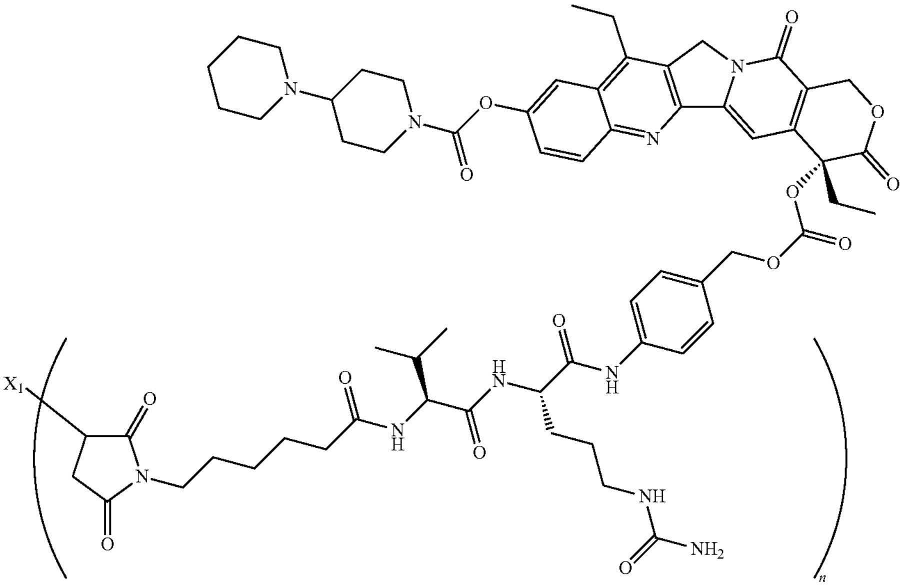 |
| B-45 Fluorouracil Conjugation Cleavable linker | 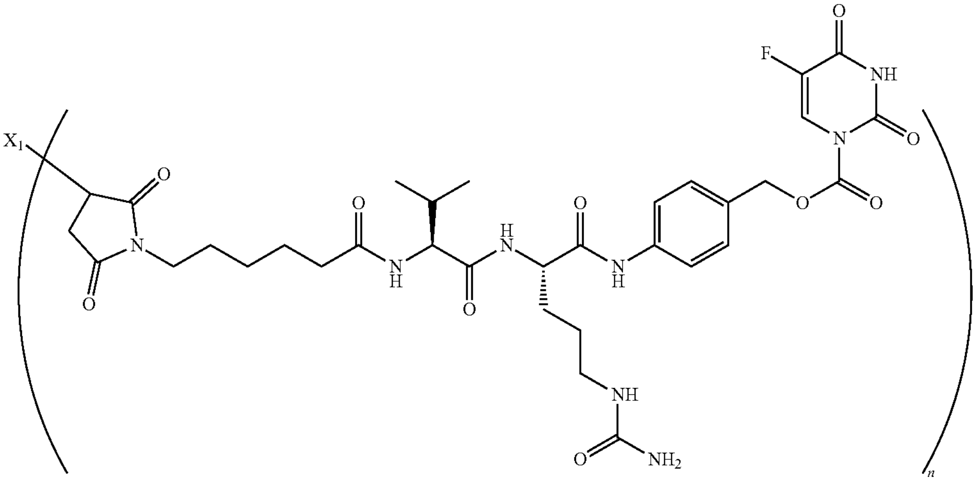 |
| B-46 Methotrexate Conjugation Cleavable linker | 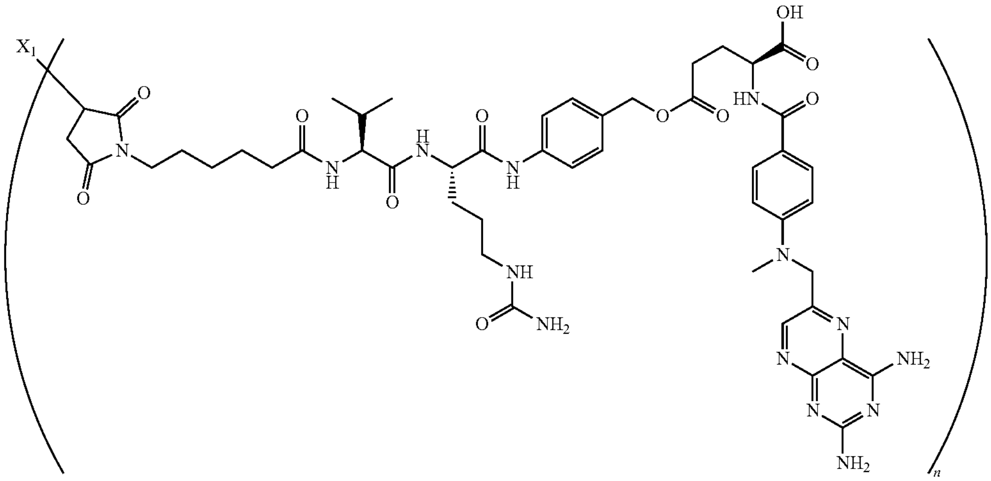 |

TABLE 7-continued

| Exemplary Compounds of Formula (II) or Formula (III) for Treating Cancer | |
|---|---|
| Compound Information | Structure |
| B-47 Doxorubicin Conjugation Cleavable linker | 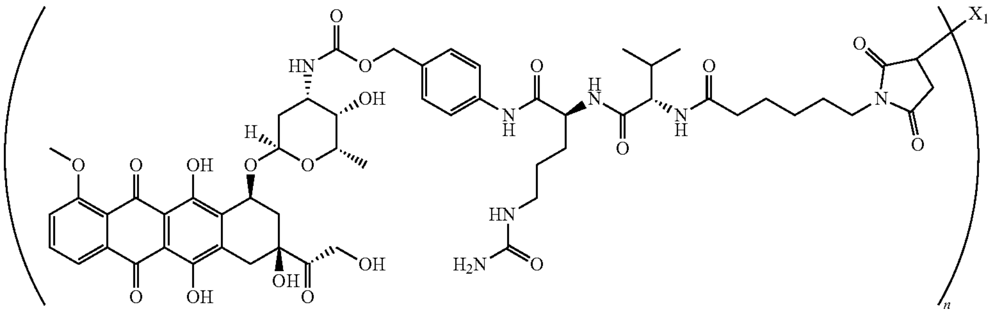 |
| B-50 MMAE Conjugation Cleavable linker | 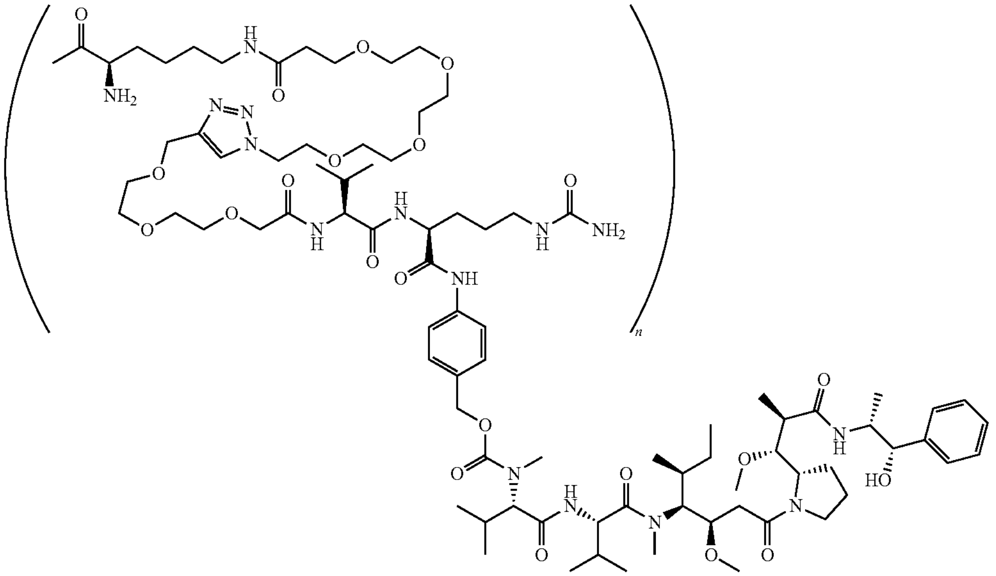 |

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49.

In some embodiments, the compound of Formula (II) or Formula (III), or a pharmaceutically acceptable salt, solvate, hydrate, isomer, or tautomer thereof, is B-32.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 1, 2, 3, 4, 5, or 6, and $X_1$ is an IL-2 polypeptide or a bio-active homolog polypeptide thereof comprising an amino acid sequence set forth in SEQ ID NO: 1 or SEQ ID NO:2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 1, 2, 3, 4, 5, or 6, and $X_1$ is an IL-2 polypeptide or a bio-active homolog polypeptide thereof comprising an amino acid sequence set forth in SEQ ID NO: 1 or SEQ ID NO:2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 1, 2, 3, 4, 5, or 6, and $X_1$ is an IL-2 polypeptide or a bio-active homolog polypeptide thereof comprising an amino acid sequence set forth in SEQ ID NO:1 or SEQ ID NO:2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO: 1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 1, 2, 3, 4, 5, or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the IL-2 polypeptide or the bio-active homolog polypeptide thereof comprises the amino acid sequence set forth in SEQ ID NO:2. In some-embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 1, 2, 3, 4, 5, or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 1, 2, 3, 4, 5, or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 1 or 2, and $X_1$ is an IL-2 polypeptide or a bio-active homolog polypeptide thereof comprising an amino acid sequence set forth in SEQ ID NO: 1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 1 or 2, and $X_1$ is an IL-2 polypeptide or a bio-active homolog polypeptide thereof comprising an amino acid sequence set forth in SEQ ID NO:1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 1 or 2, and $X_1$ is an IL-2 polypeptide or a bio-active homolog polypeptide thereof comprising an amino acid sequence set forth in SEQ ID NO:1 or SEQ ID NO:2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO: 1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 1 or 2, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 1 or 2, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 1 or 2, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 3 or 4, and $X_1$ is an IL-2 polypeptide or a bio-active homolog polypeptide thereof comprising an amino acid sequence set forth in SEQ ID NO: 1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 3 or 4, and $X_1$ is an IL-2 polypeptide or a bio-active homolog polypeptide thereof comprising an amino acid sequence set forth in SEQ ID NO:1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 3 or 4, and $X_1$ is an IL-2 polypeptide or a bio-active homolog polypeptide thereof comprising an amino acid sequence set forth in SEQ ID NO: 1 or SEQ ID NO:2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO: 1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 3 or 4, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 3 or 4, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 3 or 4, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 5 or 6, and $X_1$ is an IL-2 polypeptide or a bio-active homolog polypeptide thereof comprising an amino acid sequence set forth in SEQ ID NO:1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 5 or 6, and $X_1$ is an IL-2 polypeptide or a bio-active homolog polypeptide thereof comprising an amino acid sequence set forth in SEQ ID NO:1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 5 or 6, and $X_1$ is an IL-2 polypeptide or a bio-active homolog polypeptide thereof comprising an amino acid sequence set forth in SEQ ID NO: 1 or SEQ ID NO:2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO: 1.

In some embodiments, the compound of Formula (II) or Formula (III), or a pharmaceutically acceptable salt, solvate, hydrate, isomer, or tautomer thereof, is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 5 or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is selected from the group consisting of B-1, B-30, B-31, B-48, and B-49, wherein n is 5 or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2. In certain such embodiments, the IL-2 polypeptide or the bio-active homolog polypeptide thereof comprises the amino acid sequence set forth in SEQ ID NO:2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, is B-32, wherein n is 5 or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2. In certain such embodiments, the IL-2 polypeptide or the bio-active homolog polypeptide thereof comprises the amino acid sequence set forth in SEQ ID NO: 2. In some embodiments, the IL-2 polypeptide or the bio-active homolog polypeptide thereof comprises the amino acid sequence set forth in SEQ ID NO:1.

In some embodiments, the compound of Formula (II) or Formula (III), or a pharmaceutically acceptable salt, solvate, hydrate, isomer, or tautomer thereof, $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein the combination of n1 and n2 has a sum of 1, 2, 3, 4, 5, or 6, and $X_1$ is an IL-2 polypeptide or a bio-active homolog polypeptide thereof comprising an amino acid sequence set forth in SEQ ID NO: 1 or SEQ ID NO:2. In certain such embodiments, the compound of Formula (II) or Formula (III), or a pharmaceutically acceptable salt, solvate, hydrate, isomer, or tautomer thereof, is B-49. In certain such embodiments, n1 is 2 or 3 and n2 is 1. In certain such embodiments, n1 is 2 and n2 is 1. In some embodiments, n1 is 3 and n2 is 1. In some embodiments, the compound of Formula (II) or Formula (III), or a pharmaceutically acceptable salt, solvate, hydrate, isomer, or tautomer thereof, is B-49, wherein $X_1$ is an IL-2 polypeptide or a bio-active homolog polypeptide thereof comprising an amino acid sequence set forth in SEQ ID NO:1 or SEQ ID NO: 2, and n1 is 2 or 3 and n2 is 1. In some embodiments, the compound of Formula (II) or Formula (III), or a pharmaceutically acceptable salt, solvate, hydrate, isomer, or tautomer thereof, is B-49, wherein $X_1$ is an IL-2 polypeptide or a bio-active homolog polypeptide thereof comprising an amino acid sequence set forth in SEQ ID NO:2, and n1 is 2 or 3 and n2 is 1. In some embodiments, the compound of Formula (II) or Formula (III), or a pharmaceutically acceptable salt, solvate, hydrate, isomer, or tautomer thereof, is B-49, wherein $X_1$ is an IL-2 polypeptide or a bio-active homolog polypeptide thereof comprising an amino acid sequence set forth in SEQ ID NO:1, and n1 is 2 or 3 and n2 is 1.

In some embodiments, the compound of Formula (II) or Formula (III), or a pharmaceutically acceptable salt, solvate, hydrate, isomer, or tautomer thereof, $X_2$ is a mixture of $X_{2b}$ and $X_{2c}$, wherein $X_{2b}$ is a linker that is bound to one Cys residue on $X_1$, $X_{2c}$ is a linker that is bound to two different Cys residues on $X_1$, n is a combination of n1 and n2, wherein the combination of n1 and n2 has a sum of 2, 3, 4, 5, or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2. In certain such embodiments, the compound of Formula (II) or Formula (III), or a pharmaceutically acceptable salt, solvate, hydrate, isomer, or tautomer thereof, is B-49. In certain such embodiments, n1 is 2 or 3 and n2 is 1. In certain such embodiments, n1 is 2 and n2 is 1. In some embodiments, n1 is 3 and n2 is 1. In some embodiments, the compound of Formula (II) or Formula (III), or a pharmaceutically acceptable salt, solvate, hydrate, isomer, or tautomer thereof, is B-49, wherein $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2, and n1 is 2 or 3 and n2 is 1. In some embodiments, the compound of Formula (II) or Formula (III), or a pharmaceutically acceptable salt, solvate, hydrate, isomer, or tautomer thereof, is B-49, wherein $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:2, and n1 is 2 or 3 and n2 is 1. In some embodiments, the compound of Formula (II) or Formula (III), or a pharmaceutically acceptable salt, solvate, hydrate, isomer, or tautomer thereof, is B-49, wherein $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1, and n1 is 2 or 3 and n2 is 1.

The disclosure is directed to compounds as described herein and pharmaceutically acceptable salts, solvates, hydrates, isomers, or tautomers thereof. The use of the terms "salt," "hydrate," "solvate," and the like, is intended to equally apply to the salt, hydrate, or solvate of isomers, tautomers, or racemates of the disclosed compounds.

It should be understood that all isomeric forms are included within the present disclosure, including mixtures thereof. The term "isomer" may refer to compounds that have the same composition and molecular weight but differ in physical and/or chemical properties. The structural difference may be in constitution (geometric or positional isomers) or in the ability to rotate the plane of polarized light (stereoisomers). With regard to stereoisomers, the compounds of the disclosure may have one or more asymmetric carbon atom and may occur as racemates, racemic mixtures and as individual enantiomers or diastereomers. Individual isomers of the compounds of the disclosure may, for example, be substantially free of other isomers, or may be admixed, for example, as racemates or with all other, or other selected, isomers. If the compound contains a double bond, the substituent may be in the E or Z configuration or cis or trans configuration or mixtures of any of the foregoing. Disclosed assay results may reflect the data collected for the racemic form, the enantiomerically pure form, or any other form in terms of stereochemistry or constitution (e.g., geometric or positional isomers).

The compounds of the disclosure may contain asymmetric or chiral centers, and, therefore, exist in different stereoisomeric forms. The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer. It is intended that all stereoisomeric forms of the compounds of the disclosure as well as mixtures thereof, including racemic mixtures, form part of the present disclosure.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. Each compound herein disclosed may include all the enantiomers (which may exist even in the absence of asymmetric carbons) that conform to the general structure of the compound, unless the stereochemistry is specifically indicated. The compounds may be in a racemic or enantiomerically pure form, or any other form in terms of stereochemistry. The chiral centers of the present disclosure may have the S or R configuration as defined by the IUPAC 1974 Recommendations. In some examples presented, the synthetic route may produce a single enantiomer or a mixture of enantiomers. In some embodiments of the disclosure, the compounds of the disclosure are enantiomers. In some embodiments, the compounds of the disclosure are the(S)-enantiomer. In other embodiments, the compounds of the disclosure are the (R)-enantiomer. In yet other embodiments, the compounds of the disclosure may be (+) or (−) enantiomers.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations may be considered to be diastereomers. The term "diastereomer" may refer to any member of this set of compounds. In some examples presented, the synthetic route may produce a single diastereomer or a mixture of diastereomers. The disclosure may include diastereomers of the compounds described herein.

In some embodiments, pharmaceutical compositions of the disclosure may be enriched to provide predominantly one enantiomer of a compound described herein. An enantiomerically enriched mixture may comprise, for example, at least 60 mol percent of one enantiomer, or more preferably at least 75, at least 80, at least 85, at least 90, at least 95, at least 96, at least 97, at least 98, at least 99, at least 99.5 or even 100 mol percent. In some embodiments, the compound described herein enriched in one enantiomer may be substantially free of the other enantiomer, wherein substantially free may mean that the substance in question makes up less than 10%, or less than 5%, or less than 4%, or less than 3%, or less than 2%, or less than 1% as compared to the amount of the other enantiomer, e.g., in the pharmaceutical composition or compound mixture. For example, if a pharmaceutical composition or compound mixture contains 98 grams of a first enantiomer and 2 grams of a second enantiomer, it would be said to contain 98 mol percent of the first enantiomer and only 2 mol percent of the second enantiomer.

In some embodiments, the pharmaceutical compositions of the disclosure may be enriched to provide predominantly one diastereomer of a compound disclosed herein. A diastereomerically enriched mixture may comprise, for example, at least 60 mol percent of one diastereomer, or more preferably at least 75, at least 80, at least 85, at least 90, at least 95, at least 96, at least 97, at least 98, at least 99, at least 99.5, or even 100 mol percent. In some embodiments, the compound described herein enriched in one diastereomer may be substantially free of other diastereomers, wherein substantially free may mean that the substance in question makes up less than 10%, or less than 5%, or less than 4%, or less than 3%, or less than 2%, or less than 1% as compared to the amount of other disastereomers, e.g., in the pharmaceutical composition or compound mixture.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column. Also, some of the compounds of the disclosure may be atropisomers or rotameric forms and are considered as part of this disclosure.

Compounds of the disclosure may exist in their tautomeric form (for example, as an amide or imino ether). All such tautomeric forms are contemplated herein as part of the present disclosure.

In some embodiments, the present disclosure provides compounds of Formula (I), (II), or (III), or pharmaceutically acceptable salts, solvates, hydrates, or tautomers thereof, or pharmaceutical compositions comprising the compounds, or pharmaceutically acceptable salts, solvates, hydrates, or tautomers thereof, wherein the isomeric form and/or stereochemistry is not determined. All isomers, including stereoisomers, of Formula (I), (II), or (III), or pharmaceutically acceptable salts, solvates, hydrates, or tautomers thereof, are hereby included in the disclosure.

The disclosure may include pharmaceutically acceptable salts of the compounds disclosed herein. A "pharmaceutically acceptable salt" may be acceptable for use in humans or domestic animals and may refer to those salts that retain the biological effectiveness and properties of the free forms, which are not biologically or otherwise undesirable. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

Pharmaceutically acceptable salts may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

Compounds of the disclosure may exist as solvates. The term "solvate" may refer to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

The compounds described herein further include all pharmaceutically acceptable isotopically labeled compounds. An "isotopically" or "radio-labeled" compound may be a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^{3}H$, and carbon 14, i.e., $^{14}C$, may be particularly useful for this purpose in view of their ease of incorporation and ready means of detection. Substitution with heavier isotopes such as deuterium, i.e., 2H, may afford certain therapeutic advantages resulting from greater metabolic stability, for example, increased in vivo half-life or reduced dosage requirements, and hence may be preferred in some circumstances. Suitable isotopes that may be incorporated in compounds described herein include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. Substitution with positron emitting isotopes, such as $^{11}C$, $^{18}F$, $^{15}O$, and $^{13}N$, can be useful in Positron Emission Topography (PET) studies.

Methods of Synthesizing the Compounds

The compounds of the present disclosure (e.g., a compound of Formula (I), (II), or (III)), or pharmaceutically acceptable salts, hydrates, solvates, isomers, or tautomers thereof, may be made by a variety of methods, including standard chemistry. Suitable synthetic routes are depicted in the schemes given herein.

The compounds disclosed herein (e.g., a compound of Formula (I), (II), or (III)), or pharmaceutically acceptable salts, hydrates, solvates, isomers, or tautomers thereof, may be prepared by methods known in the art of organic synthesis as set forth in part by the following synthetic schemes. In the schemes described herein, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of disclosed herein (e.g., a compound of Formula (I), (II), or (III)), or pharmaceutically acceptable salts, hydrates, solvates, isomers, or tautomers thereof.

Those skilled in the art will recognize if a stereocenter exists in the compounds disclosed herein (e.g., a compound of Formula (I), (II), or (III)), or pharmaceutically acceptable salts, hydrates, solvates, isomers, or tautomers thereof. Compounds disclosed herein can exist as enantiomeric or diastereomeric stereoisomers. Accordingly, the present disclosure includes all possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. For example, enantiomerically pure compounds of of the disclosure can be prepared using enantiomerically pure chiral building blocks. Alternatively, racemic mixtures of the final compounds or a racemic mixture of an advanced intermediate can be subjected to chiral purification as described herein to deliver the desired enantiomerically pure intermediates or final compounds. In the instances where an advanced intermediate is purified into its individual enantiomers, each individual enantiomer can be carried on separately to deliver the final enantiomerically pure compounds of of the disclosure. Resolution of the final product, an intermediate, or a starting material may be affected by any suitable method known in the art. See, for example, "Stereochemistry of Organic Compounds," by E. L. Eliel, S. H. Wilen, and L. N. Mander (Wiley-Interscience, 1994).

The compounds described herein (e.g., a compound of Formula (I), (II), or (III)), or pharmaceutically acceptable salts, hydrates, solvates, isomers, or tautomers thereof, may be made from commercially available starting materials or synthesized using known organic, inorganic, and/or enzymatic processes.

In certain aspects, such as for the production of bioactive polypeptides or hormones utilized in the disclosure or for evaluating the biological activities of the compounds of the disclosure (e.g., a compound of Formula (I), (II), or (III)), or pharmaceutically acceptable salts, hydrates, solvates, isomers, or tautomers thereof, the practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature: "*Molecular Cloning: A Laboratory Manual*," second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*," (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Cleavable Linkers

In some cases, the dipeptide based linkers described herein have been utilized as cleavable groups for the delivery of therapeutic compound payloads in other constructs to cells or tissue of interest. Several combinations of dipeptides have been utilized, with the valine-citrulline (Val-Cit) and valinealanine (Val-Ala) as the most successful combinations. [15, 16, 17, 18, 19] The synthetic pathway leading to the synthesis of Val-Cit and Val-Ala dipeptides are very similar and shown in the Scheme 1 herein. The amino group of Valine is initially protected with a Fluorenylmethyloxycarbonyl (Fmoc) group, followed by the activation of the carboxylic acid group with N-Hydroxysuccinimide (NHS) to form compound 3. Compound 3 can then be reacted with either citrulline or alanine in an aqueous solution of $NaHCO_3$ with DMF and THF present to ensure proper solubility. The resulting compound 4 can be coupled to para-aminobenzylalcohol group (PABOH) using N-ethoxycarbonyl-2-ethoxy-1,2-dihydroquinoline ("EEDQ"), which leads to the formation of compound 5. [20] Removal of the Fmoc group may be carried out with diethyl amine in DMF at room temperature to give amino-alcohol 6.

Scheme 1
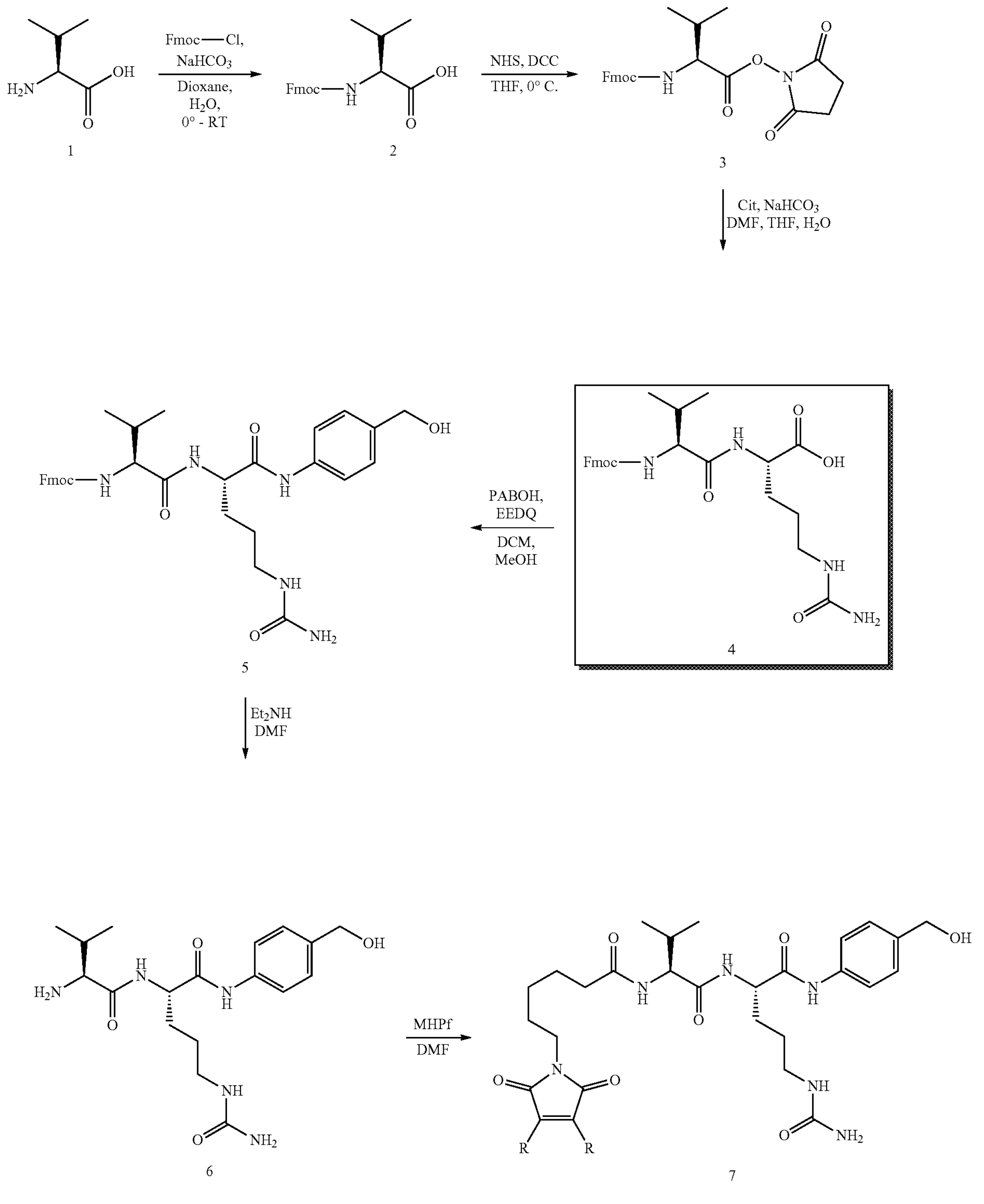
R is H, Cl, Br, or I.

To improve the stability of the heterobifunctional cross-linking reagent, 6-maleimidohexanoic acid pentafluorophenyl ester (MHPf) may be prepared as a substitute for the more popular 6-Maleimidohexanoic acid N-hydroxysuccinimide ester (MHSu). MHPf is prepared in two steps in very good yields to give compound 11-a as shown herein in Scheme 2.[14] Subsequent reaction of compound 6 with MHPf in DMF can provide a very good yield of compound MC-Val-Cit-PABOH, compound 7.

Scheme 2

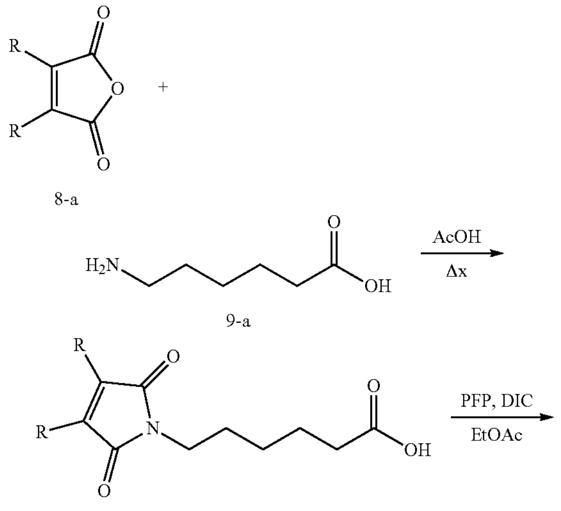

8-a
9-a
10-a

-continued

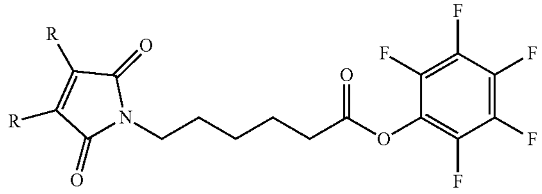

11-a

R is H, Cl, Br, or I.

As shown in Scheme 3, the MC-Val-Cit-PABOH 7 may be activated using two different methods to facilitate the attachment of various therapeutic compound payloads to either Cys or Lys residues of biologically active polypeptides, such as IL-2 polypeptides.

Initially, Bis(4-nitrophenyl) carbonate was reacted with compound 7 in the presence of N,N-Diisopropylethylamine and DMF to give carbonate 12. [22] Alternatively, N,N-disuccinimidyl carbonate can be used in a similar fashion under the same conditions. Both the p-Nitrophenol and the N-Hydroxysuccinimde are great leaving groups in the subsequent reaction.

Scheme 3

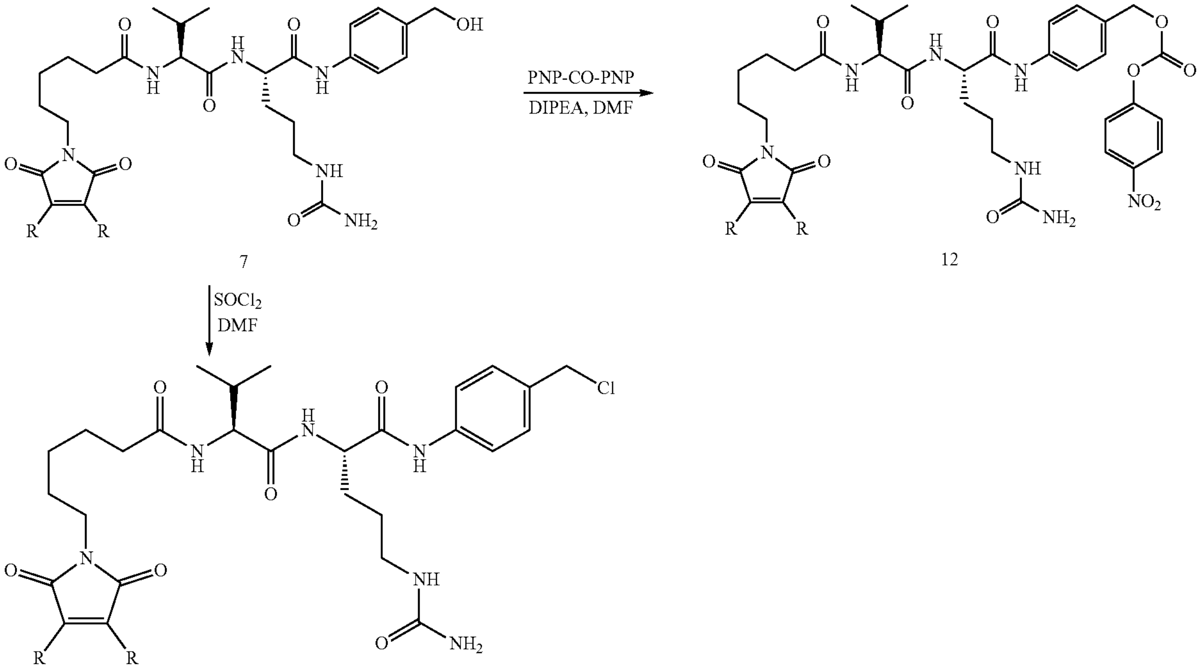

7
12
13

R is H, Cl, Br, or I.

As shown in Scheme 4, compound 12 may be reacted with the therapeutic compound to form the resulting carbonyl compound 14. Compound 14 can take the form of a carbamate or a carbonate, depending on whether the reactive site on the therapeutic compound is an amine or an alcohol. The Fmoc group may then be removed from compound 14 using diethylamine in DMF to give a near quantitative yield of compound 15.

Scheme 4

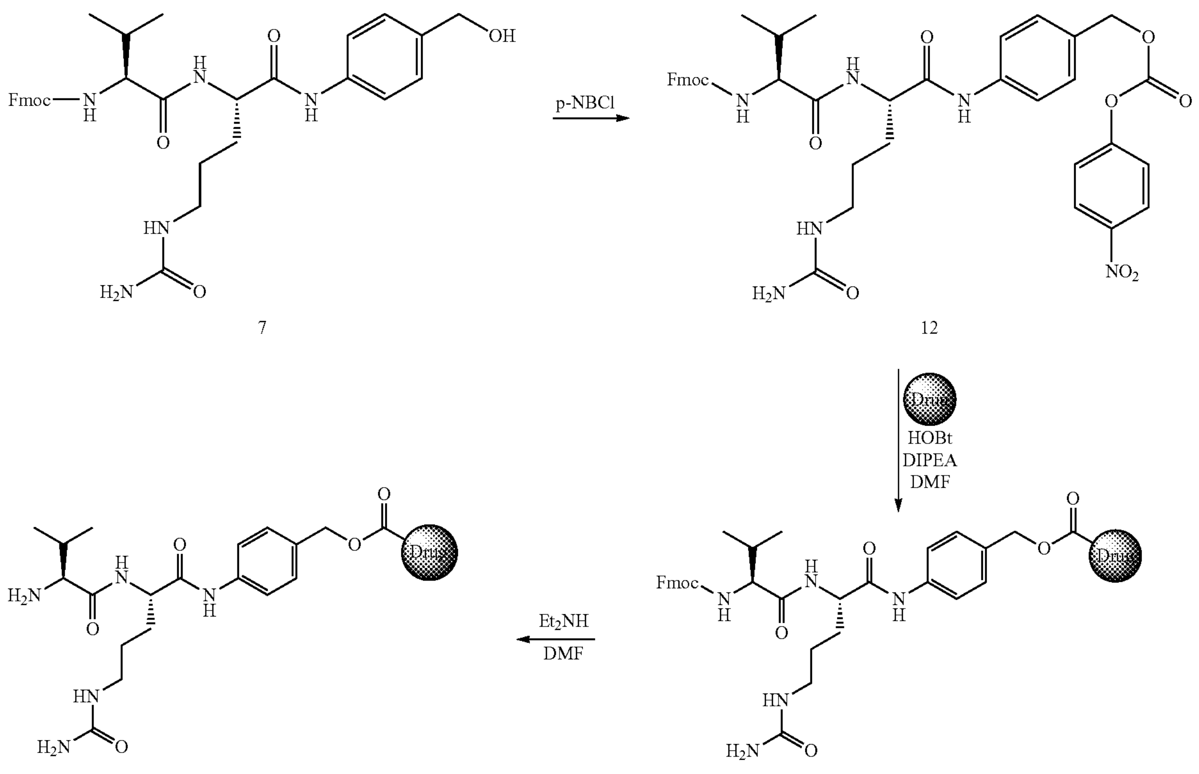

7 12 15 14

As shown in Scheme 5, the free amine may then then reacted with PEGylated bis(sulfosuccinimidyl) suberate (BS $(PEG)_5$) to effect the formation of the monosubstituted amide or compound 16.

Scheme 5

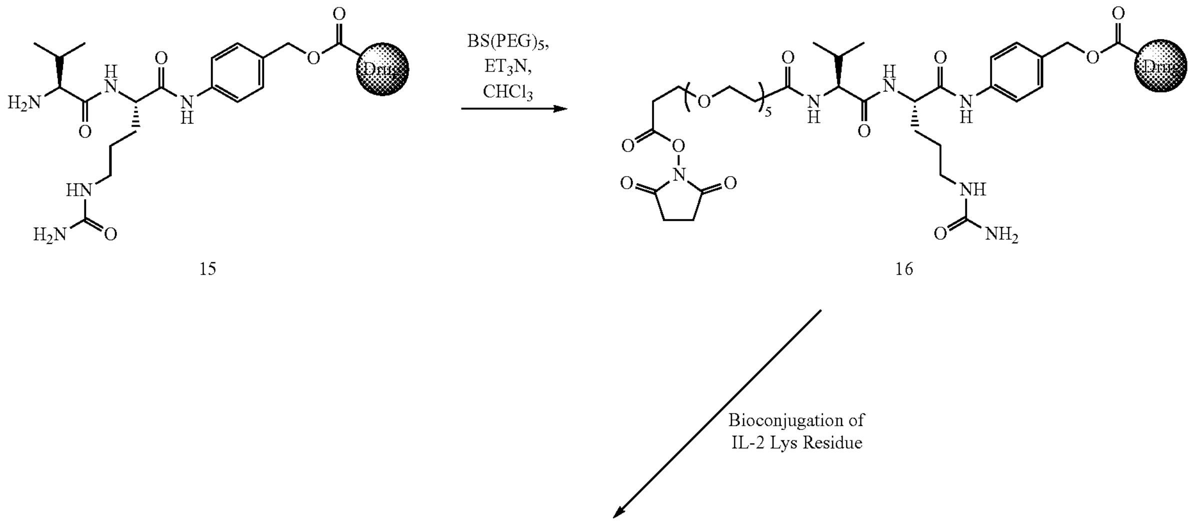

15 16

-continued

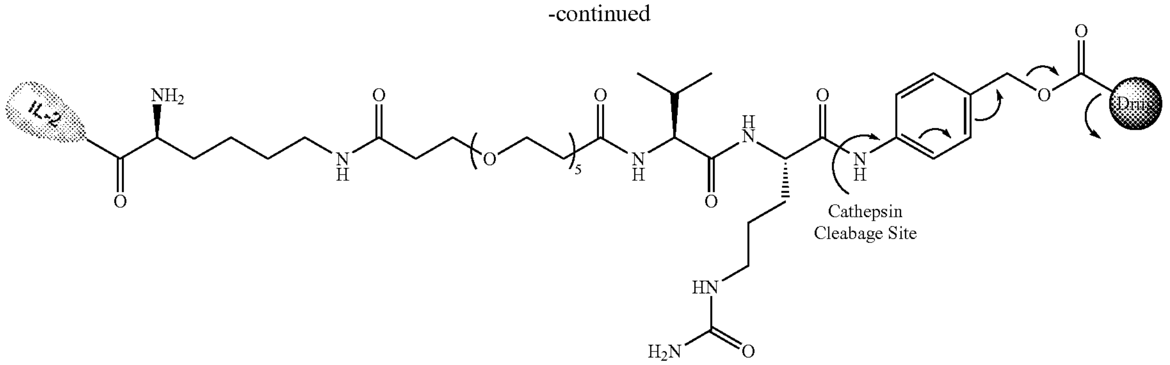

Alternatively, as shown in Scheme 6, the α, β-Bis(pentafluorphenyl-propionate) penta (ethylene-glycol) (Bis-dPEG$_5$-PFP ester) can be used to generate the mono-substituted amide for greater stability in the subsequent conjugation to proteins in aqueous solutions. The second activation occurs by transforming the hydroxyl group into a chloride atom forming compound 13. This reaction may be conducted in DMF, using thionyl chloride as the halogen source. After isolation of the chloride through precipitation of the product, the chloride product 13 undergoes an in-situ Finklestein reaction to generate the more reactive iodide species. The iodide species which reacts with secondary, tertiary and heteroaryl amines, either on the therapeutic compound or a linker attached to the therapeutic compound, to form a quaternary ammonium linkage that is stable under physiological conditions. [22] Compound 17 may then be purified and used for the conjugation with Cys residues to form the desired bio-conjugate. If R in Scheme 6 is Cl, I, or Br, and not H, the linker may form bonds with two different Cys residues on the bioactive polypeptide. Functional rebridging of native disulfides may be utilized to retain the structural integrity of the polypeptide and preserves receptor binding and function. The two Cys residues which result from the reduction of the disulfide bond may be rebridged into a functional disulfide using the dihalomaleimide.

Scheme 6

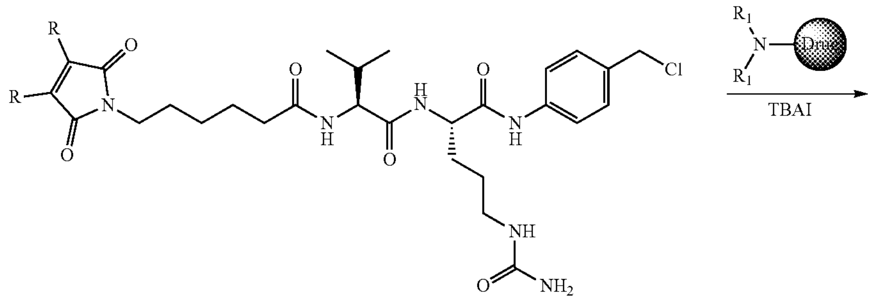

(MC-Val-Cit-PAB-Cl)
13

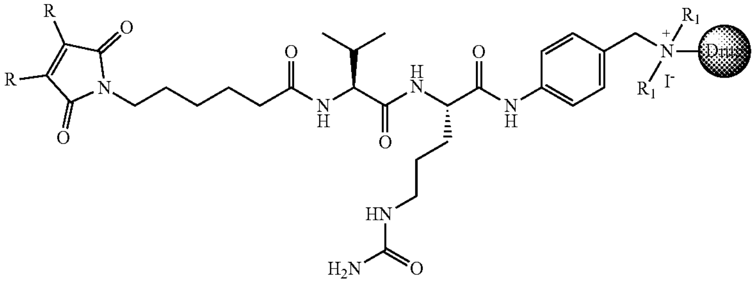

17

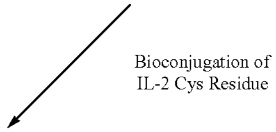

-continued

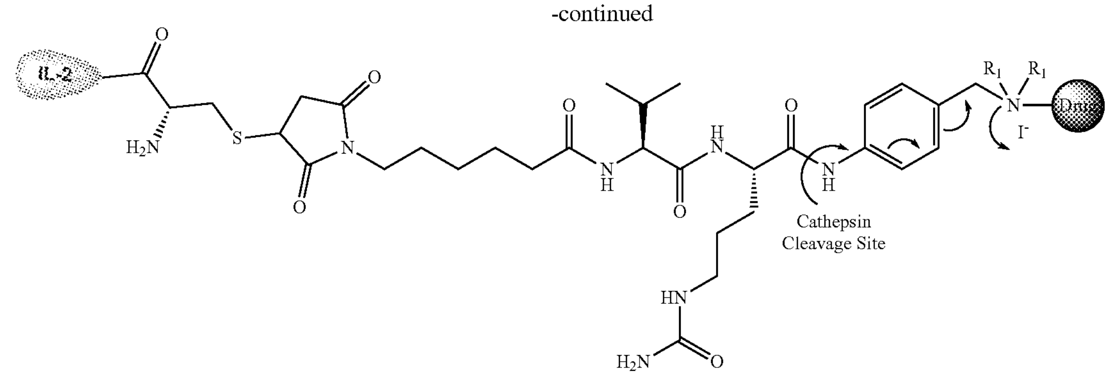

or

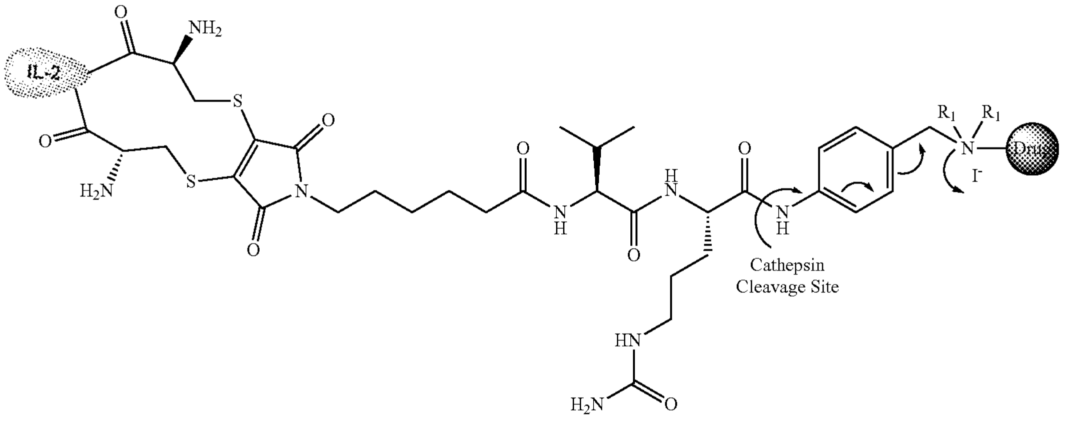

R = H, Cl, I, or Br; $R_1$ = H, alkyl, aryl, arylalkyl, protecting groups, and the like.

Glucuronide-Based Linkers

Glucuronide is another scaffold that has utility in assisting the transport of active biological agents and therapeutic compound payloads to a specific location. [23, 24, 25, 26, 27] As shown in Scheme 7, the synthesis of the transport molecule may be initiated with the commercially available (2S,3R,4S,5S,6S)-6-(methoxycarbonyl)tetrahydro-2H-pyran-2,3,4,5-tetrayl tetraacetate) undergoing a mild bromide substitution of the acetate group through the reaction of compound 18 with HBr in acetic acid to form compound 19. The bromide may be replaced by reacting 4-hydroxy-3-nitrobenzaldehyde with silver oxide in acetonitrile resulting in the formation of compound 20. Reduction of the formal group with sodium borohydride in methanol to give compound 21, may be followed by the reduction of the nitro group by palladium hydroxide to give the amino alcohol 22.

Scheme 7

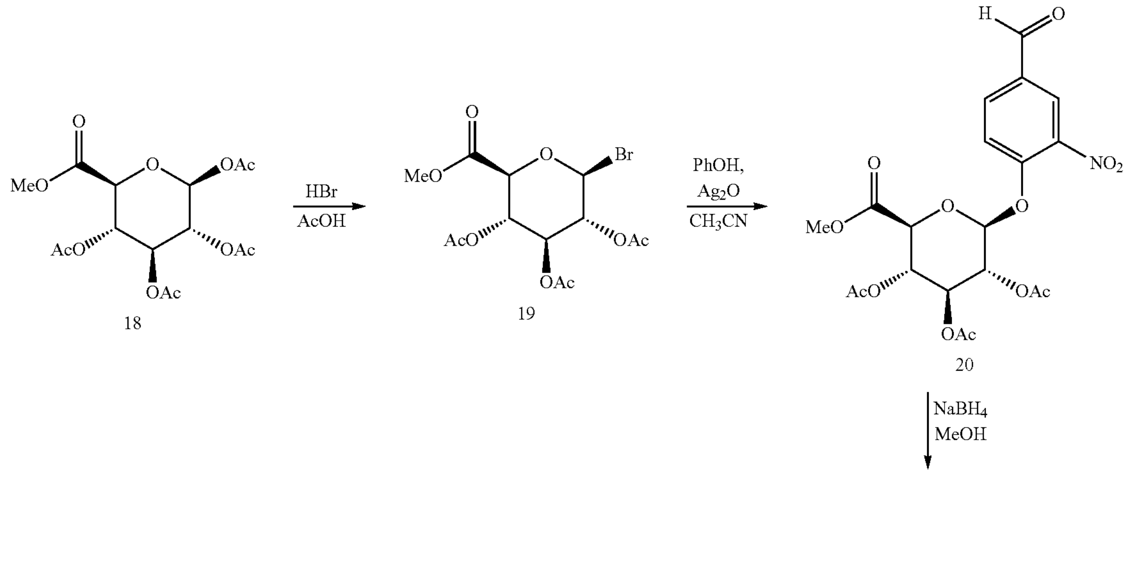

-continued

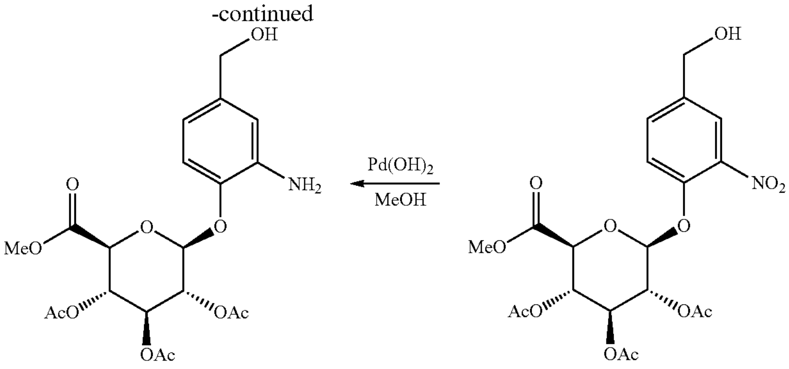

21 21

As shown in Scheme 8, the amino group of compound 22 can be selectively reacted with (9H-fluoren-9-yl)methyl (3-chloro-3-oxopropyl) carbamate followed by the formation of the unsymmetrical p-nitrophenyl carbonate using Bis(4-nitrophenyl) carbonate. The resulting carbonate 24 can be reacted with the therapeutic compound resulting in the formation of either a carbonate or a carbamate, depending on whether the reacting group on the therapeutic compound is an alcohol or an amine. Deprotection of the acetate groups with LiOH, followed by the removal of the Fmoc group with diethylamine gives compound 27.

Scheme 8

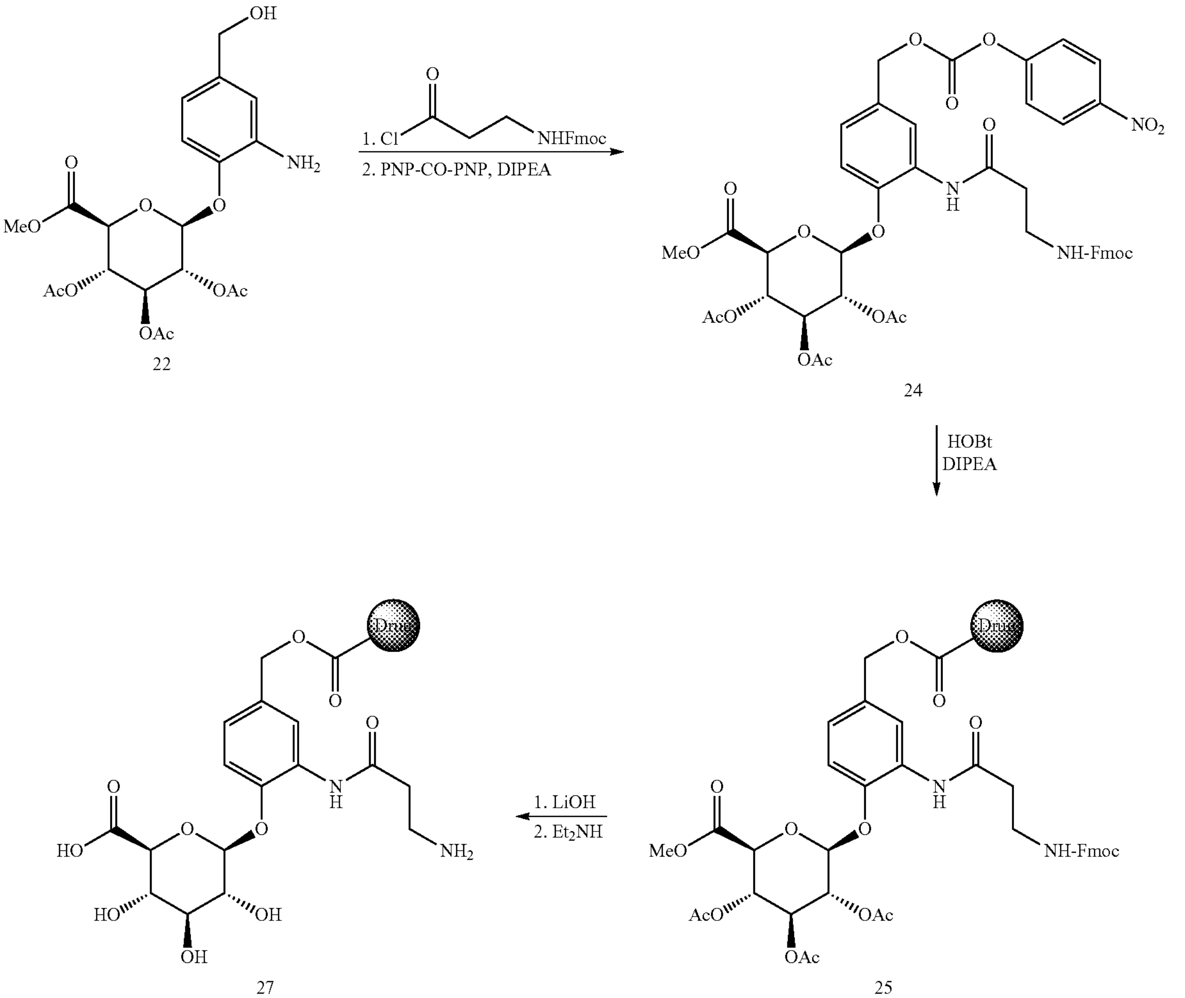

22

24

27 25

As shown in Schemes 9 and 10, Compound 27 can be functionalized to react with either the Cys or Lys residues on biologically active polypeptides, such as IL-2 polypeptides. For a bioconjugation to the Cys residue, the free amine on compound 27 can be reacted with the heterobifunctional cross-linking reagent MC-OSu, or the highly reactive and more stable MHPf. For the bioconjugation to the Lys residue, the free amine can be reacted with PEGylated bis (sulfosuccinimidyl) suberate ($BS(PEG)_5$) to effect the formation of the mono-substituted amide or alternatively with the more stable Bis-dPEG$_5$-PFP ester.

Scheme 9

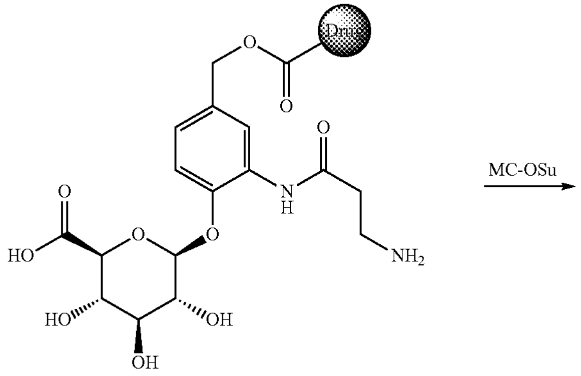

27

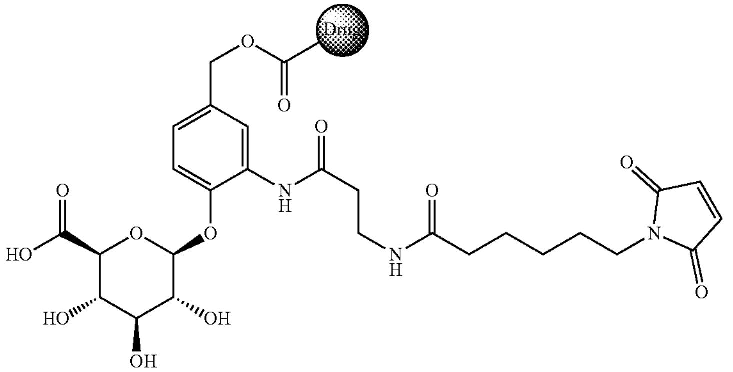

28

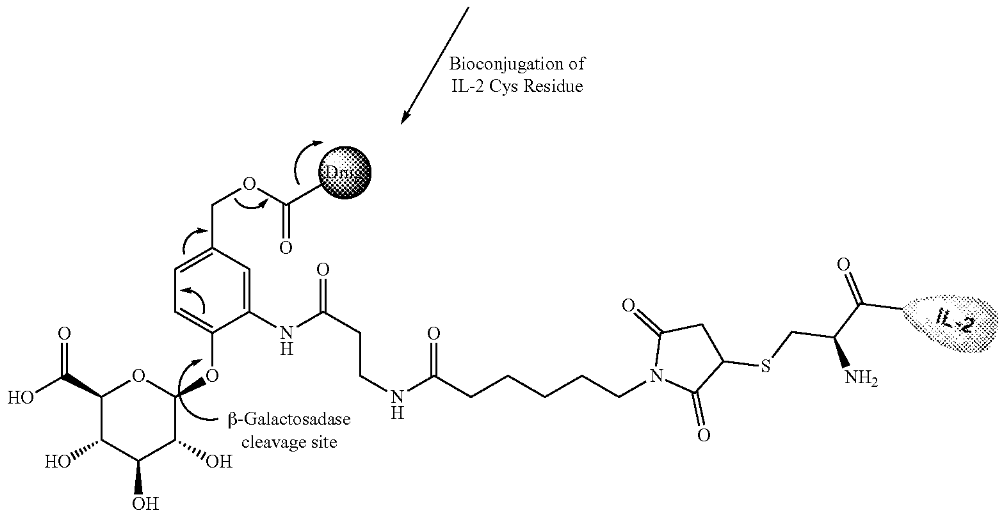

Scheme 10
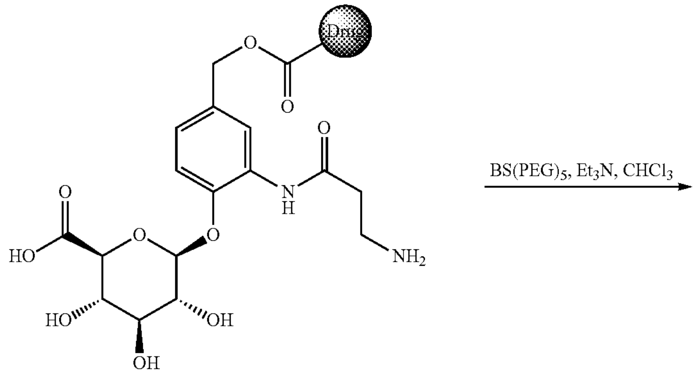
27
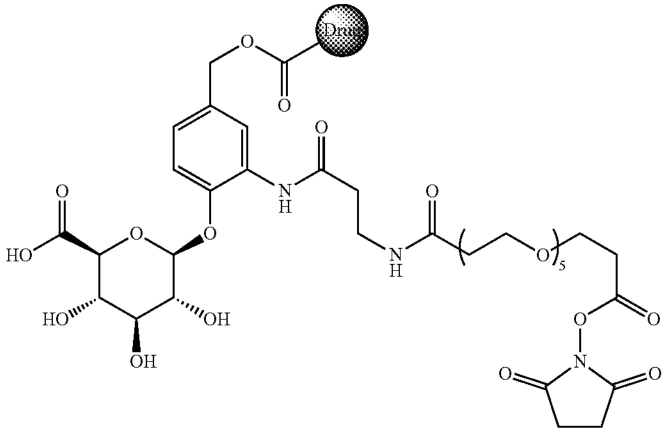
29
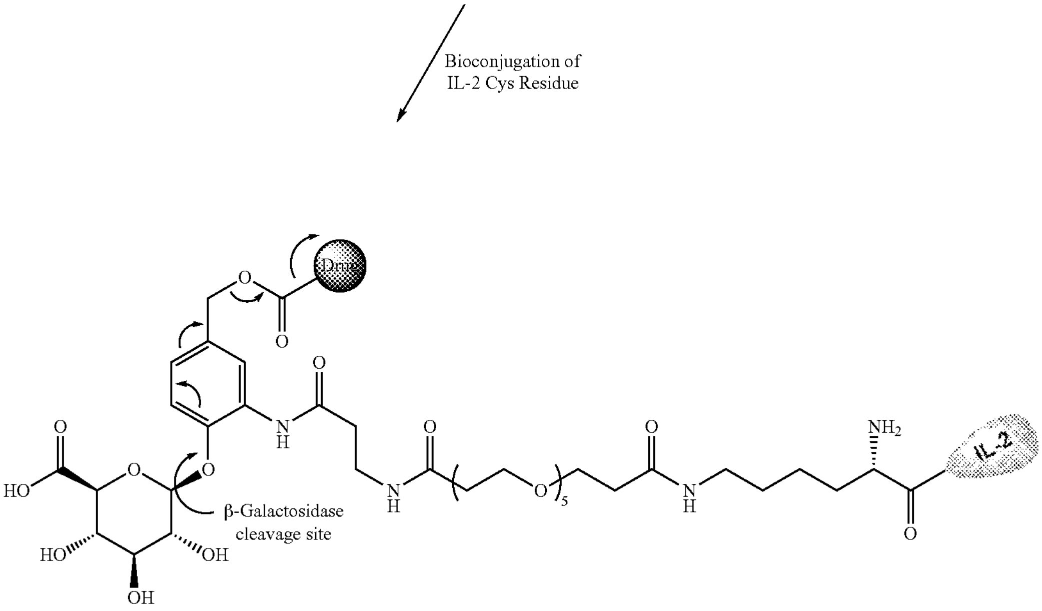

Non-Cleavable Linkers

Scheme 11

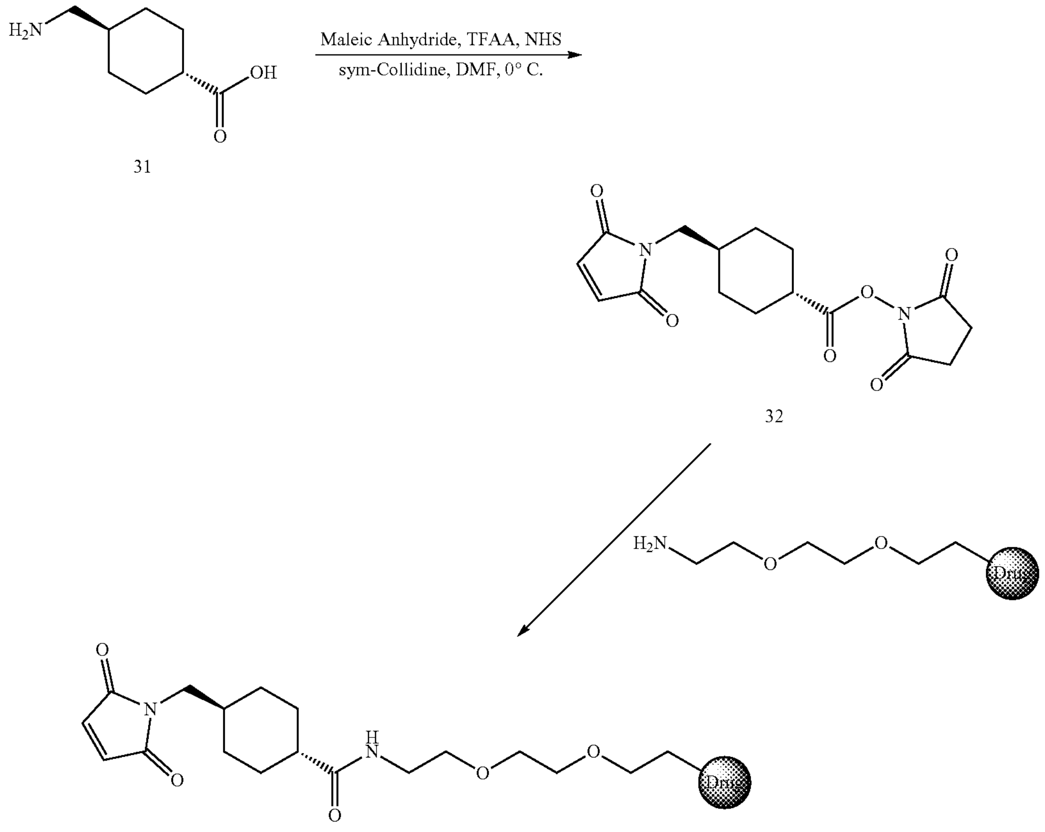

31

32

33

The use of succinimidyl-4-(N-maleimidomethyl)cyclohexane-1-carboxylate (SMCC, 32) as a heterobifunctional group for labeling and conjugation of proteins has met with great success. As shown in Scheme 11, recently, a one pot synthesis of this material was established on multigram scale starting with trans-4-(aminomethyl)cyclohexane carboxylic acid 31. Through the in situ formation of TFA-NHS, a 92% yield of compound 32 was obtained. Reacting compound 32 with amino groups linked to drug payloads can produce non-cleavable conjugates that can be reacted with available cysteine residues on proteins.

Scheme 12

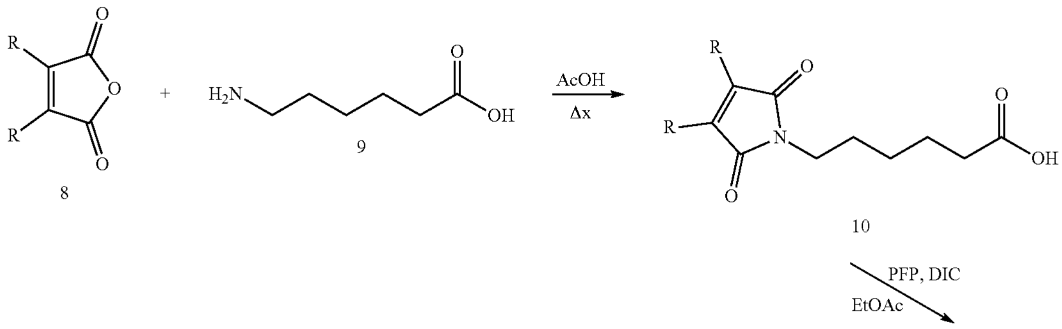

8 9 10

-continued

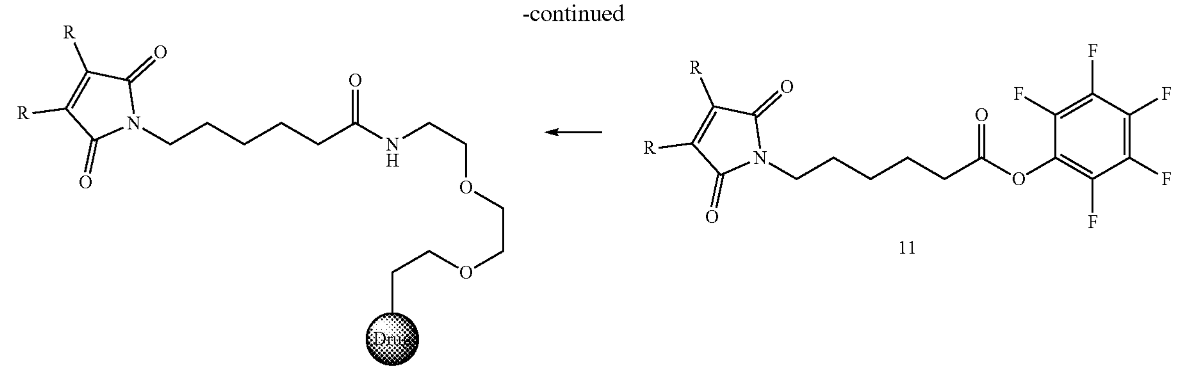

11

R = H, Cl, Br and I

Scheme 12 shows the synthesis of a non-cleavable linker using the maleiminde as the key group to attach to a cysteine residue. With the incorporation of halogens on the maleimide, multiple cysteine residues or sulfides resulting from the cleavage of a disulfide bond can react at both halogenated positions. The synthesis of this versatile linker begins with the condensation of maleic anhydride (with or without halogens) with 6-aminohexanoic acid in refluxing acid to give a near quantitative yield of compound 10. Carboxylic acid 10 was converted to the pentafluoro ester through a DCC coupling in ethyl acetate to give compound 11. The pentafluoro ester 11 is very amenable to displacement by amines under mild conditions to give a non-cleavable drug conjugate, which can react with available cysteine residues.

Representative Syntheses of Linkers of the Disclosure

Scheme 13

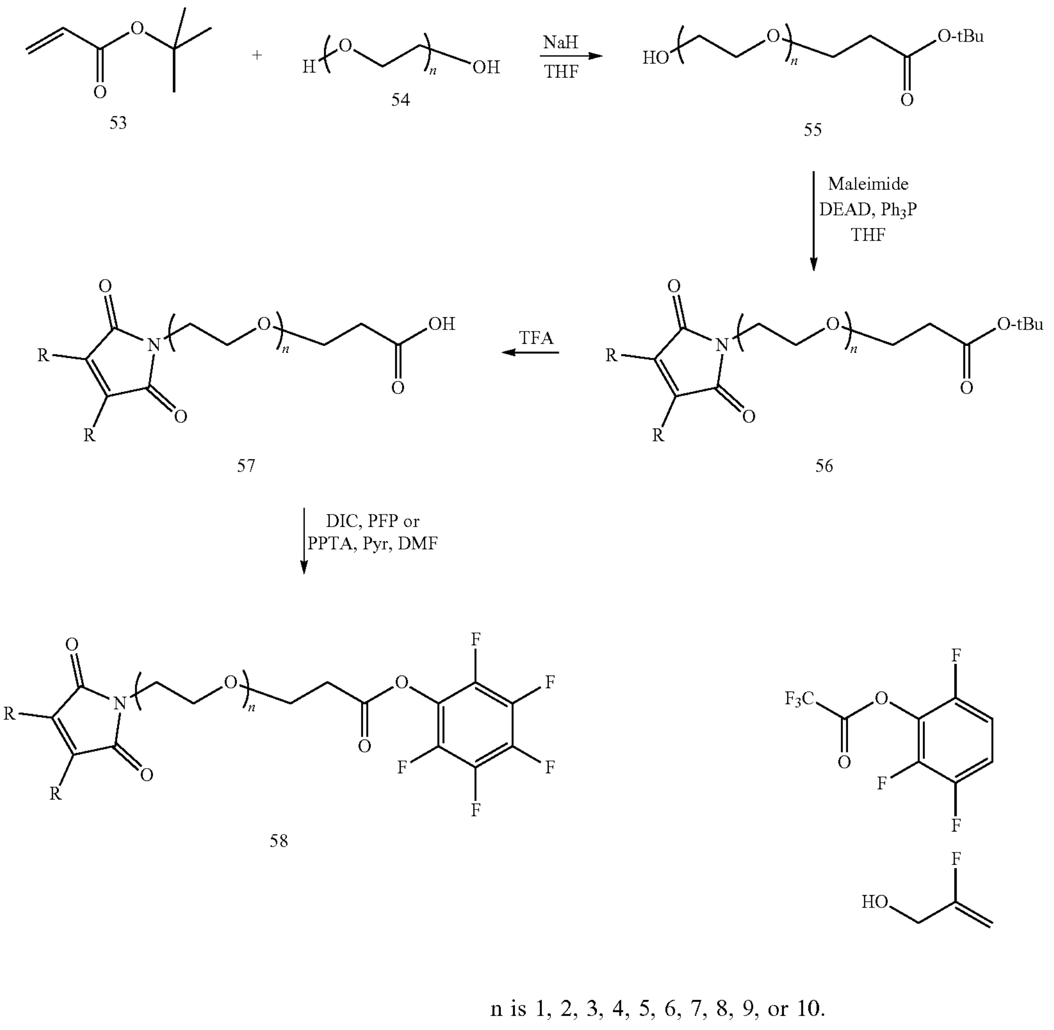

53 54 55 56 57 58 n is 1, 2, 3, 4, 5, 6, 7, 8, 9, or 10.

As shown in Scheme 13, glycols of various lengths may be reacted with a catalytic amount of sodium metal under anhydrous condition to promote the addition to tert-butyl acrylate for the Michael Addition product 55. Next, maleimide may be reacted with glycol under Mitsunobu conditions to produce compound 56 in good yields. [28] Deprotection of the tert-butyl ester with trifluoroacetic acid may be followed by the esterification under Steglich conditions with DIC and pentafluorophenol to give compound 58. An alternative approach to the formation of the pentafluorophenol ester is the reaction of the carboxylic acid with perfluorophenyl 2,2,2-trifluoroacetate (PPTA) in the presence of pyridine in DMF. The conditions are very mild and produce very good yields of the pentafluoroester. NHS has frequently been used to form the activated ester. These methods allow for the introduction of halogenated maleimides as well as the thiophenol derivatives.

Attachment of the payload to the drug conjugate often requires a functional linker with very good solubility properties as well as serum stability. Glycols may be used in this capacity. Below in schemes 14, 15, and 16, there are several approaches for the synthesis of glycol side chains that allow for easy attachment of both the payload as well as the conjugate linkers. In Scheme 14, an ethylene glycol may be reacted with Tosyl chloride to produce the Bis-Tosylate. The Bis-Tosylate may then be reacted with the Bis-tert-butyl carbamate to form compound 66. Subsequent reaction with LiBr results in the bromide substitution of the tosylate to give compound 67. In Schemes 14, 15, and 16, n is 1, 2, 3, 4, 5, 6, 7, 8, 9, or 10.

Scheme 14

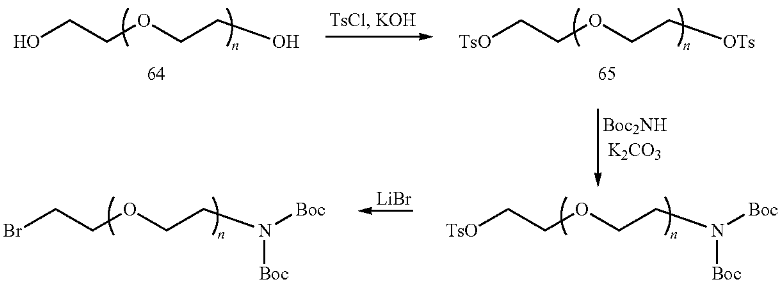

64 65 66 67

Glycol 68 in Scheme 15 has a terminal chloride, which is available for substitution. Sodium azide may be used to displace the chloride atom and the azide was then reduced with triphenylphosphine followed by protection of the amine with Boc anhydride to give compound 70. The hydroxyl group may then be finally converted to a bromide using triphenylphosphine and carbon tetrabromide.

Scheme 15

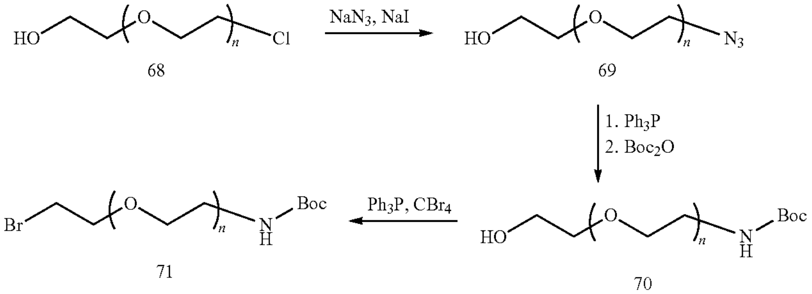

68 69 70 71

In Scheme 16, the diiodinated glycol is reacted with the Bis-Boc-carbamate to produce the Bis-Boc protected amino-iodo-glycol 73.

Scheme 16

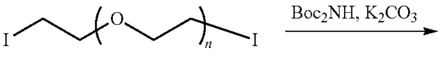

72

-continued

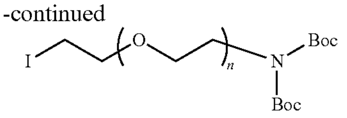

73

Pharmaceutical Compositions and Administration

Compounds of the present disclosure (e.g., a compound of Formula (II) or (III)), or pharmaceutically acceptable salts, hydrates, solvates, isomers, or tautomers thereof, may be used on their own but will generally be administered in the form of a pharmaceutical composition, in which one or more disclosed compounds, is in association with a pharmaceutically acceptable carrier. Conventional procedures for the selection and preparation of suitable pharmaceutical compositions are described in, for example, "Pharmaceuticals—The Science of Dosage Form Designs," M. E. Aulton, Churchill Livingstone, 1988, which is hereby incorporated by reference in its entirety. The pharmaceutical compositions described herein may be used in connection with the methods of treatment, uses, and medicaments described herein. The formulation and provision of suitable pharmaceutical compositions will be understood by those having ordinary skill in the art.

Compounds of the present disclosure (e.g., a compound of Formula (II) or (III)), or pharmaceutically acceptable salts, hydrates, solvates, isomers, or tautomers thereof, and pharmaceutical compositions of the disclosure can be administered in a variety of ways including enteral, parenteral and topical routes of administration. For example, suitable modes of administration include subcutaneous, iontophoretic, intravenous, intramuscular, intraperitoneal, subdural, intratumor, intertumor, and the like.

In some embodiments, the compounds of the present disclosure (e.g., a compound of Formula (II) or (III)), or pharmaceutically acceptable salts, hydrates, solvates, isomers, or tautomers thereof, and pharmaceutical compositions of the present disclosure may be administered parenterally, subcutaneous, iontophoretic, intravenous, intramuscular, intraperitoneal, subdural, intratumorally, intertumorally, or topically in dosage unit formulations containing conventional nontoxic pharmaceutically acceptable carriers as desired. The term parenteral as used herein includes subcutaneous injections, intravenous (both bolus and infusion), intramuscular, intrasternal injection, or infusion techniques. In some embodiments, the pharmaceutical composition of disclosure comprising one or more compounds of the disclosure (e.g., a compound of Formula (II) or (III)), or pharmaceutically acceptable salts, hydrates, solvates, isomers, or tautomers thereof, is for intravenous administration.

The terms "administer," "administering," or "administration" as used in this disclosure may refer to either directly administering one or more disclosed compounds, or pharmaceutically acceptable salts, hydrates, solvates, isomers, or tautomers thereof, or pharmaceutical compositions to a subject.

A "patient" or "subject" may be an animal. In some embodiments, the animal is a mammal, e.g., a human, mouse, rat, guinea pig, dog, cat, horse, cow, pig, or non-human primate, such as a monkey, chimpanzee, baboon, or rhesus. In some embodiments, the animal is a fish, bird, amphibian, reptile, or the like. In some embodiments, the subject is a human.

The disclosure includes pharmaceutical compositions comprising one or more compounds disclosed herein (e.g., a compound of Formula (II) or (III)), or pharmaceutically acceptable salts, hydrates, solvates, isomers, or tautomers thereof, and a pharmaceutically acceptable carrier. Suitable pharmaceutically acceptable carriers include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-8-cyclodextrin, polyvinylpyrrolidinone, low melting waxes, ion exchange resins, and the like, as well as combinations of any two or more thereof. Other suitable pharmaceutically acceptable carriers are described in Remington's Pharmaceutical Sciences, Mack Pub. Co., New Jersey (1991), which is incorporated herein by reference.

The disclosure includes pharmaceutical compositions comprising one or more compounds Formula (II), or pharmaceutically acceptable salts, hydrates, solvates, isomers, or tautomers thereof, and a pharmaceutically acceptable carrier.

The disclosure includes pharmaceutical compositions comprising one or more compounds of Formula (II), or pharmaceutically acceptable salts, hydrates, solvates, isomers, or tautomers thereof, and a pharmaceutically acceptable carrier, wherein the one or more compounds of Formula (II) are selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

The disclosure includes pharmaceutical compositions comprising one or more compounds of Formula (II), or pharmaceutically acceptable salts, hydrates, solvates, isomers, or tautomers thereof, and a pharmaceutically acceptable carrier, wherein the one or more compounds of Formula (II) is B-32.

The disclosure includes pharmaceutical compositions comprising one or more compounds Formula (III), or pharmaceutically acceptable salts, hydrates, solvates, isomers, or tautomers thereof, and a pharmaceutically acceptable carrier.

The disclosure includes pharmaceutical compositions comprising one or more compounds of Formula (III), or pharmaceutically acceptable salts, hydrates, solvates, isomers, or tautomers thereof, and a pharmaceutically acceptable carrier, wherein the one or more compounds of Formula (III) are selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

The disclosure includes pharmaceutical compositions comprising one or more compounds of Formula (III), or pharmaceutically acceptable salts, hydrates, solvates, isomers, or tautomers thereof, and a pharmaceutically acceptable carrier, wherein the one or more compounds of Formula (III) is B-32.

The term "carrier," as used in this disclosure, may encompass carriers, excipients, and diluents, and means a material, composition, or vehicle, such as a liquid or solid filler, diluent, excipient, solvent or encapsulating material, involved in carrying or transporting a pharmaceutical agent from one organ, or portion of the body, to another organ, or portion of the body of a subject. As used herein "pharmaceutically acceptable carrier" may include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier that has been approved by the United States Food and Drug Administration as being acceptable for use in humans or domestic animals. In some embodiments, the term "pharmaceutically acceptable carrier" may mean a non-toxic, inert solid, semi-solid or liquid filler, diluent, encapsulating material or formulation auxiliary of any type.

Pharmaceutical compositions of the present disclosure may be in any form suitable for the intended method of administration, including, for example, a solution, a suspension, or an emulsion. Liquid carriers are typically used in preparing solutions, suspensions, and emulsions. Liquid carriers contemplated for use in the practice of the present disclosure include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Pharmaceutical compositions of the present disclosure may also be in the form of microparticles, microcapsules, liposomal encapsulates, and the like, as well as combinations of any two or more thereof.

Injectable pharmaceutical compositions, for example, sterile injectable aqueous or oleaginous suspensions may be formulated according to the known art using suitable dispersing or wetting agents and suspending agents. The sterile injectable pharmaceutical compositions may also be sterile injectable solutions or suspensions in a nontoxic parenterally acceptable carrier, for example, as a solution in 1,3-propanediol or 1,3-butanediol. Among the acceptable carriers that may be employed are water, Ringer's solution, and isotonic sodium chloride solution. In addition, sterile, fixed oils are conventionally employed as a carrier. For this purpose, any bland fixed oil may be employed including synthetic monoor diglycerides. In addition, fatty acids such as oleic acid can be useful in the preparation of injectable pharmaceutical compositions.

The injectable pharmaceutical compositions can be sterilized, for example, by filtration through a bacterial-retaining filter, or by incorporating sterilizing agents in the form of sterile solid pharmaceutical compositions that can be dissolved or dispersed in sterile water or other sterile injectable medium prior to use.

In order to prolong the effect of one or more compounds of the disclosure, it may desirable to slow the absorption of the one or more compounds of the disclosure from subcutaneous or intramuscular injection. This may be accomplished by the use of a liquid suspension of crystalline or amorphous material with poor water solubility. The rate of absorption of the one or more compounds of the disclosure then depends upon its rate of dissolution that, in turn, may depend upon crystal size and crystalline form. Alternatively, delayed absorption of a parenterally administered one or more compounds of the disclosure may be accomplished by dissolving or suspending the one or more compounds of the disclosure in an oil vehicle. Injectable depot forms are made by forming microencapsule matrices of the one or more compounds of the disclosure in biodegradable polymers such as polylactide-polyglycolide. Depending upon the ratio of the one or more compounds of the disclosure to polymer and the nature of the particular polymer employed, the rate of release for the one or more compounds of the disclosure can be controlled. Examples of other biodegradable polymers include poly(orthoesters) and poly(anhydrides). Depot injectable pharmaceutical compositions may also be prepared by entrapping the one or more compounds of the disclosure in liposomes or microemulsions that are compatible with body tissues.

The compounds of the present disclosure (e.g., a compound of Formula (II) or (III)), or pharmaceutically acceptable salts, hydrates, solvates, isomers, or tautomers thereof, or pharmaceutical compositions of the disclosure can also be administered in the form of liposomes. As is known in the art, liposomes are generally derived from phospholipids or other lipid substances. Liposomes are formed by monoor multilamellar hydrated liquid crystals that are dispersed in an aqueous medium. Any non-toxic, physiologically acceptable and metabolizable lipid capable of forming liposomes can be used. The present pharmaceutical compositions in liposome form can contain, in addition to compounds of the present disclosure (e.g., a compound of Formula (II) or (III)), or pharmaceutically acceptable salts, hydrates, solvates, isomers, or tautomers thereof, carriers, stabilizers, preservatives, excipients, and the like. Possible lipids may include the phospholipids and phosphatidyl cholines (lecithins), both natural and synthetic. Methods to form liposomes are known in the art.

Methods of, and Uses for Treating Cancers and Immunological Disorders

In another aspect, the present disclosure provides methods for treating a disorder comprising administering to a subject a therapeutically effective amount of a compound, or pharmaceutically acceptable salt, hydrate, solvate, isomer, or tautomer thereof, having the structure of any of the compounds disclosed herein (e.g., a compound of Formula (II) or (III)), or pharmaceutically acceptable salts, hydrates, solvates, isomers, or tautomers thereof. In another aspect, the present disclosure provides methods for treating a disorder comprising administering to a subject a therapeutically effective amount of pharmaceutical compositions of the disclosure.

"Therapeutically effective" amounts of the compounds of the disclosure (e.g., a compound of Formula (II) or (III)), or pharmaceutically acceptable salts, hydrates, solvates, isomers, or tautomers thereof, or pharmaceutical compositions of the disclosure may refer to a sufficient amount of a compound of the disclosure (e.g., a compound of Formula (II) or (III)), or a pharmaceutically acceptable salt, hydrate, solvate, isomer, or tautomer thereof, or a pharmaceutical composition of the disclosure to provide the desired biological result. That result can be reduction and/or alleviation of the signs, symptoms, or causes of a disorder, or any other desired alteration of a biological system. For example, a "therapeutically effective amount" or "effective amount" for therapeutic use may be the amount of the pharmaceutical composition comprising a compound of the disclosure (e.g., a compound of Formula (II) or (III)), or a pharmaceutically acceptable salt, hydrate, solvate, isomer, or tautomer thereof, required to provide a clinically significant decrease in a disorder. An appropriate "therapeutically effective amount" or "effective amount" in any individual case may be determined by one of ordinary skill in the art using routine experimentation.

The term "treating" with regard to a subject, may refer to improving at least one symptom of the subject's disorder. Treating may include curing, improving, or at least partially ameliorating the disorder.

The present disclosure provides a method for treating a disorder in a subject, comprising administering to a subject in need thereof a therapeutically effective amount of a compound of the present disclosure (e.g., a compound of Formula (II) or (III)), or pharmaceutically acceptable salts, hydrates, solvates, isomers, or tautomers thereof, wherein the disorder is an immunological disorder or cancer.

The present disclosure provides a method for treating a disorder in a subject, comprising administering to a subject in need thereof a therapeutically effective amount of a pharmaceutical composition of the disclosure (e.g., a composition comprising a compound of Formula (II) or (III), or a pharmaceutically acceptable salt, hydrate, solvate, isomer, or tautomer thereof), wherein the disorder is an immunological disorder or cancer.

The present disclosure provides for use of a compound of the present disclosure (e.g., a compound of Formula (II) or (III)), or pharmaceutically acceptable salts, hydrates, solvates, isomers, or tautomers thereof, in the manufacture of a medicament for treating a disorder in a subject in need thereof, wherein the disorder is an immunological disorder or cancer.

The present disclosure provides for use of a pharmaceutical composition of the disclosure (e.g., a composition comprising a compound of Formula (II) or (III), or a pharmaceutically acceptable salt, hydrate, solvate, isomer, or tautomer thereof) in the manufacture of a medicament for treating a disorder in a subject in need thereof, wherein the disorder is an immunological disorder or cancer.

The present disclosure provides for use of a compound of the present disclosure (e.g., a compound of Formula (II) or (III)), or pharmaceutically acceptable salts, hydrates, solvates, isomers, or tautomers thereof, for treating a disorder in a subject in need thereof.

The present disclosure provides for use of a pharmaceutical composition of the disclosure (e.g., a composition comprising a compound of Formula (II) or (III), or a pharmaceutically acceptable salt, hydrate, solvate, isomer, or tautomer thereof) for treating a disorder in a subject in need thereof.

The present disclosure provides for use of a compound of the present disclosure (e.g., a compound of Formula (II) or (III)), or pharmaceutically acceptable salts, hydrates, solvates, isomers, or tautomers thereof, for treating a disorder in a subject in need thereof, wherein the disorder is an immunological disorder or cancer.

The present disclosure provides for use of a pharmaceutical composition of the disclosure (e.g., a composition comprising a compound of Formula (II) or (III), or a pharmaceutically acceptable salt, hydrate, solvate, isomer, or tautomer thereof) for treating a disorder in a subject in need thereof, wherein the disorder is an immunological disorder or cancer.

The present disclosure provides a compound of the present disclosure (e.g., a compound of Formula (II) or (III)), or pharmaceutically acceptable salts, hydrates, solvates, isomers, or tautomers thereof, for use in a method of treating a disorder in a subject in need thereof, wherein the disorder is an immunological disorder or cancer.

The present disclosure provides a pharmaceutical composition of the disclosure (e.g., a composition comprising a compound of Formula (II) or (III), or a pharmaceutically acceptable salt, hydrate, solvate, isomer, or tautomer thereof) for use in a method of treating a disorder in a subject in need thereof, wherein the disorder is an immunological disorder or cancer.

In some embodiments, the methods, uses, medicaments, or compounds for use of the disclosure include one or more compounds Formula (II), or pharmaceutically acceptable salts, hydrates, solvates, isomers, or tautomers thereof.

In some embodiments, the methods, uses, medicaments, or compounds for use of the disclosure include one or more compounds of Formula (II), or pharmaceutically acceptable salts, hydrates, solvates, isomers, or tautomers thereof, wherein the one or more compounds of Formula (II) are selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

In some embodiments, the methods, uses, medicaments, or compounds for use of the disclosure include one or more compounds of Formula (II), or pharmaceutically acceptable salts, hydrates, solvates, isomers, or tautomers thereof, wherein the one or more compounds of Formula (II) is B-32.

In some embodiments, the methods, uses, medicaments, or compounds for use of the disclosure include one or more compounds Formula (III), or pharmaceutically acceptable salts, hydrates, solvates, isomers, or tautomers thereof.

In some embodiments, the methods, uses, medicaments, or compounds for use of the disclosure include one or more compounds of Formula (III), or pharmaceutically acceptable salts, hydrates, solvates, isomers, or tautomers thereof, wherein the one or more compounds of Formula (III) are selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

In some embodiments, the methods, uses, medicaments, or compounds for use of the disclosure include one or more compounds of Formula (III), or pharmaceutically acceptable salts, hydrates, solvates, isomers, or tautomers thereof, wherein the one or more compounds of Formula (III) is B-32.

In some embodiments, the methods, uses, medicaments, or pharmaceutical compositions for use of the disclosure include pharmaceutical compositions comprising one or more compounds Formula (II), or pharmaceutically acceptable salts, hydrates, solvates, isomers, or tautomers thereof, and a pharmaceutically acceptable carrier.

In some embodiments, the methods, uses, medicaments, or pharmaceutical compositions for use of the disclosure include pharmaceutical compositions comprising one or more compounds of Formula (II), or pharmaceutically acceptable salts, hydrates, solvates, isomers, or tautomers thereof, and a pharmaceutically acceptable carrier, wherein the one or more compounds of Formula (II) are selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

In some embodiments, the methods, uses, medicaments, or pharmaceutical compositions for use of the disclosure include pharmaceutical compositions comprising one or more compounds of Formula (II), or pharmaceutically acceptable salts, hydrates, solvates, isomers, or tautomers thereof, and a pharmaceutically acceptable carrier, wherein the one or more compounds of Formula (II) is B-32.

In some embodiments, the methods, uses, medicaments, or pharmaceutical compositions for use of the disclosure include pharmaceutical compositions comprising one or more compounds Formula (III), or pharmaceutically acceptable salts, hydrates, solvates, isomers, or tautomers thereof, and a pharmaceutically acceptable carrier.

In some embodiments, the methods, uses, medicaments, or pharmaceutical compositions for use of the disclosure include pharmaceutical compositions comprising one or more compounds of Formula (III), or pharmaceutically acceptable salts, hydrates, solvates, isomers, or tautomers thereof, and a pharmaceutically acceptable carrier, wherein the one or more compounds of Formula (III) are selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

In some embodiments, the methods, uses, medicaments, or pharmaceutical compositions for use of the disclosure include pharmaceutical compositions comprising one or more compounds of Formula (III), or pharmaceutically acceptable salts, hydrates, solvates, isomers, or tautomers thereof, and a pharmaceutically acceptable carrier, wherein the one or more compounds of Formula (III) is B-32.

In some embodiments of the methods, uses, compounds for use, medicaments, or pharmaceutical compositions for use of the disclosure, the disorder is an immunological disorder. Immunological disorders of the methods, uses, compounds for use, medicaments, or pharmaceutical compositions for use of the disclosure include, but are not limited to: Achalasia, Addison's disease, Adult Still's disease, Agammaglobulinemia, Alopecia areata, Amyloidosis, Ankylosing spondylitis, Anti-GBM/Anti-TBM nephritis, Antiphospholipid syndrome, Asthma, Atherosclerosis, Autoimmune angioedema, Autoimmune dysautonomia, Autoimmune encephalomyelitis, Autoimmune hepatitis, Autoimmune inner ear disease (AIED), Autoimmune myocarditis, Autoimmune oophoritis, Autoimmune orchitis, Autoimmune pancreatitis, Autoimmune retinopathy, Autoimmune thyroid disease, Autoimmune urticaria, Axonal & neuronal neuropathy (AMAN), Balo disease, Behcet's disease, Benign mucosal pemphigoid, Bullous pemphigoid, Castleman disease (CD), Celiac disease, Chagas disease, Chronic inflammatory demyelinating polyneuropathy (CIDP), Chronic recurrent multifocal osteomyelitis (CRMO), Churg-Strauss Syndrome (CSS) or Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Discoid lupus, Dressler's syndrome, Endometriosis, Eosinophilic esophagitis (EoE), Eosinophilic fasciitis, Erythema nodosum, Essential mixed cryoglobulinemia, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves's disease, Graft-versus-Host disease (GVHD), Guillain-Barre syndrome, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenia purpura (ITP), Inclusion body myositis (IBM), Interstitial cystitis (IC), inflammatory bowel disease, Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, or III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Sarcoidosis, Schmidt syndrome, Scleritis, Scleroderma, serious allergies, Sjogren's syndrome, Sperm & testicular autoimmunity, Stiff person syndrome (SPS), Subacute bacterial endocarditis (SBE), Susac's syndrome, Sympathetic ophthalmia (SO), Systemic lupus erythematosus (SLE), Takayasu's arteritis, Temporal arteritis/Giant cell arteritis, Thrombocytopenia purpura (TTP), Tolosa-Hunt syndrome (THS), Transverse myelitis, Type 1 diabetes, Ulcerative colitis (UC), Undifferentiated connective tissue disease (UCTD), Uveitis, Vasculitis, HCV-related vasculitis, Systemic vasculitis, Vitiligo, Vogt-Koyanagi-Harada Disease, and Wegener's granulomatosis (or Granulomatosis with Polyangiitis (GPA)).

In some embodiments of the methods, uses, compounds for use, medicaments, or pharmaceutical compositions for use of the disclosure, the disorder is cancer. Cancers of the methods, uses, compounds for use, medicaments, or pharmaceutical compositions for use of the disclosure include, but are not limited to: non-small cell lung cancer (NSCLC), melanoma, kidney cancer, bladder cancer, head and neck cancer, or claudin-low breast cancer.

While the compounds of the disclosure (e.g., a compound of Formula (II) or (III)), or pharmaceutically acceptable salts, hydrates, solvates, isomers, or tautomers thereof, or pharmaceutical compositions of the disclosure can be administered as the sole active pharmaceutical agent, they can also be used in combination with one or more other compounds (e.g., a compound of Formula (II) or (III)), or pharmaceutically acceptable salts, hydrates, solvates, isomers, or tautomers thereof, or pharmaceutical compositions as described herein, or in combination with other agents used in the treatment or prevention of disorder, or both.

The term "prevent" or "preventing" with regard to a subject may refer to keeping a disorder from afflicting the subject. Preventing may include prophylactic treatment.

In addition, the compounds of the present disclosure (e.g., a compound of Formula (II) or (III)), or pharmaceutically acceptable salts, hydrates, solvates, isomers, or tautomers thereof, or pharmaceutical compositions of the disclosure can be used, either singly or in combination, or in combination with other modalities for preventing or treating disorders. Such other treatment modalities include without limitation, surgery, radiation, hormone supplementation, and diet regulation. These can be performed sequentially (e.g., treatment with a compound of the disclosure (e.g., a compound of Formula (II) or (III)), or a pharmaceutically acceptable salt, hydrate, solvate, isomer, or tautomer thereof, or pharmaceutical composition of the disclosure following surgery or radiation) or in combination (e.g., in addition to a diet regimen).

The additional active agents may generally be employed in therapeutic amounts as indicated by sources well known to those having ordinary skill in the art, e.g., the Physician's Desk Reference (PDR) $53^{rd}$ Edition (1999), which is incorporated herein by reference, or such therapeutically useful amounts as would be known to one of ordinary skill in the art. The compounds of the disclosure (e.g., a compound of Formula (II) or (III)), or pharmaceutically acceptable salts, hydrates, solvates, isomers, or tautomers thereof, pharmaceutical compositions of the disclosure, and the other therapeutically active agents can be administered at the recommended maximum clinical dosage or at lower doses. Dosage levels of the active compounds (e.g., a compound of Formula (II) or (III)), or pharmaceutically acceptable salts, hydrates, solvates, isomers, or tautomers thereof, in the pharmaceutical compositions of the disclosure may be varied to obtain a desired therapeutic response depending on the route of administration, severity of the disorder and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

In accordance with yet other embodiments, the present disclosure provides methods for treating or preventing a disorder in a human or animal subject in which an amount of a compound of the disclosure (e.g., a compound of Formula (II) or (III)), or a pharmaceutically acceptable salt, hydrate, solvate, isomer, or tautomer thereof, or a pharmaceutical composition of the disclosure that is effective to at least ameliorate disorder symptoms.

The amount of a compound of the disclosure (e.g., a compound of Formula (II) or (III)), or a pharmaceutically acceptable salt, hydrate, solvate, isomer, or tautomer thereof, that may be combined with the carrier materials to produce a single dosage form will vary depending upon the host treated and the particular mode of administration. It will be understood, however, that the specific dose level for any particular patient will depend upon a variety of factors including the activity of the specific compounds, or pharmaceutically acceptable salts, hydrates, solvates, isomers, or tautomers thereof, employed, the age, body weight, general health, sex, diet, time of administration, route of administration, rate of excretion, drug combination, and the severity of the particular disorder undergoing therapy. The therapeutically effective amount for a given situation can be readily determined by routine experimentation and is within the skill and judgment of the ordinary clinician.

For exemplary purposes of the present disclosure, a prophylactically or therapeutically effective dose will generally be from about 0.1 mg $kg^{-1}$ $d^{-1}$ to 100 mg $kg^{-1}$ $d^{-1}$, preferably from about 1 mg $kg^{-1}$ $d^{-1}$ to about 20 mg $kg^{-1}$ $d^{-1}$, and most preferably from about 10 mg $kg^{-1}$ $d^{-1}$ to about 10 mg $kg^{-1}$ $d^{-1}$ of a compound of the present disclosure (e.g., a compound of Formula (II) or (III)), or a pharmaceutically acceptable salt, hydrate, solvate, isomer, or tautomer thereof, which may be administered in one or multiple doses.

A low dose of IL-2 polypeptide is generally at least about 10-fold lower than a conventional high dose, (where a high dose may be, for example, from about 600 to 700 IU/kg/day, or from about $50\times10^6$ to $150\times10^6$ IU/day for an average human body weight). Dosage ranges described herein are provided as the dose that is administered in a one day period of time, in terms of the body surface area ($m^2$), and international units (IU). A daily dose may be fractionated into 1, 2, 3, or 4 separate doses over a day. Accordingly, a low dose of a compound of the disclosure (e.g., a compound of Formula (II) or (III)), or a pharmaceutically acceptable salt, hydrate, solvate, isomer, or tautomer thereof, or a pharmaceutical composition comprising said compound, may be administered at a dose of about $0.05\times10^6$ to not more than about $5\times10^6$ international unit (IU)/$m^2$/day, not more than about $4\times10^6$ IU/$m^2$/day, not more than about $3\times10^6$ IU/$m^2$/day, not more than about $2\times10^6$ IU/$m^2$/day, not more than about $1\times10^6$ IU/$m^2$/day. Preferably the dose is at least about $0.1\times10^6$ IU/$m^2$/day, at least about $0.2\times10^6$ IU/$m^2$/day, at least about $0.3\times10^6$ IU/$m^2$/day; and may be from about $0.4\times10^6$ IU/$m^2$/day, $0.5\times10^6$ IU/$m^2$/day, $0.6\times10^6$ IU/$m^2$/day, $0.7\times10^6$ IU/$m^2$/day, $0.8\times10^6$ IU/$m^2$/day, $0.9\times10^6$ IU/$m^2$/day, $1\times10^6$ IU/$m^2$/day, or $2\times10^6$ IU/$m^2$/day.

Kits

A "kit" as used herein may include a container for containing at least one pharmaceutical composition or compound (e.g., a compound of Formula (II) or (III)), or a pharmaceutically acceptable salt, hydrate, solvate, isomer, or tautomer thereof, of the disclosure and may also include divided containers such as a divided bottle or a divided foil packet. The container can be in any conventional shape or form as known in the art that is made of a pharmaceutically acceptable material, for example a paper or cardboard box, a glass or plastic bottle or jar, or a resealable bag. The container employed can depend on the exact dosage form involved. It is feasible that more than one container can be used together in a single package to market a single dosage form.

A specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter, that indicates the number of daily doses that has been dispensed. Another example of such a memory-aid is a battery-powered micro-chip memory coupled with a liquid crystal readout, or audible reminder signal that, for example, reads out the date that the last daily dose has been taken and/or reminds one when the next dose is to be taken.

The kits of the present disclosure may also include, in addition to one or more compounds (e.g., a compound of Formula (II), or (III)), or pharmaceutically acceptable salts, hydrates, solvates, isomers, or tautomers thereof, or pharmaceutical compositions of the present disclosure, one or more additional pharmaceutically active compounds or pharmaceutical compositions. The additional compounds or pharmaceutical compositions may be administered in the same dosage form as the one or more compounds (e.g., a compound of Formula (II) or (III)), or pharmaceutically acceptable salts, hydrates, solvates, isomers, or tautomers thereof, or pharmaceutical compositions of the present disclosure or in a different dosage form. Likewise, the additional compounds or pharmaceutical compositions can be administered at the same time as the one or more compounds (e.g., a compound of Formula (II) or (III)), or pharmaceutically acceptable salts, hydrates, solvates, isomers, or tautomers thereof, or pharmaceutical compositions of the present disclosure or at different times.

In some embodiments, the kit of the present disclosure has a notice in the form prescribed by a governmental agency regulating the manufacture, use or sale of pharmaceuticals or biological products, which notice reflects (a) approval by the agency of manufacture, use or sale for human administration, (b) directions for use, or both.

The foregoing may be better understood by reference to the following examples, that are presented for illustration and not to limit the scope of the disclosed concepts.

EXEMPLARY EMBODIMENTS

Some embodiments of this disclosure are of Embodiment I, as follows:

Embodiment I-1. A compound having the structure:

$X_1$—[$X_2$—$(X_3)_m$]$_n$, and its pharmaceutically acceptable salts, hydrates, and coordination compounds, wherein:

m is an integer between 1 and 10;

n is an integer between 1 and 11;

$X_1$ is IL-2 or a bio-active homolog thereof;

$X_2$ is a linker; and $X_3$ is a therapeutic compound.

Embodiment I-2. The compound of Embodiment I-1, wherein $X_3$ is a oncolytic drug.

Embodiment I-3. The compound of Embodiment I-1, wherein $X_3$ is an immunosuppressive drug.

Embodiment I-4. The compound of Embodiment I-1, wherein $X_2$ is a cleavable linker.

Embodiment I-5. The compound of Embodiment I-1, wherein $X_2$ is a non-cleavable linker.

Embodiment I-6. The compound of Embodiment I-1, wherein $X_2$ is bound to $X_1$ at a Cys residue thereof.

Embodiment I-7. The compound of Embodiment I-6, wherein $X_3$ is a oncolytic drug.

Embodiment I-8. The compound of Embodiment I-6, wherein $X_3$ is an immunosuppressive drug.

Embodiment I-9. The compound of Embodiment I-6, wherein $X_2$ is a cleavable linker.

Embodiment I-10. The compound of Embodiment I-6, wherein $X_2$ is a non-cleavable linker.

Embodiment I-11. The compound of Embodiment I-1, wherein $X_2$ is bound to $X_1$ at a Lys residue thereof.

Embodiment I-12. The compound of Embodiment I-11, wherein $X_3$ is a oncolytic drug.

Embodiment I-13. The compound of Embodiment I-11, wherein $X_3$ is an immunosuppressive drug.

Embodiment I-14. The compound of Embodiment I-11, wherein $X_2$ is a cleavable linker.

Embodiment I-15. The compound of Embodiment I-11, wherein $X_2$ is a non-cleavable linker.

Embodiment I-16. The compound of Embodiment I-1, wherein n is an integer between 2 and 9.

Embodiment I-17. The compound of Embodiment I-18, wherein n is an integer between 3 and 8.

Embodiment I-18. The compound of Embodiment I-1, wherein n is an integer between 4 and 7.

Embodiment I-19. The compound of Embodiment I-17, wherein n is 5 or 6.

Embodiment I-20. A method of treating a disease in a subject, comprising administering to said subject a therapeutically effective amount of the compound of Embodiment I-1 in a pharmaceutically effective carrier.

Some embodiments of this disclosure are of Embodiment II, as follows:

Embodiment II-1. A compound having a structure of Formula (I):

$$X_{2a}—(X_3)_m \quad (I),$$

or a pharmaceutically acceptable salt, solvate, hydrate, isomer, or tautomer thereof, wherein:

m is 1, 2, 3, 4, 5, 6, 7, 8, 9, or 10;

$X_{2a}$ is a linker; and $X_3$ is a therapeutic compound.

Embodiment II-2. The compound, or a pharmaceutically acceptable salt, solvate, hydrate, isomer, or tautomer thereof, of Embodiment II-1, wherein m is 1.

Embodiment II-3. The compound, or a pharmaceutically acceptable salt, solvate, hydrate, isomer, or tautomer thereof, of Embodiment II-1, wherein m is 2, 3, 4, 5, 6, 7, or 8.

Embodiment II-4. The compound, or a pharmaceutically acceptable salt, solvate, hydrate, isomer, or tautomer thereof, of Embodiment II-1, wherein m is 1, 2, or 3.

Embodiment II-5. The compound, or a pharmaceutically acceptable salt, solvate, hydrate, isomer, or tautomer thereof, of Embodiment II-1, wherein m is 2, 3, 4, or 5.

Embodiment II-6. The compound, or a pharmaceutically acceptable salt, solvate, hydrate, isomer, or tautomer thereof, of any one of Embodiments II-1 to II-5, wherein $X_{2a}$ is a cleavable linker.

Embodiment II-7. The compound, or a pharmaceutically acceptable salt, solvate, hydrate, isomer, or tautomer thereof, of any one of Embodiments II-1 to II-5, wherein $X_{2a}$ is a non-cleavable linker.

Embodiment II-8. The compound, or a pharmaceutically acceptable salt, solvate, hydrate, isomer, or tautomer thereof, of Embodiment II-6, wherein $X_{2a}$ is selected from the group consisting of L-1, L-2, L-3, L-4, L-5, L-6, L-7, L-8, L-9, L-10, L-11, L-12, L-13, L-14, L-15, L-16, and L-19, wherein R is H, alkyl, aryl, arylalkyl, a glycol ether, or a glycol linker.

Embodiment II-9. The compound, or a pharmaceutically acceptable salt, solvate, hydrate, isomer, or tautomer thereof, of Embodiment II-8, wherein $X_{2a}$ is selected from the group consisting of L-1 and L-19.

Embodiment II-10. The compound, or a pharmaceutically acceptable salt, solvate, hydrate, isomer, or tautomer thereof, of Embodiment II-7, wherein $X_{2a}$ is selected from the group consisting of L-17 and L-18.

Embodiment II-11. The compound, or a pharmaceutically acceptable salt, solvate, hydrate, isomer, or tautomer thereof, of any one of Embodiments II-1 to II-10, wherein $X_3$ is an immunomodulating agent.

Embodiment II-12. The compound, or a pharmaceutically acceptable salt, solvate, hydrate, isomer, or tautomer thereof, of any one of Embodiments II-1 to II-11, wherein $X_3$ is selected from the group consisting of an immunosuppressive drug, an antianemic, an antianginal, an antiarryhythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a ubiquitin-activating enzyme inhibitor, a ubiquitin-activating enzyme E1 inhibitor, and a proteasome inhibitor.

Embodiment II-13. The compound, or a pharmaceutically acceptable salt, solvate, hydrate, isomer, or tautomer thereof, of any one of Embodiments II-1 to II-12, wherein $X_3$ is selected from the group consisting of: pevonedistat; TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate); Piperacillin; M22 (1-benzyl-N-(2,4-dichlorophenethyl) piperidin-4-amine); 6,6'-Biapigenin; Thieno-pyridine; Imidazo-pyrimidine; Largazole; Pyr-41 (4 [4-(5-nitro-furan-2-ylmethylene)-3,5-dioxo-pyrazolidin-1-yl]-benzoic acid ethyl ester); Phorbol 12-myristate 13-acetate; 2,3-dihydropyrrolo [2,1-b]quinazolin-9 (1H)-one; Ofloxacin; Panepophenanthin; Himeic Acid A; Hyrtioreticulins A; Phytol; ABPA3 ([(2R,3S,4R,5R)-5-[6-(3-ethynylanilino) purin-9-yl]-3,4-dihydroxyoxolan-2-yl]methyl sulfamate); Benzothiazole; a Deoxyvasicinone derivative; Coumarin A; Coumarin B; and Imidazolium-quinoxaline, wherein $R_1$ is alkyl, aryl, arylalkyl, arylalkyne, arylalkene, heterocyclyl, or heteroaryl and $R_2$ is H, alkyl, or aryl.

Embodiment II-14. The compound, or a pharmaceutically acceptable salt, solvate, hydrate, isomer, or tautomer thereof, of any one of Embodiments II-1 to II-13, wherein $X_3$ is selected from the group consisting of: Pevonedistat, TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d] pyrimidin-7-yl)-3,4-dihydroxytetrahydrofuran-2-yl)methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), and TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate).

Embodiment II-14a. The compound, or a pharmaceutically acceptable salt, solvate, hydrate, isomer, or tautomer thereof, of any one of Embodiments II-1 to II-14, wherein $X_3$ is Pevonedistat.

Embodiment II-15. The compound, or a pharmaceutically acceptable salt, solvate, hydrate, isomer, or tautomer thereof, of any one of Embodiments II-1 to II-10, wherein $X_3$ is a cancer chemotherapeutic.

Embodiment II-16. The compound, or a pharmaceutically acceptable salt, solvate, hydrate, isomer, or tautomer thereof, of any one of Embodiments II-1 to II-10 or II-15, wherein $X_3$ is selected from the group consisting of an oncolytic drug, a genotoxic agent, an alkylating agent, a tubulin inhibitor, a microtubule assembly inhibitor, an antineoplastic drug, a kinase inhibitor, a vinca alkaloid, an antibiotic, an anthracycline, an antimetabolite, an aromatase inhibitor, a topoisomerase inhibitor, a mTor inhibitor, a retinoid, an antimitotic agent, a protease inhibitor, a tyrosine kinase inhibitor, a microtubule destabilizer, and a proteasome inhibitor.

Embodiment II-17. The compound, or a pharmaceutically acceptable salt, solvate, hydrate, isomer, or tautomer thereof, of any one of Embodiments II-1 to II-10 or II-15 to II-16, wherein $X_3$ is selected from the group consisting of vincristine, vinorelbine, vinflunine, crytophycin 52, a halichondrin, a dolastatin, a hemiasterlin, colchicine, a combretastatin, 2-methoxyestradiol, a methoxybenzenesulfonamide, epothilone, and discodermolide.

Embodiment II-18. The compound, or a pharmaceutically acceptable salt, solvate, hydrate, isomer, or tautomer thereof, of any one of Embodiments II-1 to II-10 or II-15 to II-16, wherein $X_3$ is selected from the group consisting of: Monomethyl Auristatin E; Docetaxel; Etoposide; Gemcitabine; Vinblastine; Paclitaxel; Irinotecan; Fluorouracil; Methotrexate; Carboplatin; Oxaliplatin; Cisplatin; Doxorubicin HCl; Fulvestrant; Isotretinoin; Buserelin; Everolimus; Carfilzomib; Rifabutin; Clindamycin; Tubulysin A; Indibulin; Gefitinib; and Dasatinib.

Embodiment II-19. The compound, or a pharmaceutically acceptable salt, solvate, hydrate, isomer, or tautomer thereof, of any one of Embodiments II-1 to II-10, II-15 to II-16, or II-18, wherein $X_3$ is Monomethyl Auristatin E.

Embodiment II-20. The compound, or a pharmaceutically acceptable salt, solvate, hydrate, isomer, or tautomer thereof, of Embodiment II-1, wherein the compound of Formula (I) is selected from the group consisting of: A-1, A-2, A-3, A-4, A-5, A-6, A-7, A-8, A-9, A-10, A-11, A-12, A-13, A-14, A-15, A-16, A-17, A-18, A-19, A-20, A-21, A-22, A-23, A-24, A-25, A-26, A-27, A-28, A-29, A-30, A-31, A-32 A-33, A-34, A-35, A-36, A-37, A-38, A-39, A-40, A-41, A-42, A-43, A-44, A-45, A-46, A-47, A-48, A-49, A-50, and A-51, wherein R is H, alkyl, aryl, arylalkyl, a glycol ether, or a glycol linker and p is 1, 2, 3, 4, 5, or 6.

Embodiment II-21. The compound, or a pharmaceutically acceptable salt, solvate, hydrate, isomer, or tautomer thereof, of Embodiment II-20, wherein the compound of Formula (I) is selected from the group consisting of A-1, A-2, A-3, A-4, A-5, A-6, A-7, A-8, A-9, A-10, A-11, A-12, A-13, A-14, A-15, A-16, A-17, A-18, A-30, A-31, and A-51.

Embodiment II-22. The compound, or a pharmaceutically acceptable salt, solvate, hydrate, isomer, or tautomer thereof, of Embodiment II-20, wherein the compound of Formula (I) is selected from the group consisting of A-1, A-30, A-31, and A-51.

Embodiment II-23. The compound, or a pharmaceutically acceptable salt, solvate, hydrate, isomer, or tautomer thereof, of Embodiment II-20, wherein the compound of Formula (I) is A-32.

Embodiment II-24. A compound having a structure of Formula (II):

$$X_1—[X_2—(X_3)_m]_n \quad \text{(II)},$$

or a pharmaceutically acceptable salt, solvate, hydrate, isomer, or tautomer thereof, wherein:

m is 1, 2, 3, 4, 5, 6, 7, 8, 9, or 10;

n is 1, 2, 3, 4, 5, 6, 7, 8, 9, 10 or 11;

$X_1$ is a biologically active polypeptide or hormone;

$X_2$ is a linker; and $X_3$ is a therapeutic compound.

Embodiment II-25. The compound, or a pharmaceutically acceptable salt, solvate, hydrate, isomer, or tautomer thereof, of Embodiment II-24, wherein $X_1$ is selected from the group consisting of an Acylation stimulating protein polypeptide, an Adipokine polypeptide, an Albinterferon polypeptide, a Cerberus polypeptide, a Colony-stimulating factor polypeptide, an Erythropoietin polypeptide, a FMS-like tyrosine kinase 3 ligand polypeptide, a Globulin component polypeptide, a Macrophage Activating Factor polypeptide, a Granulocyte colony-stimulating factor polypeptide, a Granulocyte-macrophage colony-stimulating factor polypeptide, a Hepatocyte growth factor polypeptide, an IL-17 polypeptide, an IL-10 polypeptide, an Inflammasome polypeptide, an Interferome polypeptide, an Interferon polypeptide, an Interferon beta-la polypeptide, an Interferon beta-1b polypeptide, an Interferon gamma polypeptide, an Interferon type I polypeptide, an Interferon type II polypeptide, an Interferon type III polypeptide, an Interleukin polypeptide, an Interleukin 1 receptor antagonist polypeptide, an Interleukin 8 polypeptide, a Leukemia inhibitory factor polypeptide, a Leukocyte-promoting factor polypeptide, a Lymphokine polypeptide, a Lymphotoxin polypeptide, a Lymphotoxin alpha polypeptide, a Lymphotoxin beta polypeptide, a Macrophage colony-stimulating factor polypeptide, a Macrophage inflammatory protein polypeptide, a Macrophage-activating factor polypeptide, a Monokine polypeptide, a Myokine polypeptide, a Myonectin polypeptide, a Nicotinamide phosphoribosyltransferase polypeptide, an Oncostatin M polypeptide, an Oprelvekin polypeptide, a Platelet factor 4 polypeptide, a Proinflammatory cytokine polypeptide, a Promegapoietin polypeptide, a Receptor activator of nuclear factor kappa-B ligand polypeptide, a Stromal cell-derived factor 1 polypeptide, an adrenomedullin polypeptide, an angiopoietin polypeptide, an Autocrine motility factor polypeptide, a Bone morphogenetic protein polypeptide, a Ciliary neurotrophic factor polypeptide, an Interleukin-6 polypeptide, an Epidermal growth factor polypeptide, an Ephrin A1 polypeptide, an Ephrin A2 polypeptide, an Ephrin A3 polypeptide, an Ephrin A4 polypeptide, an Ephrin A5 polypeptide, an Ephrin B1 polypeptide, an Ephrin B2 polypeptide, an Ephrin B3 polypeptide, a Fibroblast growth factor polypeptide, a Fibroblast growth factor 1 polypeptide, a fibroblast growth factor 2 polypeptide, a Fibroblast growth factor 3 polypeptide, a Fibroblast growth factor 4 polypeptide, a fibroblast growth factor 5 polypeptide, a Fibroblast growth factor 6 polypeptide, a Fibroblast growth factor 7 polypeptide, a fibroblast growth factor 8 polypeptide, a Fibroblast growth factor 9 polypeptide, a Fibroblast growth factor 10 polypeptide, a Fibroblast growth factor 11 polypeptide, a Fibroblast growth factor 12 polypeptide, a Fibroblast growth factor 13 polypeptide, a Fibroblast growth factor 14 polypeptide, a Fibroblast growth factor 15 polypeptide, a Fibroblast growth factor 16 polypeptide, a Fibroblast growth factor 17 polypeptide, a Fibroblast growth factor 18 polypeptide, a Fibroblast growth factor 19 polypeptide, a Fibroblast growth factor 20 polypeptide, a Fibroblast growth factor 21 polypeptide, a Fibroblast growth factor 22 polypeptide, a Fibroblast growth factor 23 polypeptide, a Foetal Bovine Somatotrophin polypeptide, a Glial cell line-derived neurotrophic factor polypeptide, a Neurturin polypeptide, a Persephin polypeptide, an Artemin polypeptide, a Growth differentiation factor-9 polypeptide, a Hepatoma-derived growth factor polypeptide, an Insulin polypeptide, an Insulin-like growth factor polypeptide, an Insulin-like growth factor-1 polypeptide, an Insulin-like growth factor-2 polypeptide, an IL-1 polypeptide, an IL-2 polypeptide or bio-active homolog thereof, an IL-3 polypeptide, an IL-4 polypeptide, an IL-5 polypeptide, an IL-6 polypeptide, an IL-7 polypeptide, a Keratinocyte growth factor polypeptide, a Migration-stimulating factor polypeptide, a Macrophage-stimulating protein polypeptide, a Myostatin polypeptide, a Neuregulin 1 polypeptide, a Neuregulin 2 polypeptide, a Neuregulin 3 polypeptide, a Neuregulin 4 polypeptide, a Brain-derived neurotrophic factor polypeptide, a Nerve growth factor polypeptide, a Neurotrophin-3 polypeptide, a Neurotrophin-4 polypeptide, a Placental growth factor polypeptide, a Platelet-derived growth factor polypeptide, a Renalase polypeptide, an anti-apoptotic survival factor polypeptide, a T-cell growth factor polypeptide, a Thrombopoietin polypeptide, a Transforming growth factor alpha polypeptide, a Transforming growth factor beta polypeptide, a Tumor necrosis factor-alpha polypeptide, a Vascular endothelial growth factor polypeptide, and a Wnt Signaling Pathway polypeptide.

Embodiment II-26. A compound having a structure of Formula (III):

$$X_1—[X_2—(X_3)_m]^n \quad \text{(III)},$$

or a pharmaceutically acceptable salt, solvate, hydrate, isomer, or tautomer thereof, wherein:

m is 1, 2, 3, 4, 5, 6, 7, 8, 9, or 10;

n is 1, 2, 3, 4, 5, 6, 7, 8, 9, 10, or 11;

$X_1$ is an IL-2 polypeptide or a bio-active homolog polypeptide thereof;

$X_2$ is a linker; and $X_3$ is a therapeutic compound.

Embodiment II-27. The compound, or a pharmaceutically acceptable salt, solvate, hydrate, isomer, or tautomer thereof, of Embodiment II-25 or II-26, wherein the IL-2 polypeptide or the bio-active homolog polypeptide thereof comprises an amino acid sequence set forth in Table 4.

Embodiment II-28. The compound, or a pharmaceutically acceptable salt, solvate, hydrate, isomer, or tautomer thereof, of Embodiment II-25 or II-26, wherein the IL-2 polypeptide or the bio-active homolog polypeptide thereof comprises an amino acid sequence set forth in SEQ ID NO: 1 or SEQ ID NO:2.

Embodiment II-29. The compound, or a pharmaceutically acceptable salt, solvate, hydrate, isomer, or tautomer thereof, of any one of Embodiments II-24 to II-28, wherein $X_2$ is a cleavable linker.

Embodiment II-30. The compound, or a pharmaceutically acceptable salt, solvate, hydrate, isomer, or tautomer thereof, of any one of Embodiments II-24 to II-28, wherein $X_2$ is a non-cleavable linker.

Embodiment II-31. The compound, or a pharmaceutically acceptable salt, solvate, hydrate, isomer, or tautomer thereof, of Embodiment II-29, wherein $X_2$ is selected from the group consisting of: K-1, K-2, K-3, K-4, K-5, K-6, K-7, K-8, K-9, K-10, K-11, K-12, K-13, K-14, K-15, K-16, K-19, and K-20, wherein the left side of $X_2$, as drawn, is bound to $X_1$, and the right side of $X_2$, as drawn, is bound to $X_3$ and R is H, alkyl, aryl, arylalkyl, a glycol ether, or a glycol linker.

Embodiment II-32. The compound, or a pharmaceutically acceptable salt, solvate, hydrate, isomer, or tautomer thereof, of Embodiment II-31, wherein $X_2$ is selected from the group consisting of K-1 and K-19.

Embodiment II-33. The compound, or a pharmaceutically acceptable salt, solvate, hydrate, isomer, or tautomer thereof, of Embodiment II-30, wherein $X_2$ is selected from the group consisting of K-17 and K-18, wherein the left side of $X_2$, as drawn, is bound to $X_1$, and the right side of $X_2$, as drawn, is bound to $X_3$.

Embodiment II-34. The compound, or a pharmaceutically acceptable salt, solvate, hydrate, isomer, or tautomer thereof, of any one of Embodiments II-24 to II-33, wherein $X_2$ is bound to $X_1$ at a Cys residue thereof.

Embodiment II-35. The compound, or a pharmaceutically acceptable salt, solvate, hydrate, isomer, or tautomer thereof, of any one of Embodiments II-24 to II-31, wherein $X_2$ is bound to $X_1$ at a Lys residue thereof.

Embodiment II-36. The compound, or a pharmaceutically acceptable salt, solvate, hydrate, isomer, or tautomer thereof, of any one of Embodiments II-24 to II-35, wherein m is 1.

Embodiment II-37. The compound, or a pharmaceutically acceptable salt, solvate, hydrate, isomer, or tautomer thereof, of any one of Embodiments II-24 to II-35, wherein m is 2, 3, 4, 5, 6, 7, or 8.

Embodiment II-38. The compound, or a pharmaceutically acceptable salt, solvate, hydrate, isomer, or tautomer thereof, of any one of Embodiments II-24 to II-35, wherein m is 1, 2, or 3.

Embodiment II-39. The compound, or a pharmaceutically acceptable salt, solvate, hydrate, isomer, or tautomer thereof, of any one of Embodiments II-24 to II-35, wherein m is 2, 3, 4, or 5.

Embodiment II-40. The compound, or a pharmaceutically acceptable salt, solvate, hydrate, isomer, or tautomer thereof, of any one of Embodiments II-24 to II-39, wherein $X_3$ is an immunomodulating agent.

Embodiment II-41. The compound, or a pharmaceutically acceptable salt, solvate, hydrate, isomer, or tautomer thereof, of any one of Embodiments II-24 to II-40, wherein $X_3$ is selected from the group consisting of an immunosuppressive drug, an antianemic, an antianginal, an antiarryhythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a ubiquitin-activating enzyme inhibitor, a ubiquitin-activating enzyme E1 inhibitor, and a proteasome inhibitor.

Embodiment II-42. The compound, or a pharmaceutically acceptable salt, solvate, hydrate, isomer, or tautomer thereof, of any one of Embodiments II-24 to II-41, wherein $X_3$ is selected from the group consisting of: pevonedistat; TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate); Piperacillin; M22 (1-benzyl-N-(2,4-dichlorophenethyl) piperidin-4-amine); 6,6'-Biapigenin; Thieno-pyridine; Imidazopyrimidine; Largazole; Pyr-41 (4 [4-(5-nitro-furan-2-ylmethylene)-3,5-dioxo-pyrazolidin-1-yl]-benzoic acid ethyl ester); Phorbol 12-myristate 13-acetate; 2,3-dihydropyrrolo [2,1-b]quinazolin-9 (1H)-one; Ofloxacin; Panepophenanthin; Himeic Acid A; Hyrtioreticulins A; Phytol; ABPA3 ([(2R,3S,4R,5R)-5-[6-(3-ethynylanilino) purin-9-yl]-3,4-dihydroxyoxolan-2-yl]methyl sulfamate); Benzothiazole; a Deoxyvasicinone derivative; Coumarin A; Coumarin B; and Imidazolium-quinoxaline, $R_1$ is alkyl, aryl, arylalkyl, arylalkyne, arylalkene, heterocyclyl, or heteroaryl, and $R_2$ is H, alkyl, or aryl.

Embodiment II-43. The compound, or a pharmaceutically acceptable salt, solvate, hydrate, isomer, or tautomer thereof, of any one of Embodiments II-24 to II-42, wherein $X_3$ is selected from the group consisting of: Pevonedistat, TAS1 (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), and TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate).

Embodiment II-43a. The compound, or a pharmaceutically acceptable salt, solvate, hydrate, isomer, or tautomer thereof, of any one of Embodiments II-24 to II-43, wherein $X_3$ is Pevonedistat.

Embodiment II-44. The compound, or a pharmaceutically acceptable salt, solvate, hydrate, isomer, or tautomer thereof, of any one of Embodiments II-24 to II-39, wherein $X_3$ is a cancer chemotherapeutic.

Embodiment II-45. The compound, or a pharmaceutically acceptable salt, solvate, hydrate, isomer, or tautomer thereof, of any one of Embodiments II-24 to II-39 or II-44, wherein $X_3$ is selected from the group consisting of an oncolytic drug, a genotoxic agent, an alkylating agent, a tubulin inhibitor, a microtubule assembly inhibitor, an antineoplastic drug, a kinase inhibitor, a vinca alkaloid, an antibiotic, an anthracycline, an antimetabolite, an aromatase inhibitor, a topoisomerase inhibitor, a mTor inhibitor, a retinoid, an antimitotic agent, a protease inhibitor, a tyrosine kinase inhibitor, a microtubule destabilizer, and a proteasome inhibitor.

Embodiment II-46. The compound, or a pharmaceutically acceptable salt, solvate, hydrate, isomer, or tautomer thereof, of any one of Embodiments II-24 to II-39 or II-44 to II-45, wherein $X_3$ is selected from the group consisting of vincristine, vinorelbine, vinflunine, crytophycin 52, a halichondrin, a dolastatin, a hemiasterlin, colchicine, a combretastatin, 2-methoxyestradiol, a methoxybenzenesulfonamide, epothilone, and discodermolide.

Embodiment II-47. The compound, or a pharmaceutically acceptable salt, solvate, hydrate, isomer, or tautomer thereof, of any one of Embodiments II-24 to II-39 or II-44 to II-45, wherein $X_3$ is selected from the group consisting of: Monomethyl Auristatin E; Docetaxel; Etoposide; Gemcitabine; Vinblastine; Paclitaxel; Irinotecan; Fluorouracil; Methotrexate; Carboplatin; Oxaliplatin; Cisplatin; Doxorubicin HCl; Fulvestrant; Isotretinoin; Buserelin; Everolimus; Carfilzomib; Rifabutin; Clindamycin; Tubulysin A; Indibulin; Gefitinib; and Dasatinib.

Embodiment II-48. The compound, or a pharmaceutically acceptable salt, solvate, hydrate, isomer, or tautomer thereof, of any one of Embodiments II-24 to II-39, II-44 to II-45, or II-47, wherein $X_3$ is Monomethyl Auristatin E.

Embodiment II-49. The compound, or a pharmaceutically acceptable salt, solvate, hydrate, isomer, or tautomer thereof, of any one of Embodiments II-24 to II-28, wherein the compound of Formula (II) or Formula (III) is selected from the group consisting of: B-1, B-2, B-3, B-4, B-5, B-6, B-7, B-8, B-9, B-10, B-11, B-12, B-13, B-14, B-15, B-16, B-17, B-18, B-19, B-20, B-21, B-22, B-23, B-24, B-25, B-26, B-27, B-28, B-29, B-30, B-31, B-48, and B-49, R is H, alkyl, aryl, arylalkyl, a glycol ether, or a glycol linker; q is 1, 2, 3, or 4; n1 is 1, 2, 3, 4, 5, 6, 7, 8, 9, or 10; and n2 is 1, 2, 3, 4, 5, 6, 7, 8, 9, or 10, wherein the combination of n1 and n2 has a sum of 2, 3, 4, 5, 6, 7, 8, 9, 10, or 11.

Embodiment II-50. The compound, or a pharmaceutically acceptable salt, solvate, hydrate, isomer, or tautomer thereof, Embodiment II-49, wherein the compound of Formula (II) or Formula (III) is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

Embodiment II-51. The compound, or a pharmaceutically acceptable salt, solvate, hydrate, isomer, or tautomer thereof, Embodiment II-50, wherein the compound of Formula (II) or Formula (III) is selected from the group consisting of B-1, B-30, B-31, B-48, and B-49.

Embodiment II-52. The compound, or a pharmaceutically acceptable salt, solvate, hydrate, isomer, or tautomer thereof, of any one of Embodiments II-24 to II-28, wherein the compound of Formula (II) or Formula (III) is selected from the group consisting of: B-32, B-33, B-34, B-35, B-36, B-37, B-38, B-39, B-40, B-41, B-42, B-43, B-44, B-45, B-46, B-47, and B-50.

Embodiment II-53. The compound, or a pharmaceutically acceptable salt, solvate, hydrate, isomer, or tautomer thereof, Embodiment II-52, wherein the compound of Formula (II) or Formula (III) is B-32.

Embodiment II-54. The compound, or a pharmaceutically acceptable salt, solvate, hydrate, isomer, or tautomer thereof, of any one of Embodiments II-24 to II-53, wherein n is 2, 3, 4, 5, 6, 7, 8, or 9.

Embodiment II-55. The compound, or a pharmaceutically acceptable salt, solvate, hydrate, isomer, or tautomer thereof, of any one of Embodiments II-24 to II-53, wherein n is 3, 4, 5, 6, 7, or 8.

Embodiment II-56. The compound, or a pharmaceutically acceptable salt, solvate, hydrate, isomer, or tautomer thereof, of any one of Embodiments II-24 to II-53, wherein n is 4, 5, 6, or 7.

Embodiment II-57. The compound, or a pharmaceutically acceptable salt, solvate, hydrate, isomer, or tautomer thereof, of any one of Embodiments II-24 to II-53, wherein n is 5 or 6.

Embodiment II-58. A pharmaceutical composition comprising a compound, or a pharmaceutically acceptable salt, solvate, hydrate, or tautomer thereof, of any one of Embodiments II-24 to II-57, II-87 to II-101, or II-104 to II-122 and a pharmaceutically acceptable carrier.

Embodiment II-59. A method for treating a disorder in a subject, comprising administering to a subject in need thereof a therapeutically effective amount of a compound, or a pharmaceutically acceptable salt, solvate, hydrate, or tautomer thereof, of any one of Embodiments II-24 to II-57, II-87 to II-101, or II-104 to II-122, wherein the disorder is an immunological disorder or cancer.

Embodiment II-60. A method for treating a disorder in a subject, comprising administering to a subject in need thereof a therapeutically effective amount of a pharmaceutical composition according to Embodiment II-58, wherein the disorder is an immunological disorder or cancer.

Embodiment II-61. The method of Embodiment II-59 or II-60, wherein the disorder is an immunological disorder.

Embodiment II-62. The method of Embodiment II-61, wherein the immunological disorder is multiple sclerosis, type 1 diabetes, inflammatory bowel disease, rheumatoid arthritis, or psoriasis.

Embodiment II-63. The method of Embodiment II-59 or II-60, wherein the disorder is cancer.

Embodiment II-64. The method of Embodiment II-61, wherein the cancer is non-small cell lung cancer (NSCLC), melanoma, kidney cancer, bladder cancer, head and neck cancer, or claudin-low breast cancer.

Embodiment II-65. Use of a compound, or a pharmaceutically acceptable salt, solvate, hydrate, or tautomer thereof, of any one of Embodiments II-24 to II-57, II-87 to II-101, or II-104 to II-122, in the manufacture of a medicament for treating a disorder in a subject in need thereof, wherein the disorder is an immunological disorder or cancer.

Embodiment II-66. Use of a pharmaceutical composition according to Embodiment II-58 in the manufacture of a medicament for treating a disorder in a subject in need thereof, wherein the disorder is an immunological disorder or cancer.

Embodiment II-67. Use of a compound, or a pharmaceutically acceptable salt, solvate, hydrate, or tautomer thereof, of any one of Embodiments II-24 to II-57, II-87 to II-101, or II-104 to II-122 for treating a disorder in a subject in need thereof.

Embodiment II-68. Use of a pharmaceutical composition according to Embodiment II-58 for treating a disorder in a subject in need thereof.

Embodiment II-69. Use of a compound, or a pharmaceutically acceptable salt, solvate, hydrate, or tautomer thereof, of any one of Embodiments II-24 to II-57, II-87 to II-101, or II-104 to II-122 for treating a disorder in a subject in need thereof, wherein the disorder is an immunological disorder or cancer.

Embodiment II-70. Use of a pharmaceutical composition according to Embodiment II-58 for treating a disorder in a subject in need thereof, wherein the disorder is an immunological disorder or cancer.

Embodiment II-71. The use of any one of Embodiments II-65 to II-70, wherein the disorder is an immunological disorder.

Embodiment II-72. The use of Embodiment II-71, wherein the immunological disorder is multiple sclerosis, type 1 diabetes, inflammatory bowel disease, rheumatoid arthritis, or psoriasis.

Embodiment II-73. The use of any one of Embodiments II-65 to II-70, wherein the disorder is cancer.

Embodiment II-74. The use of Embodiment II-73, wherein the cancer is non-small cell lung cancer (NSCLC), melanoma, kidney cancer, bladder cancer, head and neck cancer, or claudin-low breast cancer.

Embodiment II-75. A compound, or a pharmaceutically acceptable salt, solvate, hydrate, or tautomer thereof, of any one of Embodiments II-24 to II-57, II-87 to II-101, or II-104 to II-122 for use in a method of treating a disorder in a subject in need thereof, wherein the disorder is an immunological disorder or cancer.

Embodiment II-76. The compound for use of Embodiment II-75, wherein the disorder is an immunological disorder.

Embodiment II-77. The compound for use of Embodiment II-76, wherein the immunological disorder is multiple sclerosis, type 1 diabetes, inflammatory bowel disease, rheumatoid arthritis, or psoriasis.

Embodiment II-78. The compound for use of Embodiment II-75, wherein the disorder is cancer.

Embodiment II-79. The compound for use of Embodiment II-78, wherein the cancer is non-small cell lung cancer (NSCLC), melanoma, kidney cancer, bladder cancer, head and neck cancer, or claudin-low breast cancer.

Embodiment II-80. A pharmaceutical composition according to Embodiment II-58 for use in a method of treating a disorder in a subject in need thereof, wherein the disorder is an immunological disorder or cancer.

Embodiment II-81. The pharmaceutical composition for use of Embodiment II-80, wherein the disorder is an immunological disorder.

Embodiment II-82. The pharmaceutical composition for use of Embodiment II-81, wherein the immunological disorder is multiple sclerosis, type 1 diabetes, inflammatory bowel disease, rheumatoid arthritis, or psoriasis.

Embodiment II-83. The pharmaceutical composition for use of Embodiment II-80, wherein the disorder is cancer.

Embodiment II-84. The pharmaceutical composition for use of Embodiment II-83, wherein the cancer is non-small cell lung cancer (NSCLC), melanoma, kidney cancer, bladder cancer, head and neck cancer, or claudin-low breast cancer.

Embodiment II-85. An IL-2 polypeptide or a bio-active homolog polypeptide thereof comprising an amino acid sequence set forth in Table 4.

Embodiment II-86. An IL-2 polypeptide or a bio-active homolog polypeptide thereof comprising an amino acid sequence set forth in SEQ ID NO:1 or SEQ ID NO:2.

Embodiment II-87. The compound, or a pharmaceutically acceptable salt, solvate, hydrate, isomer, or tautomer thereof, of any one of Embodiments II-24 to II-48 or II-54 to II-57, wherein $X_2$ is bound to $X_1$ at two different sites on $X_1$.

Embodiment II-88. The compound, or a pharmaceutically acceptable salt, solvate, hydrate, isomer, or tautomer thereof, of any one of Embodiments II-24 to II-34, II-36 to II-48, or II-54 to II-57, wherein $X_2$ is bound to $X_1$ at two different Cys residues on $X_1$.

Embodiment II-89. The compound, or a pharmaceutically acceptable salt, solvate, hydrate, isomer, or tautomer thereof, of any one of Embodiments II-24 to II-33, II-35 to II-48, or II-54 to II-57, wherein $X_2$ is bound to $X_1$ at two different Lys residues on $X_1$.

Embodiment II-90. The compound, or a pharmaceutically acceptable salt, solvate, hydrate, isomer, or tautomer thereof, of any one of Embodiments II-1 to II-11, wherein $X_3$ is selected from the group consisting of: an antianemic, an antianginal, an antiarryhythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a proteasome inhibitor, and an enzyme inhibitor.

Embodiment II-91. The compound, or a pharmaceutically acceptable salt, solvate, hydrate, isomer, or tautomer thereof, of any one of Embodiments II-24 to II-40, wherein $X_3$ is selected from the group consisting of: an antianemic, an antianginal, an antiarryhythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a proteasome inhibitor, and an enzyme inhibitor.

Embodiment II-92. The compound, or a pharmaceutically acceptable salt, solvate, hydrate, isomer, or tautomer thereof, of any one of Embodiments II-1 to II-10 or II-15, wherein $X_3$ is selected from the group consisting of: an alkylating agent, a kinase inhibitor, a vinca alkaloid, an anthracycline, an antimetabolite, an aromatase inhibitor, a topoisomerase inhibitor, an mTor inhibitor, a retinoid, an antimitotic agent, an antibiotic, and a proteasome inhibitor.

Embodiment II-93. The compound, or a pharmaceutically acceptable salt, solvate, hydrate, isomer, or tautomer thereof, of any one of Embodiments II-24 to II-39 or II-44, wherein $X_3$ is selected from the group consisting of: an alkylating agent, a kinase inhibitor, a vinca alkaloid, an anthracycline, an antimetabolite, an aromatase inhibitor, a topoisomerase inhibitor, an mTor inhibitor, a retinoid, an antimitotic agent, an antibiotic, and a proteasome inhibitor.

Embodiment II-94. The compound, or a pharmaceutically acceptable salt, solvate, hydrate, isomer, or tautomer thereof, of any one of Embodiments II-1 to II-10 or II-15 to II-16, wherein $X_3$ is selected from the group consisting of: buserelin, carboplatin, carfilzomib, cisplatin, clindamycin, dasatinib, docetaxel, doxorubicin, etoposide, everolimus, fluorouracil, fulvestrant, gefitinib, gemcitabine, indibulin, irinotecan, isotretinoin, methotrexate, monomethyl, auristatin E, oxaliplatin, paclitaxel, rifabutin, tubulysin, and vinblastine.

Embodiment II-95. The compound, or a pharmaceutically acceptable salt, solvate, hydrate, isomer, or tautomer thereof, of any one of Embodiments II-24 to II-39 or II-44 to II-45, wherein $X_3$ is selected from the group consisting of: buserelin, carboplatin, carfilzomib, cisplatin, clindamycin, dasatinib, docetaxel, doxorubicin, etoposide, everolimus, fluorouracil, fulvestrant, gefitinib, gemcitabine, indibulin, irinotecan, isotretinoin, methotrexate, monomethyl, auristatin E, oxaliplatin, paclitaxel, rifabutin, tubulysin, and vinblastine.

Embodiment II-96. The compound, or a pharmaceutically acceptable salt, solvate, hydrate, isomer, or tautomer thereof, of Embodiment II-25 or II-26, wherein the IL-2 polypeptide or the bio-active homolog polypeptide thereof comprises an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to an amino acid sequence of Table 4.

Embodiment II-97. The compound, or a pharmaceutically acceptable salt, solvate, hydrate, isomer, or tautomer thereof, of Embodiment II-25 or II-26, wherein the IL-2 polypeptide or the bio-active homolog polypeptide thereof comprises an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO: 2.

Embodiment II-98. The compound, or a pharmaceutically acceptable salt, solvate, hydrate, isomer, or tautomer thereof, of any one of Embodiments II-24 to II-35 or II-40 to II-48, wherein m=n.

Embodiment II-99. The compound, or a pharmaceutically acceptable salt, solvate, hydrate, isomer, or tautomer thereof, of any one of Embodiments II-24 to II-35 or II-40 to II-48, wherein n is greater than m.

Embodiment II-100. The compound, or a pharmaceutically acceptable salt, solvate, hydrate, isomer, or tautomer thereof, of any one of Embodiments II-24 to II-35 or II-40 to II-48, wherein m is 1 and n is 1, 2, 3, 4, 5, 6, 7, 8, 9, 10, or 11.

Embodiment II-101. The compound, or a pharmaceutically acceptable salt, solvate, hydrate, isomer, or tautomer thereof, of any one of Embodiments II-24 to II-35 or II-40 to II-48, wherein m is 2 and n is 1, 2, 3, 4, 5, 6, 7, 8, 9, 10, or 11.

Embodiment II-102. An IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to an amino acid sequence of Table 4.

Embodiment II-103. An IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2.

Embodiment II-104. The compound, or a pharmaceutically acceptable salt, solvate, hydrate, isomer, or tautomer thereof, of any one of Embodiments II-24 to II-34 or II-36 to II-48, wherein $X_2$ is a mixture of $X_{2b}$ and $X_{2c}$, $X_{2b}$ is a linker that is bound to one Cys residue on $X_1$, $X_{2c}$ is a linker that is bound to two different Cys residues on $X_1$, wherein n is a combination of n1 and n2, wherein n1 corresponds to the number of $X_{2b}$ moieties bound to $X_1$ and n2 corresponds to the number of $X_{2c}$ moieties bound to $X_1$, and the combination of n1 and n2 has a sum of 2, 3, 4, 5, 6, 7, 8, 9, 10, or 11.

Embodiment II-105. The compound, or a pharmaceutically acceptable salt, solvate, hydrate, isomer, or tautomer thereof, of Embodiment II-104, wherein $X_{2b}$ is selected from the group consisting of K-1, K-2, K-4, K-6, K-8, K-11, K-13, K-15, K-17, and K-18 and $X_{2c}$ is K-19.

Embodiment II-106. The compound, or a pharmaceutically acceptable salt, solvate, hydrate, isomer, or tautomer thereof, of Embodiment II-104 or II-105, wherein $X_{2b}$ is K-1 and $X_{2c}$ is K-19.

Embodiment II-107. The compound, or a pharmaceutically acceptable salt, solvate, hydrate, isomer, or tautomer thereof, of any one of Embodiments II-104 to II-106, wherein n1 is 2 or 3 and n2 is 1.

Embodiment II-108. The compound, or a pharmaceutically acceptable salt, solvate, hydrate, isomer, or tautomer thereof, of any one of Embodiments II-104 to II-106, wherein n1 is 2 and n2 is 1.

Embodiment II-109. The compound, or a pharmaceutically acceptable salt, solvate, hydrate, isomer, or tautomer thereof, of any one of Embodiments II-104 to II-106, wherein n1 is 3 and n2 is 1.

Embodiment II-110. The compound, or a pharmaceutically acceptable salt, solvate, hydrate, isomer, or tautomer thereof, of any one of Embodiments II-104 to II-106, wherein n1 is 1, 2, 3, 4, or 5 and n2 is 1, 2 or 3.

Embodiment II-111. The compound, or a pharmaceutically acceptable salt, solvate, hydrate, isomer, or tautomer thereof, of any one of Embodiments II-24 to II-28, selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 1, 2, 3, 4, 5, or 6, and $X_1$ is an IL-2 polypeptide or a bio-active homolog polypeptide thereof comprising an amino acid sequence set forth in SEQ ID NO:1 or SEQ ID NO:2.

Embodiment II-112. The compound, or a pharmaceutically acceptable salt, solvate, hydrate, isomer, or tautomer thereof, of any one of Embodiments II-24 to II-28, selected from the group consisting of B-1, B-30, B-31, B-48, and B-49, wherein n is 1, 2, 3, 4, 5, or 6, and $X_1$ is an IL-2 polypeptide or a bio-active homolog polypeptide thereof comprising an amino acid sequence set forth in SEQ ID NO:1 or SEQ ID NO:2.

Embodiment II-113. The compound, or a pharmaceutically acceptable salt, solvate, hydrate, isomer, or tautomer thereof, of any one of Embodiments II-24 to II-28, wherein $X_2$ is a mixture of $X_{2b}$ and $X_{2c}$, $X_{2b}$ is a linker that is bound to one Cys residue on $X_1$, $X_{2c}$ is a linker that is bound to two different Cys residues on $X_1$, n is a combination of n1 and n2, wherein the combination of n1 and n2 has a sum of 2, 3, 4, 5, or 6, and $X_1$ is an IL-2 polypeptide or a bio-active homolog polypeptide thereof comprising an amino acid sequence set forth in SEQ ID NO: 1 or SEQ ID NO:2.

Embodiment II-114. The compound, or a pharmaceutically acceptable salt, solvate, hydrate, isomer, or tautomer thereof, of any one of Embodiments II-24 to II-28, wherein the compound of Formula (II) or Formula (III) is B-49 and $X_1$ is an IL-2 polypeptide or a bio-active homolog polypeptide thereof comprising an amino acid sequence set forth in SEQ ID NO:1 or SEQ ID NO:2, and n1 is 2 or 3 and n2 is 1.

Embodiment II-115. The compound, or a pharmaceutically acceptable salt, solvate, hydrate, isomer, or tautomer thereof, of any one of Embodiments II-111 to II-114, wherein the IL-2 polypeptide or the bio-active homolog polypeptide thereof comprises the amino acid sequence set forth in SEQ ID NO:2.

Embodiment II-116. The compound, or a pharmaceutically acceptable salt, solvate, hydrate, isomer, or tautomer thereof, of any one of Embodiments II-24 to II-28, selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 1, 2, 3, 4, 5, or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2.

Embodiment II-117. The compound, or a pharmaceutically acceptable salt, solvate, hydrate, isomer, or tautomer thereof, of any one of Embodiments II-24 to II-28, selected from the group consisting of B-1, B-30, B-31, B-48, and B-49, wherein n is 1, 2, 3, 4, 5, or 6 and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2.

Embodiment II-118. The compound, or a pharmaceutically acceptable salt, solvate, hydrate, isomer, or tautomer thereof, of any one of Embodiments II-24 to II-28, wherein $X_2$ is a mixture of $X_{2b}$ and $X_{2c}$, $X_{2b}$ is a linker that is bound to one Cys residue on $X_1$, $X_{2c}$ is a linker that is bound to two different Cys residues on $X_1$, n is a combination of n1 and n2, wherein the combination of n1 and n2 has a sum of 2, 3, 4, 5, or 6, and $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO:1 or SEQ ID NO:2.

Embodiment II-119. The compound, or a pharmaceutically acceptable salt, solvate, hydrate, isomer, or tautomer thereof, of any one of Embodiments II-24 to II-28, wherein the compound is B-49, $X_1$ is an IL-2 polypeptide or a bio-active homolog polypeptide thereof comprising an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 1 or SEQ ID NO:2, and n1 is 2 or 3 and n2 is 1.

Embodiment II-120. The compound, or a pharmaceutically acceptable salt, solvate, hydrate, isomer, or tautomer thereof, of any one of Embodiments II-116 to II-119, wherein the IL-2 polypeptide or the bio-active homolog polypeptide thereof comprises an amino acid sequence having at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to SEQ ID NO: 2.

Embodiment II-121. The compound, or a pharmaceutically acceptable salt, solvate, hydrate, isomer, or tautomer thereof, of any one of Embodiments II-24 to II-34, II-36 to II-48, or II-54 to II-57, wherein $X_2$ is $X_2$b, wherein $X_{2b}$ is a linker that is bound to one Cys residue on $X_1$, and n is n1, wherein n1 corresponds to the number of $X_{2b}$ moieties bound to $X_1$.

Embodiment II-122. The compound, or a pharmaceutically acceptable salt, solvate, hydrate, isomer, or tautomer thereof, of any one of Embodiments II-24 to II-34, II-36 to II-48, or II-54 to II-57, wherein $X_2$ is $X_{2c}$, wherein $X_{2c}$ is a linker that is bound to two different Cys residues on $X_1$, wherein n is n2, wherein n2 corresponds to the number of $X_{2c}$ moieties bound to $X_1$.

Some embodiments of this disclosure are of Embodiment III, as follows:

Embodiment III-1. A compound having a structure of Formula (I):

$$X_{2a}\text{—}(X_3)_m \quad \text{(I)},$$

or a pharmaceutically acceptable salt, solvate, hydrate, isomer, or tautomer thereof, wherein:

m is 1, 2, 3, 4, 5, 6, 7, 8, 9, or 10;

$X_{2a}$ is a linker; and $X_3$ is a therapeutic compound.

Embodiment III-2. The compound, or a pharmaceutically acceptable salt, solvate, hydrate, isomer, or tautomer thereof, of embodiment III-1, wherein m is 1.

Embodiment III-3. The compound, or a pharmaceutically acceptable salt, solvate, hydrate, isomer, or tautomer thereof, of embodiment III-1, wherein m is 2, 3, 4, 5, 6, 7, or 8.

Embodiment III-4. The compound, or a pharmaceutically acceptable salt, solvate, hydrate, isomer, or tautomer thereof, of embodiment III-1, wherein m is 1, 2, or 3.

Embodiment III-5. The compound, or a pharmaceutically acceptable salt, solvate, hydrate, isomer, or tautomer thereof, of embodiment III-1, wherein m is 2, 3, 4, or 5.

Embodiment III-6. The compound, or a pharmaceutically acceptable salt, solvate, hydrate, isomer, or tautomer thereof, of any one of embodiments III-1 to III-5, wherein $X_{2a}$ is a cleavable linker.

Embodiment III-7. The compound, or a pharmaceutically acceptable salt, solvate, hydrate, isomer, or tautomer thereof, of any one of embodiments III-1 to III-5, wherein $X_{2a}$ is a non-cleavable linker.

Embodiment III-8. The compound, or a pharmaceutically acceptable salt, solvate, hydrate, isomer, or tautomer thereof, of embodiment III-6, wherein $X_{2a}$ is selected from the group consisting of:

| Compound Number | Structure |
|---|---|
| L-1 | 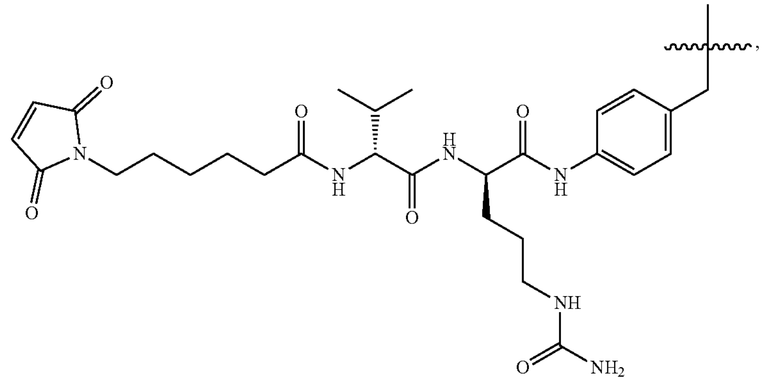 [SMILES: *Cc1ccc(NC(=O)[C@@H](CCCNC(N)=O)NC(=O)[C@H](NC(=O)CCCCCN2C(=O)C=CC2=O)C(C)C)cc1], |
| L-2 | 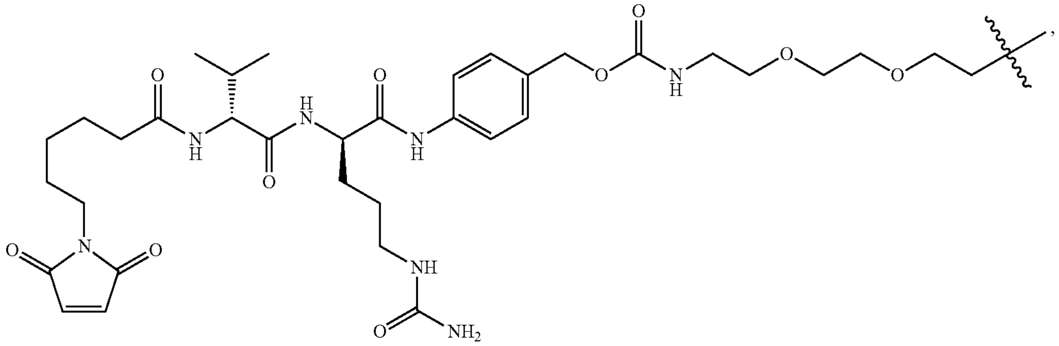 [SMILES: *CCOCCOCCNC(=O)OCc1ccc(NC(=O)[C@@H](CCCNC(N)=O)NC(=O)[C@H](NC(=O)CCCCCN2C(=O)C=CC2=O)C(C)C)cc1], |
| L-3 | 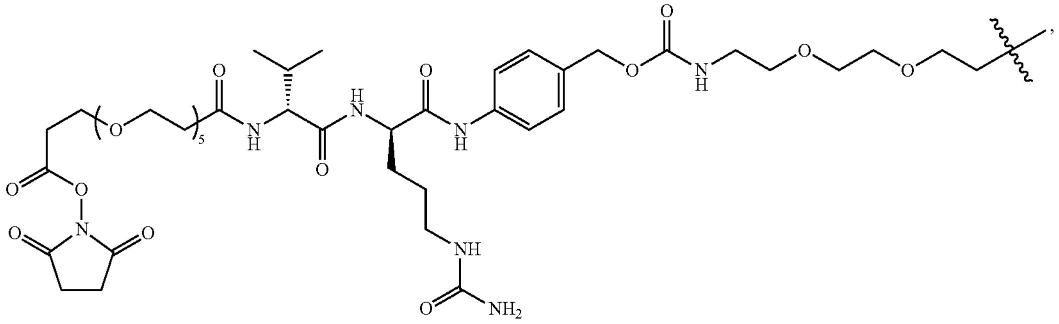, |

-continued
| Compound Number | Structure |
|---|---|
| L-4 | 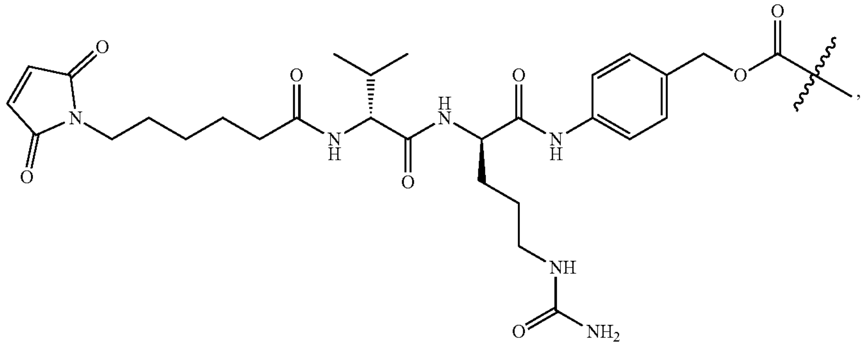 [SMILES: *C(=O)OCc1ccc(NC(=O)[C@@H](CCCNC(N)=O)NC(=O)[C@H](NC(=O)CCCCCN2C(=O)C=CC2=O)C(C)C)cc1] |
| L-5 | 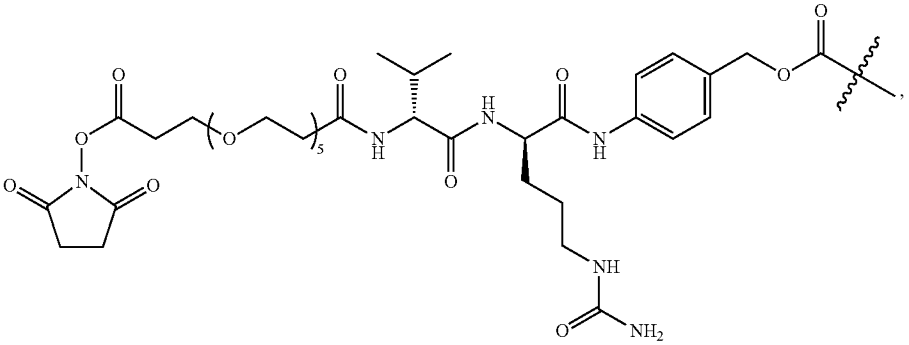 |
| L-6 | 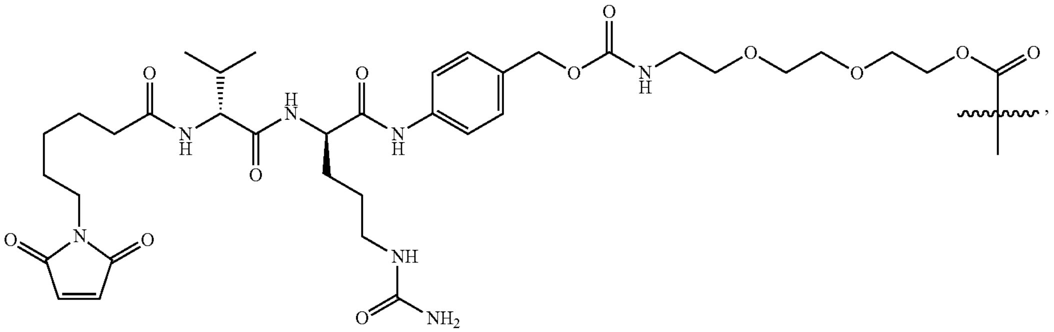 [SMILES: *C(=O)OCCOCCOCCNC(=O)OCc1ccc(NC(=O)[C@@H](CCCNC(N)=O)NC(=O)[C@H](NC(=O)CCCCCN2C(=O)C=CC2=O)C(C)C)cc1] |
| L-7 | 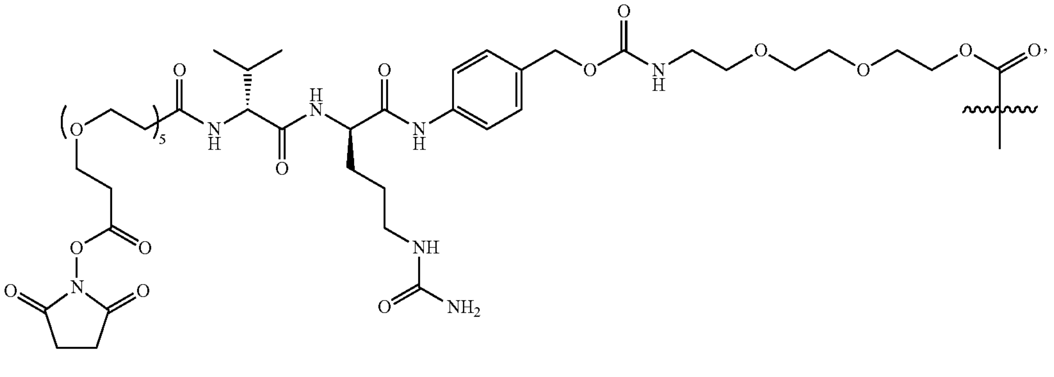 |

-continued
| Compound Number | Structure |
|---|---|
| L-8 | 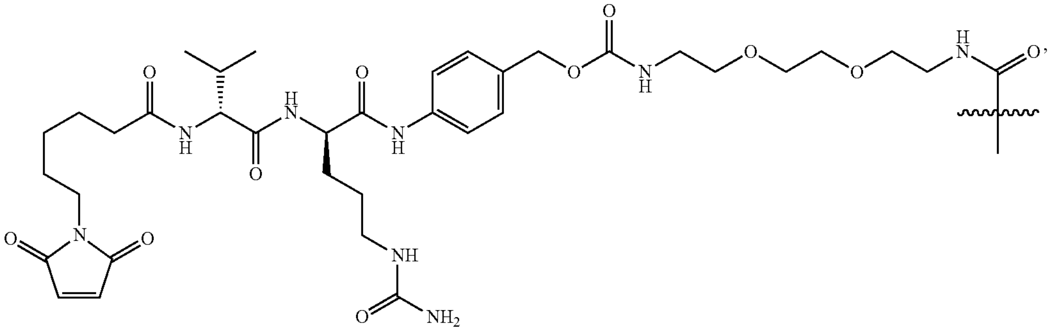 [SMILES: *C(=O)NCCOCCOCCNC(=O)OCc1ccc(NC(=O)[C@@H](CCCNC(N)=O)NC(=O)[C@H](NC(=O)CCCCCN2C(=O)C=CC2=O)C(C)C)cc1] |
| L-9 | 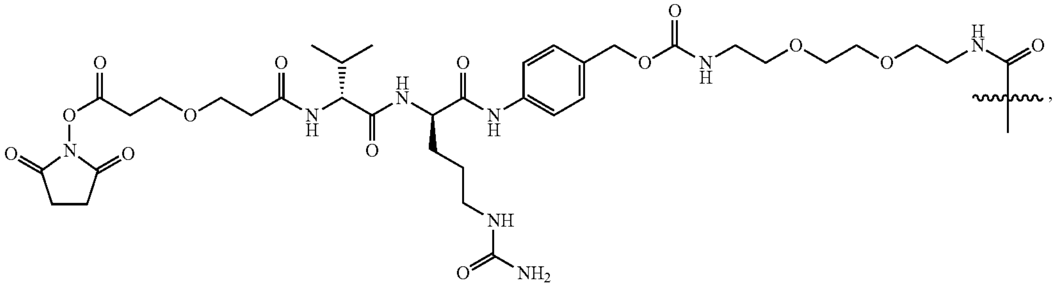 [SMILES: *C(=O)NCCOCCOCCNC(=O)OCc1ccc(NC(=O)[C@@H](CCCNC(N)=O)NC(=O)[C@H](NC(=O)CCOCCC(=O)ON2C(=O)CCC2=O)C(C)C)cc1] |
| L-10 | 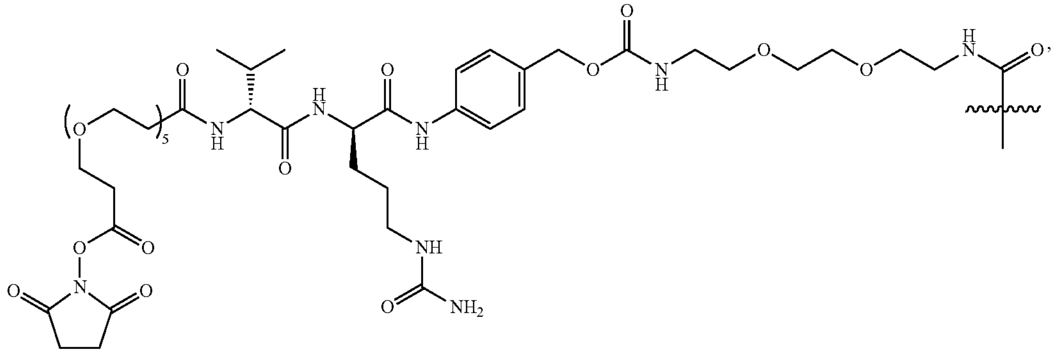 |
| L-11 | 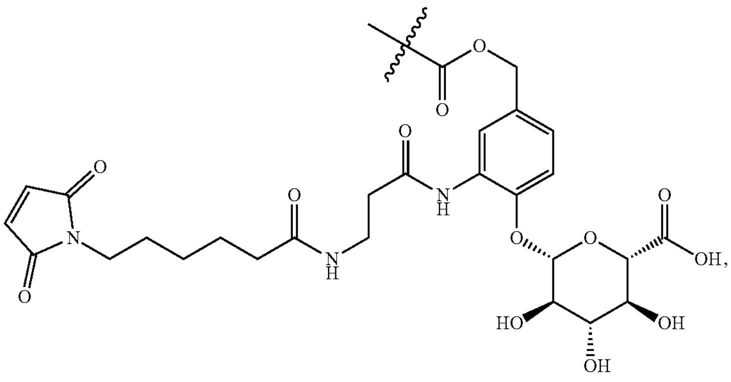 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1] |

-continued
| Compound Number | Structure |
| --- | --- |
| L-12 | 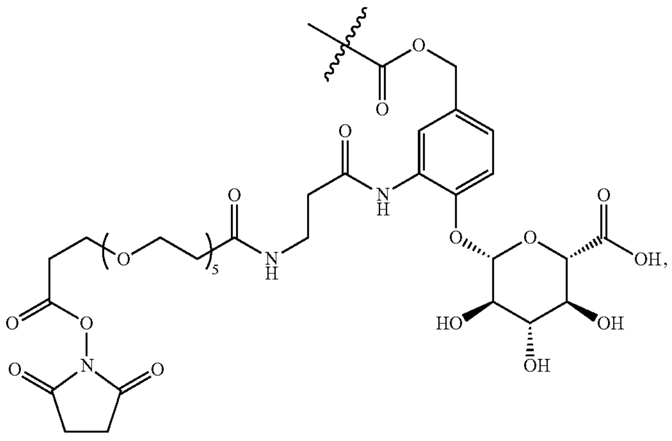 |
| L-13 | 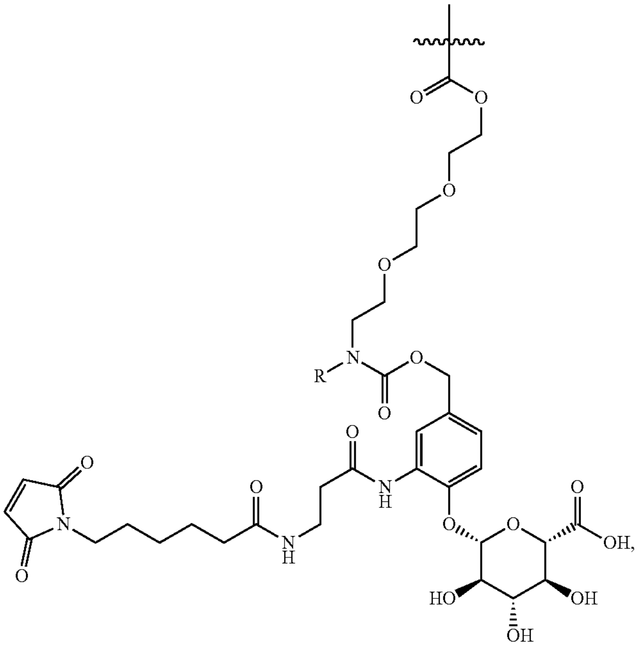 |

-continued
| Compound Number | Structure |
| --- | --- |
| L-14 | 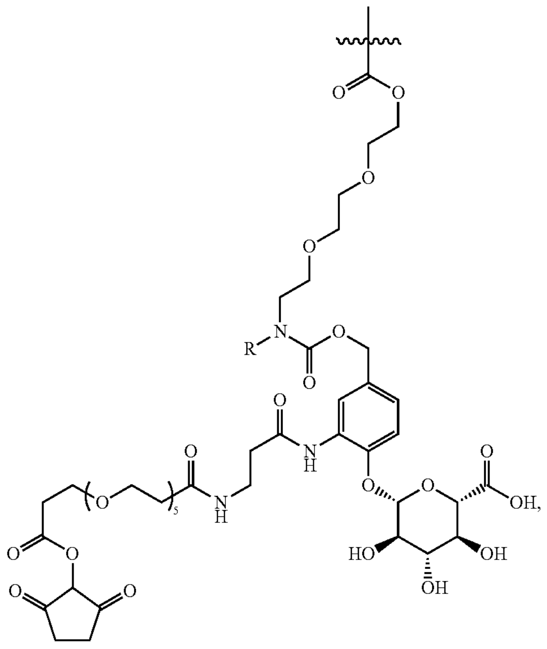 |
| L-15 | 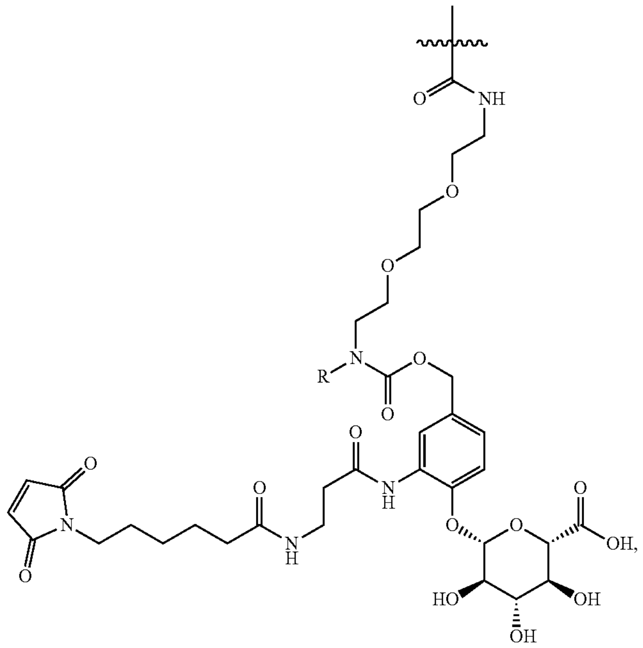 |

-continued
| Compound Number | Structure |
| --- | --- |
| L-16 | 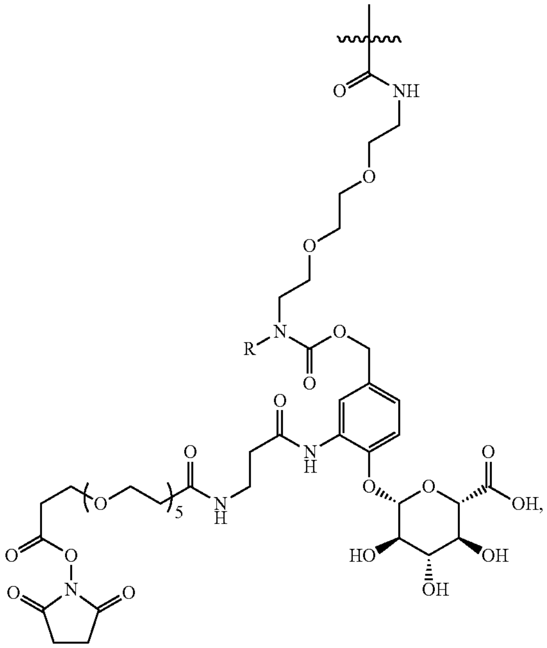 and |
| L-19 | 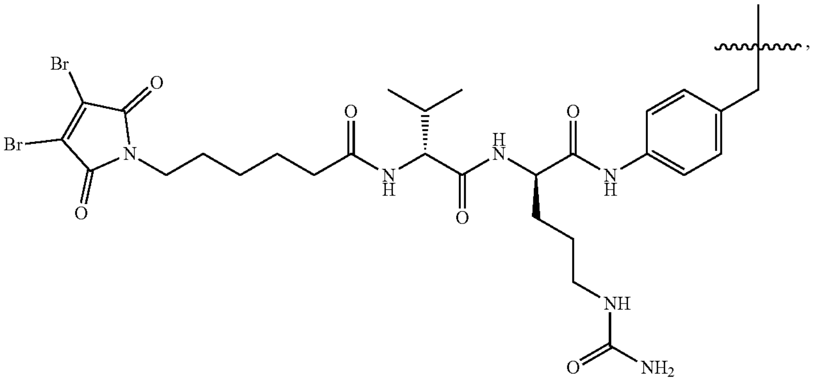 [SMILES: *Cc1ccc(NC(=O)[C@@H](CCCNC(N)=O)NC(=O)[C@H](NC(=O)CCCCCN2C(=O)C(Br)=C(Br)C2=O)C(C)C)cc1] , |
wherein R is H, alkyl, aryl, arylalkyl, a glycol ether, or a glycol linker.

Embodiment III-9. The compound, or a pharmaceutically acceptable salt, solvate, hydrate, isomer, or tautomer thereof, of embodiment III-8, wherein $X_{2a}$ is selected from the group consisting of L-1 and L-19.

Embodiment III-10. The compound, or a pharmaceutically acceptable salt, solvate, hydrate, isomer, or tautomer thereof, of embodiment III-7, wherein $X_{2a}$ is selected from the group consisting of:

| Compound Number | Structure |
|---|---|
| L-17 | 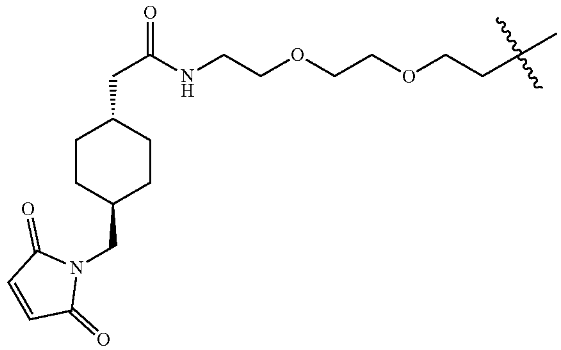 and |
| L-18 | 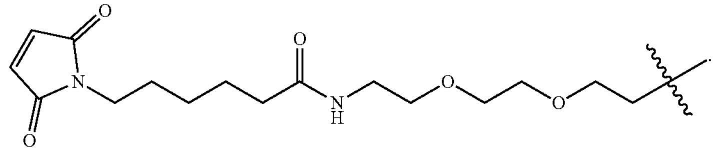 [SMILES: *CCOCCOCCNC(=O)CCCCCN1C(=O)C=CC1=O] |

,

Embodiment III-11. The compound, or a pharmaceutically acceptable salt, solvate, hydrate, isomer, or tautomer thereof, of any one of embodiments III-1 to III-10, wherein $X_3$ is an immunomodulating agent.

Embodiment III-12. The compound, or a pharmaceutically acceptable salt, solvate, hydrate, isomer, or tautomer thereof, of any one of embodiments III-1 to III-11, wherein $X_3$ is selected from the group consisting of an immunosuppressive drug, an antianemic, an antianginal, an antiarrythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a ubiquitin-activating enzyme inhibitor, a ubiquitin-activating enzyme E1 inhibitor, and a proteasome inhibitor.

Embodiment III-13. The compound, or a pharmaceutically acceptable salt, solvate, hydrate, isomer, or tautomer thereof, of any one of embodiments III-1 to III-12, wherein $X_3$ is selected from the group consisting of:

| Compound Name | Structure |
|---|---|
| Pevonedistat | 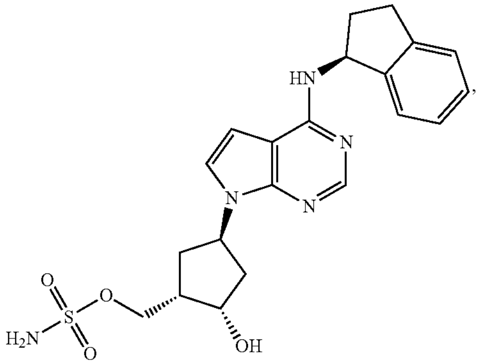 [SMILES: NS(=O)(=O)OC[C@@H]1C[C@@H](n2ccc3c(N[C@H]4CCc5ccccc54)ncnc32)C[C@@H]1O], |

-continued

| Compound Name | Structure |
| --- | --- |
| TAS1 (((2S,3S,4R,5R)-5-(4-amino-5-((4,7-dimethyl-3,4-dihydro-2H-benzo[b][1,4]oxazin-8-yl)ethynyl)-7H-pyrrolo[2,3-d]pyrimidin-7-yl)-3,4-dihydroxytetrahydrofuran-2-yl)methyl sulfamate) | 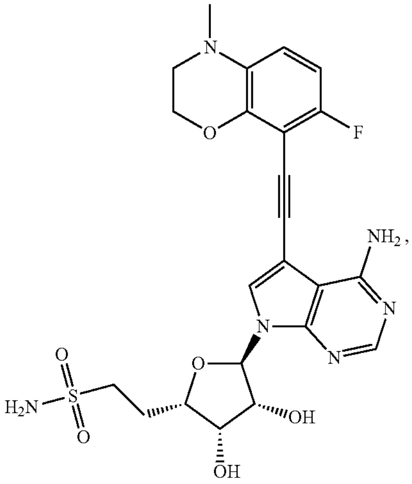 [SMILES: CN1CCOc2c1ccc(F)c2C#Cc1cn([C@@H]2O[C@@H](CCS(N)(=O)=O)[C@@H](O)[C@H]2O)c2ncnc(N)c12] |
| TAS2 (((1S,2R,3S,4R)-4-(4-amino-5-((4,7-dimethyl-3,4-dihydro-2H-benzo[b][1,4]oxazin-8-yl)ethynyl)-7H-pyrrolo[2,3-d]pyrimidin-7-yl)-2,3-dihydroxycyclopentyl)methyl sulfamate) | 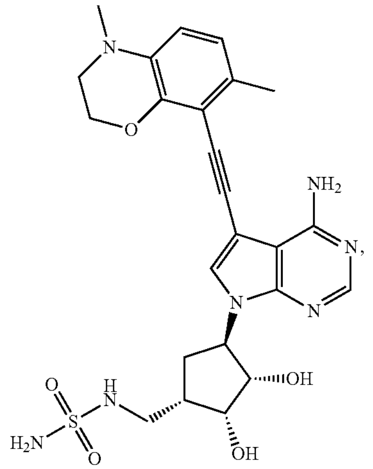 [SMILES: Cc1ccc2c(c1C#Cc1cn([C@@H]3C[C@@H](CNS(N)(=O)=O)[C@@H](O)[C@H]3O)c3ncnc(N)c13)OCCN2C] |
| TAK7243 (((1R,2R,3S,4R)-2,3-dihydroxy-4-((2-(3-(trifluoromethyl)phenyl)pyrazolo[1,5-a]pyrimidin-7-yl)amino)cyclopentyl)methyl sulfamate) | 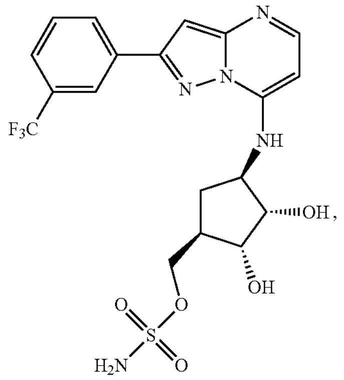 [SMILES: NS(=O)(=O)OC[C@H]1C[C@@H](Nc2ccnc3cc(-c4cccc(C(F)(F)F)c4)nn23)[C@H](O)[C@@H]1O] |
| Piperacillin | 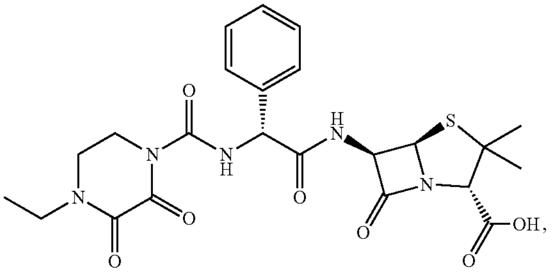 [SMILES: CCN1CCN(C(=O)N[C@@H](C(=O)N[C@@H]2C(=O)N3[C@@H]2SC(C)(C)[C@@H]3C(=O)O)c2ccccc2)C(=O)C1=O] |

-continued
| Compound Name | Structure |
| --- | --- |
| M22 (1-benzyl-N-(2,4-dichlorophenethyl)piperidin-4-amine) | 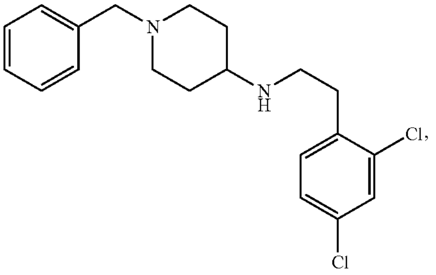 [SMILES: Clc1ccc(CCNC2CCN(Cc3ccccc3)CC2)c(Cl)c1] |
| 6,6'-Biapigenin | 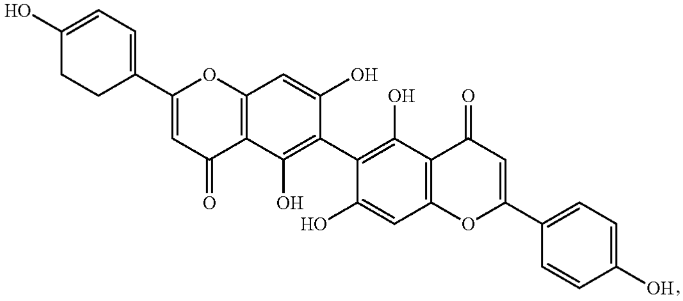 [SMILES: O=c1cc(C2=CC=C(O)CC2)oc2cc(O)c(-c3c(O)cc4oc(-c5ccc(O)cc5)cc(=O)c4c3O)c(O)c12] |
| Thieno-pyridine | 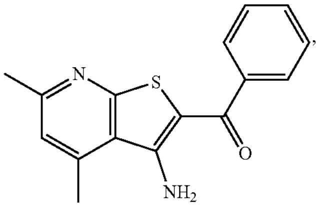 [SMILES: Cc1cc(C)c2c(N)c(C(=O)c3ccccc3)sc2n1] |
| Imidazo-pyrimidine | 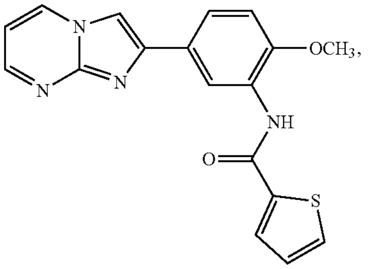 [SMILES: COc1ccc(-c2cn3cccnc3n2)cc1NC(=O)c1cccs1] |
| Largazole | 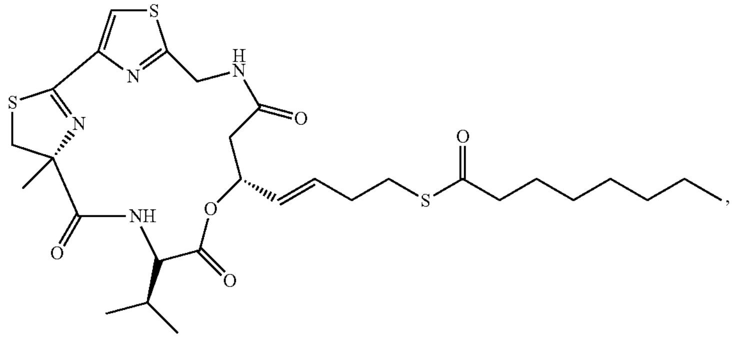 |

-continued
| Compound Name | Structure |
| --- | --- |
| Pyr-41 (4[4-(5-nitro-furan-2-ylmethylene)-3,5-dioxo-pyrazolidin-1-yl]-benzoic acid ethyl ester) | 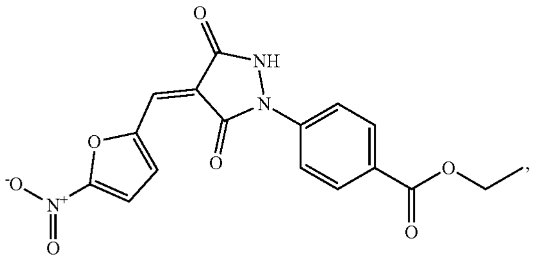 |
| Phorbol 12-myristate 13-acetate | 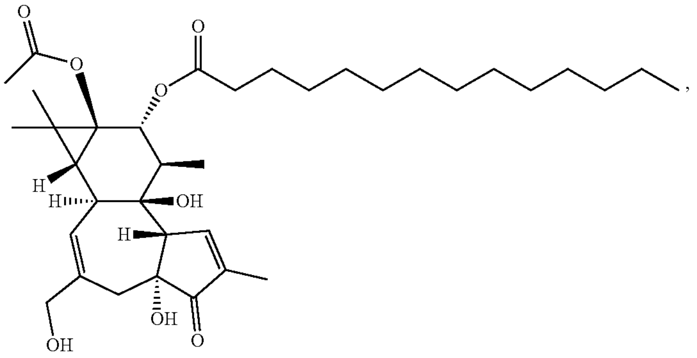 |
| 2,3-dihydropyrrolo[2,1-b]quinazolin-9(1H)-one | 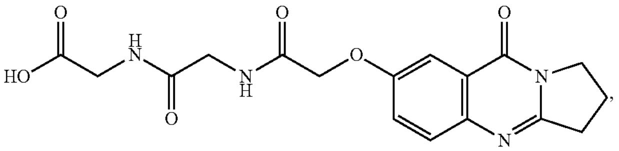 [SMILES: O=C(O)CNC(=O)CNC(=O)COc1ccc2nc3n(c(=O)c2c1)CCC3] |
| Ofloxacin | 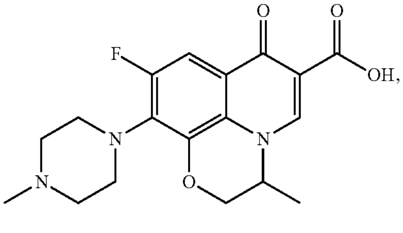 [SMILES: CC1COc2c(N3CCN(C)CC3)c(F)cc3c(=O)c(C(=O)O)cn1c23] |
| Panepophenanthin | 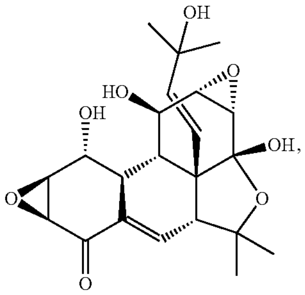 [SMILES: CC(C)(O)/C=C/[C@@]12[C@H]3[C@@H](O)[C@@H]4O[C@@H]4[C@]1(O)OC(C)(C)[C@@H]2C=C1C(=O)[C@H]2O[C@H]2[C@H](O)[C@H]13] |
| Himeic Acid A | 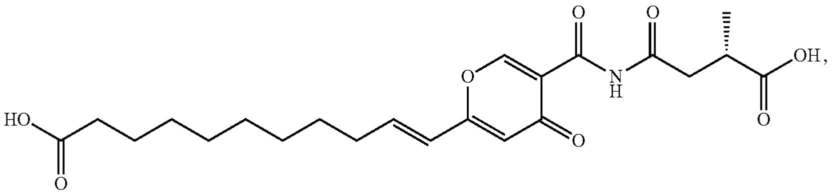 [SMILES: C[C@@H](CC(=O)NC(=O)c1coc(/C=C/CCCCCCCCC(=O)O)cc1=O)C(=O)O] |

-continued
| Compound Name | Structure |
| --- | --- |
| Hyrtioreticulins A | 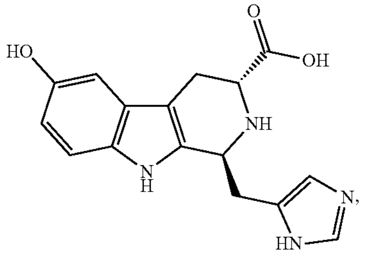 [SMILES: O=C(O)[C@H]1Cc2c([nH]c3ccc(O)cc23)[C@H](Cc2cnc[nH]2)N1] |
| Phytol | 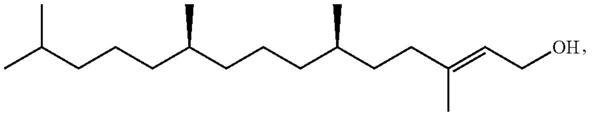 [SMILES: C/C(=C\CO)CC[C@H](C)CCC[C@H](C)CCCC(C)C] |
| ABPA3 ([(2R,3S,4R,5R)-5-[6-(3-ethynylanilino)purin-9-yl]-3,4-dihydroxyoxolan-2-yl]methyl sulfamate) | 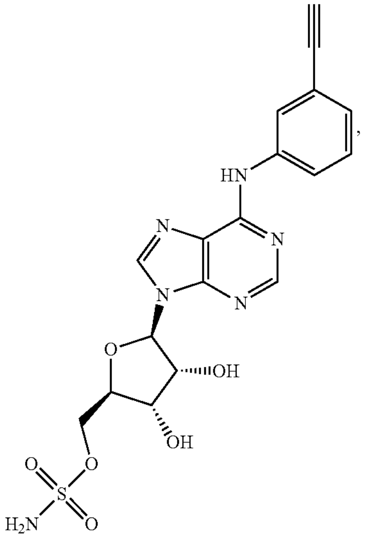 [SMILES: C#Cc1cccc(Nc2ncnc3c2ncn3[C@@H]2O[C@H](COS(N)(=O)=O)[C@@H](O)[C@H]2O)c1] |
| Benzothiazole | 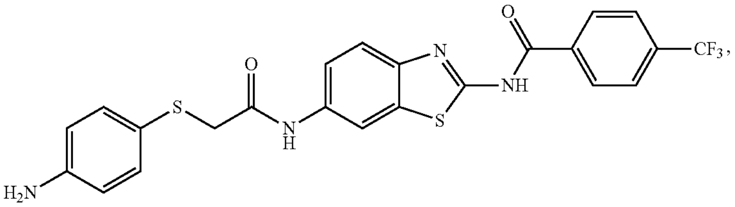 [SMILES: Nc1ccc(SCC(=O)Nc2ccc3nc(NC(=O)c4ccc(C(F)(F)F)cc4)sc3c2)cc1] |
| Deoxyvasicinone derivative | 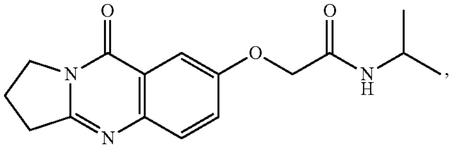 [SMILES: CC(C)NC(=O)COc1ccc2nc3n(c(=O)c2c1)CCC3] |
| Coumarin A | 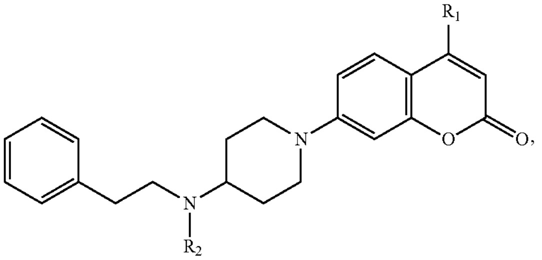 |

-continued

| Compound Name | Structure |
|---|---|
| Coumarin B | 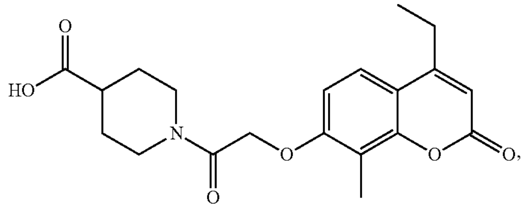 [SMILES: CCc1cc(=O)oc2c(C)c(OCC(=O)N3CCC(C(=O)O)CC3)ccc12] , |
| Deoxyvasicinone derivative | 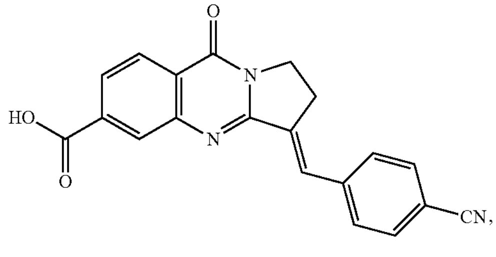 [SMILES: N#Cc1ccc(/C=C2\CCn3c2nc2cc(C(=O)O)ccc2c3=O)cc1] , |
| Imidazolium-quinoxaline | 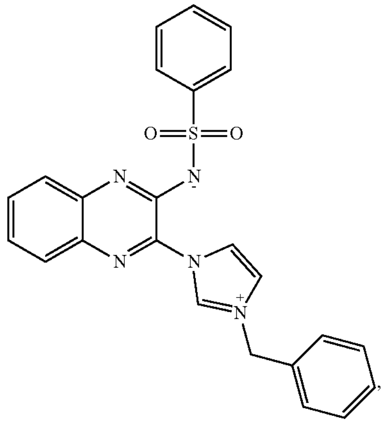 , and |
| TAS4464 (7H-Pyrrolo[2,3-d]pyrimidin-4-amine, 7-[5-[(aminosulfonyl)amino]-5-deoxy-beta-D-ribofuranosyl]-5-[2-(2-ethoxy-6-fluorophenyl)ethynyl]-) | 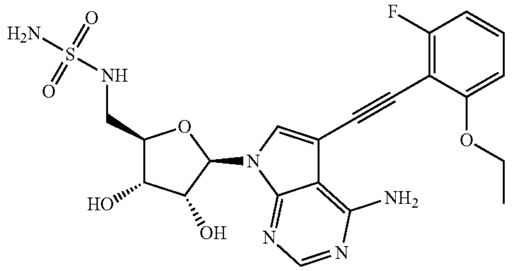 [SMILES: CCOc1cccc(F)c1C#Cc1cn([C@@H]2O[C@H](CNS(N)(=O)=O)[C@@H](O)[C@H]2O)c2ncnc(N)c12] |

wherein $R_1$ is alkyl, aryl, arylalkyl, arylalkyne, arylalkene, heterocyclyl, or heteroaryl and $R_2$ is H, alkyl, or aryl.

Embodiment III-14. The compound, or a pharmaceutically acceptable salt, solvate, hydrate, isomer, or tautomer thereof, of any one of embodiments III-1 to III-13, wherein $X_3$ is selected from the group consisting of: Pevonedistat, TAS1 (((2S,3S,4R,5R)-5-(4-amino-5-((4,7-dimethyl-3,4-dihydro-2H-benzo[b][1,4]oxazin-8-yl) ethynyl)-7H-pyrrolo [2,3-d]pyrimidin-7-yl)-3,4-dihydroxytetrahydrofuran-2-yl) methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), and TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate).

Embodiment III-15. The compound, or a pharmaceutically acceptable salt, solvate, hydrate, isomer, or tautomer thereof, of any one of embodiments III-1 to III-10, wherein $X_3$ is a cancer chemotherapeutic.

Embodiment III-16. The compound, or a pharmaceutically acceptable salt, solvate, hydrate, isomer, or tautomer thereof, of any one of embodiments III-1 to III-10 or 15, wherein $X_3$ is selected from the group consisting of an oncolytic drug, a genotoxic agent, an alkylating agent, a tubulin inhibitor, a microtubule assembly inhibitor, an antineoplastic drug, a kinase inhibitor, a vinca alkaloid, an antibiotic, an anthracycline, an antimetabolite, an aromatase inhibitor, a topoisomerase inhibitor, a mTor inhibitor, a retinoid, an antimitotic agent, a protease inhibitor, a tyrosine kinase inhibitor, a microtubule destabilizer, and a proteasome inhibitor.

Embodiment III-17. The compound, or a pharmaceutically acceptable salt, solvate, hydrate, isomer, or tautomer thereof, of any one of embodiments III-1 to III-10 or III-15 to III-16, wherein $X_3$ is selected from the group consisting of vincristine, vinorelbine, vinflunine, crytophycin 52, a halichondrin, a dolastatin, a hemiasterlin, colchicine, a combretastatin, 2-methoxyestradiol, a methoxybenzenesulfonamide, epothilone, and discodermolide.

Embodiment III-18. The compound, or a pharmaceutically acceptable salt, solvate, hydrate, isomer, or tautomer thereof, of any one of embodiments III-1 to III-10 or III-15 to III-16, wherein $X_3$ is selected from the group consisting of:

| Compound Name | Structure |
| --- | --- |
| Monomethyl Auristatin E | 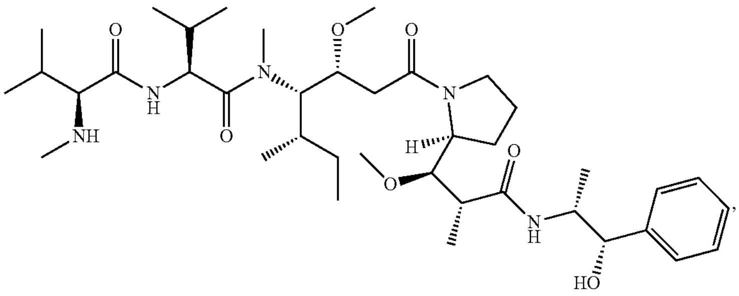 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C] |
| Docetaxel | 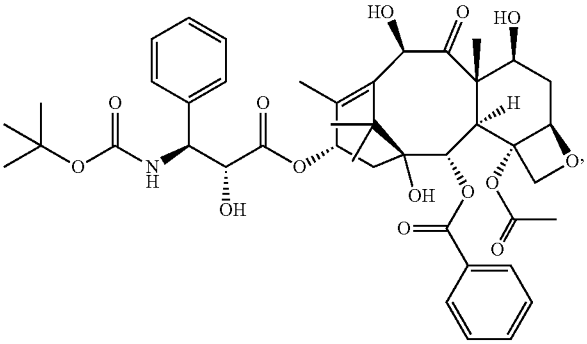 |
| Etoposide | 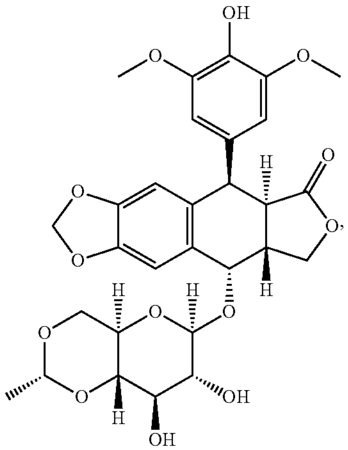 |

-continued
| Compound Name | Structure |
| --- | --- |
| Gemcitabine | 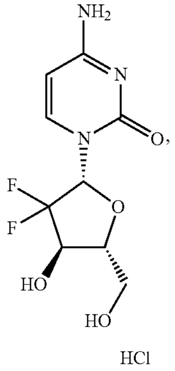 [SMILES: Nc1ccn([C@@H]2O[C@H](CO)[C@@H](O)C2(F)F)c(=O)n1 ; Cl] |
| Vinblastine | 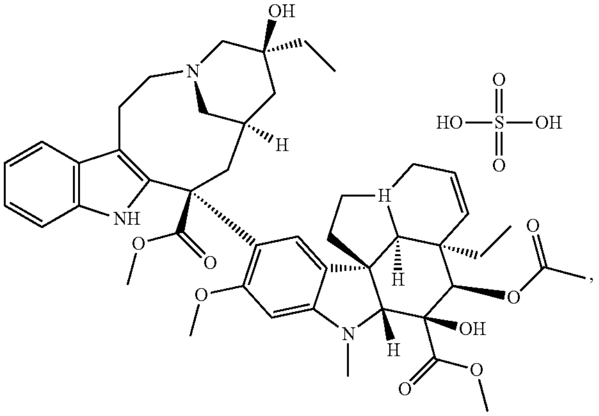 |
| Paclitaxel | 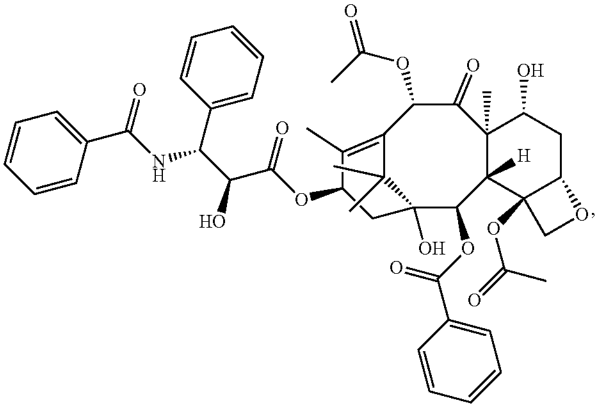 |
| Irinotecan | 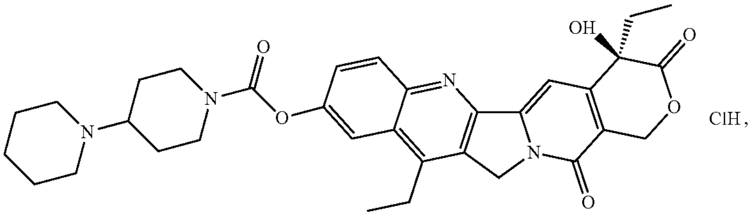 [SMILES: CCc1c2c(nc3ccc(OC(=O)N4CCC(N5CCCCC5)CC4)cc13)-c1cc3c(c(=O)n1C2)COC(=O)[C@@]3(O)CC ; Cl] |
| Fluorouracil | 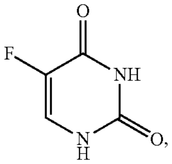 |

-continued
| Compound Name | Structure |
| --- | --- |
| Methotrexate | 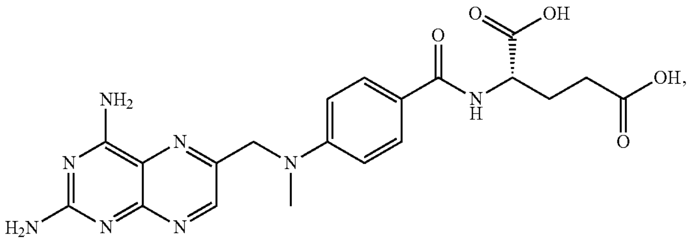 [SMILES: CN(Cc1cnc2nc(N)nc(N)c2n1)c1ccc(C(=O)N[C@@H](CCC(=O)O)C(=O)O)cc1] |
| Carboplatin | 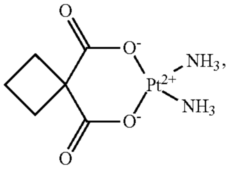 |
| Oxaliplatin | 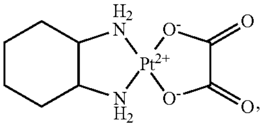 |
| Cisplatin | 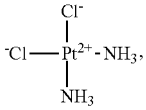 |
| Doxorubicin HCl | 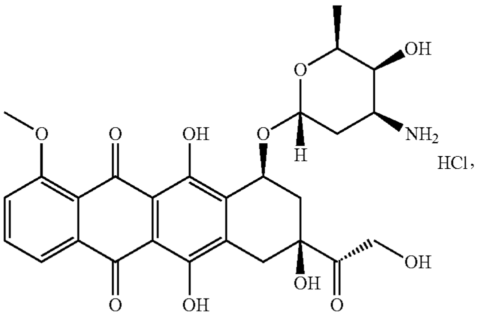 |
| Fulvestrant | 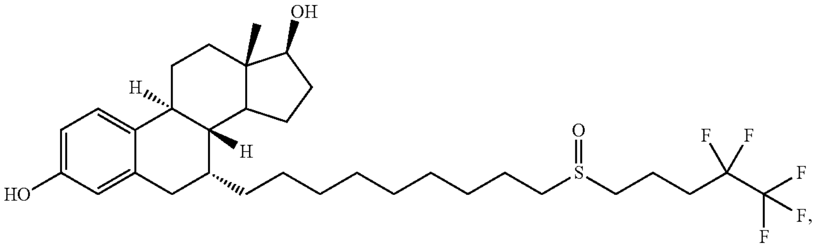 [SMILES: C[C@]12CC[C@@H]3c4ccc(O)cc4C[C@@H](CCCCCCCCCS(=O)CCCC(F)(F)C(F)(F)F)[C@H]3C1CC[C@@H]2O] |
| Isotretinoin | 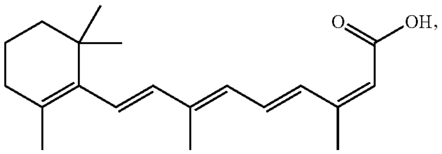 [SMILES: CC1=C(/C=C/C(C)=C/C=C/C(C)=C\C(=O)O)C(C)(C)CCC1] |

-continued
| Compound Name | Structure |
|---|---|
| Buserelin | 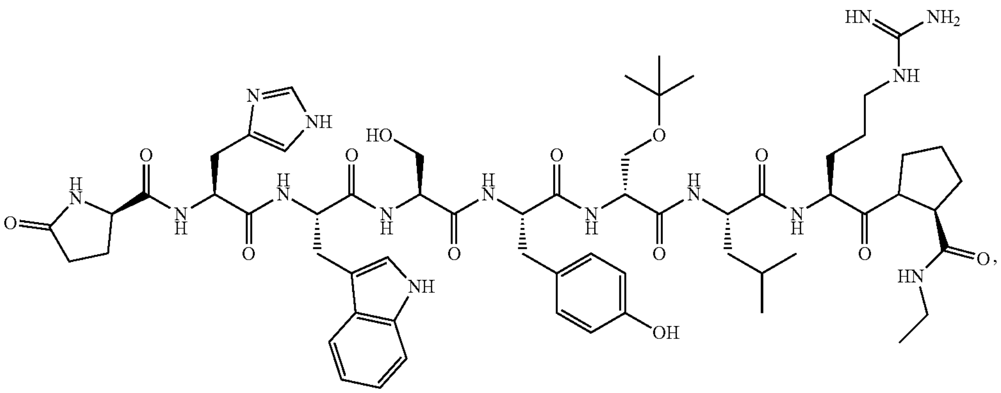 [SMILES: CCNC(=O)[C@@H]1CCCC1C(=O)[C@H](CCCNC(=N)N)NC(=O)[C@H](CC(C)C)NC(=O)[C@@H](COC(C)(C)C)NC(=O)[C@H](Cc1ccc(O)cc1)NC(=O)[C@H](CO)NC(=O)[C@H](Cc1c[nH]c2ccccc12)NC(=O)[C@H](Cc1c[nH]cn1)NC(=O)[C@H]1CCC(=O)N1] |
| Everolimus | 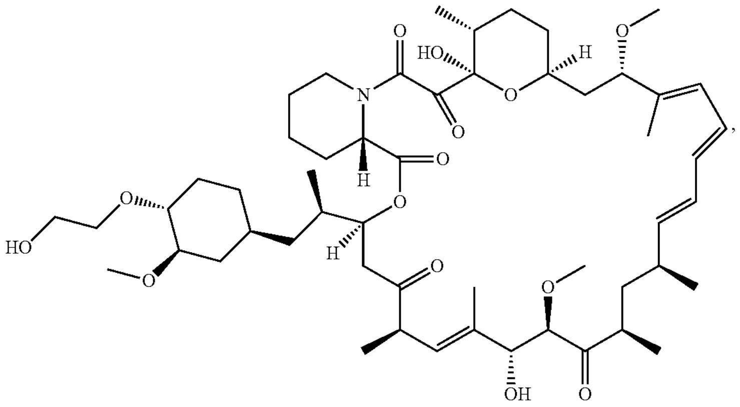 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C] |
| Carfilzomib | 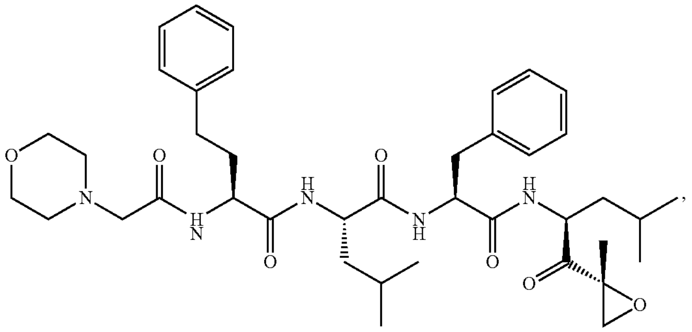 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1] |
| Rifabutin | 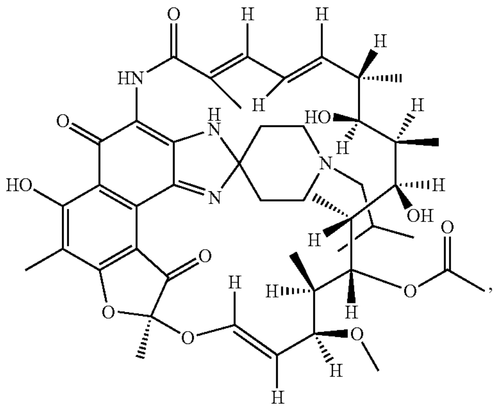 [SMILES: CO[C@H]1/C=C/O[C@@]2(C)Oc3c(C)c(O)c4c(c3C2=O)C2=NC3(CCN(CC(C)C)CC3)NC2=C(NC(=O)/C(C)=C/C=C/[C@H](C)[C@H](O)[C@@H](C)[C@@H](O)[C@@H](C)[C@H](OC(C)=O)[C@@H]1C)C4=O] |

-continued

| Compound Name | Structure |
| --- | --- |
| Clindamycin | 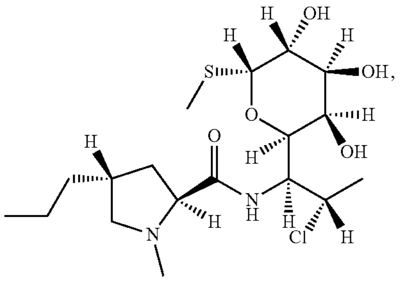 [SMILES: CCC[C@@H]1C[C@@H](C(=O)N[C@@H]([C@H]2O[C@H](SC)[C@H](O)[C@@H](O)[C@H]2O)[C@H](C)Cl)N(C)C1] |
| Tubulysin A | 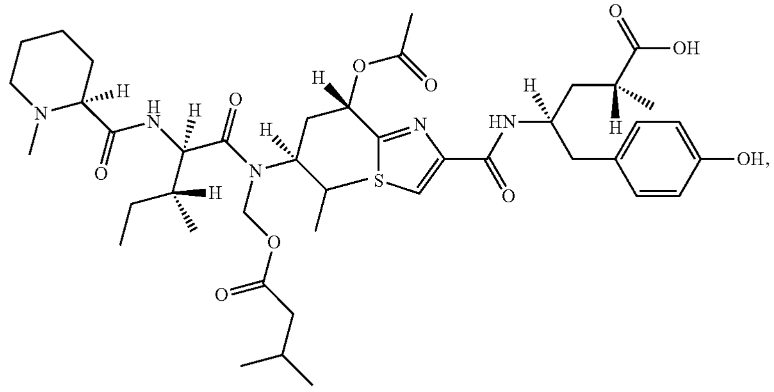 [SMILES: CC[C@@H](C)[C@@H](NC(=O)[C@@H]1CCCCN1C)C(=O)N(COC(=O)CC(C)C)[C@@H](C[C@H](OC(C)=O)c1nc(C(=O)N[C@H](Cc2ccc(O)cc2)C[C@@H](C)C(=O)O)cs1)C(C)C] |
| Indibulin | 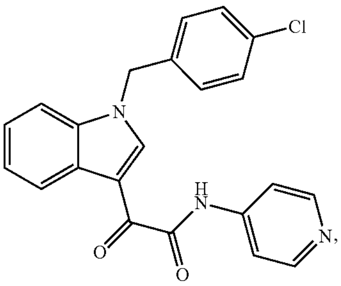 [SMILES: O=C(Nc1ccncc1)C(=O)c1cn(Cc2ccc(Cl)cc2)c2ccccc12] |
| Gefitinib | 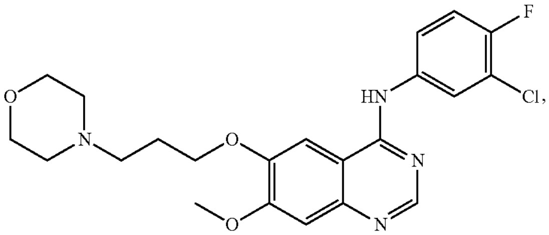 and |
| Dasatinib | 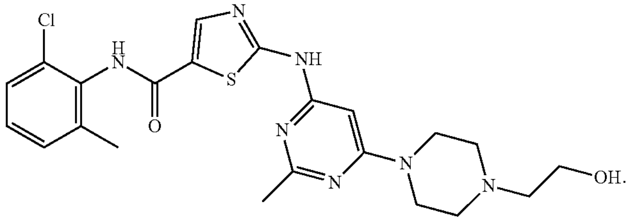 [SMILES: Cc1nc(Nc2ncc(C(=O)Nc3c(C)cccc3Cl)s2)cc(N2CCN(CCO)CC2)n1] |

Embodiment III-19. The compound, or a pharmaceutically acceptable salt, solvate, hydrate, isomer, or tautomer thereof, of any one of embodiments III-1 to III-10, III-15 to III-16, or III-18, wherein $X_3$ is Monomethyl Auristatin E.

Embodiment III-20. The compound, or a pharmaceutically acceptable salt, solvate, hydrate, isomer, or tautomer thereof, of embodiment III-1, wherein the compound of Formula (I) is selected from the group consisting of:

| Compound | Structure |
| --- | --- |
| A-1 | 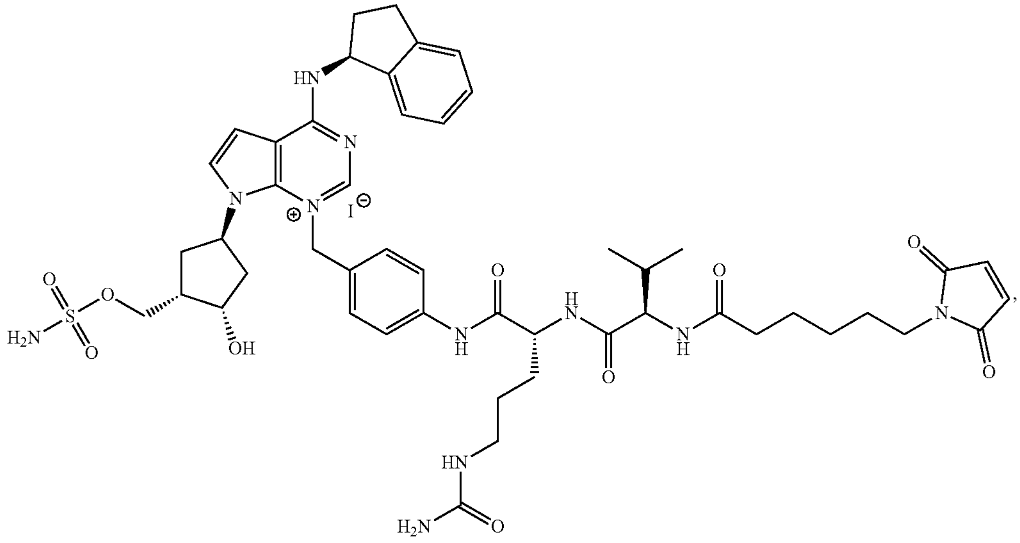 [SMILES: CC(C)[C@@H](NC(=O)CCCCCN1C(=O)C=CC1=O)C(=O)N[C@H](CCCNC(N)=O)C(=O)Nc1ccc(C[n+]2cnc(N[C@H]3CCc4ccccc43)c3ccn([C@@H]4C[C@@H](COS(N)(=O)=O)[C@@H](O)C4)c32)cc1 ; [I-]], |
| A-2 | 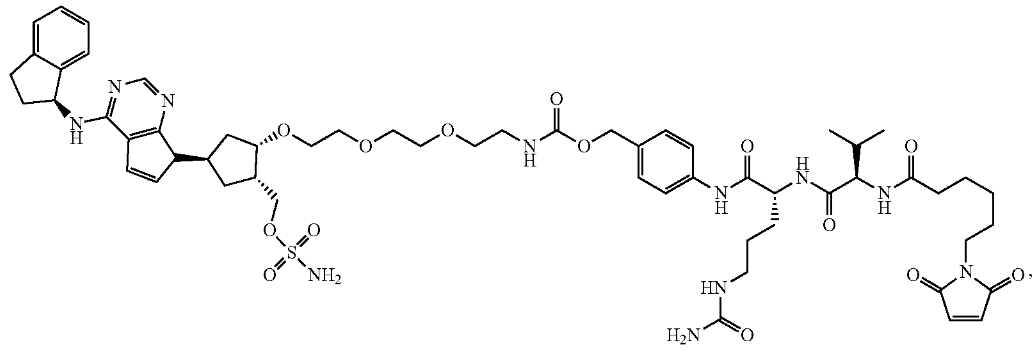 [SMILES: CC(C)[C@@H](NC(=O)CCCCCN1C(=O)C=CC1=O)C(=O)N[C@H](CCCNC(N)=O)C(=O)Nc1ccc(COC(=O)NCCOCCOCCO[C@H]2C[C@H](C3C=Cc4c(N[C@H]5CCc6ccccc65)ncnc43)C[C@H]2COS(N)(=O)=O)cc1], |
| A-3 | 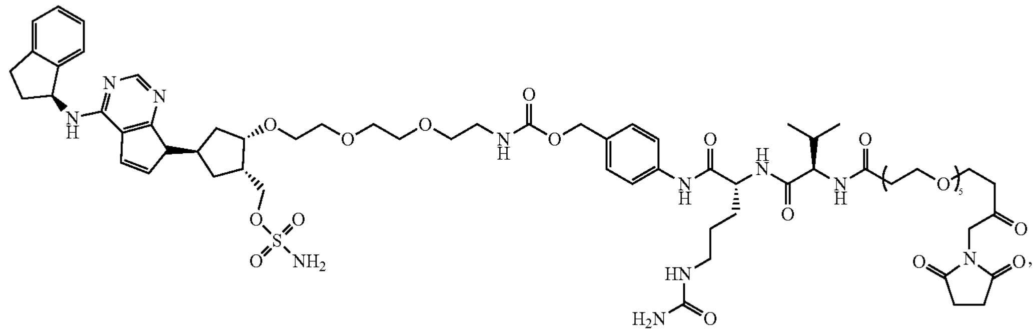, |

-continued
| Compound | Structure |
|---|---|
| A-4 | 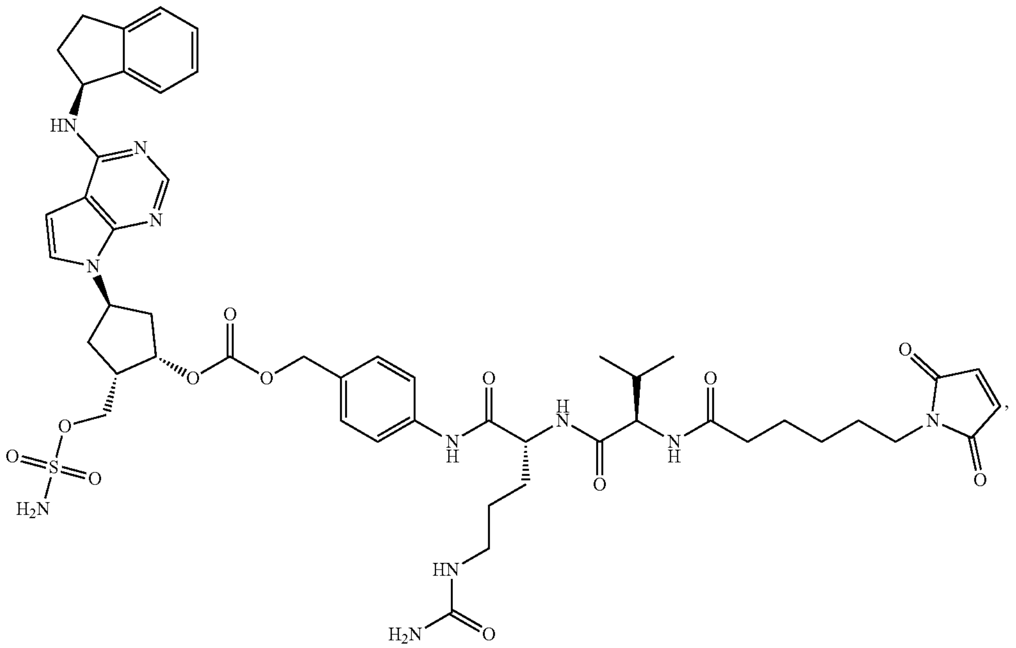 [SMILES: CC(C)[C@@H](NC(=O)CCCCCN1C(=O)C=CC1=O)C(=O)N[C@H](CCCNC(N)=O)C(=O)Nc1ccc(COC(=O)O[C@H]2C[C@H](n3ccc4c(N[C@H]5CCc6ccccc65)ncnc43)C[C@H]2COS(N)(=O)=O)cc1] |
| A-5 | 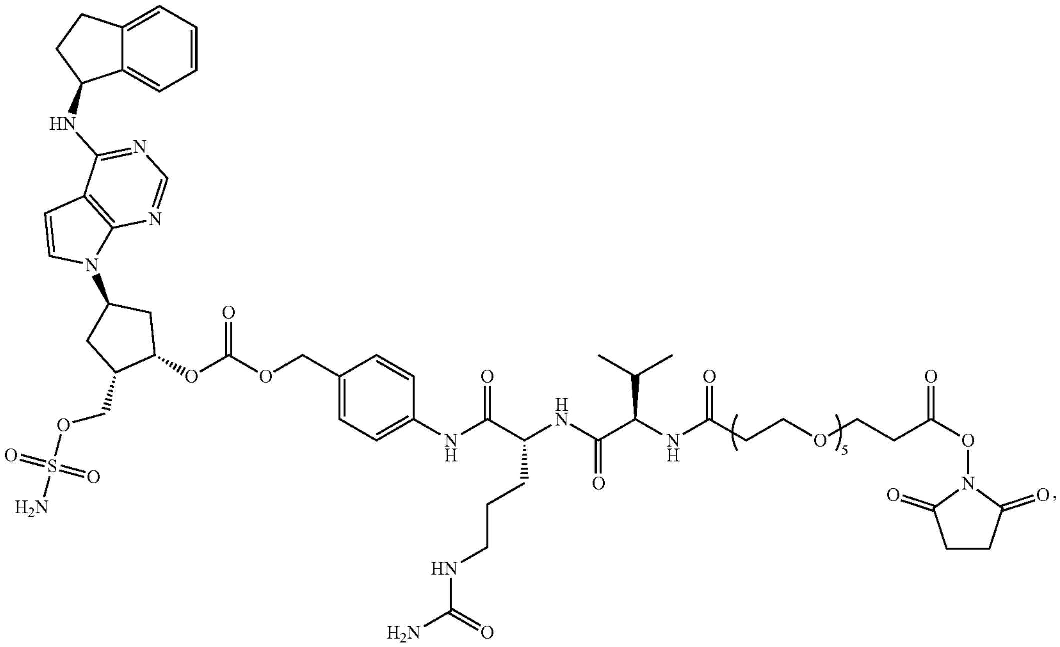 |
| A-6 | 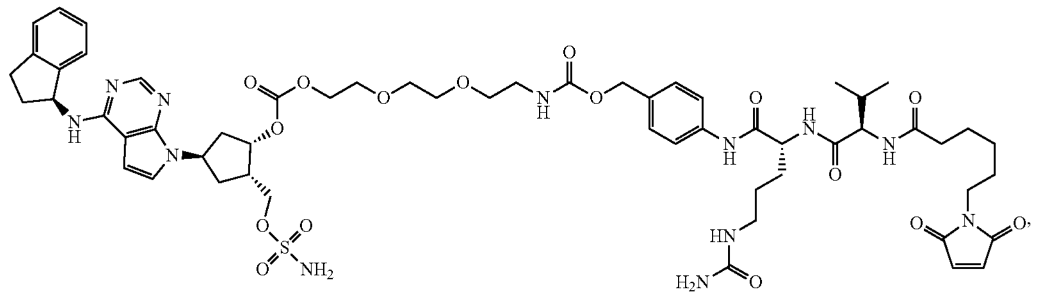 [SMILES: CC(C)[C@@H](NC(=O)CCCCCN1C(=O)C=CC1=O)C(=O)N[C@H](CCCNC(N)=O)C(=O)Nc1ccc(COC(=O)NCCOCCOCCOC(=O)O[C@H]2C[C@H](n3ccc4c(N[C@H]5CCc6ccccc65)ncnc43)C[C@H]2COS(N)(=O)=O)cc1] |

-continued
| Compound | Structure |
| --- | --- |
| A-7 | 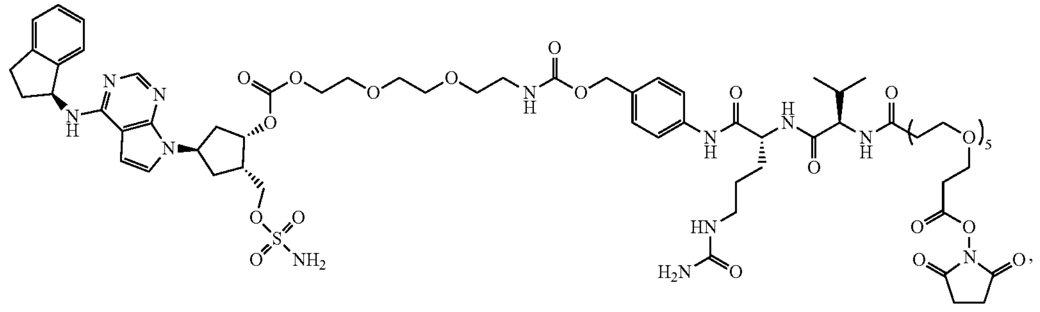 |
| A-8 | 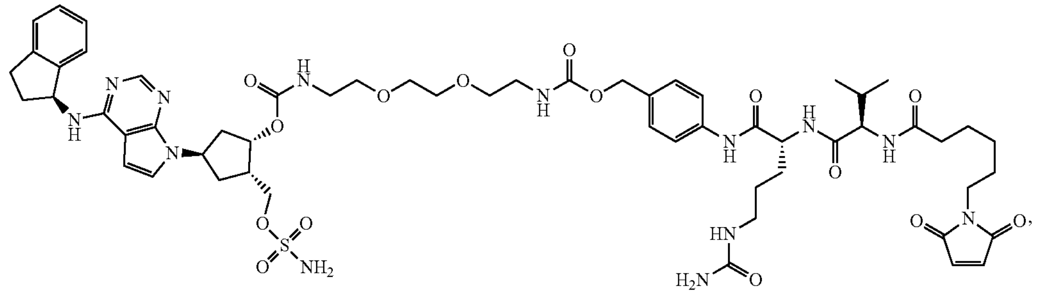 [SMILES: CC(C)[C@@H](NC(=O)CCCCCN1C(=O)C=CC1=O)C(=O)N[C@H](CCCNC(N)=O)C(=O)Nc1ccc(COC(=O)NCCOCCOCCNC(=O)O[C@H]2C[C@H](n3ccc4c(N[C@H]5CCc6ccccc65)ncnc43)C[C@H]2COS(N)(=O)=O)cc1] |
| A-9 | 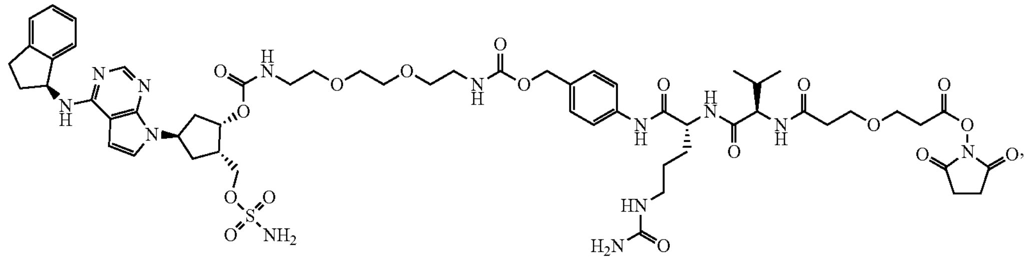 [SMILES: CC(C)[C@@H](NC(=O)CCOCCC(=O)ON1C(=O)CCC1=O)C(=O)N[C@H](CCCNC(N)=O)C(=O)Nc1ccc(COC(=O)NCCOCCOCCNC(=O)O[C@H]2C[C@H](n3ccc4c(N[C@H]5CCc6ccccc65)ncnc43)C[C@H]2COS(N)(=O)=O)cc1] |
| A-10 | 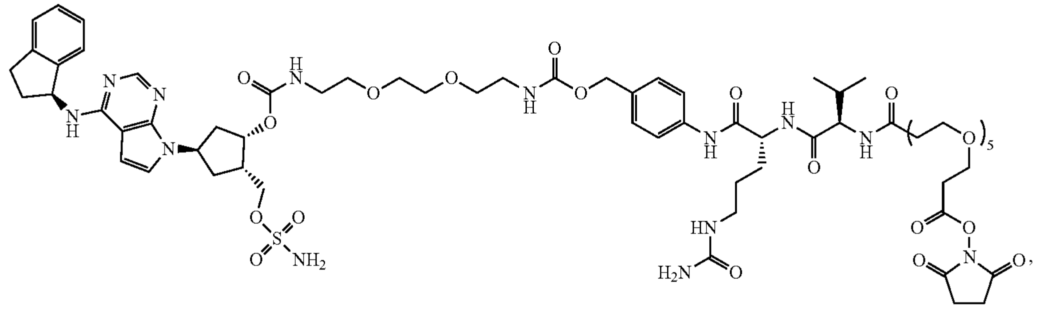 |

-continued
| Compound | Structure |
| --- | --- |
| A-11 | 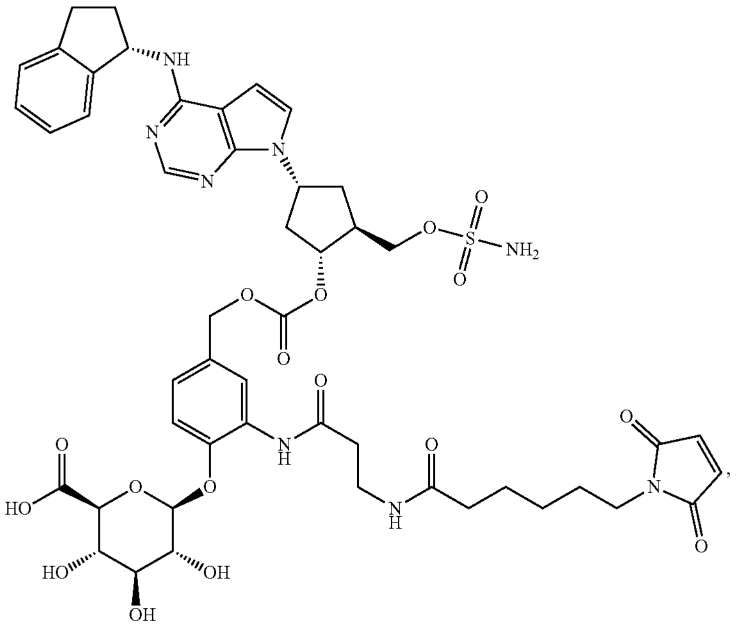 [SMILES: NS(=O)(=O)OC[C@@H]1C[C@@H](n2ccc3c(N[C@H]4CCc5ccccc54)ncnc32)C[C@H]1OC(=O)OCc1ccc(O[C@@H]2O[C@H](C(=O)O)[C@@H](O)[C@H](O)[C@H]2O)c(NC(=O)CCNC(=O)CCCCCN2C(=O)C=CC2=O)c1] |
| A-12 | 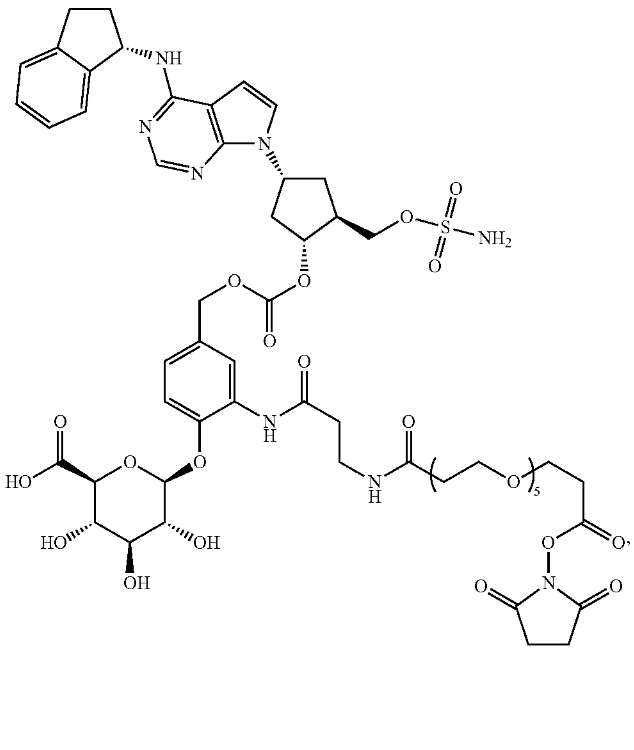 |

-continued
| Compound | Structure |
| --- | --- |
| A-13 | 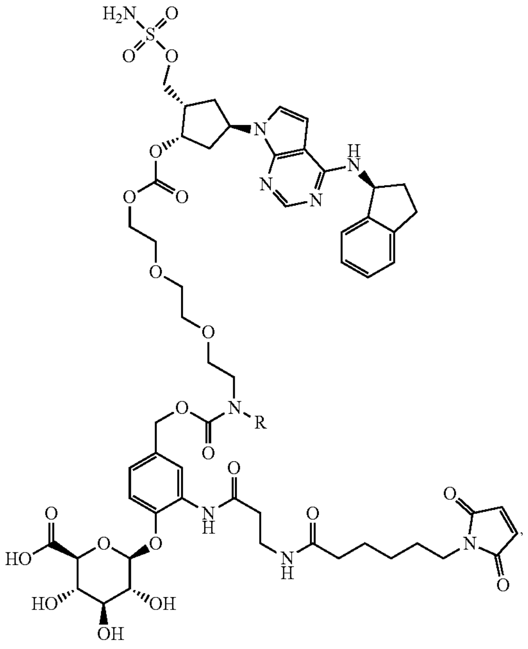 |
| A-14 | 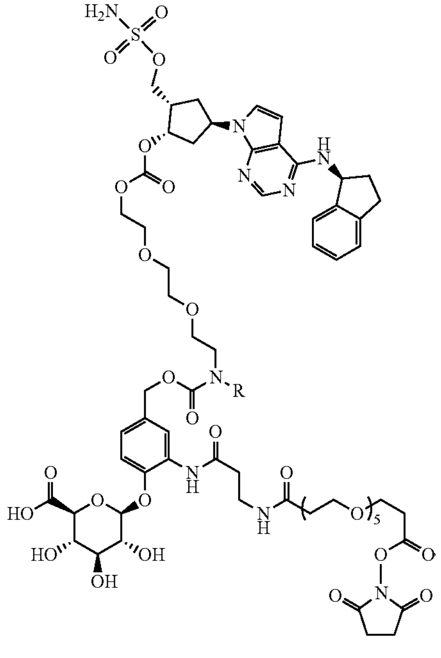 |

-continued
| Compound | Structure |
|---|---|
| A-15 | 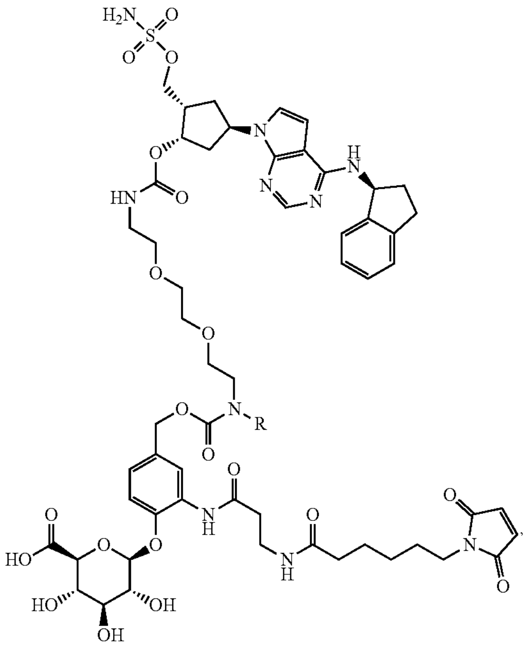 |
| A-16 | 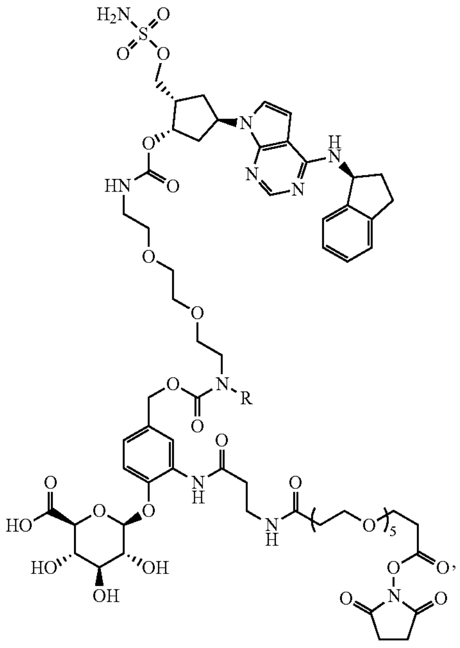 |

-continued
| Compound | Structure |
| --- | --- |
| A-17 | 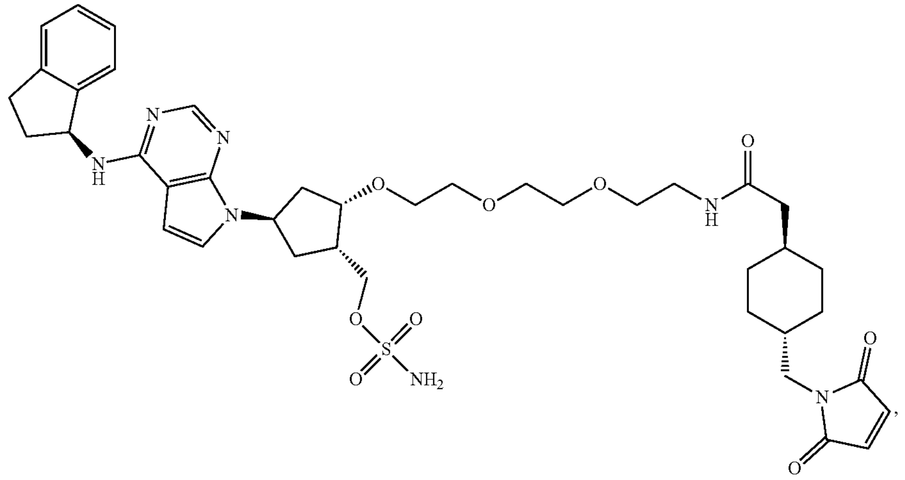 [SMILES: NS(=O)(=O)OC[C@@H]1C[C@@H](n2ccc3c(N[C@H]4CCc5ccccc54)ncnc32)C[C@@H]1OCCOCCOCCNC(=O)C[C@H]1CC[C@H](CN2C(=O)C=CC2=O)CC1] |
| A-18 | 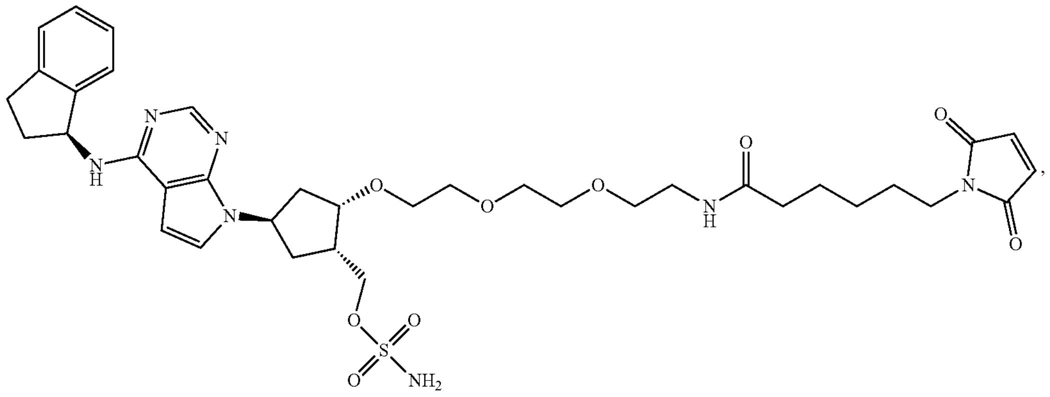 [SMILES: NS(=O)(=O)OC[C@@H]1C[C@@H](n2ccc3c(N[C@H]4CCc5ccccc54)ncnc32)C[C@@H]1OCCOCCOCCNC(=O)CCCCCN1C(=O)C=CC1=O] |
| A-19 | 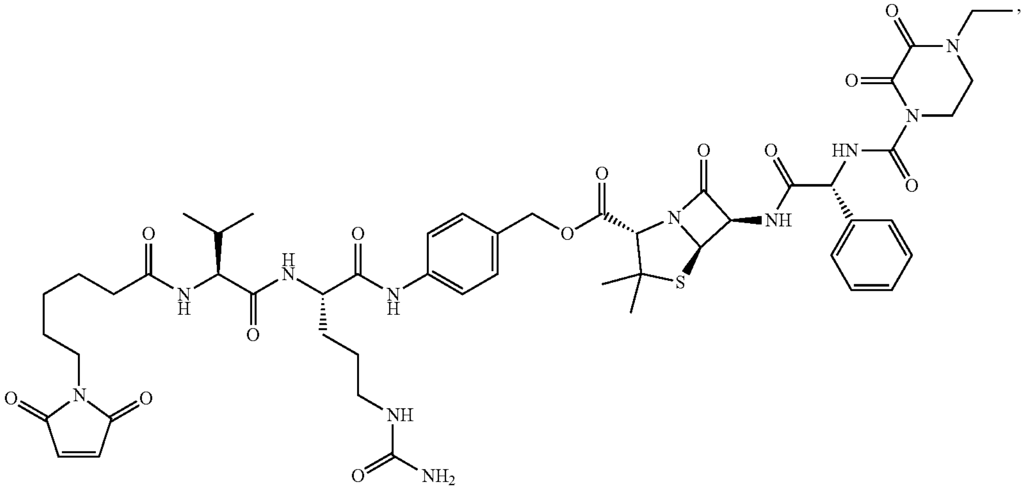 [SMILES: CCN1CCN(C(=O)N[C@@H](C(=O)N[C@@H]2C(=O)N3[C@@H]2SC(C)(C)[C@@H]3C(=O)OCc2ccc(NC(=O)[C@H](CCCNC(N)=O)NC(=O)[C@@H](NC(=O)CCCCCN3C(=O)C=CC3=O)C(C)C)cc2)c2ccccc2)C(=O)C1=O] |

-continued
| Compound | Structure |
| --- | --- |
| A-20 | 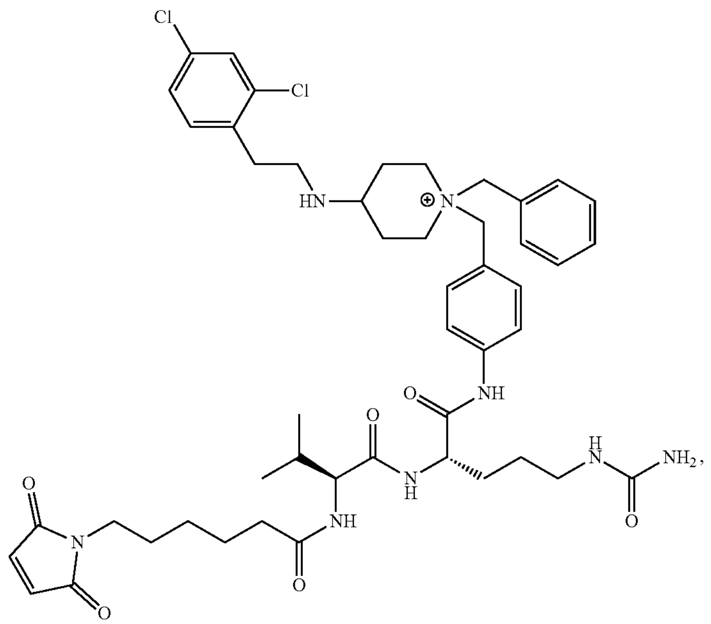 [SMILES: CC(C)[C@H](NC(=O)CCCCCN1C(=O)C=CC1=O)C(=O)N[C@@H](CCCNC(N)=O)C(=O)Nc1ccc(C[N+]2(Cc3ccccc3)CCC(NCCc3ccc(Cl)cc3Cl)CC2)cc1] |
| A-21 | 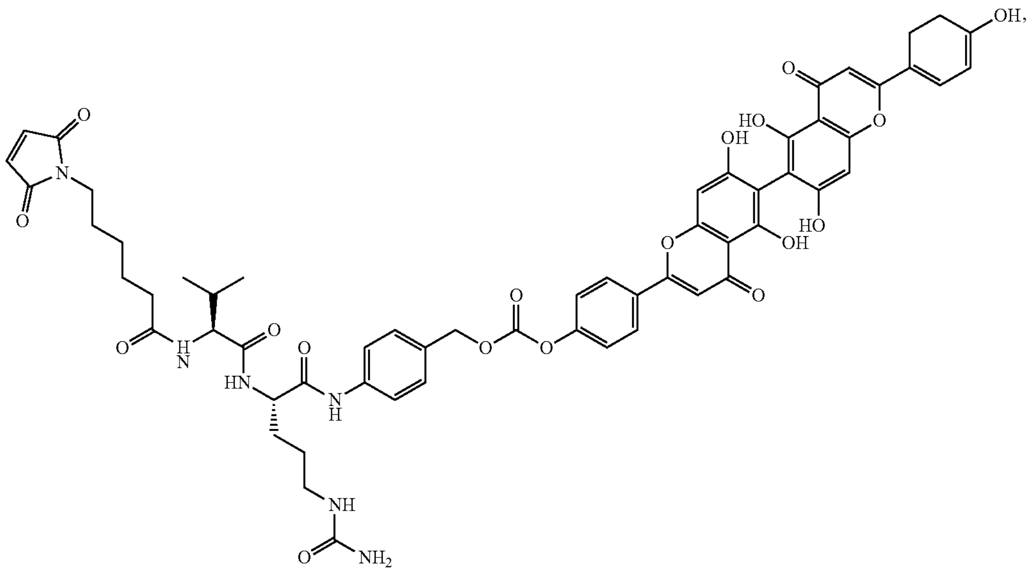 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc(-c3cc(=O)c4c(O)c(-c5c(O)cc6oc(C7=CC=C(O)CC7)cc(=O)c6c5O)c(O)cc4o3)cc2)cc1] |

-continued
| Compound | Structure |
| --- | --- |
| A-22 | 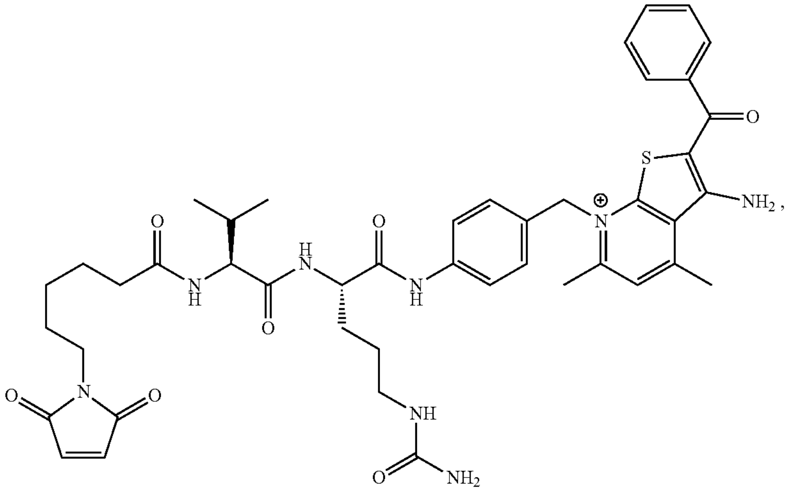 [SMILES: Cc1cc(C)[n+](Cc2ccc(NC(=O)[C@H](CCCNC(N)=O)NC(=O)[C@@H](NC(=O)CCCCCN3C(=O)C=CC3=O)C(C)C)cc2)c2sc(C(=O)c3ccccc3)c(N)c12] |
| A-23 | 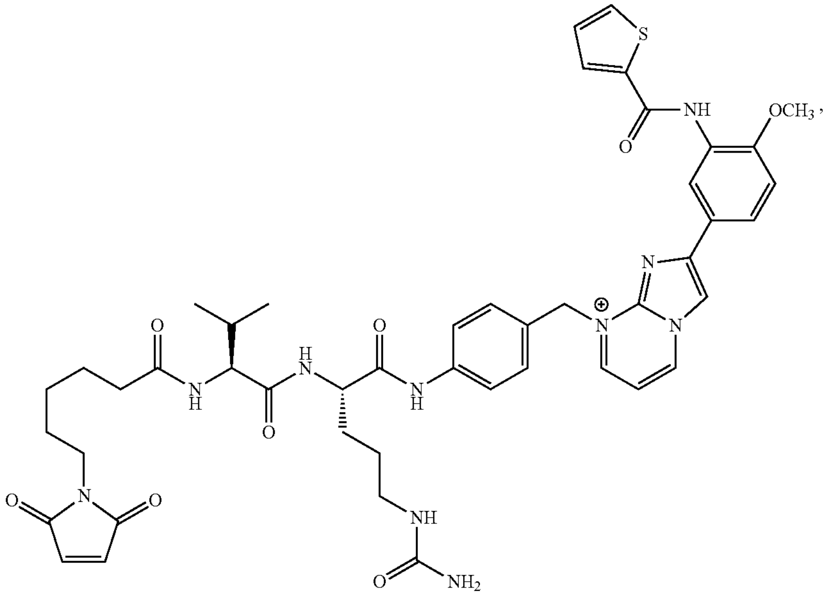 [SMILES: COc1ccc(-c2cn3ccc[n+](Cc4ccc(NC(=O)[C@H](CCCNC(N)=O)NC(=O)[C@@H](NC(=O)CCCCCN5C(=O)C=CC5=O)C(C)C)cc4)c3n2)cc1NC(=O)c1cccs1] |
| A-24 | 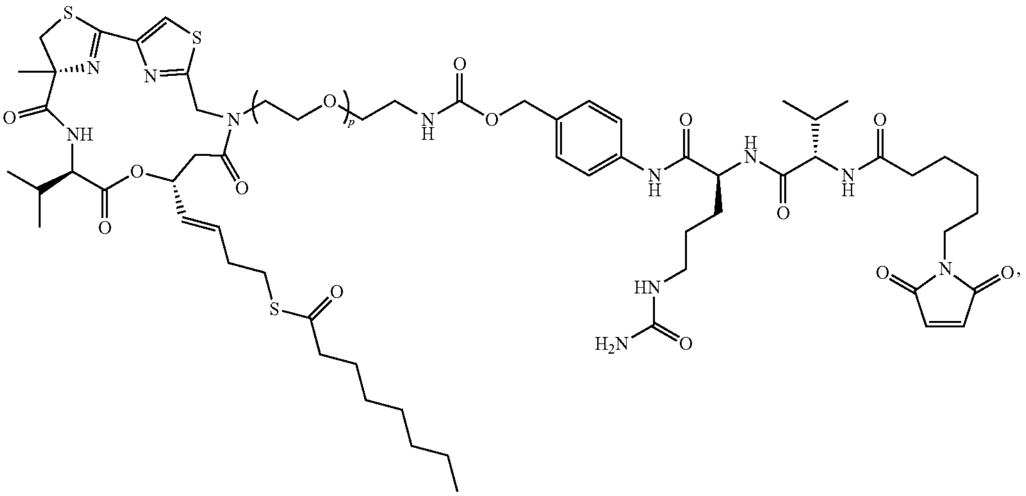 |

-continued
| Compound | Structure |
| --- | --- |
| A-25 | 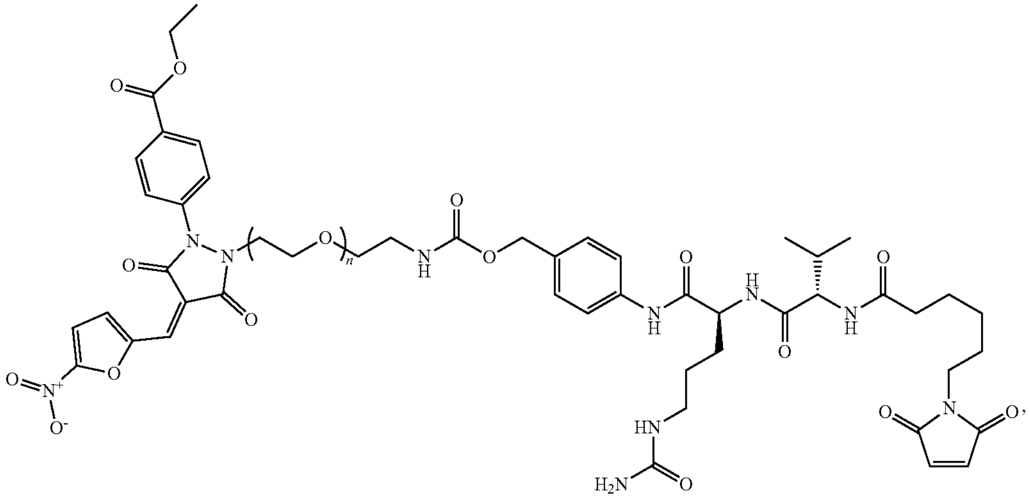 |
| A-26 | 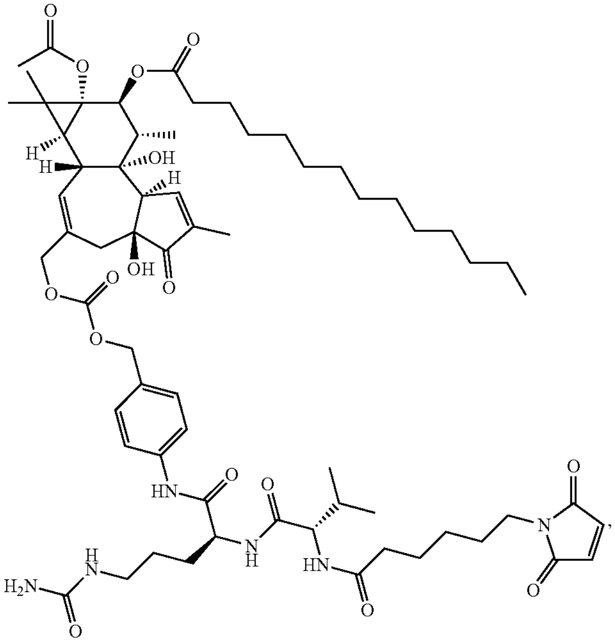 [SMILES: CCCCCCCCCCCCCC(=O)O[C@H]1[C@H](C)[C@]2(O)[C@H](C=C(COC(=O)OCc3ccc(NC(=O)[C@H](CCCNC(N)=O)NC(=O)[C@@H](NC(=O)CCCCCN4C(=O)C=CC4=O)C(C)C)cc3)C[C@@]3(O)C(=O)C(C)=C[C@H]23)[C@H]2C(C)(C)[C@@]12OC(C)=O] |
| A-27 | 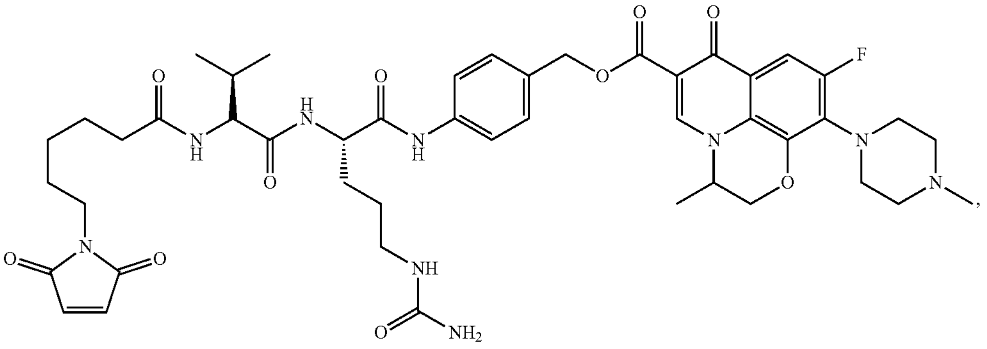 |

-continued
| Compound | Structure |
| --- | --- |
| A-28 | 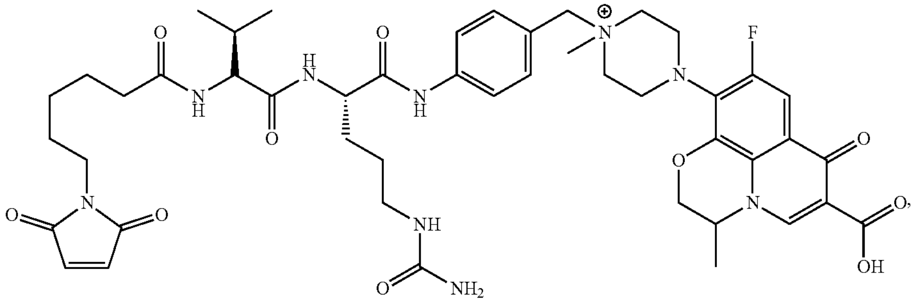 |
| A-29 | 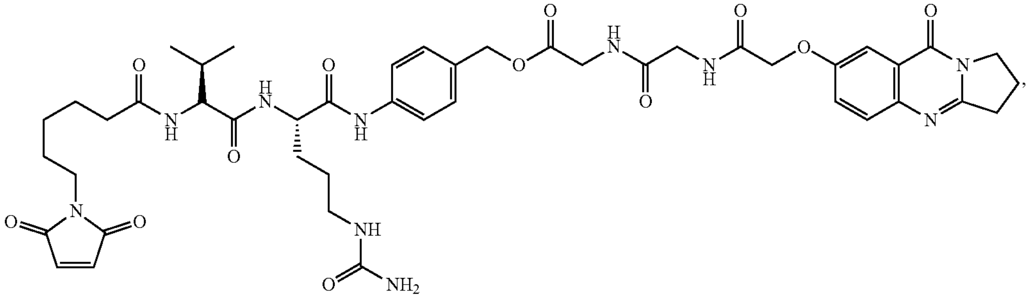 |
| A-30 | 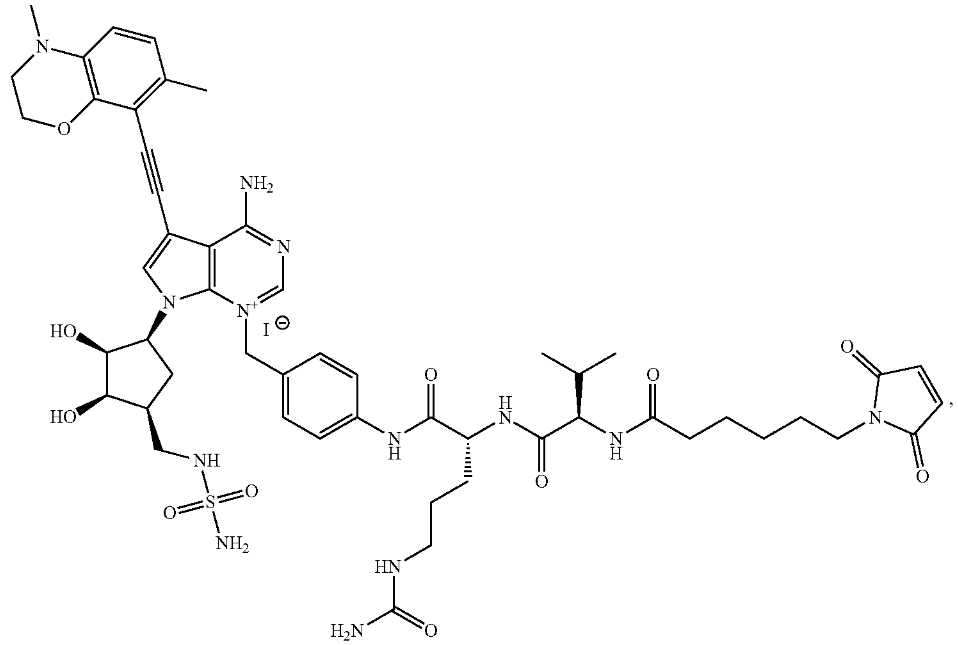 [SMILES: Cc1ccc2c(c1C#Cc1cn([C@H]3C[C@@H](CNS(N)(=O)=O)[C@@H](O)[C@H]3O)c3c1c(N)nc[n+]3Cc1ccc(NC(=O)[C@@H](CCCNC(N)=O)NC(=O)[C@H](NC(=O)CCCCCN3C(=O)C=CC3=O)C(C)C)cc1)OCCN2C ; [I-]] |

-continued
| Compound | Structure |
| --- | --- |
| A-31 | 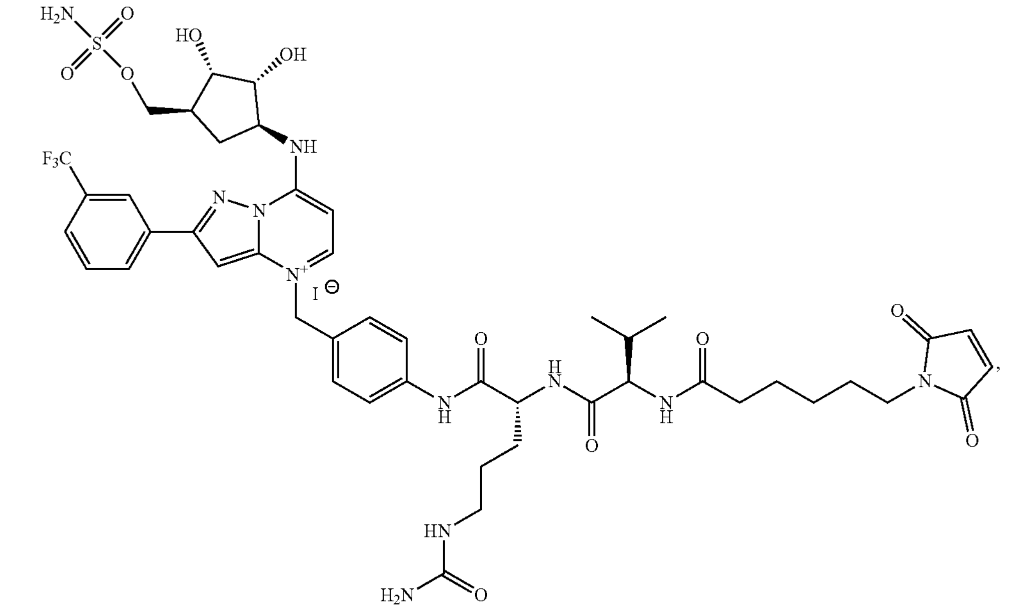 [SMILES: CC(C)[C@@H](NC(=O)CCCCCN1C(=O)C=CC1=O)C(=O)N[C@H](CCCNC(N)=O)C(=O)Nc1ccc(C[n+]2ccc(N[C@H]3C[C@@H](COS(N)(=O)=O)[C@H](O)[C@@H]3O)n3nc(-c4cccc(C(F)(F)F)c4)cc32)cc1 ; [I-]] |
| A-32 | 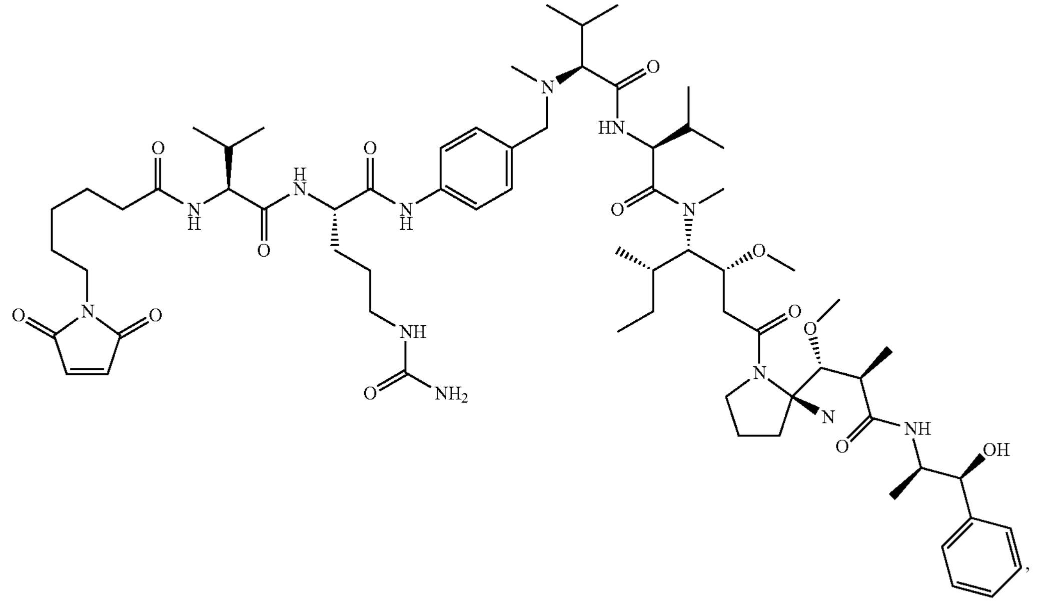 [SMILES: CC[C@H](C)[C@@H]([C@@H](CC(=O)N1CCC[C@@]1(N)[C@H](OC)[C@@H](C)C(=O)N[C@H](C)[C@@H](O)c1ccccc1)OC)N(C)C(=O)[C@@H](NC(=O)[C@H](C(C)C)N(C)Cc1ccc(NC(=O)[C@H](CCCNC(N)=O)NC(=O)[C@@H](NC(=O)CCCCCN2C(=O)C=CC2=O)C(C)C)cc1)C(C)C] |
| A-33 | 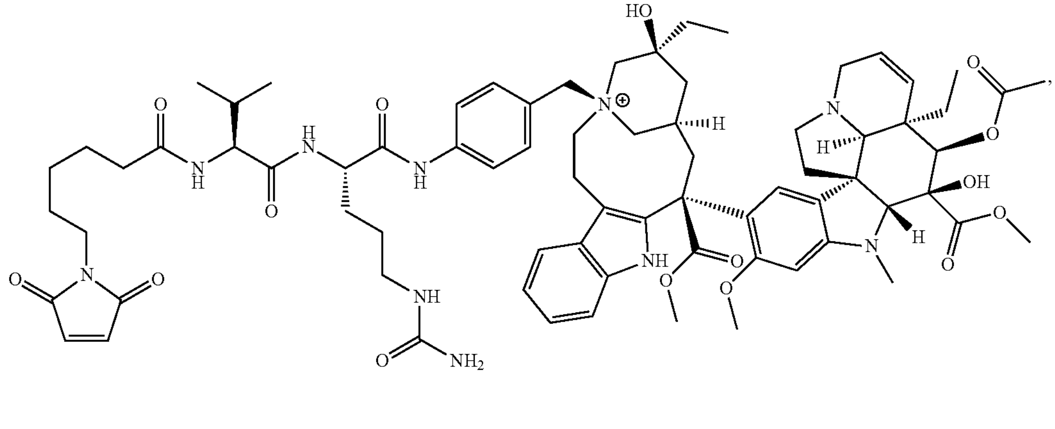 |

-continued
| Compound | Structure |
| --- | --- |
| A-34 | 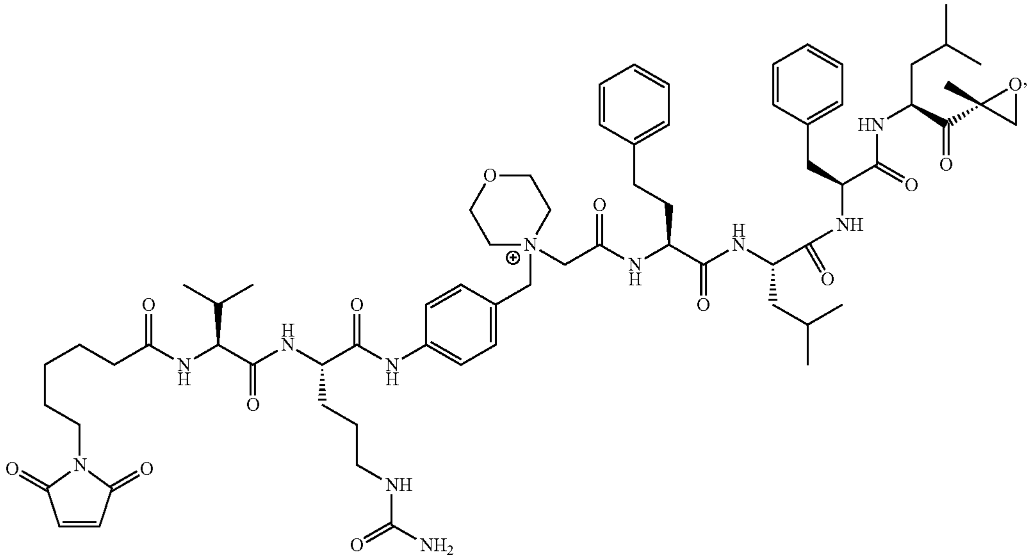 [SMILES: CC(C)C[C@H](NC(=O)[C@H](CCc1ccccc1)NC(=O)C[N+]1(Cc2ccc(NC(=O)[C@H](CCCNC(N)=O)NC(=O)[C@@H](NC(=O)CCCCCN3C(=O)C=CC3=O)C(C)C)cc2)CCOCC1)C(=O)N[C@@H](Cc1ccccc1)C(=O)N[C@@H](CC(C)C)C(=O)[C@@]1(C)CO1] |
| A-35 | 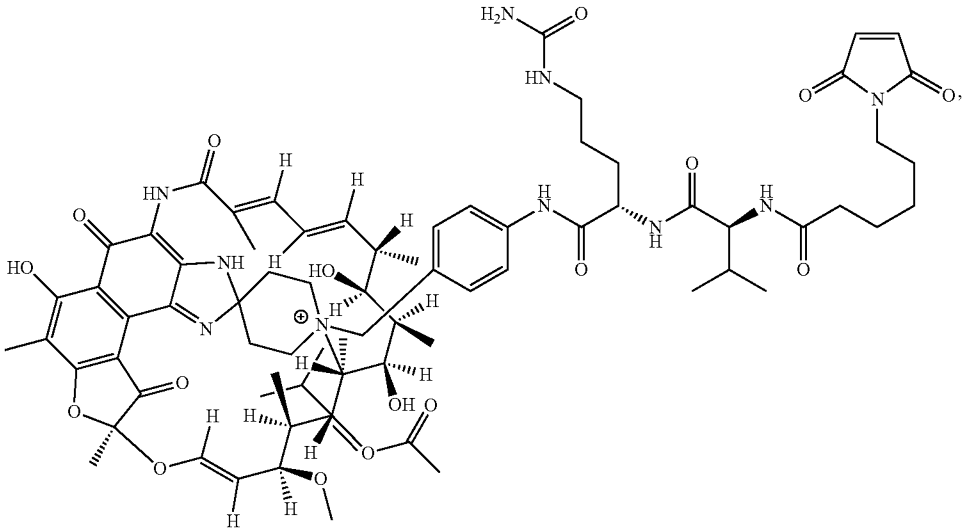 |
| A-36 | 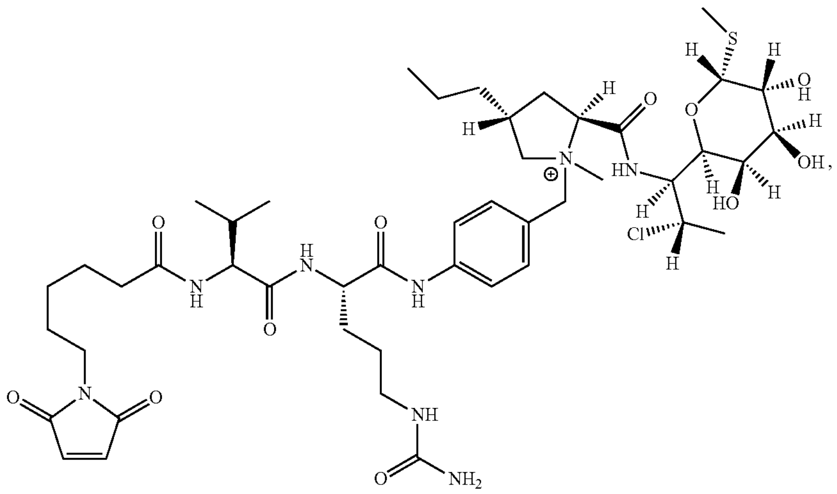 [SMILES: CCC[C@@H]1C[C@@H](C(=O)N[C@@H]([C@H]2O[C@H](SC)[C@H](O)[C@@H](O)[C@H]2O)[C@H](C)Cl)[N+](C)(Cc2ccc(NC(=O)[C@H](CCCNC(N)=O)NC(=O)[C@@H](NC(=O)CCCCCN3C(=O)C=CC3=O)C(C)C)cc2)C1] |

-continued
| Compound | Structure |
| --- | --- |
| A-37 | 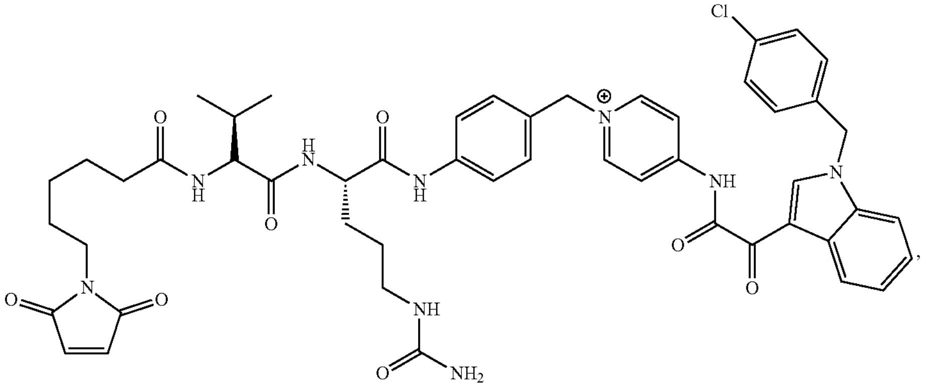 |
| A-38 | 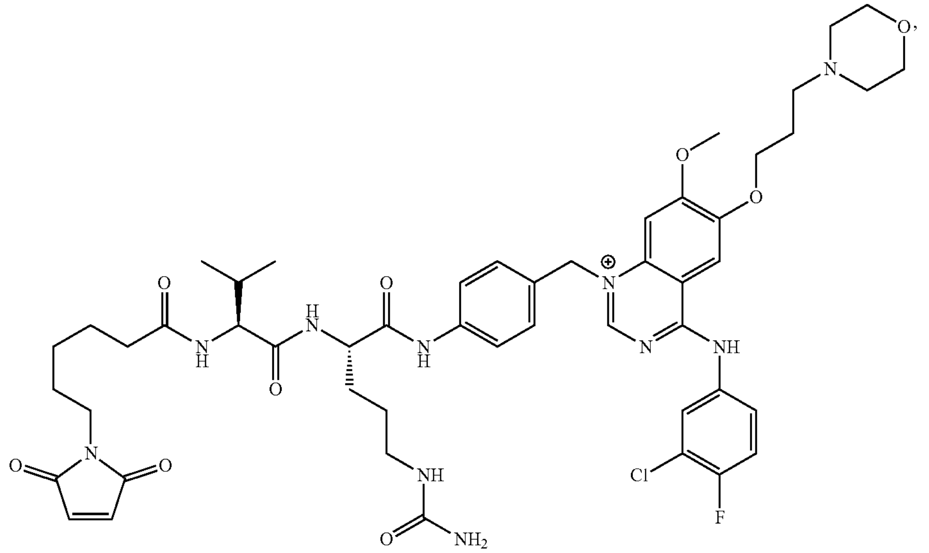 [SMILES: COc1cc2c(cc1OCCCN1CCOCC1)c(Nc1ccc(F)c(Cl)c1)nc[n+]2Cc1ccc(NC(=O)[C@H](CCCNC(N)=O)NC(=O)[C@@H](NC(=O)CCCCCN2C(=O)C=CC2=O)C(C)C)cc1] |
| A-39 | 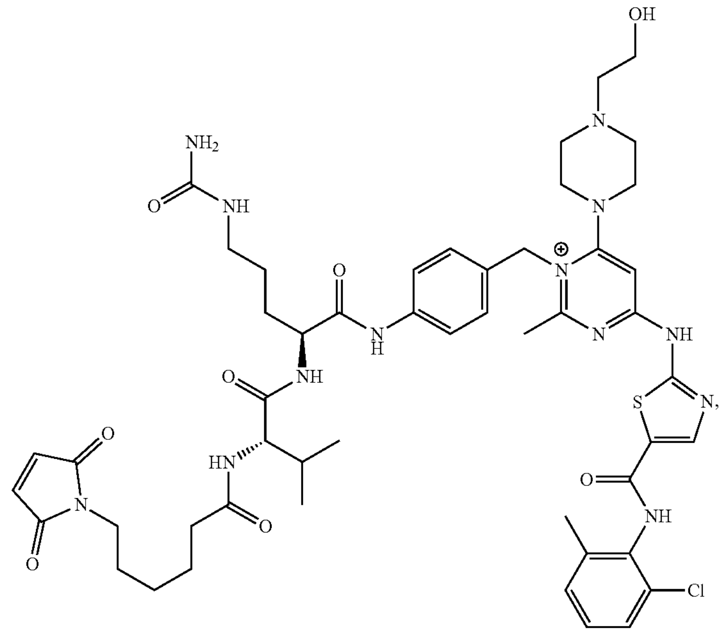 [SMILES: Cc1cccc(Cl)c1NC(=O)c1cnc(Nc2cc(N3CCN(CCO)CC3)[n+](Cc3ccc(NC(=O)[C@H](CCCNC(N)=O)NC(=O)[C@@H](NC(=O)CCCCCN4C(=O)C=CC4=O)C(C)C)cc3)c(C)n2)s1] |

-continued
| Compound | Structure |
| --- | --- |
| A-40 | 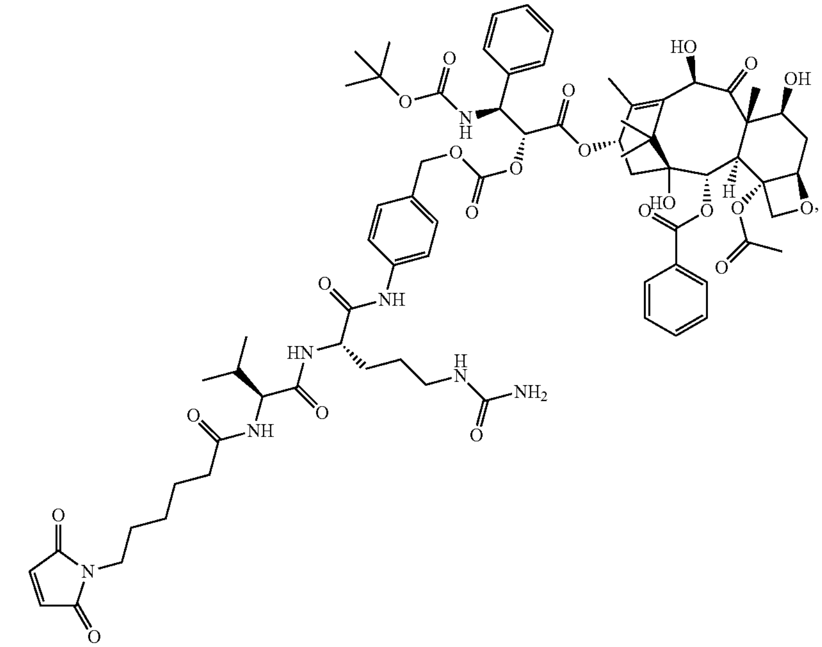 [SMILES: CC(=O)O[C@@]12CO[C@@H]1C[C@H](O)[C@@]1(C)C(=O)[C@H](O)C3=C(C)[C@@H](OC(=O)[C@H](OC(=O)OCc4ccc(NC(=O)[C@H](CCCNC(N)=O)NC(=O)[C@@H](NC(=O)CCCCCN5C(=O)C=CC5=O)C(C)C)cc4)[C@@H](NC(=O)OC(C)(C)C)c4ccccc4)C[C@@](O)([C@@H](OC(=O)c4ccccc4)[C@H]21)C3(C)C] |
| A-41 | 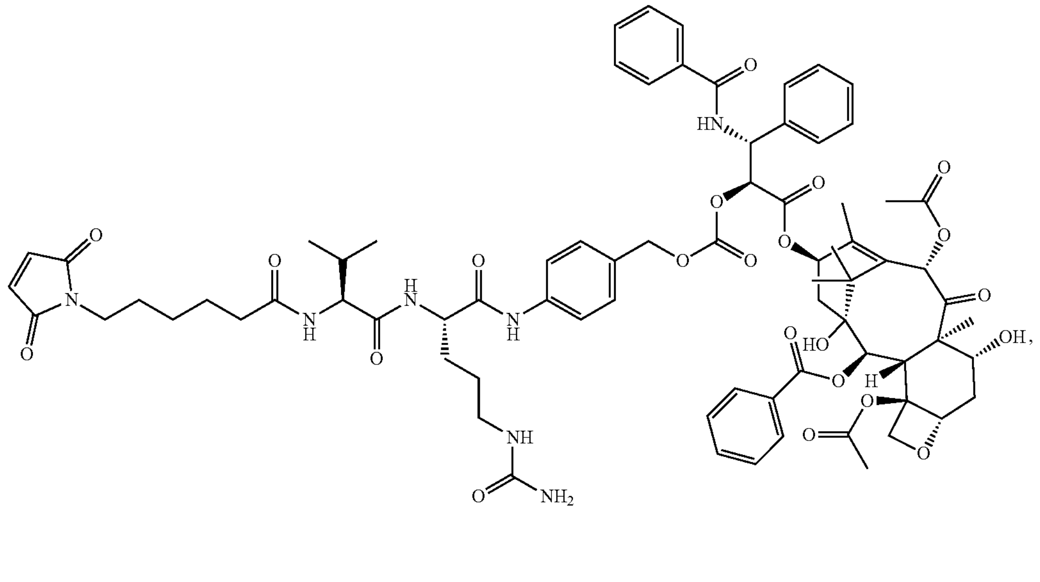 [SMILES: CC(=O)O[C@@H]1C(=O)[C@@]2(C)[C@H](O)C[C@@H]3OC[C@]3(OC(C)=O)[C@@H]2[C@@H](OC(=O)c2ccccc2)[C@@]2(O)C[C@@H](OC(=O)[C@@H](OC(=O)OCc3ccc(NC(=O)[C@H](CCCNC(N)=O)NC(=O)[C@@H](NC(=O)CCCCCN4C(=O)C=CC4=O)C(C)C)cc3)[C@H](NC(=O)c3ccccc3)c3ccccc3)C(C)=C1C2(C)C] |

-continued
| Compound | Structure |
| --- | --- |
| A-42 | 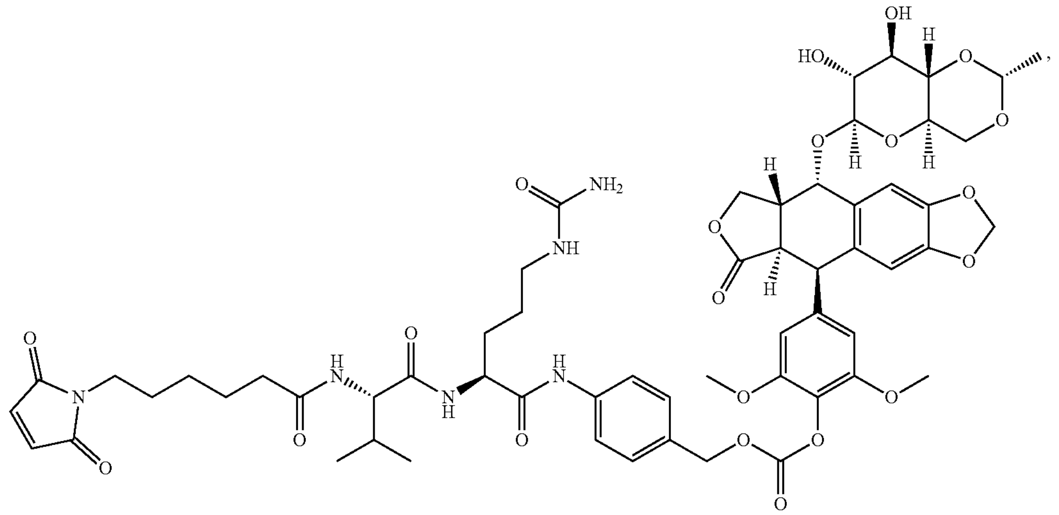 [SMILES: COc1cc([C@@H]2c3cc4c(cc3[C@@H](O[C@@H]3O[C@@H]5CO[C@@H](C)O[C@H]5[C@H](O)[C@H]3O)[C@H]3COC(=O)[C@H]23)OCO4)cc(OC)c1OC(=O)OCc1ccc(NC(=O)[C@H](CCCNC(N)=O)NC(=O)[C@@H](NC(=O)CCCCCN2C(=O)C=CC2=O)C(C)C)cc1] |
| A-43 | 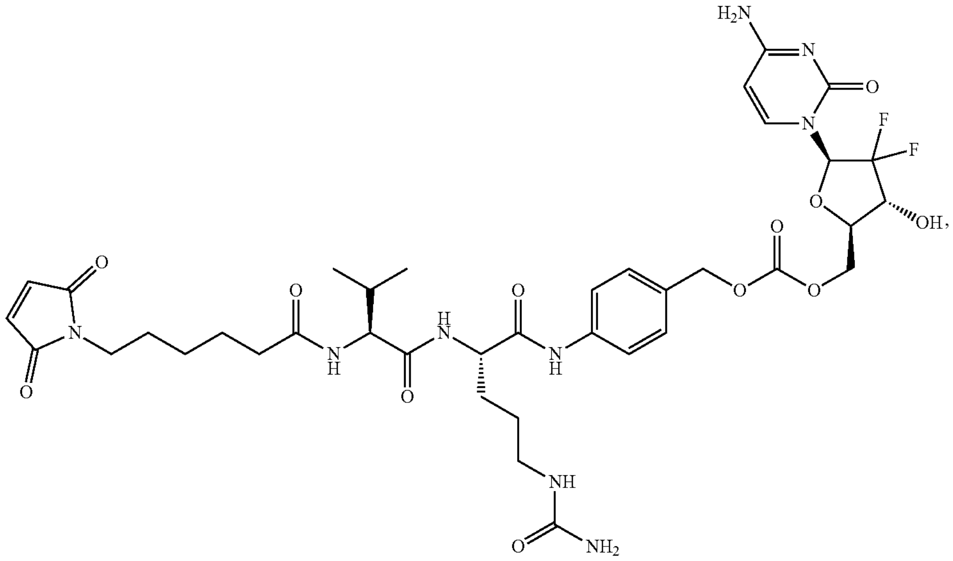 [SMILES: CC(C)[C@H](NC(=O)CCCCCN1C(=O)C=CC1=O)C(=O)N[C@@H](CCCNC(N)=O)C(=O)Nc1ccc(COC(=O)OC[C@H]2O[C@@H](n3ccc(N)nc3=O)C(F)(F)[C@@H]2O)cc1] |

-continued
| Compound | Structure |
| --- | --- |
| A-44 | 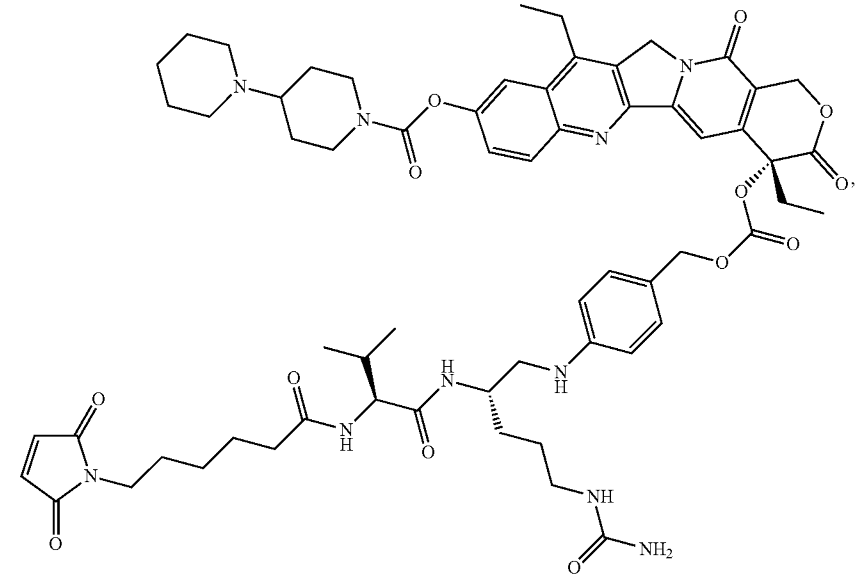 [SMILES: CCc1c2c(nc3ccc(OC(=O)N4CCC(N5CCCCC5)CC4)cc13)-c1cc3c(c(=O)n1C2)COC(=O)[C@]3(CC)OC(=O)OCc1ccc(NC[C@H](CCCNC(N)=O)NC(=O)[C@@H](NC(=O)CCCCCN2C(=O)C=CC2=O)C(C)C)cc1] |
| A-45 | 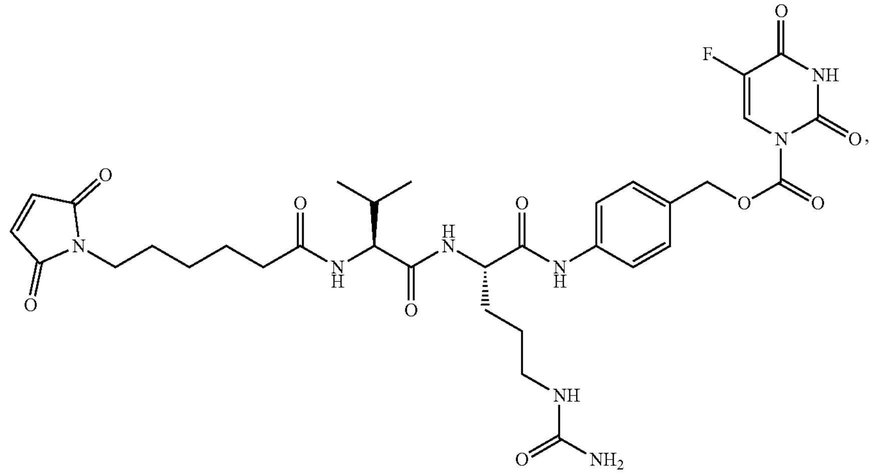 [SMILES: CC(C)[C@H](NC(=O)CCCCCN1C(=O)C=CC1=O)C(=O)N[C@@H](CCCNC(N)=O)C(=O)Nc1ccc(COC(=O)n2cc(F)c(=O)[nH]c2=O)cc1] |
| A-46 | 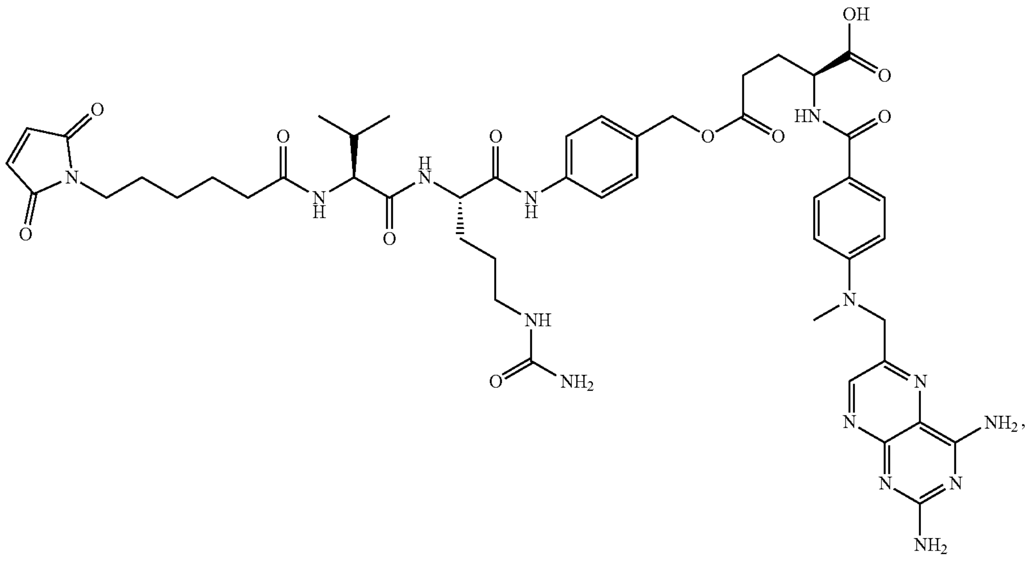 [SMILES: CC(C)[C@H](NC(=O)CCCCCN1C(=O)C=CC1=O)C(=O)N[C@@H](CCCNC(N)=O)C(=O)Nc1ccc(COC(=O)CC[C@H](NC(=O)c2ccc(N(C)Cc3cnc4nc(N)nc(N)c4n3)cc2)C(=O)O)cc1] |

-continued
| Compound | Structure |
| --- | --- |
| A-47 | 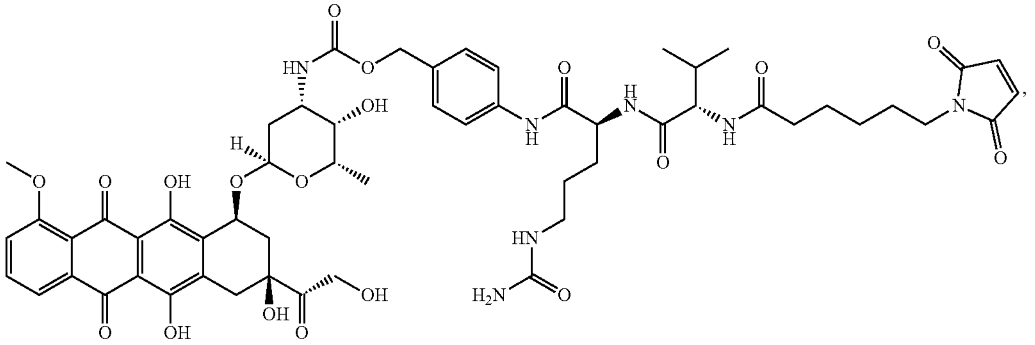 |
| A-48 | 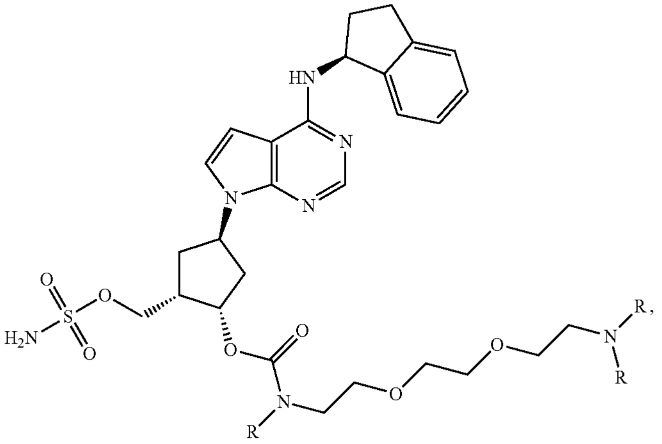 |
| A-49 | 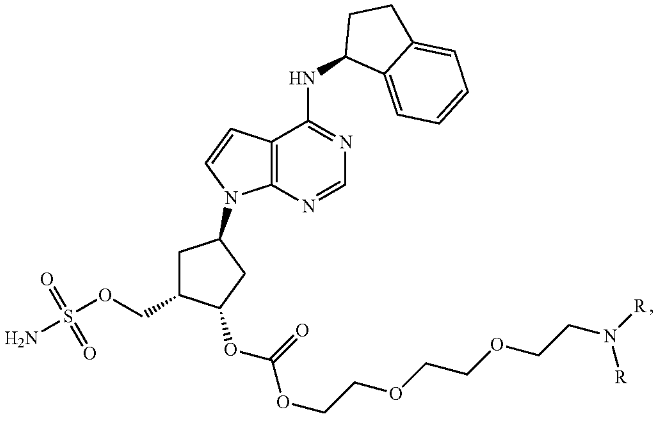 |

-continued

| Compound | Structure |
| --- | --- |
| A-50 | 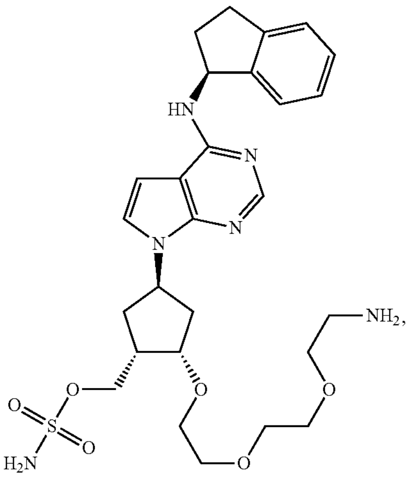 and |
| A-51 | 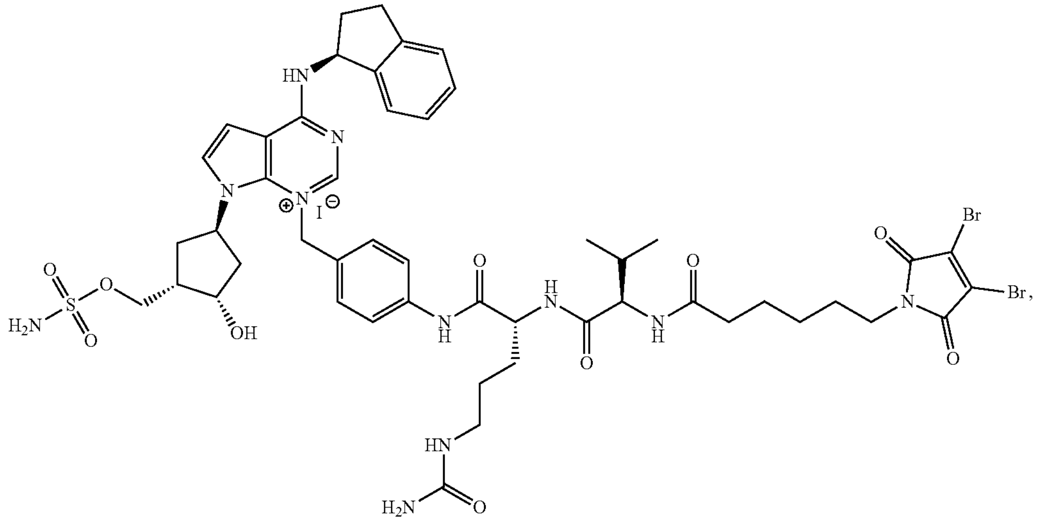 [SMILES: CC(C)[C@@H](NC(=O)CCCCCN1C(=O)C(Br)=C(Br)C1=O)C(=O)N[C@H](CCCNC(N)=O)C(=O)Nc1ccc(C[n+]2cnc(N[C@H]3CCc4ccccc43)c3ccn([C@@H]4C[C@@H](COS(N)(=O)=O)[C@@H](O)C4)c32)cc1 ; [I-]] , |

wherein R is H, alkyl, aryl, arylalkyl, a glycol ether, or a glycol linker and p is 1, 2, 3, 4, 5, or 6.

Embodiment III-21. The compound, or a pharmaceutically acceptable salt, solvate, hydrate, isomer, or tautomer thereof, of embodiment III-20, wherein the compound of Formula (I) is selected from the group consisting of A-1, A-2, A-3, A-4, A-5, A-6, A-7, A-8, A-9, A-10, A-11, A-12, A-13, A-14, A-15, A-16, A-17, A-18, A-30, A-31, and A-51.

Embodiment III-22. The compound, or a pharmaceutically acceptable salt, solvate, hydrate, isomer, or tautomer thereof, of embodiment III-20, wherein the compound of Formula (I) is selected from the group consisting of A-1, A-30, A-31, and A-51.

Embodiment III-23. The compound, or a pharmaceutically acceptable salt, solvate, hydrate, isomer, or tautomer thereof, of embodiment III-20, wherein the compound of Formula (I) is A-32.

Embodiment III-24. A compound having a structure of Formula (II):

$$X_1\text{—}[X_2\text{—}(X_3)_m]_n \qquad \text{(II)},$$

or a pharmaceutically acceptable salt, solvate, hydrate, isomer, or tautomer thereof, wherein:

m is 1, 2, 3, 4, 5, 6, 7, 8, 9, or 10;

n is 1, 2, 3, 4, 5, 6, 7, 8, 9, 10 or 11;

$X_1$ is a biologically active polypeptide or hormone;

$X_2$ is a linker; and $X_3$ is a therapeutic compound.

Embodiment III-25. The compound, or a pharmaceutically acceptable salt, solvate, hydrate, isomer, or tautomer thereof, of embodiment III-24, wherein $X_1$ is selected from the group consisting of an Acylation stimulating protein polypeptide, an Adipokine polypeptide, an Albinterferon polypeptide, a Cerberus polypeptide, a Colony-stimulating factor polypeptide, an Erythropoietin polypeptide, a FMS-like tyrosine kinase 3 ligand polypeptide, a Globulin component polypeptide, a Macrophage Activating Factor polypeptide, a Granulocyte colony-stimulating factor polypeptide, a Granulocyte-macrophage colony-stimulating factor polypeptide, a Hepatocyte growth factor polypeptide, an IL-17 polypeptide, an IL-10 polypeptide, an Inflammasome polypeptide, an Interferome polypeptide, an Interferon polypeptide, an Interferon beta-la polypeptide, an Interferon beta-1b polypeptide, an Interferon gamma polypeptide, an Interferon type I polypeptide, an Interferon type II polypeptide, an Interferon type III polypeptide, an Interleukin polypeptide, an Interleukin 1 receptor antagonist polypeptide, an Interleukin 8 polypeptide, a Leukemia inhibitory factor polypeptide, a Leukocyte-promoting factor polypeptide, a Lymphokine polypeptide, a Lymphotoxin polypeptide, a Lymphotoxin alpha polypeptide, a Lymphotoxin beta polypeptide, a Macrophage colony-stimulating factor polypeptide, a Macrophage inflammatory protein polypeptide, a Macrophage-activating factor polypeptide, a Monokine polypeptide, a Myokine polypeptide, a Myonectin polypeptide, a Nicotinamide phosphoribosyltransferase polypeptide, an Oncostatin M polypeptide, an Oprelvekin polypeptide, a Platelet factor 4 polypeptide, a Proinflammatory cytokine polypeptide, a Promegapoietin polypeptide, a Receptor activator of nuclear factor kappa-B ligand polypeptide, a Stromal cell-derived factor 1 polypeptide, an adrenomedullin polypeptide, an angiopoietin polypeptide, an Autocrine motility factor polypeptide, a Bone morphogenetic protein polypeptide, a Ciliary neurotrophic factor polypeptide, an Interleukin-6 polypeptide, an Epidermal growth factor polypeptide, an Ephrin A1 polypeptide, an Ephrin A2 polypeptide, an Ephrin A3 polypeptide, an Ephrin A4 polypeptide, an Ephrin A5 polypeptide, an Ephrin B1 polypeptide, an Ephrin B2 polypeptide, an Ephrin B3 polypeptide, a Fibroblast growth factor polypeptide, a Fibroblast growth factor 1 polypeptide, a fibroblast growth factor 2 polypeptide, a Fibroblast growth factor 3 polypeptide, a Fibroblast growth factor 4 polypeptide, a fibroblast growth factor 5 polypeptide, a Fibroblast growth factor 6 polypeptide, a Fibroblast growth factor 7 polypeptide, a fibroblast growth factor 8 polypeptide, a Fibroblast growth factor 9 polypeptide, a Fibroblast growth factor 10 polypeptide, a Fibroblast growth factor 11 polypeptide, a Fibroblast growth factor 12 polypeptide, a Fibroblast growth factor 13 polypeptide, a Fibroblast growth factor 14 polypeptide, a Fibroblast growth factor 15 polypeptide, a Fibroblast growth factor 16 polypeptide, a Fibroblast growth factor 17 polypeptide, a Fibroblast growth factor 18 polypeptide, a Fibroblast growth factor 19 polypeptide, a Fibroblast growth factor 20 polypeptide, a Fibroblast growth factor 21 polypeptide, a Fibroblast growth factor 22 polypeptide, a Fibroblast growth factor 23 polypeptide, a Foetal Bovine Somatotrophin polypeptide, a Glial cell line-derived neurotrophic factor polypeptide, a Neurturin polypeptide, a Persephin polypeptide, an Artemin polypeptide, a Growth differentiation factor-9 polypeptide, a Hepatoma-derived growth factor polypeptide, an Insulin polypeptide, an Insulin-like growth factor polypeptide, an Insulin-like growth factor-1 polypeptide, an Insulin-like growth factor-2 polypeptide, an IL-1 polypeptide, an IL-2 polypeptide or bio-active homolog thereof, an IL-3 polypeptide, an IL-4 polypeptide, an IL-5 polypeptide, an IL-6 polypeptide, an IL-7 polypeptide, a Keratinocyte growth factor polypeptide, a Migration-stimulating factor polypeptide, a Macrophage-stimulating protein polypeptide, a Myostatin polypeptide, a Neuregulin 1 polypeptide, a Neuregulin 2 polypeptide, a Neuregulin 3 polypeptide, a Neuregulin 4 polypeptide, a Brain-derived neurotrophic factor polypeptide, a Nerve growth factor polypeptide, a Neurotrophin-3 polypeptide, a Neurotrophin-4 polypeptide, a Placental growth factor polypeptide, a Platelet-derived growth factor polypeptide, a Renalase polypeptide, an anti-apoptotic survival factor polypeptide, a T-cell growth factor polypeptide, a Thrombopoietin polypeptide, a Transforming growth factor alpha polypeptide, a Transforming growth factor beta polypeptide, a Tumor necrosis factor-alpha polypeptide, a Vascular endothelial growth factor polypeptide, and a Wnt Signaling Pathway polypeptide.

Embodiment III-26. A compound having a structure of Formula (III):

$$X_1—[X_2—(X_3)_m]_n \quad \text{(III)},$$

or a pharmaceutically acceptable salt, solvate, hydrate, isomer, or tautomer thereof, wherein:

m is 1, 2, 3, 4, 5, 6, 7, 8, 9, or 10;

n is 1, 2, 3, 4, 5, 6, 7, 8, 9, 10, or 11;

$X_1$ is an IL-2 polypeptide or a bio-active homolog polypeptide thereof;

$X_2$ is a linker; and $X_3$ is a therapeutic compound.

Embodiment III-27. The compound, or a pharmaceutically acceptable salt, solvate, hydrate, isomer, or tautomer thereof, of embodiment III-25 or III-26, wherein the IL-2 polypeptide or the bio-active homolog polypeptide thereof comprises an amino acid sequence set forth in Table 4.

Embodiment III-28. The compound, or a pharmaceutically acceptable salt, solvate, hydrate, isomer, or tautomer thereof, of embodiment III-25 or III-26, wherein the IL-2 polypeptide or the bio-active homolog polypeptide thereof comprises an amino acid sequence set forth in SEQ ID NO: 1 or SEQ ID NO:2.

Embodiment III-29. The compound, or a pharmaceutically acceptable salt, solvate, hydrate, isomer, or tautomer thereof, of any one of embodiments III-24 to III-28, wherein $X_2$ is a cleavable linker.

Embodiment III-30. The compound, or a pharmaceutically acceptable salt, solvate, hydrate, isomer, or tautomer thereof, of any one of embodiments III-24 to III-28, wherein $X_2$ is a non-cleavable linker.

Embodiment III-31. The compound, or a pharmaceutically acceptable salt, solvate, hydrate, isomer, or tautomer thereof, of embodiment III-29, wherein $X_2$ is selected from the group consisting of:

| Compound | Structure |
|---|---|
| K-1 | 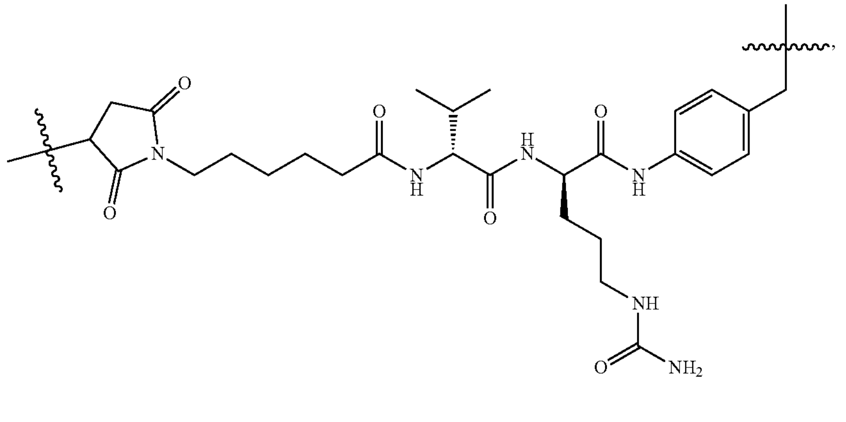 [SMILES: *Cc1ccc(NC(=O)[C@@H](CCCNC(N)=O)NC(=O)[C@H](NC(=O)CCCCCN2C(=O)CC(*)C2=O)C(C)C)cc1] |

-continued
| Compound | Structure |
|---|---|
| K-2 | 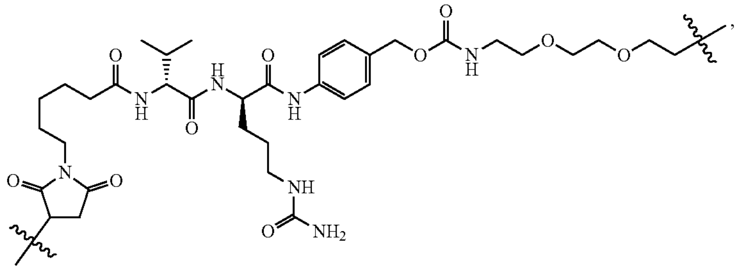 [SMILES: *CCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |
| K-3 | 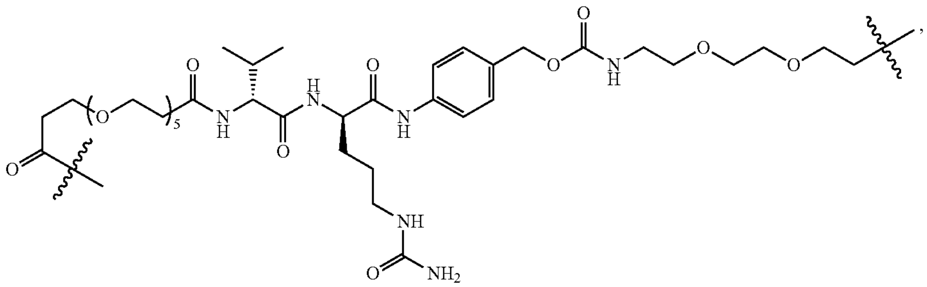 |
| K-4 | 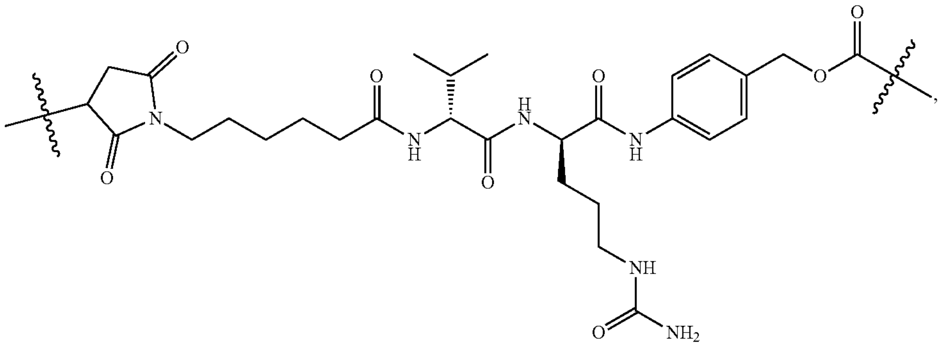 [SMILES: *C(=O)OCc1ccc(NC(=O)[C@@H](CCCNC(N)=O)NC(=O)[C@H](NC(=O)CCCCCN2C(=O)CC(*)C2=O)C(C)C)cc1] |
| K-5 | 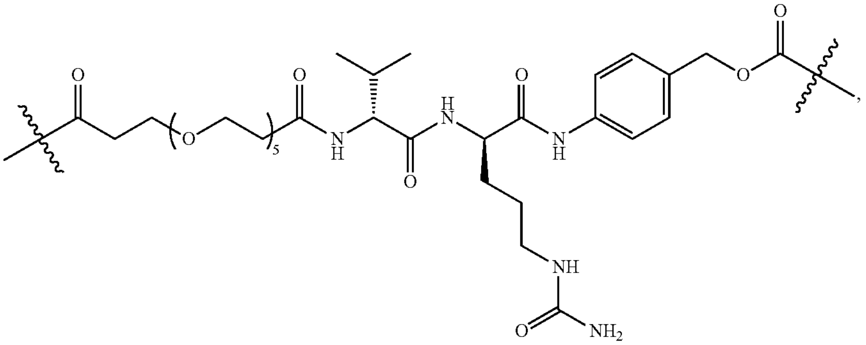 |
| K-6 | 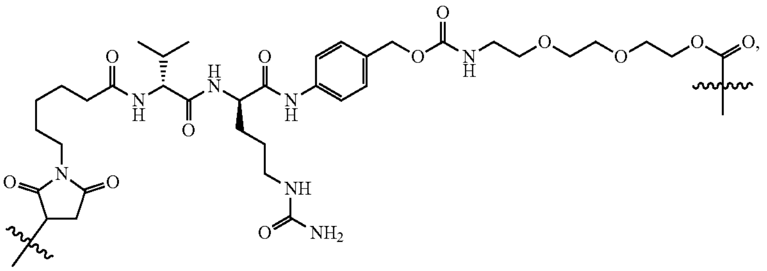 [SMILES: *C(=O)OCCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |

-continued
| Compound | Structure |
|---|---|
| K-7 | 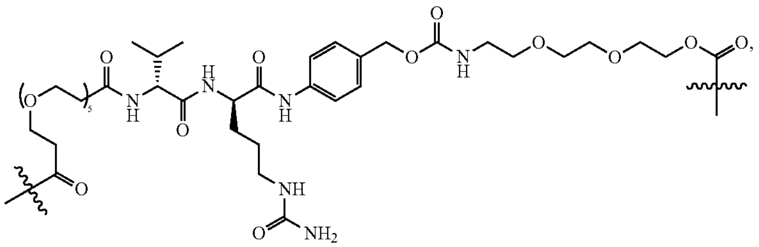 |
| K-8 | 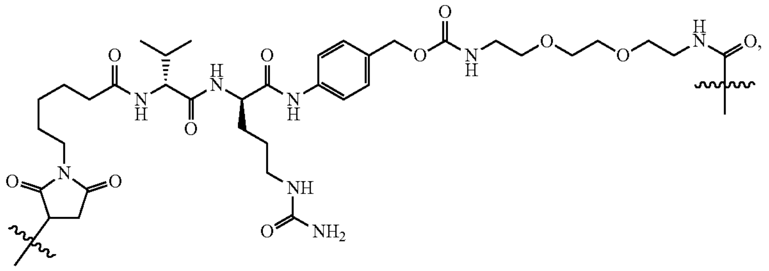 [SMILES: *C(=O)NCCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |
| K-9 | 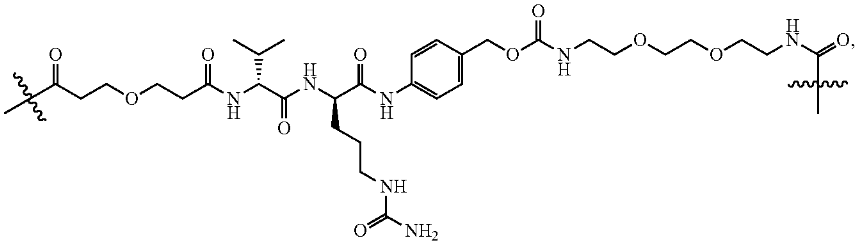 [SMILES: *C(=O)CCOCCC(=O)N[C@@H](C(=O)N[C@H](CCCNC(N)=O)C(=O)Nc1ccc(COC(=O)NCCOCCOCCNC(*)=O)cc1)C(C)C] |
| K-10 | 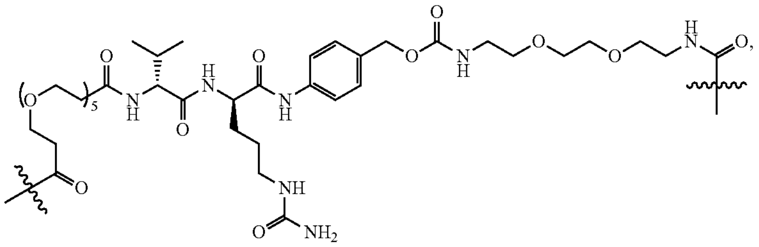 |
| K-11 | 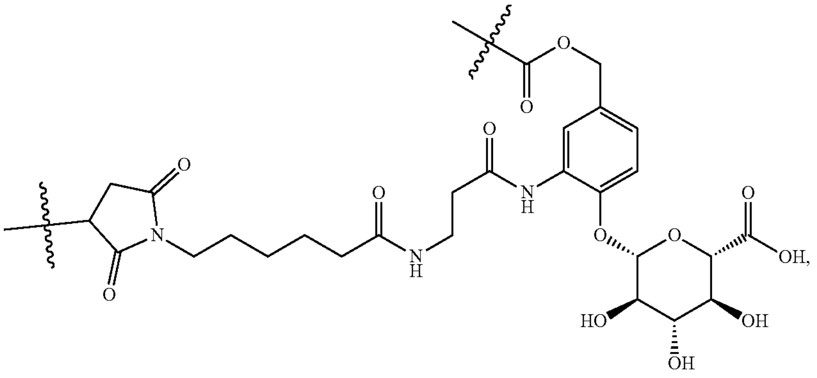 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)CC(*)C2=O)c1] |

-continued
| Compound | Structure |
| --- | --- |
| K-12 | 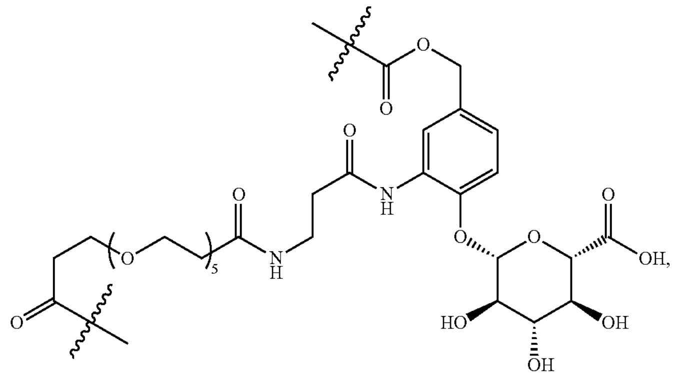 |
| K-13 | 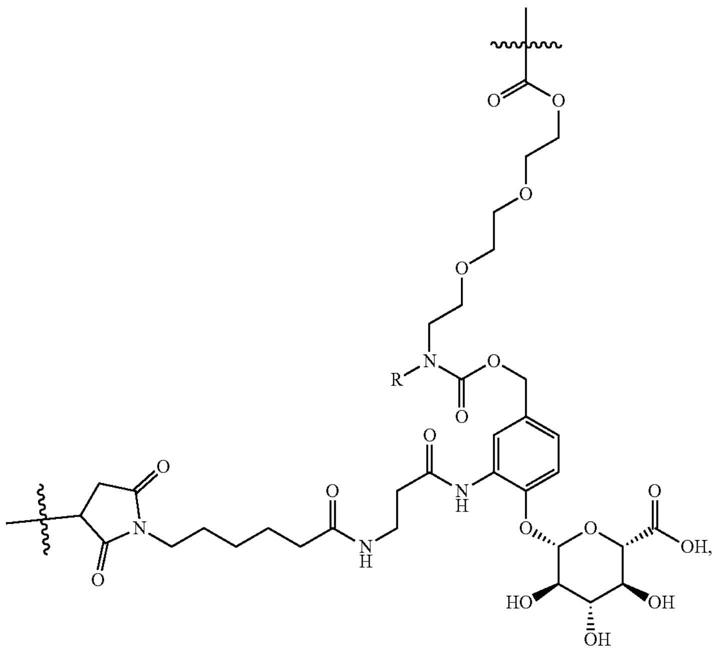 |

-continued
| Compound | Structure |
| --- | --- |
| K-14 | 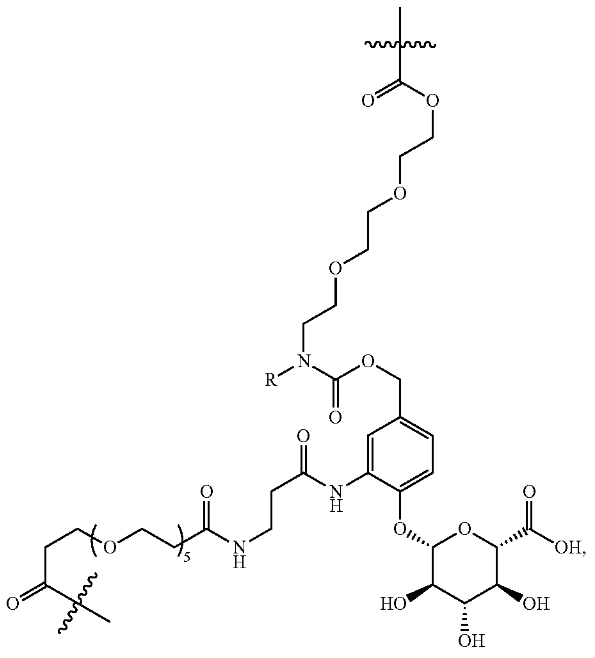 |
| K-15 | 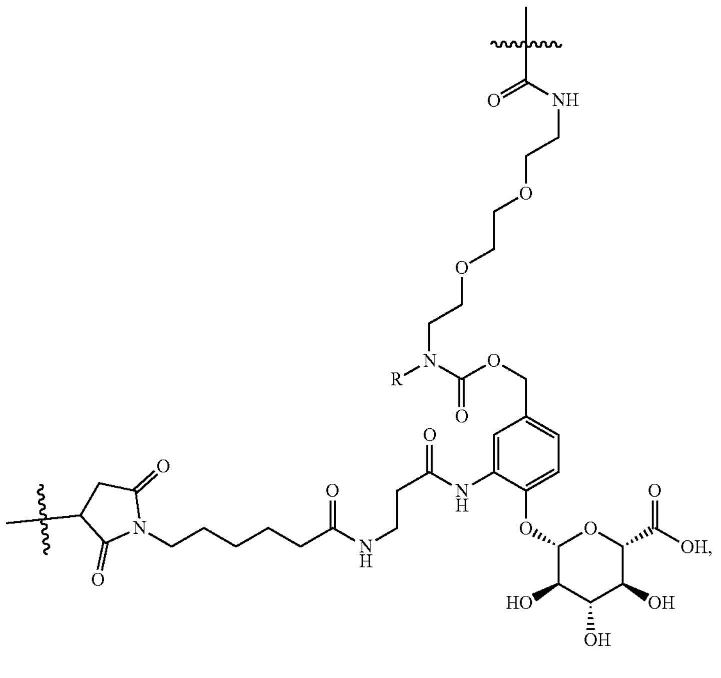 |

-continued
| Compound | Structure |
| --- | --- |
| K-16 | 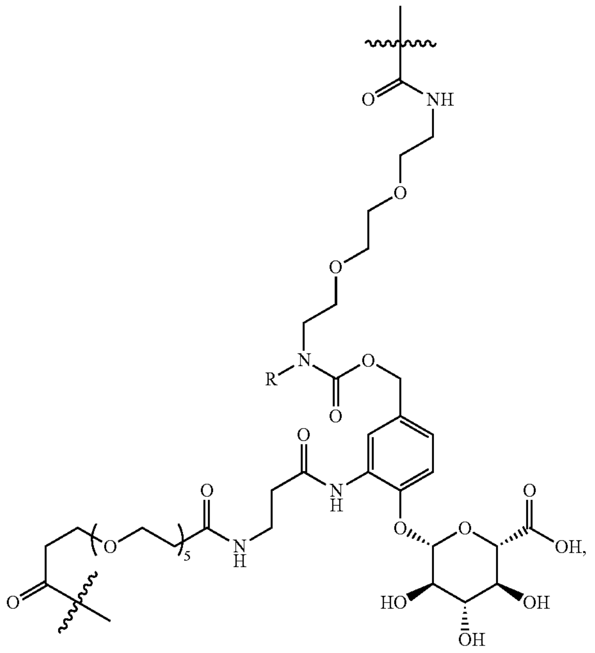 |
| K-19 | 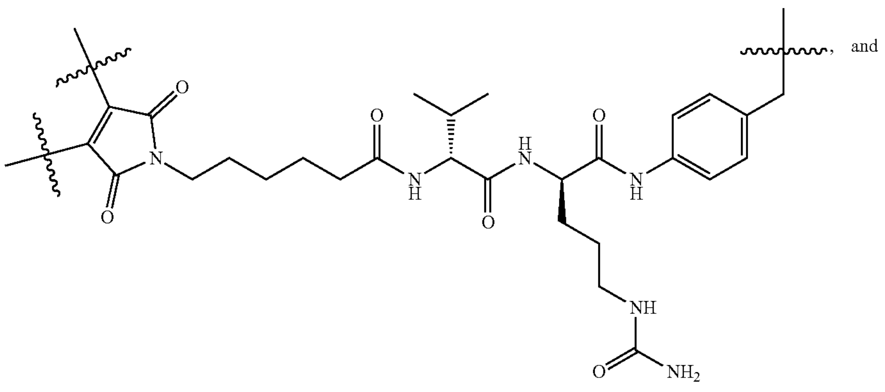 [SMILES: *Cc1ccc(NC(=O)[C@@H](CCCNC(N)=O)NC(=O)[C@H](NC(=O)CCCCCN2C(=O)C(*)=C(*)C2=O)C(C)C)cc1] |
and -continued

| Compound | Structure |
| --- | --- |
| K-20 | 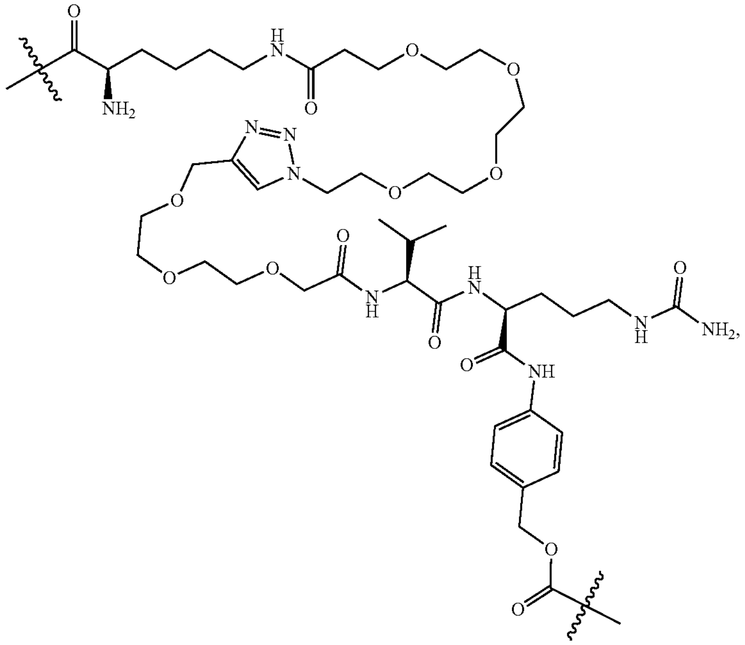 [SMILES: *C(=O)OCc1ccc(NC(=O)[C@H](CCCNC(N)=O)NC(=O)[C@@H](NC(=O)COCCOCCOCc2cn(CCOCCOCCOCCOCCC(=O)NCCCC[C@@H](N)C(*)=O)nn2)C(C)C)cc1] |

wherein the left side of $X_2$, as drawn, is bound to $X_1$, and the right side of $X_2$, as drawn, is bound to $X_3$ and wherein R is H, alkyl, aryl, arylalkyl, a glycol ether, or a glycol linker.

Embodiment III-32. The compound, or a pharmaceutically acceptable salt, solvate, hydrate, isomer, or tautomer thereof, of embodiment III-31, wherein $X_2$ is selected from the group consisting of K-1 and K-19.

Embodiment III-33. The compound, or a pharmaceutically acceptable salt, solvate, hydrate, isomer, or tautomer thereof, of embodiment III-30, wherein $X_2$ is selected from the group consisting of:

| Compound | Structure |
| --- | --- |
| K-17 | 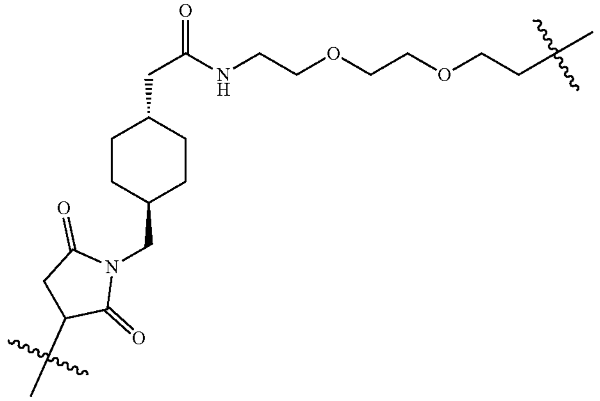 and |
| | and |
| K-18 | 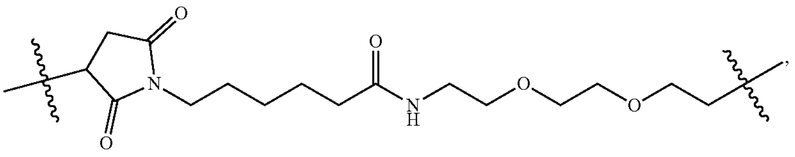 [SMILES: *CCOCCOCCNC(=O)CCCCCN1C(=O)CC(*)C1=O] |

wherein the left side of $X_2$, as drawn, is bound to $X_1$, and the right side of $X_2$, as drawn, is bound to $X_3$.

Embodiment III-34. The compound, or a pharmaceutically acceptable salt, solvate, hydrate, isomer, or tautomer thereof, of any one of embodiments III-24 to III-33, wherein $X_2$ is bound to $X_1$ at a Cys residue thereof.

Embodiment III-35. The compound, or a pharmaceutically acceptable salt, solvate, hydrate, isomer, or tautomer thereof, of any one of embodiments III-24 to III-31, wherein $X_2$ is bound to $X_1$ at a Lys residue thereof.

Embodiment III-36. The compound, or a pharmaceutically acceptable salt, solvate, hydrate, isomer, or tautomer thereof, of any one of embodiments III-24 to III-35, wherein m is 1.

Embodiment III-37. The compound, or a pharmaceutically acceptable salt, solvate, hydrate, isomer, or tautomer thereof, of any one of embodiments III-24 to III-35, wherein m is 2, 3, 4, 5, 6, 7, or 8.

Embodiment III-38. The compound, or a pharmaceutically acceptable salt, solvate, hydrate, isomer, or tautomer thereof, of any one of embodiments III-24 to III-35, wherein m is 1, 2, or 3.

Embodiment III-39. The compound, or a pharmaceutically acceptable salt, solvate, hydrate, isomer, or tautomer thereof, of any one of embodiments III-24 to III-35, wherein m is 2, 3, 4, or 5.

Embodiment III-40. The compound, or a pharmaceutically acceptable salt, solvate, hydrate, isomer, or tautomer thereof, of any one of embodiments III-24 to III-39, wherein $X_3$ is an immunomodulating agent.

Embodiment III-41. The compound, or a pharmaceutically acceptable salt, solvate, hydrate, isomer, or tautomer thereof, of any one of embodiments III-24 to III-40, wherein $X_3$ is selected from the group consisting of an immunosuppressive drug, an antianemic, an antianginal, an antiarryhythmic, an antiarthritic, an antiasthmatic, a leukotriene antagonist, an antibacterial, an antibiotic, an anticoagulant, an anticonvulsant, an antidepressant, an antidiabetic, an antiemetic, a glucocorticoid, an anti-TNF agent, a cytotoxic agent, a neddylation inhibitor, a ubiquitin-activating enzyme inhibitor, a ubiquitin-activating enzyme E1 inhibitor, and a proteasome inhibitor.

Embodiment III-42. The compound, or a pharmaceutically acceptable salt, solvate, hydrate, isomer, or tautomer thereof, of any one of embodiments III-24 to III-41, wherein $X_3$ is selected from the group consisting of: pevonedistat; TAS1 (((2S,3S,4R,5R)-5-(4-amino-5-((4,7-dimethyl-3,4-dihydro-2H-benzo[b][1,4]oxazin-8-yl) ethynyl)-7H-pyrrolo [2,3-d]pyrimidin-7-yl)-3,4-dihydroxytetrahydrofuran-2-yl) methyl sulfamate); TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl)phenyl) pyrazolo [1,5-a]pyrimidin-7-yl)amino)cyclopentyl)methyl sulfamate); Piperacillin; M22 (1-benzyl-N-(2,4-dichlorophenethyl) piperidin-4-amine); 6,6'-Biapigenin; Thienopyridine; Imidazo-pyrimidine; Largazole; Pyr-41 (4 [4-(5-nitro-furan-2-ylmethylene)-3,5-dioxo-pyrazolidin-1-yl]-benzoic acid ethyl ester); Phorbol 12-myristate 13-acetate; 2,3-dihydropyrrolo[2,1-b]quinazolin-9 (1H)-one; Ofloxacin; Panepophenanthin; Himeic Acid A; Hyrtioreticulins A; Phytol; ABPA3 ([(2R,3S,4R,5R)-5-[6-(3-ethynylanilino) purin-9-yl]-3,4-dihydroxyoxolan-2-yl]methyl sulfamate); Benzothiazole; a Deoxyvasicinone derivative; Coumarin A; Coumarin B; Imidazolium-quinoxaline, and TAS4464 (7H-Pyrrolo[2,3-d]pyrimidin-4-amine, 7-[5-[(aminosulfonyl) amino]-5-deoxy-beta-D-ribofuranosyl]-5-[2-(2-ethoxy-6-fluorophenyl) ethynyl]-), wherein $R^1$ is alkyl, aryl, arylalkyl, arylalkyne, arylalkene, heterocyclyl, or heteroaryl and $R_2$ is H, alkyl, or aryl.

Embodiment III-43. The compound, or a pharmaceutically acceptable salt, solvate, hydrate, isomer, or tautomer thereof, of any one of embodiments III-24 to III-42, wherein $X_3$ is selected from the group consisting of: Pevonedistat, TAS1 (((2S,3S,4R,5R)-5-(4-amino-5-((4,7-dimethyl-3,4-dihydro-2H-benzo[b][1,4]oxazin-8-yl) ethynyl)-7H-pyrrolo [2,3-d]pyrimidin-7-yl)-3,4-dihydroxytetrahydrofuran-2-yl) methyl sulfamate), TAS2 (((1S,2R,3S,4R)-4-(4-amino-5-((4,7-dimethyl-3,4-dihydro-2H-benzo[b][1,4]oxazin-8-yl) ethynyl)-7H-pyrrolo[2,3-d]pyrimidin-7-yl)-2,3-dihydroxycyclopentyl)methyl sulfamate), and TAK7243 (((1R,2R,3S,4R)-2,3-dihydroxy-4-((2-(3-(trifluoromethyl)phenyl) pyrazolo[1,5-a]pyrimidin-7-yl)amino)cyclopentyl)methyl sulfamate).

Embodiment III-44. The compound, or a pharmaceutically acceptable salt, solvate, hydrate, isomer, or tautomer thereof, of any one of embodiments III-24 to III-39, wherein $X_3$ is a cancer chemotherapeutic.

Embodiment III-45. The compound, or a pharmaceutically acceptable salt, solvate, hydrate, isomer, or tautomer thereof, of any one of embodiments III-24 to III-39 or III-44, wherein $X_3$ is selected from the group consisting of an oncolytic drug, a genotoxic agent, an alkylating agent, a tubulin inhibitor, a microtubule assembly inhibitor, an antineoplastic drug, a kinase inhibitor, a vinca alkaloid, an antibiotic, an anthracycline, an antimetabolite, an aromatase inhibitor, a topoisomerase inhibitor, a mTor inhibitor, a retinoid, an antimitotic agent, a protease inhibitor, a tyrosine kinase inhibitor, a microtubule destabilizer, and a proteasome inhibitor.

Embodiment III-46. The compound, or a pharmaceutically acceptable salt, solvate, hydrate, isomer, or tautomer thereof, of any one of embodiments III-24 to III-39 or III-44 to III-45, wherein $X_3$ is selected from the group consisting of vincristine, vinorelbine, vinflunine, crytophycin 52, a halichondrin, a dolastatin, a hemiasterlin, colchicine, a combretastatin, 2-methoxyestradiol, a methoxybenzenesulfonamide, epothilone, and discodermolide.

Embodiment III-47. The compound, or a pharmaceutically acceptable salt, solvate, hydrate, isomer, or tautomer thereof, of any one of embodiments III-24 to III-39 or III-44 to III-45, wherein $X_3$ is selected from the group consisting of: Monomethyl Auristatin E; Docetaxel; Etoposide; Gemcitabine; Vinblastine; Paclitaxel; Irinotecan; Fluorouracil; Methotrexate; Carboplatin; Oxaliplatin; Cisplatin; Doxorubicin HCl; Fulvestrant; Isotretinoin; Buserelin; Everolimus; Carfilzomib; Rifabutin; Clindamycin; Tubulysin A; Indibulin; Gefitinib; and Dasatinib.

Embodiment III-48. The compound, or a pharmaceutically acceptable salt, solvate, hydrate, isomer, or tautomer thereof, of any one of embodiments III-24 to III-39, III-44 to III-45, or III-47, wherein $X_3$ is Monomethyl Auristatin E.

Embodiment III-49. The compound, or a pharmaceutically acceptable salt, solvate, hydrate, isomer, or tautomer thereof, of any one of embodiments III-24 to III-28, wherein the compound of Formula (II) or Formula (III) is selected from the group consisting of:

| Compound | Structure |
| --- | --- |
| B-1 | 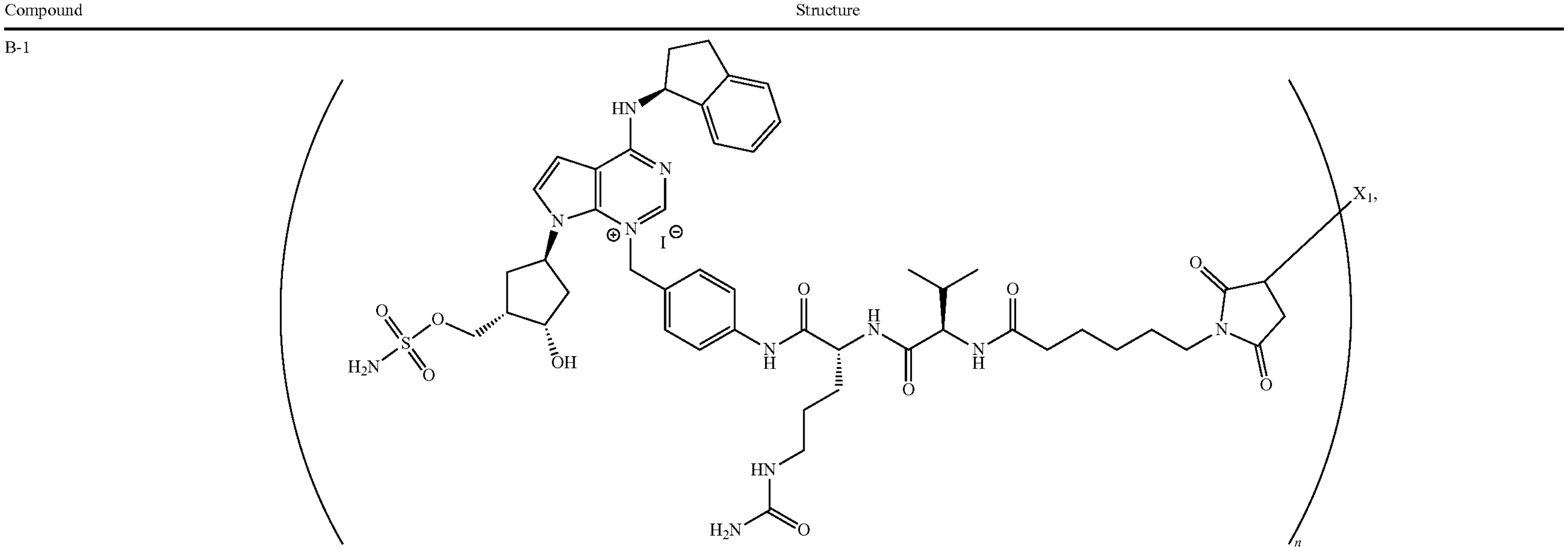 |

-continued
| Compound | Structure |
| --- | --- |
| B-2 | 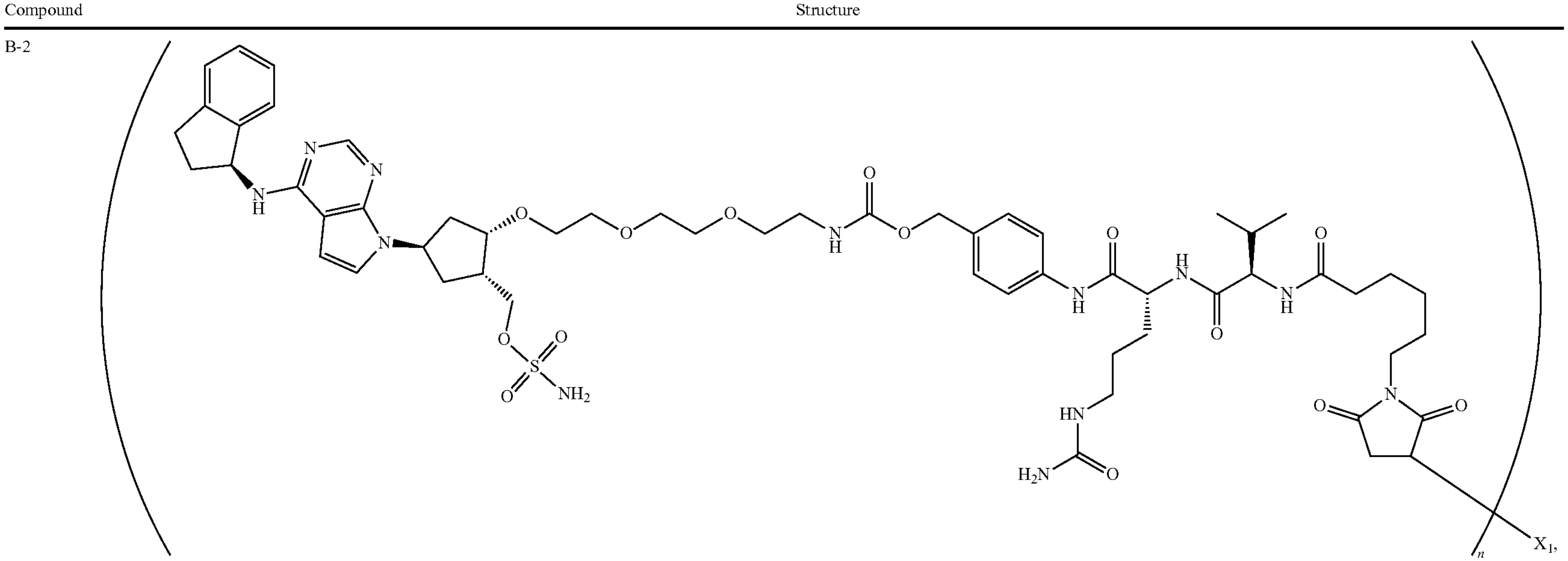 |

-continued
| Compound | Structure |
| --- | --- |
| B-3 | 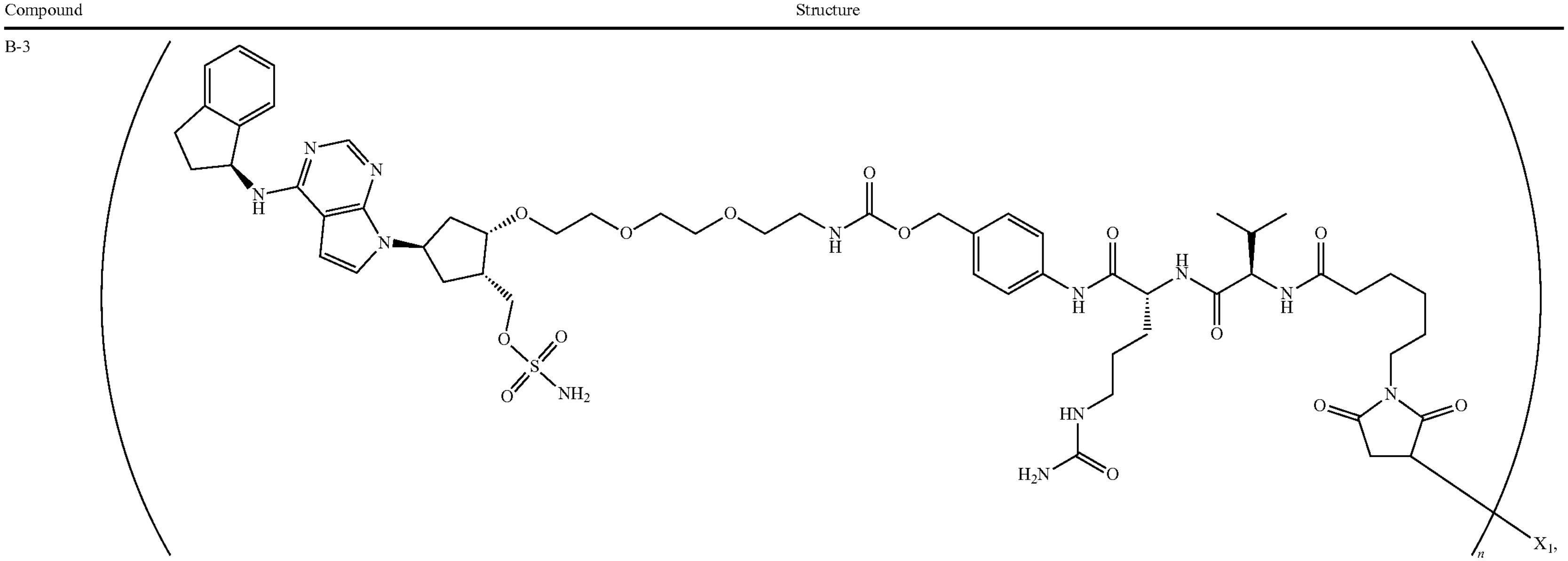 |

-continued
| Compound | Structure |
|---|---|
| B-4 | 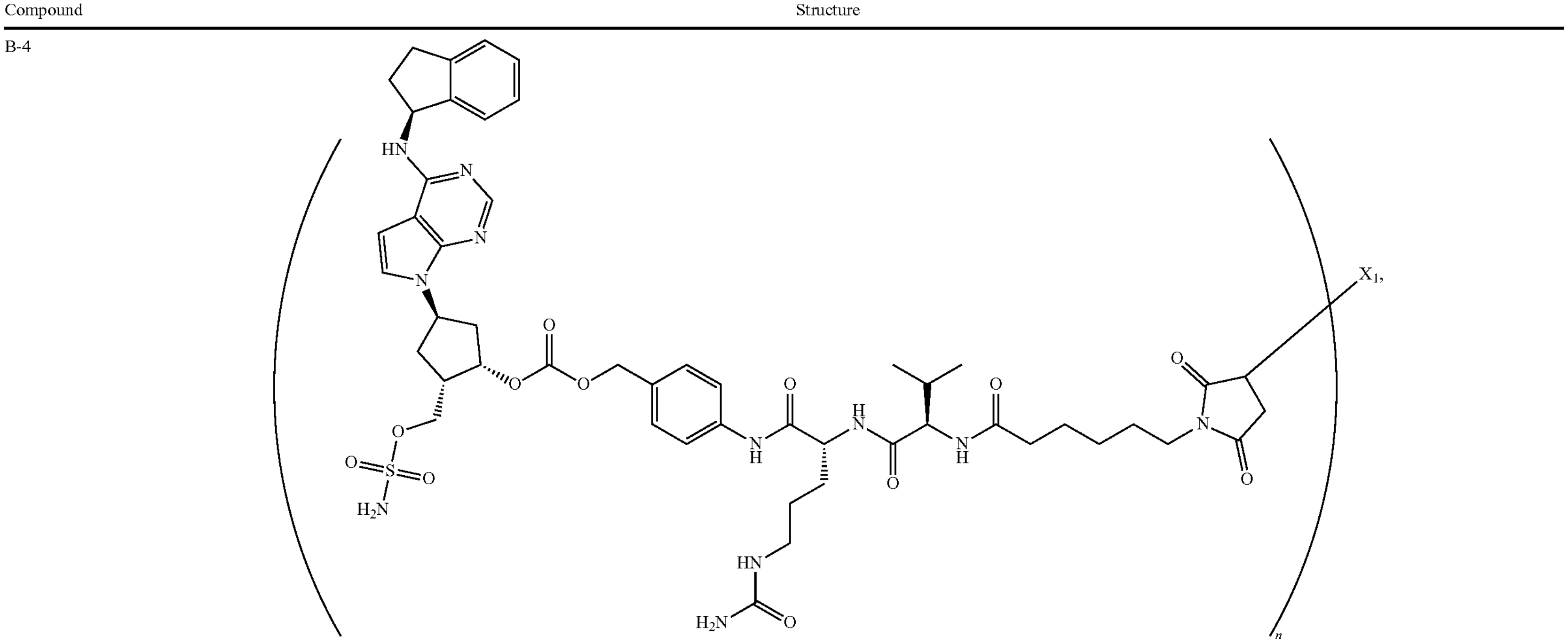 |

-continued
| Compound | Structure |
| --- | --- |
| B-5 | 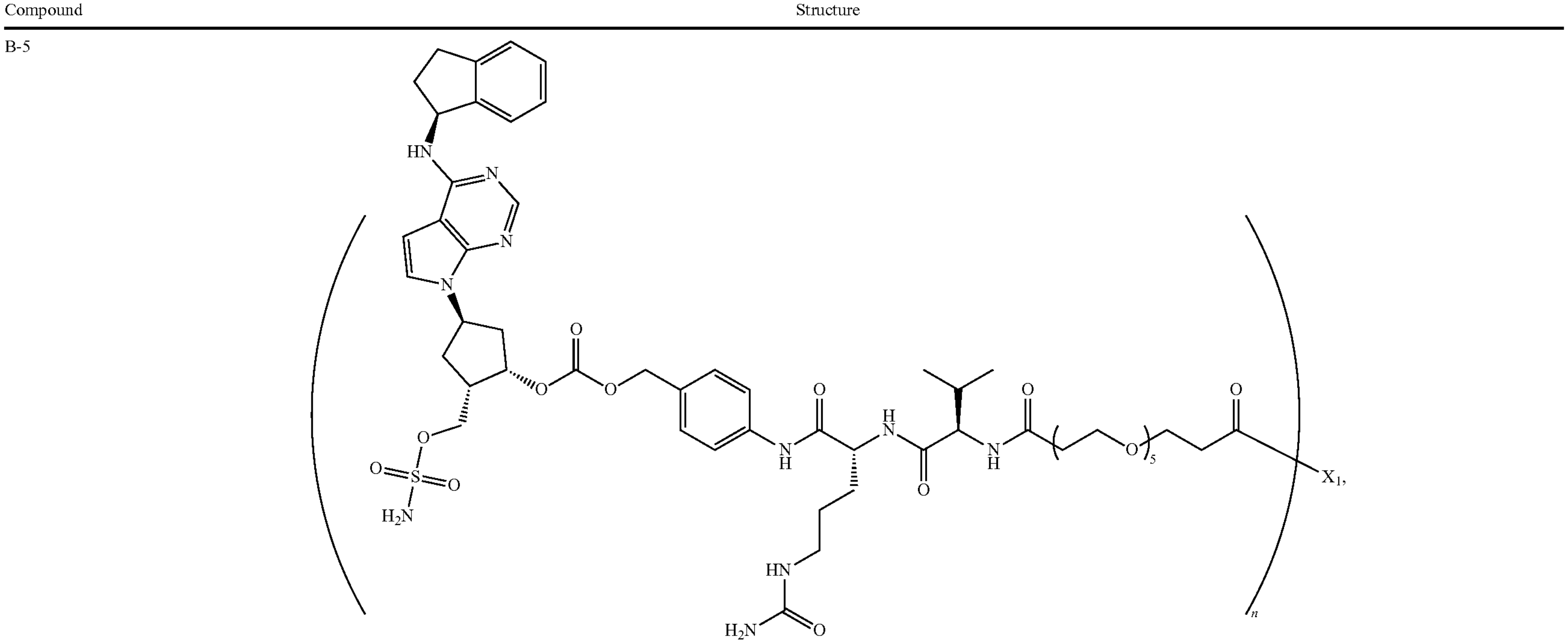 |

-continued
| Compound | Structure |
| --- | --- |
| B-6 | 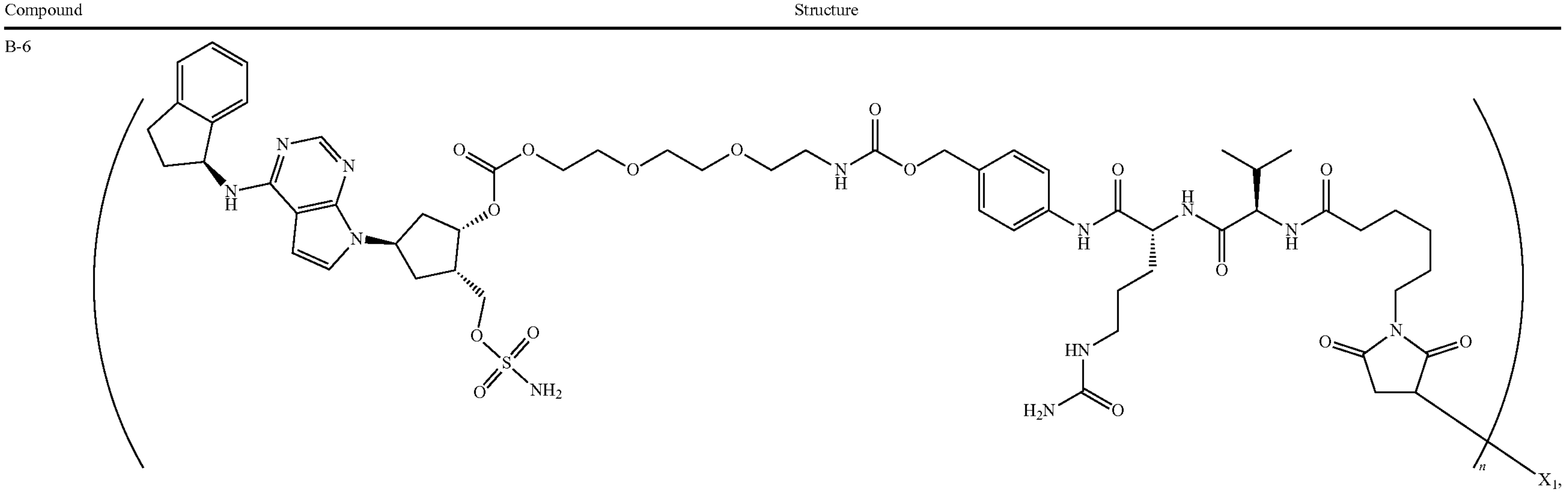 |
| B-7 | 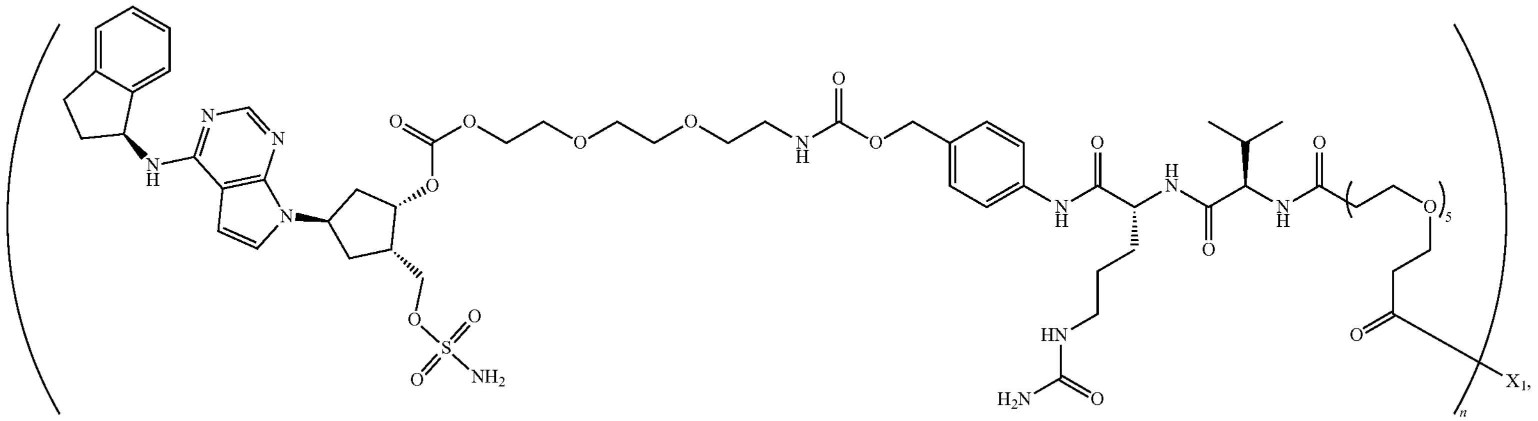 |

-continued
| Compound | Structure |
| --- | --- |
| B-8 | 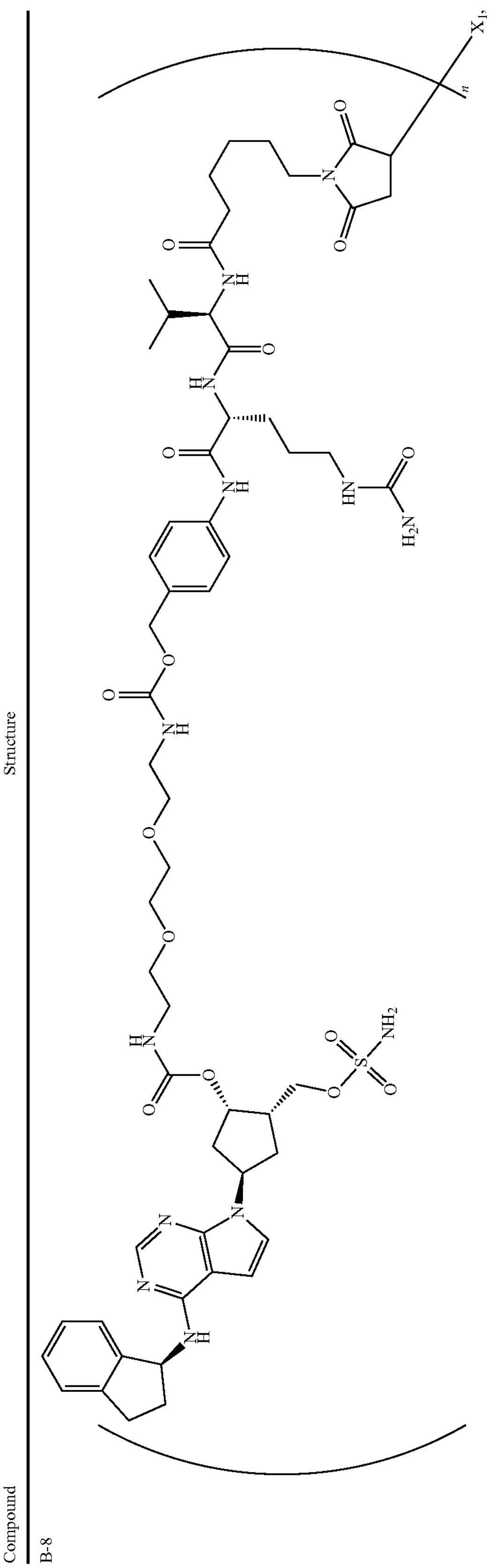 |
| B-9 | 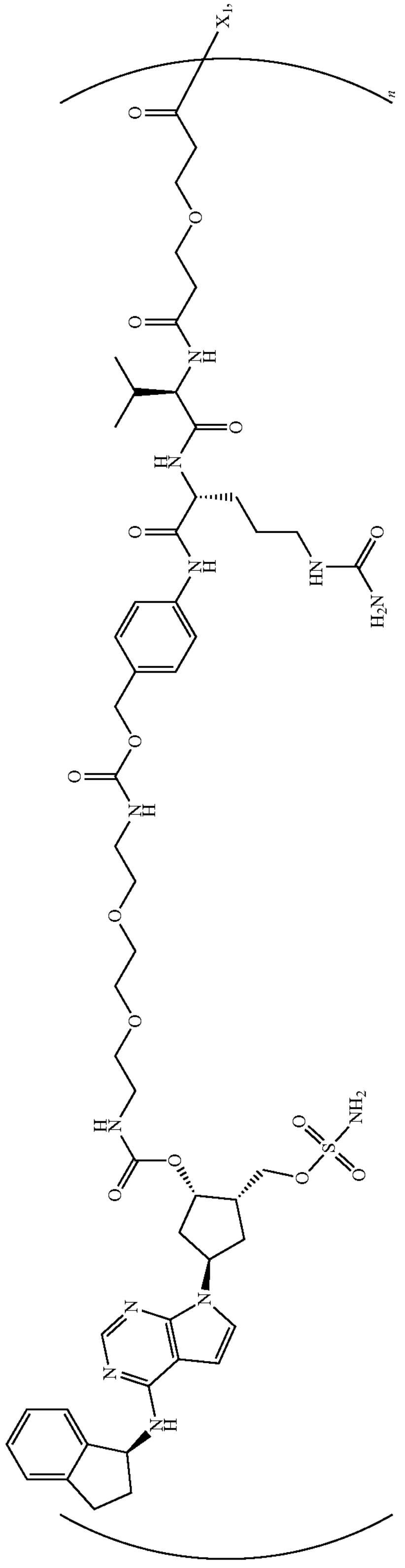 |

-continued
| Compound | Structure |
| --- | --- |
| B-10 | 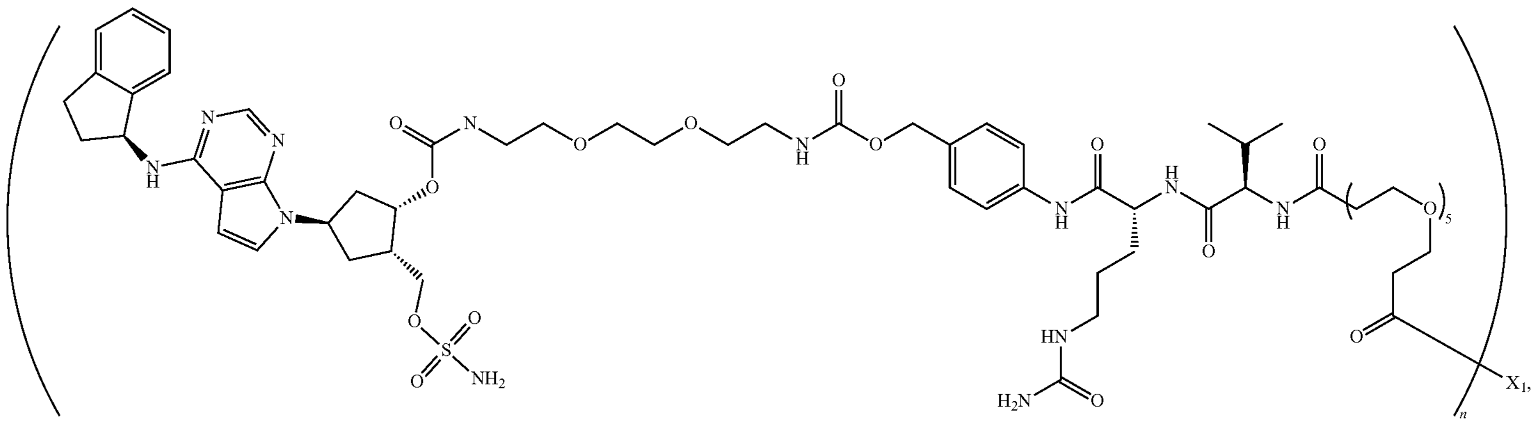 |
| B-11 | 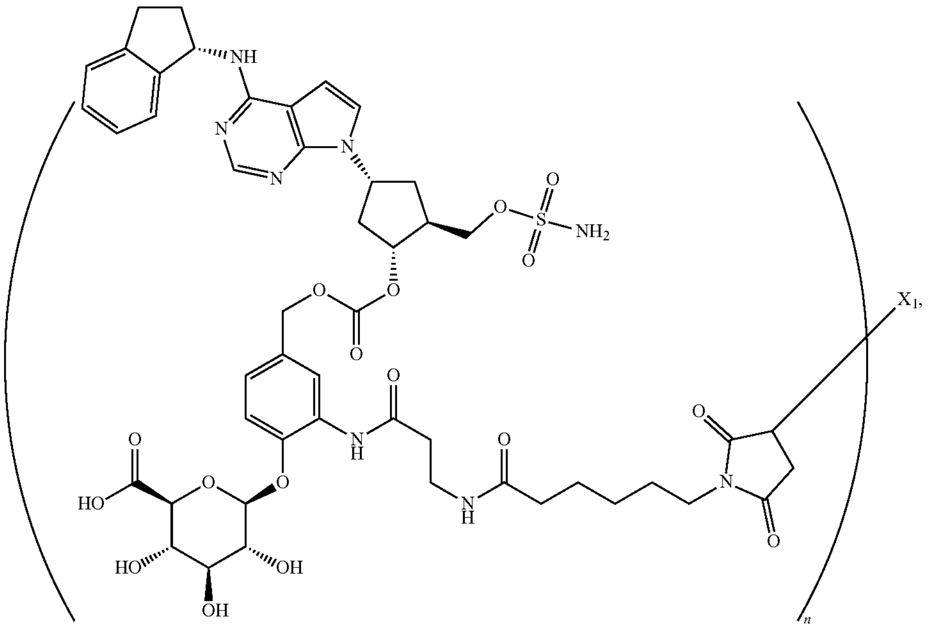 |

-continued
| Compound | Structure |
| --- | --- |
| B-12 | 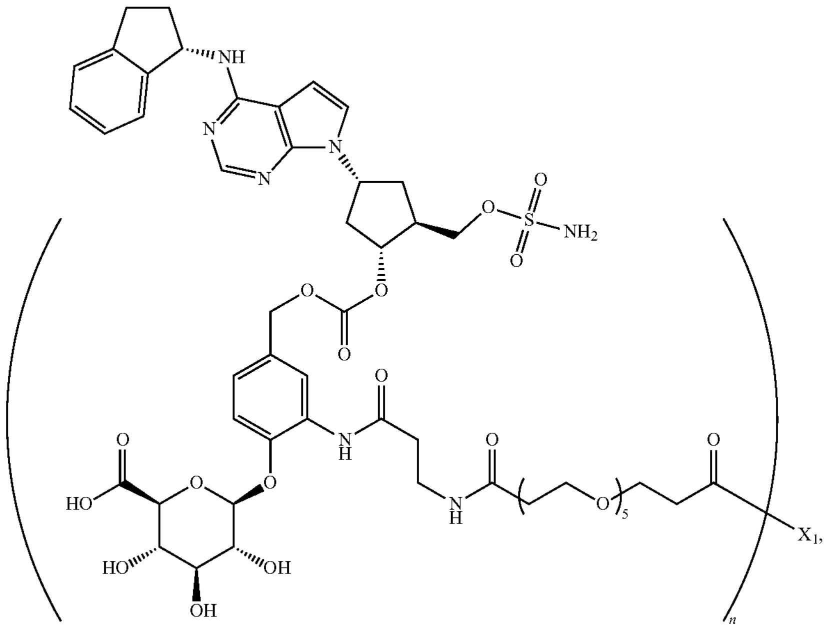 |

-continued
| Compound | Structure |
|---|---|
| B-13 | 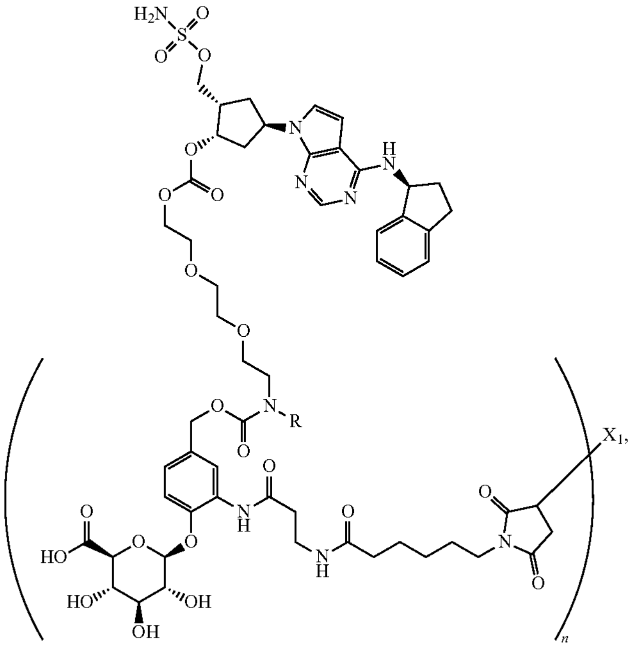 |

-continued
| Compound | Structure |
| --- | --- |
| B-14 | 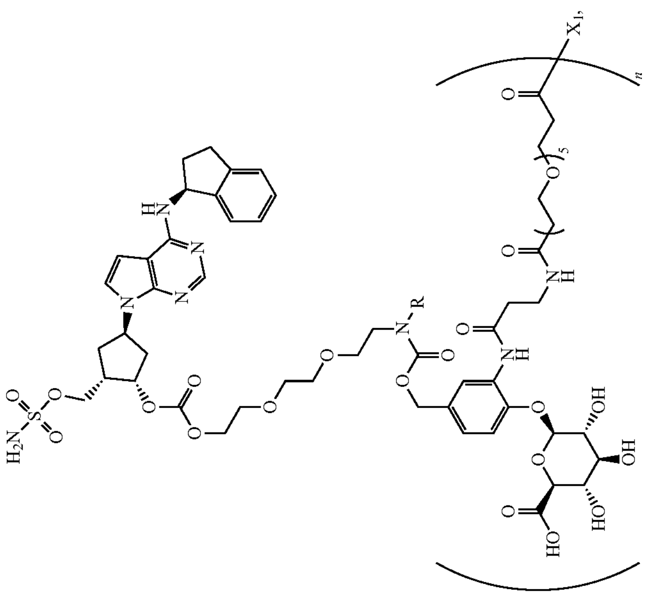 |

-continued
| Compound | Structure |
| --- | --- |
| B-15 | 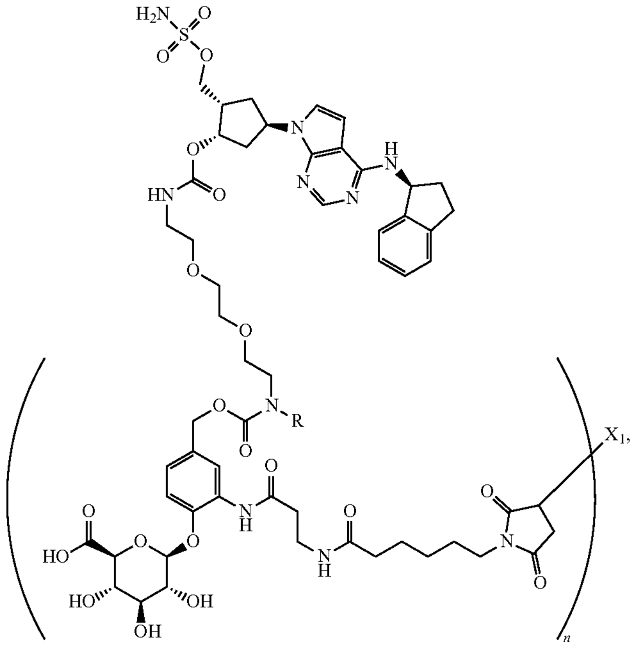 |

-continued
| Compound | Structure |
|---|---|
| B-16 | 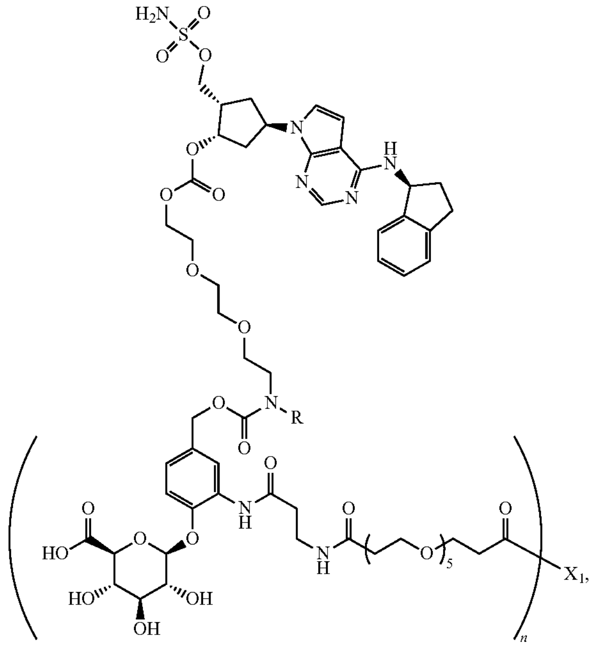 |

-continued
| Compound | Structure |
| --- | --- |
| B-17 | 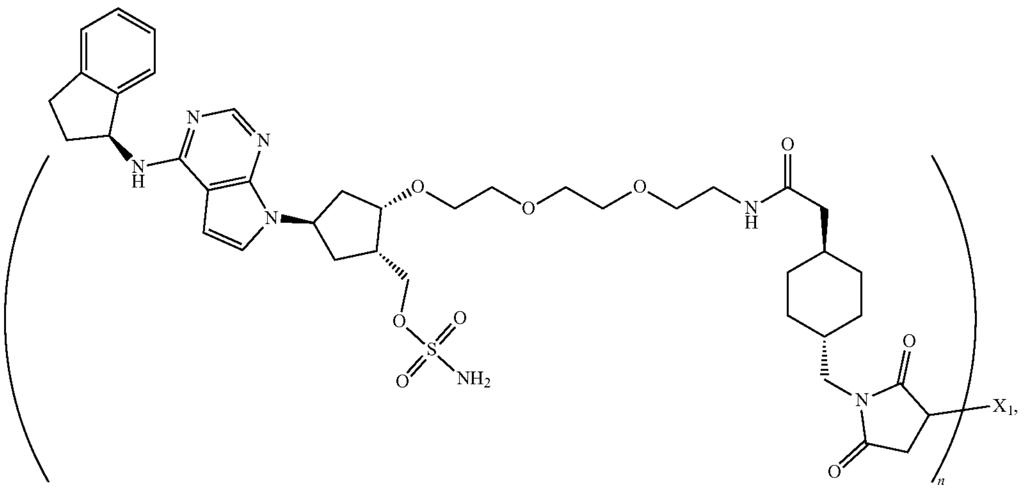 |
| B-18 | 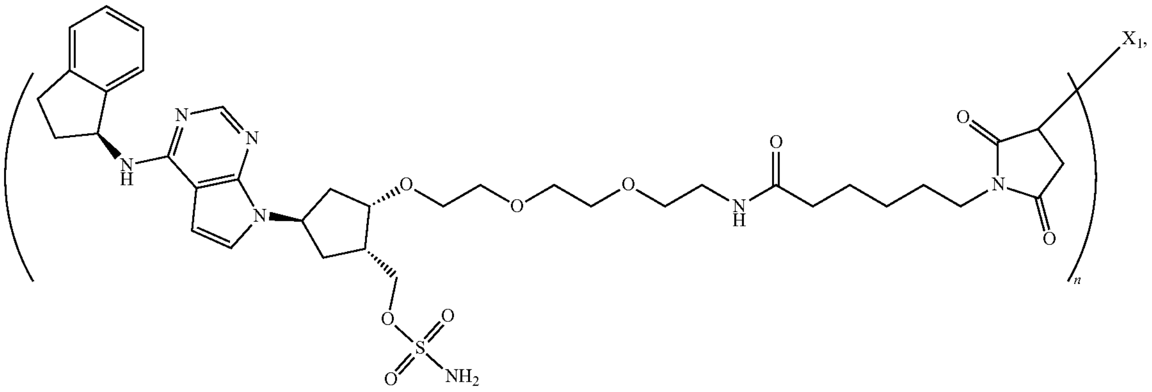 |

-continued
| Compound | Structure |
| --- | --- |
| B-19 | 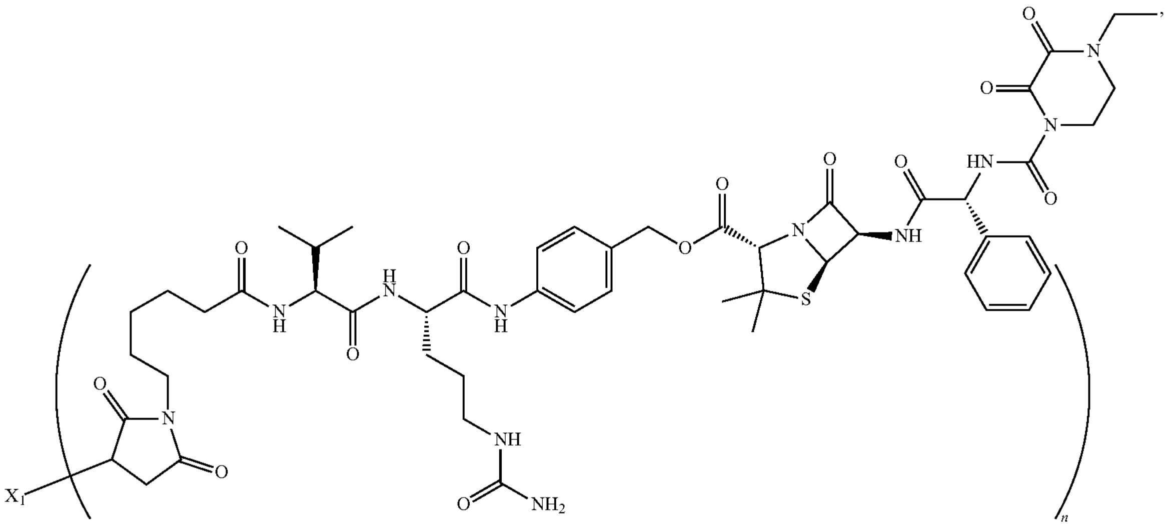 |

-continued
| Compound | Structure |
| --- | --- |
| B-20 | 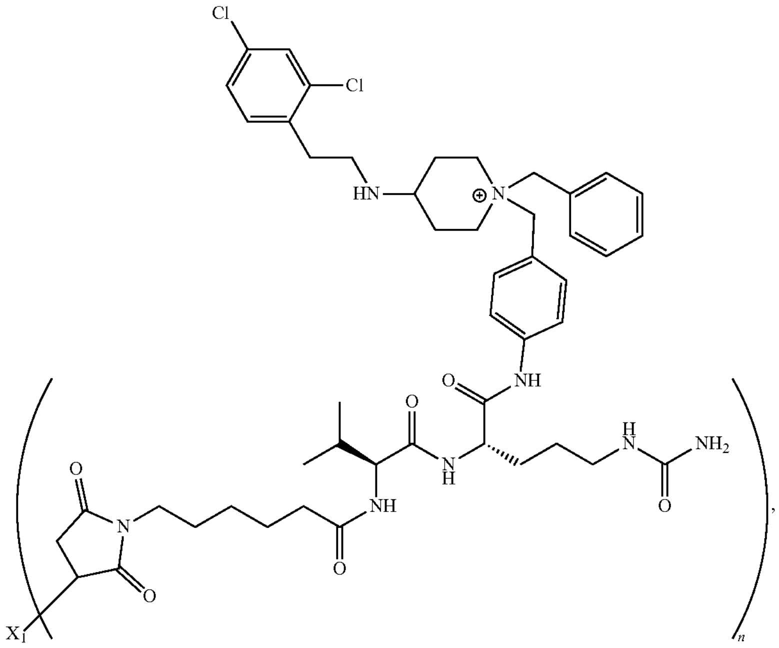 |

-continued
| Compound | Structure |
| --- | --- |
| B-21 | 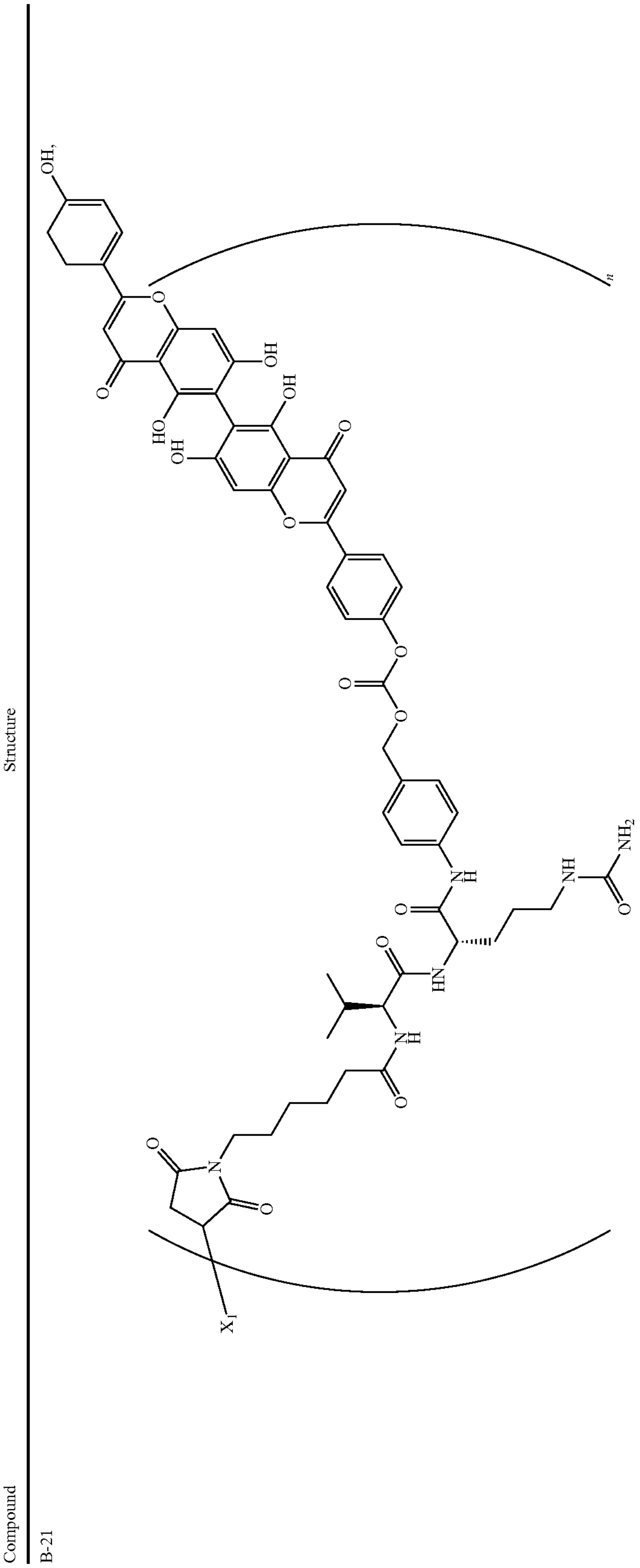 |

-continued
| Compound | Structure |
| --- | --- |
| B-22 | 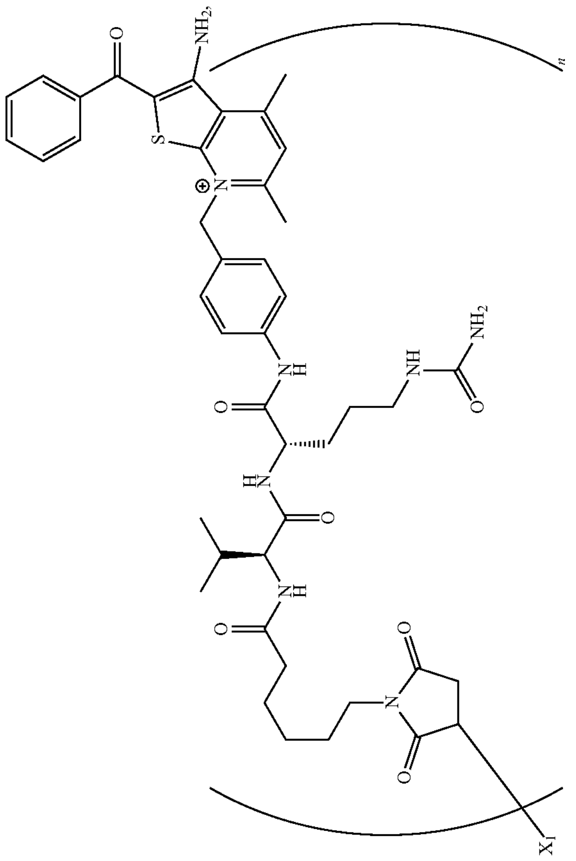 |

-continued
| Compound | Structure |
| --- | --- |
| B-23 | 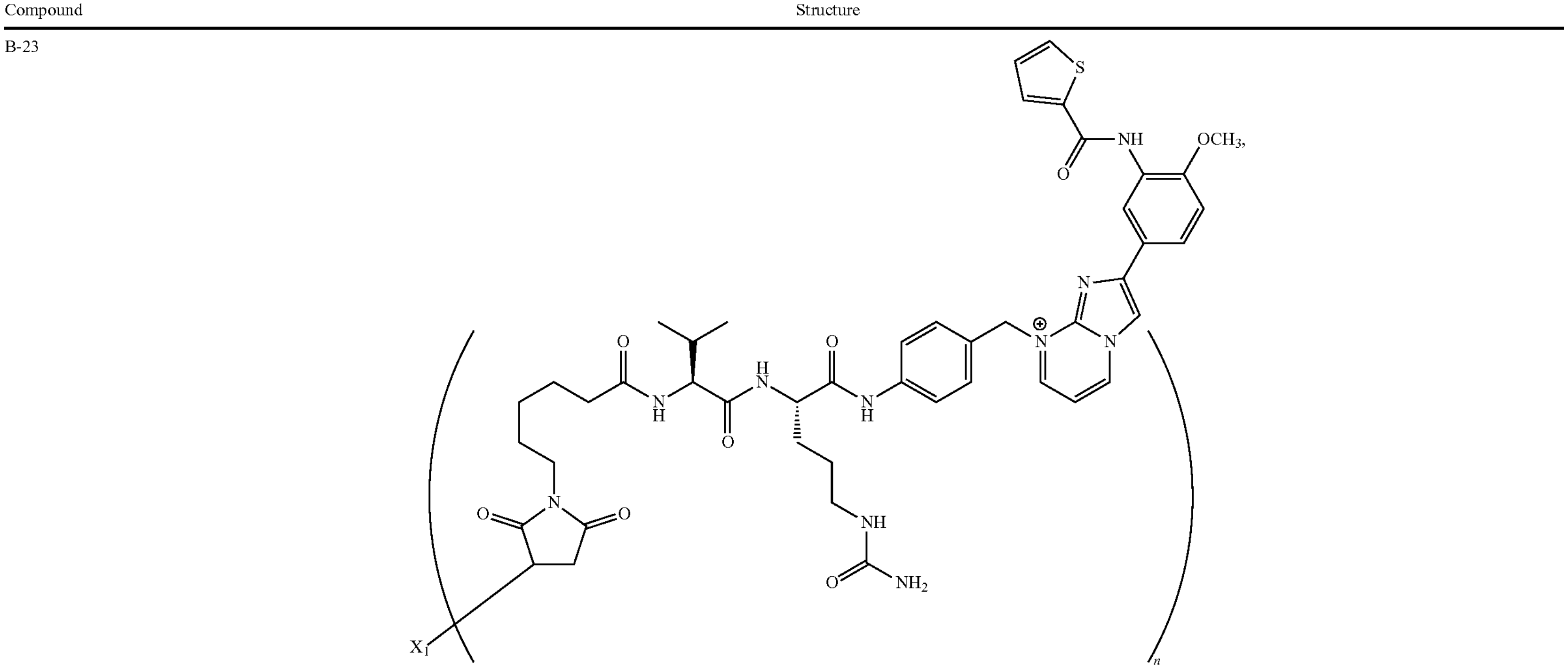 |

-continued
| Compound | Structure |
| --- | --- |
| B-24 | 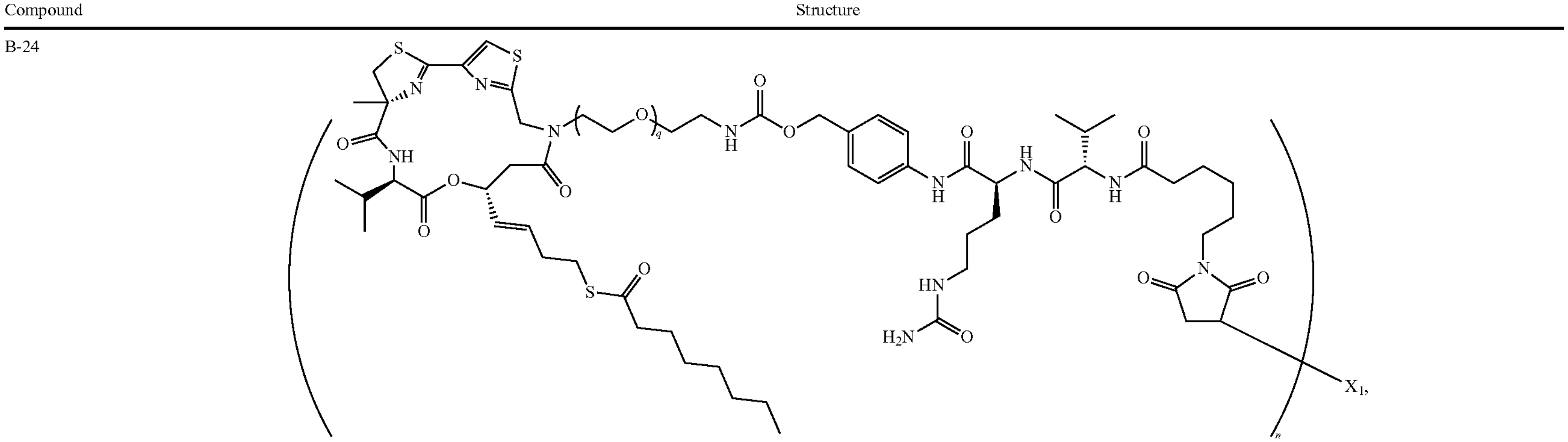 |
| B-25 | 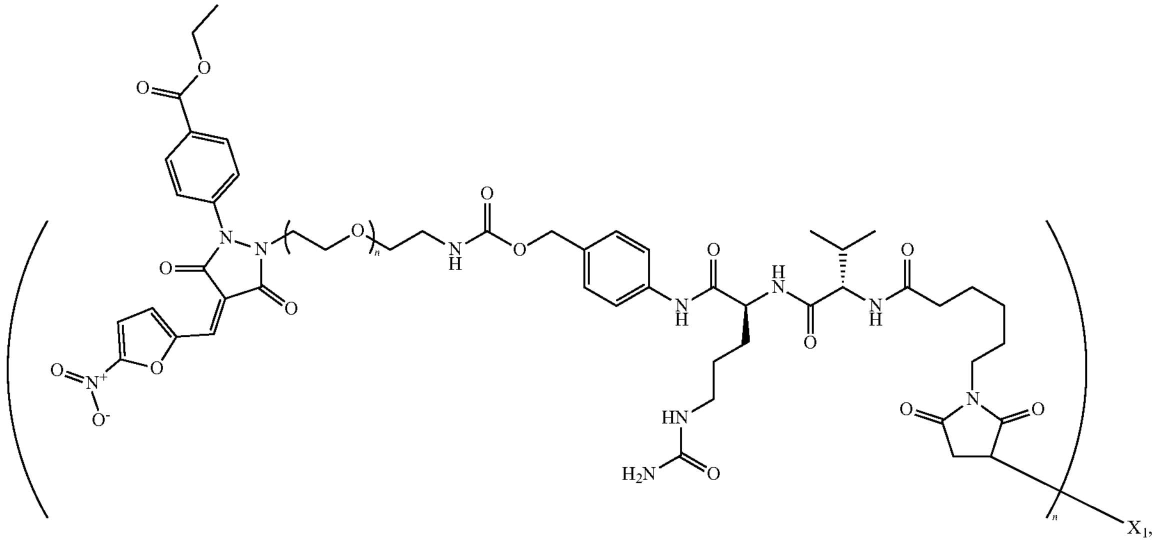 |

-continued
| Compound | Structure |
| --- | --- |
| B-26 | 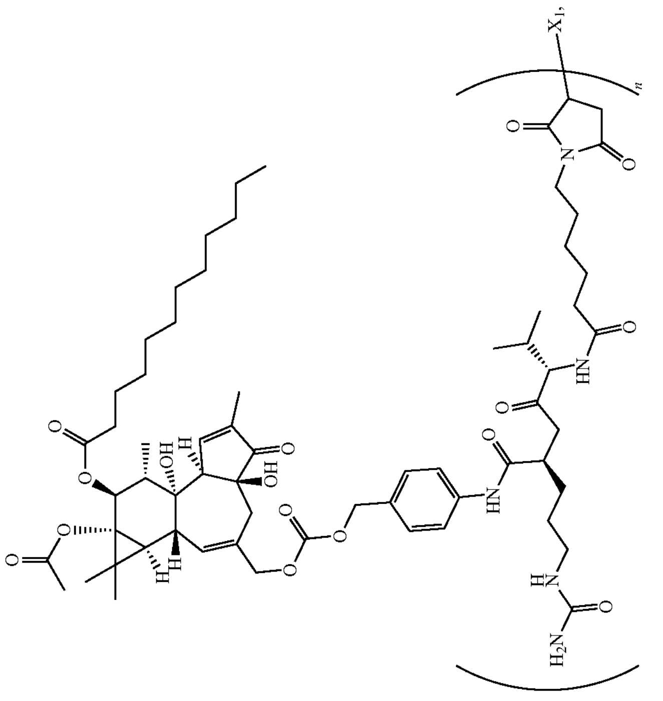 |

-continued
| Compound | Structure |
| --- | --- |
| B-27 | 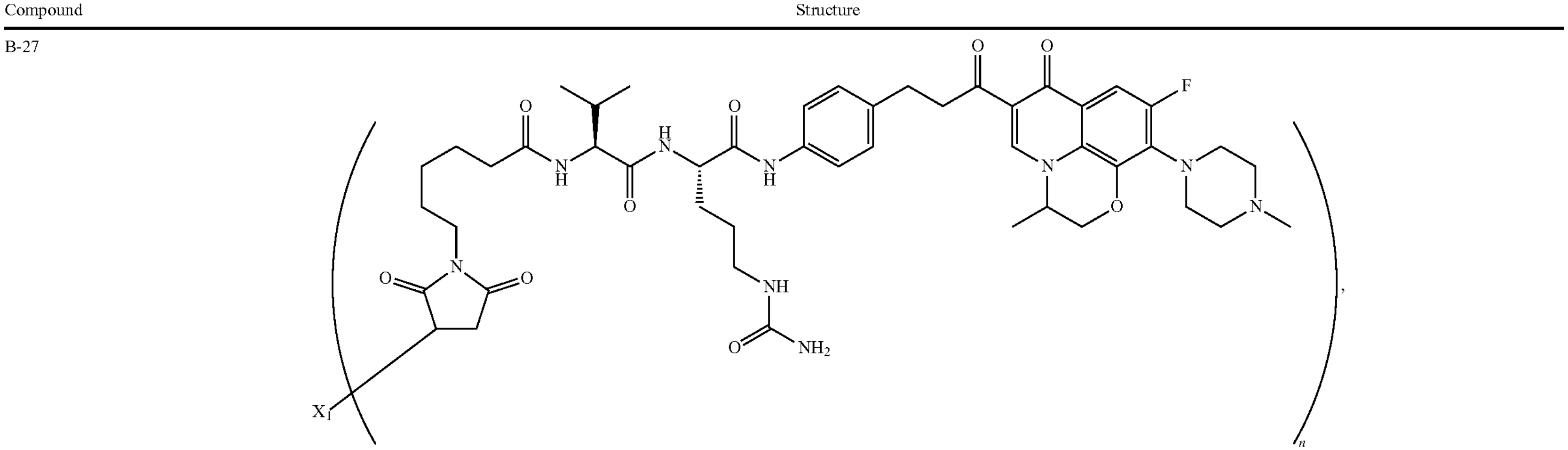 |
| B-28 | 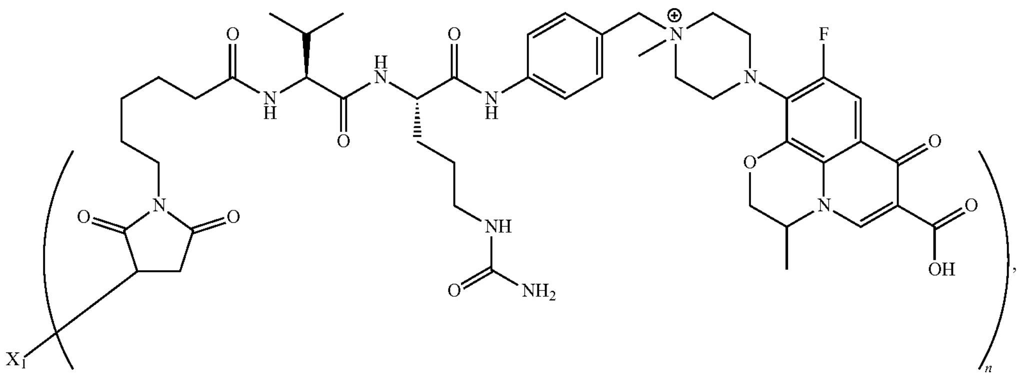 |

-continued
| Compound | Structure |
| --- | --- |
| B-29 | 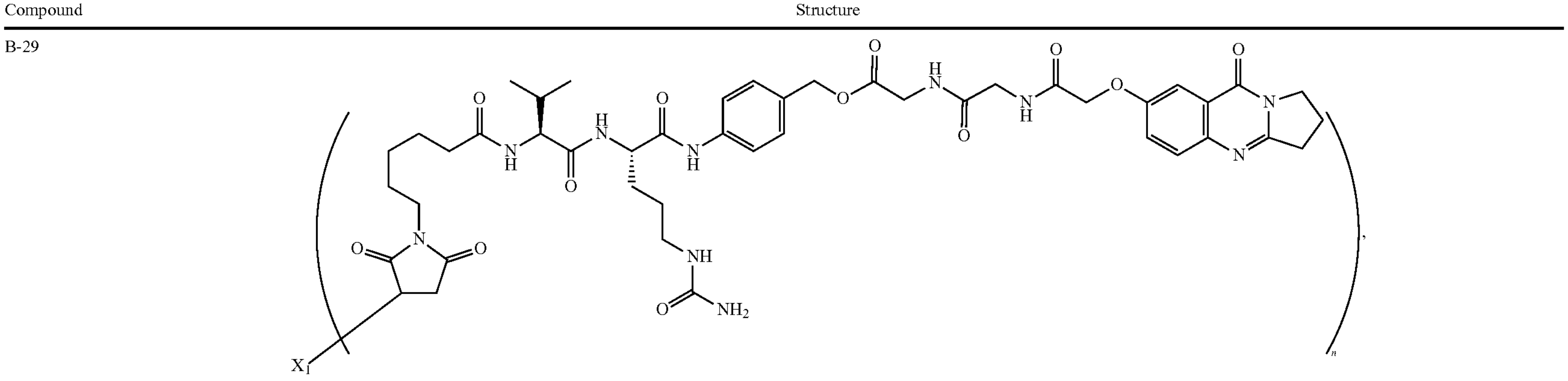 |
| B-30 | 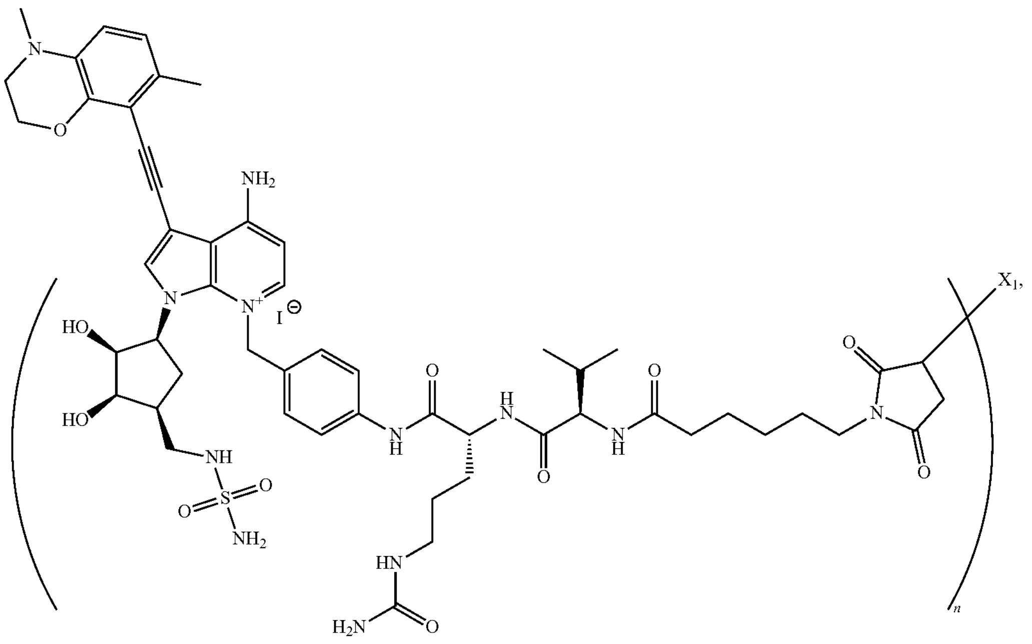 |

-continued
| Compound | Structure |
| --- | --- |
| B-31 | 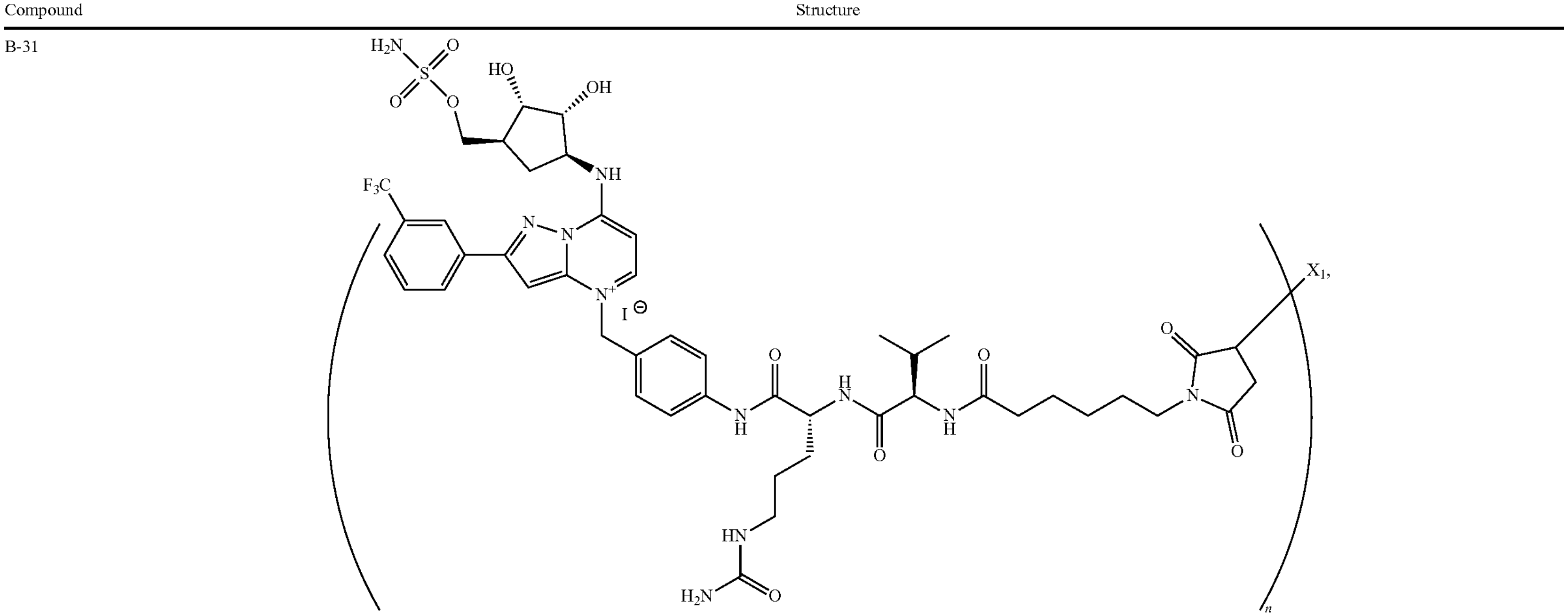 |

-continued
| Compound | Structure |
|---|---|
| B-48 | 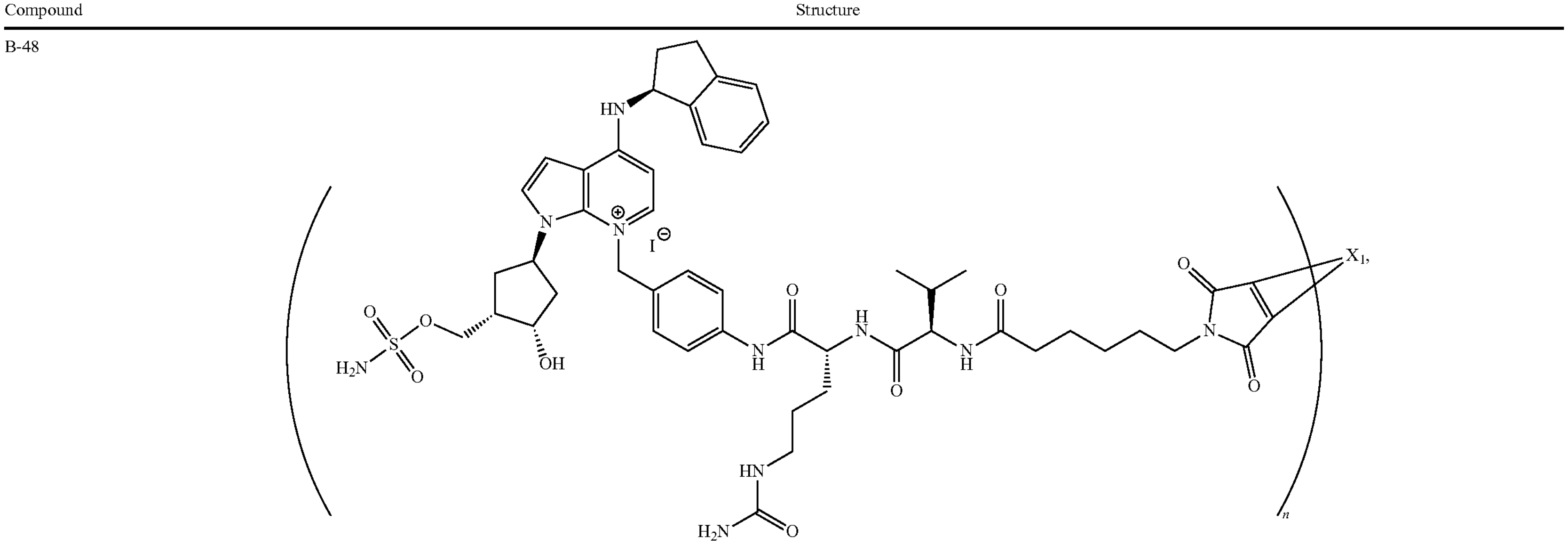 |
| | and |
| B-49 | 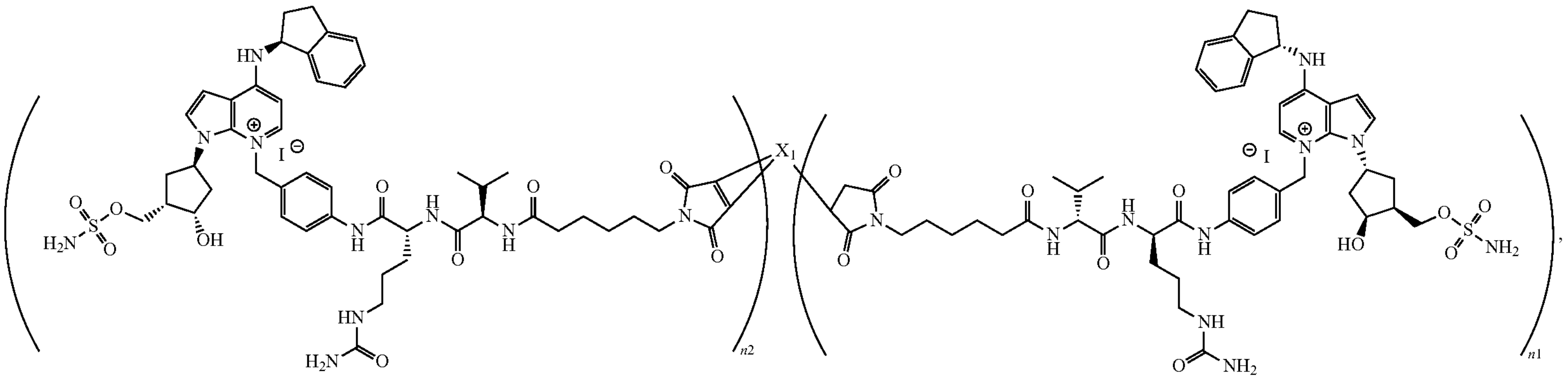 | wherein R is H, alkyl, aryl, arylalkyl, a glycol ether, or a glycol linker; q is 1, 2, 3, or 4; n1 is 1, 2, 3, 4, 5, 6, 7, 8, 9, or 10; and n2 is 1, 2, 3, 4, 5, 6, 7, 8, 9, or 10, wherein the combination of n1 and n2 has a sum of 2, 3, 4, 5, 6, 7, 8, 9, 10, or 11.

Embodiment III-50. The compound, or a pharmaceutically acceptable salt, solvate, hydrate, isomer, or tautomer thereof, embodiment III-49, wherein the compound of Formula (II) or Formula (III) is selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49.

Embodiment III-51. The compound, or a pharmaceutically acceptable salt, solvate, hydrate, isomer, or tautomer thereof, embodiment III-50, wherein the compound of Formula (II) or Formula (III) is selected from the group consisting of B-1, B-30, B-31, B-48, and B-49.

Embodiment III-52. The compound, or a pharmaceutically acceptable salt, solvate, hydrate, isomer, or tautomer thereof, of any one of embodiments III-24 to III-28, wherein the compound of Formula (II) or Formula (III) is selected from the group consisting of:

| Compound | Structure |
|---|---|
| B-32 | 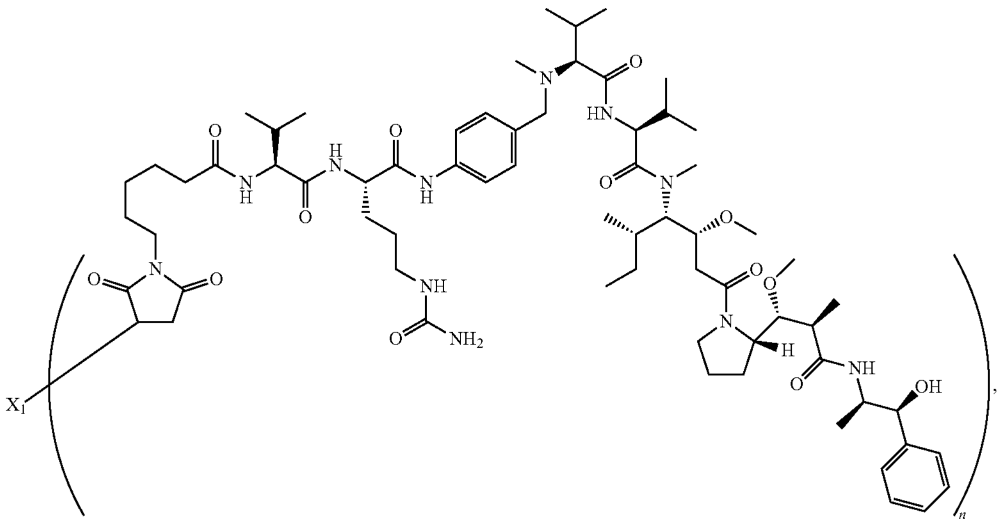 , |
| B-33 | 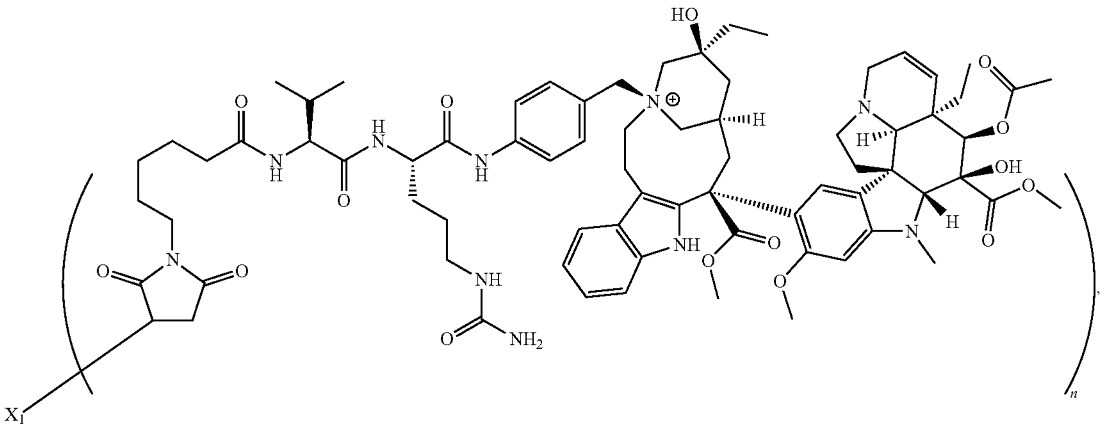 , |

-continued
| Compound | Structure |
| --- | --- |
| B-34 | 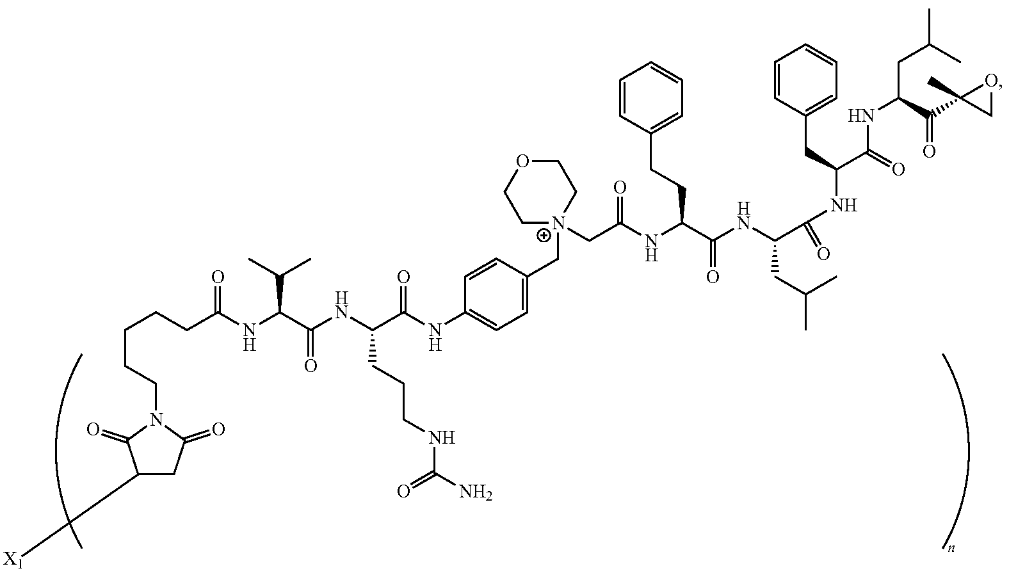 |
| B-35 | 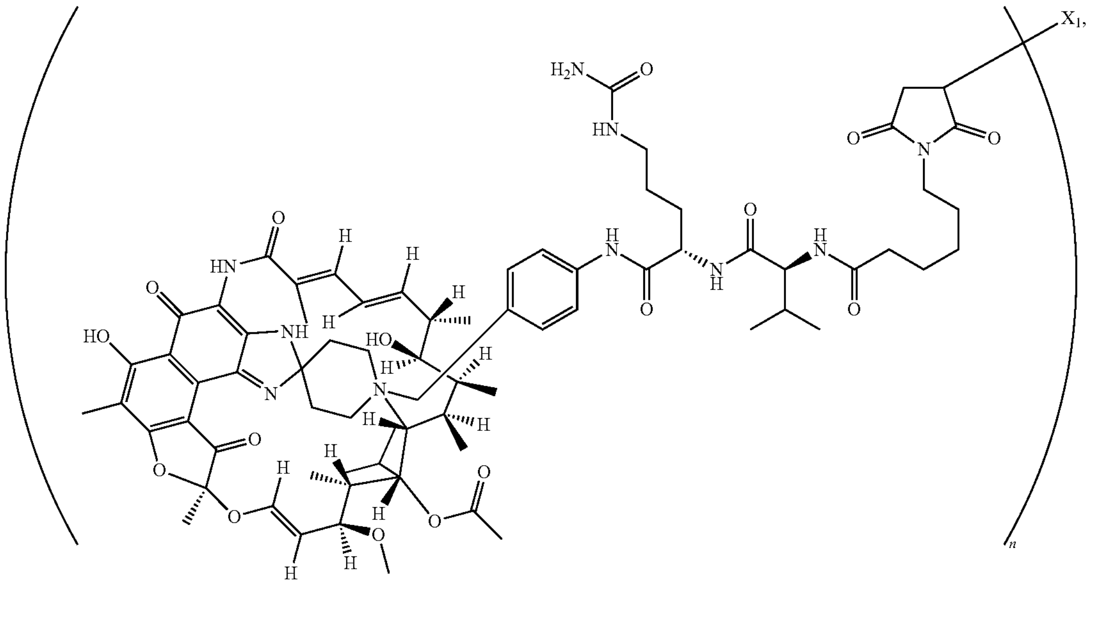 |

-continued
| Compound | Structure |
| --- | --- |
| B-36 | 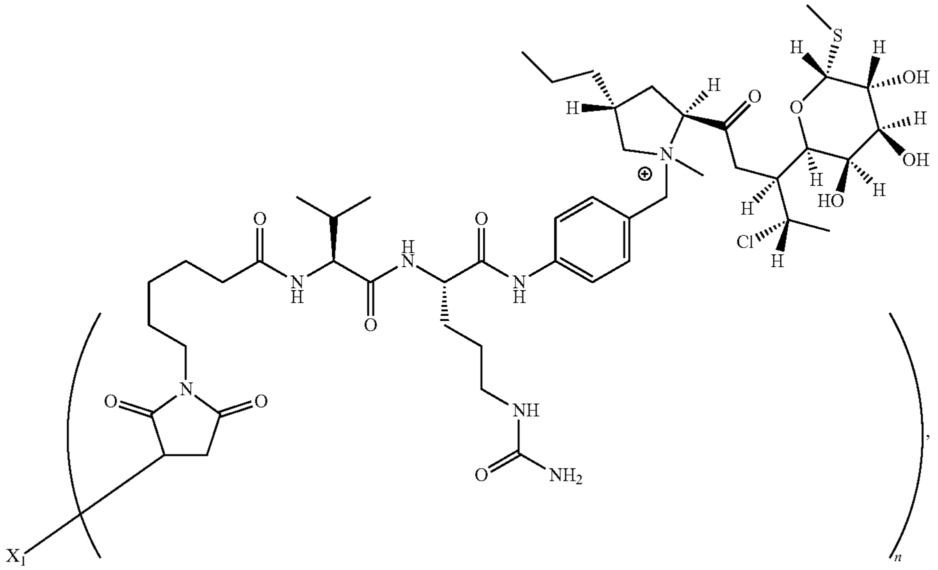 |
| B-37 | 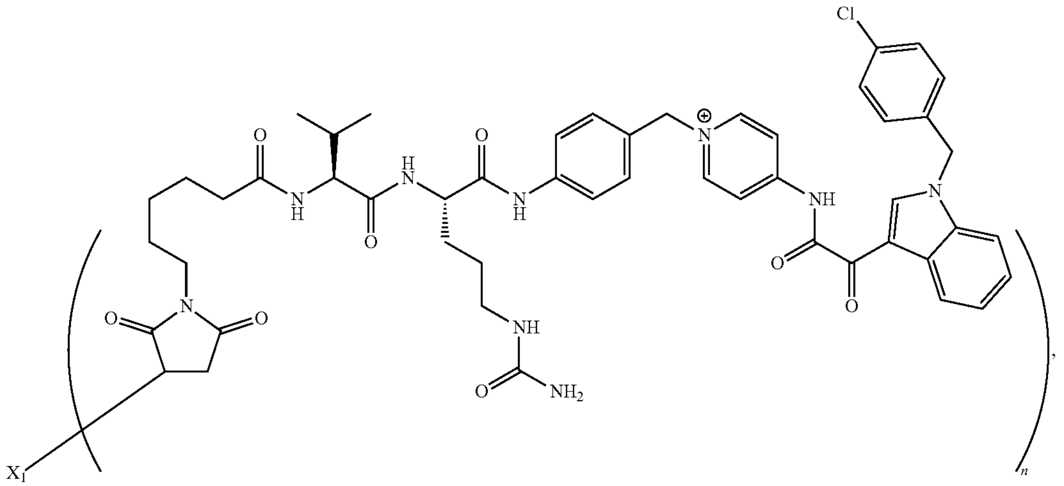 |

-continued
| Compound | Structure |
|---|---|
| B-38 | 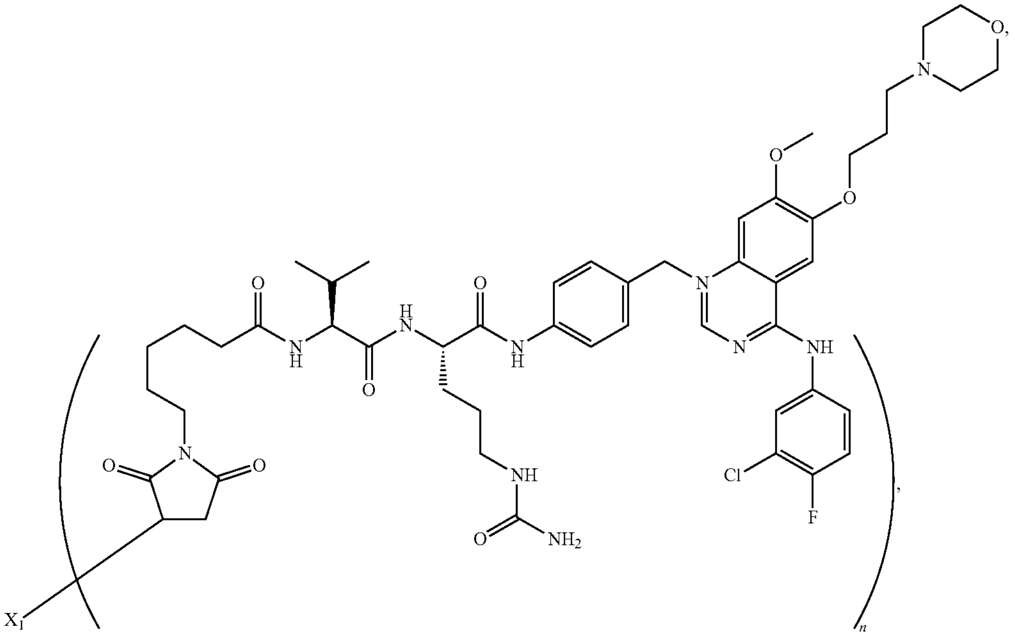 |
| B-39 | 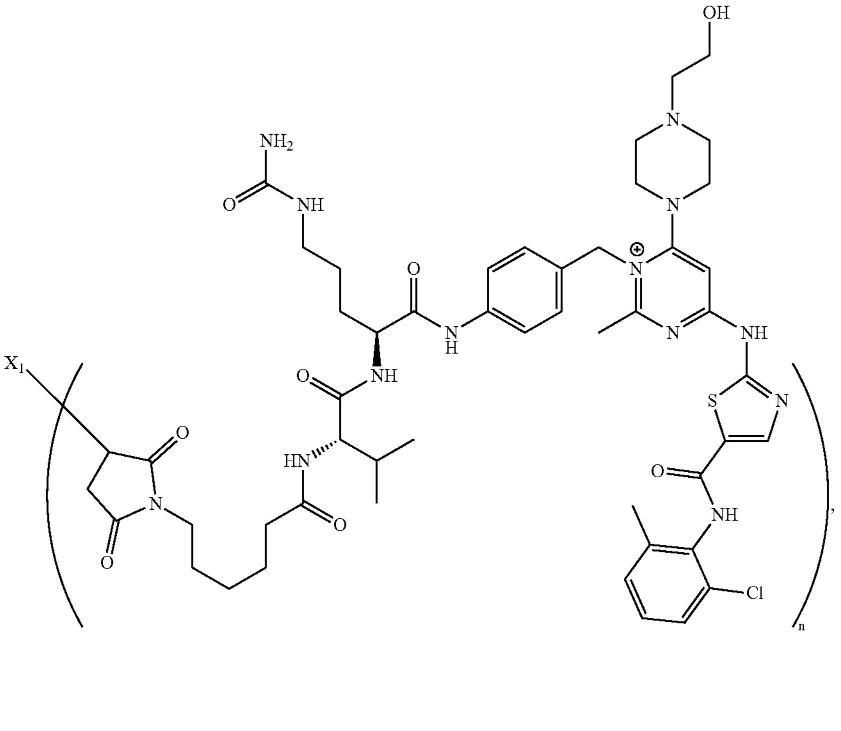 |

-continued
| Compound | Structure |
| --- | --- |
| B-40 | 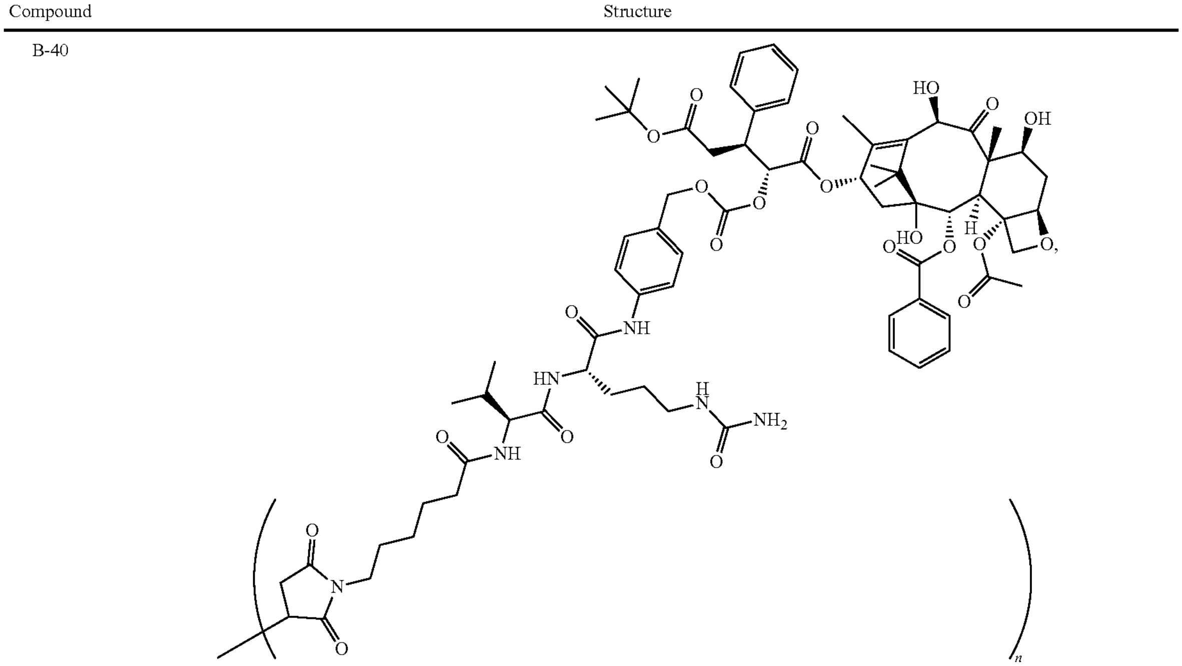 |
| B-41 | 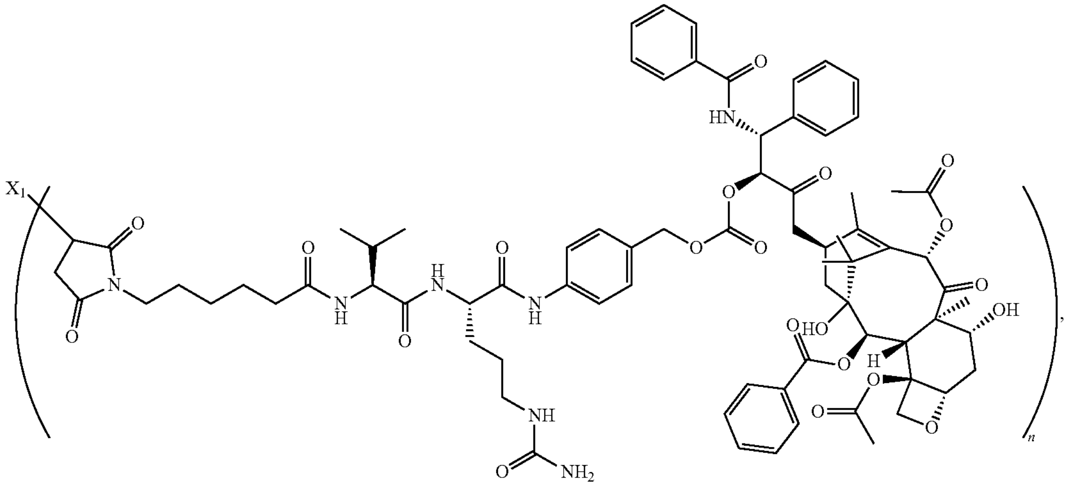 |
| B-42 | 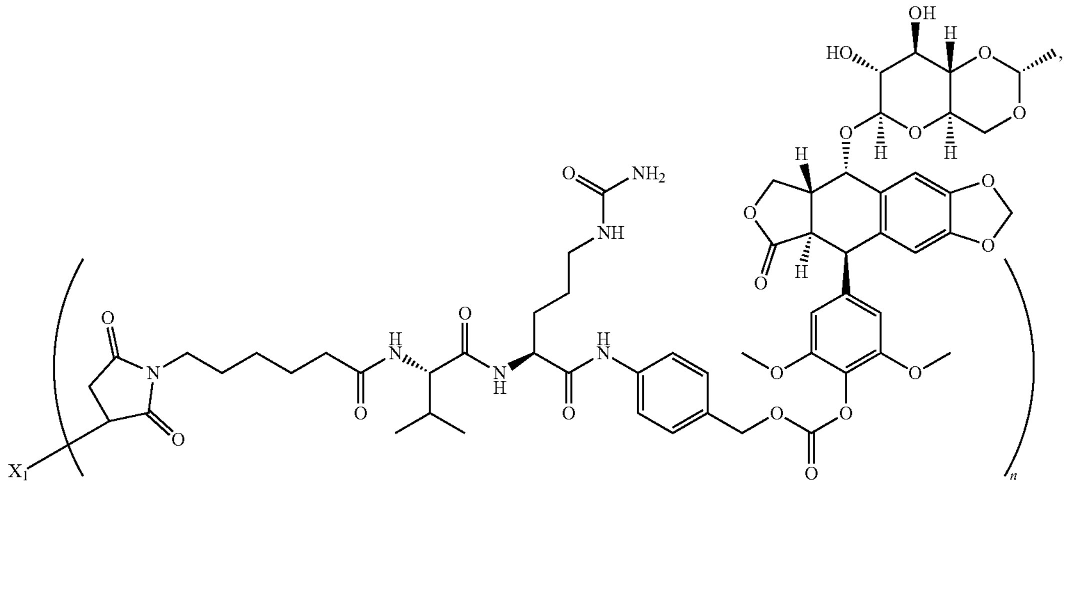 |

-continued
| Compound | Structure |
|---|---|
| B-43 | 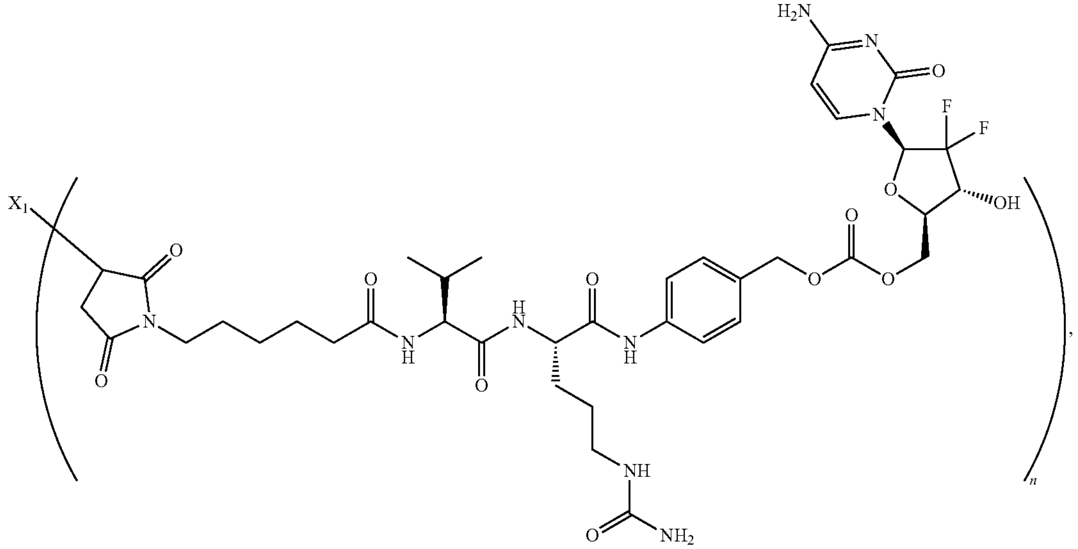 |
| B-44 | 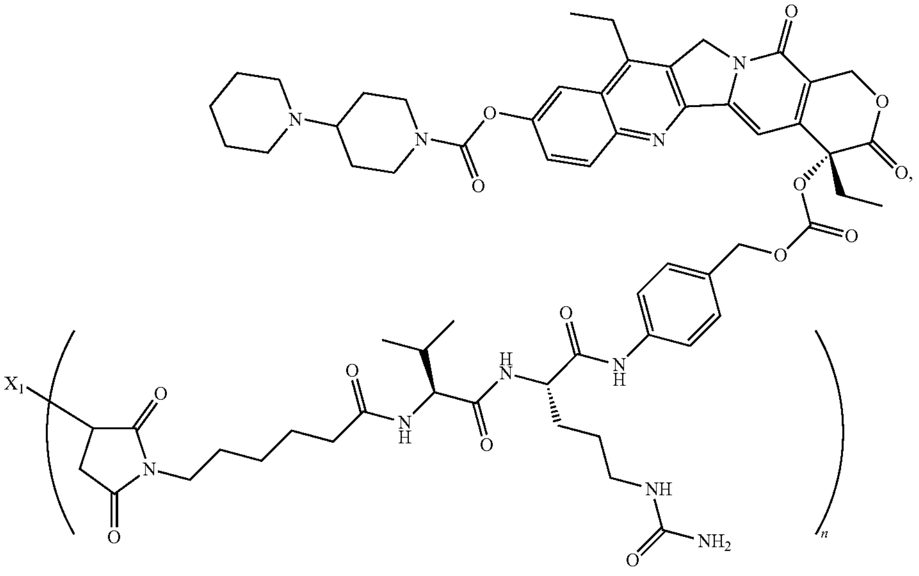 |
| B-45 | 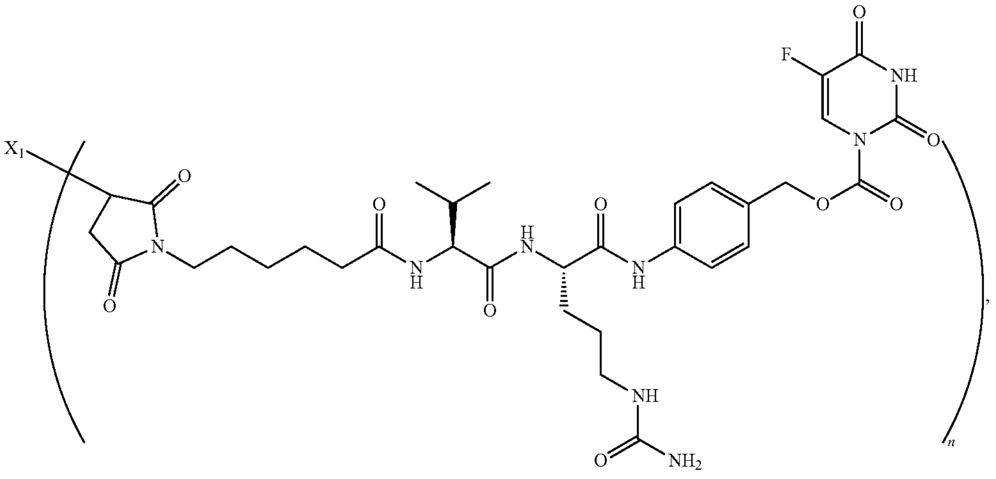 |

-continued
| Compound | Structure |
|---|---|
| B-46 | 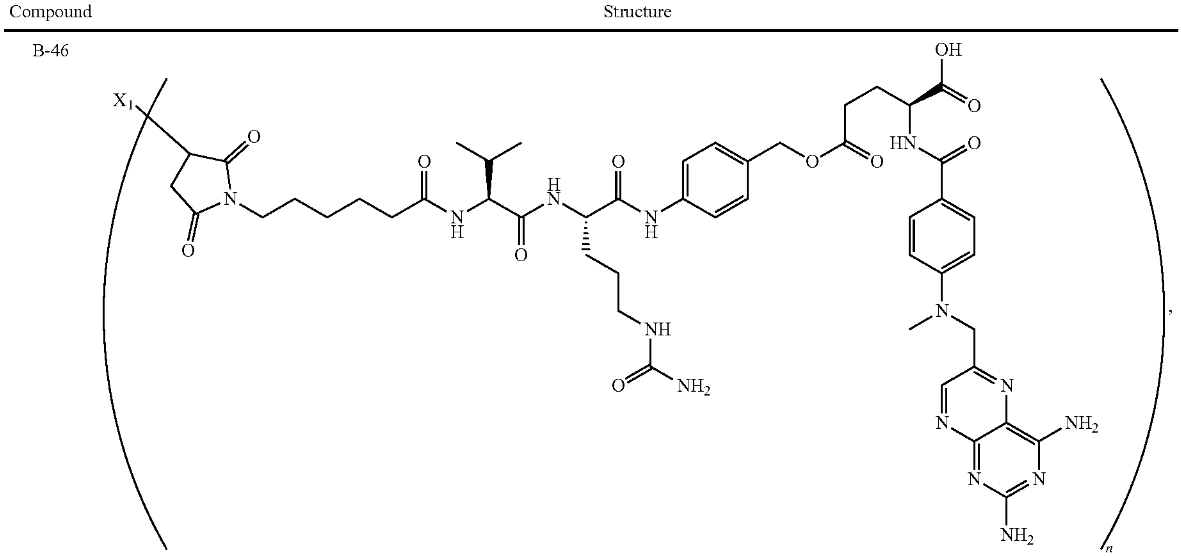, |
| B-47 | 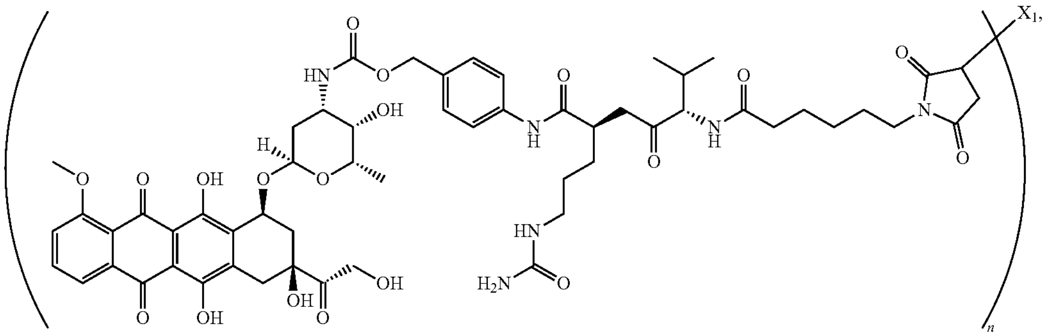 and |
| | and |
| B-50 | 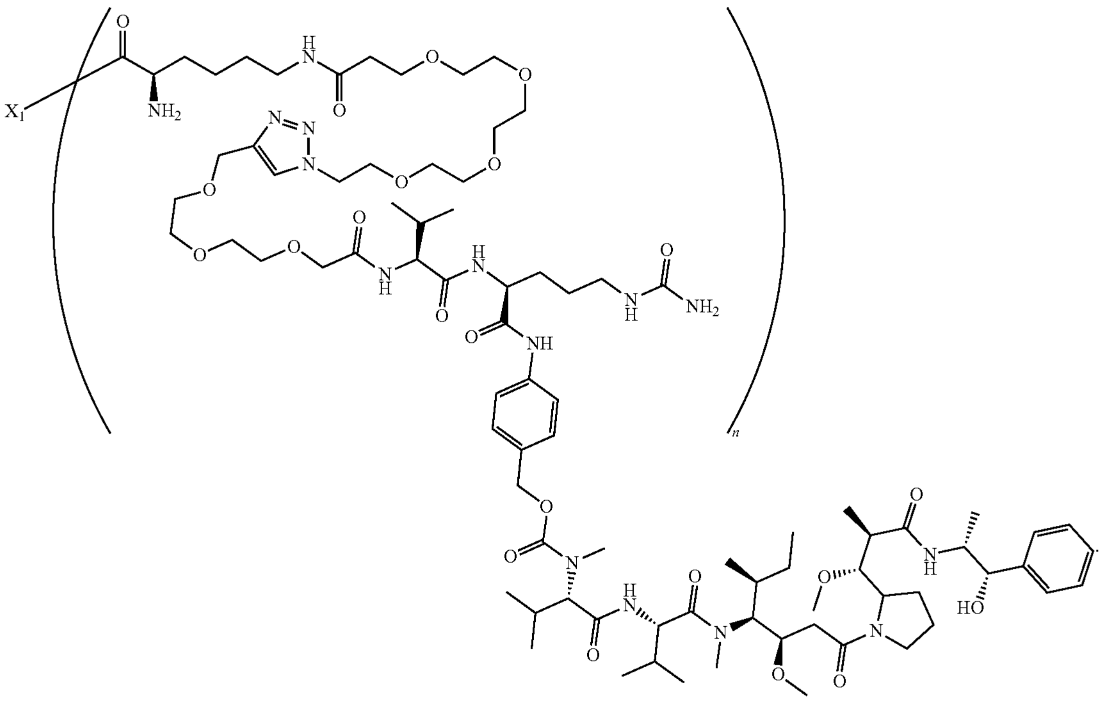 |

Embodiment III-53. The compound, or a pharmaceutically acceptable salt, solvate, hydrate, isomer, or tautomer thereof, embodiment III-52, wherein the compound of Formula (II) or Formula (III) is B-32.

Embodiment III-54. The compound, or a pharmaceutically acceptable salt, solvate, hydrate, isomer, or tautomer thereof, of any one of embodiments III-24 to III-53, wherein n is 2, 3, 4, 5, 6, 7, 8, or 9.

Embodiment III-55. The compound, or a pharmaceutically acceptable salt, solvate, hydrate, isomer, or tautomer thereof, of any one of embodiments III-24 to III-53, wherein n is 3, 4, 5, 6, 7, or 8.

Embodiment III-56. The compound, or a pharmaceutically acceptable salt, solvate, hydrate, isomer, or tautomer thereof, of any one of embodiments III-24 to III-53, wherein n is 4, 5, 6, or 7.

Embodiment III-57. The compound, or a pharmaceutically acceptable salt, solvate, hydrate, isomer, or tautomer thereof, of any one of embodiments III-24 to III-53, wherein n is 5 or 6.

Embodiment III-58. A pharmaceutical composition comprising a compound, or a pharmaceutically acceptable salt, solvate, hydrate, or tautomer thereof, of any one of embodiments III-24 to III-57 or III-87 to III-105 and a pharmaceutically acceptable carrier.

Embodiment III-59. A method for treating a disorder in a subject, comprising administering to a subject in need thereof a therapeutically effective amount of a compound, or a pharmaceutically acceptable salt, solvate, hydrate, or tautomer thereof, of any one of embodiments III-24 to III-57 or III-87 to III-105, wherein the disorder is an immunological disorder or cancer.

Embodiment III-60. A method for treating a disorder in a subject, comprising administering to a subject in need thereof a therapeutically effective amount of a pharmaceutical composition according to embodiment III-58, wherein the disorder is an immunological disorder or cancer.

Embodiment III-61. The method of embodiment III-59 or III-60, wherein the disorder is an immunological disorder.

Embodiment III-62. The method of embodiment III-61, wherein the immunological disorder is multiple sclerosis, type 1 diabetes, inflammatory bowel disease, rheumatoid arthritis, psoriasis, or systemic lupus erythematosus.

Embodiment III-63. The method of embodiment III-59 or III-60, wherein the disorder is cancer.

Embodiment III-64. The method of embodiment III-61, wherein the cancer is non-small cell lung cancer (NSCLC), melanoma, kidney cancer, bladder cancer, head and neck cancer, or claudin-low breast cancer.

Embodiment III-65. Use of a compound, or a pharmaceutically acceptable salt, solvate, hydrate, or tautomer thereof, of any one of embodiments III-24 to III-57 or III-87 to III-105, in the manufacture of a medicament for treating a disorder in a subject in need thereof, wherein the disorder is an immunological disorder or cancer.

Embodiment III-66. Use of a pharmaceutical composition according to embodiment III-58 in the manufacture of a medicament for treating a disorder in a subject in need thereof, wherein the disorder is an immunological disorder or cancer.

Embodiment III-67. Use of a compound, or a pharmaceutically acceptable salt, solvate, hydrate, or tautomer thereof, of any one of embodiments III-24 to III-57 or III-87 to III-105 for treating a disorder in a subject in need thereof.

Embodiment III-68. Use of a pharmaceutical composition according to embodiment III-58 for treating a disorder in a subject in need thereof.

Embodiment III-69. Use of a compound, or a pharmaceutically acceptable salt, solvate, hydrate, or tautomer thereof, of any one of embodiments III-24 to III-57 or III-87 to III-105 for treating a disorder in a subject in need thereof, wherein the disorder is an immunological disorder or cancer.

Embodiment III-70. Use of a pharmaceutical composition according to embodiment III-58 for treating a disorder in a subject in need thereof, wherein the disorder is an immunological disorder or cancer.

Embodiment III-71. The use of any one of embodiments III-65 to III-70, wherein the disorder is an immunological disorder.

Embodiment III-72. The use of embodiment III-71, wherein the immunological disorder is multiple sclerosis, type 1 diabetes, inflammatory bowel disease, rheumatoid arthritis, psoriasis, or systemic lupus erythematosus.

Embodiment III-73. The use of any one of embodiments III-65 to III-70, wherein the disorder is cancer.

Embodiment III-74. The use of embodiment III-73, wherein the cancer is non-small cell lung cancer (NSCLC), melanoma, kidney cancer, bladder cancer, head and neck cancer, or claudin-low breast cancer.

Embodiment III-75. A compound, or a pharmaceutically acceptable salt, solvate, hydrate, or tautomer thereof, of any one of embodiments III-24 to III-57 or III-87 to III-105 for use in a method of treating a disorder in a subject in need thereof, wherein the disorder is an immunological disorder or cancer.

Embodiment III-76. The compound for use of embodiment III-75, wherein the disorder is an immunological disorder.

Embodiment III-77. The compound for use of embodiment III-76, wherein the immunological disorder is multiple sclerosis, type 1 diabetes, inflammatory bowel disease, rheumatoid arthritis, psoriasis, or systemic lupus erythematosus.

Embodiment III-78. The compound for use of embodiment III-75, wherein the disorder is cancer.

Embodiment III-79. The compound for use of embodiment III-78, wherein the cancer is non-small cell lung cancer (NSCLC), melanoma, kidney cancer, bladder cancer, head and neck cancer, or claudin-low breast cancer.

Embodiment III-80. A pharmaceutical composition according to embodiment III-58 for use in a method of treating a disorder in a subject in need thereof, wherein the disorder is an immunological disorder or cancer.

Embodiment III-81. The pharmaceutical composition for use of embodiment III-80, wherein the disorder is an immunological disorder.

Embodiment III-82. The pharmaceutical composition for use of embodiment III-81, wherein the immunological disorder is multiple sclerosis, type 1 diabetes, inflammatory bowel disease, rheumatoid arthritis, psoriasis, or systemic lupus erythematosus.

Embodiment III-83. The pharmaceutical composition for use of embodiment III-80, wherein the disorder is cancer.

Embodiment III-84. The pharmaceutical composition for use of embodiment III-83, wherein the cancer is non-small cell lung cancer (NSCLC), melanoma, kidney cancer, bladder cancer, head and neck cancer, or claudin-low breast cancer.

Embodiment III-85. An IL-2 polypeptide or a bio-active homolog polypeptide thereof comprising an amino acid sequence set forth in Table 4.

Embodiment III-86. An IL-2 polypeptide or a bio-active homolog polypeptide thereof comprising an amino acid sequence set forth in SEQ ID NO: 1 or SEQ ID NO:2.

Embodiment III-87. The compound, or a pharmaceutically acceptable salt, solvate, hydrate, isomer, or tautomer thereof, of any one of embodiments III-24 to III-48 or III-54 to III-57, wherein $X_2$ is bound to $X_1$ at two different sites on $X_1$.

Embodiment III-88. The compound, or a pharmaceutically acceptable salt, solvate, hydrate, isomer, or tautomer thereof, of any one of embodiments III-24 to III-34, III-36 to III-48, or III-54 to III-57, wherein $X_2$ is bound to $X_1$ at two different Cys residues on $X_1$.

Embodiment III-89. The compound, or a pharmaceutically acceptable salt, solvate, hydrate, isomer, or tautomer thereof, of any one of embodiments III-24 to III-33, III-35 to III-48, or III-54 to III-57, wherein $X_2$ is bound to $X_1$ at two different Lys residues on $X_1$.

Embodiment III-90. The compound, or a pharmaceutically acceptable salt, solvate, hydrate, isomer, or tautomer thereof, of any one of embodiments III-24 to III-34 or III-36 to III-48, wherein $X_2$ is a mixture of $X_{2b}$ and $X_{2c}$, $X_{2b}$ is a linker that is bound to one Cys residue on $X_1$, $X_{2c}$ is a linker that is bound to two different Cys residues on $X_1$, n is a combination of n1 and n2, wherein n1 corresponds to the number of $X_{2b}$ moieties bound to $X_1$ and n2 corresponds to the number of $X_{2c}$ moieties bound to $X_1$, and the combination of n1 and n2 has a sum of 2, 3, 4, 5, 6, 7, 8, 9, 10, or 11.

Embodiment III-91. The compound, or a pharmaceutically acceptable salt, solvate, hydrate, isomer, or tautomer thereof, of embodiment III-90, wherein $X_{2b}$ is selected from the group consisting of K-1, K-2, K-4, K-6, K-8, K-11, K-13, K-15, K-17, and K-18 and $X_{2c}$ is K-19.

Embodiment III-92. The compound, or a pharmaceutically acceptable salt, solvate, hydrate, isomer, or tautomer thereof, of embodiment III-90 or III-91, wherein $X_{2b}$ is K-1 and $X_2$c is K-19.

Embodiment III-93. The compound, or a pharmaceutically acceptable salt, solvate, hydrate, isomer, or tautomer thereof, of any one of embodiments III-90 to III-92, wherein n1 is 2 or 3 and n2 is 1.

Embodiment III-94. The compound, or a pharmaceutically acceptable salt, solvate, hydrate, isomer, or tautomer thereof, of any one of embodiments III-90 to III-92, wherein n1 is 2 and n2 is 1.

Embodiment III-95. The compound, or a pharmaceutically acceptable salt, solvate, hydrate, isomer, or tautomer thereof, of any one of embodiments III-90 to III-92, wherein n1 is 3 and n2 is 1.

Embodiment III-96. The compound, or a pharmaceutically acceptable salt, solvate, hydrate, isomer, or tautomer thereof, of any one of embodiments III-90 to III-92, wherein n1 is 1, 2, 3, 4, or 5 and n2 is 1, 2 or 3.

Embodiment III-97. The compound, or a pharmaceutically acceptable salt, solvate, hydrate, isomer, or tautomer thereof, of any one of embodiments III-24 to III-28, selected from the group consisting of B-1, B-2, B-3, B-4, B-5, B-6, B-7, B-8, B-9, B-10, B-11, B-12, B-13, B-14, B-15, B-16, B-17, B-18, B-30, B-31, B-48, and B-49, wherein n is 1, 2, 3, 4, 5, or 6, and $X_1$ is an IL-2 polypeptide or a bio-active homolog polypeptide thereof comprising an amino acid sequence set forth in SEQ ID NO:1 or SEQ ID NO:2.

Embodiment III-98. The compound, or a pharmaceutically acceptable salt, solvate, hydrate, isomer, or tautomer thereof, of any one of embodiments III-24 to III-28, selected from the group consisting of B-1, B-30, B-31, B-48, and B-49, wherein n is 1, 2, 3, 4, 5, or 6, and $X_1$ is an IL-2 polypeptide or a bio-active homolog polypeptide thereof comprising an amino acid sequence set forth in SEQ ID NO: 1 or SEQ ID NO:2.

Embodiment III-99. The compound, or a pharmaceutically acceptable salt, solvate, hydrate, isomer, or tautomer thereof, of any one of embodiments III-24 to III-28, wherein $X_2$ is a mixture of $X_{2b}$ and $X_{2c}$, $X_{2b}$ is a linker that is bound to one Cys residue on $X_1$, $X_{2c}$ is a linker that is bound to two different Cys residues on $X_1$, n is a combination of n1 and n2, wherein the combination of n1 and n2 has a sum of 2, 3, 4, 5, or 6, and $X_1$ is an IL-2 polypeptide or a bio-active homolog polypeptide thereof comprising an amino acid sequence set forth in SEQ ID NO: 1 or SEQ ID NO:2.

Embodiment III-100. The compound, or a pharmaceutically acceptable salt, solvate, hydrate, isomer, or tautomer thereof, of any one of embodiments III-24 to III-28, wherein the compound of Formula (II) or Formula (III) is B-49, $X_1$ is an IL-2 polypeptide or a bio-active homolog polypeptide thereof comprising an amino acid sequence set forth in SEQ ID NO:1 or SEQ ID NO:2, and n1 is 2 or 3 and n2 is 1.

Embodiment III-101. The compound, or a pharmaceutically acceptable salt, solvate, hydrate, isomer, or tautomer thereof, of embodiments III-97 to III-100, wherein the IL-2 polypeptide or the bio-active homolog polypeptide thereof comprises the amino acid sequence set forth in SEQ ID NO:2.

Embodiment III-102. The compound, or a pharmaceutically acceptable salt, solvate, hydrate, isomer, or tautomer thereof, of any one of embodiments III-24 to III-34, III-36 to III-48, or III-54 to III-57, wherein $X_2$ is $X_2$b, wherein $X_{2b}$ is a linker that is bound to one Cys residue on $X_1$, and n is n1, wherein n1 corresponds to the number of $X_{2b}$ moieties bound to $X_1$.

Embodiment III-103. The compound, or a pharmaceutically acceptable salt, solvate, hydrate, isomer, or tautomer thereof, of any one of embodiments III-24 to III-34, III-36 to III-48, or III-54 to III-57, wherein $X_2$ is $X_{2c}$, wherein $X_{2c}$ is a linker that is bound to two different Cys residues on $X_1$, wherein n is n2, wherein n2 corresponds to the number of $X_{2c}$ moieties bound to $X_1$.

Embodiment III-104. The compound, or a pharmaceutically acceptable salt, solvate, hydrate, isomer, or tautomer thereof, of any one of embodiments III-1 to III-14, wherein $X_3$ is Pevonedistat.

Embodiment III-105. The compound, or a pharmaceutically acceptable salt, solvate, hydrate, isomer, or tautomer thereof, of any one of embodiments III-24 to III-43, wherein $X_3$ is Pevonedistat.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Synthesis of Compounds

The compounds of the present disclosure can be synthesized using techniques and materials known to those of skill in the art. Starting materials for the compounds of the disclosure may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Aspin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the disclosure may include one or more steps of protection and deprotection (e.g., the formation and removal of acetal groups). In addition, the synthetic procedures disclosed herein can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance (1H and 13C NMR), infrared and ultraviolet spectroscopy ("IR" and "UV"), X-ray crystallography, elemental analysis ("EA"). HPLC and mass spectroscopy ("MS") can be used for identification, quantitation and purification as well.

In certain aspects, such as for the production of bioactive polypeptides or hormones utilized in the disclosure or for evaluating the biological acitivties of the compounds of the disclosure (e.g., a compound of Formula (I), (II), or (III)), or pharmaceutically acceptable salts, hydrates, solvates, isomers, or tautomers thereof, the practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature: "*Molecular Cloning: A Laboratory Manual*," second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*," (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Although the schemes herein illustrate specific starting materials and products, those having ordinary skill in the art will understand that many substitution patterns can be made using known methods and materials in combination with the teachings herein.

Synthetic Example 1: Traceless Ammonium Linker Synthesis

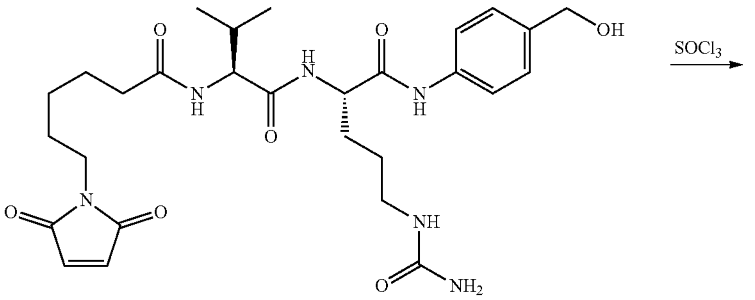

7

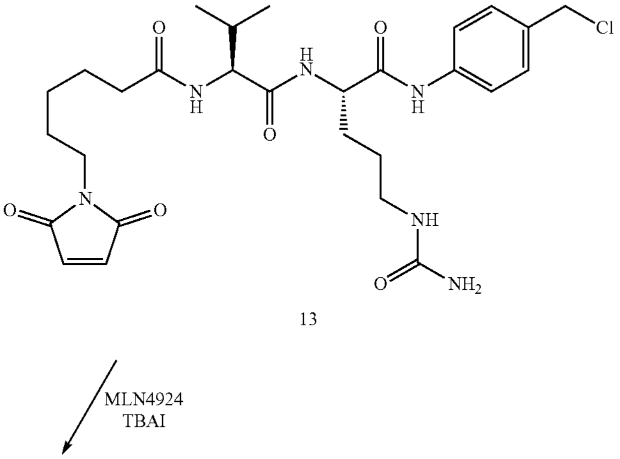

13

-continued

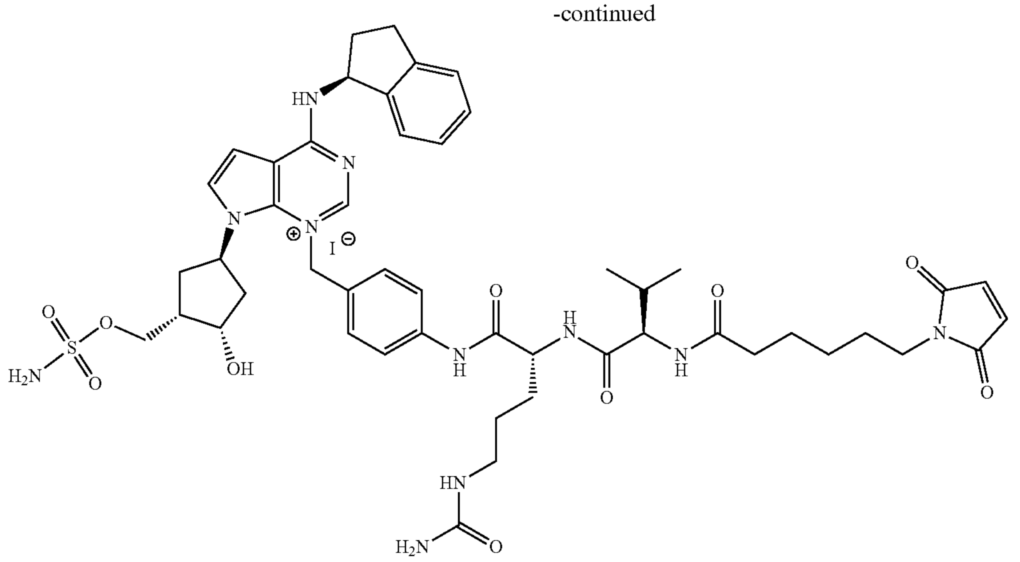

Synthesis of N—((S)-1-(((S)-1-((4-(chloromethyl)phenyl)amino)-1-oxo-5-ureidopentan-2-yl)amino)-3-methyl-1-oxobutan-2-yl)-6-(2,5-dioxo-2,5-dihydro-1H-pyrrol-1-yl) hexanamide 13: Compound 7 (800 mg, 1.39 mmol) was combined with DMF (4 mL) and heated at 80° C. until the solution was homogeneous. After 15 minutes, the reaction mixture was allowed to cool to room temperature and was subsequently cooled to 0° C. To this solution was added thionyl chloride (113 µL, 1.54 mmol) dropwise. The reaction mixture was stirred for 30 minutes at 0° C., and then slowly quenched with ice cold water to form a solid, which was filtered and collected 380 mg. The filtrate was evaporated to dryness and titurated with ethyl ether to give an additional 400 mg of product for a 96% yield. MS (ESI): m/e 590.3 (MH)+, 591, 592.

Synthesis of 4-(((S)-2,3-dihydro-1H-inden-1-yl)amino)-1-(4-((R)-2-((R)-2-(6-(2,5-dioxo-2,5-dihydro-1H-pyrrol-1-yl) hexanamido)-3-methylbutanamido)-5-ureidopentanamido)benzyl)-7-((1R,3S,4S)-3-hydroxy-4-((sulfamoyloxy) methyl) cyclopentyl)-7H-pyrrolo[2,3-d]pyrimidin-1-ium: To a solution of compound 13 (70.3 mg, 0.119 mmol) and MLN 4924 (50.5 mg, 0.113 mmol) in DMF (1.0 mL) was added tetrabutylammonium iodide (20 mg, 0.062 umol) and DIPEA (47 µL, 0.27 mmol). The reaction mixture was stirred at 40° C. for 48 hours. The solvent was evaporated to dryness and the product was purified by flash silica gel chromatography to give 15 mg of the desired product for a 11% yield.

Synthetic Example 2: Glucuronide Linker Synthesis

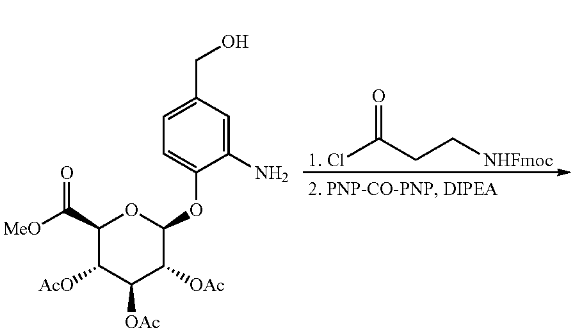

-continued

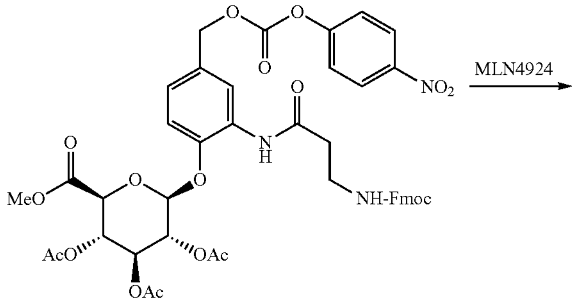

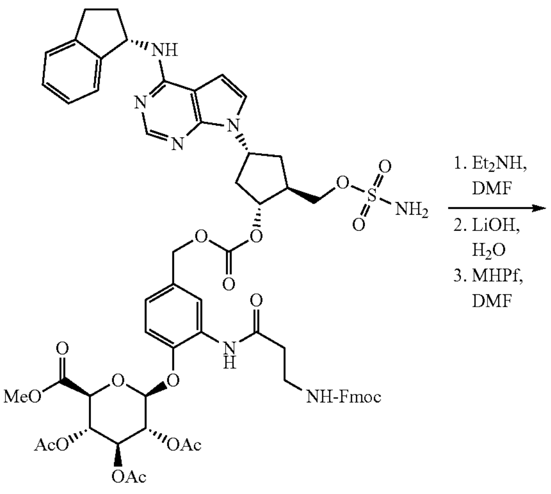

-continued

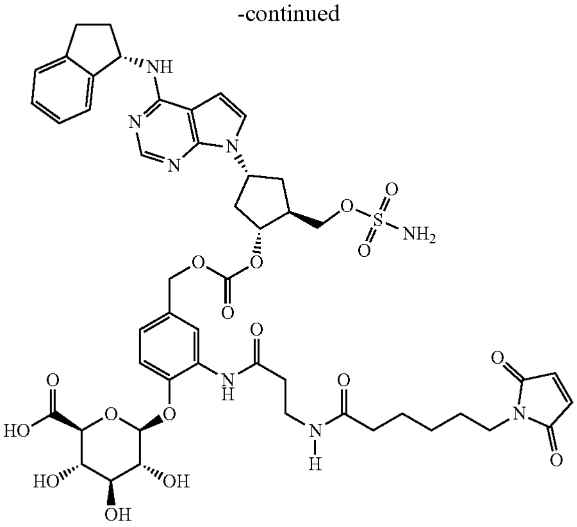

The amino alcohol was reacted with the acid chloride of Fmoc-β-alanine to selective form the Fmoc protected amino amide of the glucuronide. The alcohol can be activated with the formation of the 4-nitrophenyl carbonate using the bis-4-nitrophenyl carbonate. The reaction with the drug payload can result in the attachment of the drug to the glucuronide through a carbonate linkage. Deprotection of the Fmoc group, followed by hydrolysis of the acetates and formation of the amide bond to the maleimide linker, results in a compound ready for conjugation to available cysteine residues.

Synthetic Example 3: Non-Cleavable Cysteine Conjugation

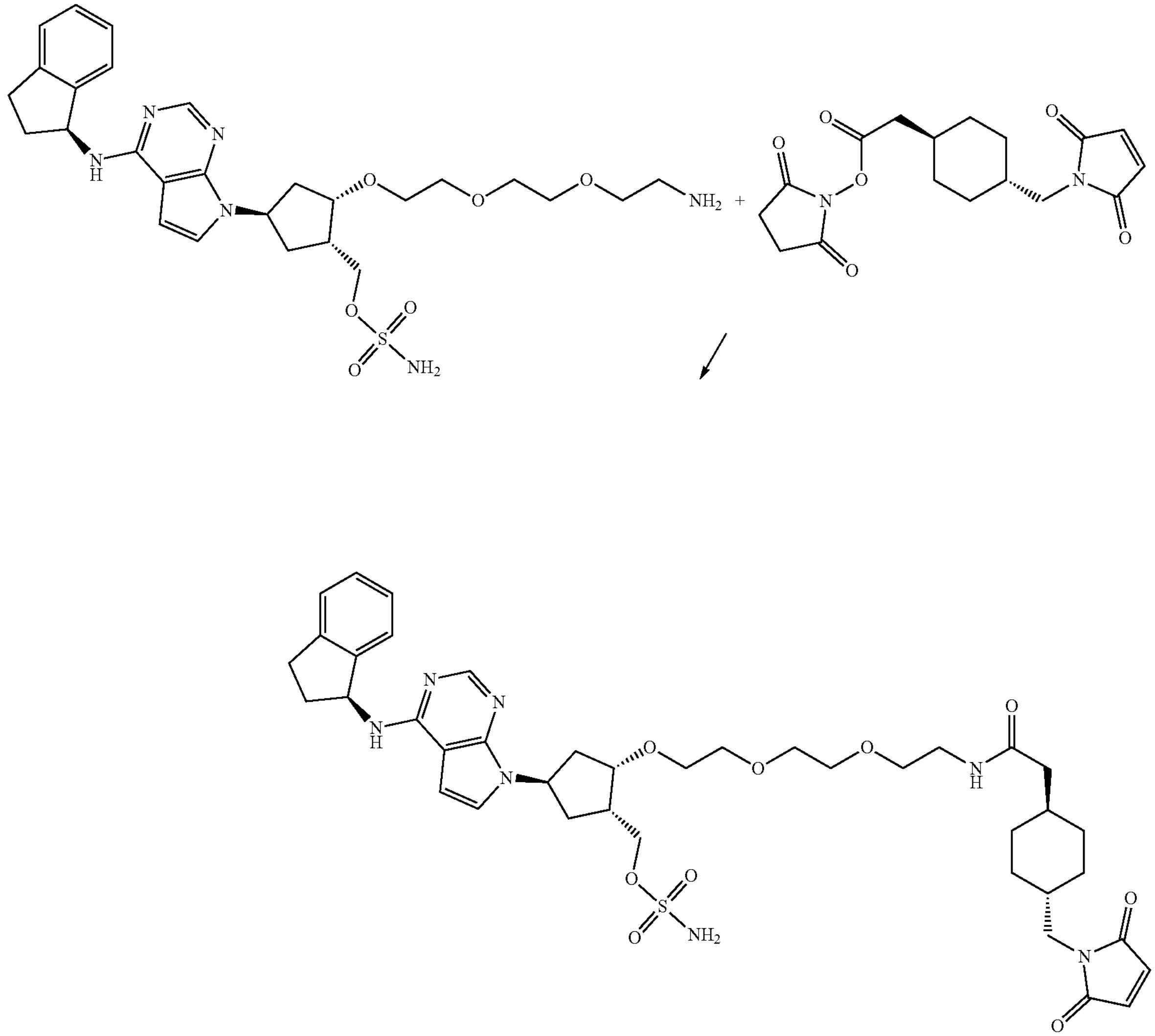

The hydroxy group on MLN4924 can be deprotonated with base and reacted with 1-azido-2-(2-(2-chloroethoxy) ethoxy) ethane, resulting in a compound that can undergo reduction to produce a derivative of MLN4924 that has an amino glycol side chain. The amino glycol side chain can react with SMCC to produce a non-cleavable linkage of MLN4924. Cysteine residues of proteins can add to the maleimide portion of this compound leading to the bioconjugation of a non-cleavable drug conjugate.

Synthetic Example 4: Non-Cleavable Cysteine Conjugation

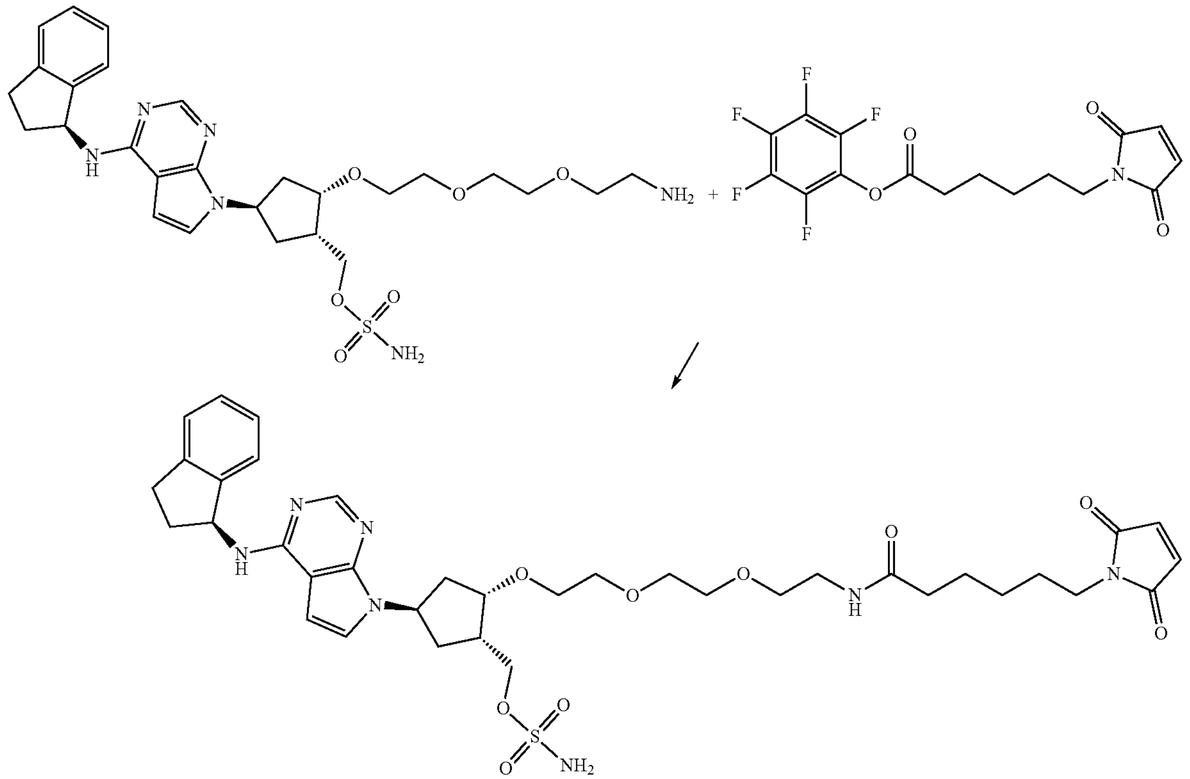

In a similar fashion to Synthetic Example 3, the same amino-glycol derivative of MLN4924 can react with the perfluorophenyl 6-(2,5-dioxo-2,5-dihydro-1H-pyrrol-1-yl) hexanoate to give the hexanamide linkage to the drug payload. This is another example of a non-cleavable linker that can used to attach cysteines of proteins of interest.

Synthetic Example 5: General Synthesis of Linkers

Linker 1

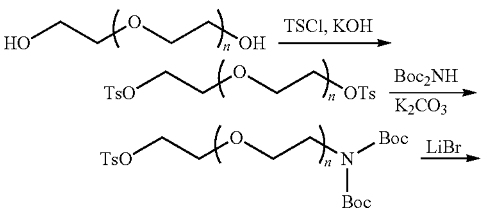

-continued

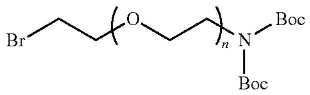

n is 1, 2, 3, 4, 5, 6, 7, 8, 9, or 10.

The ethylene glycol was reacted with aqueous potassium hydroxide and toluenesulfonyl chloride to sulfonylate both hydroxy groups in very good yields. The resulting bis-tosylglycol was reacted with one equivalent of Di-tertbutyl-iminodicarboxylate using mild conditions to produce Bis-Boc-aminoglycol tosylate. Subsequent reaction with lithium bromide gave the corresponding Bis-Boc-aminoglycol bromide.

Linker 2

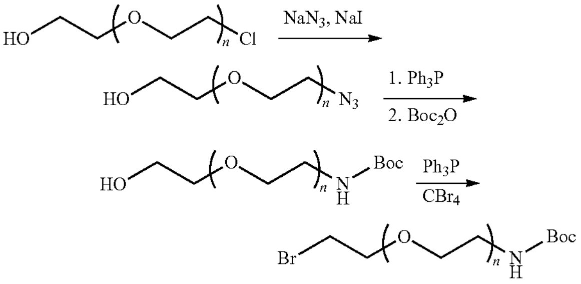

n is 1, 2, 3, 4, 5, 6, 7, 8, 9, or 10.

The synthesis of Linker 2 was initiated with the substitution of the chloride atom of chloroethoxy-ethoxyethanol with an azide group through an in situ Finklestein reaction using sodium iodide and sodium azide. Reduction of the azide was then carried out with triphenylphosphine under very mild conditions. The resulting amino group was immediately protected with a Boc group using Boc anhydride. And finally, the hydroxy group was converted into a bromide using carbon tetrabromide and triphenylphosphine.

Carbonyl Linkers

The carbonyl linkers shown below can be synthesized through the initial deprotonation of the hydroxy group on MLN4924 using BuLi at −78° C., followed by the addition of N,N'-disuccinimidyl carbonate (DSC) to form the succinimidyl carbonate of MLN4924. This intermediate is very reactive with amino groups and hydroxy groups, leading to the formation of both carbonates and carbamates. In the first example, a hydroxy displaces the N-hydroxysuccinimde leading to the formation of the carbonate. In the second example, an amino group is used for the displacement, leading to the formation of a carbamate group.

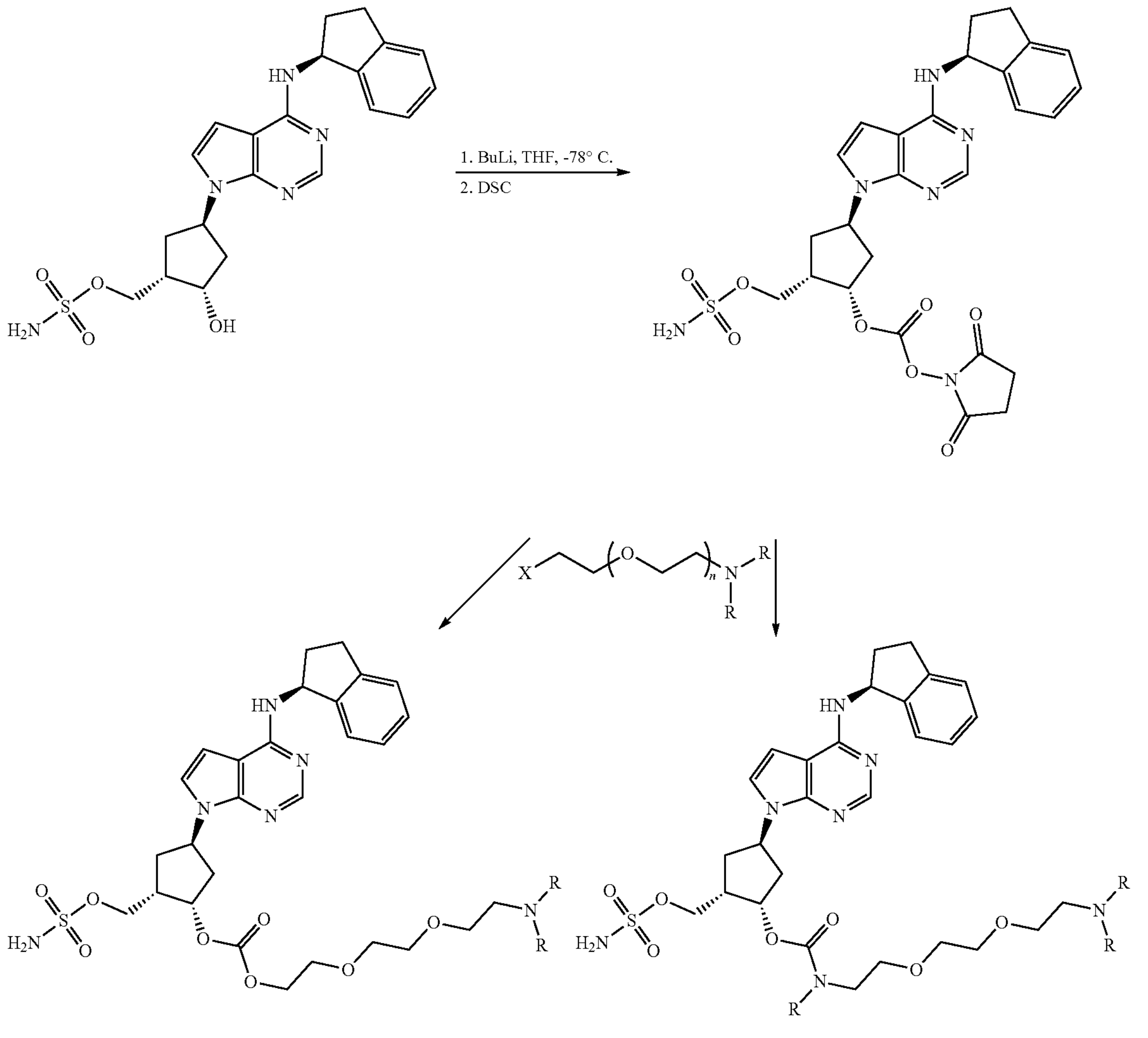

Linker 3

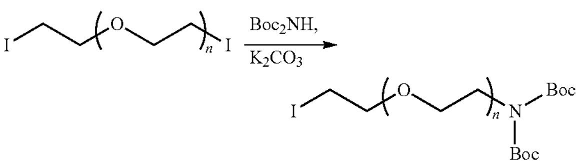

n is 1, 2, 3, 4, 5, 6, 7, 8, 9, or 10.

Linker 3 was synthesized in one step from 1,2-bis(2-iodoethoxy) ethane using Di-tert-butyliminodicarboxylate and potassium carbonate to give the product in good yield.

X is a leaving group such as halogen, mesylate, tosylate, and the like; n is 1, 2, 3, 4, 5, 6, 7, 8, 9, or 10.

Ether Linkers

For the ether linker shown below, the hydroxyl group of MLN4924 was again deprotonated with a strong base and reacted with a protected amino glycol side chain with a good leaving group. The hydroxy anion reacts with the side chain through a substitution reaction and forming the ether linkage. The amino protection groups are then removed under mild conditions. The amino group can react with a variety of reactions to attach the drug linkers.

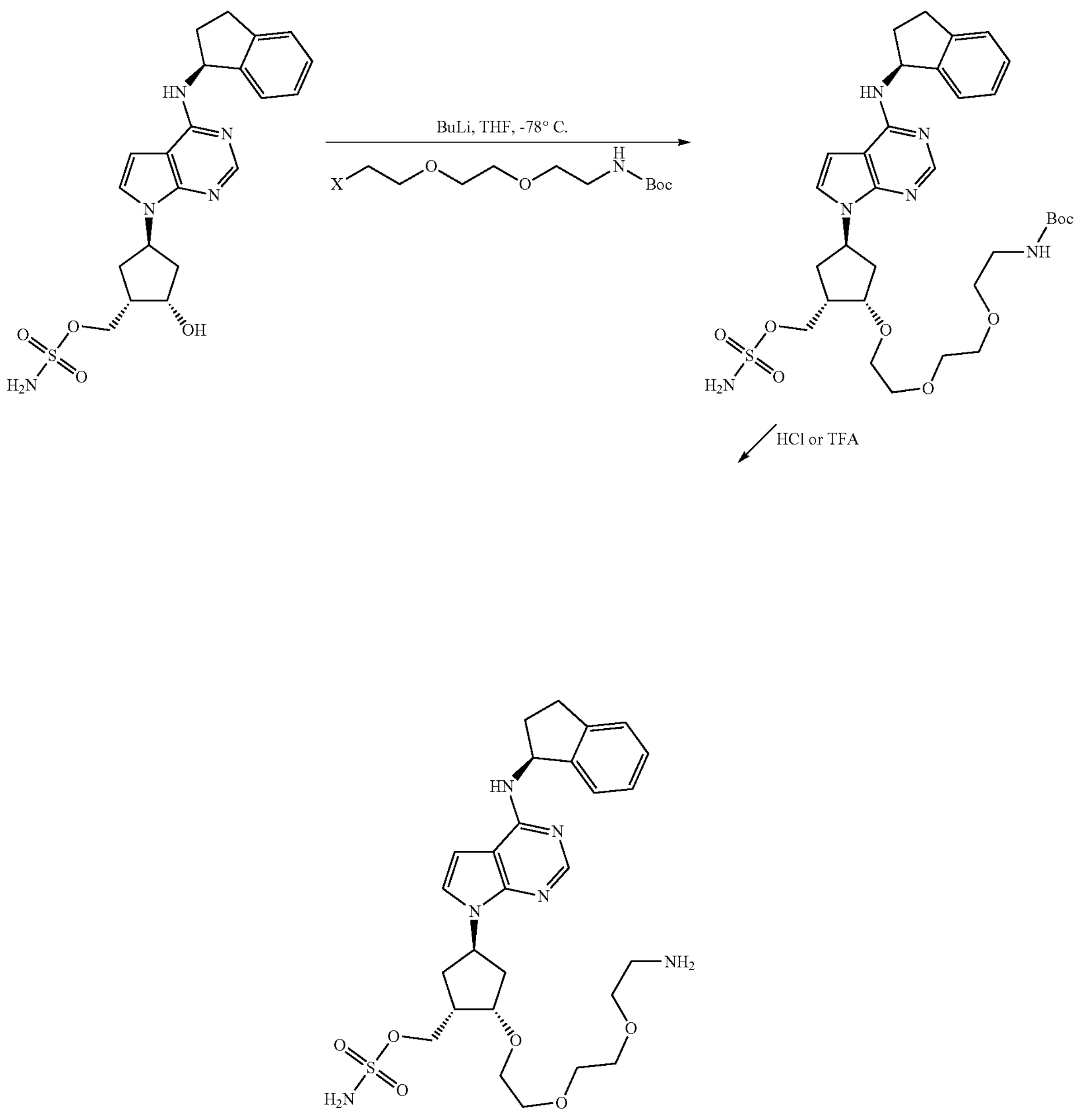
X is a leaving group such as halogen, mesylate, tosylate, and the like.
Cleavable Linker 1
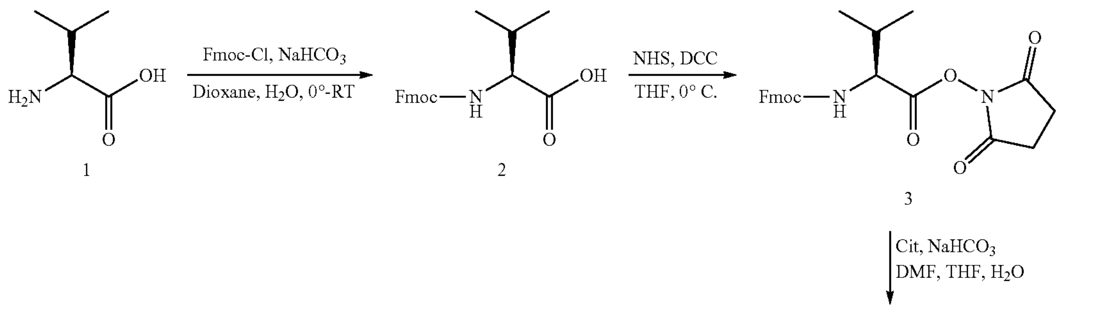

-continued

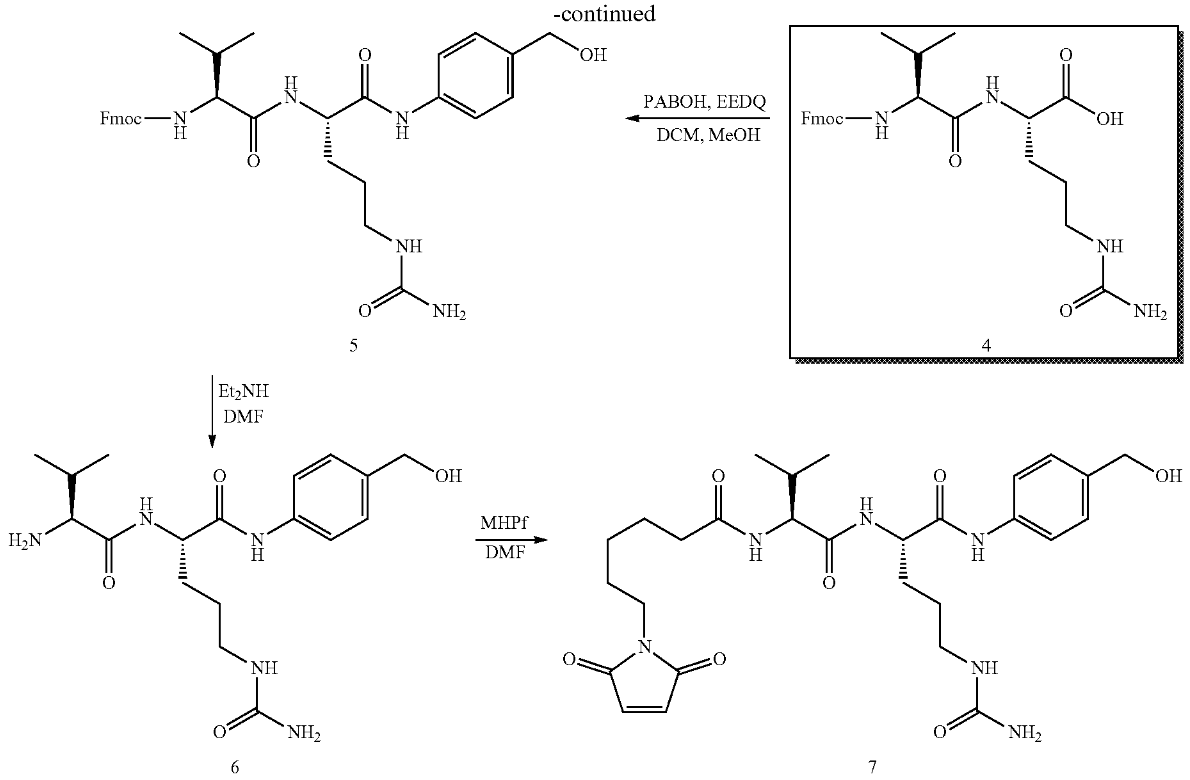

5 4 6 7

Synthesis of Fmoc-Valine 2: The valine (5.0 g, 42.7 mmol) was combined with water (100 mL) and dioxane (100 mL) and stirred rapidly as solid $NaHCO_3$ (71.8 g, 85.4 mmol) was added in portions. The resulting mixture was stirred rapidly and cooled to 0° C. To this mixture was added solid Fmoc chloride (12.2 g, 46.9 mmol) in portions, keeping the reaction temperature below 5° C. The resulting mixture was stirred at 0° C. for 90 minutes was then allowed to warm to room temperature overnight.

The resulting mixture was acidified to pH 2.0 with 1.0 M HCl and extracted with EtOAc. The combined organic layers were dried over $MgSO_4$, filtered and evaporated to give a residue. The residue was purified by gravity chromatography with EtOAc/Hexanes (25-40%) to give a white solid in 10.1 g for a 70% yield.

Synthesis of 2,5-dioxopyrrolidin-1-yl(((9H-fluoren-9-yl) methoxy) carbonyl)-L-valinate 3: Fmoc-Val (1.0 g, 2.95 mmol) was combined with N-hydroxy succinimide (510 mg, 4.43 mmol) and dissolved in THF (10 mL). The resulting solution was cooled to 0° C. and a solution of DCC (609 mg, 12.95 mmol) dissolved in THF (3 mL) was added. The reaction mixture was maintained at 0° C. for 2 hours, then allowed to warm to room temperature overnight.

The mixture was filtered and the solid was washed with THF. The resulting filtrate was dried over $MgSO_4$, filtered, and evaporated to dryness. The residue was purified with gravity chromatography using 40% EtOAc/Hexanes to obtain 1.23 g for a 96% yield. Calc. 436.46; MS (ESI): m/e $(M+Na)^+$, 459.

Synthesis of(S)-2-((S)-2-((((9H-fluoren-9-yl) methoxy) carbonyl)amino)-3-methylbutanamido)-5-ureidopentanoic acid 4: Citrulline (420 mg, 2.41 mmol) was combined with solid $NaHCO_3$ (200 mg, 2.38 mmol) and dissolved in water (6.0 mL). To this mixture was added a solution of compound 3 (1.0 g, 2.29 mmol) in DMF (6 mL). The mixture was stirred for 5 minutes and THF (5 mL) was added and the reaction mixture was stirred overnight at room temperature.

A 15% Citric acid solution (11.5 mL) was added to the reaction mixture with stirring and a precipitate formed. The mixture was extracted with a 9:1 mixture of EtOAc/i-PrOH (3x15 mL). the combined organic layers were washed with brine twice, dried over $MgSO_4$, filtered and evaporated to dryness to give a residue. The residue was sonicated with ether and iterated. A white solid formed, which was collected by filtration and dried under vacuum to give 1.0 g for a 87% yield. MS (ESI): m/e 496.56 (MH)+, 497, $(M+Na)^+$, 519.

Synthesis of (9H-fluoren-9-yl)methyl((S)-1-(((S)-1-((4-(hydroxymethyl)phenyl)amino)-1-oxo-5-ureidopentan-2-yl) amino)-3-methyl-1-oxobutan-2-yl) carbamate 5: The Fmoc-Val-Cit 4 (1.0 g, 2.01 mmol) and p-aminobenzyl alcohol (492 mg, 4.0 mmol) were dissolved in a 1:1 solution of dichloromethane/methanol (30 mL). To this mixture was added N-Ethoxycarbonyl-2-ethoxy-1,2-dihydroquinoline (992 mg, 4.0 mmol). The reaction flask was wrapped in foil and the hood lights were turned off, while the reaction was stirred at room temperature for 48 hours.

The reaction mixture was evaporated to dryness and the resulting solid was titurated with ether. The suspension was stirred overnight in ether, then filtered to give a yellow solid. The solids were again washed with ether to give 990 mg for a 87% yield. MS (ESI): m/e 572.66 (MH)+, 573, $(M+Na)^+$, 595.

Synthesis of(S)-2-((S)-2-amino-3-methylbutanamido)-N-(4-(hydroxymethyl)phenyl)-5-ureidopentanamide 6: Compound 5 (4.0 g, 6.65 mmol) was dissolved in DMF (80 mL) and diethylamine (14 mL) was added. The reaction mixture was stirred for 24 hours.

The reaction mixture was evaporated to dryness to give a residue. The residue was titurated with dichloromethane to give a light brown solid in 2.5 g for a quantitative yield. The compound was used in the next step without further purification.

Synthesis of 6-(2,5-dioxo-2,5-dihydro-1H-pyrrol-1-yl)-N—((S)-1-(((S)-1-((4-(hydroxymethyl)phenyl)amino)-1-oxo-5-ureidopentan-2-yl)amino)-3-methyl-1-oxobutan-2-yl) hexanamide 7: Compound 6 (400 mg, 1.05 mmol) was combined with 6-maleimidohexannoic acid pentylfluorophenyl ester, MHPf (437 mg, 1.15 mmol) and DMF (10 mL) was added. The resulting mixture was stirred at room temperature overnight.

The solvent was evaporated from the reaction mixture to leave a residue. The residue was titurated with ether and the resulting slid was filtered. The solid was washed with ethyl ether and dried under vacuum to give a solid in 570 mg for a 95% % yield. MS (ESI): m/e 572.66, (MH)+, 573, $(M+Na)^+$, 595.

Synthesis of 11-b

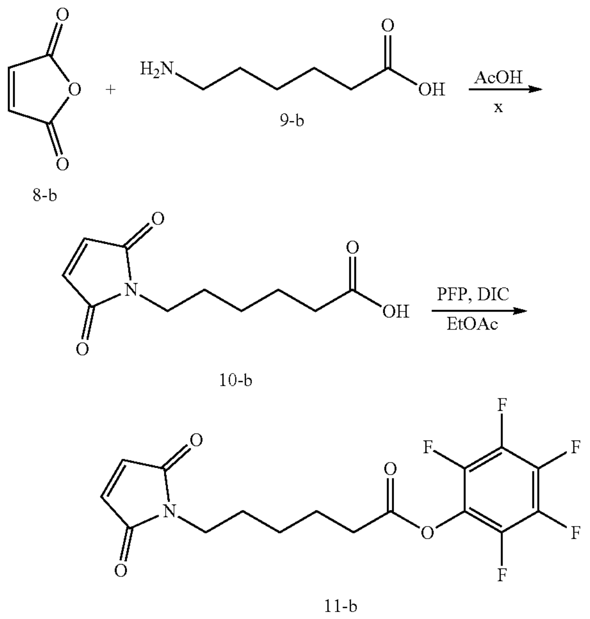

8-b 9-b 10-b 11-b

Synthesis of 6-(2,5-dioxo-2,5-dihydro-1H-pyrrol-1-yl) hexanoic acid 10-b: Maleic anhydride (5.0 g, 50.98 mmol) was combined with 6-aminocaproic acid (6.69 g, 50.98 mmol) and acetic acid (45 mL) was added. The resulting mixture was heated at 120° C. overnight. (Initially, the reaction mixture became a clear light orange solution followed by the formation of a white slurry).

The orange solution was allowed to cool to room temperature. Toluene (100 mL) was added and the reaction mixture was evaporated to dryness. The Toluene azeotrope was repeated two more times. The resulting mixture was dissolved in $CH_2Cl_2$ and washed with water followed by brine. The organic layer was dried over $MgSO_4$, filtered and evaporated to give an orange solid in quantitative yield.

Synthesis of perfluorophenyl 6-(2,5-dioxo-2,5-dihydro-1H-pyrrol-1-yl) hexanoate 11-b: Carboxylic acid 10-b (4.00 g, 17.6 mmol) and pentafluorophenol (3.56 g, 19.36 mmol) were dissolved in EtOAc (70 mL) and cooled to 0° C. To this solution was added a solution of DCC (4.0 g, 19.36 mmol) in EtOAc (25 mL). The solution was stirred at 0° C. for 2 hours, then allowed to warm to room temperature overnight.

The reaction mixture was evaporated to dryness to give a residue. The residue was purified by flash silica gel chromatography using 100% $CH_2Cl_2$ to give 5.98 g for a 90% yield.

Cleavable Linker 2

12-b

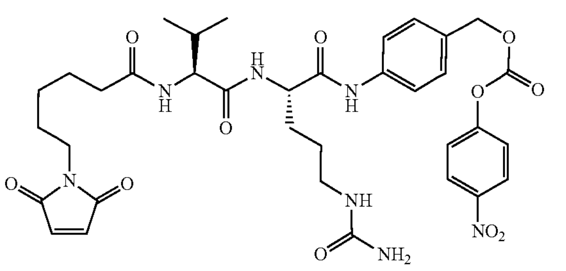

Synthesis of 4-((S)-2-((S)-2-(6-(2,5-dioxo-2,5-dihydro-1H-pyrrol-1-yl) hexanamido)-3-methylbutanamido)-5-ureidopentanamido)benzyl (4-nitrophenyl) carbonate 12-b: Compound 7 (1.3 g, 2.16 mmol) and bis(4-nitrophenyl) carbonate (1.34 g, 4.34 mmol) were combined and dissolved in DMF (6 mL). To this solution was added DIPEA (0.75 mL, 4.35 mmol). The mixture was stirred overnight at room temperature. The reaction mixture was evaporated to dryness and the residue was washed with ether.

Cleavable Linker 3

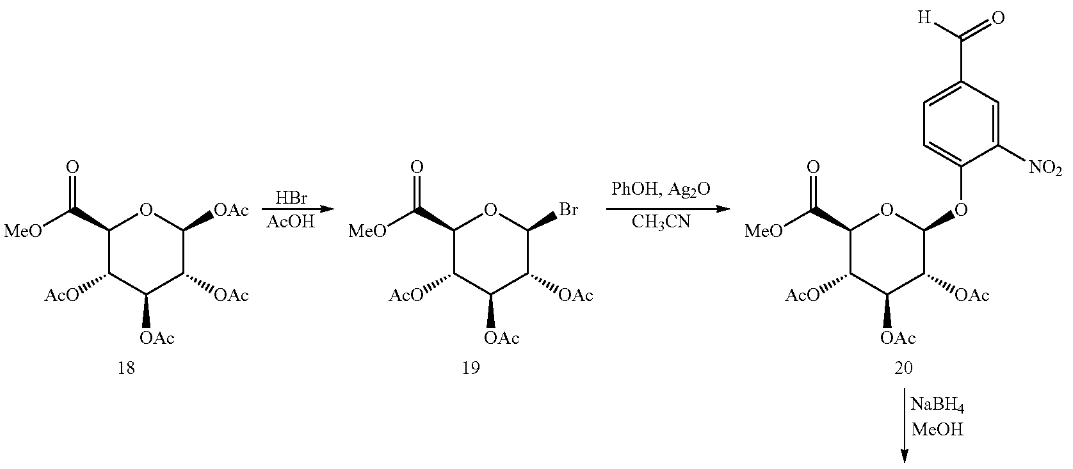

18 19 20

-continued

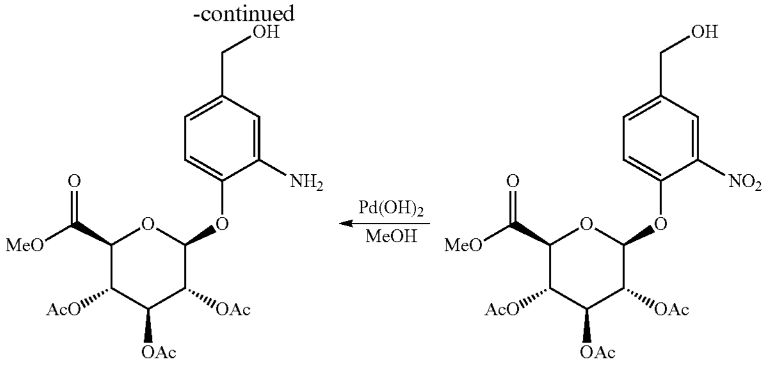

22 21

Synthesis of (2R,3R,4S,5S,6S)-2-bromo-6-(methoxycarbonyl)tetrahydro-2H-pyran-3,4,5-triyl triacetate 19: (2S,3R,4S,5S,6S)-6-(methoxycarbonyl)tetrahydro-2H-pyran-2,3,4,5-tetrayl tetraacetate 18 (2.0 g, 5.31 mmol) was dissolved in $CH_2Cl_2$ (20 mL) and cooled to 0° C. To this solution was added a solution of 33% HBr in AcOH (10 mL) dropwise over 10 minutes. The mixture was stirred at 0° C. for 30 minutes and then allowed to warm to room temperature. The reaction mixture was diluted with $CH_2Cl_2$ and washed with sodium bicarbonate solution, followed by brine. The organic layer was dried over $MgSO_4$, filtered and evaporated to give an orange syrup. Toluene was added and the residue evaporated to dryness three more times. The same azeotroping process was repeated with ether to give a light beige solid in 1.75 g for a 82% yield.

Synthesis of (2S,3R,4S,5S,6S)-2-(4-formyl-2-nitrophenoxy)-6-(methoxycarbonyl)tetrahydro-2H-pyran-3,4,5-triyl triacetate 20: The above bromide (2.0 g, 5.04 mmol), 4-hydroxy-3-nitrobenzaldehyde (822 mg, 4.92 mmol), and silver oxide (1.5 g, 6.47 mmol) were combined with acetonitrile (25 mL). the resulting mixture was stirred overnight in the dark.

The reaction mixture was filtered through celite and the solids were washed with acetonitrile. The filtrate was evaporated to ⅓ the original volume and EtOAc (150 mL) was added. To the organic layer was added saturated sodium bicarbonate and the mixture was stirred for 30 minutes. The reaction mixture was filtered through celite and the organic layer was washed with saturated sodium bicarbonate and brine. The organic layer was dried over $MgSO_4$, filtered and evaporated to give a yellow solid in 1.75 g for a 73.5% yield. MS (ESI): m/e 483.4 (MH)+, 506

Synthesis of (2S,3R,4S,5S,6S)-2-(4-(hydroxymethyl)-2-nitrophenoxy)-6-(methoxycarbonyl)tetrahydro-2H-pyran-3,4,5-triyl triacetate 21: The aryl aldehyde (1.5 g, 3.10 mmol) above was dissolved in $CH_2Cl_2$ (15 mL) and IPA (3.5 mL). The resulting mixture was cooled to 0° C. and solid $NaBH_4$ (71 mg, 1.87 mmol) was added in three portions over 10 minutes. After the addition, temperature was maintained at 0° C. for 1 hour. The reaction was poured into ice water (40 mL) which was followed by $CH_2Cl_2$ (200 mL). The reaction mixture was stirred for 30 minutes and the layers were separated. The aqueous layer was back extracted with $CH_2Cl_2$ and the combined organic layers were dried over $MgSO_4$, filtered and evaporated to give an oily solid. Toluene was added to the mixture and evaporated to dryness two more times to give 1.35 g of a white solid for a 90% yield. MS (ESI): m/e 485.4, $(M+Na)^+$, 508.

Synthesis of (2S,3R,4S,5S,6S)-2-(2-amino-4-(hydroxymethyl) phenoxy)-6-(methoxycarbonyl)tetrahydro-2H-pyran-3,4,5-triyl triacetate 22: The nitro-benzyl alcohol (1.0 g, 2.06 mmol) from above was combined with 10% Pd/C (50 mg) and EtOAc (50 mL) was added. Hydrogen gas in a balloon was added and the mixture was stirred for three days at room temperature.

The hydrogen atmosphere was evacuated and replaced with nitrogen three times. The Pd/C from the reaction was filtered through celite and the filtrate was evaporated to dryness. Isolated a quantitative yield of 937 mg as a solid. MS (ESI): m/e 455.4, (MH)+, 456, $(M+Na)^+$, 478.

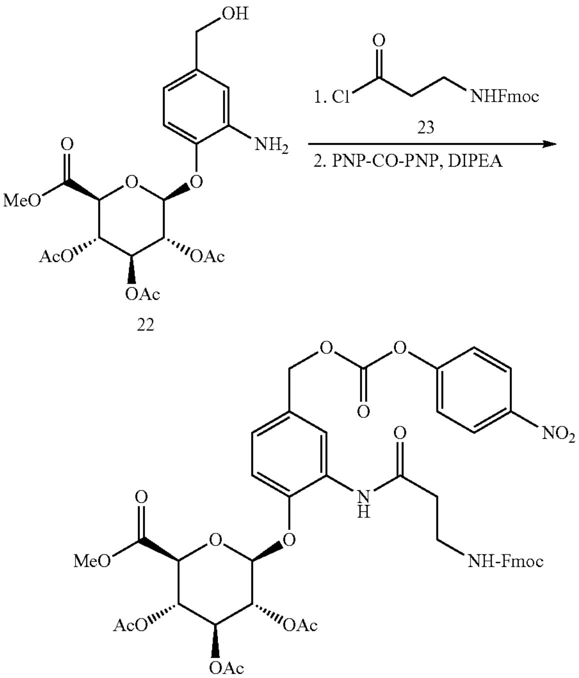

22

24

Synthesis of (9H-fluoren-9-yl)methyl (3-chloro-3-oxopropyl) carbamate 23: Fmoc-β-alanine (3.5 g, 11.2 mmol) was suspended in $CH_2Cl_2$ (40 mL) and thionyl chloride (6.0 mL, 82.6 mmol) was added. The resulting mixture was sonicated at room temperature under an atmosphere of nitrogen. After 2 hours, the reaction was evaporated to dryness to give a residue. Toluene was added to the residue and the mixture was evaporated to dryness 2 more times to give a 95% yield of a white solid as product.

Synthesis of (2S,3R,4S,5S,6S)-2-(2-(3-((((9H-fluoren-9-yl) methoxy) carbonyl)amino) propanamido)-4-((((4-nitrophenoxy) carbonyl)oxy)methyl) phenoxy)-6-(methoxycarbonyl)tetrahydro-2H-pyran-3,4,5-triyl triacetate 24: The aniline (1.0 g, 2.2 mmol) was dissolved in $CH_2Cl_2$ (20 mL) and DIPEA (0.766 mL, 4.4 mmol) was added. The mixture was stirred for 5 minutes and the (9H-fluoren-9-yl)methyl (3-chloro-3-oxopropyl) carbamate (890 mg, 2.7 mmol) was added. The mixture was stirred for 30 minutes and quenched with aqueous saturated $NaHCO_3$. The resulting mixture was extracted with EtOAc and the combined organic layers were dried with $MgSO_4$, filtered, and evaporated to give a residue. The residue was purified by flash silica gel chromatography using 0 to 100% EtOAc/Hexanes. Isolated 1.43 g of a yellow sticky solid for an 87% yield. MS (ESI): m/e 748.7, (MH)+, 749, $(M+Na)^+$, 771.

The benzyl alcohol (1.5 g, 2.00 mmol) was dissolved in DMF (10 mL) and DIPEA (0.52 mL, 3.01 mmol) was added. To this mixture was added a solution of bis(4-nitrophenyl) carbonate (1.22 g, 4.38 mmol) in DMF (10 mL) slowly through dropwise addition. The resulting mixture was allowed to stir at room temperature overnight. The reaction was evaporated to dryness and purified by flash silica gel chromatography.

Synthetic Example 6: Synthesis of an Ether Linker

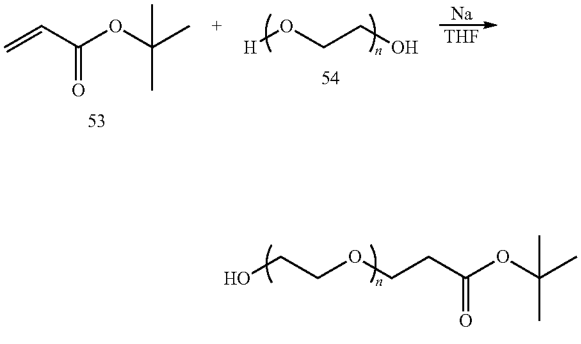

53 54 55

Synthesis of tert-butyl 3-(2-(2-(2-hydroxyethoxy) ethoxy) ethoxy) propanoate 55: Triethylene glycol (26.7 g, 177.8 mmol) was dissolved in dry THF (125 mL) and sodium metal (50 mg, 2.18 mmol) was added. The resulting mixture was stirred for 3 hours until all the sodium was dissolved. To the light-yellow solution was added tert-butyl-acrylate (12.0 mL, 82.0 mmol) and the resulting mixture was stirred at room temperature overnight.

The organic solvent was removed by evaporation and brine was added to the resulting residue and extracted with EtOAc. The combined organic layers were dried over $MgSO_4$, filtered and evaporated to dryness to give 15.8 g (69.2% yield) of a clear oil, which was used without further purification.

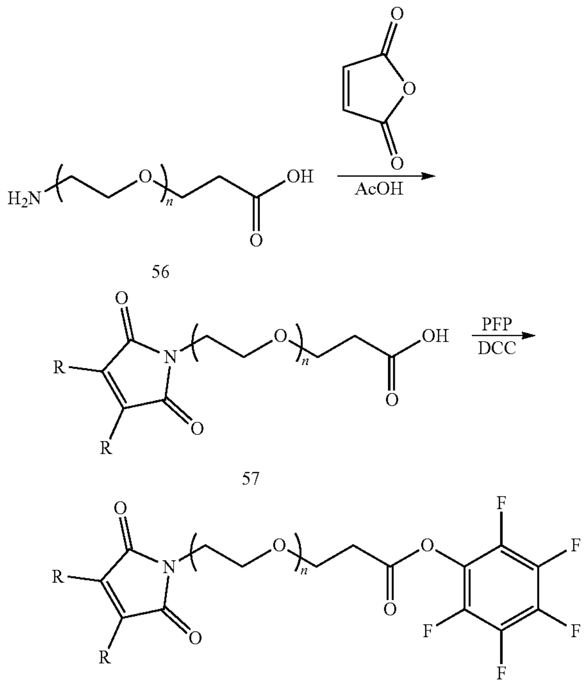

56 57 58

R is H or Br; n is 1, 2, 3, 4, 5, 6, 7, 8, 9, or 10.

Synthesis of 3-(2-(2-(2-(2,5-dioxo-2,5-dihydro-1H-pyrrol-1-yl) ethoxy) ethoxy) ethoxy) propanoic acid 57A: Maleic anhydride (111 mg, 1.13 mmol, R is H) was combined with 3-(2-(2-(2-aminoethoxy) ethoxy) ethoxy) propanoic acid (250 mg, 1.13 mmol) and AcOH (5 mL) was added. The resulting solution was heated to 105° C. overnight. The reaction was allowed to cool to room temperature and the solvent was evaporated to dryness. Toluene (5 mL) was added and the mixture was evaporated to dryness 2 more times. The reaction product was very pure and used in the next reaction without purification.

Synthesis of perfluorophenyl 3-(2-(2-(2-(2,5-dioxo-2,5-dihydro-1H-pyrrol-1-yl) ethoxy) ethoxy) ethoxy) propanoate 58A: The acid (340 mg, 1.13 mmol) was combined with pentafluorophenol (207 mg, 1.13 mmol) and dissolved in EtOAc (5 mL). The resulting mixture was cooled to 0° C. and a solution of DCC (233 mg, 1.13 mmol) in EtOAc (3 mL) was added dropwise. The reaction mixture was stirred for 2 hours at 0° C., then allowed to warm to room temperature overnight. The mixture was evaporated to dryness and the residue was purified by flash silica gel chromatography to give 230 mg a semisolid for a 44% yield.

Synthesis of 3-(2-(2-(2-(3,4-dibromo-2,5-dioxo-2,5-dihydro-1H-pyrrol-1-yl) ethoxy) ethoxy) ethoxy) propanoic acid 57B: Dibromomaleic anhydride (289 mg, 1.13 mmol, R is Br) was combined with 3-(2-(2-(2-aminoethoxy) ethoxy) ethoxy) propanoic acid (250 mg, 1.13 mmol) and AcOH (5 mL) was added. The resulting solution was heated to 105° C. overnight. The reaction was allowed to cool to room temperature and the solvent was evaporated to dryness. Toluene (5 mL) was added and the mixture was evaporated to dryness 2 more times. The reaction product was very pure and used in the next reaction without purification.

Synthesis of perfluorophenyl 3-(2-(2-(2-(3,4-dibromo-2,5-dioxo-2,5-dihydro-1H-pyrrol-1-yl) ethoxy) ethoxy) ethoxy) propanoate 58B: The acid (518.8 mg, 1.13 mmol)

was combined with pentafluorophenol (207 mg, 1.13 mmol) and dissolved in EtOAc (5 mL). the resulting mixture was cooled to 0° C. and a solution of DCC (233 mg, 1.13 mmol) in EtOAc (3 mL) was added dropwise. The reaction mixture was stirred for 2 hours at 0° C., then allowed to warm to room temperature overnight. The mixture was evaporated to dryness and the residue was purified by flash silica gel chromatography to give 298 mg a semisolid for a 42% yield.

Synthetic Example 7: Conjugation of Therapeutic Compounds to Biologically Active Polypeptides IL2-FITC Conjugate Recombinant human IL-2 (SEQ ID NO:4, Table 4) (20 μmol) and FITC-Maleimide (2 equiv.) were stirred overnight in 50 mM phosphate buffer, pH 7.4 at 21° C. The reaction mixture was purified by size exclusion chromatography using a Hitrap 5 mL desalting column and an AKTA Start chromatography system to obtain the conjugate IL2-FITC. This conjugate is the conjugate used in FIG. 7 and Biological Example 3.

IL2-Bis-VC-MLN-4924 Conjugate

Thioredoxin-IL-2 fusion protein (SEQ ID NO:2, Table 4) labeling step, 50 μM of protein was first reacted with five equivalents of maleimide-dipeptide-MLN-4924 linker (Structure A-1, Table 3) and stirred at 21° C. for 4 hours. The reaction mixture was purified by size exclusion chromatography as above and then reacted with five equivalents of tris(2-carboxyethyl) phosphine (TCEP) in 50 mM Phosphate buffer, pH 7.8 at 37° C., for 30 minutes. Then, a dibromo-maleimide-dipeptide-MLN-4924 linker (Structure A-51, Table 3) (4 equivalents) was added and the reaction was stirred at 21° C. for 24 hours. The reaction mixture was purified by size exclusion chromatography as above to yield the conjugate IL2-Bis-VC-MLN-4924. This conjugate is the 3-4:1 conjugate used in the bottom panel of FIG. 6B, in FIG. 13, in FIG. 14, and Biological Examples 2, and 9-11.

IL2-VC-MLN-4924 Conjugate

Thioredoxin-IL-2 fusion protein (SEQ ID NO:2, Table 4) labeling step, 50 μM of protein was reacted with five equivalents of maleimide-dipeptide-MLN-4924 linker (Structure A-1, Table 3) and stirred at 21° C. for 4 hours. The reaction mixture was purified by size exclusion chromatography using a Hitrap 5 mL desalting column and an AKTA Start chromatography system to obtain the conjugate IL2-VC-MLN-4924. This conjugate is the 1:1 conjugate used in the bottom panel of FIG. 6B, and Biological Example 2.

IL2-VC-MMAE Conjugate 1

Figure 8:
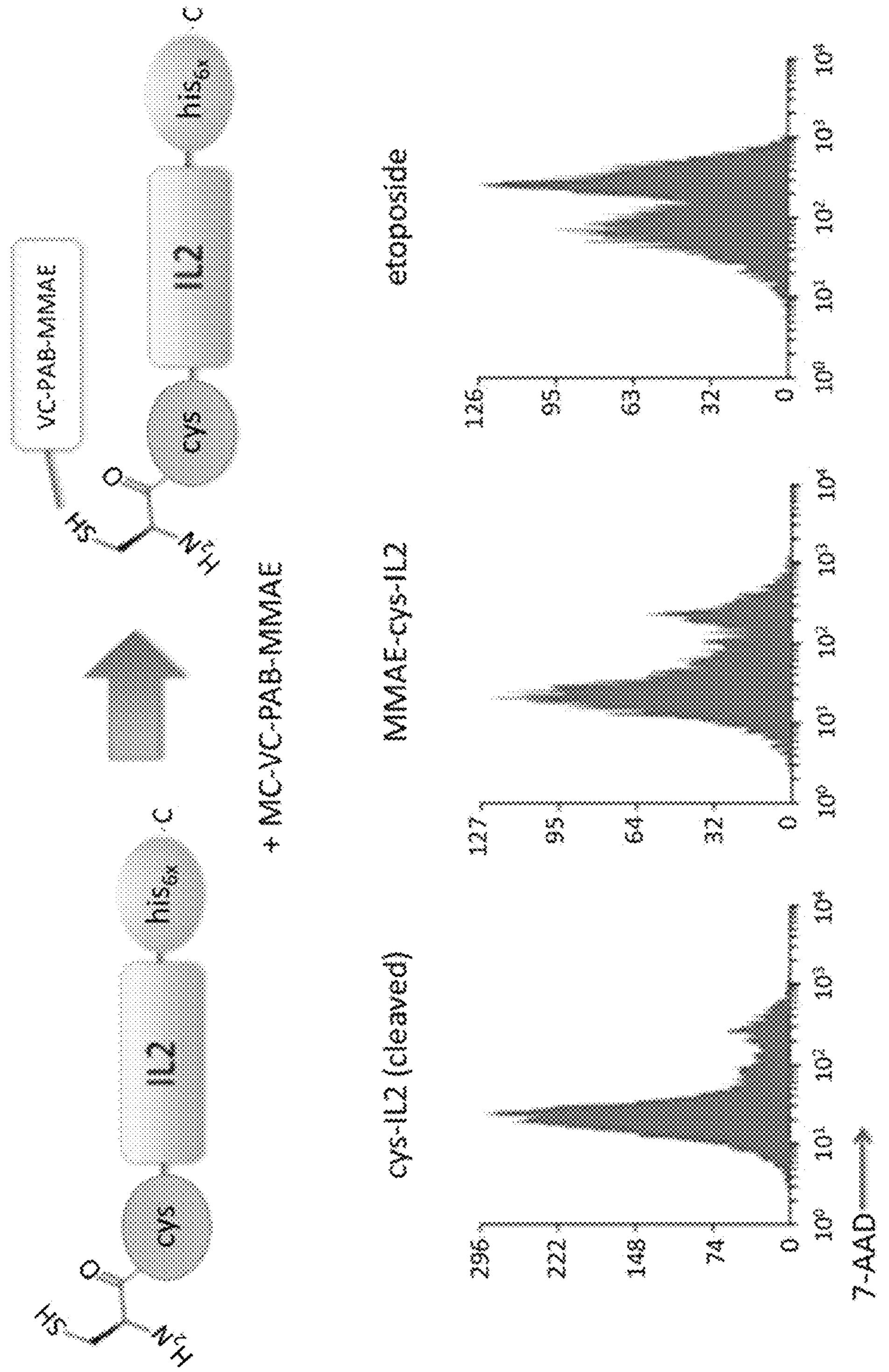
FIG. 8 illustrates targeted Treg cell death after cysteine residues of IL-2 polypeptides were conjugated to a linker comprising a cytotoxic payload, MMAE. Selective delivery of MMAE, an antimitotic agent, to target T cells was observed, with approximately 25% of cell death occurring every cell cycle. Cell death caused by treatment of the MMAE-IL-2 conjugate was compared to cell death caused by etoposide, a cancer chemotherapeutic genotoxic agent.

For IL-2 labeled with MMAE, 50 μM of protein (SEQ ID NO:4, Table 4) was first reacted with 5 equivalents of maleimide-dipeptide-MMAE linker (Structure A-32, Table 3) in phosphate buffer pH 7.4 and stirred at 21° C. for 4 hours. The reaction mixture was purified by size exclusion chromatography as above to yield the conjugate IL2-VC-MMAE. This conjugate is the 1:1 conjugate used in the bottom panel of FIG. 6A and in FIG. 8 and in Biological Examples 1 and 4.

IL2-VC-MMAE Conjugate 2

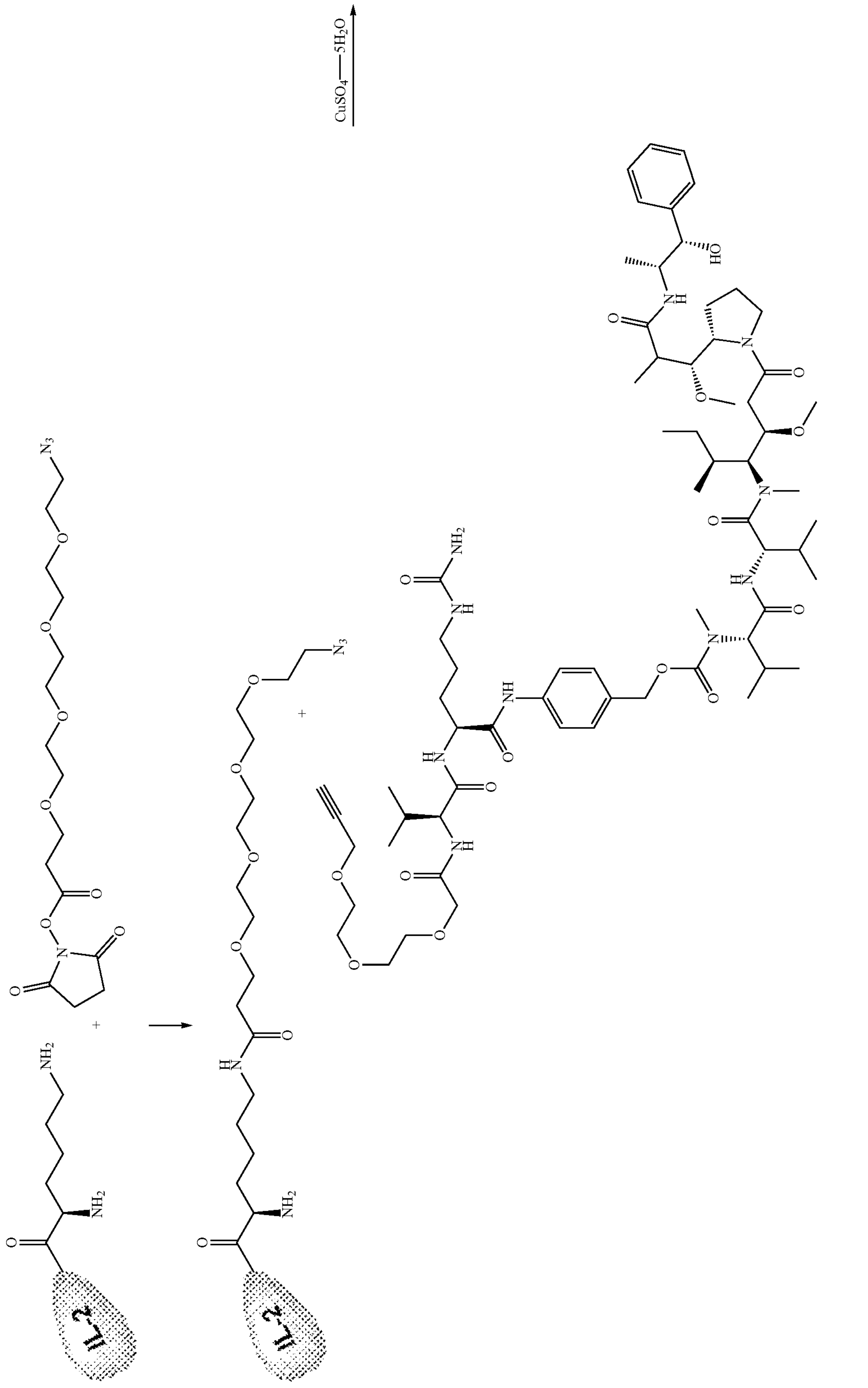
$CuSO_4$—$5H_2O$

-continued
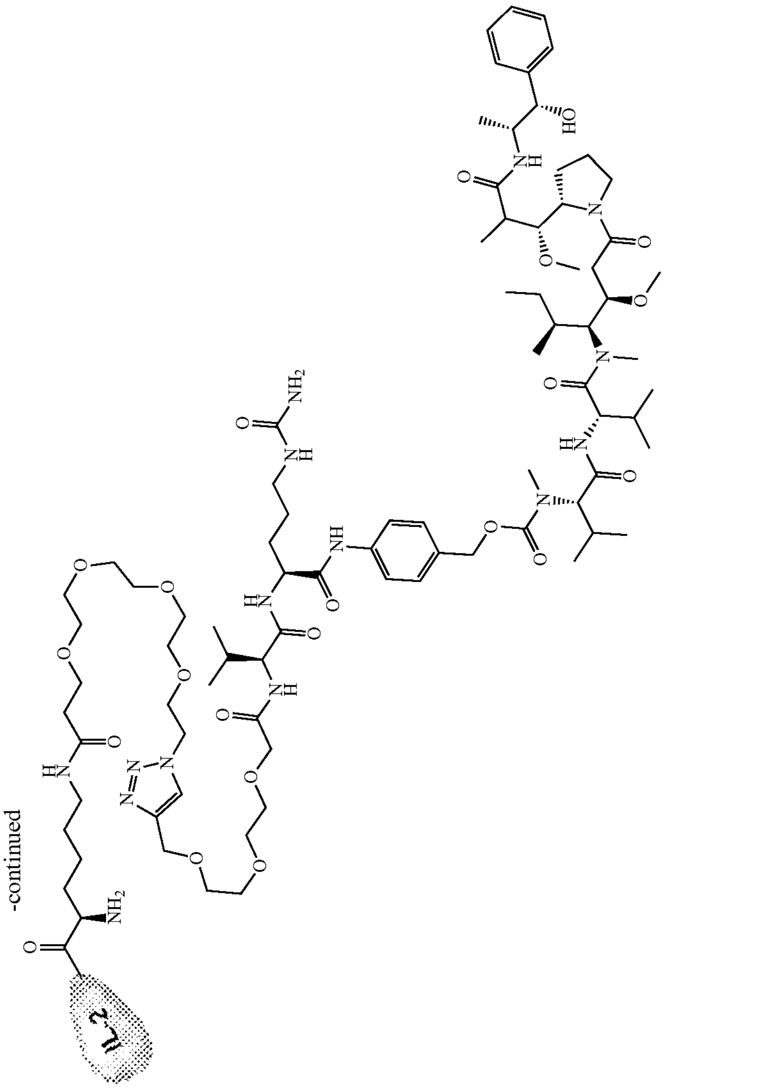

IL-2 (SEQ ID NO:4, Table 4) was prepared in PBS, with a protein concentration of 5 mg/mL. NHS-PEG4-Azide (Thermo) was prepared in DMSO as a 100 mM solution stock solution. The NHS reagent was reacted to the protein sample at a final concentration of 1 mM (15 eq.) and the reaction was incubated at room temperature for 30 minutes. Reaction was stopped by the addition of Tris-HCl at 50 mM followed by incubation on ice for 5 minutes. The whole reaction mixture was then desalted using a Hitrap desalting column in an Akta starter chromatography setup.

60 µM of the azide-derivatized IL-2 was then incubated with a 10 molar excess of a acetylene-valine-Citruline-MMAE conjugating construct (Medchem Express) at 21° C. for 16 hours in PBS buffer containing 0.5 mM of a Cu-TBTA complex and 0.5 mM of ascorbic acid. IL2-VC-MMAE was purified by size exclusion chromatography (Hiload Superdex S75 pg, GE Life Sciences). Drug to protein molar ratio was calculated as described Wakankar A, Chen Y, Gokam Y, Jacobson F S. Analytical methods for physicochemical characterization of antibody drug conjugates. *MAbs.* 2011; 3 (2): 161-72. This conjugate is the 3:1 conjugate used in the bottom panel of FIG. 6A and in Biological Example 1.

General Biological Information

IL-2 polypeptides used herein are produced in *E. coli*, using known techniques, e.g., those from "Biological activity of recombinant human interleukin-2 produced in *Escherichia coli*," Rosenberg S A, Grimm E A, McGrogan M, Doyle M, Kawasaki E, Koths K, Mark D F, 1984 Mar. 30; 223 (4643): 1412-4.

Figure 6A:
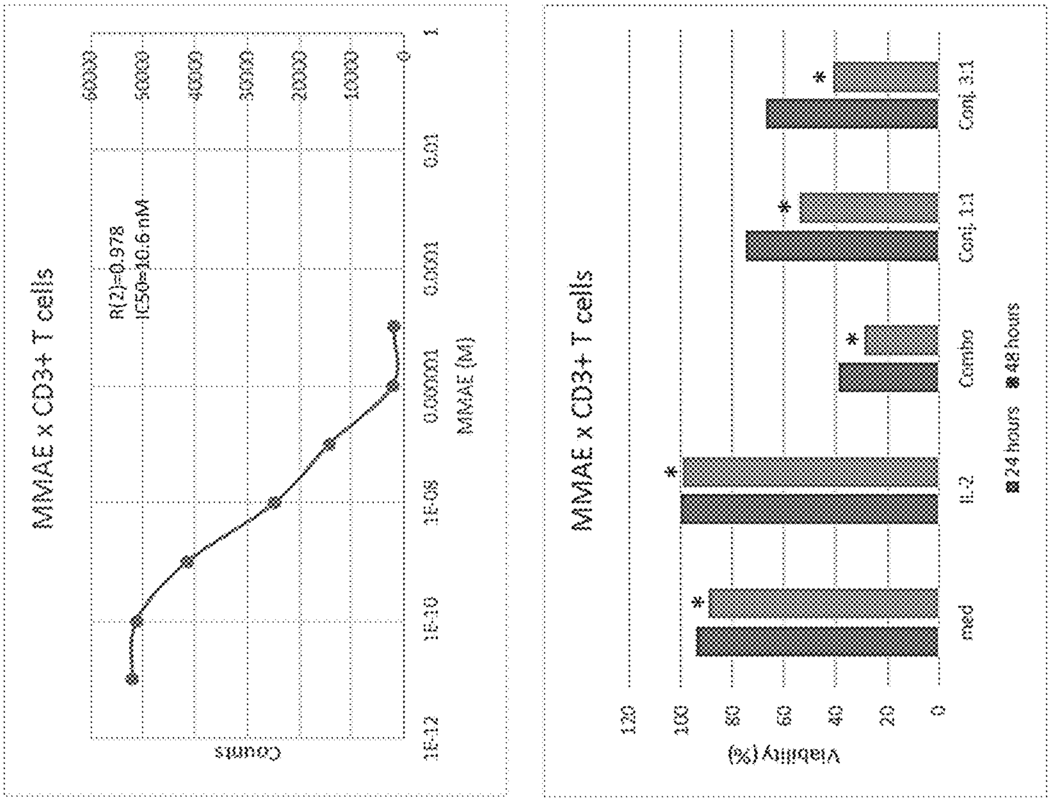
FIG. 6A, top panel, illustrates IL-2 (60 pM)-stimulated CD3+ T cell blasts (measures proliferation) treated with varying concentrations of monomethyl auristatin E (MMAE), a chemotherapy agent.

Biological Example 1: Treatment of CD3+ T Cell Blasts with a Cancer Chemotherapeutic-IL-2 Polypeptide Conjugate A primary murine IL-2 dependent cell line, CTLL-2 (ATCC) was stimulated for 72 hours with 10 U/mL of recombinant murine IL-2 (Biolegend). Cells were washed extensively and rested in complete media (RPMI/10% FCS) for 20 hours before being subjected to stimulation with 60 pM of recombinant Human IL-2 (SEQ ID NO:1, Table 4) along with increasing concentrations of monomethyl auristatin (MMAE) (Medchem Express) in 96 well plates, at 50,000 cells/well in 100 µL of complete media. 48 hours after stimulation, culture wells were pulsed with 20 µL of the Celltiter 96 AqueousOne reagent (Promega) and incubated for another 4 hours. Plates were measured for absorbance at 490 nM and the results plotted as a relation between Absorbance and MMAE concentration (FIG. 6A, Top panel).

A primary murine IL-2 dependent cell line, CTLL-2 (ATCC) was stimulated for 72 hours with 10 U/mL of recombinant murine IL-2 (Biolegend). Cells were washed extensively and rested in complete media (RPMI/10% FCS) for 20 hours before being subjected to stimulation with a either complete media alone (med), recombinant IL-2 at 60 pM (IL-2), recombinant IL-2 at 60 pM along with MMAE at 50 nM (Combo), recombinant IL-2 (60 pM) conjugated to MMAE via dipeptide linker at a 1:1 molar ratio (Conj. 1:1) or recombinant IL-2 (60 pM) conjugated to MMAE via dipeptide linker at a 3:1 molar ratio (Conj. 3:1), prepared as described in Synthetic Example 7. Culture sets were incubated for 24 and 48 hours and cells analyzed for viability with the LIVE/DEAD® Viability/Cytotoxicity Kit (Thermo Scientific). Results were plotted as the measurement of the percentage of live cells in the period using the value obtained with IL-2 at 48 hours as 100% (FIG. 6A, Bottom panel).

Figure 6B:
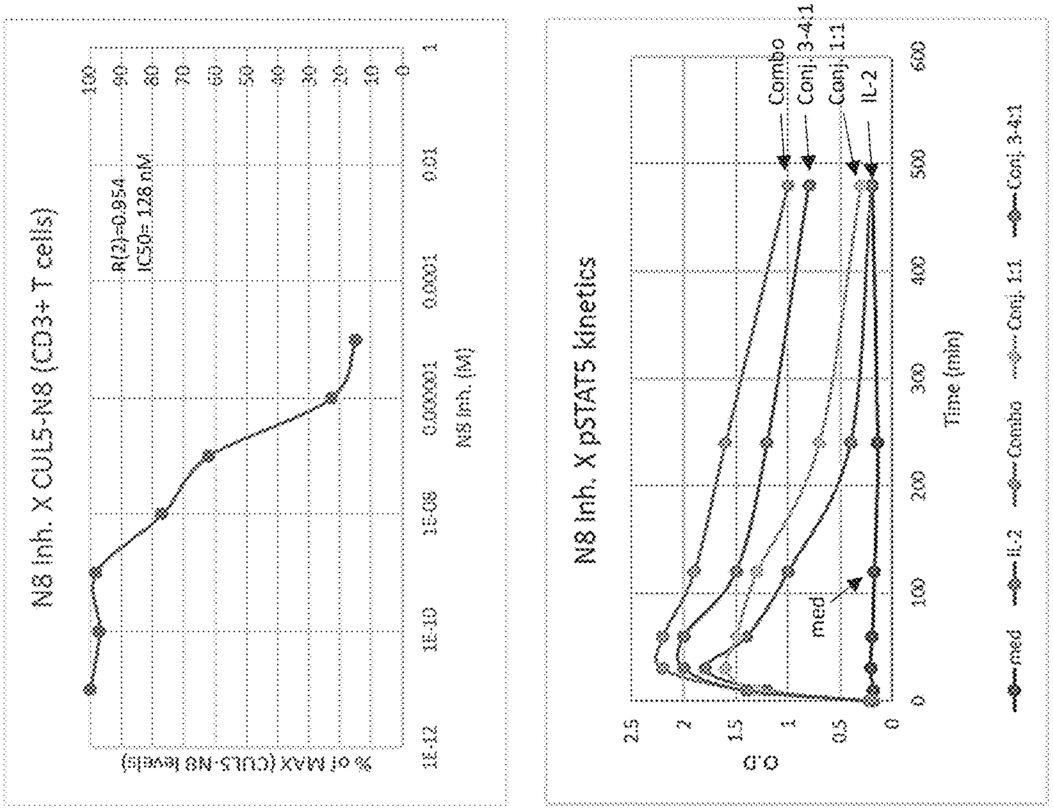
FIG. 6B, top panel, illustrates IL-2 (100 pM)-stimulated CD3+ T cell blasts (measures NEDD8 (N8) associated to cullin-5 (CUL5) via Western blot) after treatment with varying concentrations of a NEDD8 activating enzyme (NAE) inhibitor, MLN4924 (pevonedistat, N8 Inh.).

Biological Example 2: Treatment of CD3+ T Cell Blasts with a Neddylation Inhibitor-IL-2 Polypeptide Conjugate CTLL-2 cultures were established as in Biological Example 1 except that cells for every treatment condition were cultivated at 100,000 cells/mL in T75 flasks in 25 mL of media containing 100 pM of recombinant Human Thioredoxin-IL-2 fusion protein (SEQ ID NO:2, Table 4) along with increasing concentrations of a Nedd8 inhibitor (MLN4924, N8 Inh) (Medchem Express). After 24 hours cells were washed, pelleted by centrifugation and lysed for 30 minutes on ice in IP Lysis buffer (50 mM Tris, pH 7.6, 150 mM NaCl, 1% Triton X-100, 0.05% sodium deoxycholate and protease inhibitors). Lysates were centrifuged at 21,000×g for 15 minutes at 4° C. and the supernatants collected and subjected to immunoprecipitation with an anti-mouse/rat/human CUL5 antibody (F6) (Santa Cruz Biotechnology). Immunocomplexes were captured by protein A/G agarose beads, washed extensively and heated at 95° C. for 5 minutes in SDS sample buffer (Bio-Rad). Samples were electrophoresed, blotted into a PVDF membrane and sequentially probed with an HRP-conjugated anti-Nedd8 antibody (H2) (Santa Cruz Biotechnology) and HRP-conjugate anti-CUL5 (F6). Western blots were developed with a chemiluminescent substrate (SuperSignal Western Pico) (Thermo) and exposed to film. Films were scanned and images were acquired as TIFF files and subjected to densitometric measurement using the imageJ software (National Institutes of Health). Data is plotted as a function of the densitometric levels of the gel bands produced by the anti-Nedd8-HRP signal on film normalized against the signal produced by the anti-CUL5-HRP antibody for each sample (FIG. 6B, Top panel).

Cultures were established as above in Biological Example 2 and stimulated for the indicated periods of time with either 100 pM of recombinant Human IL-2 (IL-2), complete media (med), 100 pM IL-2 along with 200 nM of a Nedd8 inhibitor (Combo), a Nedd8 inhibitor conjugated to an IL-2 polypeptide via a dipeptide linker at a 1:1 molar ratio (Conj. 1:1) or 3-4:1 (Conj. 3-4:1), prepared as described in Synthetic Example 7. Lysates were prepared as above except that the cell lysis buffer was provided by the pSTAT5 ELISA kit. pSTAT5 levels were measured a according to the ELISA kit manufacturer's instructions (Cell Signaling Technology) using an Absorbance plate reader. Data is plotted as the O.D. (Absorbance) signal as a function of time (FIG. 6B, Bottom panel).

Biological Example 3: Analysis of IL-2 Polypeptide Conjugates with MC-FITC

Figure 7:
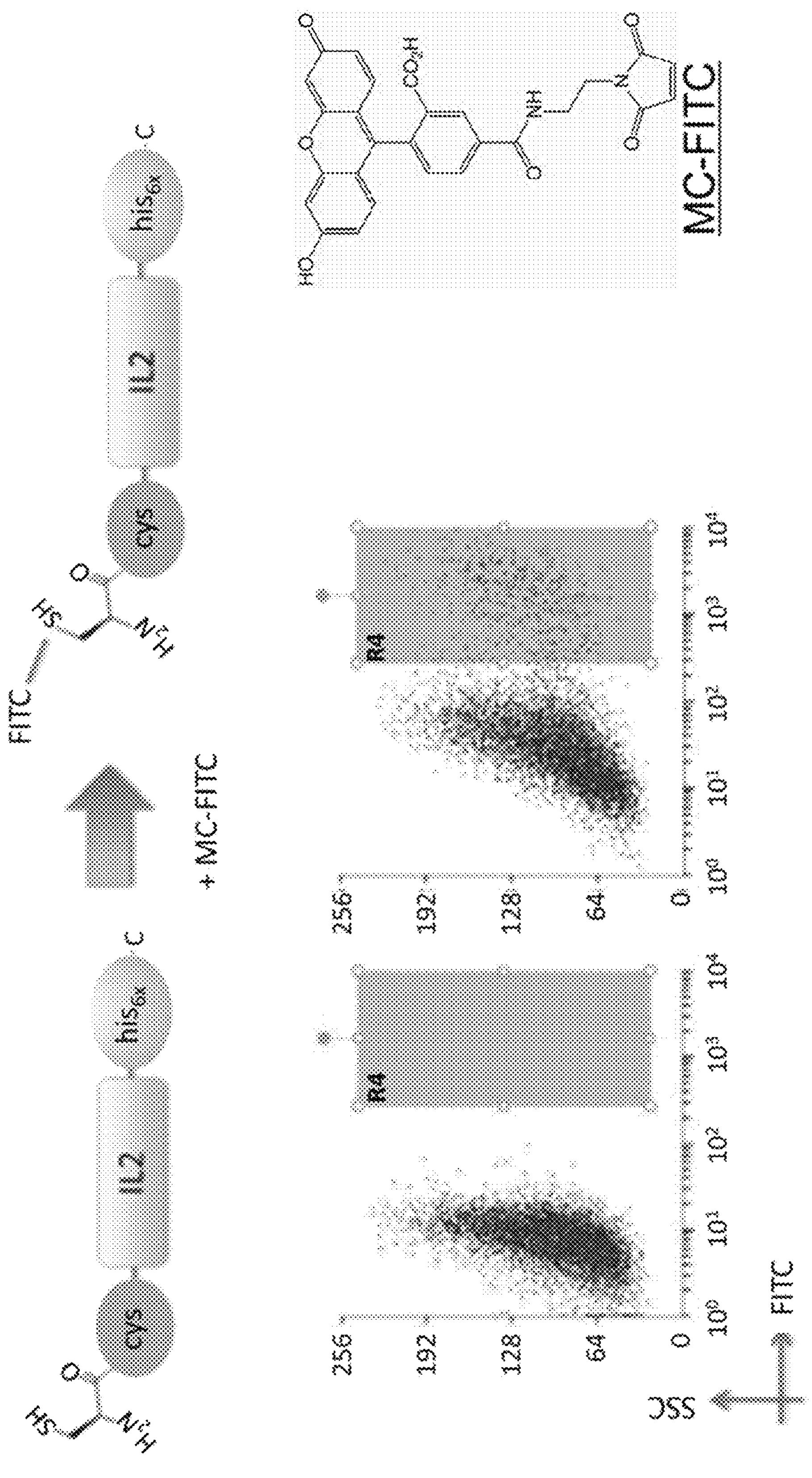
FIG. 7 illustrates that IL-2 polypeptides conjugated with MC-FITC selectively labeled a sub-population of T cells corresponding to regulatory T cells (Tregs).

C57B16 mice were sacrificed and spleens and lymph nodes were pooled and single cell suspensions prepared as described elsewhere (1). Cells were stained with an anti-CD3-Cy 5.5 and anti-CD4-PE antibodies and double positive cells were sorted on a S3 cell sorter (Bio-Rad). Sorted cells were washed and incubated with a FITC-conjugated recombinant IL-2 (SEQ ID NO: 4, Table 4, prepared as described in Synthetic Example 7) for 1 hour at 4° C. followed by extensive washing at 4° C. to prevent receptor internalization. Cells were analyzed by FACS (Bio-RAD S3) for FITC fluorescence (FIG. 7).

(1) Su L, Creusot R J, Gallo E M, Chan S M, Utz P J, Fathman C G, Ermann J. Murine CD4+CD25+ regulatory T cells fail to undergo chromatin remodeling across the proximal promoter region of the IL-2 gene. J Immunol. 2004 Oct. 15; 173 (8): 4994-5001. PubMed PMID: 15470042.

Biological Example 4: Analysis of the Impact of IL-2 Polypeptide-Cancer Chemotherapeutic Conjugates on Cell Viability C57B16 mice were sacrificed and spleens and lymph nodes were pooled and single cell suspensions prepared as described elsewhere (1). Cells were stained with an anti-CD3-Cy 5.5 and anti-CD4-PE antibodies and double positive cells were sorted on a S3 cell sorter (Bio-Rad). Sorted cells were washed and stimulated with a combination of anti-mouse CD3 and anti-CD28 antibody coupled to magnetic beads (Dynabeads, mouse T cell activator, Thermo Scientific) in complete media for 72 hours. Cells were then washed, rested in complete media for 24 hours and stimulated with 1 nM of recombinant IL-2 alone, MMAE conjugated to recombinant IL-2 (SEQ ID NO: 3, Table 4, prepared as described in Synthetic Example 7) via a dipeptide linker or 50 μM of the genotoxic drug Etoposide for 24 hours. Cells were analyzed for viability with the LIVE/DEAD® Viability/Cytotoxicity Kit (Thermo Scientific) using a FACS instrument (Bio-Rad S3, FIG. 8).

(1) Su L, Creusot R J, Gallo E M, Chan S M, Utz P J, Fathman C G, Ermann J. Murine CD4+CD25+ regulatory T cells fail to undergo chromatin remodeling across the proximal promoter region of the IL-2 gene. J Immunol. 2004 Oct. 15; 173 (8): 4994-5001. PubMed PMID: 15470042.

Biological Example 5: Identification of a Common Defect in Patients with Allergy and Autoimmune Diseases Tregs were purified from three healthy blood bank controls, and the pSTAT5 of the Tregs was measured at 30 minutes following low dose IL-2 (1 ng/ml). The relative percentage of STAT5 phosphorylation (pSTAT5 percentage) was then measured in human Teffs and in human Tregs from three patients having food allergies compared to the pSTAT5 of the Tregs from the healthy controls. Cultures were harvested from the food allergy participants, and the relative pSTAT5 percentage was measured from the cultures, following low dose IL-2 (1 ng/ml), after 30 minutes, 2 hours, and 3 hours. The time course in the cell cultures is depicted in FIG. 9, graphed with $p<0.05$ for * with two-way ANOVA.

It was found that, in patients with serious food allergies, defective inhibition of Treg IL-2R desensitization is demonstrated by a more rapid loss of pSTAT5 in their Tregs than in normal subjects' Tregs activated by low dose IL-2 in vitro (FIG. 9).

Biological Example 6: Use of Low Dose IL-2 or Combination IL-2/MLN for Treatment of Type 1 Diabetes in Mouse Model Female Non Obese Diabetic (NOD) mice, aged 8 weeks (The Jackson Laboratory) were used in a study of low dose IL-2, MLN4929 (a pathway inhibitor) or a combination of IL-2 and MLN4928 (referred to herein as IL-2/MLN). The NOD mice are known to spontaneously develop hyperglycemia around 14 weeks of age, with incidence reaching approximately 80% by 25 weeks of age. Normoglycemic mice are entered into the study when they are 12 weeks old, a period when the normoglycemic mice have frank insulitis and are antibody positive.

Figure 10:
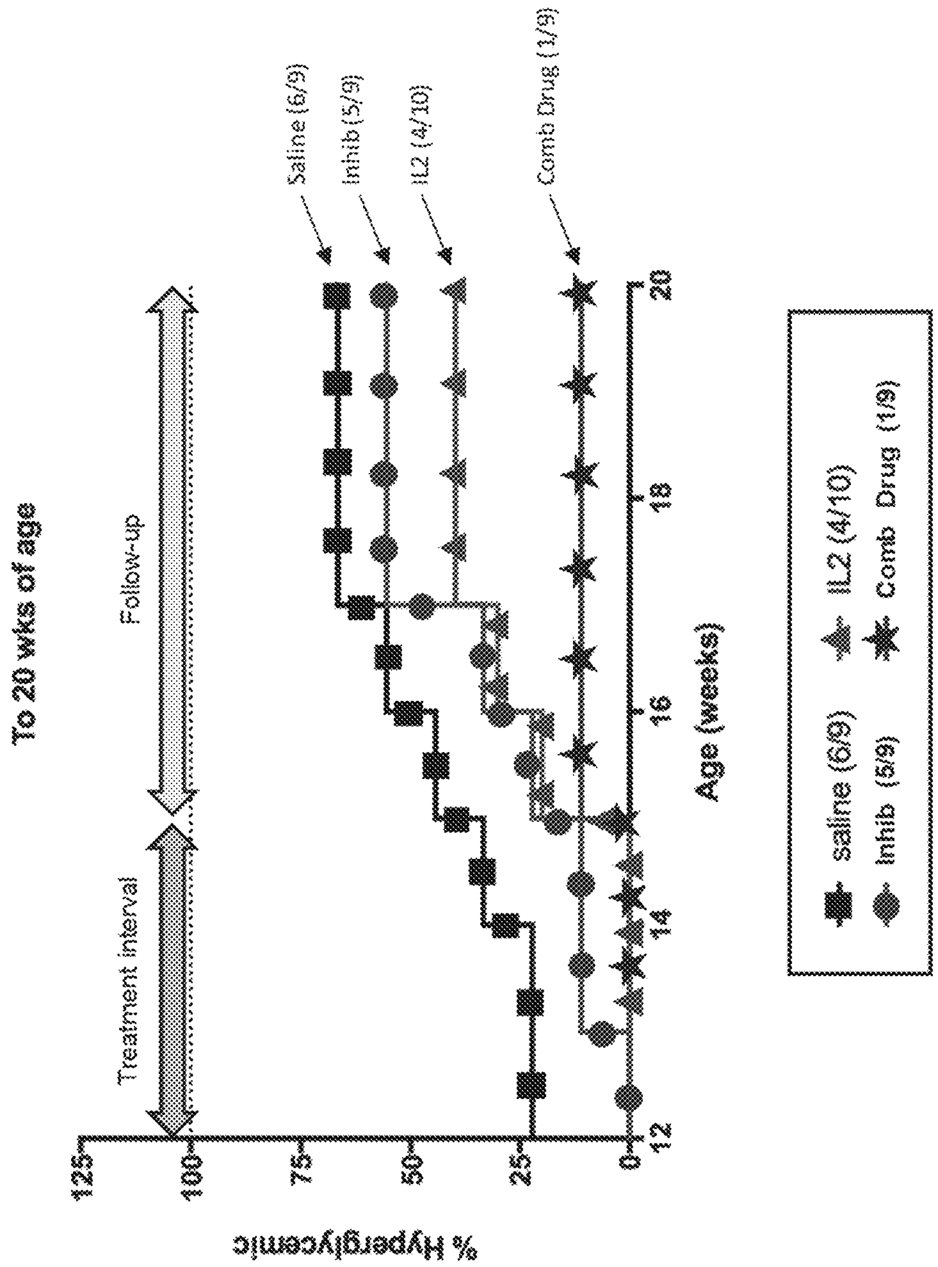
FIG. 10 illustrates that a combination of low dose IL-2 (1 ng) with a NAE inhibitor MLN4924 (400 μg) prevented the progression to hyperglycemia in Non Obese Diabetic (NOD) mice. Groups of 7-9 mice were either treated with low dose IL-2, MLN4924, a combination of the two drugs, or saline (as control), once daily by intraperitoneal (i.p.) injection for three weeks, beginning at age 12 coincident with severe inflammation of the islets of Langerhans in the pancreas (insulitis). Mice were assayed for hyperglycemia weekly using a glucometer and tail vein blood and considered hyperglycemia when two separate bleedings were >250 mg/dl.

Four groups of 7-9 NOD female mice were treated for 21 days, beginning at 12 weeks of age, coincident with severe inflammation of the islets of Langerhans in the pancreas as an indicator of insulitis. The administered treatments were either saline, low dose IL-2, the pathway inhibitor MLN4924, or the IL-2/MLN combination. The mice were monitored by blood glucose and assayed for hyperglycemia weekly until 20 weeks of age using a glucometer and tail vein blood, and considered hyperglycemic when two separate bleedings were >250 mg/dl. It was shown that the IL-2/MLN combination could help to prevent the progression to hyperglycemia in the NOD mice (FIG. 10).

Figure 11:
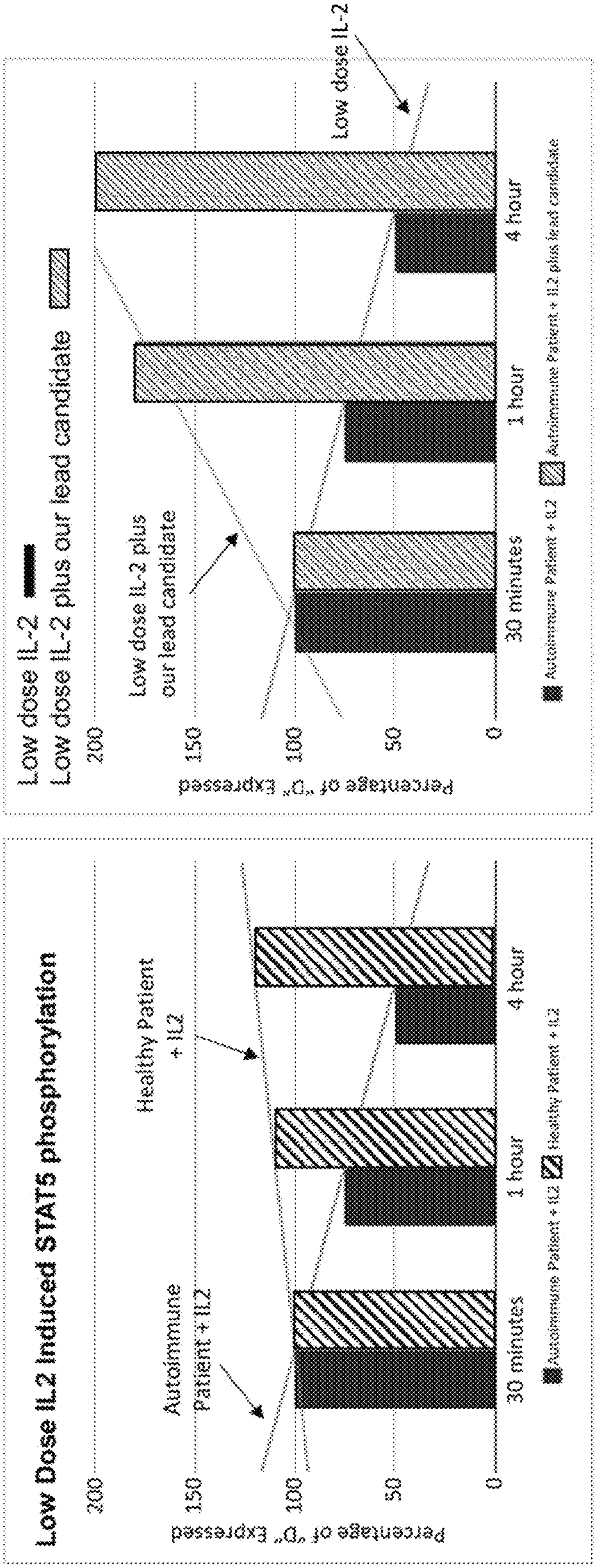
FIG. 11 illustrates that a combination of low dose IL-2 and a NAE inhibitor MLN4924 is capable of restoring pSTAT5 expression of regulatory T cells in humans with autoimmune type 1 diabetes when administered in vitro.

Biological Example 7: Use of Low Dose IL-2 or Combination IL-2/MLN for Treatment of Type 1 Diabetes in Humans The IL-2/MLN combination was tested in vitro in healthy patients and patients with autoimmune type 1 diabetes. The pSTAT5 levels (indicated as percentage of "D" expressed in FIG. 11) was measured at 30 minutes, 1 hour, and 4 hours in healthy patients and autoimmune patients using IL-2, and the IL-2/MLN combination. It was shown that the combination of low dose IL-2 and the NAE inhibitor MLN4924 was capable of restoring pSTAT5 expression of regulatory T cells in humans with autoimmune type 1 diabetes when administered in vitro. (FIG. 11).

Biological Example 8: Use of IL-2/MLN Combination Drug Therapy for Treatment of Asthma in Mouse Model Asthma Model The asthma model was elicited in 10 week old female C57BL/6J mice by intranasal (i.n.) challenge with 5 micrograms (mcg) cockroach antigen (CRA)/0.03 mL in PBS for 5 times each, at days 1, 2, 15, 18, and 21. Five groups of four mice were antigen-sensitized on days 1 and 2.

Treatment

The asthma model mice were subjected to i.p. injection with the following within 30 minutes after i.n. challenge with CRA on days 15, 18, and 21 (for a total of 3 treatments):

(1) 0.1 mL PBS (control);

(2) Saline/DMSO, 50 ul PBS+50 ul PBS containing 40% DMSO (control);

(3) 50 ul MLN [400 μg in 40% DMSO]+50 ul PBS;

(4) 50 ul IL-2 [100 ng in PBS]+50 ul PBS containing 40% DMSO; or (5) 50 ul MLN [400 μg in 40% DMSO]+50 ul IL-2 [100 ng in PBS].

Necropsy

Figure 12:
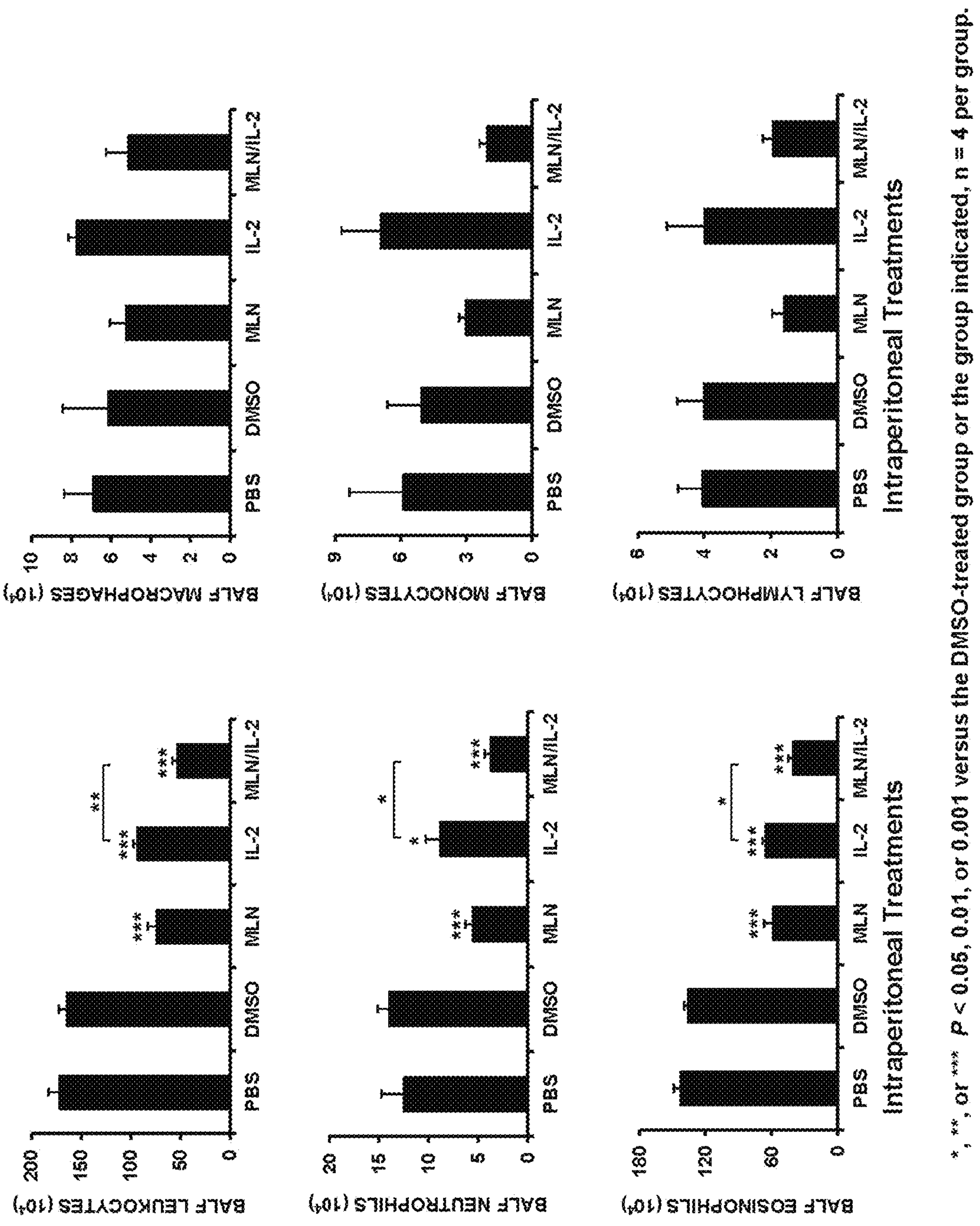
FIG. 12 illustrates therapeutic effects assessed by bronchoalveolar lavage in a mouse asthma model (cockroach antigen (CRA) inhalant asthma), showing the therapeutic effects of administration of either low dose IL-2, a NAE inhibitor MLN294, or low dose IL-2 in combination with the NAE inhibitor MLN4924. B6 mice in groups of 5 were sensitized to CRA (5 mg in 0.03 ml saline inhaled daily for two days) and at days 15, 18 and 21 following sensitization, as a challenge. Within 30 minutes of each challenge, the mice received one of four treatments: either saline as control, low dose IL-2 (100 ng), MLN4924 (200 μg) or the combination of low dose IL-2 and MLN4924.

The mice were sacrificed on day 22, 24 hours after the last antigen challenge and treatment. Bronchoalveolar lavage fluid (BALF) was collected for evaluating the recruitment of leukocytes, neutrophils, macrophages, monocytes, lymphocytes and eosinophils into the lung air spaces, and the lung tissues were fixed for assessing lung tissue leukocyte, neutrophil, and eosinophil infiltration. The results of the therapeutic effects assessed by bronchoalveolar lavage in the mouse asthma model are shown in FIG. 12.

Biological Example 9: BAL Analysis of CRA Sensitized Mice Treated with MLN4924-IL2 Protein Drug Conjugate, Low Dose IL-2, or Saline Asthma Model To further assess the therapeutic effect of the NAE inhibitor (MLN4924) protein drug conjugate (MLN4924-IL2) in the treatment of a mouse model of asthma, mice were used according to the methods described in Biological Example 7. The protein drug conjugate used was the IL2-Bis-VC-MLN-4924 conjugate as described herein. The effects of the MLN4924-IL2 conjugate were also compared to a comparable dose of low dose IL-2 administered at the same time. Groups of five female C57BL/6J mice were sensitized with cockroach antigen (CRA) for two days. Two weeks later they were i.n. challenged with CRA three times, three days apart.

Treatment

The asthma model mice from each of the five groups were subjected to intraperitoneal (i.p.) injection with the following within 30 minutes after i.n. challenge with CRA on days 15, 18, and 21 (for a total of 3 treatments):

(1) 0.1 mL saline (control);

(2) 1 μg IL-2/0.1 mL saline (as the low dose IL-2 treatment); or (3) 2 μg modified IL-2/0.1 mL saline (as the protein drug conjugate treatment).

Necropsy

Figure 13:
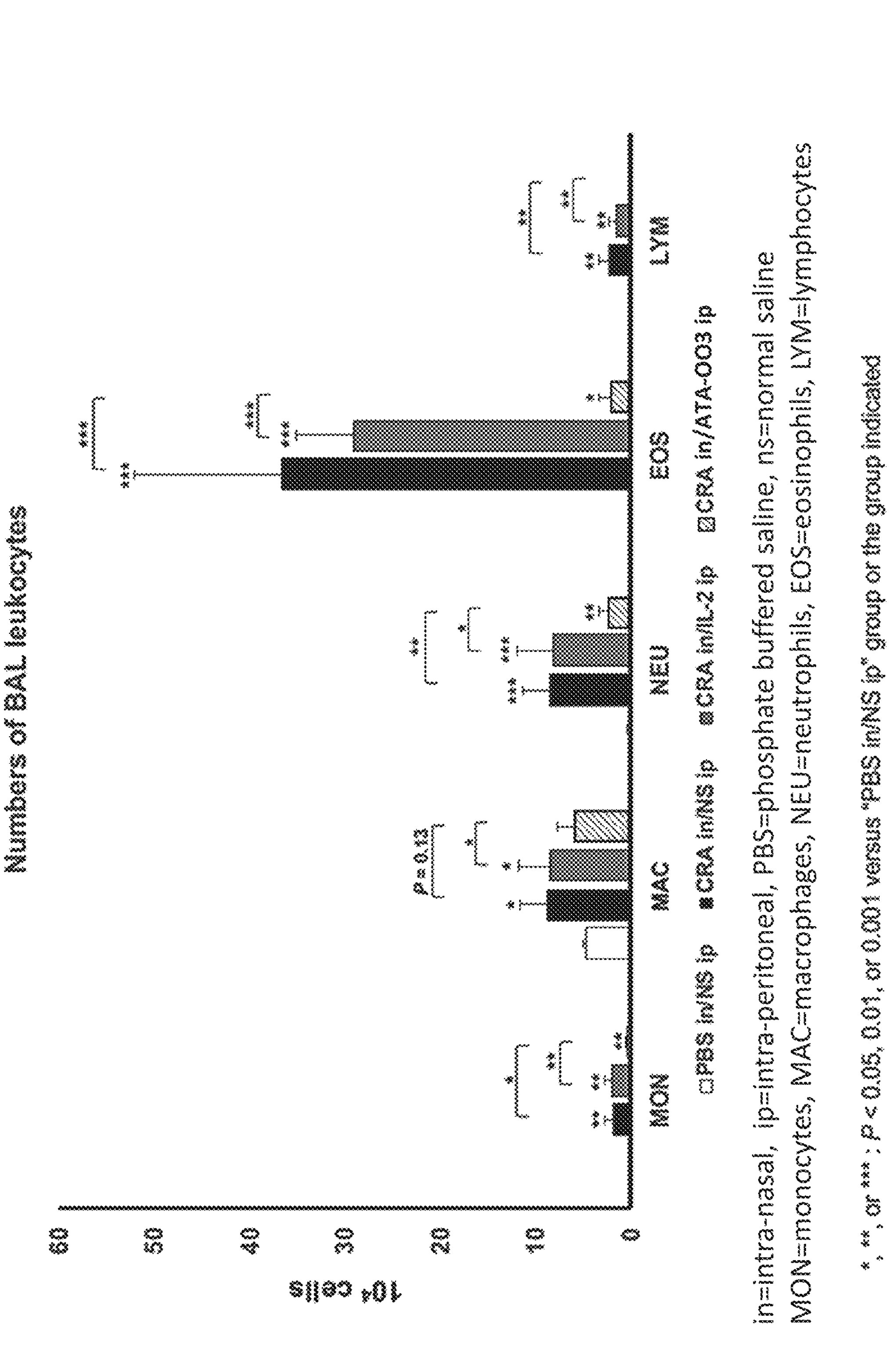
FIG. 13 shows the results of a bronchoalveolar lavage (BAL) analysis performed on cells harvested from the alveoli of mice in the same mouse model of asthma as in FIG. 12. B6 mice in groups of 5 were sensitized to CRA (5 mg in 0.03 ml saline inhaled daily for two days) at days 15, 18 and 21 following sensitization. Within 30 minutes of each challenge, the mice received one of three treatments: saline as control, or low dose IL-2, or MLN4924-IL2 protein drug conjugate (PDC). These studies showed that the PDC was more effective in treatment of asthma than was the combination therapy seen in FIG. 12.

The mice were sacrificed on day 22, 24 hours after the last antigen challenge and treatment. Bronchoalveolar lavage fluid (BALF) was collected for evaluating the recruitment of monocytes, macrophages, lymphocytes, neutrophils, and eosinophils into the lung air spaces, and the lung tissues were fixed for assessing lung tissue leukocyte, neutrophil, and eosinophil infiltration. The results of the therapy are shown in FIG. 13.

Biological Example 10: Use of MLN4924-IL2 Protein Drug Conjugate for Treatment of Lupus Nephritis in Mouse Model NZB/W F1 hybrid mice were bred from male NZW/LacJ and female NZB/BINJ (The Jackson Laboratory). Female progeny were kept and aged to spontaneously develop the disease mimicking systemic human lupus nephritis. At 24 weeks of age the F1 progeny begin weekly urine testing to measure the total amount of urine protein to determine the onset and severity of the disease. These mice are known to begin developing the disease at approximately 29 weeks of age.

Urine protein was measured using the Pierce™ Coomassie (Bradford) Protein Assay Kit according to manufacturer's instructions and absorbance (595 nm) was read and calculated using the ProteinMax Pro software. Once the animals reached a total urine protein concentration of over 300 mg/dL for two consecutive weeks, the animals were placed into groups.

Groups of (NZB×NZW) F1 mice aged more than 24 weeks who had achieved a proteinuria score of greater than 500 mg/dl were either given 2 μg of intraperitoneal injections of the MLN4924 PDC, 1 μg of wild type IL-2 without MLN4924, or a PBS vehicle control for 5 consecutive days. Eight mice were treated with the MLN4924-IL2 conjugate, and five mice were treated with low dose IL-2. Five untreated control mice rapidly increased their proteinuria.

The protein drug conjugate used was the IL2-Bis-VC-MLN-4924 conjugate as described herein. All MLN4924-IL2 conjugate and control treatments were diluted to the prescribed dose in 1×PBS and sterile filtered using a 0.22 uM syringe filter to minimize loss and frozen in daily aliquots at −20° C.

Figure 14:
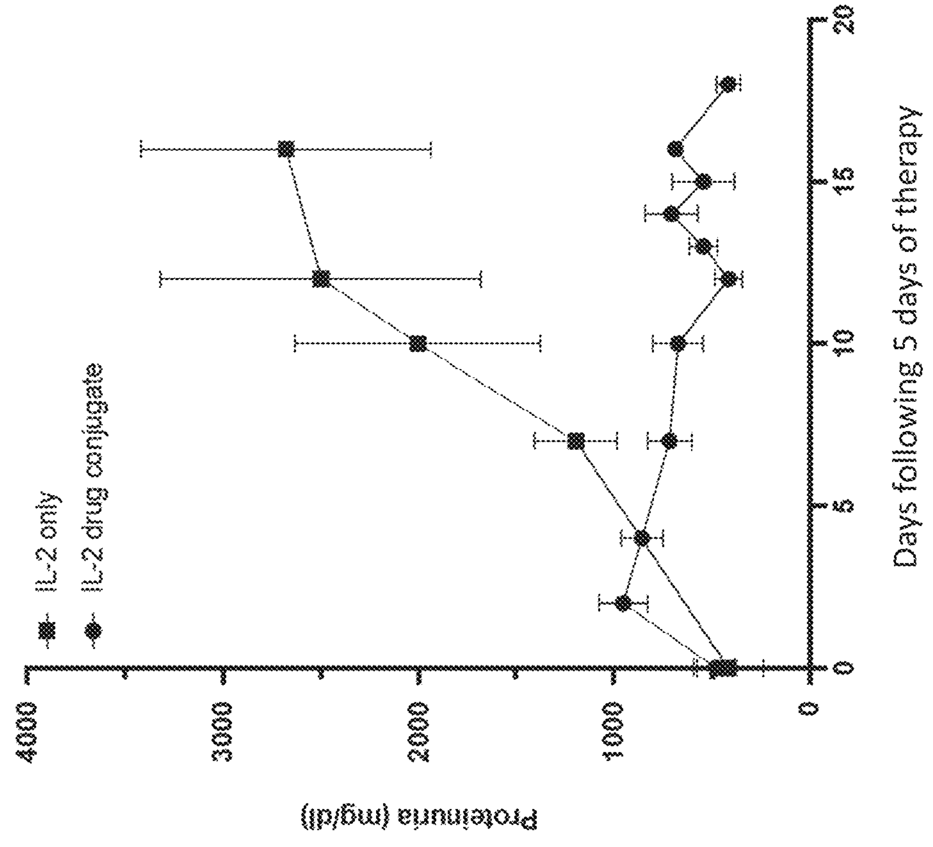
FIG. 14 shows the results of proteinuria measured from a mouse model of lupus nephritis as an indicator of severity of the disease. These data demonstrate the therapeutic effect of MLN4924-IL2 protein drug conjugate compared to low dose IL-2 without the drug attached. Groups of (NZBxNZW) F1 mice aged more than 24 weeks who had achieved a proteinuria score of greater than 500 mg/dl were either given the MLN4924-IL2 protein drug conjugate or a similar amount of low dose IL-2 absent the drug ip daily for five days. There were eight mice treated with the PDC and five mice treated with low dose IL-2. Five untreated control mice rapidly increased their proteinuria and were sacrificed. These data suggest that treatment with the MLN4924-IL2 PDC was more effective than low dose IL-2 in treatment of lupus nephritis.

For the duration of the treatment period and one week following the treatment period, a urine sample and animal weight were measured every other day. When the animals reached a total urine protein concentration over 4500 mg/dL for two consecutive weeks, the animals were humanely sacrificed via CO2 inhalation in accordance to IACUC standard operating procedures of small animal euthanasia. The therapeutic effects of the MLN4924-IL2 conjugate are shown to be more effective than the therapeutic effects of low dose IL-2 (without the drug attached) in treatment of lupus nephritis (FIG. 14).

Biological Example 11: Pulmonary Function Testing Using MLN4924 Protein Drug Conjugate A separate cohort of mice (of the same strain, sex and age as described in Biological Examples 7-9) are sensitized, challenged and treated in an identical manner as described in Biological Examples 7-9, using the IL2-Bis-VC-MLN-4924 protein drug conjugate as described herein, and are assessed for their pulmonary function.

Invasive measurements of airway reactivity in anesthetized, tracheostomized, mechanically ventilated mice are performed 24 hours after the last antigen challenge or PBS challenge. Aerosolized methacholine is administered in increasing concentrations (0, 1.25, 2.5, 5, and 10 mg/ml), with individual doses separated by 2 minutes. Pulmonary resistance (RL) and dynamic compliance (Cdyn) as measurements of functions of respiratory frequency are continuously computed by fitting flow, volume, and pressure to an equation of motion for each aerosol challenge period, which consists of a 0.5-minute aerosol exposure and a 1.5-minute period after exposure.

The description of the embodiments, alternative embodiments, and specific examples herein are given by way of illustration and should not be viewed as limiting. Further, many changes and modifications within the scope of the present embodiments may be made without departing from the spirit thereof, and the present disclosure includes such changes and modifications.

Each patent and non-patent publication cited herein is included by reference in its entirety and for all purposes.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

REFERENCES

[1] Bart de Goeij and John M Lambert. "New developments for antibody-drug conjugate-based therapeutic approaches." In: *Current Opinion in Immunology* 40 (2016), pp. 14-23.

[2] A. Beck et al. "Strategies and challenges for the next generation of antibody drug conjugates." In: *Nat Rev Drug Discov* 16.5 (2017), pp. 315-337.

[3] Angiolo Gadducci et al. "Treatment options in recurrent cervical cancer." In: *Oncology Letters* (2010), pp. 3-11.

[4] K Tsuchikama and Z. An. "Antibody-drug conjugates: recent advances in conjugation and linker chemistries." In: *Protein Cell* 9.1 (2018), pp. 33-46.

[5] Imran Vhora et al. "Protein and Peptide-Drug Conjugates: An Emerging Drug Delivery Technology." In: *Advances in Protein Chemistry and Structural Biology* 98.

[6] A Warnecke et al. "Synthesis, cleavage profile, and antitumor efficacy of an albumin-binding prodrug of methotrexate that is cleaved by plasmin and cathepsin B." In: *Arch Pharm* (*Weinheim*) 340.8 (2007), pp. 389-95.

[7] Z. Wang et al. "Ontak-like human IL-2 fusion toxin." In: *J. Immunol. Methods* 448 (2017), pp. 51-58.

[8] S. Cazzamalli et al. "Enhanced Therapeutic Activity of Non-Internalizing Small Molecule-Drug Conjugates Targeting Carbonic Anhydrase IX in Combination With Targeted Interleukin-2." In: *Clinical Cancer Research* 17 (2018), p. 3458.

[9] G. M. Burslem and C. M. Crews. "Small-Molecule Modulation of Protein Homeostasis. Chem Rev." In: *Chem. Rev.* 117.17 (2017), pp. 11269-11301.

[10] T. Kotte et al. "Treg Depletion-enhanced IL-2 Treatment Facilitates Therapy of Established Tumors Using Systemically Delivered Oncolytic Virus." In: *Molecular Therapy* 16.7 (2008), pp. 1217-1226.

[11] J. N. deGruyter, L. R. Malins, and P. S. Baran. "Residue-Specific Peptide Modification: A Chemist's Guide." In: *Biochemistry* 56.30 (2017), pp. 3863-3873.

[12] E. Basle, N. Joubert, and M. Pucheault. "Protein chemical modification on endogenous amino acids." In: *Chem Biol* 17.3 (2010), pp. 213-27.

[13] C. S. Mckay and M. G. Finn. "Click chemistry in complex mixtures: bioorthogonal bioconjugation." In: *Chem Biol* 21.9 (2014), pp. 1075-101.

[14] O. Koniev and A. Wagner. "Developments and recent advancements in the field of endogenous amino acid selective bond forming reactions for bioconjugation." In: *Chem Soc Rev* 448.15 (2015), pp. 5495-551.

[15] G. M. Dubowchik, A. Raymond, and I. Firestone. "Cathepsin B-sensitive dipeptide prodrugs. 1. A model study of structural requirements for efficient release of doxorubicin." In: *Bioorganic & Medicinal Chemistry Letters* 8 (1998), pp. 33413346.

[16] G. M. Dubowchik, A. Raymond, et al. "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity." In: *Bioconjugate Chem.* 13 (2002), pp. 855-869.

[17] A. Dal Corso et al. "Protease-Cleavable Linkers Modulate the Anticancer Activity of Noninternalizing Antibody-Drug Conjugates." In: *Bioconjug Chem* 28.7 (2017), pp. 1826-1833.

[18] M. Dorywalska et al. "Molecular Basis of Valine-Citrulline-PABC Linker Instability in Site-Specific ADCs and Its Mitigation by Linker Design." In: *Mol Cancer Ther* 15.5 (2016), pp. 958-70.

[19] N. Joubert, M. C. Viaud-Massuard, R. Respaud, et al. United States Patent Application 20160151515.

[20] Z. Boulous, T. P. Conolly, and C. P. Penney. "A Simple One-Step Conversion of Carboxylic Acids to Esters Using EEDQ." In: *J. Org. Chem* 60 (1995), pp. 7072-7074.

[21] Shinya Kida et al. "Studies on Heterobifunctional Cross-Linking Reagents, 6-Maleimidohexanoic Acid Active Esters." In: *Chem. Pharm. Bull.* 55.4 (2007), pp. 685-687.

[22] Yanming Wang et al. "Development and Properties of Valine-Alanine based Antibody-Drug Conjugates with Monomethyl Auristatin E as the Potent Payload." In: *Int. J. Mol. Sci.* 18 (2007), p. 1860.

[23] M. de Graaf et al. "Beta-Glucuronidase-Mediated Drug Release." In: *Current Pharmaceutical Design* 18 (2002).

[24] Hatanaka Yasumaru, Hashimoto Makoto, and Yuichi Kanaoka. "A Novel Biotinylated Heterobifunctional Cross-linking Reagent Bearing an Aromatic Diazirine." In: *Bioorganic & Medicinal Chemistry* 2.12 (1994).

[25] S. C. Jeffrey et al. "Development and Properties of a-Glucuronide Linkers for Monoclonal Antibody-Drug Conjugates." In: *Bioconjugate Chem* 17 (2006).

[26] S. C. Jeffrey, M. T. Nguyen, et al. "Minor groove binder antibody conjugates employing a water soluble beta-glucuronide linker." In: *Bioorg Med Chem Lett* 17.8 (2007).

[27] S. Kolodych, C. Michel, et al. "Development and evaluation of beta-galactosidase sensitive antibody-drug conjugates." In: *Eur J Med Chem* 142 (2017).

[28] European Patent No. EP2478912B1.

What is claimed is:

1. A compound having a structure of Formula (III):

$$X_1\text{—}[X_2\text{—}(X_3)_m] \quad \text{(III)},$$

or a pharmaceutically acceptable salt, solvate, hydrate, isomer, or tautomer thereof, wherein:

m is 1, 2, 3, 4, 5, 6, 7, 8, 9, or 10;

n is 1, 2, 3, 4, 5, 6, 7, 8, 9, 10, or 11;

$X_1$ is an IL-2 polypeptide or a bio-active homolog polypeptide thereof comprising an amino acid sequence set for in SEQ ID NO:2;

$X_2$ comprises is at least one linker, wherein the at least one linker includes one or more linker types is conjugated to the IL-2 polypeptide or a bio-active homolog polypeptide thereof; and $X_3$ is a therapeutic compound payload for treating immunological disorders, wherein $X_3$ is a neddylation inhibitor wherein the therapeutic compound payload is conjugated to the at least one linker.

2. The compound, or a pharmaceutically acceptable salt, solvate, hydrate, isomer, or tautomer thereof, of claim 1, wherein X2 is a non-cleavable linker.

3. The compound, or a pharmaceutically acceptable salt, solvate, hydrate, isomer, or tautomer thereof, of claim 1, wherein X2 is a cleavable linker selected from the group consisting of:
| Compound | Structure |
|---|---|
| K-1 | 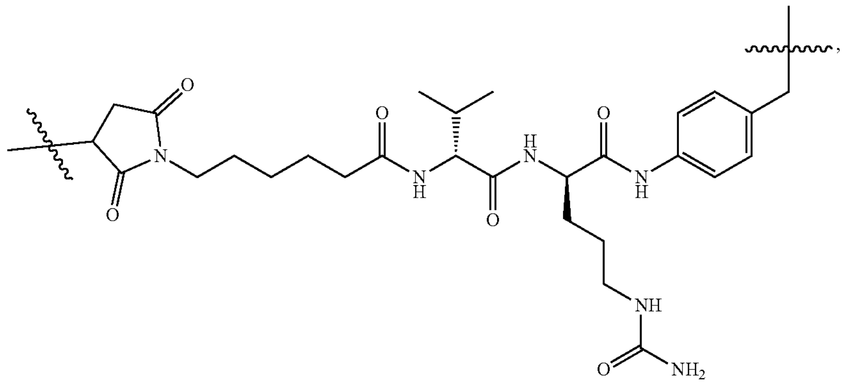 [SMILES: *Cc1ccc(NC(=O)[C@@H](CCCNC(N)=O)NC(=O)[C@H](NC(=O)CCCCCN2C(=O)CC(*)C2=O)C(C)C)cc1] |
| K-2 | 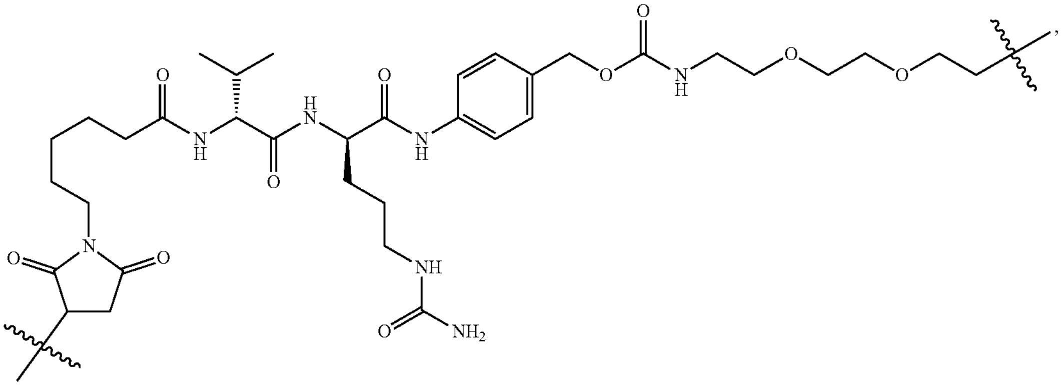 [SMILES: *CCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |
| K-3 | 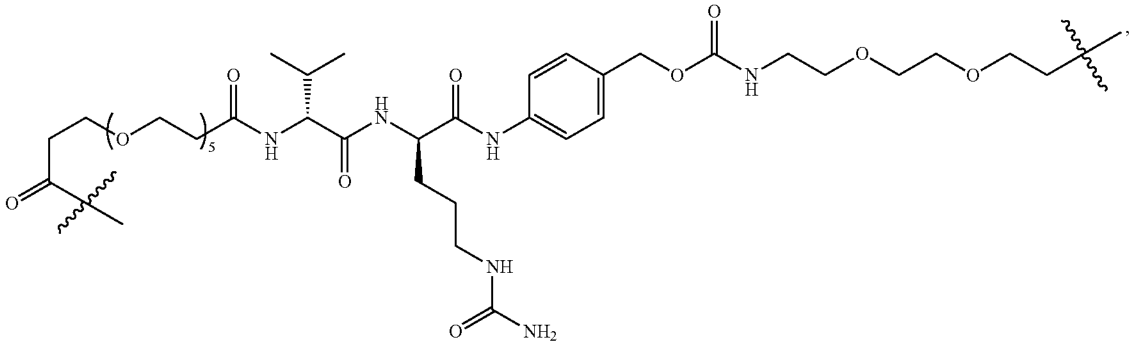 |
| K-4 | 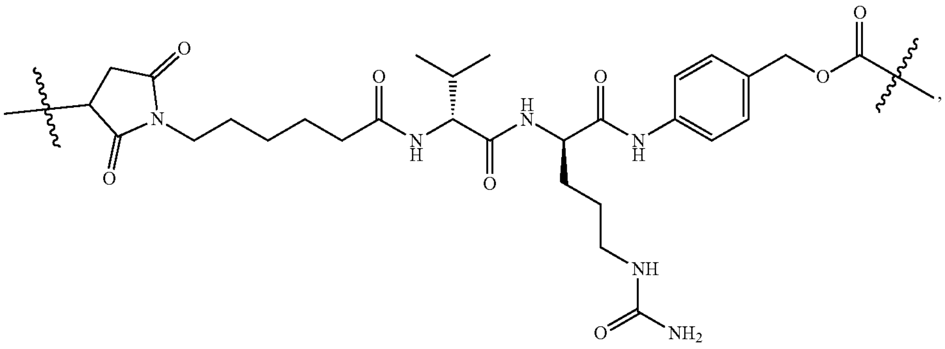 [SMILES: *C(=O)OCc1ccc(NC(=O)[C@@H](CCCNC(N)=O)NC(=O)[C@H](NC(=O)CCCCCN2C(=O)CC(*)C2=O)C(C)C)cc1] |

-continued
| Compound | Structure |
|---|---|
| K-5 | 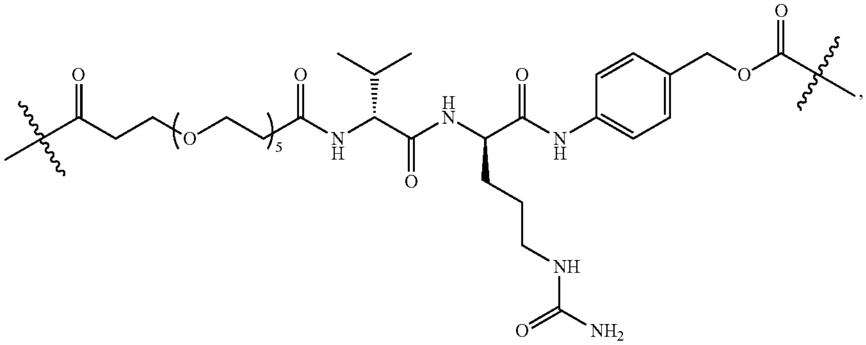 |
| K-6 | 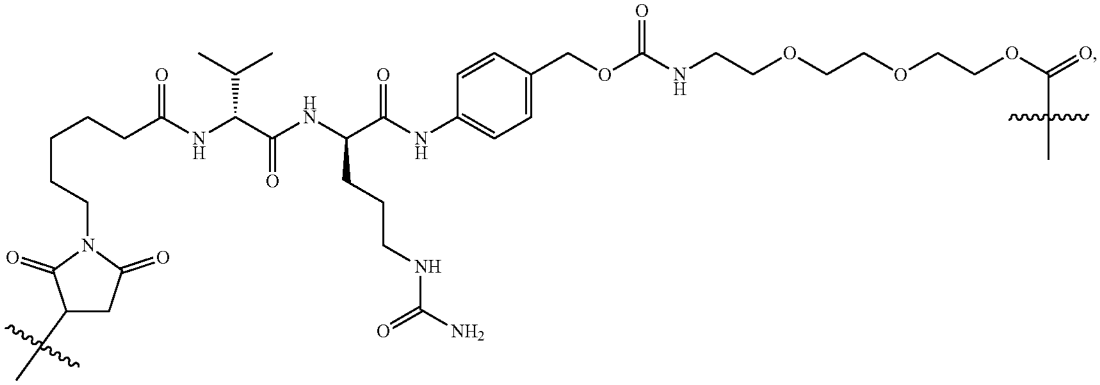 [SMILES: *C(=O)OCCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |
| K-7 | 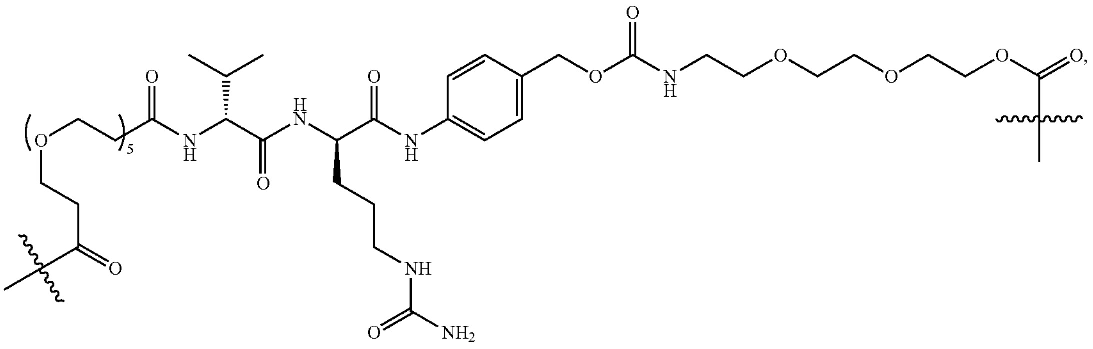 |
| K-8 | 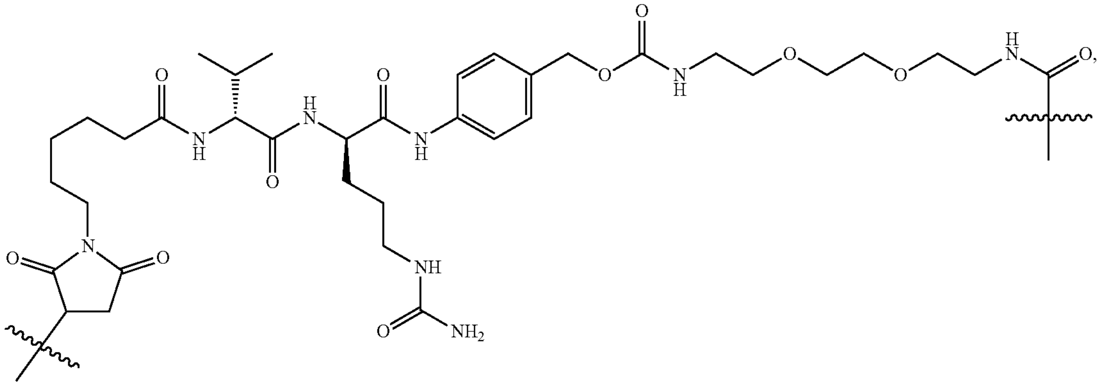 [SMILES: *C(=O)NCCOCCOCCNC(=O)OCc1ccc(NC(=O)[C@@H](CCCNC(N)=O)NC(=O)[C@H](NC(=O)CCCCCN2C(=O)CC(*)C2=O)C(C)C)cc1] |

-continued
| Compound | Structure |
|---|---|
| K-9 | 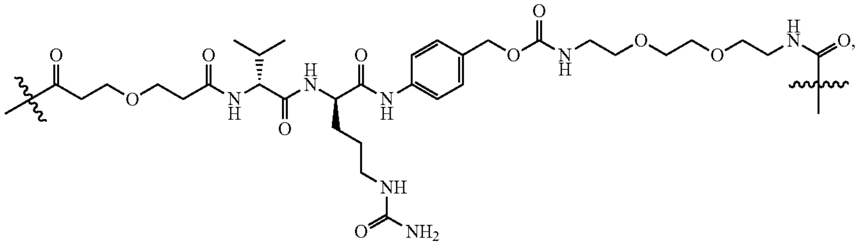 [SMILES: *C(=O)CCOCCC(=O)N[C@@H](C(=O)N[C@H](CCCNC(N)=O)C(=O)Nc1ccc(COC(=O)NCCOCCOCCNC(*)=O)cc1)C(C)C] |
| K-10 | 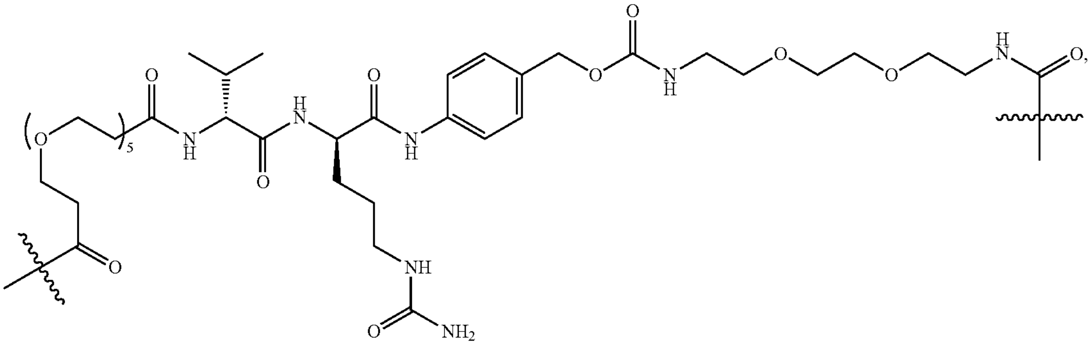 |
| K-11 | 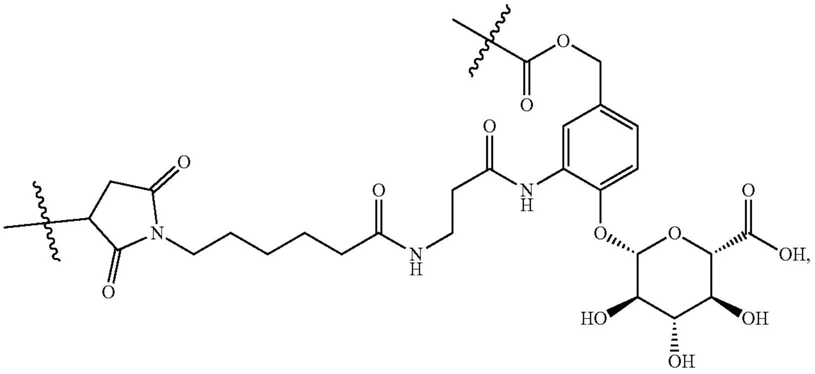 [SMILES: *C(=O)OCc1ccc(O[C@@H]2O[C@H](C(=O)O)[C@@H](O)[C@H](O)[C@H]2O)c(NC(=O)CCNC(=O)CCCCCN2C(=O)CC(*)C2=O)c1] |
| K-12 | 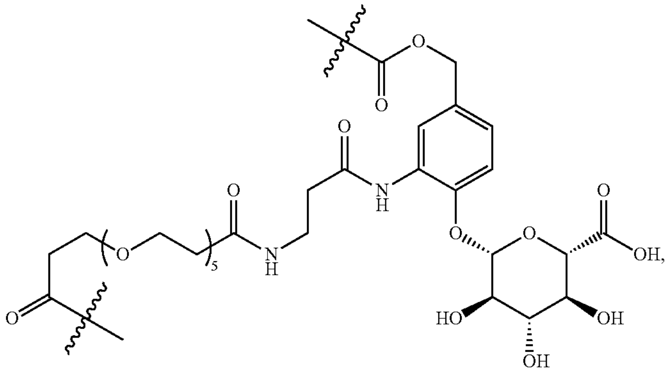 |

-continued
| Compound | Structure |
|---|---|
| K-13 | 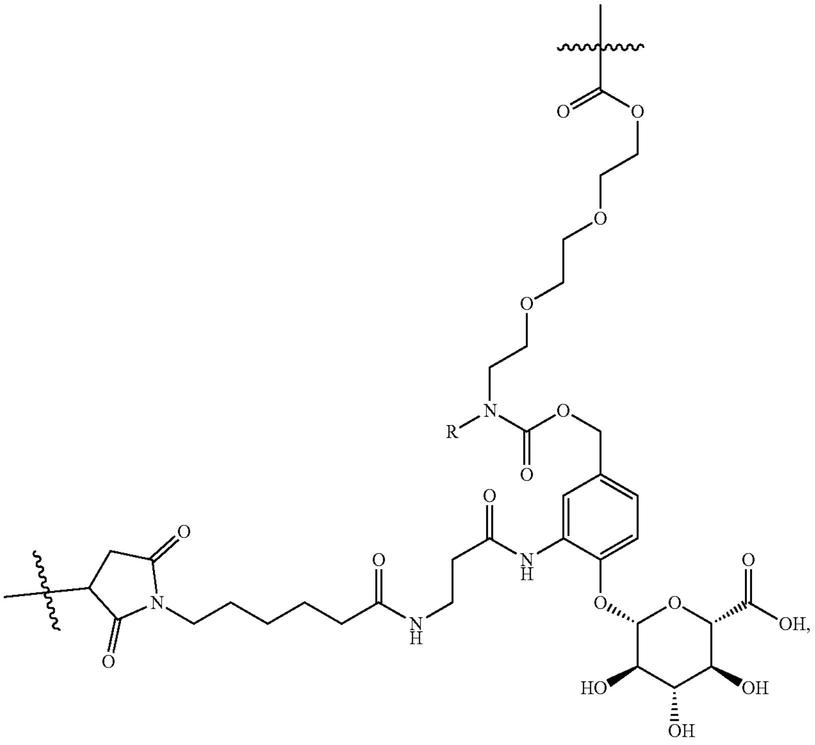 |
| K-14 | 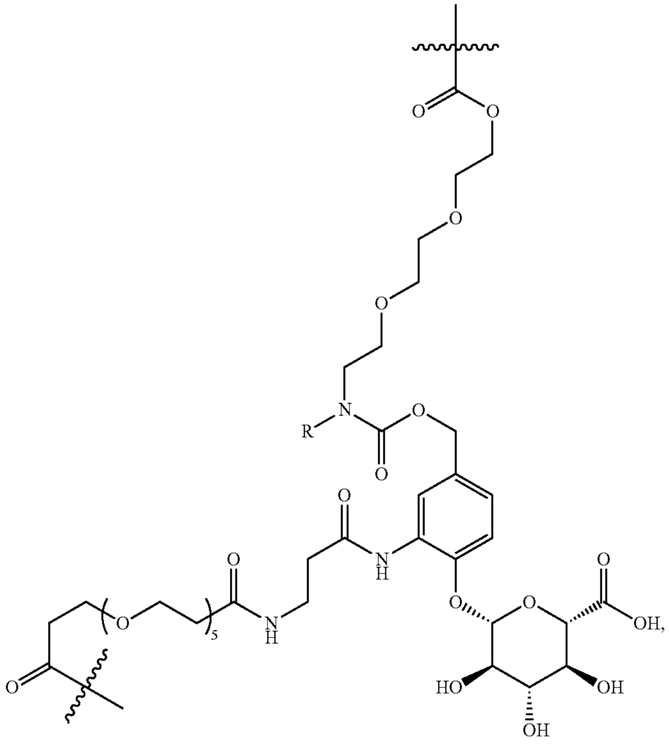 |

-continued
| Compound | Structure |
| --- | --- |
| K-15 | 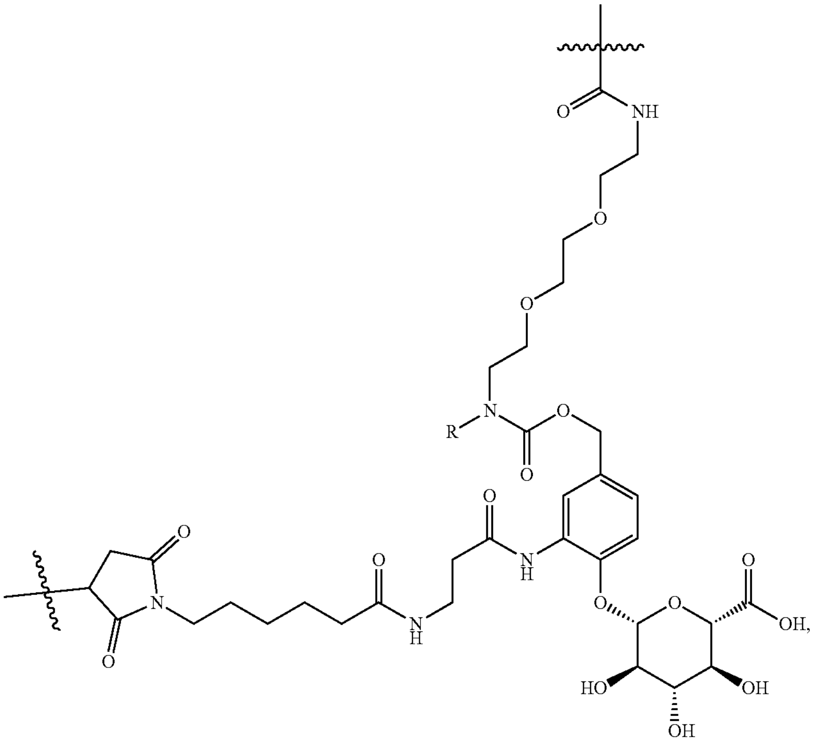 |
| K-16 | 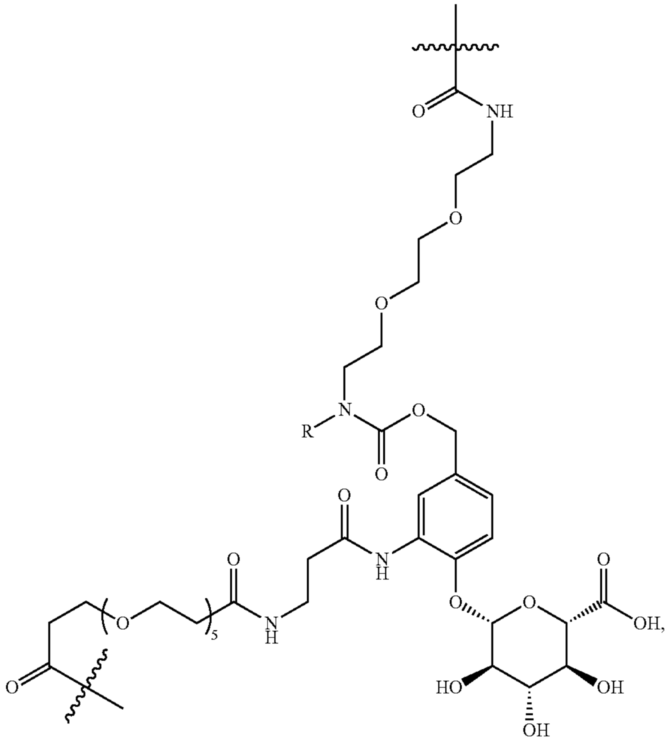 |

-continued

| Compound | Structure |
| --- | --- |
| K-19 | 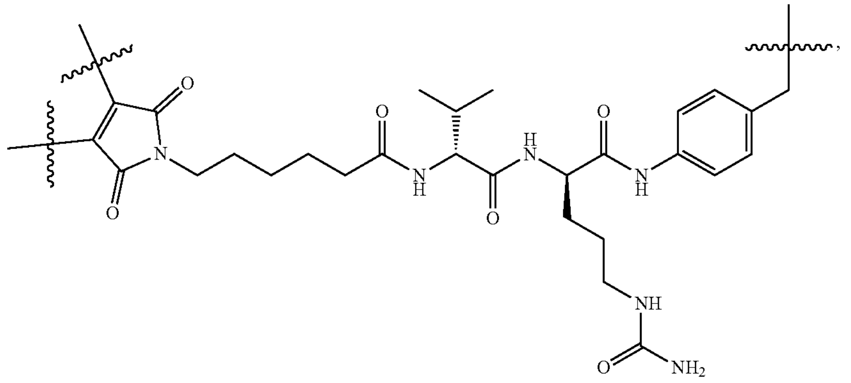 [SMILES: *Cc1ccc(NC(=O)[C@@H](CCCNC(N)=O)NC(=O)[C@H](NC(=O)CCCCCN2C(=O)C(*)=C(*)C2=O)C(C)C)cc1] |
| | and |
| K-20 | 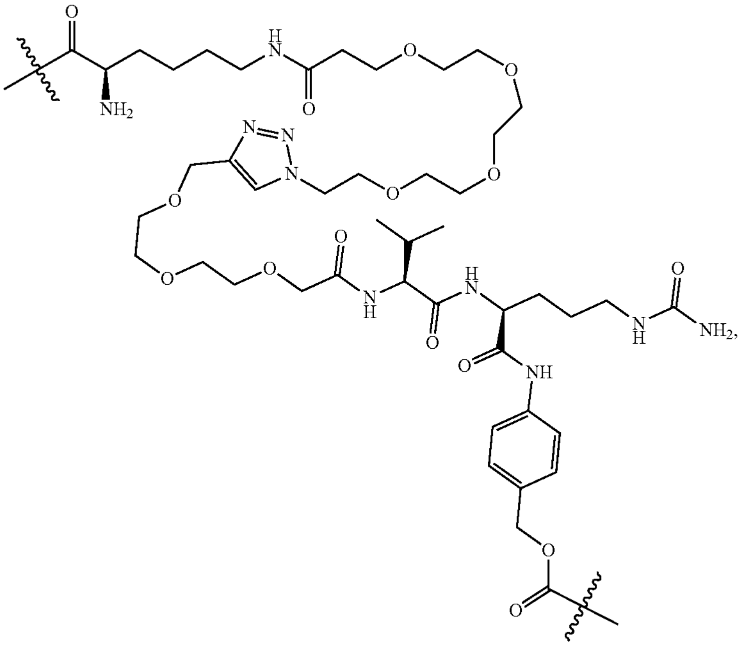 [SMILES: *C(=O)OCc1ccc(NC(=O)[C@H](CCCNC(N)=O)NC(=O)[C@@H](NC(=O)COCCOCCOCc2cn(CCOCCOCCOCCOCCC(=O)NCCCC[C@@H](N)C(*)=O)nn2)C(C)C)cc1] |

wherein the left side of X2, as drawn, is bound to X1, and the right side of X2, as drawn, is bound to X3 and wherein R is H, alkyl, aryl, arylalkyl, a glycol ether, or a glycol linker.

4. The compound, or a pharmaceutically acceptable salt, solvate, hydrate, isomer, or tautomer thereof, of claim 1, wherein X2 is bound to X1 at a Cys residue thereof or a Lys residue thereof.

5. The compound, or a pharmaceutically acceptable salt, solvate, hydrate, isomer, or tautomer thereof, of claim 1, wherein X3 is an immunomodulating agent.

6. The compound, or a pharmaceutically acceptable salt, solvate, hydrate, isomer, or tautomer thereof, of claim 1, wherein X3 is selected from the group consisting of: pevonedistat; TASI (((2S,3S,4R,5R)-5-(4-amino-5-((4,7-dimethyl-3,4-dihydro-2H-benzo[b][1,4]oxazin-8-yl) ethynyl)-7H-pyrrolo[2,3-d]pyrimidin-7-yl)-3,4-dihydroxytetrahydrofuran-2-yl)methyl sulfamate); TAS2 (((1S,2R,3S,4R)-4-(4-amino-5-((4,7-dimethyl-3,4-dihydro-2H-benzo[b][1,4] oxazin-8-yl) ethynyl)-7H-pyrrolo[2,3-d]pyrimidin-7-yl)-2,3-dihydroxycyclopentyl)methyl sulfamate); TAK7243 (((1R,2R,3S,4R)-2,3-dihydroxy-4-((2-(3-(trifluoromethyl) phenyl) pyrazolo[1,5-a]pyrimidin-7-yl)amino)cyclopentyl) methyl sulfamate); ABPA3 ([(2R,3S,4R,5R)-5-[6-(3-ethynylanilino) purin-9-yl]-3,4-dihydroxyoxolan-2-yl]methyl sulfamate); and TAS4464 (7H-Pyrrolo[2,3-d]pyrimidin-4-amine, 7-[5-[(aminosulfony 1)amino]-5-deoxy-beta-D-ribofuranosyl]-5-[2-(2-ethoxy-6-fluorophenyl) ethynyl]-), wherein $R^1$ is alkyl, aryl, arylalkyl, arylalkyne, arylalkene, heterocyclyl, or heteroaryl and R2 is H, alkyl, or aryl.

7. The compound, or a pharmaceutically acceptable salt, solvate, hydrate, isomer, or tautomer thereof, of claim 1, wherein the compound of Formula (III) is selected from the group consisting of:

| Compound | Structure |
|---|---|
| B-1 | 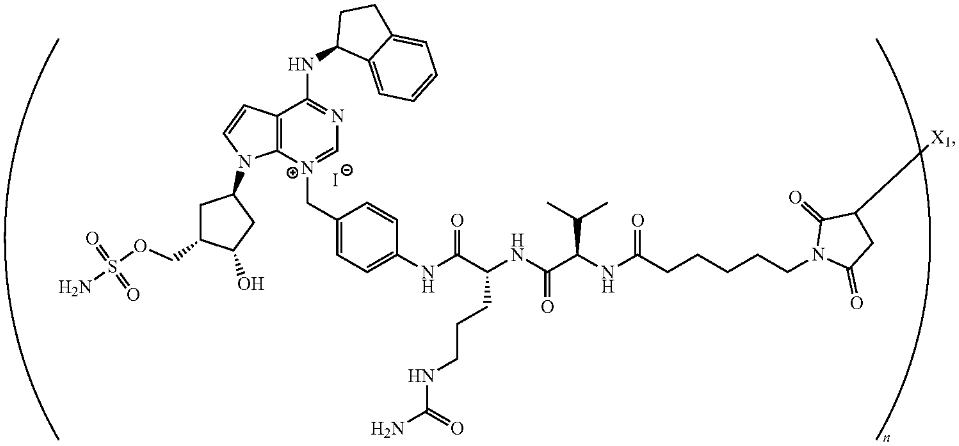 |
| B-2 | 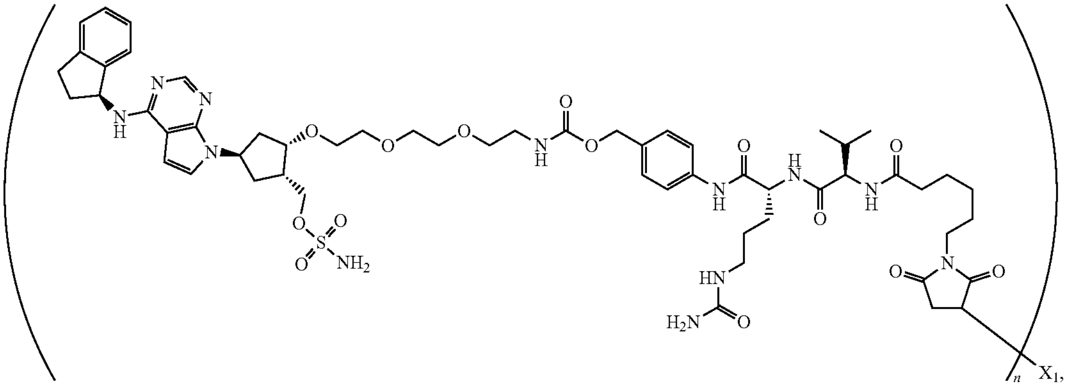 |
| B-3 | 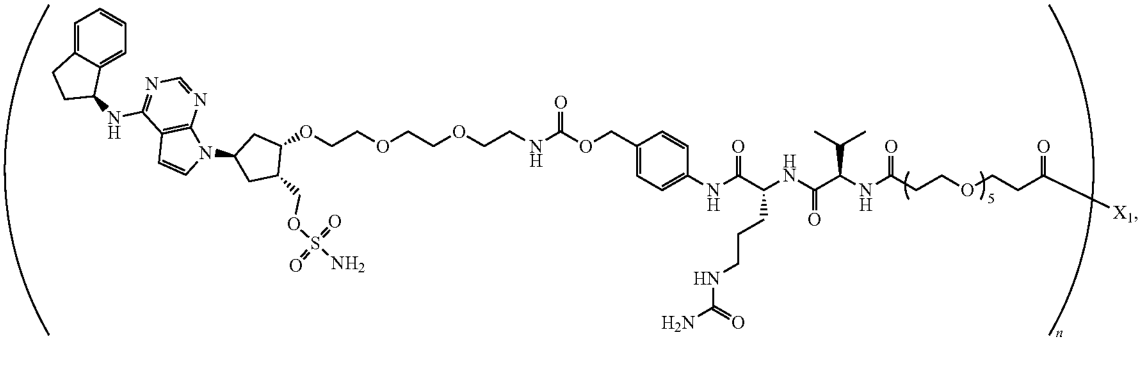 |

-continued
| Compound | Structure |
|---|---|
| B-4 | 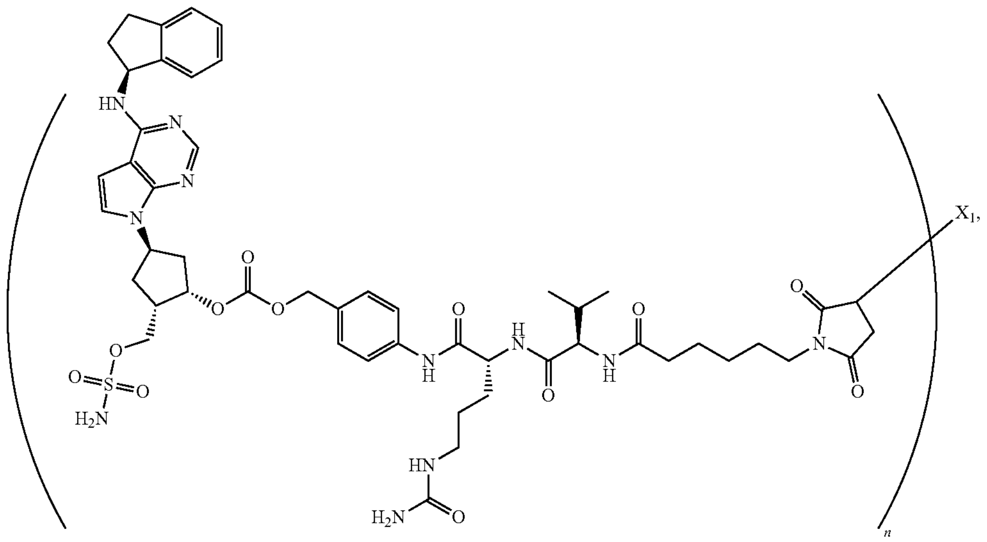 |
| B-5 | 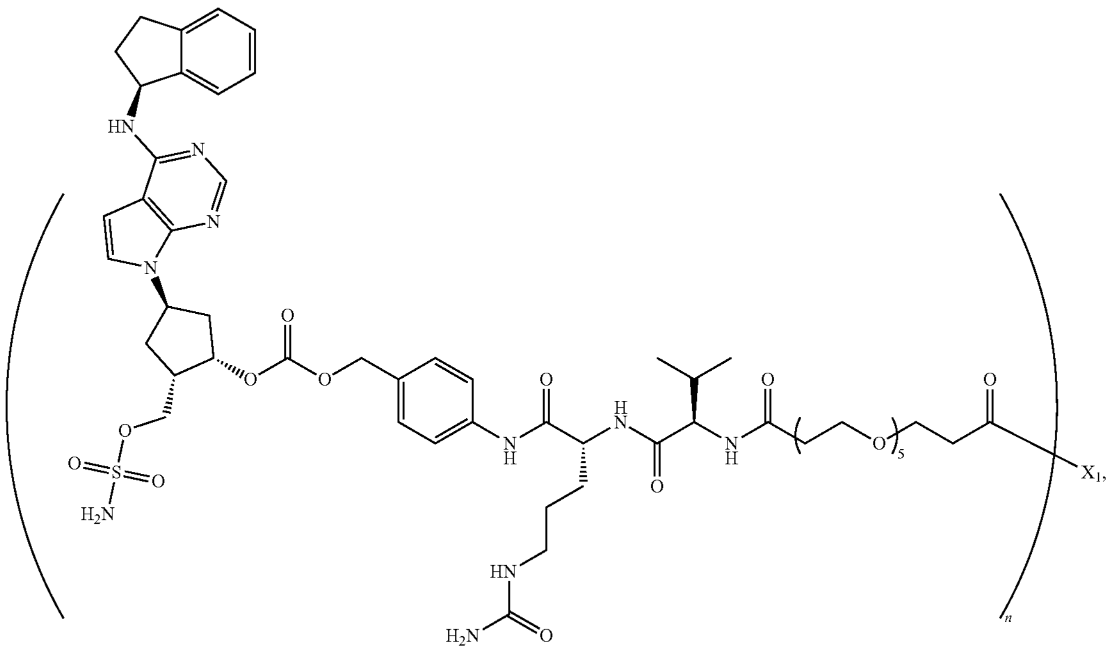 |
| B-6 | 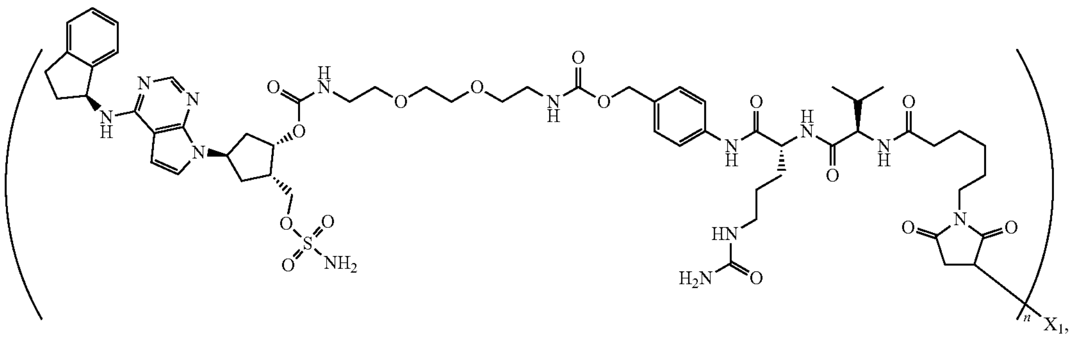 |

-continued
| Compound | Structure |
| --- | --- |
| B-7 | 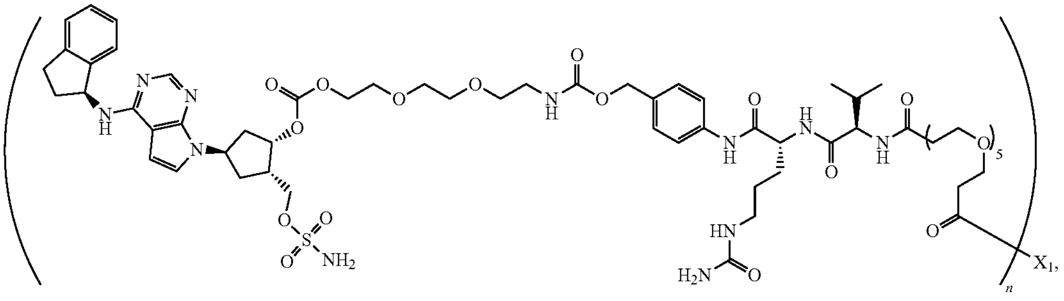 |
| B-8 | 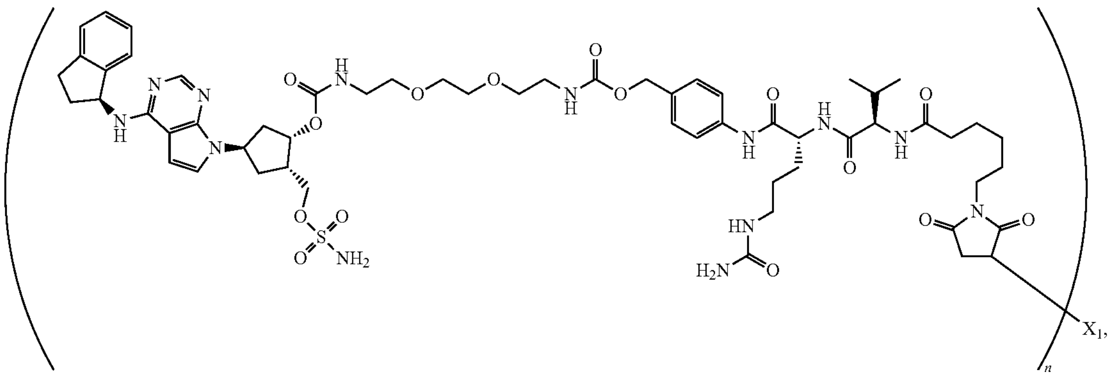 |
| B-9 | 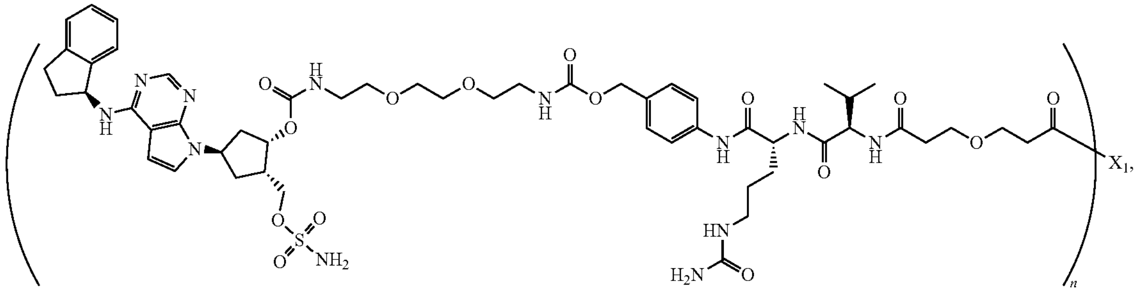 |
| B-10 | 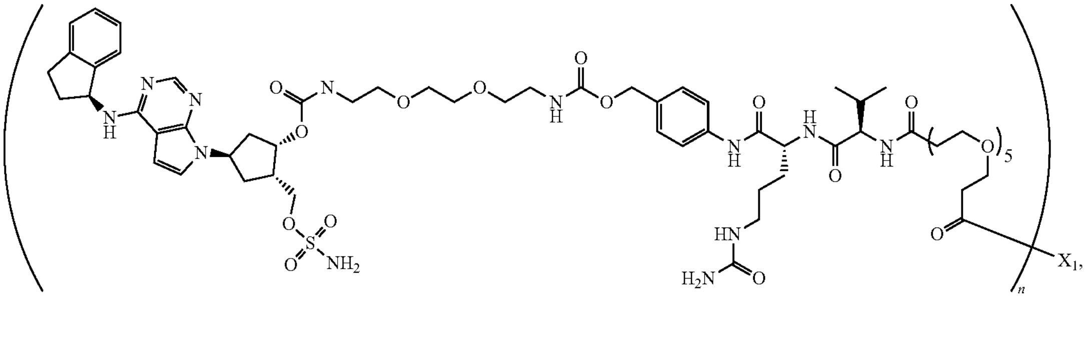 |

-continued
| Com-pound | Structure |
|---|---|
| B-11 | 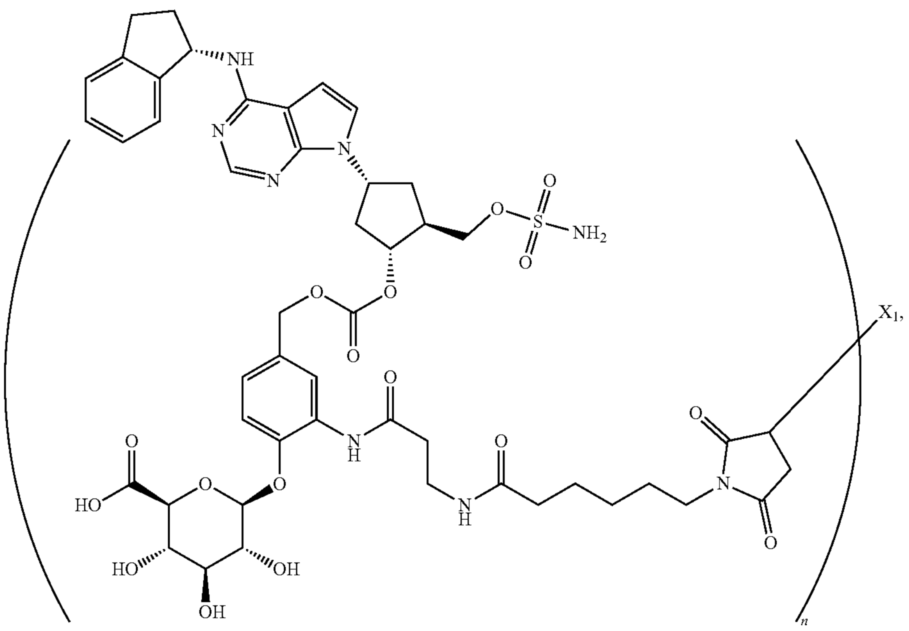 |
| B-12 | 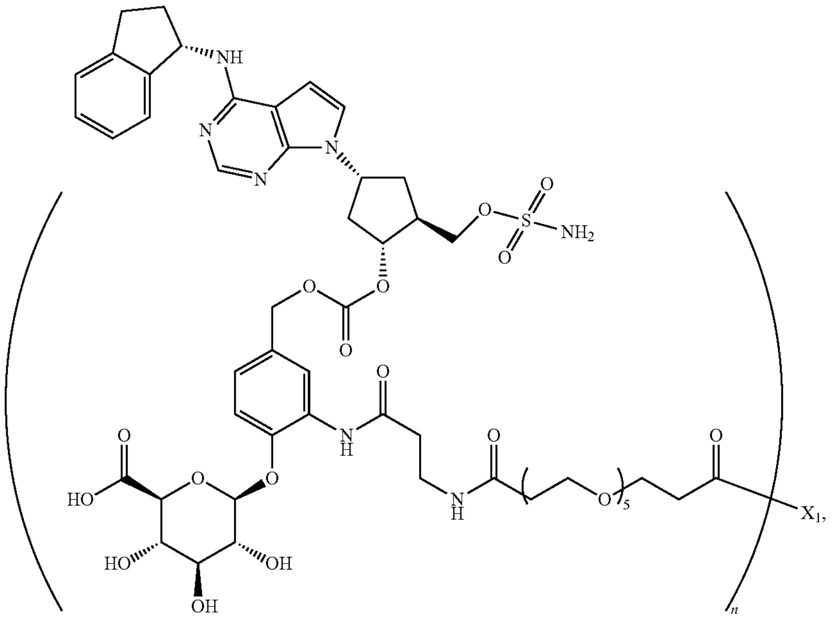 |

-continued
| Compound | Structure |
|---|---|
| B-13 | 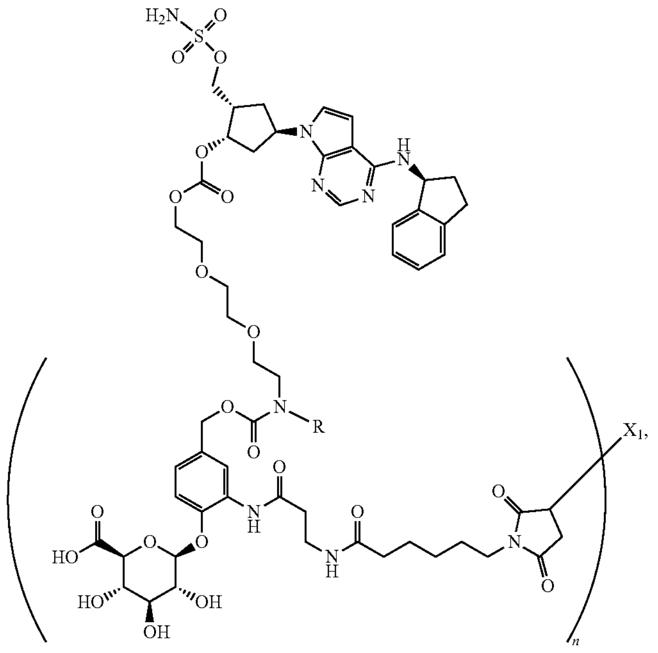 |
| B-14 | 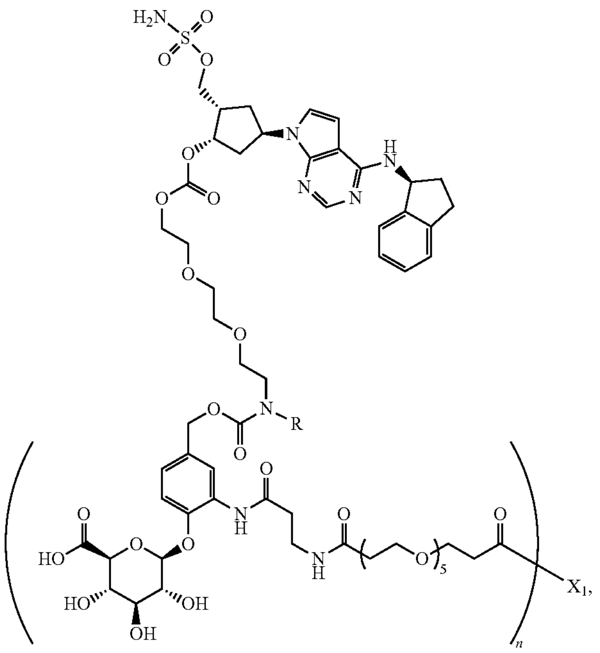 |

-continued
| Compound | Structure |
|---|---|
| B-15 | 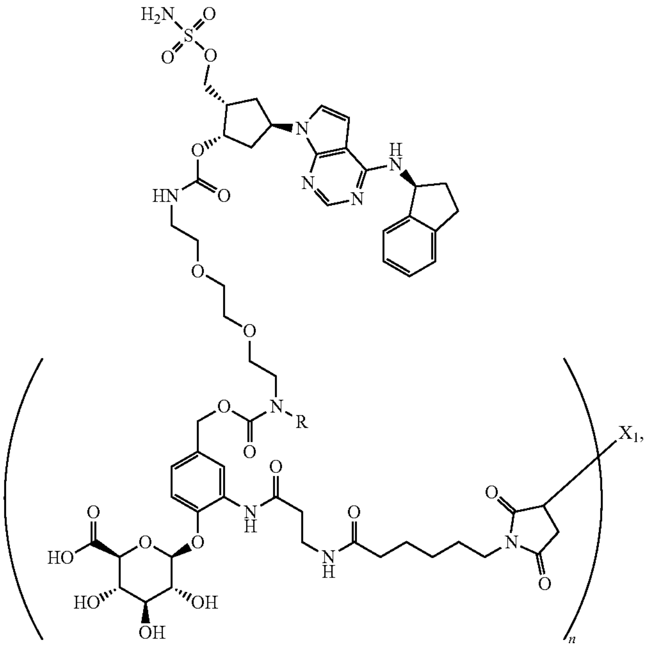 |
| B-16 | 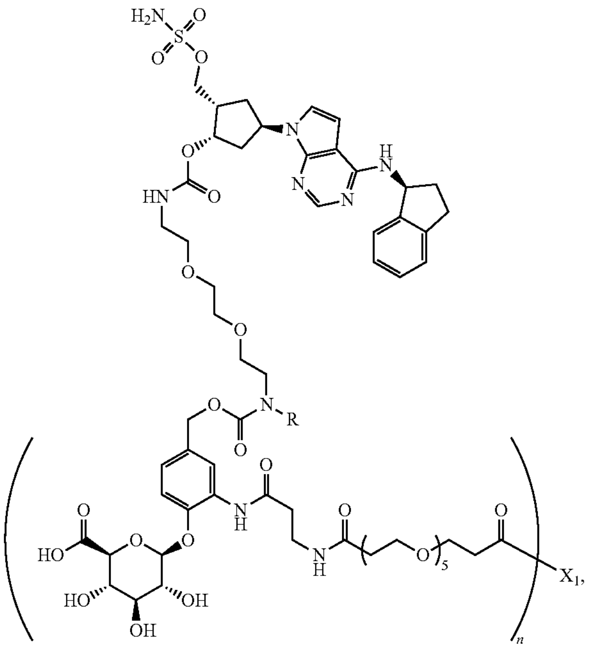 |

-continued
| Compound | Structure |
|---|---|
| B-17 | 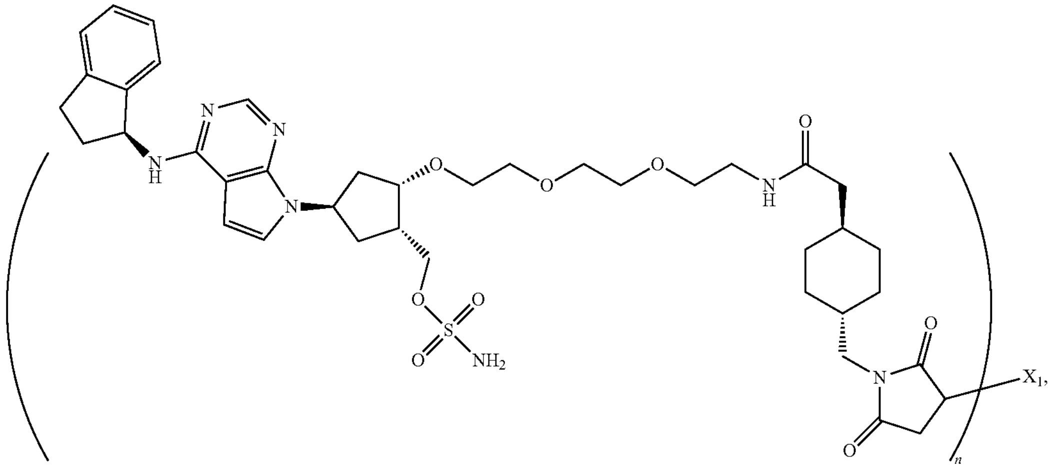 |
| B-18 | 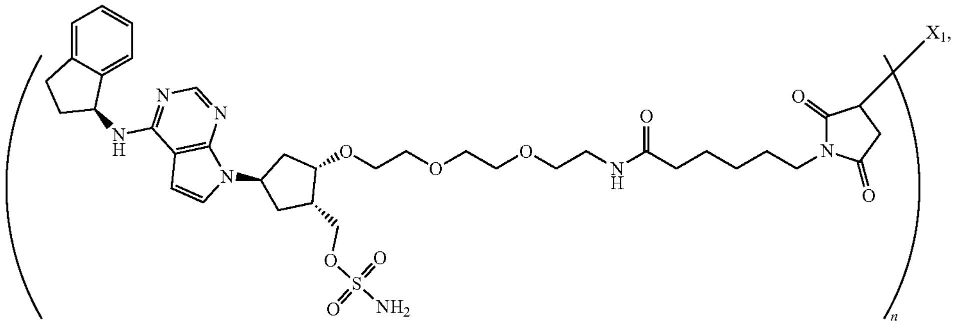 |
| B-30 | 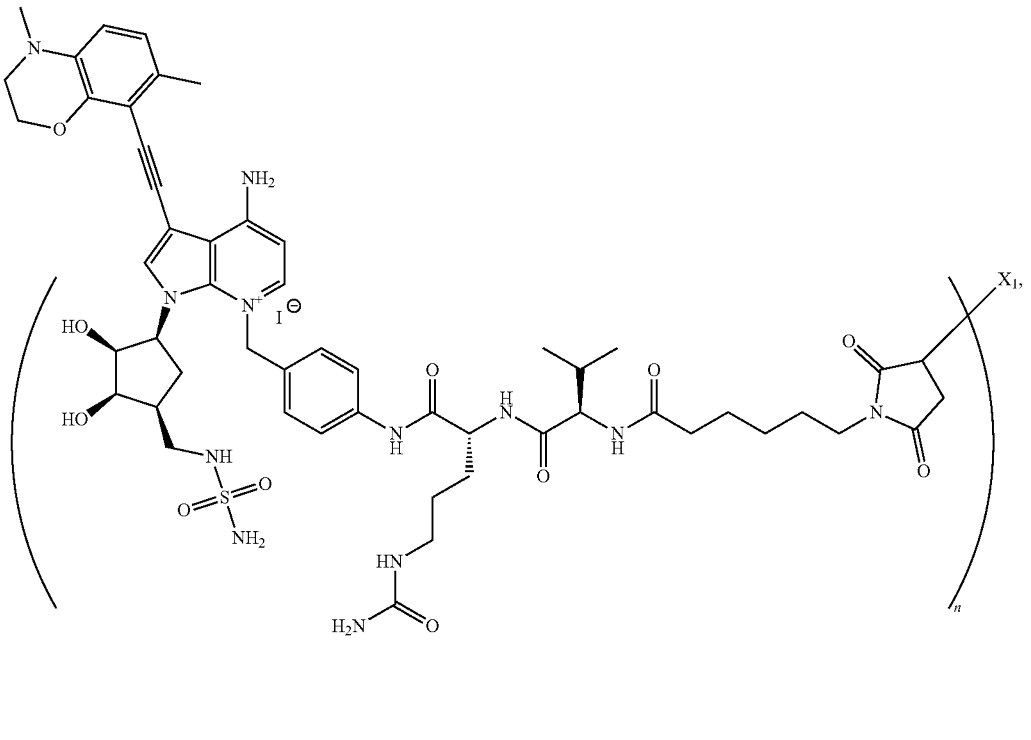 |

-continued
| Compound | Structure |
|---|---|
| B-31 | 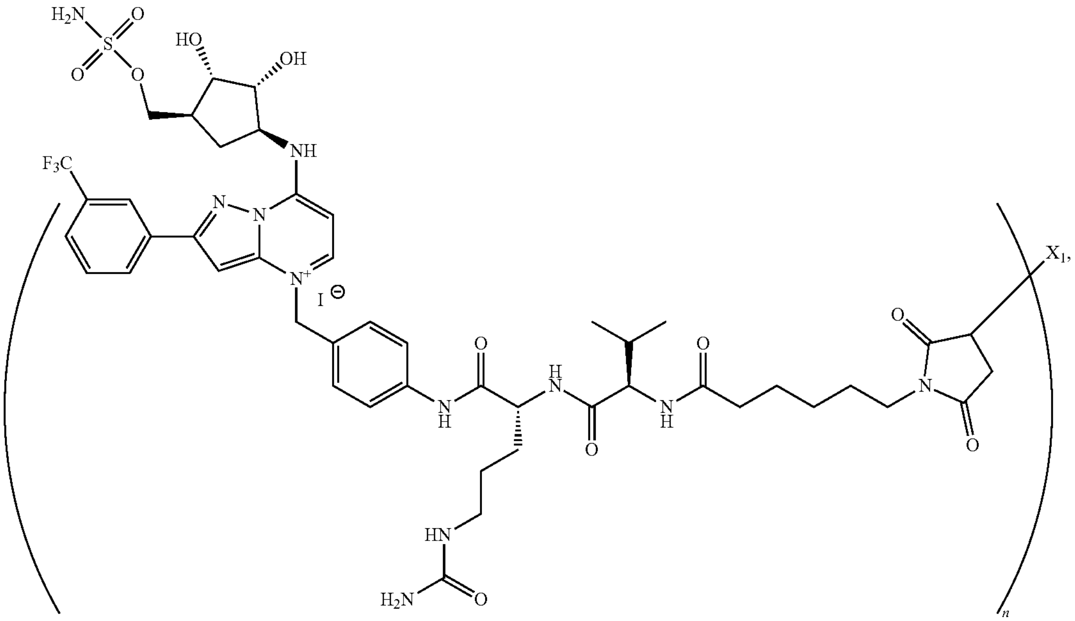 |
| B-48 | 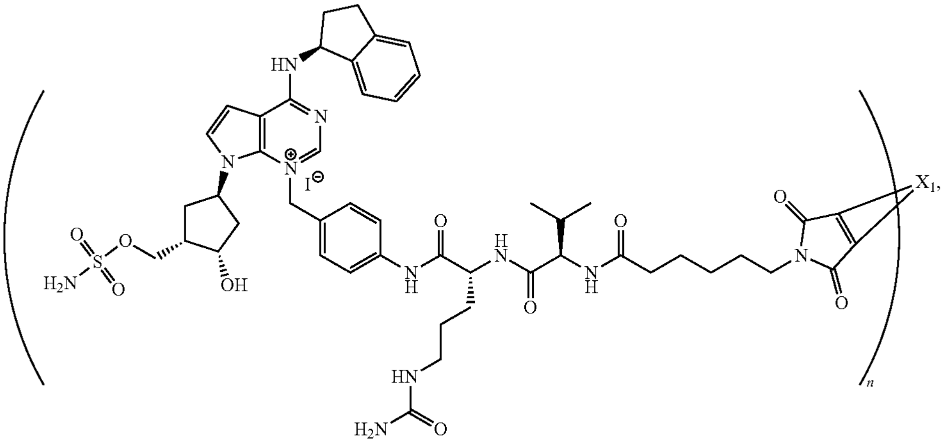 |
| | and |
| B-49 | 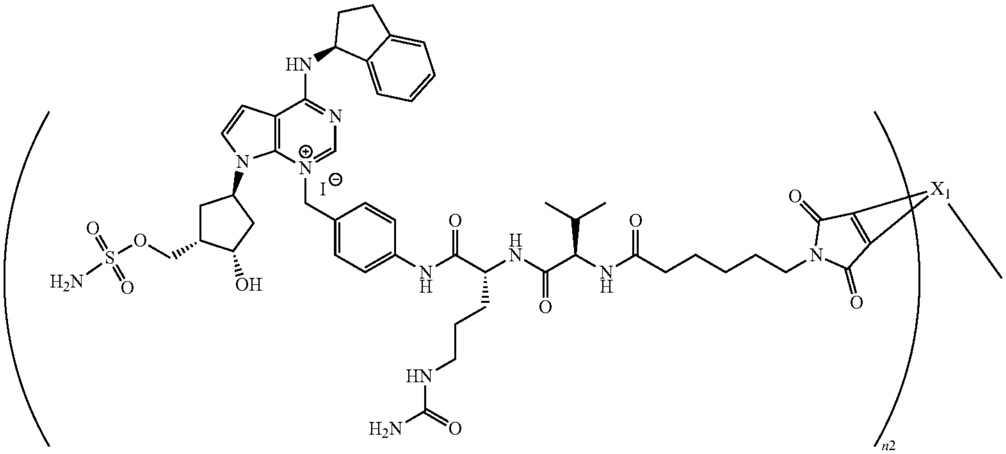 |

-continued

| Compound | Structure |
|---|---|
| | 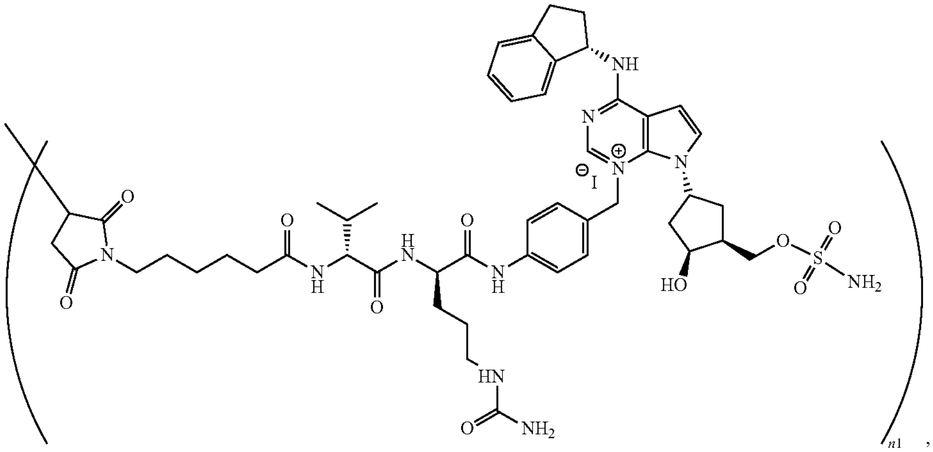 , |

wherein R is H, alkyl, aryl, arylalkyl, a glycol ether, or a glycol linker; q is 1, 2, 3, or 4; n1 is 1, 2, 3, 4, 5, 6, 7, 8, 9, or 10; and n2 is 1, 2, 3, 4, 5, 6, 7, 8, 9, or 10.

8. A pharmaceutical composition comprising a compound, or a pharmaceutically acceptable salt, solvate, hydrate, or tautomer thereof, of claim 1 and a pharmaceutically acceptable carrier.

9. The compound, or a pharmaceutically acceptable salt, solvate, hydrate, isomer, or tautomer thereof, of claim 1, wherein X2 is a mixture of $X_{2b}$ and $X_{2c}$, $X_{2b}$ is a linker that is bound to one Cys residue on $X_1$, $X_{2c}$ is a linker that is bound to two different Cys residues on $X_1$, wherein n is 2, 3, 4, 5, or 6, and wherein SEQ ID NO:2 has with amino acid sequence MVKQIESKTAFQEALDAAGDKL VVVDFSATWCGPCKMIKPFFHSLSEKYSNVI-FLEVDVDDCQDVASECEVKCMPTFQF FKKGQKVGEFSGANKEKLEATINELVGSA-MAPTSSSTKKTQLQLEHLLLDLQMILNGI NNYKNPKLTRMLTFKFYMPK-KATELKHLQCLEEELKPLEEVLNLAQSKNFHLR-PRDLI SNINVIVLELKGSETTFMCEYADETATIVE-FLNRWITFSQSIISTLT.

10. The compound, or a pharmaceutically acceptable salt, solvate, hydrate, isomer, or tautomer thereof, of claim 1, wherein the compound of Formula (III) is B-49.

11. The compound, or a pharmaceutically acceptable salt, solvate, hydrate, isomer, or tautomer thereof, of claim 1, wherein X2 is X2b or X2c, wherein X2b is a linker that is bound to one Cys residue on X1, and n is n1, wherein n1 corresponds to the number of X2b moieties bound to X1, and wherein X2c is a linker that is bound to two different Cys residues on X1, wherein n is n2, wherein n2 corresponds to the number of X2c moieties bound to X1.

12. The compound, or a pharmaceutically acceptable salt, solvate, hydrate, isomer, or tautomer thereof, of claim 1, wherein the compound of Formula (III) is B-49.

13. The compound of claim 1, wherein the linker is cleavable under intracellular conditions and facilitates endocytic release of the therapeutic compound payload.

* * * * *